(12) United States Patent
Demopulos et al.

(10) Patent No.: US 12,351,648 B2
(45) Date of Patent: Jul. 8, 2025

(54) METHODS OF INHIBITING MASP-2 FOR THE TREATMENT AND/OR PREVENTION OF CORONAVIRUS-INDUCED ACUTE RESPIRATORY DISTRESS SYNDROME

(71) Applicant: Omeros Corporation, Seattle, WA (US)

(72) Inventors: Gregory A. Demopulos, Seattle, WA (US); Tineka J. Quinton, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 17/194,054

(22) Filed: Mar. 5, 2021

(65) Prior Publication Data

US 2021/0292436 A1    Sep. 23, 2021

Related U.S. Application Data

(60) Provisional application No. 62/986,566, filed on Mar. 6, 2020, provisional application No. 63/008,540, filed on Apr. 10, 2020, provisional application No. 63/015,299, filed on Apr. 24, 2020, provisional application No. 63/054,298, filed on Jul. 21, 2020, provisional application No. 63/062,843, filed on Aug. 7, 2020, provisional application No. 63/104,229, filed on Oct. 22, 2020, provisional application No. 63/105,637, filed on Oct. 26, 2020, provisional application No. 63/140,591, filed on Jan. 22, 2021.

(51) Int. Cl.
| | | |
|---|---|---|
| A61K 39/395 | (2006.01) | |
| A61K 39/00 | (2006.01) | |
| A61P 11/00 | (2006.01) | |
| C07K 16/40 | (2006.01) | |

(52) U.S. Cl.
CPC .............. *C07K 16/40* (2013.01); *A61P 11/00* (2018.01); *A61K 2039/505* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,331,647 | A | 5/1982 | Goldenberg |
| 4,816,567 | A | 3/1989 | Cabilly et al. |
| 4,946,778 | A | 8/1990 | Ladner et al. |
| 5,211,657 | A | 5/1993 | Yamada et al. |
| 5,223,409 | A | 6/1993 | Ladner et al. |
| 5,403,484 | A | 4/1995 | Ladner et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,571,698 | A | 11/1996 | Ladner et al. |
| 5,610,288 | A | 3/1997 | Rubenstein |
| 5,693,762 | A | 12/1997 | Queen et al. |
| 5,718,709 | A | 2/1998 | Considine et al. |
| 5,738,868 | A | 4/1998 | Shinkarenko |
| 5,739,119 | A | 4/1998 | Galli et al. |
| 5,741,516 | A | 4/1998 | Webb et al. |
| 5,759,829 | A | 6/1998 | Shewmaker et al. |
| 5,789,573 | A | 8/1998 | Baker et al. |
| 5,795,587 | A | 8/1998 | Gao et al. |
| 5,801,154 | A | 9/1998 | Baracchini et al. |
| 6,649,592 | B1 | 11/2003 | Larson |
| 2002/0019369 | A1 | 2/2002 | Li et al. |
| 2012/0282263 | A1 | 11/2012 | Dudler et al. |
| 2013/0344073 | A1 | 12/2013 | Schwaeble et al. |

(Continued)

FOREIGN PATENT DOCUMENTS

| | | | | |
|---|---|---|---|---|
| CN | 104717975 A | | 6/2015 | |
| CN | 112237630 A | * | 1/2021 | ............. A61K 45/00 |

(Continued)

OTHER PUBLICATIONS

Huang et al. Clinical features of patients infected with 2019 novel coronavirus in Wuhan, China,. The Lancet 395(10223) p. 497-506, published Jan. 2020) (Year: 2020).*

World Health Organization (WHO): WHO advice for international travel and trade in relation to the outbreak of pneumonia caused by a new coronavirus in China. pp. 1-3, Jan. 10, 2020. (Year: 2020).*

Ian M Mackay. Viral pneumonia cluster in Wuhan, centralChina: 44 cases and counting. Virology Down Under, pp. 1-8, Jan. 3, 2020. (Year: 2020).*

(Continued)

*Primary Examiner* — Maher M Haddad
(74) *Attorney, Agent, or Firm* — Tineka J. Quinton

(57) ABSTRACT

In one aspect, the invention provides methods for treating, inhibiting, alleviating, or preventing acute respiratory distress syndrome, pneumonia, or some other pulmonary or other manifestation of coronavirus infection, such as thrombosis, in a mammalian subject infected with coronavirus, such as SARS-CoV-2. The methods comprise the step of administering to a subject infected with coronavirus an amount of a MASP-2 inhibitory agent effective to inhibit MASP-2-dependent complement activation. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound. In one embodiment, the subject is a human subject suffering from COVID-19-induced acute respiratory distress syndrome (ARDS) and requires supplemental oxygen prior to treatment and the MASP-2 inhibitory agent is administered in an amount sufficient to discontinue the need for supplemental oxygen.

6 Claims, 71 Drawing Sheets

Specification includes a Sequence Listing.

(56) References Cited

U.S. PATENT DOCUMENTS

| | | |
|---|---|---|
| 2016/0058850 A1 | 3/2016 | Igonin et al. |
| 2019/0127484 A1 | 5/2019 | Schwaeble et al. |

FOREIGN PATENT DOCUMENTS

| | | | |
|---|---|---|---|
| EP | 0 321 201 A2 | 6/1989 | |
| WO | WO 88/04300 | 6/1988 | |
| WO | WO 91/11465 | 8/1991 | |
| WO | WO 2004/009664 A2 | 1/2004 | |
| WO | WO 2004/106384 A1 | 12/2004 | |
| WO | WO-2005123128 A2 * | 12/2005 | ......... A01K 67/0276 |
| WO | WO 2012/151481 A1 | 11/2012 | |
| WO | WO 2013/192240 A2 | 12/2013 | |
| WO | WO 2014/144542 A2 | 9/2014 | |
| WO | WO 2019/231933 A2 | 12/2019 | |
| WO | WO 2019/231933 A3 | 12/2019 | |
| WO | WO 2019/231935 | 12/2019 | |
| WO | WO 2019/246367 A1 | 12/2019 | |
| WO | WO 2021/113682 A1 | 6/2021 | |
| WO | WO 2021/113686 A1 | 6/2021 | |
| WO | WO 2021/113690 A1 | 6/2021 | |
| WO | WO 2021/113698 A1 | 6/2021 | |

OTHER PUBLICATIONS

Yang et al. Clinical course and outcomes of critically ill patients with SARS-CoV-2 pneumonia in Wuhan, China: a single-centered, retrospective, observational study. Lancet Respir Med, Feb. 2020, 8:475-81. (Year: 2020).*

Chen, C., et al., "Stoichiometry of Complexes between Mannose—binding Protein and Its Associated Serine Proteases," *The Journal of Biological Chemistry* 276(28):25894-25902 (2001).

Feinberg, H., et al., "Crystal structure of the CUB1-EGF-CUB2 region of mannose-binding protein associated serine protease-2," *The EMBO Journal* 22(10):2348-2359 (2003).

Stover, C.M., et al., "The rat and mouse homologues of MASP-2 and Map19, components of the lectin activation pathway of complement," *J Immunol* 163(12):6848-6859 (1999).

Thiel, S., et al., "A second serine protease associated with mannan-binding lectin that activates complement," *Nature* 386:506-510 (1997).

Thielens, N.M., et al., "Interaction Properties of Human Mannan-Binding Lectin (MBL)-Associated Serine Proteases-1 and -2, MBL-Associated Protein 19, and MBL," *The Journal of Immunology* 166:5068-5077 (2001).

Matsushita, M., et al., "Cutting Edge: Complement-Activatting Complex of Ficolin and Mannose-Binding Lectin-Associated Serine Protease," *The Journal of Immunology* 164:2281-2284 (2000).

Rodrigues, M.L., et al., "Engineering Fab' Fragments for Efficient F(ab)$_2$ Formation in *Escherichia coli* and for Improved In Vivo Stability," *The Journal of Immunology* 151(12):6954-6961 (1993).

Riedemann, N.C., et al., "Complement in Ischemia Reperfusion Injury," *American Journal of Pathology* 162(2):363-367 (2003).

Matsushita, M. et al., "Activation of the Lectin Complement Pathway by H-Ficolin (Hakata Antigen)," *The Journal of Immunology* 168:3502-3506 (2002).

Stengaard-Pedersen, K., et al., "Inherited Deficiency of Mannan-Binding Lectin-Associated Serine Protease 2," *The New Englad Journal of Medicine* 349(6):554-560 (2003).

Moller-Kristensen, M., et al., "Levels of mannan-binding lectin-associated serine protease-2 in healthy individuals," *Journal of Immunological Methods* 282:159-167 (2003).

Petersen, S.V., et al., "Control of the Classical and MBL Pathway of Complement Activation," *Mol. Immunol* 37(14):803-811 (2000).

Petersen, S.V., et al., "An assay for the mannan-binding lectin pathway of complement activation," *Journal of Immunological Methods* 257:107-116 (2001).

Liszewski, M. Kathryn and Atkinson, John P., The Complement System, Chapter 26, pp. 917-939. *Fundamentals in Immunology*, Third Edition, William E. Paul, Ed. Raven Press Ltd, New York, 1993.

Collard, C.D., et al., "Complement Activation after Oxidative Stress: Role of the Lectin Complement Pathway," *American Journal of Pathology* 156(5):1549-1556 (2000).

Jordan, J.E., et al., "Inhibition of Mannose-Binding Lectin Reduces Postischemic Myocardial Reperfusion Injury," *Circulation* 104:1413-1418 (2001).

Collard, C.D., et al., "Endothelial Oxidative Stress Activates the Lectin Complement Pathway," *American Journal of Pathology* 159(3):1045-1054 (2001).

Kilpatrick, D.C., "Mannan-binding lectin: clinical significance and applications," *Biochimica et Biophysica Acta* 1572:401-413 (2002).

Kalli, K., et al., "Therapeutic Uses of Recombinant Complement Protein Inhibitors," Springer Seminars in Immunopathology 15(4):417-431 (1994).

Wallis, R., et al., "Localization of the Serine Protease-binding Sites in the Collagen-like Domain of Mannose-binding Protein," *The Journal of Biological Chemistry* 279(14):14065-14073 (2004).

Wallis, R., et al., "Interaction of Mannose-binding Protein with Associated Serine Proteases: Effects of Naturally Occurring Mutations," *The Journal of Biological Chemistry* 275(40):30962-30969 (2000).

Petersen, S.V., et al., "Generation of Antibodies Towards MASP-1 and MASP-2 Using Bacterial Expression Systems," *Molecular Immunology* 35(6-7):409 (1998) (meeting abstract).

Cech, T.R., et al., "Biological Catalysis by RNA," *Ann. Rev. Biochem.* 55:599-629 (1986).

Clackson, T., et al., "Making antibody fragments using phage display libraries," *Nature* 352:624-628 (1991).

Chen, P.-F., et al., "Development of the Non-palindromatic Adaptor Polymerase Chain Reaction (NPA-PCR) for the Amplification of Alpha- and Beta-Chain T-Cell Receptor of cDNAs." *Scand J Immunol* 35:539-549 (1992).

Bird, R.E., et al., "Single-Chain Antigen-Binding Proteins," *Science* 242:423-426 (1988).

Climie, S., et al., "Chemical synthesis of the thymidylate synthase gene," *Proc. Natl. Acad. Sci.* 87:633-637 (1990).

Carter, P., et al., "Humanization of an anti-p185$^{HER2}$ antibody for human cancer therapy," *Proc. Natl. Acad. Sci.* 89:4285-4289 (1992).

Altschul, S.F., et al., "Gapped Blast and PSI-Blast: a new generation of protein database search programs," *Nucleic Acids Research* 25(17):3389-3402 (1997).

Makino, K., et al., "A Microcapsule Self-Regulating Delivery System for Insulin," *Journal of Controlled Release* 12:235-239 (1990).

Lee, V.H.L., "Protease Inhibitors and Penetration Enhancers as Approaches to Modify Peptide Absorption," *Journal of Controlled Release* 13:213-223 (1990).

Jolliffe, L.K., et al., "Humanized Antibodies: Enhancing Therapeutic Utility Through Antibody Engineering," *Intern. Rev. Immunol* 10:241-250 (1993).

Jackson, D.Y., et al., "Potent α4β1 Peptide Antagonists as Potential Anti-Inflammatory Agents," *J. Med. Chem.* 40:3359-3368 (1997).

Hori, R., et al., "Enhanced Bioavailability of Subcutaneously Injected Insulin Coadministered with Collagen in Rats and Humans," *Pharmaceutical Research* 6(9):813-816 (1989).

Satomura, A., et al., "Significant Elevations in Serum Mannose-Binding Lectin Levels in Patients with Chromic Renal Failure," *Nephron* 92:702-704 (2002).

Greenspan, N.S., et al., "Idiotypes: structure and immunogenicity," *FASEB J.* 7:437-444 (1993).

De Boer, A.G., et al., "Rectal Absorption Enhancement of Peptide Drugs," *Journal of Controlled Release* 13:241-246 (1990).

Fuertges, R., et al., "The Clinical Efficacy of Poly(ethylene glycol)-Modified Proteins," *The Journal of Controlled Release* 11:139-148 (1990).

Riechmann, L., et al., "Reshaping human antibodies for therapy," *Nature* 332:323-327 (1988).

Singer, I.I., et al., "Optimal Humanization of 1B4, an Anti-CD18 Murine Monoclonal Antibody, Is Achieved by Correct Choice of Human V-Region Framework Sequences," *The Journal of Immunology* 150(7):2844-2857 (1993).

Sandhu, J.S., et al., "Protein Engineering of Antibodies," *Critical Reviews in Biotechnology* 12(5/6):437-462 (1992).

(56) References Cited

OTHER PUBLICATIONS

Ravetch, J.V., et al., "Fc Receptors," *Annu. Rev. Immunol.* 9:457-92 (1991).
Rosenblatt, J., et al., "The Effect of Collagen Fiber Size Distribution on the Release Rate of Proteins from Collagen Matrices by Diffusion," *Journal of Controlled Release* 9:195-203 (1989).
Porter, R.R., "The Hydrolysis of Rabbit γ-Globulin and Antibodies with Crystalline Papain," *Biochem. J.* 73:119-126 (1959).
Merrifield, R.B., "Solid Phase Peptide Synthesis. I. The Synthesis of a Tetrapeptide," *J. Amer. Chem. Soc.* 85:2149-2154 (1963).
Presta, L.G., "Antibody engineering," *Current Opinion in Structural Biology* 2:593-596 (1992).
Lee, V.H.L., "Enzymatic Barriers to Peptide and Protein Absorption," *CRC Critical Reviews in Therapeutic Drug Carrier Systems* 5(2):69-97 (1988).
Yamakawa, I., et al., "Sustained Release of Insulin by Double-Layered Implant Using Poly(D,L-Lactic Acid)," *Journal of Pharmaceutical Sciences* 79(6):505-509 (1990).
Ohman, E.M., et al., "Early clinical experience with integrelin, and inhibitor of the platelet glycoprotein IIb/IIIa integrin receptor," *European Heart Journal* 16(Supplement L):50-55 (1995).
Pack, P., et al., "Improved Bivalent Miniantibodies, with Identical Avidity as Whole Antibodies, Produced by High Cell Density Fermentation of *Escherichia coli*," *Bio/Technology* 11:1271-1277 (1993).
Zhang, L., et al., "A Discrete Site Modulates Activation of I Domains: Application to Integrin $\alpha_M\beta_2$," *The Journal of Biological Chemistry* 271(47):29953-29957 (1996).
Taylor, L.D., et al., "Human immunoglobulin transgenes undergo rearrangement, somatic mutation and class switching in mice that lack endogenous IgM," *International Immunology* 6(4):579-591 (1994).
Takakura, Y. et al., "Control of Pharmaceutical Properties of Soybean Trypsin Inhibitor by Conjugation with Dextran I: Synthesis and Characterization," *Journal of Pharmaceutical Sciences* 78(2):117-121 (1989).
Takakura, Y., et al., "Control of Pharmaceutical Properties of Soybean Trypsin Inhibitor by Conjugation with Dextran II: Biopharmaceutical and Pharmacological Properties," *Journal of Pharmaceutical Sciences* 78(3):219-222 (1989).
Van de Winkel, J.G.J., et al., "Human IgG Fc receptor heterogeneity: molecular aspects and clinical implications," *Immunology Today* 14(5):215-221 (1993).
Vaughan, T.J., et al., "Human antibodies by design," *Nature Biotechnology* 16:535-539 (1998).
Scatchard, G., "The Attractions of Proteins for Small Molecules and Ions," *Annals New York Academy of Sciences* 51:660-672 (1949).
Green, L.L., et al., "Antigen-specific human monoclonal antibodies from mice engineered with human Ig heavy and light chain YACs," *Nature Genetics* 7:13-21 (1994).
Glover, G.I., et al., "Synthetic Peptide Inhibitors of Complement Serine Proteases—I. Identification of Functionally Equivalent Protease Inhibitor Sequences in Serpins and Inhibition of C1s and D," *Molecular Immunology* 25(12):1261-1267 (1988).
Fedor, M.J., et al., "Substrate sequence effects on "hammerhead" RNA catalytic efficiency," *Proc. Natl. Acad. Sci. USA* 87:1668-1672 (1990).
Duncan, A.R., et al., "The binding site for C1q and IgG," *Nature* 332:738-740 (1988).
Dodds, A.W., et al., "Small-Scale Preparation of Complement Components C3 and C4," *Methods in Enzymology* 223:47-61 (1993).
Haseloff, J. et al., "Simple RNA enzymes with new and highly specific endoribonuclease activities," *Nature* 334:585-591 (1988).
Matsushita, M., et al., "Activation of the Classical Complement Pathway by Mannose-binding Protein in Association with a Novel C1s-like Serine Protease," *J. Exp. Med.* 176:1497-1502 (1992).
Itakura, K. et al., "Synthesis and Use of Synthetic Oligonucleotides," *Ann. Rev. Biochem.* 53:323-356 (1984).
Kuntz, I.D., "Structure-Based Strategies for Drug Design and Discovery," *Science* 257:1078-1082 (1992).
Ikeda, K., et al., "Serum Lectin with Known Structure Activates Complement through the Classical Pathway," *The Journal of Biological Chemistry* 262(16):7451-7454 (1987).
Lloyd, B.H., et al., "Determination of optimal sites of antisense oligonucleotide cleavage within TNFα mRNA," *Nucleic Acids Research* 29(17):3664-3673 (2001).
DesJarlais, R.L., et al., "Structure-based design of nonpeptide inhibitors specific for the human immunodeficiency virus 1 protease," *Proc. Natl. Acad. Sci. USA* 87:6644-6648 (1990).
Bae, Y.H., et al., "Insulin Permeation Through Thermo-Sensitive Hydrogels," *Journal of Controlled Release* 9:271-279 (1989).
Asano, M. et al., "In Vivo Characteristics of Low Molecular Weight Copoly($_L$-Lactic Acid/Glycolic Acid) Formulations with Controlled Release of Lutenizing Hormone-Releasing Hormone Agonist," *Journal of Controlled Release* 9:111-122 (1989).
Köhler, G., et al., "Continuous cultures of fused cells secreting antibody of predefined specificity," *Nature* 256:495-497 (1975).
Levy, M., et al., "H deficiency in two brothers with atypical dense intramembranous deposit disease," *Kidney International* 30:949-956 (1986).
Kuntz, I.D., et al., "A Geometric Approach to Macromolecule-Ligand Interactions," *J. Mol. Biol.* 161:269-288 (1982).
Marks, J.D., et al., "By-passing Immunization: Human Antibodies from V-gene Libraries Displayed on Phage," *J. Mol. Biol.* 222:581-597 (1991).
Murayama, O., et al., "Novel Peptide Ligands for Integrin α6β1 Selected from a Phage Display Library," *J. Biochem.* 120:445-451 (1996).
Nisonoff, A., et al., "Separation of Univalent Fragments from the Bivalent Rabbit Antibody Molecule by Reduction of Disulfide Bonds," *Archives of Biochemistry and Biophysics* 89:230-244 (1960).
Scherr, M., et al., "Rapid determination and quantitation of the accessibility to native RNAs by antisense oligodeoxynucleotides in murine cell extracts," *Nucleic Acids Research* 26(22):5079-5085 (1998).
Isaacs, J.D., et al., "Therapy with Monoclonal Antibodies: An in Vivo Model for the Assessment of Therapeutic Potential," *The Journal of Immunology* 148(10):3062-3071 (1992).
Whitlow, M., et al., "Single-Chain Fv Proteins and their Fusion Proteins," *Methods: A Companion to Methods in Enzymology* 2(2):97-105 (1991).
Larrick, J.W., et al., "PCR Amplification of Antibody Genes," *Methods: A Companion to Methods in Enzymology* 2(2):106-110 (1991).
Jones, P.T., et al., "Replacing the complementarity-determining regions in a human antibody with those from a mouse," *Nature* 321:522-525 (1986).
Ward, E.S., et al., "Genetic Manipulation and Expression of Antibodies," *Monoclonal Antibodies: Principles and Applications* pp. 137-185 (Wiley-Liss, Inc.) (1995).
Courtenay-Luck, N.S., "Genetic manipulation of monoclonal antibodies," *Monoclonal Antibodies: Production, engineering and clinical application*, Ritter and Ladyman, eds., (Cambridge University Press) pp. 166-179 (1995).
Kelley, R.F., "Engineering Therapeutic Antibodies," *Protein Engineering: Principles and Practice*, Cleland and Craik, eds., (Wiley-Liss, Inc.) pp. 399-434 (1996).
Baines, M.G., et al., "Purification of Immunoglobulin G (IgG)," *Methods in Molecular Biology, vol. 10: Immunochemical Protocols*, Manson, ed., (The Humana Press, Inc.) pp. 79-104 (1992).
Green, J.A., et al., "Production of Polyclonal Antisera," *Methods in Molecular Biology, vol. 10: Immunochemical Protocols*, Manson, Ed., (The Humans Press, Inc.) pp. 1-5 (1992).
Hovind, P., et al., "Mannone-binding Lectin as a Predictor of Microalbuminuria in Type 1 Diabetes: An Inception Cohort Study," *Diabetes* 54:1523-1527 (2005).
Harlow, E., et al., "Antibodies: a laboratory manual," Cold springs Harbor Laboratory, Cold Springs Harbor, New York, 1988. pp. 567-569.
Krarup, A., et al., "Simultaneous activation of complement and coagulation by MBL-associated serine protease 2," *PLos ONE* 7(e623):1-8 (2007).

(56) References Cited

OTHER PUBLICATIONS

Schwaeble, H-W., et al. "Targeting of mannan-binding lectin-ssociated serine protease-2 confers protection from myocardial and gastrointestinal ischemia/reperfusion injury," *PNAS* 108(18):7523-7528 (2011).
Olesen, H.V., et al., "The mannan-binding lectin pathway and lung disease in systic fibrosis-dysfunction of mannan=binding lectin-associated serine protease 2 (MASP-2) may be a major modifier," *Clinical Immunology* 121:324-331 (2006).
Endo, M., et al., "Glomerular deposition of mannose-binding lectin (MBL) ndicates a novel mechanism of complement activation in IgA nephropathy," *Nephrol Dial Transplant* 13:1984-1990 (1998).
Hisano, S., et al., "Activation of the lectin complement pathway in Henoch-Schonlein purpura nephritis," *Am J Kidney Dis* 45(2):295-302 (2005).
Roos, A., et al., "Glomerular activation of the lectin pathway of complement in IgA nephropathy is associated with more severe renal disease," *J Am Soc Nephrol* 17(6):1724-1734 (2006).
Lhotta, K., et al., "Glomerular deposition of mannose-binding lectin in human glomerulonephritis," *Nephrol Dial Transplant* 14(4):881-886 (1999).
Heja, D., et al., "Monospecific Inhibitors Show That Both Mannan-binding Lectin-associated Serine Protease-1 (MASP-1) and -2 Are Essential for Lectin Pathway Activation and Reveal Structural Plasticity of MASP-2," *J Biol Chem* 287(24):20290-20300 (2012).
Kaufman, R.J., et al., "Improved vectors for stable expression of foreign genes in mammalian cells by use of the untranslated leader sequence from EMC virus," *Nucleic Acids Research* 19:4485-90 (1991).
Kaufman, R.J., "Selection and coamplification of heterologous genes in mammalian cells," *Methods in Enzymology*, 185:537-66 (1990).
Maniatis, A., et al., "Intermediate-dose melphalan for refractory myeloma," *Blood* 74(3):1177 (1989).
Shea, K.J., "Molecular Imprinting of Synthetic Network Polymers: The De Novo synthesis of Macromolecular Binding and Catalytic Sties," *Trip* 2(5):166-173 (1994).
Colligan, "Production of Monoclonal Antibosies," *Current Protocols in Immunology*, vol. 1., John Wiley & Sons, pp. 2.5.1-2.6.7, (1991).
Gal et al., "A true autoactivating enzyme. Structural insight into mannose-binding lectin-associated serine protease-2 activations," *J. Biol. Chem.* 280(39):33435-44 (2005).
Thadhani, R., et al., "Acute renal failure," *New Engl J Med* 334(22):1448-1460 (1996).
Gulla, K.C., et al., "Activation of mannan-binding lectin-associated serine proteases leads to generation of a fibrin clot," *Immunology* 129:482-495 (2009).
Kaufman, R. J., "Selection and Coamplification of Heterologous Genes in Mammalian Cells," *Methods in Enzymology* 185:537-566 (1990).
Heja, D., et al., "Revised mechanism of complement lectin-pathway activation revealing the role of serine protease MASP-1 as the exclusive activator of MASP-2," *Proc Natl Acad Sci U S A* 109(26):10498-10503 (2012).
Megyeri, M., et al., "Quantitative characterization of the activation steps of mannan-binding lectin (MBL)-associated serine proteases (MASPs) points to the central role of MASP-1 in the initiation of the complement lectin pathway," *J Biol Chem* 288(13):8922-8934 (2013).
Yaseen, S., et al., "Lectin pathway effector enzyme mannan-binding lectin-associated serine protease-2 can activate native complement C3 in absence of C4 and/or C2." *The FASEB Journal* 31:2210-2219 (2017).
Lee, W.A., "Permeation enhancers for the nasal delivery of protein and peptide therapeutics," *Biopharm*. 3:22-25 (1990).
Gunn, B. M., et al., "Mannose binding lectin is required for alphavirus-induced arthritis/myositis," *PLoS Pathog* 8(3):e1002586 (2012).

Berger, S. P., et al., "Association between mannose-binding lectin levels and graft survival in kidney transplantation," *Am J Transplant* 5(6):1361-1366 (2005).
Yoshihiro, I., et al., "An Insulin-Releasing System that is Responsive to Glucose," *J. Controlled Release* 10:195-203 (1989).
King, L.A., et al., "Propagation, titration and purification of AcMNPV in cell culture," *The Baculovirus Expression System: A Laboratory Guide*, Chapman and Hall Ltd., London, pp. 106-126 (1992).
Asgari, E., et al., "Mannan-binding lectin-associated serine protease 2 is critical for the development of renal ischemia reperfusion injury and mediates tissue injury in the absence of complement C4," *FASEB J* 28(9):3996-4003 (2014).
Tampe, D., et al., "Potential approaches to reverse or repair renal fibrosis," *Nat Rev Nephrol* 10(4):226-237 (2014).
Fearn, A., et al., "The influence of complement activation on chronic renal inflammation and fibrosis," *Molecular Immunology* 48(14):1721 (2011).
Pippin, J. W., et al., "Inducible rodent models of acquired podocyte diseases," *Am J Physiol Renal Physiol* 296(2):F213-F229 (2009).
Pickering, M. C., et al., "C3 glomerulopathy: consensus report," *Kidney Int* 84(6):1079-1089 (2013).
Sheerin, N. S., et al., "Synthesis of complement protein C3 in the kidney is an important mediator of local tissue injury," *FASEB J* 22(4):1065-1072 (2008).
Chevalier, R. L., et al., "Ureteral obstruction as a model of renal interstitial fibrosis and obstructive nephropathy," *Kidney Int* 75(11):1145-1152 (2009).
Wynn, T. A., "Fibrotic disease and the T(H)1/T(H)2 paradigm," *Nat Rev Immunol* 4(8):583-594 (2004).
Boor, P., et al., "Complement C5 mediates experimental tubulointerstitial fibrosis," *J Am Soc Nephrol* 18(5):1508-1515 (2007).
Abbate, M., et al., "How does proteinuria cause progressive renal damage?" *J Am Soc Nephrol* 17(11):2974-2984 (2006).
Mathern, D. R., et al., "Molecules Great and Small: The Complement System," *Clin J Am Soc Nephrol* 10(9):1636-1650 (2015).
Liu et al., "Glomerular mannose-binding lectin deposition is a useful prognostic predictor in immunoglobulin A nephropathy," *Clin Exp Immunol* 174(1):152-60 (2013).
Rensen et al., "Activation of the Complement System in Human Nonalcoholic Fatty Liver Disease," *Hepatology* 50(6):1809-17 (2009).
Quigg R.J, "Complement and the Kidney," *J Immunol* 171:3319-3324, (2003).
Naik A., et al., "Complement regulation in renal disease models," *Semin Nephrol* 33:575-585 (2013).
Tang, Z., et al., "C3a mediates epithelial-to-mesenchymal transition in proteinuric nephropathy," *J Am Soc Nephrol* 20(3):593-603 (2009).
Bao, L., et al., "Distinct roles for C3a and C5a in complement-induced tubulointerstitial injury," *Kidney Int* 80(5):524-534 (2011).
Gharaee-Kermani, M., et al., "Animal Models of Pulmonary Fibrosis," *Methods Mol. Med*. 117:251-259 (2005).
Brown, K. S., et al., "Severe fibrosis in hepatitis C virus-infected patients is associated with increased activity of the mannan-binding lectin (MBL)/MBL-associated serine protease 1 (MASP-1) complex," *Clin Exp Immunol*. 147(1):90-8 (2007).
El Saadany, S. A., et al., "Fibrosis severity and mannan-binding lectin (MBL)/MBL-associated serine protease 1 (MASP-1) complex in HCV-infected patients," *Arab J Gastroenterol* 12(2):68-73 (2011).
Saeed, A., et al., "Mannan binding lectin-associated serine protease 1 is induced by hepatitis C virus infection and activates human hepatic stellate cells," *Clin Exp Immunol* 174(2):265-273 (2013).
Risdon, R. A., et al., "Relationship between renal function and histological changes found in renal-biopsy specimens from patients with persistent glomerular nephritis," *Lancet* 2(7564):363-366 (1968).
Schainuck, L. I., et al., "Structural-functional correlations in renal disease. II. The correlations," *Hum Pathol* 1(4):631-641 (1970).
Nath K.A., "Tubulointerstitial changes as a major determinant in the progression of renal damage," *Am J Kid Dis* 20:1-17 (1992).
Liu, Y., "Cellular and molecular mechanisms of renal fibrosis," *Nat Rev Nephrol* 7(12):684-696 (2011).
Duffield, J. S., "Cellular and molecular mechanisms in kidney fibrosis," *J Clin Invest* 124(6):2299-2306 (2014).

(56) References Cited

OTHER PUBLICATIONS

Whittaker, P., et al., "Quantitative assessment of myocardial collagen with picrosirius red staining and circularly polarized light," *Basic Res Cardiol* 89(5):397-410 (1994).
Furness, P. N., et al., "Semiautomatic quantitation of macrophages in human renal biopsy specimens in proteinuric states," *J Clin Pathol* 50(2):118-122 (1997).
Yang, H. C., et al., "Models of chronic kidney disease," *Drug Discov Today Dis Models* 7(1-2):13-19 (2010).
Brunskill, N. J., "Albumin signals the coming of age of proteinuric nephropathy," *J Am Soc Nephrol* 15(2):504-505 (2004).
Tryggvason, K., et al., "Causes and consequences of proteinuria: the kidney filtration barrier and progressive renal failure," *J Intern Med* 254(3):216-224 (2003).
Williams, M. E., "Diabetic nephropathy: the proteinuria hypothesis," *Am J Nephrol* 25(2):77-94 (2005).
Baines, R. J., et al., "Tubular toxicity of proteinuria," *Nat Rev Nephrol* 7(3):177-180 (2011).
Lozano, R., et al., "Global and regional mortality from 235 causes of death for 20 age groups in 1990 and 2010: a systematic analysis for the Global Burden of Disease Study 2010," *Lancet* 380(9859):2095-2128 (2012).
Clark, W. F., et al., "Excessive fluid intake as a novel cause of proteinuria," *CMAJ* 178(2):173-175 (2008).
Ishola, D. A., Jr., et al., "In mice, proteinuria and renal inflammatory responses to albumin overload are strain-dependent," *Nephrol Dial Transplant* 21(3):591-597 (2006).
David, S., et al., "Alternative pathway complement activation induces proinflammatory activity in human proximal tubular epithelial cells," *Nephrol Dial Transplant* 12(1):51-56 (1997).
Lee, V. W., et al., "Adriamycin nephropathy: a model of focal segmental glomerulosclerosis," *Nephrology (Carlton)* 16(1):30-38 (2011).
Drawz, P., et al., "Chronic kidney disease," *Ann Intern Med* 162(11):1-16 (2015).
Wyatt, R. J., et al., "IgA nephropathy," *N Engl J Med* 368(25):2402-2414 (2013).
Goto, M., et al., "A scoring system to predict renal outcome in IgA nephropathy: a nationwide 10-year prospective cohort study," *Nephrol Dial Transplant* 24(10):3068-3074 (2009).
Berthoux, F., et al., "Predicting the risk for dialysis or death in IgA nephropathy," *J Am Soc Nephrol* 22(4):752-761 (2011).
Coppo, R., et al., "Factors predicting progression of IgA nephropathies," *J Nephrol* 18(5):503-512 (2005).
Reich, H. N., et al., "Remission of proteinuria improves prognosis in IgA nephropathy," *J Am Soc Nephrol* 18(12):3177-3183 (2007).
D'Amico, G., "Natural history of idiopathic IgA nephropathy: role of clinical and histological prognostic factors," *Am J Kidney Dis* 36(2):227-237 (2000).
Matsuda, M., et al., "Deposition of mannan binding protein and mannan binding protein-mediated complement activation in the glomeruli of patients with IgA nephropathy," *Nephron* 80(4):408-413 (1998).
Liu, L. L., et al., "Urinary mannose-binding lectin is a biomarker for predicting the progression of immunoglobulin (Ig)A nephropathy," *Clin Exp Immunol* 169(2):148-155 (2012).
KDIGO, "KDIGO Clinical Practice Guideline for Glomerulonephritis," *Int. Soc of Nephrol* 2(2):139-274 (2012).
Harlow, E., Antibodies, A Laboratory Manual. 1988, pp. 37-59.
Kerr, H., et al., "Comlement-mediated injury and protection of endothelium: Lessons from atypical haemolytic uraemic syndrome," *Immunobiology* 217(2):195-203 (2012).
Sato, Y., et al., "Pulmonary tumor thrombotic microangiopathy," *Pathology International* 45:436-440 (1995).
Dobó, J., et al., "Be on target: Strategies of targeting alternative and lectin pathway components in complement-mediated diseases," *Frontiers in Immunology* 9:1851 (2018).
Hui, D.S., et al., "The continuing 2019-nCoV epidemic threat of novel coronaviruses to global health—The latest 2019 novel coronavirus outbreak in Wuhan, China," *International Journal of Infectious Diseases* 91:264-266 (2020).
Hilleman, M.R., et al., "Realities and enigmas of human viral influenza: pathogenesis, epidemiology and control," *Vaccine* 20:3068-3097 (2002).
Su, S., et al., "Novel influenza D virus: Epidemiology, pathology, evolution and biological characteristics," *Virulance* 8(8):1580-1591 (2017).
Fouchier, R.A., et al., "Avian influenza A virus (H7N7) associated with human conjunctivitis and a fatal case of acute respiratory distress syndrome," *PNAS* 101(5):1356-1361 (2004).
World Health Organization, Weekly epidemiological record, Nov. 14, 2008, 83$^{rd}$ year, Geneva, Switzerland. No. 46, 2008, 83, 413-420, "Health conditions for travellers to Saudi Arabia for the pilgrimage to Mecca (Hajj)".
Eccles, R., "Understanding the symptoms of the common cold and influenza," *Lancet Infect Dis* 5:718-725 (2005).
Schmitz, N., et al., "Interleukin-1 is responsible for acute lung immunopathology but increases survival of respiratory influenza virus infection," *Journal of Virology* 79(10):6441-6448 (2005).
Cheung, C.Y., et al., "Induction of proinflammatory cytokines in human macrophaegs by Influenza A (H5N1) viruses: a mechanism for the unusual severity of human disease?" *The Lancet* 360:1831-37 (2002).
Kash, J.C., et al., "Genomic analysis of increased host immune and cell death responses induced by 1918 influenza virus," *Nature* 443(7111):578-581 (2006).
Berge, S.M., et al., "Pharmaceutical salts," *J Pharmaceut Sci* 66(1):1-19 (1977).
Pétursson, S., "Protecting groups in carbohydrate chemistry," *Journal of Chemical Education* 74(11):1287-1303 (1997).
Janeway, C.A., et al., "The interaction of the antibody molecule with specific antigen", 3.6-3.9 (pp. 1-5), in Immunobilogy: The Immune System in Health and Disease, 5$^{th}$ Edition, New York: Garland Science; 2001.
Szymanski, L.J., et al., "Coronary artery aneurysms and thrombosis in Kawasaki disease," *Aced Forensic Path* 8(2):416-423 (2018).
Hauang, M.-J., et al., "Impact of acute kidney injury on coagulation in adult minimal change nephropathy," *Medicine* 95:46(e5366) (2016).
Rota, P.A., et al., "Characterization of a novel coronavirus associated with severe acute respiratory syndrome," *Science* 300(5624):1394-1399 (2003).
Zaki, A.M., et al., "Isolation of a novel coronavirus from a man with pneumonia in Saudi Arabia," *NEJM* 367(19):1814-20 (2012).
World Health Organization, Novel Coronavirus(2019-nCoV), Siutation Report-22. Data as reported by Feb. 11, 2020.
Guan, W., et al., "Clinical characteristics of coronavirus disease 2019 in China," *NEJM* 382(18):1708-20 (2020).
Gralinski, L.E., et al., "Complement activation contributes to severe acute respiratory syndrome coronavirus pathogenesis," *mBio* 9(5):e1753-18 (2018).
Hui, D.S., et al., "The 1-year impact of sever acute respiratory syndrome on pulmonary function, exercise capacity, and quality of life in a cohort of survivors," *Chest* 128(4):2247-2261 (2005).
Gross, T.J., et al., "Idiopathic pulmonary fibrosis," *NEJM* 345(7):517-525 (2001).
World Health Organiation, WHO Director-General's opening remarks at the media briefing on Covid-19—Mar. 3, 2020.
Sweeny, R.M., et al., "Acute respiratory distress syndrome," *The Lancet* 388:2416-30 (2016).
The ARDS Definition Task Force, "Acute respiratory distress syndrome," *JAMA* 307(23):2526-2533 (2012).
Zhou, F., et al., "Clinical course and risk factors for mortality of adult inpatients with Covid-19 in Wuhan, China: a retrospective cohort study," *The Lancet* 395:1054-62 (2020).
Remuzzi, A., et al., "Covid-19 and Italy: what next?" *The Lancet* 395:1225-28 (2020).
Wichmann, D., et al., "Autopsy findings and venous thromboembolism in patients with Covid-19," *Annals of Internal Medicine* doi:10.7326/M20-2003 1-14 (2020).

(56) References Cited

OTHER PUBLICATIONS

Xu, Z., et al., "Pathological finding of Covid-19 associated with acute respiratory distress syndrome," *Lancet Respir Med* 8:420-422 (2020).

Horby, P.W., et al., "Effect of dexamethasone in hospitalized patients with Covid-19—Preliminary Report," *medRxiv* (https://doi.org/10.1101/2020.06.22.20137273).

Gritti, G., et a., "IL-6 signalling pathway inactivation with siltuximab in patients with Covid-19 respiratory failure: an observational cohort study," *medRxiv* (https://doi.org/10.1101/2020.04.01.20048561).

Magro, C., et al., "Complement associated microvascular injury and thrombosis in the pathogenesis of severe Covid-19 infection: A report of five cases," *Translational Research* 220:1-13 (2020).

Sun, S., et al., "Inhibition of complement activation alleviates acute ling injury induced by highly pathogenic avian influenza H5N1 virus infection," *Am J Respir Cell Mol Biol* 49(2):221-230 (2013).

Garcia Suquia, A., et al.,"High D-dimer levels after stopping anticoagulants in pulmonary embolism with sleep apnoea," *Eur Respir J* 46:1691-1700 (2015).

Varga, Z., et al., "Endotheial cell infection and endotheliitis in Covid-19," *The Lancet* 395:1427-1418 (2020).

Ackermann, M., et al., Pulmonary vascular endothelialitis, thrombosis, and engiogenesis in Covid-19, *New Engl J Med* 383(2):120-128 (2020).

Green, S.J., "Covid-19 accelerates endothelial dysfuction and nitric oxide," *Microbes and Infection* 22:149-150 (2020).

Teuwen, L.-A., at al., "Covid-19: the vasculature unleashed," *Nat Rev Immunol* 20(7):389-391 (2020).

Goshua, G., et al., "Endotheliopathy in Covid-19-associated coagulopathy: evidence from a single-centre, cross-sectional study," *Lancet Haematol* 7:e575-82 (2020).

Jaramillo-Rocha, V., "Acute respiratory distress syndrome," *N Engl J Med* 377(19):1903-4 (2017).

Ferguson, N.D., et al., "The Berlin definition of ARDS: an expanded rationale, justification, and supplementary material," *Intensive Care Med* 38:1573-1582 (2012).

Fagiuoli, S., et al., "Adaptations and lessons in the province of Bergamo," *N Engl J Med* 382(21):e71(1)-e72(2) 2020).

Corman, V.M., et al., "Detection of 2019 novel coronavirus (2019-nCoV) by real-time RT-PCR," *Euro Surveill* 25(3):pii=2000045 (https://doi.org/10.2807/1560-7917.ES_2020.25.3.2000045) 2020.

Farinacci, M., et al., "Circulating endothelial cells as biomarker for cardiovascular diseases," *Res Pract Thromb Haemost* 3:49-58 (2019).

Moussa, M.D., et al., "Evaluation of endothelial damage in sepsis-related ARDS using circulating endothelial cells," *Intensive Care Med* 41:231-238 (2015).

Almici, C., et al., "Circulating endothelial cell count: a reliable marker of endothelial damage in patients undergoing hematopoietic stem cell transplantation," *Bone Marrow Transplantation* 52:1637-1643 (2017).

Thompson, B.T., et al., "Acute respiratory distress syndrome," *N Engl J Med* 377(6):562-72 (2017).

Gao, T., et al., "Highly pathogenic coronavirus N protein aggravates lung injury by MASP-2-mediated complement over-activation," *MedRxiv* (https://doi.org/10.1101/2020.03.29.20041962).

Xiong, Y., et al., "Transscriptomic characterists of bronchoalveolar lavage fluid and peripheral blood mononuclear cells in Covid-19 patients," *Emerging Microbes and Infection* 9(1):761-770 (2020).

Mastaglio, S. et al., "The first case of Covid-19 treated with the complement C3 inhibitor AMY-101," *Clinical Immunology* 215:108450 (2020).

Diurno, F., et al., "Eculizumab treatment in patients with Covid-19: preliminary results from real life ASL Napoli 2 Nord experience," *European Review for Medical and Pharmacological Sciences* 24:4040-4047 (2020).

Veronese, N., et al., "Use of corticosteroids in cornovirus disease 2019 pneumonia: a systematic review of the literature," *Frontiers in Medicine* 7 (Article 170) (2020).

Marshall, M., "Covid-19's lasting misery," *Nature* 585:339-341 (2020).

Troyer, E.A., et al., "Are we facing a crashing wave of neuropsychiatric sequelae of Covid-19? Neuropsychiatric symptoms and potential immunologic mechanisms," *Brain, Behavior, and Immunity* 87:34-39 (2020).

Babapoor-Farrokhran, S., et al., "Myocardiol injury and Covid-19: Possible mechanisms," *Life Sciences* 253:117723 (2020).

Heneka, M.T., et al., "Immediate and long-term consequences of Covid-19 infections for the development of neurological disease," *Alzheimer's Research & Therapy* 12:69 (2020).

Yelin, D, et al., "Long-term consequences of Covid-19: research needs," *The Lancet* 20:1115-1117 (2020).

Diorio, C., et al., "Evidence of thrombotic microangiopathy in children with SARS-CoV-2 across the spectrum of clinical presentations," *Blood Advances* 4(23):6051-6063 (2020).

Radia, T., et al., "Multi-system inflammatory syndrome in children & adolescents (MIS-C): A systemic review of clinical features and presentation," *Peadiatric Respiratory Reviews* (https://doi.org/10.1016/j.prrv.2020.08.001).

Bonow. R.O., et al., "Association of Coronavirus Disease 2019 (Covid-19) with Myocardial Injury and Mortality," *JAMA Cardiology* 5(7):751-753 (2020).

Del Rio, C., et al., "Long-term health consequences of Covid-19," *JAMA* 324(17):1723-1724 (2020).

Marchiano, S., et al., "SARS-CoV-2 infects human pluripotent stem cell-derived cardiomyocytes, impairing electrical and mechanical function," *bioRxiv* (https://doi.org/10.1101/2020.08.30.274464).

Puntmann, V.O., et al., "Outcomes of cardiovascular magnetic resonance imaging in patient recently recovered from coronavirus disease 2019 (Covid-19)," *JAMA Cardiol* 5(11):1265-1273 (2020(.

Lindner, D., et al., "Associateion of cardiac infection with SARS-CoV-2 in confirmed Covid-19 autopsy cases," *JAMA Cardiology* 5(11):1281-1285 (2020).

Chen, X., et al., "Detectable serum SARS-CoV-2 viral load (RNAeamia) isclosely associated with drastically elevated interleukin 6 (IL-6) level in critically Covid-19 patients," *medRxiv* Mar. 3, 2020. .https://doi.org/10.1101/2020.02.29.20029520.

Beltrame, M.H., et al., "MBL-associated serine proteases (MASPs) and infectious diseases," *Mol Imuunol* 67:85-100 (2015).

Rambaldi, A., et al., "Endothelial injury and thrombotic microangiopathy in Covid-19: Treatment with the lectin-pathway inhibitor Narsoplimab," *Immunobiology* 225:152001 (2020).

Szakacs, D., et al., "Novel MASP-2 inhibitors developed via directed evolution of human TFPI1 are potent lectin pathway inhibitors," *J Biol Chem* 294(20):8227-8237 (2019).

Liu, et al., "Clinical features and progression of acute respiratory distress syndrome in coronavirus disease 2019," *medRxiv* https://doi.org/10.1101/2020.02.17.20024166 (this version posted Feb. 27, 2020).

Campbell, C. M., et al., "Will complement inhibition be the new target in treating Covid-19-elated systemic thrombosis?", *Circulation* 141:1739-1741 (2020).

Pandya, P. H., et al., "Complement system in lung disease." *Am J Respir Cell Mol Biol* 51(4):467-473 (2014).

* cited by examiner

*p=0.0388

*p=0.0182

*p = 0.0324
**p=0.0349

SEQUENCE LISTING

```
<160> NUMBER OF SEQ ID NOS: 85

<210> SEQ ID NO 1
<211> LENGTH: 725
<212> TYPE: DNA
<213> ORGANISM: Homo sapiens
<220> FEATURE:
<221> NAME/KEY: CDS
<222> LOCATION: (27)..(584)

<400> SEQUENCE: 1
ggccaggcca gctggacggg cacacc atg agg ctg ctg acc ctc ctg ggc ctt     53
                                Met Arg Leu Leu Thr Leu Leu Gly Leu
                                1               5 ctg tgt ggc tcg gtg gcc acc ccc ttg ggc ccg aag tgg cct gaa cct     101
Leu Cys Gly Ser Val Ala Thr Pro Leu Gly Pro Lys Trp Pro Glu Pro
10                  15                  20                  25 gtg ttc ggg cgc ctg gca tcc ccc ggc ttt cca ggg gag tat gcc aat     149
Val Phe Gly Arg Leu Ala Ser Pro Gly Phe Pro Gly Glu Tyr Ala Asn
                30                  35                  40 gac cag gag cgg cgc tgg acc ctg act gca ccc ccc ggc tac cgc ctg     197
Asp Gln Glu Arg Arg Trp Thr Leu Thr Ala Pro Pro Gly Tyr Arg Leu
            45                  50                  55 cgc ctc tac ttc acc cac ttc gac ctg gag ctc tcc cac ctc tgc gag     245
Arg Leu Tyr Phe Thr His Phe Asp Leu Glu Leu Ser His Leu Cys Glu
        60                  65                  70 tac gac ttc gtc aag ctg agc tcg ggg gcc aag gtg ctg gcc acg ctg     293
Tyr Asp Phe Val Lys Leu Ser Ser Gly Ala Lys Val Leu Ala Thr Leu
    75                  80                  85 tgc ggg cag gag agc aca gac acg gag cgg gcc cct ggc aag gac act     341
Cys Gly Gln Glu Ser Thr Asp Thr Glu Arg Ala Pro Gly Lys Asp Thr
90                  95                  100                 105 ttc tac tcg ctg ggc tcc agc ctg gac att acc ttc cgc tcc gac tac     389
Phe Tyr Ser Leu Gly Ser Ser Leu Asp Ile Thr Phe Arg Ser Asp Tyr
                110                 115                 120
```

```
tcc aac gag aag ccg ttc acg ggg ttc gag gcc ttc tat gca gcc gag      437
Ser Asn Glu Lys Pro Phe Thr Gly Phe Glu Ala Phe Tyr Ala Ala Glu
        125                 130                 135 gac att gac gag tgc cag gtg gcc ccg gga gag gcg ccc acc tgc gac      485
Asp Ile Asp Glu Cys Gln Val Ala Pro Gly Glu Ala Pro Thr Cys Asp
        140                 145                 150 cac cac tgc cac aac cac ctg ggc ggt ttc tac tgc tcc tgc cgc gca      533
His His Cys His Asn His Leu Gly Gly Phe Tyr Cys Ser Cys Arg Ala
        155                 160                 165 ggc tac gtc ctg cac cgt aac aag cgc acc tgc tca gag cag agc ctc      581
Gly Tyr Val Leu His Arg Asn Lys Arg Thr Cys Ser Glu Gln Ser Leu
170                 175                 180                 185 tag cctccctgg agctccggcc tgcccagcag gtcagaagcc agagccagcc             634
tgctggcctc agctccgggt tgggctgaga tggctgtgcc ccaactccca ttcacccacc     694
atggacccaa taataaacct ggccccaccc c                                    725

<210> SEQ ID NO 2
<211> LENGTH: 185
<212> TYPE: PRT
<213> ORGANISM: Homo sapiens

<400> SEQUENCE: 2

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185

<210> SEQ ID NO 3
<211> LENGTH: 170
<212> TYPE: PRT
<213> ORGANISM: Homo sapiens

<400> SEQUENCE: 3

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30
```

```
Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
 50                  55                  60

Ser Ser Gly Ala Lys Val Leu Ala Thr Leu Cys Gly Gln Glu Ser Thr
 65                  70                  75                  80

Asp Thr Glu Arg Ala Pro Gly Lys Asp Thr Phe Tyr Ser Leu Gly Ser
                 85                  90                  95

Ser Leu Asp Ile Thr Phe Arg Ser Asp Tyr Ser Asn Glu Lys Pro Phe
                100                 105                 110

Thr Gly Phe Glu Ala Phe Tyr Ala Ala Glu Asp Ile Asp Glu Cys Gln
                115                 120                 125

Val Ala Pro Gly Glu Ala Pro Thr Cys Asp His His Cys His Asn His
130                 135                 140

Leu Gly Gly Phe Tyr Cys Ser Cys Arg Ala Gly Tyr Val Leu His Arg
145                 150                 155                 160

Asn Lys Arg Thr Cys Ser Glu Gln Ser Leu
                165                 170

<210> SEQ ID NO 4
<211> LENGTH: 2460
<212> TYPE: DNA
<213> ORGANISM: Homo sapiens
<220> FEATURE:
<221> NAME/KEY: CDS
<222> LOCATION: (22)..(2082)

<400> SEQUENCE: 4
ggccagctgg acgggcacac c atg agg ctg ctg acc ctc ctg ggc ctt ctg      51
                        Met Arg Leu Leu Thr Leu Leu Gly Leu Leu
                         1               5                  10 tgt ggc tcg gtg gcc acc ccc ttg ggc ccg aag tgg cct gaa cct gtg      99
Cys Gly Ser Val Ala Thr Pro Leu Gly Pro Lys Trp Pro Glu Pro Val
             15                  20                  25 ttc ggg cgc ctg gca tcc ccc ggc ttt cca ggg gag tat gcc aat gac     147
Phe Gly Arg Leu Ala Ser Pro Gly Phe Pro Gly Glu Tyr Ala Asn Asp
         30                  35                  40 cag gag cgg cgc tgg acc ctg act gca ccc ccc ggc tac cgc ctg cgc     195
Gln Glu Arg Arg Trp Thr Leu Thr Ala Pro Pro Gly Tyr Arg Leu Arg
     45                  50                  55 ctc tac ttc acc cac ttc gac ctg gag ctc tcc cac ctc tgc gag tac     243
Leu Tyr Phe Thr His Phe Asp Leu Glu Leu Ser His Leu Cys Glu Tyr
 60                  65                  70 gac ttc gtc aag ctg agc tcg ggg gcc aag gtg ctg gcc acg ctg tgc     291
Asp Phe Val Lys Leu Ser Ser Gly Ala Lys Val Leu Ala Thr Leu Cys
 75                  80                  85                  90 ggg cag gag agc aca gac acg gag cgg gcc cct ggc aag gac act ttc     339
Gly Gln Glu Ser Thr Asp Thr Glu Arg Ala Pro Gly Lys Asp Thr Phe
                 95                 100                 105 tac tcg ctg ggc tcc agc ctg gac att acc ttc cgc tcc gac tac tcc     387
Tyr Ser Leu Gly Ser Ser Leu Asp Ile Thr Phe Arg Ser Asp Tyr Ser
            110                 115                 120 aac gag aag ccg ttc acg ggg ttc gag gcc ttc tat gca gcc gag gac     435
Asn Glu Lys Pro Phe Thr Gly Phe Glu Ala Phe Tyr Ala Ala Glu Asp
            125                 130                 135 att gac gag tgc cag gtg gcc ccg gga gag gcg ccc acc tgc gac cac     483
Ile Asp Glu Cys Gln Val Ala Pro Gly Glu Ala Pro Thr Cys Asp His
        140                 145                 150
```

-continued

| | |
|---|---|
| cac tgc cac aac cac ctg ggc ggt ttc tac tgc tcc tgc cgc gca ggc<br>His Cys His Asn His Leu Gly Gly Phe Tyr Cys Ser Cys Arg Ala Gly<br>155                        160                      165                      170 | 531 |
| tac gtc ctg cac cgt aac aag cgc acc tgc tca gcc ctg tgc tcc ggc<br>Tyr Val Leu His Arg Asn Lys Arg Thr Cys Ser Ala Leu Cys Ser Gly<br>                175                      180                      185 | 579 |
| cag gtc ttc acc cag agg tct ggg gag ctc agc agc cct gaa tac cca<br>Gln Val Phe Thr Gln Arg Ser Gly Glu Leu Ser Ser Pro Glu Tyr Pro<br>                    190                      195                      200 | 627 |
| cgg ccg tat ccc aaa ctc tcc agt tgc act tac agc atc agc ctg gag<br>Arg Pro Tyr Pro Lys Leu Ser Ser Cys Thr Tyr Ser Ile Ser Leu Glu<br>205                        210                      215 | 675 |
| gag ggg ttc agt gtc att ctg gac ttt gtg gag tcc ttc gat gtg gag<br>Glu Gly Phe Ser Val Ile Leu Asp Phe Val Glu Ser Phe Asp Val Glu<br>                220                      225                      230 | 723 |
| aca cac cct gaa acc ctg tgt ccc tac gac ttt ctc aag att caa aca<br>Thr His Pro Glu Thr Leu Cys Pro Tyr Asp Phe Leu Lys Ile Gln Thr<br>235                        240                      245                      250 | 771 |
| gac aga gaa gaa cat ggc cca ttc tgt ggg aag aca ttg ccc cac agg<br>Asp Arg Glu Glu His Gly Pro Phe Cys Gly Lys Thr Leu Pro His Arg<br>                        255                      260                      265 | 819 |
| att gaa aca aaa agc aac acg gtg acc atc acc ttt gtc aca gat gaa<br>Ile Glu Thr Lys Ser Asn Thr Val Thr Ile Thr Phe Val Thr Asp Glu<br>                270                      275                      280 | 867 |
| tca gga gac cac aca ggc tgg aag atc cac tac acg agc aca gcg cag<br>Ser Gly Asp His Thr Gly Trp Lys Ile His Tyr Thr Ser Thr Ala Gln<br>285                        290                      295 | 915 |
| cct tgc cct tat ccg atg gcg cca cct aat ggc cac gtt tca cct gtg<br>Pro Cys Pro Tyr Pro Met Ala Pro Pro Asn Gly His Val Ser Pro Val<br>                300                      305                      310 | 963 |
| caa gcc aaa tac atc ctg aaa gac agc ttc tcc atc ttt tgc gag act<br>Gln Ala Lys Tyr Ile Leu Lys Asp Ser Phe Ser Ile Phe Cys Glu Thr<br>315                        320                      325                      330 | 1011 |
| ggc tat gag ctt ctg caa ggt cac ttg ccc ctg aaa tcc ttt act gca<br>Gly Tyr Glu Leu Leu Gln Gly His Leu Pro Leu Lys Ser Phe Thr Ala<br>                335                      340                      345 | 1059 |
| gtt tgt cag aaa gat gga tct tgg gac cgg cca atg ccc gcg tgc agc<br>Val Cys Gln Lys Asp Gly Ser Trp Asp Arg Pro Met Pro Ala Cys Ser<br>350                        355                      360 | 1107 |
| att gtt gac tgt ggc cct cct gat gat cta ccc agt ggc cga gtg gag<br>Ile Val Asp Cys Gly Pro Pro Asp Asp Leu Pro Ser Gly Arg Val Glu<br>                365                      370                      375 | 1155 |
| tac atc aca ggt cct gga gtg acc acc tac aaa gct gtg att cag tac<br>Tyr Ile Thr Gly Pro Gly Val Thr Thr Tyr Lys Ala Val Ile Gln Tyr<br>380                        385                      390 | 1203 |
| agc tgt gaa gag acc ttc tac aca atg aaa gtg aat gat ggt aaa tat<br>Ser Cys Glu Glu Thr Phe Tyr Thr Met Lys Val Asn Asp Gly Lys Tyr<br>395                        400                      405                      410 | 1251 |
| gtg tgt gag gct gat gga ttc tgg acg agc tcc aaa gga gaa aaa tca<br>Val Cys Glu Ala Asp Gly Phe Trp Thr Ser Ser Lys Gly Glu Lys Ser<br>                415                      420                      425 | 1299 |
| ctc cca gtc tgt gag cct gtt tgt gga cta tca gcc cgc aca aca gga<br>Leu Pro Val Cys Glu Pro Val Cys Gly Leu Ser Ala Arg Thr Thr Gly<br>                430                      435                      440 | 1347 |
| ggg cgt ata tat gga ggg caa aag gca aaa cct ggt gat ttt cct tgg<br>Gly Arg Ile Tyr Gly Gly Gln Lys Ala Lys Pro Gly Asp Phe Pro Trp<br>                445                      450                      455 | 1395 |
| caa gtc ctg ata tta ggt gga acc aca gca gca ggt gca ctt tta tat<br>Gln Val Leu Ile Leu Gly Gly Thr Thr Ala Ala Gly Ala Leu Leu Tyr<br>460                        465                      470 | 1443 |

| | | |
|---|---|---|
| gac aac tgg gtc cta aca gct gct cat gcc gtc tat gag caa aaa cat<br>Asp Asn Trp Val Leu Thr Ala Ala His Ala Val Tyr Glu Gln Lys His<br>475                        480                        485                        490 | 1491 |
| gat gca tcc gcc ctg gac att cga atg ggc acc ctg aaa aga cta tca<br>Asp Ala Ser Ala Leu Asp Ile Arg Met Gly Thr Leu Lys Arg Leu Ser<br>                  495                        500                        505 | 1539 |
| cct cat tat aca caa gcc tgg tct gaa gct gtt ttt ata cat gaa ggt<br>Pro His Tyr Thr Gln Ala Trp Ser Glu Ala Val Phe Ile His Glu Gly<br>                510                        515                        520 | 1587 |
| tat act cat gat gct ggc ttt gac aat gac ata gca ctg att aaa ttg<br>Tyr Thr His Asp Ala Gly Phe Asp Asn Asp Ile Ala Leu Ile Lys Leu<br>            525                        530                        535 | 1635 |
| aat aac aaa gtt gta atc aat agc aac atc acg cct att tgt ctg cca<br>Asn Asn Lys Val Val Ile Asn Ser Asn Ile Thr Pro Ile Cys Leu Pro<br>540                        545                        550 | 1683 |
| aga aaa gaa gct gaa tcc ttt atg agg aca gat gac att gga act gca<br>Arg Lys Glu Ala Glu Ser Phe Met Arg Thr Asp Asp Ile Gly Thr Ala<br>555                        560                        565                        570 | 1731 |
| tct gga tgg gga tta acc caa agg ggt ttt ctt gct aga aat cta atg<br>Ser Gly Trp Gly Leu Thr Gln Arg Gly Phe Leu Ala Arg Asn Leu Met<br>                575                        580                        585 | 1779 |
| tat gtc gac ata ccg att gtt gac cat caa aaa tgt act gct gca tat<br>Tyr Val Asp Ile Pro Ile Val Asp His Gln Lys Cys Thr Ala Ala Tyr<br>            590                        595                        600 | 1827 |
| gaa aag cca ccc tat cca agg gga agt gta act gct aac atg ctt tgt<br>Glu Lys Pro Pro Tyr Pro Arg Gly Ser Val Thr Ala Asn Met Leu Cys<br>                605                        610                        615 | 1875 |
| gct ggc tta gaa agt ggg ggc aag gac agc tgc aga ggt gac agc gga<br>Ala Gly Leu Glu Ser Gly Gly Lys Asp Ser Cys Arg Gly Asp Ser Gly<br>        620                        625                        630 | 1923 |
| ggg gca ctg gtg ttt cta gat agt gaa aca gag agg tgg ttt gtg gga<br>Gly Ala Leu Val Phe Leu Asp Ser Glu Thr Glu Arg Trp Phe Val Gly<br>635                        640                        645                        650 | 1971 |
| gga ata gtg tcc tgg ggt tcc atg aat tgt ggg gaa gca ggt cag tat<br>Gly Ile Val Ser Trp Gly Ser Met Asn Cys Gly Glu Ala Gly Gln Tyr<br>                655                        660                        665 | 2019 |
| gga gtc tac aca aaa gtt att aac tat att ccc tgg atc gag aac ata<br>Gly Val Tyr Thr Lys Val Ile Asn Tyr Ile Pro Trp Ile Glu Asn Ile<br>            670                        675                        680 | 2067 |
| att agt gat ttt taa cttgcgtgtc tgcagtcaag gattcttcat ttttagaaat<br>Ile Ser Asp Phe<br>            685 | 2122 |
| gcctgtgaag accttggcag cgacgtggct cgagaagcat tcatcattac tgtggacatg | 2182 |
| gcagttgttg ctccacccaa aaaaacagac tccaggtgag gctgctgtca tttctccact | 2242 |
| tgccagttta attccagcct tacccattga ctcaagggga cataaaccac gagagtgaca | 2302 |
| gtcatctttg cccacccagt gtaatgtcac tgctcaaatt acatttcatt accttaaaaa | 2362 |
| gccagtctct tttcatactg gctgttggca tttctgtaaa ctgcctgtcc atgctctttg | 2422 |
| ttttttaaact tgttcttatt gaaaaaaaaa aaaaaaaa | 2460 |

<210> SEQ ID NO 5
<211> LENGTH: 686
<212> TYPE: PRT
<213> ORGANISM: Homo sapiens

<400> SEQUENCE: 5

Met Arg Leu Leu Thr Leu Leu Gly Leu Leu Cys Gly Ser Val Ala Thr
1               5                    10                      15

```
Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
            35                  40                  45

Leu Thr Ala Pro Pro Gly Tyr Arg Leu Arg Leu Tyr Phe Thr His Phe
 50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
            275                 280                 285

Trp Lys Ile His Tyr Thr Ser Thr Ala Gln Pro Cys Pro Tyr Pro Met
290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
            355                 360                 365

Pro Asp Asp Leu Pro Ser Gly Arg Val Glu Tyr Ile Thr Gly Pro Gly
            370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430
```

-continued

Val Cys Gly Leu Ser Ala Arg Thr Gly Gly Arg Ile Tyr Gly Gly
            435                 440                 445

Gln Lys Ala Lys Pro Gly Asp Phe Pro Trp Gln Val Leu Ile Leu Gly
    450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
            500                 505                 510

Trp Ser Glu Ala Val Phe Ile His Glu Gly Tyr Thr His Asp Ala Gly
            515                 520                 525

Phe Asp Asn Asp Ile Ala Leu Ile Lys Leu Asn Asn Lys Val Val Ile
530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
            595                 600                 605

Arg Gly Ser Val Thr Ala Asn Met Leu Cys Ala Gly Leu Glu Ser Gly
            610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
            660                 665                 670

Ile Asn Tyr Ile Pro Trp Ile Glu Asn Ile Ile Ser Asp Phe
            675                 680                 685

<210> SEQ ID NO 6
<211> LENGTH: 671
<212> TYPE: PRT
<213> ORGANISM: Homo sapiens

<400> SEQUENCE: 6

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
            35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
            115                 120                 125

```
Val Ala Pro Gly Glu Ala Pro Thr Cys Asp His His Cys His Asn His
    130                 135                 140
Leu Gly Gly Phe Tyr Cys Ser Cys Arg Ala Gly Tyr Val Leu His Arg
145                 150                 155                 160
Asn Lys Arg Thr Cys Ser Ala Leu Cys Ser Gly Gln Val Phe Thr Gln
                165                 170                 175
Arg Ser Gly Glu Leu Ser Ser Pro Glu Tyr Pro Arg Pro Tyr Pro Lys
            180                 185                 190
Leu Ser Ser Cys Thr Tyr Ser Ile Ser Leu Glu Glu Gly Phe Ser Val
        195                 200                 205
Ile Leu Asp Phe Val Glu Ser Phe Asp Val Glu Thr His Pro Glu Thr
    210                 215                 220
Leu Cys Pro Tyr Asp Phe Leu Lys Ile Gln Thr Asp Arg Glu His
225                 230                 235                 240
Gly Pro Phe Cys Gly Lys Thr Leu Pro His Arg Ile Glu Thr Lys Ser
                245                 250                 255
Asn Thr Val Thr Ile Thr Phe Val Thr Asp Glu Ser Gly Asp His Thr
                260                 265                 270
Gly Trp Lys Ile His Tyr Thr Ser Thr Ala Gln Pro Cys Pro Tyr Pro
        275                 280                 285
Met Ala Pro Pro Asn Gly His Val Ser Pro Val Gln Ala Lys Tyr Ile
    290                 295                 300
Leu Lys Asp Ser Phe Ser Ile Phe Cys Glu Thr Gly Tyr Glu Leu Leu
305                 310                 315                 320
Gln Gly His Leu Pro Leu Lys Ser Phe Thr Ala Val Cys Gln Lys Asp
                325                 330                 335
Gly Ser Trp Asp Arg Pro Met Pro Ala Cys Ser Ile Val Asp Cys Gly
                340                 345                 350
Pro Pro Asp Asp Leu Pro Ser Gly Arg Val Glu Tyr Ile Thr Gly Pro
            355                 360                 365
Gly Val Thr Thr Tyr Lys Ala Val Ile Gln Tyr Ser Cys Glu Glu Thr
        370                 375                 380
Phe Tyr Thr Met Lys Val Asn Asp Gly Lys Tyr Val Cys Glu Ala Asp
385                 390                 395                 400
Gly Phe Trp Thr Ser Ser Lys Gly Glu Lys Ser Leu Pro Val Cys Glu
                405                 410                 415
Pro Val Cys Gly Leu Ser Ala Arg Thr Thr Gly Gly Arg Ile Tyr Gly
                420                 425                 430
Gly Gln Lys Ala Lys Pro Gly Asp Phe Pro Trp Gln Val Leu Ile Leu
        435                 440                 445
Gly Gly Thr Thr Ala Ala Gly Ala Leu Leu Tyr Asp Asn Trp Val Leu
    450                 455                 460
Thr Ala Ala His Ala Val Tyr Glu Gln Lys His Asp Ala Ser Ala Leu
465                 470                 475                 480
Asp Ile Arg Met Gly Thr Leu Lys Arg Leu Ser Pro His Tyr Thr Gln
                485                 490                 495
Ala Trp Ser Glu Ala Val Phe Ile His Glu Gly Tyr Thr His Asp Ala
                500                 505                 510
Gly Phe Asp Asn Asp Ile Ala Leu Ile Lys Leu Asn Asn Lys Val Val
            515                 520                 525
Ile Asn Ser Asn Ile Thr Pro Ile Cys Leu Pro Arg Lys Glu Ala Glu
530                 535                 540
```

| | | | | | | | | | | | | |
|---|---|---|---|---|---|---|---|---|---|---|---|---|
|Ser|Phe|Met|Arg|Thr|Asp|Asp|Ile|Gly|Thr|Ala|Ser|Gly|Trp|Gly|Leu|
|545| | | | |550| | | | |555| | | | |560|

Thr Gln Arg Gly Phe Leu Ala Arg Asn Leu Met Tyr Val Asp Ile Pro
              565                    570                    575

Ile Val Asp His Gln Lys Cys Thr Ala Ala Tyr Glu Lys Pro Pro Tyr
            580                    585                    590

Pro Arg Gly Ser Val Thr Ala Asn Met Leu Cys Ala Gly Leu Glu Ser
          595                    600                    605

Gly Gly Lys Asp Ser Cys Arg Gly Asp Ser Gly Ala Leu Val Phe
         610                    615                  620

Leu Asp Ser Glu Thr Glu Arg Trp Phe Val Gly Gly Ile Val Ser Trp
625                  630                    635                  640

Gly Ser Met Asn Cys Gly Glu Ala Gly Gln Tyr Gly Val Tyr Thr Lys
            645                    650                    655

Val Ile Asn Tyr Ile Pro Trp Ile Glu Asn Ile Ile Ser Asp Phe
         660                    665                  670

<210> SEQ ID NO 7
<211> LENGTH: 4900
<212> TYPE: DNA
<213> ORGANISM: Homo sapiens

<400> SEQUENCE: 7

```
cctgtcctgc ctgcctggaa ctctgagcag gctggagtca tggagtcgat tcccagaatc      60
ccagagtcag ggaggctggg ggcaggggca ggtcactgga caaacagatc aaaggtgaga     120
ccagcgtagg actgcagacc aggccaggcc agctggacgg gcacaccatg aggtaggtgg     180
gcgccacagc ctccctgcag ggtgtggggt gggagcacag gcctgggcct caccgcccct     240
gccctgccca taggctgctg accctcctgg gccttctgtg tggctcggtg gccaccccct     300
taggcccgaa gtggcctgaa cctgtgttcg ggcgcctggc atccccggc tttccagggg      360
agtatgccaa tgaccaggag cggcgctgga ccctgactgc acccccggc taccgcctgc      420
gcctctactt cacccacttc gacctggagc tctcccacct ctgcgagtac gacttcgtca     480
aggtgccgtc agacgggagg gctggggttt ctcagggtcg ggggtcccc aaggagtagc      540
cagggttcag ggacacctgg gagcagggc caggcttggc caggagggag atcaggcctg     600
ggtcttgcct tcactccctg tgacacctga ccccacagct gagctcgggg gccaaggtgc     660
tggccacgct gtgcgggcag gagagcacag acacggagcg ggcccctggc aaggacactt     720
tctactcgct gggctccagc ctggacatta ccttccgctc cgactactcc aacgagaagc     780
cgttcacggg gttcgaggcc ttctatgcag ccgagggtga gccaagaggg gtcctgcaac     840
atctcagtct cgcgcagctgg ctgtggggt aactctgtct taggccaggc agccctgcct    900
tcagtttccc caccttttccc agggcagggg agaggcctct ggcctgacat catccacaat    960
gcaaagacca aaacagccgt gacctccatt cacatgggct gagtgccaac tctgagccag   1020
ggatctgagg acagcatcgc ctcaagtgac gcagggactg gccgggcgcg gcagctcacg   1080
cctgtaattc cagcactttg ggaggccgag gctggcttga aatttgagg gtcaggagtt   1140
caaggccagc cagggcaaca cggtgaaact ctatctccac taaaactaca aaaattagct   1200
gggcgtggtg gtgcgcacct ggaatcccag ctactaggga ggctgaggca ggagaattgc   1260
ttgaacctgc gaggtggagg ctgcagtgaa cagagattgc accactacac tccacctggg   1320
cgacagacta gactccgtct caaaaaacaa aaacaaaaa ccacgcaggg ccgagggccc   1380
atttacaagc tgacaaagtg ggccctgcca gcgggagcgc tgcaggatgt ttgattttca   1440
```

```
gatcccagtc cctgcagaga ccaactgtgt gacctctggc aagtggctca atttctctgc    1500
tccttagaag ctgctgcaag ggttcagcgc tgtagccccg cccctgggt ttgattgact     1560 cccctcatta gctgggtgac ctcggccgga cactgaaact cccactggtt taacagaggt    1620
gatgtttgca tctttctccc agcgctgctg ggagcttgca gcgaccctag gcctgtaagg    1680
tgattggccc ggcaccagtc ccgcacccta gacaggacct aggcctcctc tgaggtccac    1740
tctgaggtca tggatctcct gggaggagtc caggctggat cccgcctctt tccctcctga    1800
cggcctgcct ggccctgcct ctcccccaga cattgacgag tgccaggtgg cccgggaga    1860 ggcgcccacc tgcgaccacc actgccacaa ccacctgggc ggtttctact gctcctgccg    1920
cgcaggctac gtcctgcacc gtaacaagcg cacctgctca ggtgagggag ctgcctggg    1980 ccccaacgca ccctctcctg ggatacccgg ggctcctcag ggccattgct gctctgccca    2040
ggggtgcgga gggcctgggc ctggacactg ggtgcttcta ggccctgctg cctccagctc    2100
cccttctcag ccctgcttcc cctctcagca gccaggctca tcagtgccac cctgccctag    2160
cactgagact aattctaaca tcccactgtg tacctggttc cacctgggct ctgggaaccc    2220
ctcatgtagc cacgggagag tcggggtatc taccctcgtt ccttggactg ggttcctgtt    2280
ccctgcactg ggggacgggc cagtgctctg gggcgtgggc agccccaccc tgtggcgctg    2340
accctgctcc cccgactcgg tttctcctct cggggtctct ccttgcctct ctgatctctc    2400
ttccagagca gagcctctag cctcccctgg agctccggct gcccagcagg tcagaagcca    2460
gagccaggct gctggcctca gctccgggtt gggctgagat gctgtgcccc aactcccatt    2520
cacccaccat ggacccaata taaacctggg ccccacccca cctgctgccg cgtgtctctg    2580
gggtgggagg gtcggggaggc ggtggggcgc gctcctctct gcctaccctc ctcacagcct    2640
catgaacccc aggtctgtgg gagcctcctc catggggcca cacggtcctt ggcctcaccc    2700
cctgttttga agatgggca ctgaggccgg agaggggtaa ggcctcgctc gagtccaggt     2760
ccccagaggc tgagcccaga gtaatcttga accacccca ttcagggtct ggcctggagg    2820
agcctgaccc acagaggaga caccctggga gatattcatt gaggggtaat ctggtccccc    2880
gcaaatccag gggtgattcc cactgcccca taggcacagc cacgtggaag aaggcaggca    2940 atgttgggc tcctcacttc ctagaggcct cacaactcaa atgcccccca ctgcagctgg    3000
gggtggggtg gtggtatggg atggggacca agccttcctt gaaggataga gcccagccca    3060
acaccccgcc ccgtggcagc agcatcacgt gttccagcga ggaaggagag caccagactc    3120
agtcatgatc actgttgcct tgaacttcca agaacagccc cagggcaagg gtcaaaacag    3180
gggaaagggg gtgatgagag atccttcttc cggatgttcc tccaggaacc agggggctgg    3240
ctggtcttgg ctgggttcgg gtaggagacc catgatgaat aaacttggga atcactgggg    3300
tggctgtaag ggaatttagg ggagctccga aggggccctt aggctcgagg agatgctcct    3360
ctcttttccc gaattcccag ggacccagga gagtgtccct tcttcctctt cctgtgtgtc    3420
catccacccc cgcccccgc cctggcagag ctggtggaac tcagtgctct agcccctacc     3480
ctggggttgc gactctggct caggacacca ccacgctccc tgggggtgtg agtgagggcc    3540
tgtgcgctcc atcccgagtg ctgcctgttt cagctaaagc ctcaaagcaa gagaaacccc    3600
ctctctaagc ggcccctcag ccatcgggtg ggtcgtttgg tttctgggta ggcctcaggg    3660
gctggccacc tgcagggccc agcccaaccc agggatgcag atgtcccagc cacatccctg    3720
tcccagtttc ctgctcccca aggcatccac cctgctgttg gtgcgagggc tgatagaggg    3780
```

```
cacgccaagt cactcccctg cccttccctc cttccagccc tgtgctccgg ccaggtcttc    3840
acccagaggt ctggggagct cagcagccct gaatacccac ggccgtatcc caaactctcc    3900
agttgcactt acagcatcag cctggaggag gggttcagtg tcattctgga ctttgtggag    3960
tccttcgatg tggagacaca ccctgaaacc ctgtgtccct acgactttct caaggtctgg    4020
ctcctgggcc cctcatcttg tccccagatcc tcccccttca gcccagctgc accccctact    4080
tcctgcagca tggcccccac cacgttcccg tcaccctcgg tgaccccacc tcttcaggtg    4140
ctctatggag gtcaaggctg gggcttcgag tacaagtgtg ggaggcagag tggggagggg    4200
caccccaatc catggcctgg gttggcctca ttggctgtcc ctgaaatgct gaggaggtgg    4260
gttacttccc tccgcccagg ccagacccag gcagctgctc cccagctttc atgagcttct    4320
ttctcagatt caaacagaca gagaagaaca tgcccattc tgtgggaaga cattgcccca    4380
caggattgaa acaaaaagca acacggtgac catcacctttt gtcacagatg aatcaggaga    4440
ccacacaggc tggaagatcc actacacgag cacagtgagc aagtgggctc agatccttgg    4500
tggaagcgca gagctgcctc tctctggagt gcaaggagct gtagagtgta gggctcttct    4560
gggcaggact aggaagggac accaggtta gtggtgctga ggtctgaggc agcagcttct    4620
aaggggaagc acccgtgccc tcctcagcag cacccagcat cttcaccact cattcttcaa    4680
ccacccattc acccatcact catctttttac ccacccaccc tttgccactc atccttctgt    4740
ccctcatcct tccaaccatt catcaatcac ccacccatcc atcctttgcc acacaaccat    4800
ccacccattc ttctacctac ccatcctatc catccatcct tctatcagca tccttctacc    4860
acccatcctt cgttcggtca tccatcatca tccatccatc                          4900

<210> SEQ ID NO 8
<211> LENGTH: 136
<212> TYPE: PRT
<213> ORGANISM: Homo sapiens

<400> SEQUENCE: 8

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala
    130                 135

<210> SEQ ID NO 9
<211> LENGTH: 181
<212> TYPE: PRT
<213> ORGANISM: Homo sapiens
```

<400> SEQUENCE: 9

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser
            180
```

<210> SEQ ID NO 10
<211> LENGTH: 293
<212> TYPE: PRT
<213> ORGANISM: Homo sapiens

<400> SEQUENCE: 10

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175
```

```
Lys Arg Thr Cys Ser Ala Leu Cys Ser Gly Gln Val Phe Thr Gln Arg
                180                 185                 190

Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
                275                 280                 285

Trp Lys Ile His Tyr
            290

<210> SEQ ID NO 11
<211> LENGTH: 41
<212> TYPE: PRT
<213> ORGANISM: Homo sapiens

<400> SEQUENCE: 11

Glu Asp Ile Asp Glu Cys Gln Val Ala Pro Gly Glu Ala Pro Thr Cys
1               5                   10                  15

Asp His His Cys His Asn Leu Gly Gly Phe Tyr Cys Ser Cys Arg
                20                  25                  30

Ala Gly Tyr Val Leu His Arg Asn Lys
            35                  40

<210> SEQ ID NO 12
<211> LENGTH: 242
<212> TYPE: PRT
<213> ORGANISM: Homo sapiens

<400> SEQUENCE: 12

Ile Tyr Gly Gly Gln Lys Ala Lys Pro Gly Asp Phe Pro Trp Gln Val
1               5                   10                  15

Leu Ile Leu Gly Gly Thr Thr Ala Ala Gly Ala Leu Leu Tyr Asp Asn
                20                  25                  30

Trp Val Leu Thr Ala Ala His Ala Val Tyr Glu Gln Lys His Asp Ala
            35                  40                  45

Ser Ala Leu Asp Ile Arg Met Gly Thr Leu Lys Arg Leu Ser Pro His
50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
                85                  90                  95

Lys Val Val Ile Asn Ser Asn Ile Thr Pro Ile Cys Leu Pro Arg Lys
            100                 105                 110

Glu Ala Glu Ser Phe Met Arg Thr Asp Asp Ile Gly Thr Ala Ser Gly
            115                 120                 125

Trp Gly Leu Thr Gln Arg Gly Phe Leu Ala Arg Asn Leu Met Tyr Val
        130                 135                 140

Asp Ile Pro Ile Val Asp His Gln Lys Cys Thr Ala Ala Tyr Glu Lys
145                 150                 155                 160
```

-continued

Pro Pro Tyr Pro Arg Gly Ser Val Thr Ala Asn Met Leu Cys Ala Gly
              165                 170                 175

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
        195                 200                 205

Val Ser Trp Gly Ser Met Asn Cys Gly Glu Ala Gly Gln Tyr Gly Val
    210                 215                 220

Tyr Thr Lys Val Ile Asn Tyr Ile Pro Trp Ile Glu Asn Ile Ile Ser
225                 230                 235                 240

Asp Phe

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Gly Lys Asp Ser Cys Arg Gly Asp Ala Gly Gly Ala Leu Val Phe Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Thr Pro Leu Gly Pro Lys Trp Pro Glu Pro Val Phe Gly Arg Leu
1               5                   10                  15

<210> SEQ ID NO 15
<211> LENGTH: 43
<212> TYPE: PRT
<213> ORGANISM: Artificial Sequence
<220> FEATURE:
<223> OTHER INFORMATION: Synthetic

<400> SEQUENCE: 15

Thr Ala Pro Pro Gly Tyr Arg Leu Arg Leu Tyr Phe Thr His Phe Asp
1               5                   10                  15

Leu Glu Leu Ser His Leu Cys Glu Tyr Asp Phe Val Lys Leu Ser Ser
            20                  25                  30

Gly Ala Lys Val Leu Ala Thr Leu Cys Gly Gln
            35                  40

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Thr Phe Arg Ser Asp Tyr Ser Asn
1               5

<210> SEQ ID NO 17
<211> LENGTH: 25
<212> TYPE: PRT

-continued

```
<213> ORGANISM: Artificial Sequence
<220> FEATURE:
<223> OTHER INFORMATION: Synthetic

<400> SEQUENCE: 17

Phe Tyr Ser Leu Gly Ser Ser Leu Asp Ile Thr Phe Arg Ser Asp Tyr
1               5                   10                  15

Ser Asn Glu Lys Pro Phe Thr Gly Phe
            20                  25

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ile Asp Glu Cys Gln Val Ala Pro Gly
1               5

<210> SEQ ID NO 19
<211> LENGTH: 25
<212> TYPE: PRT
<213> ORGANISM: Artificial Sequence
<220> FEATURE:
<223> OTHER INFORMATION: Synthetic

<400> SEQUENCE: 19

Ala Asn Met Leu Cys Ala Gly Leu Glu Ser Gly Gly Lys Asp Ser Cys
1               5                   10                  15

Arg Gly Asp Ser Gly Gly Ala Leu Val
            20                  25

<210> SEQ ID NO 20
<211> LENGTH: 960
<212> TYPE: DNA
<213> ORGANISM: Homo sapiens
<220> FEATURE:
<221> NAME/KEY: CDS
<222> LOCATION: (51)..(797)

<400> SEQUENCE: 20
attaactgag attaaccttc cctgagtttt ctcacaccaa ggtgaggacc atg tcc      56
                                                         Met Ser
                                                         1 ctg ttt cca tca ctc cct ctc ctt ctc ctg agt atg gtg gca gcg tct  104
Leu Phe Pro Ser Leu Pro Leu Leu Leu Leu Ser Met Val Ala Ala Ser
        5                   10                  15 tac tca gaa act gtg acc tgt gag gat gcc caa aag acc tgc cct gca  152
Tyr Ser Glu Thr Val Thr Cys Glu Asp Ala Gln Lys Thr Cys Pro Ala
    20                  25                  30 gtg att gcc tgt agc tct cca ggc atc aac ggc ttc cca ggc aaa gat  200
Val Ile Ala Cys Ser Ser Pro Gly Ile Asn Gly Phe Pro Gly Lys Asp
35                  40                  45                  50 ggg cgt gat ggc acc aag gga gaa aag ggg gaa cca ggc caa ggg ctc  248
Gly Arg Asp Gly Thr Lys Gly Glu Lys Gly Glu Pro Gly Gln Gly Leu
                55                  60                  65 aga ggc tta cag ggc ccc cct gga aag ttg ggg cct cca gga aat cca  296
Arg Gly Leu Gln Gly Pro Pro Gly Lys Leu Gly Pro Pro Gly Asn Pro
            70                  75                  80 ggg cct tct ggg tca cca gga cca aag ggc caa aaa gga gac cct gga  344
Gly Pro Ser Gly Ser Pro Gly Pro Lys Gly Gln Lys Gly Asp Pro Gly
        85                  90                  95
```

| | | | | | | | | | | | | | | |
|---|---|---|---|---|---|---|---|---|---|---|---|---|---|---|
| aaa | agt | ccg | gat | ggt | gat | agt | agc | ctg | gct | gcc | tca | gaa | aga | aaa | gct | 392 |
| Lys | Ser | Pro | Asp | Gly | Asp | Ser | Ser | Leu | Ala | Ala | Ser | Glu | Arg | Lys | Ala |
| | 100 | | | | 105 | | | | 110 | | | | | | |

```
aaa agt ccg gat ggt gat agt agc ctg gct gcc tca gaa aga aaa gct      392
Lys Ser Pro Asp Gly Asp Ser Ser Leu Ala Ala Ser Glu Arg Lys Ala
    100                 105                 110 ctg caa aca gaa atg gca cgt atc aaa aag tgg ctc acc ttc tct ctg      440
Leu Gln Thr Glu Met Ala Arg Ile Lys Lys Trp Leu Thr Phe Ser Leu
115                 120                 125                 130 ggc aaa caa gtt ggg aac aag ttc ttc ctg acc aat ggt gaa ata atg      488
Gly Lys Gln Val Gly Asn Lys Phe Phe Leu Thr Asn Gly Glu Ile Met
                135                 140                 145 acc ttt gaa aaa gtg aag gcc ttg tgt gtc aag ttc cag gcc tct gtg      536
Thr Phe Glu Lys Val Lys Ala Leu Cys Val Lys Phe Gln Ala Ser Val
            150                 155                 160 gcc acc ccc agg aat gct gca gag aat gga gcc att cag aat ctc atc      584
Ala Thr Pro Arg Asn Ala Ala Glu Asn Gly Ala Ile Gln Asn Leu Ile
        165                 170                 175 aag gag gaa gcc ttc ctg ggc atc act gat gag aag aca gaa ggg cag      632
Lys Glu Glu Ala Phe Leu Gly Ile Thr Asp Glu Lys Thr Glu Gly Gln
    180                 185                 190 ttt gtg gat ctg aca gga aat aga ctg acc tac aca aac tgg aac gag      680
Phe Val Asp Leu Thr Gly Asn Arg Leu Thr Tyr Thr Asn Trp Asn Glu
195                 200                 205                 210 ggt gaa ccc aac aat gct ggt tct gat gaa gat tgt gta ttg cta ctg      728
Gly Glu Pro Asn Asn Ala Gly Ser Asp Glu Asp Cys Val Leu Leu Leu
                215                 220                 225 aaa aat ggc cag tgg aat gac gtc ccc tgc tcc acc tcc cat ctg gcc      776
Lys Asn Gly Gln Trp Asn Asp Val Pro Cys Ser Thr Ser His Leu Ala
            230                 235                 240 gtc tgt gag ttc cct atc tga agggtcatat cactcaggcc ctccttgtct        827
Val Cys Glu Phe Pro Ile
            245 ttttactgca acccacaggc ccacagtatg cttgaaaaga taaattatat caatttcctc    887 atatccagta ttgttccttt tgtgggcaat cactaaaaat gatcactaac agcaccaaca    947 aagcaataat agt                                                       960

<210> SEQ ID NO 21
<211> LENGTH: 248
<212> TYPE: PRT
<213> ORGANISM: Homo sapiens

<400> SEQUENCE: 21

Met Ser Leu Phe Pro Ser Leu Pro Leu Leu Leu Ser Met Val Ala
1               5                   10                  15

Ala Ser Tyr Ser Glu Thr Val Thr Cys Glu Asp Ala Gln Lys Thr Cys
                20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
        50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125
```

-continued

```
Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 represents
      hydroxyproline
<220> FEATURE:
<221> NAME/KEY: MISC_FEATURE
<222> LOCATION: (4)..(4)
<223> OTHER INFORMATION: Wherein X at position 4 represents hydrophobic
      residue

<400> SEQUENCE: 22

Xaa Gly Lys Xaa Gly Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X represents hydroxyproline

<400> SEQUENCE: 23

Xaa Gly Lys Leu Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(15)
<223> OTHER INFORMATION: Wherein X at positions 9 and 15 represents
      hydroxyproline

<400> SEQUENCE: 24
```

```
Gly Leu Arg Gly Leu Gln Gly Pro Xaa Gly Lys Leu Gly Pro Xaa Gly
1               5                   10                  15

<210> SEQ ID NO 25
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(27)
<223> OTHER INFORMATION: Wherein X at positions 3, 6, 15, 21, 24, 27
      represents hydroxyproline

<400> SEQUENCE: 25

Gly Pro Xaa Gly Pro Xaa Gly Leu Arg Gly Leu Gln Gly Pro Xaa Gly
1               5                   10                  15

Lys Leu Gly Pro Xaa Gly Pro Xaa Gly Pro Xaa
            20                  25

<210> SEQ ID NO 26
<211> LENGTH: 53
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 26

Gly Lys Asp Gly Arg Asp Gly Thr Lys Gly Glu Lys Gly Glu Pro Gly
1               5                   10                  15

Gln Gly Leu Arg Gly Leu Gln Gly Pro Xaa Gly Lys Leu Gly Pro Xaa
            20                  25                  30

Gly Asn Xaa Gly Pro Ser Gly Ser Xaa Gly Pro Lys Gly Gln Lys Gly
        35                  40                  45

Asp Xaa Gly Lys Ser
    50

<210> SEQ ID NO 27
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(33)
<223> OTHER INFORMATION: Wherein X at positions 3, 6, 12, 18, 21, 30, 33
      represents hydroxyproline
```

```
<400> SEQUENCE: 27

Gly Ala Xaa Gly Ser Xaa Gly Glu Lys Gly Ala Xaa Gly Pro Gln Gly
1               5                   10                  15

Pro Xaa Gly Pro Xaa Gly Lys Met Gly Pro Lys Gly Glu Xaa Gly Asp
            20                  25                  30

Xaa

<210> SEQ ID NO 28
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(45)
<223> OTHER INFORMATION: Wherein X at positions 3, 6, 9, 27, 30, 36, 42,
      45 represents hydroxyproline

<400> SEQUENCE: 28

Gly Cys Xaa Gly Leu Xaa Gly Ala Xaa Gly Asp Lys Gly Glu Ala Gly
1               5                   10                  15

Thr Asn Gly Lys Arg Gly Glu Arg Gly Pro Xaa Gly Pro Xaa Gly Lys
            20                  25                  30

Ala Gly Pro Xaa Gly Pro Asn Gly Ala Xaa Gly Glu Xaa
            35                  40                  45

<210> SEQ ID NO 29
<211> LENGTH: 24
<212> TYPE: PRT
<213> ORGANISM: Artificial Sequence
<220> FEATURE:
<223> OTHER INFORMATION: Synthetic

<400> SEQUENCE: 29

Leu Gln Arg Ala Leu Glu Ile Leu Pro Asn Arg Val Thr Ile Lys Ala
1               5                   10                  15

Asn Arg Pro Phe Leu Val Phe Ile
            20

<210> SEQ ID NO 30
<211> LENGTH: 559
<212> TYPE: DNA
<213> ORGANISM: Homo sapiens

<400> SEQUENCE: 30
atgaggctgc tgaccctcct gggccttctg tgtggctcgg tggccacccc cttgggcccg      60
aagtggcctg aacctgtgtt cgggcgcctg catccccccg gctttccagg ggagtatgcc     120
aatgaccagg agcggcgctg gaccctgact gcaccccccg gctaccgcct gcgcctctac     180
ttcacccact cgacctgga gctctcccac ctctgcgagt acgacttcgt caagctgagc     240
tcggggccca aggtgctggc cacgtgtgc gggcaggaga gcacagacac ggagcgggcc     300
cctggcaagg acactttcta ctcgctgggc tccagcctgg acattacctt ccgctccgac     360
tactccaacg agaagccgtt cacggggttc gaggccttct atgcagccga ggacattgac     420
gagtgccagg tggccccggg agaggcgccc acctgcgacc accactgcca caaccacctg     480
ggcggtttct actgctccct ccgcgcaggc tacgtcctgc accgtaacaa cgcgcacctg     540
tcagccctgt gctccggcc                                                 559
```

```
<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
cgggcacacc atgaggctgc tgaccctcct gggc                              34

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
gacattacct tccgctccga ctccaacgag aag                               33

<210> SEQ ID NO 33
<211> LENGTH: 33
<212> TYPE: DNA
<213> ORGANISM: Artificial Sequence
<220> FEATURE:
<223> OTHER INFORMATION: Synthetic

<400> SEQUENCE: 33
agcagccctg aatacccacg gccgtatccc aaa                               33

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
cgggatccat gaggctgctg accctc                                      26

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ggaattccta ggctgcata                                              19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
ggaattccta cagggcgct                                              19

<210> SEQ ID NO 37
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 37
ggaattccta gtagtggat                                                    19

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
tgcggccgct gtaggtgctg tcttt                                             25

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ggaattcact cgttattctc gga                                               23

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
tccgagaata acgagtg                                                      17

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
cattgaaagc tttggggtag aagttgttc                                         29

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
cgcggccgca gctgctcaga gtgtaga                                           27

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
cggtaagctt cactggctca gggaaata                                          28

<210> SEQ ID NO 44
<211> LENGTH: 37
```

```
<212> TYPE: DNA
<213> ORGANISM: Artificial Sequence
<220> FEATURE:
<223> OTHER INFORMATION: Synthetic

<400> SEQUENCE: 44
aagaagcttg ccgccaccat ggattggctg tggaact                              37

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
cgggatcctc aaactttctt gtccaccttg g                                    31

<210> SEQ ID NO 46
<211> LENGTH: 36
<212> TYPE: DNA
<213> ORGANISM: Artificial Sequence
<220> FEATURE:
<223> OTHER INFORMATION: Synthetic

<400> SEQUENCE: 46
aagaaagctt gccgccacca tgttctcact agctct                               36

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
cgggatcctt ctccctctaa cactct                                          26

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Glu Pro Lys Ser Cys Asp Lys Thr His
1               5

<210> SEQ ID NO 49
<211> LENGTH: 4960
<212> TYPE: DNA
<213> ORGANISM: Homo Sapiens

<400> SEQUENCE: 49
ccggacgtgg tggcgcatgc ctgtaatccc agctactcgg gaggctgagg caggagaatt     60
gctcgaaccc cggaggcaga ggtttggtgg ctcacacctg taatcccagc actttgcgag    120
gctgaggcag gtgcatcgct ttggctcagg agttcaagac cagcctgggc aacacaggga    180
gacccccatc tctacaaaaa acaaaaacaa atataaaggg gataaaaaaa aaaaaaagac    240
aagacatgaa tccatgagga cagagtgtgg aagaggaagc agcagcctca aagttctgga    300
agctggaaga acagataaac aggtgtgaaa taactgcctg gaaagcaact tctttttttt    360 ttttttttt tttgaggtgg agtctcactc tgtcgtccag gctggagtgc agtggtgcga    420
```

-continued

```
tctcggatca ctgcaacctc cgcctcccag gctcaagcaa ttctcctgcc tcagcctccc      480
gagtagctgg gattataagt gcgcgctgcc acacctggat gattttttgta tttttagtag     540
agatgggatt tcaccatgtt ggtcaggctg gtctcaaact cccaacctcg tgatccaccc      600
accttggcct cccaaagtgc tgggattaca ggtataagcc accgagccca gccaaaagcg      660
acttctaagc ctgcaaggga atcgggaatt ggtggcacca ggtccttctg acagggttta     720
agaaattagc cagcctgagg ctgggcacgg tggctcacac ctgtaatccc agcactttgg     780
gaggctaagg caggtggatc acctgagggc aggagttcaa gaccagcctg accaacatgg     840
agaaacccca tccctaccaa aaataaaaaa ttagccaggt gtggtggtgc tcgcctgtaa     900
tcccagctac ttgggaggct gaggtgggag gattgcttga acacaggaag tagaggctgc     960
agtgagctat gattgcagca ctgcactgaa gccggggcaa cagaacaaga tccaaaaaaa    1020
agggagggggt gaggggcaga gccaggattt gtttccaggc tgttgttacc taggtccgac    1080
tcctggctcc cagagcagcc tgtcctgcct gctggaact ctgagcaggc tggagtcatg     1140
gagtcgattc ccagaatccc agagtcaggg aggctggggg caggggcagg tcactggaca    1200
aacagatcaa aggtgagacc agcgtagggc tgcagaccag gccaggccag ctggacgggc    1260
acaccatgag gtaggtgggc gcccacagcc tccctgcagg gtgtggggtg ggagcacagg    1320
cctgggccct caccgcccct gccctgccca taggctgctg accctcctgg gccttctgtg    1380
tggctcggtg gccacccct tgggcccgaa gtggcctgaa cctgtgttcg ggcgcctggc      1440
atccccggc tttccagggg agtatgccaa tgaccaggag cggcgctgga ccctgactgc      1500
accccccggc taccgcctgc gcctctactt cacccacttc gacctggagc tctcccacct    1560
ctgcgagtac gacttcgtca aggtgccgtc aggacgggag ggctgggggtt tctcagggtc    1620
gggggggtccc caaggagtag ccagggttca gggacacctg ggagcagggg ccaggcttgg    1680
ccaggaggga gatcaggcct gggtcttgcc ttcactccct gtgacacctg accccacagc    1740
tgagctcggg ggccaaggtg ctggccacgc tgtgcgggca ggagagcaca gacacggagc    1800
gggcccctgg caaggacact ttctactcgc tgggctccag cctggacatt accttccgct    1860
ccgactactc caacgagaag ccgttcacgg ggttcgaggc cttctatgca gccgagggtg    1920
agccaagagg ggtcctgcaa catctcagtc tgcgcagctg gctgtggggg taactctgtc    1980
ttaggccagg cagccctgcc ttcagtttcc ccacctttcc cagggcaggg gagaggcctc    2040
tggcctgaca tcatccacaa tgcaaagacc aaaacagccg tgacctccat tcacatgggc    2100
tgagtgccaa ctctgagcca gggatctgag gacagcatcg cctcaagtga cgcagggact    2160
ggccgggcgc agcagctcac gcctgtaatt ccagcacttt gggaggccga ggctggctga    2220
tcatttgagg tcaggagttc aaggccagcc agggcaacac ggtgaaactc tatctccact    2280
aaaactacaa aaattagctg ggcgtggtgg tgcgcacctg gaatcccagc tactagggag    2340
gctgaggcag gagaattgct tgaacctgcg aggtggaggc tgcagtgaac agagattgca    2400
ccactacact ccagcctggg cgacagagct agactccgtc tcaaaaaaca aaaaacaaaa    2460
acgacgcagg ggccgagggc cccatttaca gctgacaaag tggggccctg ccagcgggag    2520
cgctgccagg atgtttgatt tcagatccca gtccctgcag agaccaactg tgtgacctct    2580
ggcaagtggc tcaatttctc tgctccttag gaagctgctg caagggttca gcgctgtagc    2640
cccgccccct gggtttgatt gactcccctc attagctggg tgacctcggg ccggacactg    2700
aaactcccac tggtttaaca gaggtgatgt ttgcatcttt ctcccagcgc tgctgggagc    2760
```

```
ttgcagcgac cctaggcctg taaggtgatt ggcccggcac cagtcccgca ccctagacag    2820
gacgaggcct cctctgaggt ccactctgag gtcatggatc tcctgggagg agtccaggct    2880
ggatcccgcc tctttccctc ctgacggcct gcctggccct gcctctcccc cagacattga    2940
cgagtgccag gtggcccgg gagaggcgcc cacctgcgac caccactgcc acaaccacct    3000
gggcggtttc tactgctcct gccgcgcagg ctacgtcctg caccgtaaca agcgcacctg    3060
ctcagccctg tgctccggcc aggtcttcac ccagaggtct ggggagctca gcagccctga    3120 ataccacgg ccgtatccca aactctccag ttgcacttac agcatcagcc tggaggaggg    3180
gttcagtgtc attctggact tgtggagtc cttcgatgtg gagacacacc ctgaaaccct    3240
gtgtccctac gactttctca agattcaaac agacagagaa gaacatggcc cattctgtgg    3300
gaagacattg ccccacagga ttgaaacaaa aagcaacacg gtgaccatca cctttgtcac    3360
agatgaatca ggagaccaca caggctggaa gatccactac acgagcacag cgcacgcttg    3420
cccttatccg atggcgccac ctaatggcca cgtttcacct gtgcaagcca aatacatcct    3480
gaaagacagc ttctccatct tttgcgagac tggctatgag cttctgcaag gtcacttgcc    3540
cctgaaatcc tttactgcag tttgtcagaa agatggatct tgggaccggc caatgcccgc    3600
gtgcagcatt gttgactgtg gccctcctga tgatctaccc agtggccgag tggagtacat    3660
cacaggtcct ggagtgacca cctacaaagc tgtgattcag tacagctgtg aagagacctt    3720
ctacacaatg aaagtgaatg atggtaaata tgtgtgtgag gctgatggat tctggacgag    3780
ctccaaagga gaaaaatcac tcccagtctg tgagcctgtt tgtggactat cagcccgcac    3840
aacaggaggg cgtatatatg gagggcaaaa ggcaaaacct ggtgattttc cttggcaagt    3900
cctgatatta ggtggaacca cagcagcagg tgcacttttta tatgacaact gggtcctaac    3960
agctgctcat gccgtctatg agcaaaaaca tgatgcatcc gccctggaca ttcgaatggg    4020
caccctgaaa agactatcac ctcattatac acaagcctgg tctgaagctg tttttataca    4080
tgaaggttat actcatgatg ctggctttga caatgacata gcactgatta aattgaataa    4140
caaagttgta atcaatagca acatcacgcc tatttgtctg ccaagaaaag aagctgaatc    4200
ctttatgagg acagatgaca ttggaactgc atctggatgg ggattaaccc aaagggggttt    4260 tcttgctaga aatctaatgt atgtcgacat accgattgtt gaccatcaaa aatgtactgc    4320
tgcatatgaa aagccaccct atccaagggg aagtgtaact gctaacatgc tttgtgctgg    4380
cttagaaagt gggggcaagg acagctgcag aggtgacagc ggaggggcac tggtgtttct    4440
agatagtgaa acagagaggt ggtttgtggg aggaatagtg tcctggggtt ccatgaattg    4500 tgggaagca ggtcagtatg gagtctacac aaaagttatt aactatattc cctggatcga    4560
gaacataatt agtgattttt aacttgcgtg tctgcagtca aggattcttc atttttagaa    4620
atgcctgtga agaccttggc agcgacgtgg ctcgagaagc attcatcatt actgtggaca    4680
tggcagttgt tgctccaccc aaaaaaacag actccaggtg aggctgctgt catttctcca    4740
cttgccagtt taattccagc cttacccatt gactcaaggg gacataaacc acgagagtga    4800
cagtcatctt tgcccaccca gtgtaatgtc actgctcaaa ttacatttca ttaccttaaa    4860
aagccagtct ctttcatac tggctgttgg catttctgta aactgcctgt ccatgctctt    4920
tgtttttaaa cttgttctta ttgaaaaaaa aaaaaaaaa                           4960

<210> SEQ ID NO 50
<211> LENGTH: 2090
<212> TYPE: DNA
<213> ORGANISM: Murine
```

```
<220> FEATURE:
<221> NAME/KEY: CDS
<222> LOCATION: (33)..(2090)

<400> SEQUENCE: 50
ggcgctggac tgcagagcta tggtggcaca cc atg agg cta ctc atc ttc ctg           53
                                    Met Arg Leu Leu Ile Phe Leu
                                    1               5 ggt ctg ctg tgg agt ttg gtg gcc aca ctt ctg ggt tca aag tgg cct          101
Gly Leu Leu Trp Ser Leu Val Ala Thr Leu Leu Gly Ser Lys Trp Pro
        10                  15                  20 gaa cct gta ttc ggg cgc ctg gtg tcc cct ggc ttc cca gag aag tat          149
Glu Pro Val Phe Gly Arg Leu Val Ser Pro Gly Phe Pro Glu Lys Tyr
    25                  30                  35 gct gac cat caa gat cga tcc tgg aca ctg act gca ccc cct ggc tac          197
Ala Asp His Gln Asp Arg Ser Trp Thr Leu Thr Ala Pro Pro Gly Tyr
40                  45                  50                  55 cgc ctg cgc ctc tac ttc acc cac ttt gac ctg gaa ctc tct tac cgc          245
Arg Leu Arg Leu Tyr Phe Thr His Phe Asp Leu Glu Leu Ser Tyr Arg
                60                  65                  70 tgc gag tat gac ttt gtc aag ttg agc tca ggg acc aag gtg ctg gcc          293
Cys Glu Tyr Asp Phe Val Lys Leu Ser Ser Gly Thr Lys Val Leu Ala
            75                  80                  85 aca ctg tgt ggg cag gag agt aca gac act gag cag gca cct ggc aat          341
Thr Leu Cys Gly Gln Glu Ser Thr Asp Thr Glu Gln Ala Pro Gly Asn
        90                  95                 100 gac acc ttc tac tca ctg ggt ccc agc cta aag gtc acc ttc cac tcc          389
Asp Thr Phe Tyr Ser Leu Gly Pro Ser Leu Lys Val Thr Phe His Ser
    105                 110                 115 gac tac tcc aat gag aag ccg ttc aca ggg ttt gag gcc ttc tat gca          437
Asp Tyr Ser Asn Glu Lys Pro Phe Thr Gly Phe Glu Ala Phe Tyr Ala
120                 125                 130                 135 gcg gag gat gtg gat gaa tgc aga gtg tct ctg gga gac tca gtc cct          485
Ala Glu Asp Val Asp Glu Cys Arg Val Ser Leu Gly Asp Ser Val Pro
                140                 145                 150 tgt gac cat tat tgc cac aac tac ttg ggc ggc tac tat tgc tcc tgc          533
Cys Asp His Tyr Cys His Asn Tyr Leu Gly Gly Tyr Tyr Cys Ser Cys
            155                 160                 165 aga gcg ggc tac att ctc cac cag aac aag cac acg tgc tca gcc ctt          581
Arg Ala Gly Tyr Ile Leu His Gln Asn Lys His Thr Cys Ser Ala Leu
        170                 175                 180 tgt tca ggc cag gtg ttc aca gga aga tct ggg tat ctc agt agc cct          629
Cys Ser Gly Gln Val Phe Thr Gly Arg Ser Gly Tyr Leu Ser Ser Pro
    185                 190                 195 gag tac ccg cag cca tac ccc aag ctc tcc agc tgc acc tac agc atc          677
Glu Tyr Pro Gln Pro Tyr Pro Lys Leu Ser Ser Cys Thr Tyr Ser Ile
200                 205                 210                 215 cgc ctg gag gac ggc ttc agt gtc atc ctg gac ttc gtg gag tcc ttc          725
Arg Leu Glu Asp Gly Phe Ser Val Ile Leu Asp Phe Val Glu Ser Phe
                220                 225                 230 gat gtg gag acg cac cct gaa gcc cag tgc ccc tat gac tcc ctc aag          773
Asp Val Glu Thr His Pro Glu Ala Gln Cys Pro Tyr Asp Ser Leu Lys
            235                 240                 245 att caa aca gac aag ggg gaa cac gga cca ttt tgt ggg aag acg ctg          821
Ile Gln Thr Asp Lys Gly Glu His Gly Pro Phe Cys Gly Lys Thr Leu
        250                 255                 260 cct ccc agg att gaa act gac agc cac aag gtg acc atc acc ttt gcc          869
Pro Pro Arg Ile Glu Thr Asp Ser His Lys Val Thr Ile Thr Phe Ala
    265                 270                 275 act gac gag tcg ggg aac cac aca ggc tgg aag ata cac tac aca agc          917
Thr Asp Glu Ser Gly Asn His Thr Gly Trp Lys Ile His Tyr Thr Ser
```

```
                Thr Asp Glu Ser Gly Asn His Thr Gly Trp Lys Ile His Tyr Thr Ser
                280                 285                 290                 295 aca gca cgg ccc tgc cct gat cca acg gcg cca cct aat ggc agc att          965
Thr Ala Arg Pro Cys Pro Asp Pro Thr Ala Pro Pro Asn Gly Ser Ile
                        300                 305                 310 tca cct gtg caa gcc acg tat gtc ctg aag gac agg ttt tct gtc ttc         1013
Ser Pro Val Gln Ala Thr Tyr Val Leu Lys Asp Arg Phe Ser Val Phe
                315                 320                 325 tgc aag aca ggc ttc gag ctt ctg caa ggt tct gtc ccc ctg aaa tca         1061
Cys Lys Thr Gly Phe Glu Leu Leu Gln Gly Ser Val Pro Leu Lys Ser
            330                 335                 340 ttc act gct gtc tgt cag aaa gat gga tct tgg gac cgg ccg atg cca         1109
Phe Thr Ala Val Cys Gln Lys Asp Gly Ser Trp Asp Arg Pro Met Pro
        345                 350                 355 gag tgc agc att att gat tgt ggc cct ccc gat gac cta ccc aat ggc         1157
Glu Cys Ser Ile Ile Asp Cys Gly Pro Pro Asp Asp Leu Pro Asn Gly
360                 365                 370                 375 cat gtg gac tat atc aca ggc cct caa gtg act acc tac aaa gct gtg         1205
His Val Asp Tyr Ile Thr Gly Pro Gln Val Thr Thr Tyr Lys Ala Val
                380                 385                 390 att cag tac agc tgt gaa gag act ttc tac aca atg agc agc aat ggt         1253
Ile Gln Tyr Ser Cys Glu Glu Thr Phe Tyr Thr Met Ser Ser Asn Gly
            395                 400                 405 aaa tat gtg tgt gag gct gat gga ttc tgg acg agc tcc aaa gga gaa         1301
Lys Tyr Val Cys Glu Ala Asp Gly Phe Trp Thr Ser Ser Lys Gly Glu
        410                 415                 420 aaa ctc ccc ccg gtt tgt gag cct gtt tgt ggg ctg tcc aca cac act         1349
Lys Leu Pro Pro Val Cys Glu Pro Val Cys Gly Leu Ser Thr His Thr
425                 430                 435 ata gga gga cgc ata gtt gga ggg cag cct gca aag cct ggt gac ttt         1397
Ile Gly Gly Arg Ile Val Gly Gly Gln Pro Ala Lys Pro Gly Asp Phe
440                 445                 450                 455 cct tgg caa gtc ttg ttg ctg ggt caa act aca gca gca gct ggt gca         1445
Pro Trp Gln Val Leu Leu Leu Gly Gln Thr Thr Ala Ala Ala Gly Ala
                460                 465                 470 ctt ata cat gac aat tgg gtc cta aca gcc gct cat gct gta tat gag         1493
Leu Ile His Asp Asn Trp Val Leu Thr Ala Ala His Ala Val Tyr Glu
            475                 480                 485 aaa aga atg gca gcg tcc tcc ctg aac atc cga atg ggc atc ctc aaa         1541
Lys Arg Met Ala Ala Ser Ser Leu Asn Ile Arg Met Gly Ile Leu Lys
        490                 495                 500 agg ctc tca cct cat tac act caa gcc tgg ccc gag gaa atc ttt ata         1589
Arg Leu Ser Pro His Tyr Thr Gln Ala Trp Pro Glu Glu Ile Phe Ile
505                 510                 515 cat gaa ggc tac act cac ggt gct ggt ttt gac aat gat ata gca ttg         1637
His Glu Gly Tyr Thr His Gly Ala Gly Phe Asp Asn Asp Ile Ala Leu
520                 525                 530                 535 att aaa ctc aag aac aaa gtc aca atc aac gga agc atc atg cct gtt         1685
Ile Lys Leu Lys Asn Lys Val Thr Ile Asn Gly Ser Ile Met Pro Val
                540                 545                 550 tgc cta ccg cga aaa gaa gct gca tcc tta atg aga aca gac ttc act         1733
Cys Leu Pro Arg Lys Glu Ala Ala Ser Leu Met Arg Thr Asp Phe Thr
            555                 560                 565 gga act gtg gct ggc tgg ggg tta acc cag aag ggg ctt ctt gct aga         1781
Gly Thr Val Ala Gly Trp Gly Leu Thr Gln Lys Gly Leu Leu Ala Arg
        570                 575                 580 aac cta atg ttt gtg gac ata cca att gct gac cac caa aaa tgt acc         1829
Asn Leu Met Phe Val Asp Ile Pro Ile Ala Asp His Gln Lys Cys Thr
585                 590                 595
```

| | | | | | | | | | | | | | | | | |
|---|---|---|---|---|---|---|---|---|---|---|---|---|---|---|---|---|
| acc | gtg | tat | gaa | aag | ctc | tat | cca | gga | gta | aga | gta | agc | gct | aac | atg | 1877 |
| Thr | Val | Tyr | Glu | Lys | Leu | Tyr | Pro | Gly | Val | Arg | Val | Ser | Ala | Asn | Met | |
| 600 | | | | 605 | | | | | 610 | | | | | 615 | | |
| ctc | tgt | gct | ggc | tta | gag | act | ggt | ggc | aag | gac | agc | tgc | aga | ggt | gac | 1925 |
| Leu | Cys | Ala | Gly | Leu | Glu | Thr | Gly | Gly | Lys | Asp | Ser | Cys | Arg | Gly | Asp | |
| | | | | 620 | | | | | 625 | | | | | 630 | | |
| agt | ggg | ggg | gca | tta | gtg | ttt | cta | gat | aat | gag | aca | cag | cga | tgg | ttt | 1973 |
| Ser | Gly | Gly | Ala | Leu | Val | Phe | Leu | Asp | Asn | Glu | Thr | Gln | Arg | Trp | Phe | |
| | | | | 635 | | | | | 640 | | | | | 645 | | |
| gtg | gga | gga | ata | gtt | tcc | tgg | ggt | tcc | att | aat | tgt | ggg | gcg | gca | ggc | 2021 |
| Val | Gly | Gly | Ile | Val | Ser | Trp | Gly | Ser | Ile | Asn | Cys | Gly | Ala | Ala | Gly | |
| | | | 650 | | | | | 655 | | | | | 660 | | | |
| cag | tat | ggg | gtc | tac | aca | aaa | gtc | atc | aac | tat | att | ccc | tgg | aat | gag | 2069 |
| Gln | Tyr | Gly | Val | Tyr | Thr | Lys | Val | Ile | Asn | Tyr | Ile | Pro | Trp | Asn | Glu | |
| | | 665 | | | | | 670 | | | | | 675 | | | | |
| aac | ata | ata | agt | aat | ttc | taa | | | | | | | | | | 2090 |
| Asn | Ile | Ile | Ser | Asn | Phe | | | | | | | | | | | |
| 680 | | | | 685 | | | | | | | | | | | | |

<210> SEQ ID NO 51
<211> LENGTH: 685
<212> TYPE: PRT
<213> ORGANISM: Murine

<400> SEQUENCE: 51

Met Arg Leu Leu Ile Phe Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Pro Gly Phe Pro Glu Lys Tyr Ala Asp His Gln Asp Arg Ser Trp Thr
        35                  40                  45

Leu Thr Ala Pro Pro Gly Tyr Arg Leu Arg Leu Tyr Phe Thr His Phe
    50                  55                  60

Asp Leu Glu Leu Ser Tyr Arg Cys Glu Tyr Asp Phe Val Lys Leu Ser
65                  70                  75                  80

Ser Gly Thr Lys Val Leu Ala Thr Leu Cys Gly Gln Glu Ser Thr Asp
                85                  90                  95

Thr Glu Gln Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Val
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Ala Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Tyr Leu Ser Ser Pro Glu Tyr Pro Gln Pro Tyr Pro Lys Leu
        195                 200                 205

Ser Ser Cys Thr Tyr Ser Ile Arg Leu Glu Asp Gly Phe Ser Val Ile
    210                 215                 220

Leu Asp Phe Val Glu Ser Phe Asp Val Glu Thr His Pro Glu Ala Gln
225                 230                 235                 240

Cys Pro Tyr Asp Ser Leu Lys Ile Gln Thr Asp Lys Gly Glu His Gly
                245                 250                 255

```
Pro Phe Cys Gly Lys Thr Leu Pro Pro Arg Ile Glu Thr Asp Ser His
            260                 265                 270

Lys Val Thr Ile Thr Phe Ala Thr Asp Glu Ser Gly Asn His Thr Gly
            275                 280                 285

Trp Lys Ile His Tyr Thr Ser Thr Ala Arg Pro Cys Pro Asp Pro Thr
            290                 295                 300

Ala Pro Pro Asn Gly Ser Ile Ser Pro Val Gln Ala Thr Tyr Val Leu
305                 310                 315                 320

Lys Asp Arg Phe Ser Val Phe Cys Lys Thr Gly Phe Glu Leu Leu Gln
            325                 330                 335

Gly Ser Val Pro Leu Lys Ser Phe Thr Ala Val Cys Gln Lys Asp Gly
            340                 345                 350

Ser Trp Asp Arg Pro Met Pro Glu Cys Ser Ile Ile Asp Cys Gly Pro
            355                 360                 365

Pro Asp Asp Leu Pro Asn Gly His Val Asp Tyr Ile Thr Gly Pro Gln
370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
            405                 410                 415

Trp Thr Ser Ser Lys Gly Glu Lys Leu Pro Pro Val Cys Glu Pro Val
            420                 425                 430

Cys Gly Leu Ser Thr His Thr Ile Gly Gly Arg Ile Val Gly Gly Gln
            435                 440                 445

Pro Ala Lys Pro Gly Asp Phe Pro Trp Gln Val Leu Leu Leu Gly Gln
            450                 455                 460

Thr Thr Ala Ala Ala Gly Ala Leu Ile His Asp Asn Trp Val Leu Thr
465                 470                 475                 480

Ala Ala His Ala Val Tyr Glu Lys Arg Met Ala Ala Ser Ser Leu Asn
            485                 490                 495

Ile Arg Met Gly Ile Leu Lys Arg Leu Ser Pro His Tyr Thr Gln Ala
            500                 505                 510

Trp Pro Glu Glu Ile Phe Ile His Glu Gly Tyr Thr His Gly Ala Gly
            515                 520                 525

Phe Asp Asn Asp Ile Ala Leu Ile Lys Leu Lys Asn Lys Val Thr Ile
530                 535                 540

Asn Gly Ser Ile Met Pro Val Cys Leu Pro Arg Lys Glu Ala Ala Ser
545                 550                 555                 560

Leu Met Arg Thr Asp Phe Thr Gly Thr Val Ala Gly Trp Gly Leu Thr
            565                 570                 575

Gln Lys Gly Leu Leu Ala Arg Asn Leu Met Phe Val Asp Ile Pro Ile
            580                 585                 590

Ala Asp His Gln Lys Cys Thr Thr Val Tyr Glu Lys Leu Tyr Pro Gly
            595                 600                 605

Val Arg Val Ser Ala Asn Met Leu Cys Ala Gly Leu Glu Thr Gly Gly
            610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
            645                 650                 655

Ile Asn Cys Gly Ala Ala Gly Gln Tyr Gly Val Tyr Thr Lys Val Ile
            660                 665                 670
```

```
Asn Tyr Ile Pro Trp Asn Glu Asn Ile Ile Ser Asn Phe
            675                 680                 685

<210> SEQ ID NO 52
<211> LENGTH: 670
<212> TYPE: PRT
<213> ORGANISM: Murine

<400> SEQUENCE: 52

Thr Leu Leu Gly Ser Lys Trp Pro Glu Pro Val Phe Gly Arg Leu Val
1               5                   10                  15

Ser Pro Gly Phe Pro Glu Lys Tyr Ala Asp His Gln Asp Arg Ser Trp
            20                  25                  30

Thr Leu Thr Ala Pro Pro Gly Tyr Arg Leu Arg Leu Tyr Phe Thr His
        35                  40                  45

Phe Asp Leu Glu Leu Ser Tyr Arg Cys Glu Tyr Asp Phe Val Lys Leu
    50                  55                  60

Ser Ser Gly Thr Lys Val Leu Ala Thr Leu Cys Gly Gln Glu Ser Thr
65                  70                  75                  80

Asp Thr Glu Gln Ala Pro Gly Asn Asp Thr Phe Tyr Ser Leu Gly Pro
                85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
        115                 120                 125

Val Ser Leu Gly Asp Ser Val Pro Cys Asp His Tyr Cys His Asn Tyr
    130                 135                 140

Leu Gly Gly Tyr Tyr Cys Ser Cys Arg Ala Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Tyr Leu Ser Ser Pro Glu Tyr Pro Gln Pro Tyr Pro Lys
            180                 185                 190

Leu Ser Ser Cys Thr Tyr Ser Ile Arg Leu Glu Asp Gly Phe Ser Val
        195                 200                 205

Ile Leu Asp Phe Val Glu Ser Phe Asp Val Glu Thr His Pro Glu Ala
    210                 215                 220

Gln Cys Pro Tyr Asp Ser Leu Lys Ile Gln Thr Asp Lys Gly Glu His
225                 230                 235                 240

Gly Pro Phe Cys Gly Lys Thr Leu Pro Pro Arg Ile Glu Thr Asp Ser
                245                 250                 255

His Lys Val Thr Ile Thr Phe Ala Thr Asp Glu Ser Gly Asn His Thr
            260                 265                 270

Gly Trp Lys Ile His Tyr Thr Ser Thr Ala Arg Pro Cys Pro Asp Pro
        275                 280                 285

Thr Ala Pro Pro Asn Gly Ser Ile Ser Pro Val Gln Ala Thr Tyr Val
    290                 295                 300

Leu Lys Asp Arg Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Met Pro Glu Cys Ser Ile Ile Asp Cys Gly
            340                 345                 350

Pro Pro Asp Asp Leu Pro Asn Gly His Val Asp Tyr Ile Thr Gly Pro
        355                 360                 365
```

```
Gln Val Thr Thr Tyr Lys Ala Val Ile Gln Tyr Ser Cys Glu Glu Thr
    370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Leu Pro Pro Val Cys Glu Pro
                405                 410                 415

Val Cys Gly Leu Ser Thr His Thr Ile Gly Gly Arg Ile Val Gly Gly
            420                 425                 430

Gln Pro Ala Lys Pro Gly Asp Phe Pro Trp Gln Val Leu Leu Leu Gly
        435                 440                 445

Gln Thr Thr Ala Ala Gly Ala Leu Ile His Asp Asn Trp Val Leu
    450                 455                 460

Thr Ala Ala His Ala Val Tyr Glu Lys Arg Met Ala Ala Ser Ser Leu
465                 470                 475                 480

Asn Ile Arg Met Gly Ile Leu Lys Arg Leu Ser Pro His Tyr Thr Gln
                485                 490                 495

Ala Trp Pro Glu Glu Ile Phe Ile His Glu Gly Tyr Thr His Gly Ala
            500                 505                 510

Gly Phe Asp Asn Asp Ile Ala Leu Ile Lys Leu Lys Asn Lys Val Thr
        515                 520                 525

Ile Asn Gly Ser Ile Met Pro Val Cys Leu Pro Arg Lys Glu Ala Ala
    530                 535                 540

Ser Leu Met Arg Thr Asp Phe Thr Gly Thr Val Ala Gly Trp Gly Leu
545                 550                 555                 560

Thr Gln Lys Gly Leu Leu Ala Arg Asn Leu Met Phe Val Asp Ile Pro
                565                 570                 575

Ile Ala Asp His Gln Lys Cys Thr Thr Val Tyr Glu Lys Leu Tyr Pro
            580                 585                 590

Gly Val Arg Val Ser Ala Asn Met Leu Cys Ala Gly Leu Glu Thr Gly
        595                 600                 605

Gly Lys Asp Ser Cys Arg Gly Asp Ser Gly Gly Ala Leu Val Phe Leu
    610                 615                 620

Asp Asn Glu Thr Gln Arg Trp Phe Val Gly Gly Ile Val Ser Trp Gly
625                 630                 635                 640

Ser Ile Asn Cys Gly Ala Ala Gly Gln Tyr Gly Val Tyr Thr Lys Val
                645                 650                 655

Ile Asn Tyr Ile Pro Trp Asn Glu Asn Ile Ile Ser Asn Phe
            660                 665                 670

<210> SEQ ID NO 53
<211> LENGTH: 2091
<212> TYPE: DNA
<213> ORGANISM: Rat
<220> FEATURE:
<221> NAME/KEY: CDS
<222> LOCATION: (10)..(2067)

<400> SEQUENCE: 53 tggcacaca atg agg cta ctg atc gtc ctg ggt ctg ctt tgg agt ttg gtg     51
          Met Arg Leu Leu Ile Val Leu Gly Leu Leu Trp Ser Leu Val
          1               5                   10 gcc aca ctt ttg ggc tcc aag tgg cct gag cct gta ttc ggg cgc ctg     99
Ala Thr Leu Leu Gly Ser Lys Trp Pro Glu Pro Val Phe Gly Arg Leu
15                  20                  25                  30 gtg tcc ctg gcc ttc cca gag aag tat ggc aac cat cag gat cga tcc    147
Val Ser Leu Ala Phe Pro Glu Lys Tyr Gly Asn His Gln Asp Arg Ser
```

```
                    35                  40                  45
tgg acg ctg act gca ccc cct ggc ttc cgc ctg cgc ctc tac ttc acc      195
Trp Thr Leu Thr Ala Pro Pro Gly Phe Arg Leu Arg Leu Tyr Phe Thr
            50                  55                  60 cac ttc aac ctg gaa ctc tct tac cgc tgc gag tat gac ttt gtc aag      243
His Phe Asn Leu Glu Leu Ser Tyr Arg Cys Glu Tyr Asp Phe Val Lys
            65                  70              75 ttg acc tca ggg acc aag gtg cta gcc acg ctg tgt ggg cag gag agt      291
Leu Thr Ser Gly Thr Lys Val Leu Ala Thr Leu Cys Gly Gln Glu Ser
    80                  85                  90 aca gat act gag cgg gca cct ggc aat gac acc ttc tac tca ctg ggt      339
Thr Asp Thr Glu Arg Ala Pro Gly Asn Asp Thr Phe Tyr Ser Leu Gly
95              100                 105                 110 ccc agc cta aag gtc acc ttc cac tcc gac tac tcc aat gag aag cca      387
Pro Ser Leu Lys Val Thr Phe His Ser Asp Tyr Ser Asn Glu Lys Pro
                115                 120                 125 ttc aca gga ttt gag gcc ttc tat gca gcg gag gat gtg gat gaa tgc      435
Phe Thr Gly Phe Glu Ala Phe Tyr Ala Ala Glu Asp Val Asp Glu Cys
            130                 135                 140 aga aca tcc ctg gga gac tca gtc cct tgt gac cat tat tgc cac aac      483
Arg Thr Ser Leu Gly Asp Ser Val Pro Cys Asp His Tyr Cys His Asn
        145                 150                 155 tac ctg ggc ggc tac tac tgc tcc tgc cga gtg ggc tac att ctg cac      531
Tyr Leu Gly Gly Tyr Tyr Cys Ser Cys Arg Val Gly Tyr Ile Leu His
    160                 165                 170 cag aac aag cat acc tgc tca gcc ctt tgt tca ggc cag gtg ttc act      579
Gln Asn Lys His Thr Cys Ser Ala Leu Cys Ser Gly Gln Val Phe Thr
175                 180                 185                 190 ggg agg tct ggc ttt ctc agt agc cct gag tac cca cag cca tac ccc      627
Gly Arg Ser Gly Phe Leu Ser Ser Pro Glu Tyr Pro Gln Pro Tyr Pro
                195                 200                 205 aaa ctc tcc agc tgc gcc tac aac atc cgc ctg gag gaa ggc ttc agt      675
Lys Leu Ser Ser Cys Ala Tyr Asn Ile Arg Leu Glu Glu Gly Phe Ser
            210                 215                 220 atc acc ctg gac ttc gtg gag tcc ttt gat gtg gag atg cac cct gaa      723
Ile Thr Leu Asp Phe Val Glu Ser Phe Asp Val Glu Met His Pro Glu
    225                 230                 235 gcc cag tgc ccc tac gac tcc ctc aag att caa aca gac aag agg gaa      771
Ala Gln Cys Pro Tyr Asp Ser Leu Lys Ile Gln Thr Asp Lys Arg Glu
240                 245                 250 tac ggc ccg ttt tgt ggg aag acg ctg ccc ccc agg att gaa act gac      819
Tyr Gly Pro Phe Cys Gly Lys Thr Leu Pro Pro Arg Ile Glu Thr Asp
255                 260                 265                 270 agc aac aag gtg acc att acc ttt acc acc gac gag tca ggg aac cac      867
Ser Asn Lys Val Thr Ile Thr Phe Thr Thr Asp Glu Ser Gly Asn His
            275                 280                 285 aca ggc tgg aag ata cac tac aca agc aca gca cag ccc tgc cct gat      915
Thr Gly Trp Lys Ile His Tyr Thr Ser Thr Ala Gln Pro Cys Pro Asp
        290                 295                 300 cca acg gcg cca cct aat ggt cac att tca cct gtg caa gcc acg tat      963
Pro Thr Ala Pro Pro Asn Gly His Ile Ser Pro Val Gln Ala Thr Tyr
    305                 310                 315 gtc ctg aag gac agc ttt tct gtc ttc tgc aag act ggc ttc gag ctt     1011
Val Leu Lys Asp Ser Phe Ser Val Phe Cys Lys Thr Gly Phe Glu Leu
320                 325                 330 ctg caa ggt tct gtc ccc ctg aag tca ttc act gct gtc tgt cag aaa     1059
Leu Gln Gly Ser Val Pro Leu Lys Ser Phe Thr Ala Val Cys Gln Lys
335                 340                 345                 350 gat gga tct tgg gac cgg ccg ata cca gag tgc agc att att gac tgt     1107
```

|  |  |  |  |  |  |  |  |  |  |  |  |  |  |
|---|---|---|---|---|---|---|---|---|---|---|---|---|---|
|  | Asp | Gly | Ser | Trp | Asp | Arg | Pro | Ile | Pro | Glu | Cys | Ser | Ile | Ile Asp Cys |
|  |  |  |  |  | 355 |  |  |  | 360 |  |  |  |  | 365 |

```
ggc cct ccc gat gac cta ccc aat ggc cac gtg gac tat atc aca ggc     1155
Gly Pro Pro Asp Asp Leu Pro Asn Gly His Val Asp Tyr Ile Thr Gly
            370                 375                 380 cct gaa gtg acc acc tac aaa gct gtg att cag tac agc tgt gaa gag     1203
Pro Glu Val Thr Thr Tyr Lys Ala Val Ile Gln Tyr Ser Cys Glu Glu
        385                 390                 395 act ttc tac aca atg agc agc aat ggt aaa tat gtg tgt gag gct gat     1251
Thr Phe Tyr Thr Met Ser Ser Asn Gly Lys Tyr Val Cys Glu Ala Asp
    400                 405                 410 gga ttc tgg acg agc tcc aaa gga gaa aaa tcc ctc ccg gtt tgc aag     1299
Gly Phe Trp Thr Ser Ser Lys Gly Glu Lys Ser Leu Pro Val Cys Lys
415                 420                 425                 430 cct gtc tgt gga ctg tcc aca cac act tca gga ggc cgt ata att gga     1347
Pro Val Cys Gly Leu Ser Thr His Thr Ser Gly Gly Arg Ile Ile Gly
                435                 440                 445 gga cag cct gca aag cct ggt gac ttt cct tgg caa gtc ttg tta ctg     1395
Gly Gln Pro Ala Lys Pro Gly Asp Phe Pro Trp Gln Val Leu Leu Leu
            450                 455                 460 ggt gaa act aca gca gca ggt gct ctt ata cat gac gac tgg gtc cta     1443
Gly Glu Thr Thr Ala Ala Gly Ala Leu Ile His Asp Asp Trp Val Leu
        465                 470                 475 aca gcg gct cat gct gta tat ggg aaa aca gag gcg atg tcc tcc ctg     1491
Thr Ala Ala His Ala Val Tyr Gly Lys Thr Glu Ala Met Ser Ser Leu
    480                 485                 490 gac atc cgc atg ggc atc ctc aaa agg ctc tcc ctc att tac act caa     1539
Asp Ile Arg Met Gly Ile Leu Lys Arg Leu Ser Leu Ile Tyr Thr Gln
495                 500                 505                 510 gcc tgg cca gag gct gtc ttt atc cat gaa ggc tac act cac gga gct     1587
Ala Trp Pro Glu Ala Val Phe Ile His Glu Gly Tyr Thr His Gly Ala
                515                 520                 525 ggt ttt gac aat gat ata gca ctg att aaa ctc aag aac aaa gtc aca     1635
Gly Phe Asp Asn Asp Ile Ala Leu Ile Lys Leu Lys Asn Lys Val Thr
            530                 535                 540 atc aac aga aac atc atg ccg att tgt cta cca aga aaa gaa gct gca     1683
Ile Asn Arg Asn Ile Met Pro Ile Cys Leu Pro Arg Lys Glu Ala Ala
        545                 550                 555 tcc tta atg aaa aca gac ttc gtt gga act gtg gct ggc tgg ggg tta     1731
Ser Leu Met Lys Thr Asp Phe Val Gly Thr Val Ala Gly Trp Gly Leu
    560                 565                 570 acc cag aag ggg ttt ctt gct aga aac cta atg ttt gtg gac ata cca     1779
Thr Gln Lys Gly Phe Leu Ala Arg Asn Leu Met Phe Val Asp Ile Pro
575                 580                 585                 590 att gtt gac cac caa aaa tgt gct act gcg tat aca aag cag ccc tac     1827
Ile Val Asp His Gln Lys Cys Ala Thr Ala Tyr Thr Lys Gln Pro Tyr
                595                 600                 605 cca gga gca aaa gtg act gtt aac atg ctc tgt gct ggc cta gac cgc     1875
Pro Gly Ala Lys Val Thr Val Asn Met Leu Cys Ala Gly Leu Asp Arg
            610                 615                 620 ggt ggc aag gac agc tgc aga ggt gac agc gga ggg gca tta gtg ttt     1923
Gly Gly Lys Asp Ser Cys Arg Gly Asp Ser Gly Gly Ala Leu Val Phe
        625                 630                 635 cta gac aat gaa aca cag aga tgg ttt gtg gga gga ata gtt tcc tgg     1971
Leu Asp Asn Glu Thr Gln Arg Trp Phe Val Gly Gly Ile Val Ser Trp
    640                 645                 650 ggt tct att aac tgt ggg ggg tca gaa cag tat ggg gtc tac acg aaa     2019
Gly Ser Ile Asn Cys Gly Gly Ser Glu Gln Tyr Gly Val Tyr Thr Lys
655                 660                 665                 670
```

```
gtc acg aac tat att ccc tgg att gag aac ata ata aat aat ttc taa    2067
Val Thr Asn Tyr Ile Pro Trp Ile Glu Asn Ile Ile Asn Asn Phe
            675                 680                 685 tttgcaaaaa aaaaaaaaaa aaaa                                          2091
```

<210> SEQ ID NO 54
<211> LENGTH: 685
<212> TYPE: PRT
<213> ORGANISM: Rat

<400> SEQUENCE: 54

```
Met Arg Leu Leu Ile Val Leu Gly Leu Leu Trp Ser Leu Val Ala Thr
 1               5                  10                  15

Leu Leu Gly Ser Lys Trp Pro Glu Pro Val Phe Gly Arg Leu Val Ser
            20                  25                  30

Leu Ala Phe Pro Glu Lys Tyr Gly Asn His Gln Asp Arg Ser Trp Thr
        35                  40                  45

Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80

Ser Gly Thr Lys Val Leu Ala Thr Leu Cys Gly Gln Glu Ser Thr Asp
                85                  90                  95

Thr Glu Arg Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Thr
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Phe Leu Ser Ser Pro Glu Tyr Pro Gln Pro Tyr Pro Lys Leu
        195                 200                 205

Ser Ser Cys Ala Tyr Asn Ile Arg Leu Glu Glu Gly Phe Ser Ile Thr
    210                 215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
            260                 265                 270

Lys Val Thr Ile Thr Phe Thr Thr Asp Glu Ser Gly Asn His Thr Gly
        275                 280                 285

Trp Lys Ile His Tyr Thr Ser Thr Ala Gln Pro Cys Pro Asp Pro Thr
    290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350
```

Ser Trp Asp Arg Pro Ile Pro Glu Cys Ser Ile Ile Asp Cys Gly Pro
          355                 360                 365

Pro Asp Asp Leu Pro Asn Gly His Val Asp Tyr Ile Thr Gly Pro Glu
370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
          420                 425                 430

Cys Gly Leu Ser Thr His Thr Ser Gly Gly Arg Ile Ile Gly Gly Gln
          435                 440                 445

Pro Ala Lys Pro Gly Asp Phe Pro Trp Gln Val Leu Leu Leu Gly Glu
450                 455                 460

Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495

Arg Met Gly Ile Leu Lys Arg Leu Ser Leu Ile Tyr Thr Gln Ala Trp
          500                 505                 510

Pro Glu Ala Val Phe Ile His Glu Gly Tyr Thr His Gly Ala Gly Phe
          515                 520                 525

Asp Asn Asp Ile Ala Leu Ile Lys Leu Lys Asn Lys Val Thr Ile Asn
530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
          580                 585                 590

Asp His Gln Lys Cys Ala Thr Ala Tyr Thr Lys Gln Pro Tyr Pro Gly
          595                 600                 605

Ala Lys Val Thr Val Asn Met Leu Cys Ala Gly Leu Asp Arg Gly Gly
610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Gly Ser Glu Gln Tyr Gly Val Tyr Thr Lys Val Thr
          660                 665                 670

Asn Tyr Ile Pro Trp Ile Glu Asn Ile Ile Asn Asn Phe
          675                 680                 685

<210> SEQ ID NO 55
<211> LENGTH: 670
<212> TYPE: PRT
<213> ORGANISM: Rat

<400> SEQUENCE: 55

Thr Leu Leu Gly Ser Lys Trp Pro Glu Pro Val Phe Gly Arg Leu Val
1               5                   10                  15

Ser Leu Ala Phe Pro Glu Lys Tyr Gly Asn His Gln Asp Arg Ser Trp
                20                  25                  30

Thr Leu Thr Ala Pro Pro Gly Phe Arg Leu Arg Leu Tyr Phe Thr His

```
                35                  40                  45
Phe Asn Leu Glu Leu Ser Tyr Arg Cys Glu Tyr Asp Phe Val Lys Leu
 50                  55                  60
Thr Ser Gly Thr Lys Val Leu Ala Thr Leu Cys Gly Gln Glu Ser Thr
 65                  70                  75                  80
Asp Thr Glu Arg Ala Pro Gly Asn Asp Thr Phe Tyr Ser Leu Gly Pro
                 85                  90                  95
Ser Leu Lys Val Thr Phe His Ser Asp Tyr Ser Asn Glu Lys Pro Phe
                100                 105                 110
Thr Gly Phe Glu Ala Phe Tyr Ala Ala Glu Asp Val Asp Glu Cys Arg
                115                 120                 125
Thr Ser Leu Gly Asp Ser Val Pro Cys Asp His Tyr Cys His Asn Tyr
130                 135                 140
Leu Gly Gly Tyr Tyr Cys Ser Cys Arg Val Gly Tyr Ile Leu His Gln
145                 150                 155                 160
Asn Lys His Thr Cys Ser Ala Leu Cys Ser Gly Gln Val Phe Thr Gly
                165                 170                 175
Arg Ser Gly Phe Leu Ser Ser Pro Glu Tyr Pro Gln Pro Tyr Pro Lys
                180                 185                 190
Leu Ser Ser Cys Ala Tyr Asn Ile Arg Leu Glu Glu Gly Phe Ser Ile
                195                 200                 205
Thr Leu Asp Phe Val Glu Ser Phe Asp Val Glu Met His Pro Glu Ala
210                 215                 220
Gln Cys Pro Tyr Asp Ser Leu Lys Ile Gln Thr Asp Lys Arg Glu Tyr
225                 230                 235                 240
Gly Pro Phe Cys Gly Lys Thr Leu Pro Pro Arg Ile Glu Thr Asp Ser
                245                 250                 255
Asn Lys Val Thr Ile Thr Phe Thr Asp Glu Ser Gly Asn His Thr
                260                 265                 270
Gly Trp Lys Ile His Tyr Thr Ser Thr Ala Gln Pro Cys Pro Asp Pro
                275                 280                 285
Thr Ala Pro Pro Asn Gly His Ile Ser Pro Val Gln Ala Thr Tyr Val
290                 295                 300
Leu Lys Asp Ser Phe Ser Val Phe Cys Lys Thr Gly Phe Glu Leu Leu
305                 310                 315                 320
Gln Gly Ser Val Pro Leu Lys Ser Phe Thr Ala Val Cys Gln Lys Asp
                325                 330                 335
Gly Ser Trp Asp Arg Pro Ile Pro Glu Cys Ser Ile Ile Asp Cys Gly
                340                 345                 350
Pro Pro Asp Asp Leu Pro Asn Gly His Val Asp Tyr Ile Thr Gly Pro
                355                 360                 365
Glu Val Thr Thr Tyr Lys Ala Val Ile Gln Tyr Ser Cys Glu Glu Thr
                370                 375                 380
Phe Tyr Thr Met Ser Ser Asn Gly Lys Tyr Val Cys Glu Ala Asp Gly
385                 390                 395                 400
Phe Trp Thr Ser Ser Lys Gly Glu Lys Ser Leu Pro Val Cys Lys Pro
                405                 410                 415
Val Cys Gly Leu Ser Thr His Thr Ser Gly Gly Arg Ile Ile Gly Gly
                420                 425                 430
Gln Pro Ala Lys Pro Gly Asp Phe Pro Trp Gln Val Leu Leu Leu Gly
                435                 440                 445
Glu Thr Thr Ala Ala Gly Ala Leu Ile His Asp Asp Trp Val Leu Thr
450                 455                 460
```

```
Ala Ala His Ala Val Tyr Gly Lys Thr Glu Ala Met Ser Ser Leu Asp
465                 470                 475                 480

Ile Arg Met Gly Ile Leu Lys Arg Leu Ser Leu Ile Tyr Thr Gln Ala
            485                 490                 495

Trp Pro Glu Ala Val Phe Ile His Glu Gly Tyr Thr His Gly Ala Gly
        500                 505                 510

Phe Asp Asn Asp Ile Ala Leu Ile Lys Leu Lys Asn Lys Val Thr Ile
    515                 520                 525

Asn Arg Asn Ile Met Pro Ile Cys Leu Pro Arg Lys Glu Ala Ala Ser
530                 535                 540

Leu Met Lys Thr Asp Phe Val Gly Thr Val Ala Gly Trp Gly Leu Thr
545                 550                 555                 560

Gln Lys Gly Phe Leu Ala Arg Asn Leu Met Phe Val Asp Ile Pro Ile
                565                 570                 575

Val Asp His Gln Lys Cys Ala Thr Ala Tyr Thr Lys Gln Pro Tyr Pro
            580                 585                 590

Gly Ala Lys Val Thr Val Asn Met Leu Cys Ala Gly Leu Asp Arg Gly
        595                 600                 605

Gly Lys Asp Ser Cys Arg Gly Asp Ser Gly Ala Leu Val Phe Leu
    610                 615                 620

Asp Asn Glu Thr Gln Arg Trp Phe Val Gly Ile Val Ser Trp Gly
625                 630                 635                 640

Ser Ile Asn Cys Gly Gly Ser Glu Gln Tyr Gly Val Tyr Thr Lys Val
                645                 650                 655

Thr Asn Tyr Ile Pro Trp Ile Glu Asn Ile Ile Asn Asn Phe
            660                 665                 670

<210> SEQ ID NO 56
<211> LENGTH: 28
<212> TYPE: DNA
<213> ORGANISM: Artificial Sequence
<220> FEATURE:
<223> OTHER INFORMATION: Homo Sapiens

<400> SEQUENCE: 56
atgaggctgc tgaccctcct gggccttc                                        28

<210> SEQ ID NO 57
<211> LENGTH: 23
<212> TYPE: DNA
<213> ORGANISM: Artificial Sequence
<220> FEATURE:
<223> OTHER INFORMATION: Homo Sapiens

<400> SEQUENCE: 57
gtgcccctcc tgcgtcacct ctg                                             23

<210> SEQ ID NO 58
<211> LENGTH: 23
<212> TYPE: DNA
<213> ORGANISM: Artificial Sequence
<220> FEATURE:
<223> OTHER INFORMATION: Homo Sapiens

<400> SEQUENCE: 58
cagaggtgac gcaggagggg cac                                             23

<210> SEQ ID NO 59
<211> LENGTH: 27
```

```
<212> TYPE: DNA
<213> ORGANISM: Artificial Sequence
<220> FEATURE:
<223> OTHER INFORMATION: Homo Sapiens

<400> SEQUENCE: 59
ttaaaatcac taattatgtt ctcgatc                                           27

<210> SEQ ID NO 60
<211> LENGTH: 22
<212> TYPE: DNA
<213> ORGANISM: Artificial Sequence
<220> FEATURE:
<223> OTHER INFORMATION: Murine

<400> SEQUENCE: 60
atgaggctac tcatcttcct gg                                                22

<210> SEQ ID NO 61
<211> LENGTH: 23
<212> TYPE: DNA
<213> ORGANISM: Artificial Sequence
<220> FEATURE:
<223> OTHER INFORMATION: Murine

<400> SEQUENCE: 61
ctgcagaggt gacgcagggg ggg                                               23

<210> SEQ ID NO 62
<211> LENGTH: 23
<212> TYPE: DNA
<213> ORGANISM: Artificial Sequence
<220> FEATURE:
<223> OTHER INFORMATION: Murine

<400> SEQUENCE: 62
ccccccctgc gtcacctctg cag                                               23

<210> SEQ ID NO 63
<211> LENGTH: 29
<212> TYPE: DNA
<213> ORGANISM: Artificial Sequence
<220> FEATURE:
<223> OTHER INFORMATION: Murine

<400> SEQUENCE: 63
ttagaaatta cttattatgt tctcaatcc                                         29

<210> SEQ ID NO 64
<211> LENGTH: 29
<212> TYPE: DNA
<213> ORGANISM: Artificial Sequence
<220> FEATURE:
<223> OTHER INFORMATION: Rat

<400> SEQUENCE: 64
gaggtgacgc aggaggggca ttagtgttt                                         29

<210> SEQ ID NO 65
<211> LENGTH: 37
<212> TYPE: DNA
<213> ORGANISM: Artificial Sequence
<220> FEATURE:
<223> OTHER INFORMATION: Rat

<400> SEQUENCE: 65
```

```
ctagaaacac taatgcccct cctgcgtcac ctctgca                              37
```

<210> SEQ ID NO 66
<211> LENGTH: 354
<212> TYPE: DNA
<213> ORGANISM: Artificial Sequence
<220> FEATURE:
<223> OTHER INFORMATION: Synthetic

<400> SEQUENCE: 66

```
caggtcacct tgaaggagtc tggtcctgtg ctggtgaaac ccacagagac cctcacgctg     60
acctgcaccg tctctgggtt ctcactcagc aggggtaaaa tgggtgtgag ctggatccgt    120
cagcccccag ggaaggccct ggagtggctt gcacacattt tttcgagtga cgaaaaatcc    180
tacaggacat cgctgaagag caggctcacc atctccaagg acacctccaa aaaccaggtg    240
gtccttacaa tgaccaacat ggaccctgtg acacagcca cgtattactg tgcacggata     300
cgacgtggag gaattgacta ctggggccag ggaaccctgg tcactgtctc ctca          354
```

<210> SEQ ID NO 67
<211> LENGTH: 118
<212> TYPE: PRT
<213> ORGANISM: Artificial Sequence
<220> FEATURE:
<223> OTHER INFORMATION: Synthetic

<400> SEQUENCE: 67

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Arg Gly
            20                  25                  30
Lys Met Gly Val Ser Trp Ile Arg Gln Pro Pro Gly Lys Ala Leu Glu
        35                  40                  45
Trp Leu Ala His Ile Phe Ser Ser Asp Glu Lys Ser Tyr Arg Thr Ser
    50                  55                  60
Leu Lys Ser Arg Leu Thr Ile Ser Lys Asp Thr Ser Lys Asn Gln Val
65                  70                  75                  80
Val Leu Thr Met Thr Asn Met Asp Pro Val Thr Ala Thr Tyr Tyr
                85                  90                  95
Cys Ala Arg Ile Arg Arg Gly Gly Ile Asp Tyr Trp Gly Gln Gly Thr
            100                 105                 110
Leu Val Thr Val Ser Ser
        115
```

<210> SEQ ID NO 68
<211> LENGTH: 121
<212> TYPE: PRT
<213> ORGANISM: Artificial Sequence
<220> FEATURE:
<223> OTHER INFORMATION: Synthetic

<400> SEQUENCE: 68

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Thr
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
```

Val Ser Val Lys Ser Arg Ile Thr Ile Asn Pro Asp Thr Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Phe Gly Val Pro Phe Asp Ile Trp Gly
            100                 105                 110

Gln Gly Thr Met Val Thr Val Ser Ser
        115                 120

<210> SEQ ID NO 69
<211> LENGTH: 106
<212> TYPE: PRT
<213> ORGANISM: Artificial Sequence
<220> FEATURE:
<223> OTHER INFORMATION: Synthetic

<400> SEQUENCE: 69

Gln Pro Val Leu Thr Gln Pro Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 70
<211> LENGTH: 324
<212> TYPE: DNA
<213> ORGANISM: Artificial Sequence
<220> FEATURE:
<223> OTHER INFORMATION: Synthetic

<400> SEQUENCE: 70
tcctatgagc tgatacagcc accctcggtg tcagtggccc caggacagac ggccaccatt    60
acctgtgcgg gagacaacct tgggaagaaa cgtgtgcact ggtaccagca gaggccaggc   120
caggcccctg tgttggtcat ctatgatgat agcgaccggc cctcagggat ccctgaccga   180
ttctctgcct ccaactctgg gaacacggcc accctgacca tcactagggg cgaagccggg   240
gatgaggccg actattattg tcaggtgtgg gacattgcta ctgatcatgt ggtcttcggc   300
ggagggacca agctcaccgt ccta                                          324

<210> SEQ ID NO 71
<211> LENGTH: 120
<212> TYPE: PRT
<213> ORGANISM: Artificial Sequence
<220> FEATURE:
<223> OTHER INFORMATION: Synthetic

<400> SEQUENCE: 71

Ser Tyr Glu Leu Ile Gln Pro Pro Ser Val Ser Val Ala Pro Gly Gln
1               5                   10                  15

```
Thr Ala Thr Ile Thr Cys Ala Gly Asp Asn Leu Gly Lys Lys Arg Val
            20                  25                  30

His Trp Tyr Gln Gln Arg Pro Gly Gln Ala Pro Val Leu Val Ile Tyr
        35                  40                  45

Asp Asp Ser Asp Arg Pro Ser Gly Ile Pro Asp Arg Phe Ser Ala Ser
    50                  55                  60

Asn Ser Gly Asn Thr Ala Thr Leu Thr Ile Thr Arg Gly Glu Ala Gly
65                  70                  75                  80

Asp Glu Ala Asp Tyr Tyr Cys Gln Val Trp Asp Ile Ala Thr Asp His
                85                  90                  95

Val Val Phe Gly Gly Gly Thr Lys Leu Thr Val Leu Ala Ala Ala Gly
            100                 105                 110

Ser Glu Gln Lys Leu Ile Ser Glu
        115                 120

<210> SEQ ID NO 72
<211> LENGTH: 36
<212> TYPE: PRT
<213> ORGANISM: Artificial Sequence
<220> FEATURE:
<223> OTHER INFORMATION: Synthetic

<400> SEQUENCE: 72

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln
        35

<210> SEQ ID NO 73
<211> LENGTH: 33
<212> TYPE: PRT
<213> ORGANISM: Artificial Sequence
<220> FEATURE:
<223> OTHER INFORMATION: Synthetic

<400> SEQUENCE: 73

Thr Cys Glu Pro Gly Thr Thr Phe Lys Asp Lys Cys Asn Thr Cys Arg
1               5                   10                  15

Cys Gly Ser Asp Gly Lys Ser Ala Val Cys Thr Lys Leu Trp Cys Asn
            20                  25                  30

Gln

<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74

Thr Cys Arg Cys Gly Ser Asp Gly Lys Ser Ala Val Cys Thr Lys Leu
1               5                   10                  15

Trp Cys Asn Gln
        20

<210> SEQ ID NO 75
<211> LENGTH: 491
<212> TYPE: PRT
<213> ORGANISM: Artificial Sequence
```

<220> FEATURE:
<223> OTHER INFORMATION: Synthetic

<400> SEQUENCE: 75

```
Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln Gly Thr Gly Gly Ser Gly Ser Ser Gln Val
        35                  40                  45

Thr Leu Lys Glu Ser Gly Pro Val Leu Val Lys Pro Thr Glu Thr Leu
50                  55                  60

Thr Leu Thr Cys Thr Val Ser Gly Phe Ser Leu Ser Arg Gly Lys Met
65                  70                  75                  80

Gly Val Ser Trp Ile Arg Gln Pro Pro Gly Lys Ala Leu Glu Trp Leu
                85                  90                  95

Ala His Ile Phe Ser Ser Asp Glu Lys Ser Tyr Arg Thr Ser Leu Lys
            100                 105                 110

Ser Arg Leu Thr Ile Ser Lys Asp Thr Ser Lys Asn Gln Val Val Leu
        115                 120                 125

Thr Met Thr Asn Met Asp Pro Val Asp Thr Ala Thr Tyr Tyr Cys Ala
130                 135                 140

Arg Ile Arg Arg Gly Gly Ile Asp Tyr Trp Gly Gln Gly Thr Leu Val
145                 150                 155                 160

Thr Val Ser Ser Ala Ser Thr Lys Gly Pro Ser Val Phe Pro Leu Ala
                165                 170                 175

Pro Cys Ser Arg Ser Thr Ser Glu Ser Thr Ala Ala Leu Gly Cys Leu
            180                 185                 190

Val Lys Asp Tyr Phe Pro Glu Pro Val Thr Val Ser Trp Asn Ser Gly
        195                 200                 205

Ala Leu Thr Ser Gly Val His Thr Phe Pro Ala Val Leu Gln Ser Ser
210                 215                 220

Gly Leu Tyr Ser Leu Ser Ser Val Val Thr Val Pro Ser Ser Ser Leu
225                 230                 235                 240

Gly Thr Lys Thr Tyr Thr Cys Asn Val Asp His Lys Pro Ser Asn Thr
                245                 250                 255

Lys Val Asp Lys Arg Val Glu Ser Lys Tyr Gly Pro Pro Cys Pro Pro
            260                 265                 270

Cys Pro Ala Pro Glu Phe Leu Gly Gly Pro Ser Val Phe Leu Phe Pro
        275                 280                 285

Pro Lys Pro Lys Asp Thr Leu Met Ile Ser Arg Thr Pro Glu Val Thr
290                 295                 300

Cys Val Val Val Asp Val Ser Gln Glu Asp Pro Glu Val Gln Phe Asn
305                 310                 315                 320

Trp Tyr Val Asp Gly Val Glu Val His Asn Ala Lys Thr Lys Pro Arg
                325                 330                 335

Glu Glu Gln Phe Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Gly Leu Pro Ser Ser Ile Glu Lys Thr Ile Ser Lys Ala Lys
370                 375                 380

Gly Gln Pro Arg Glu Pro Gln Val Tyr Thr Leu Pro Pro Ser Gln Glu
385                 390                 395                 400
```

```
Glu Met Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
                435                 440                 445

Phe Leu Tyr Ser Arg Leu Thr Val Asp Lys Ser Arg Trp Gln Glu Gly
450                 455                 460

Asn Val Phe Ser Cys Ser Val Met His Glu Ala Leu His Asn His Tyr
465                 470                 475                 480

Thr Gln Lys Ser Leu Ser Leu Ser Leu Gly Lys
                485                 490

<210> SEQ ID NO 76
<211> LENGTH: 491
<212> TYPE: PRT
<213> ORGANISM: Artificial Sequence
<220> FEATURE:
<223> OTHER INFORMATION: Synthetic

<400> SEQUENCE: 76

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ala Gly
            435                 440                 445

Gly Ser Gly Leu Glu Val Thr Cys Glu Pro Gly Thr Thr Phe Lys Asp
        450                 455                 460

Lys Cys Asn Thr Cys Arg Cys Gly Ser Asp Gly Lys Ser Ala Val Cys
465                 470                 475                 480

Thr Lys Leu Trp Cys Asn Gln Gly Ser Gly Ala
                485                 490

<210> SEQ ID NO 77
<211> LENGTH: 258
<212> TYPE: PRT
<213> ORGANISM: Artificial Sequence
<220> FEATURE:
<223> OTHER INFORMATION: Synthetic

<400> SEQUENCE: 77

Leu Glu Val Thr Cys Glu Pro Gly Thr Thr Phe Lys Asp Lys Cys Asn
1               5                   10                  15

Thr Cys Arg Cys Gly Ser Asp Gly Lys Ser Ala Val Cys Thr Lys Leu
            20                  25                  30

Trp Cys Asn Gln Gly Thr Gly Gly Ser Gly Ser Ser Ser Gln Pro
            35                  40                  45

Val Leu Thr Gln Pro Pro Ser Leu Ser Val Ser Pro Gly Gln Thr Ala
50                  55                  60

Ser Ile Thr Cys Ser Gly Glu Lys Leu Gly Asp Lys Tyr Ala Tyr Trp
65                  70                  75                  80

Tyr Gln Gln Lys Pro Gly Gln Ser Pro Val Leu Val Met Tyr Gln Asp
                85                  90                  95

Lys Gln Arg Pro Ser Gly Ile Pro Glu Arg Phe Ser Gly Ser Asn Ser
            100                 105                 110

Gly Asn Thr Ala Thr Leu Thr Ile Ser Gly Thr Gln Ala Met Asp Glu
        115                 120                 125

Ala Asp Tyr Tyr Cys Gln Ala Trp Asp Ser Ser Thr Ala Val Phe Gly
    130                 135                 140

Gly Gly Thr Lys Leu Thr Val Leu Gly Gln Pro Lys Ala Ala Pro Ser
145                 150                 155                 160

Val Thr Leu Phe Pro Pro Ser Ser Glu Glu Leu Gln Ala Asn Lys Ala
                165                 170                 175

Thr Leu Val Cys Leu Ile Ser Asp Phe Tyr Pro Gly Ala Val Thr Val
            180                 185                 190

Ala Trp Lys Ala Asp Ser Ser Pro Val Lys Ala Gly Val Glu Thr Thr
        195                 200                 205

Thr Pro Ser Lys Gln Ser Asn Asn Lys Tyr Ala Ala Ser Ser Tyr Leu
    210                 215                 220

Ser Leu Thr Pro Glu Gln Trp Lys Ser His Arg Ser Tyr Ser Cys Gln
225                 230                 235                 240

Val Thr His Glu Gly Ser Thr Val Glu Lys Thr Val Ala Pro Thr Glu
                245                 250                 255

Cys Ser

<210> SEQ ID NO 78
<211> LENGTH: 258
<212> TYPE: PRT
<213> ORGANISM: Artificial Sequence
<220> FEATURE:
<223> OTHER INFORMATION: Synthetic

<400> SEQUENCE: 78

Gln Pro Val Leu Thr Gln Pro Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser Ala Ala Gly Gly Ser Gly Leu Glu Val Thr Cys Glu
    210                 215                 220

Pro Gly Thr Thr Phe Lys Asp Lys Cys Asn Thr Cys Arg Cys Gly Ser
225                 230                 235                 240

```
Asp Gly Lys Ser Ala Val Cys Thr Lys Leu Trp Cys Asn Gln Gly Ser
            245                 250                 255

Gly Ala

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Gly Thr Gly Gly Gly Ser Gly Ser Ser Ser
1               5                   10

<210> SEQ ID NO 80
<211> LENGTH: 6
<212> TYPE: PRT
<213> ORGANISM: Artificial Sequence
<220> FEATURE:
<223> OTHER INFORMATION: Synthetic

<400> SEQUENCE: 80

Ala Ala Gly Gly Ser Gly
1               5

<210> SEQ ID NO 81
<211> LENGTH: 4
<212> TYPE: PRT
<213> ORGANISM: Artificial Sequence
<220> FEATURE:
<223> OTHER INFORMATION: Synthetic

<400> SEQUENCE: 81

Gly Ser Gly Ala
1

<210> SEQ ID NO 82
<211> LENGTH: 1533
<212> TYPE: DNA
<213> ORGANISM: Artificial Sequence
<220> FEATURE:
<223> OTHER INFORMATION: Synthetic

<400> SEQUENCE: 82
atgatgtcct ttgtctctct gctcctggtt ggcatcctat tccatgccac ccaggccttg      60
gaagtgacgt gtgagcccgg aacgacattc aaagacaagt gcaatacttg tcggtgcggt     120
tcagatggga atcggcggt ctgcacaaag ctctggtgta accagggcac cggtggaggg     180
tcggatccaa gctcacaggt caccttgaag gagtctggtc ctgtgctggt gaaacccaca     240
gagaccctca cgctgacctg caccgtctct gggttctcac tcagcagggg taaaatgggt     300
gtgagctgga tccgtcagcc cccagggaag gccctggagt ggcttgcaca catttttttcg     360 agtgacgaaa atcctacag acatcgctg aagagcaggc tcaccatctc caaggacacc     420
tccaaaaacc aggtggtcct tacaatgacc aacatggacc ctgtggacac agccacgtat     480
tactgtgcac ggatacgacg tggaggaatt gactactggg gccagggaac cctggtcact     540
gtctcctcag cctccaccaa gggcccatcc gtcttccccc tggcgccctg ctccaggagc     600
acctccgaga gcacagccgc cctgggctgc ctggtcaagg actacttccc cgaaccggtg     660
acggtgtcgt ggaactcagg cgccctgacc agcggcgtgc acaccttccc ggctgtccta     720
cagtcctcag gactctactc cctcagcagc gtggtgaccg tgccctccag cagcttgggc     780
```

```
acgaagacct acacctgcaa cgtagatcac aagcccagca acaccaaggt ggacaagaga    840
gttgagtcca aatatggtcc cccatgccca ccatgcccag cacctgagtt cctgggggga    900
ccatcagtct tcctgttccc cccaaaaccc aaggacactc tcatgatctc ccggacccct    960
gaggtcacgt gcgtggtggt ggacgtgagc caggaagacc ccgaggtcca gttcaactgg   1020
tacgtggatg gcgtggaggt gcataatgcc aagacaaagc cgcgggagga gcagttcaac   1080
agcacgtacc gtgtggtcag cgtcctcacc gtcctgcacc aggactggct gaacggcaag   1140
gagtacaagt gcaaggtctc caacaaaggc ctcccgtcct ccatcgagaa aaccatctcc   1200
aaagccaaag ggcagccccg agagccacag gtgtacaccc tgcccccatc ccaggaggag   1260
atgaccaaga accaggtcag cctgacctgc ctggtcaaag gcttctaccc cagcgacatc   1320
gccgtggagt gggagagcaa tgggcagccg gagaacaact acaagaccac gcctcccgtg   1380
ctggactccg acggctcctt cttcctctac agcaggctaa ccgtggacaa gagcaggtgg   1440
caggagggga atgtcttctc atgctccgtg atgcatgagg ctctgcacaa ccactacaca   1500
cagaagagcc tctccctgtc tctcgggaaa tga                                1533
```

<210> SEQ ID NO 83
<211> LENGTH: 1533
<212> TYPE: DNA
<213> ORGANISM: Artificial Sequence
<220> FEATURE:
<223> OTHER INFORMATION: Synthetic

<400> SEQUENCE: 83

```
atgatgtcct ttgtctctct gctcctggtt ggcatcctat tccatgccac ccaggcccag     60
gtcaccttga aggagtctgg tcctgtgctg gtgaaaccca cagagaccct cacgctgacc    120
tgcaccgtct ctgggttctc actcagcagg ggtaaaatgg gtgtgagctg gatccgtcag    180
cccccaggga aggccctgga gtggcttgca cacatttttt cgagtgacga aaatcctac    240
aggacatcgc tgaagagcag gctcaccatc tccaaggaca cctccaaaaa ccaggtggtc    300
cttacaatga ccaacatgga ccctgtggac acagccacgt attactgtgc acggatacga    360
cgtggaggaa ttgactactg gggccaggga accctggtca ctgtctcctc agcctccacc    420
aagggcccat ccgtcttccc cctggcgccc tgctccagga gcacctccga gagcacagcc    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacgaagac ctacacctgc    660
aacgtagatc acaagcccag caacaccaag gtggacaaga gagttgagtc caaatatggt    720
cccccatgcc caccatgccc agcacctgag ttcctggggg gaccatcagt cttcctgttc    780
cccccaaaac ccaaggacac tctcatgatc tcccggaccc ctgaggtcac gtgcgtggtg    840
gtggacgtga gccaggaaga ccccgaggtc cagttcaact ggtacgtgga tggcgtggag    900
gtgcataatg ccaagacaaa gccgcgggag gagcagttca acagcacgta ccgtgtggtc    960
agcgtcctca ccgtcctgca ccaggactgg ctgaacggca aggagtacaa gtgcaaggtc   1020
tccaacaaag gcctcccgtc ctccatcgag aaaaccatct ccaaagccaa agggcagccc   1080
cgagagccac aggtgtacac cctgccccca tcccaggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acgcctcccg tgctggactc cgacggctcc   1260
```

| | |
|---|---|
| ttcttcctct acagcaggct aaccgtggac aagagcaggt ggcaggaggg gaatgtcttc | 1320 |
| tcatgctccg tgatgcatga ggctctgcac aaccactaca cacagaagag cctctccctg | 1380 |
| tctctcggga agccgctggt ggtagtggt ttggaagtga cgtgtgagcc cggaacgaca | 1440 |
| ttcaaagaca agtgcaatac ttgtcggtgc ggttcagatg ggaaatcggc ggtctgcaca | 1500 |
| aagctctggt gtaaccaggg tagtggtgct tga | 1533 |

<210> SEQ ID NO 84
<211> LENGTH: 834
<212> TYPE: DNA
<213> ORGANISM: Artificial Sequence
<220> FEATURE:
<223> OTHER INFORMATION: Synthetic

<400> SEQUENCE: 84

| | |
|---|---|
| atgatgtcct ttgtctctct gctcctggtt ggcatcctat tccatgccac ccaggccttg | 60 |
| gaagtgacgt gtgagcccgg aacgacattc aaagacaagt gcaatacttg tcggtgcggt | 120 |
| tcagatggga aatcggcggt ctgcacaaag ctctggtgta accagggcac cggtggaggg | 180 |
| tcgggatcca gctcacagcc agtgctgact cagcccccct cactgtccgt gtccccagga | 240 |
| cagacagcca gcatcacctg ctctggagag aaattggggg ataaatatgc ttactggtat | 300 |
| cagcagaagc caggccagtc ccctgtgttg gtcatgtatc aagataaaca gcggccctca | 360 |
| gggatccctg agcgattctc tggctccaac tctgggaaca gccactct gaccatcagc | 420 |
| gggacccagg ctatggatga ggctgactat tactgtcagg cgtgggacag cagcactgcg | 480 |
| gtattcggcg agggaccaa gctgaccgtc ctaggccagc ctaaggcggc gccctcggtc | 540 |
| accctgttcc cgccctcctc tgaggagctt caagccaaca ggccacact ggtgtgtctc | 600 |
| ataagtgact ctacccgg agccgtgaca gtggcctgga aggcagatag cagcccgtc | 660 |
| aaggcgggag tggagaccac cacaccctcc aaacaaagca caacaagta cgcggccagc | 720 |
| agctatctga gcctgacgcc tgagcagtgg aagtcccaca aagctacag ctgccaggtc | 780 |
| acgcatgaag ggagcaccgt ggagaagaca gtggcccta cagaatgttc atag | 834 |

<210> SEQ ID NO 85
<211> LENGTH: 834
<212> TYPE: DNA
<213> ORGANISM: Artificial Sequence
<220> FEATURE:
<223> OTHER INFORMATION: Synthetic

<400> SEQUENCE: 85

| | |
|---|---|
| atgatgtcct ttgtctctct gctcctggtt ggcatcctat tccatgccac ccaggcccag | 60 |
| ccagtgctga ctcagccccc ctcactgtcc gtgtccccag acagacagc cagcatcacc | 120 |
| tgctctggag agaaattggg ggataaatat gcttactggt atcagcagaa gccaggccag | 180 |
| tcccctgtgt tggtcatgta tcaagataaa cagcggccct cagggatccc tgagcgattc | 240 |
| tctggctcca actctgggaa cagccactct gaccatca gcgggaccca ggctatggat | 300 |
| gaggctgact attactgtca ggcgtgggac agcagcactg cggtattcgg cggagggacc | 360 |
| aagctgaccg tcctaggcca gcctaaggcg gcgccctcgg tcaccctgtt cccgccctcc | 420 |
| tctgaggagc ttcaagccaa caaggccaca ctggtgtgtc tcataagtga cttctacccg | 480 |
| ggagccgtga cagtggcctg gaaggcagat agcagcccg tcaaggcggg agtggagacc | 540 |
| accacaccct ccaaacaaag caacaacaag tacgcggcca gcagctatct gagcctgacg | 600 |
| cctgagcagt ggaagtccca cagaagctac agctgccagg tcacgcatga agggagcacc | 660 |

```
gtggagaaga cagtggcccc tacagaatgt tcagccgctg gtggtagtgg tttggaagtg    720
acgtgtgagc ccggaacgac attcaaagac aagtgcaata cttgtcggtg cggttcagat    780
gggaaatcgg cggtctgcac aaagctctgg tgtaaccagg gtagtggtgc ttag          834
```

METHODS OF INHIBITING MASP-2 FOR THE TREATMENT AND/OR PREVENTION OF CORONAVIRUS-INDUCED ACUTE RESPIRATORY DISTRESS SYNDROME

CROSS-REFERENCE TO RELATED APPLICATIONS

This application claims the benefit of U.S. Provisional Application No. 62/986,566, filed Mar. 6, 2020, and claims the benefit of U.S. Provisional Application No. 63/008,540, filed Apr. 10, 2020, and claims the benefit of U.S. Provisional Application No. 63/015,299, filed Apr. 24, 2020, and claims the benefit of U.S. Provisional Application No. 63/054,298, filed Jul. 21, 2020, and claims the benefit of U.S. Provisional Application No. 63/062,843, filed Aug. 7, 2020, and claims the benefit of U.S. Provisional Application No. 63/104,229, filed Oct. 22, 2020, and claims the benefit of U.S. Provisional Application No. 63/105,637, filed Oct. 26, 2020, and claims the benefit of U.S. Provisional Application No. 63/140,591, filed Jan. 22, 2021, all of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0312_US_Sequence_Listing_20210302_ST25.txt. The text file is 136 KB; was created on Mar. 2, 2021; and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York), in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and thus requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

The lectin pathway is widely thought to have a major role in host defense against infection in the naive host. Strong evidence for the involvement of MBL in host defense comes from analysis of patients with decreased serum levels of functional MBL (Kilpatrick, *Biochim. Biophys. Acta* 1572: 401-413, (2002)). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites, and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

In addition to its essential role in immune defense, the complement system contributes to tissue damage in many clinical conditions. Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard et al., *Am. J. Pathol.* 156:1549-1556, (2000)). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan et al., *Circulation* 104:1413-1418, (2001)). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard et al., *Am. J. Pathol.* 159:1045-1054, (2001)). Other studies have implicated the classical and alternative pathways in the pathogenesis of ischemia/reperfusion injury and the role of the lectin pathway in this disease remains controversial (Riedermann, N.C., et al., *Am. J. Pathol.* 162:363-367, 2003).

Fibrosis is the formation of excessive connective tissue in an organ or tissue, commonly in response to damage or injury. A hallmark of fibrosis is the production of excessive extracellular matrix following local trauma. The normal physiological response to injury results in the deposition of connective tissue, but this initially beneficial reparative process may persist and become pathological, altering the architecture and function of the tissue. At the cellular level, epithelial cells and fibroblasts proliferate and differentiate into myofibroblasts, resulting in matrix contraction, increased rigidity, microvascular compression, and hypoxia. An influx of inflammatory cells, including macrophages and lymphocytes, results in cytokine release and amplifies the deposition of collagen, fibronectin and other molecular markers of fibrosis. Conventional therapeutic approaches have largely been targeted towards the inflammatory process of fibrosis, using corticosteroids and immunosuppressive drugs. Unfortunately, these anti-inflammatory agents have had little to no clinical effect. Currently there are no effective treatments or therapeutics for fibrosis, but both animal studies and anecdotal human reports suggest that fibrotic tissue damage may be reversed (Tampe and Zeisberg, *Nat Rev Nephrol*, Vol 10:226-237, 2014).

The kidney has a limited capacity to recover from injury. Various renal pathologies result in local inflammation that causes scarring and fibrosis of renal tissue. The perpetuation of inflammatory stimuli drives tubulointerstitial inflammation and fibrosis and progressive renal functional impairment in chronic kidney disease. Its progression to end-stage renal failure is associated with significant morbidity and mortality. Since tubulointerstitial fibrosis is the common end point of multiple renal pathologies, it represents a key target for therapies aimed at preventing renal failure. Risk factors (e.g., proteinuria) independent of the primary renal disease contribute to the development of renal fibrosis and loss of renal excretory function by driving local inflammation, which in turn enhances disease progression.

In view of the role of fibrosis in many diseases and disorders, such as, for example, tubulointerstitial fibrosis leading to chronic kidney disease, there is a pressing need to develop therapeutically effective agents for treating diseases and conditions caused or exacerbated by fibrosis. In further view of the paucity of new and existing treatments targeting inflammatory pro-fibrotic pathways in renal disease, there is a need to develop therapeutically effective agents to treat, inhibit, prevent and/or reverse renal fibrosis and thereby prevent progressive chronic kidney disease.

Coronavirus disease 2019 (COVID-19) is an infectious disease caused by severe acute respiratory syndrome coronavirus 2 (SARS coronavirus 2 or SARS-CoV-2), a virus that is closely related to the SARS virus (World Health Organization, 2/11/2020, Novel Coronavirus Situation Report 22). Those affected by COVID-19 may develop a fever, dry cough, fatigue and shortness of breath. Cases can progress to respiratory dysfunction, including pneumonia, severe acute respiratory syndrome, and death in the most vulnerable (see e.g., Hui D. S. et al., *Int J Infect Dis* 91:264-266, Jan. 14, 2020). There is no vaccine or specific antiviral treatment, with management involving treatment of symptoms and supportive care.

Influenza (also known as "the flu") is an infectious disease caused by an RNA influenza virus. Symptoms of influenza virus infection can be mild to severe, and include high fever, runny nose, sore throat, muscle and joint pain, headache, coughing and feeling tired. These symptoms typically begin two days after exposure to the virus and most last less than a week, however, the cough may last for more than two weeks. (see "Influenza Seasonal, World Health Organization 6 Nov. 2018). Complications of influenza may include viral pneumonia, acute respiratory distress syndrome (ARDS) secondary bacterial pneumonia, sinus infections and worsening of previous health problems such as asthma or heart failure (see "Key Facts About Influenza (Flu)" Centers for Disease Control and Prevention (CDC), Sep. 9, 2014). Influenza's effects are much more severe and last longer than those of the common cold. Most people will recover completely in about one to two weeks, but others will develop life-threatening complications such as pneumonia. Thus, influenza can be deadly, especially for the weak, young and old, those with compromised immune systems, or the chronically ill. See Hilleman M R, *Vaccine*. 20 (25-26): 3068-87 (2002).

Three of the four types of influenza viruses affect humans: Type A, Type B, and Type C. (see "*Types of Influenza Viruses Seasonal Influenza (Flu)*, *Centers for Disease Control and Prevention (CDC)*. 27 Sep. 2017). Type D has not been known to infect humans but is believed to have the potential to do so (see "Novel Influenza D virus: Epidemiology, pathology, evolution and biological characteristics," *Virulence*. 8 (8): 1580-91, 2017). The serotypes of influenza A that have been confirmed in humans are: H1N1 (caused the "Spanish Flu" in 1918 and "Swine Flu" in 2009); H2N2 (caused the "Asian Flu" in 1957), H3N2 (caused the "Hong Kong Flu" in 1968), H5N1 (caused the "Bird Flu in 2004), H7N7, H1N2, H9N2, H7N2, H7N3, H10N7, H7N9 and H6N1. See World Health Organization (30 Jun. 2006). "Epidemiology of WHO-confirmed human cases of avian influenza A (H5N1) infection, *Wkly Epidemiol Rec*. 81 (26): 249-57.; Fouchier R A, et al. (2004) *PNAS* 101 (5): 1356-61; *Wkly Epidemiol Rec*. 83 (46): 415-20, Asian Lineage Avian Influenza A(F7N9) Virus, Centers for Disease Control and Prevention (CDC), 7 Dec. 2018).

Common symptoms of the influenza virus (also known as the flu) such as fever, headaches and fatigue are the result of large amounts of proinflammatory cytokines and chemokines (such as interferon or tumor necrosis factor) produced from influenza-infected cells. See Eccles R. et al., Lancet Infect Dis 5(11):718-25 (2005); Schmitz N, et al., *Journal of Virology*. 79 (10): 6441-8 (2005). This massive immune response may result in a life-threatening cytokine storm. This effect has been proposed to be the cause of the unusual lethality of both the 115N1 avian influenza, and the 1918 pandemic strain. Cheung C Y, et al., *Lancet*. 360 (9348): 1831-37 (2002); Kash J C, et al., *Nature*. 443 (7111): 578-81 (2006). Influenza also appears to trigger programmed cell death (apoptosis) see Spiro S G, et al., Clinical Respiratory Medicine, Elsevier Health Sciences. p. 311 (2012).

Thus, there is an urgent need to develop therapeutically effective agents to treat, inhibit and/or prevent coronavirus-induced pneumonia and acute respiratory distress syndrome and influenza virus induced pneumonia and acute respiratory distress syndrome.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a method for treating, inhibiting, alleviating, or preventing acute respiratory distress syndrome in a mammalian subject infected with coronavirus, comprising administering to the subject an amount of a MASP-2 inhibitory agent effective to inhibit MASP-2-dependent complement activation. In some embodiments, the subject is suffering from one or more respiratory symptoms and the method comprises administering to the subject an amount of a MASP-2 inhibitory agent effective to improve at least one respiratory symptom (i.e., improve respiratory function). In one embodiment, the method comprises administering the composition to a subject infected with SARS-CoV-2. In one embodiment, the method comprises administering the composition to a subject suffering from COVID-19, such as a subject suffering from acute-respiratory distress syndrome (ARDS) associated with COVID-19. In one embodiment, the method comprises administering the composition to a subject infected with SARS-CoV. In one embodiment, the method comprises administering the composition to a subject infected with MERS-CoV. In one embodiment, the subject is identified as having coronavirus (i.e., SARS-CoV-2, SARS-CoV or MERS-CoV) prior to administration of the MASP-2 inhibitory agent. In one embodiment, the MASP-2 inhibitory agent is a MASP-2 antibody or antigen-binding fragment thereof. In one embodiment, the MASP-2 inhibitory agent is a MASP-2 monoclonal antibody, or fragment thereof that specifically binds to a portion of SEQ ID NO:6. In one embodiment, the MASP-2 inhibitory agent selectively inhibits lectin pathway complement activation without substantially inhibiting C1q-dependent complement activation. In one embodiment, the MASP-2 inhibitory agent is a small molecule, such as a synthetic or semi-synthetic small molecule that inhibits MASP-2-dependent complement activation. In one embodiment, the MASP-2 inhibitory agent is an expression inhibitor of MASP-2. In one embodiment, the MASP-2 inhibitory antibody is a monoclonal antibody, or fragment thereof that specifically binds to human MASP-2. In one embodiment, the MASP-2 inhibitory antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum (i.e., normal human serum) with an $IC_{50}$ of 30 nM or less. In one embodiment, the MASP-2 inhibitory antibody or antigen-binding fragment thereof, comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69. In one embodiment, the MASP-2 inhibitory antibody or antigen-binding fragment thereof comprises a heavy chain variable region comprising the amino acid sequence set forth as SEQ ID NO:67 and a light chain variable region comprising the amino acid sequence set forth as SEQ ID NO:69.

In another aspect, the present invention provides a method for treating, inhibiting, alleviating, or preventing acute respiratory distress syndrome in a mammalian subject infected with influenza virus, comprising administering to the subject an amount of a MASP-2 inhibitory agent effective to inhibit MASP-2-dependent complement activation. In some embodiments, the subject is suffering from one or more respiratory symptoms and the method comprises administering to the subject an amount of a MASP-2 inhibitory agent effective to improve at least one respiratory symptom (i.e., improve respiratory function). In one embodiment, the subject is infected with an influenza virus selected from the group consisting of influenza virus Type A, influenza virus Type B and influenza virus Type C. In one embodiment, the subject is infected with influenza Type A. In one embodiment, the subject is infected with an influenza Type A serotype selected from the group consisting of H1N1, H2N2, H3N2, H5N1, H7N7, H1N2, H9N2, H7N2, H7N3, H10N7, H7N9 and H6N1. In one embodiment, the subject is identified as having influenza virus prior to administration of the MASP-2 inhibitory agent. In one embodiment, the MASP-2 inhibitory agent is a MASP-2 antibody or antigen-binding fragment thereof. In one embodiment, the MASP-2 inhibitory agent is a MASP-2 monoclonal antibody, or fragment thereof that specifically binds to a portion of SEQ ID NO:6. In one embodiment, the MASP-2 inhibitory agent selectively inhibits lectin pathway complement activation without substantially inhibiting C1q-dependent complement activation. In one embodiment, the MASP-2 inhibitory agent is a small molecule, such as a synthetic or semi-synthetic small molecule that inhibits MASP-2-dependent complement activation. In one embodiment, the MASP-2 inhibitory agent is an expression inhibitor of MASP-2. In one embodiment, the MASP-2 inhibitory antibody is a monoclonal antibody, or fragment thereof that specifically binds to human MASP-2. In one embodiment, the MASP-2 inhibitory antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum with an $IC_{50}$ of 30 nM or less. In one embodiment, the MASP-2 inhibitory antibody or antigen-binding fragment thereof, comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69. In one embodiment, the MASP-2 inhibitory antibody or antigen-binding fragment thereof comprises a heavy chain variable region comprising the amino acid sequence set forth as SEQ ID NO:67 and a light chain variable region comprising the amino acid sequence set forth as SEQ ID NO:69.

In another aspect, the invention provides a method for treating, inhibiting, alleviating or preventing fibrosis in a mammalian subject suffering, or at risk of developing a disease or disorder caused or exacerbated by fibrosis and/or inflammation, such as coronavirus infection, comprising administering to the subject an amount of a MASP-2 inhibitory agent effective to inhibit fibrosis. In one embodiment, the MASP-2 inhibitory agent is a MASP-2 antibody or fragment thereof. In one embodiment, the MASP-2 inhibitory agent is a MASP-2 monoclonal antibody, or fragment thereof that specifically binds to a portion of SEQ ID NO:6. In one embodiment, the MASP-2 inhibitory agent selectively inhibits lectin pathway complement activation without substantially inhibiting C1q-dependent complement activation.

In another aspect, the invention provides a method for treating, inhibiting, alleviating, or preventing acute respiratory distress syndrome, pneumonia, or some other pulmonary or other manifestation of coronavirus infection, such as thrombosis, in a mammalian subject infected with coronavirus, comprising administering to the subject an amount of a MASP-2 inhibitory agent effective to inhibit MASP-2- dependent complement activation. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound.

In another aspect, the invention provides a method for treating a human subject suffering from COVID-19 induced acute respiratory distress syndrome (ARDS) or pneumonia, comprising administering to the subject an amount of a MASP-2 inhibitory agent effective to inhibit MASP-2-dependent complement activation. In one embodiment, the subject is on a mechanical ventilator (an invasive mechanical ventilator or a non-invasive mechanical ventilator) prior to treatment and the MASP-2 inhibitory agent is administered at a dosage and for a time period sufficient to discontinue the need for mechanical ventilation. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound.

In another aspect, the invention provides a method for treating, preventing or reducing the severity or coagulation or thrombosis in a human subject infected with SARS-CoV-2 comprising administering to the subject an amount of a MASP-2 inhibitory agent effective to treat, prevent or reduce the severity of coagulation or thrombosis in said subject. In one embodiment, the subject has a D-Dimer level higher than the standard range prior to treatment and the MASP-2 inhibitory agent is administered in an amount and for a time sufficient to reduce the level of D-Dimer in said subject into the normal range of a healthy subject. In one embodiment, the MASP-2 inhibitory agent provides anticoagulation and/or antithrombosis effects without affecting hemostatis. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound.

In another aspect, the invention provides a method for treating, ameliorating, preventing or reducing the risk of developing one or more COVID-19-related long-term sequelae in a human subject that is currently infected with SARS-CoV-2 or has been infected with SARS-CoV-2, comprising administering to the subject an amount of a MASP-2 inhibitory agent effective to inhibit MASP-2-dependent complement activation. In one embodiment, the subject is suffering from COVID-19-induced pneumonia or ARDS and the MASP-2 inhibitory agent is administered in an amount effective to improve respiratory function. In one embodiment, the subject has recovered from COVID-19 induced pneumonia or ARDS and the MASP-2 inhibitory agent is administered in an amount to treat or ameliorate one or more long-term sequelae. In one embodiment, the subject is suffering from COVID-19-induced coagulation or thrombosis and the MASP-2 inhibitory agent is administered to the subject in an amount effective to treat, prevent or reduce the severity of coagulation or thrombosis in said subject. In one embodiment, the subject has recovered from COVID-19 induced coagulation or thrombosis and the MASP-2 inhibitory agent is administered in an amount to treat or ameliorate one or more long-term sequelae. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound.

In another aspect, the invention provides a method for treating, inhibiting, alleviating or preventing acute respiratory distress syndrome, pneumonia or some other pulmonary or other manifestation of influenza virus infection, in a mammalian subject infected with influenza virus, comprising administering to the subject an amount of a MASP-2 inhibitory agent effective to inhibit MASP-2-dependent complement activation. In one embodiment, the influenza virus is influenza virus A, influenza virus B or influenza virus C. In one embodiment, the influenza virus A is selected from the group consisting of H1N1, H2N2, H3N2, H15N1, H7N7, H1N2, H9N2, H7N2, H7N3, H10N7, H7N9 and H6N1. In one embodiment, the MASP-2 inhibitory agent is a MASP-2 monoclonal antibody, or fragment thereof that specifically binds to a portion of SEQ ID NO:6. In one embodiment, the MASP-2 inhibitory agent is a small molecule MASP-2 inhibitory compound.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

COVID-19 patients at baseline prior to treatment (day 0) and at different time points after treatment with narsoplimab, as described in Example 21.

Figure 46:
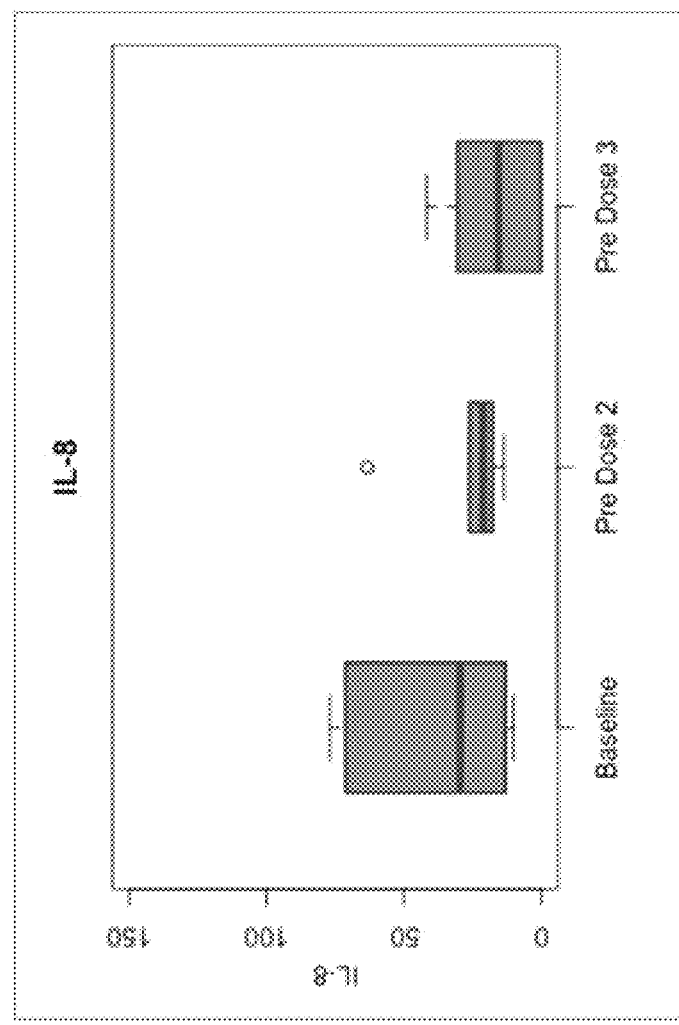

FIG. 46 graphically illustrates the serum level of Interleukin 8 (IL-8) (median; interquartile range (IQR)) in 6 COVID-19 patients at baseline prior to treatment (day 0) and at different time points after treatment with narsoplimab, as described in Example 21.

Figures 47A, 47B:
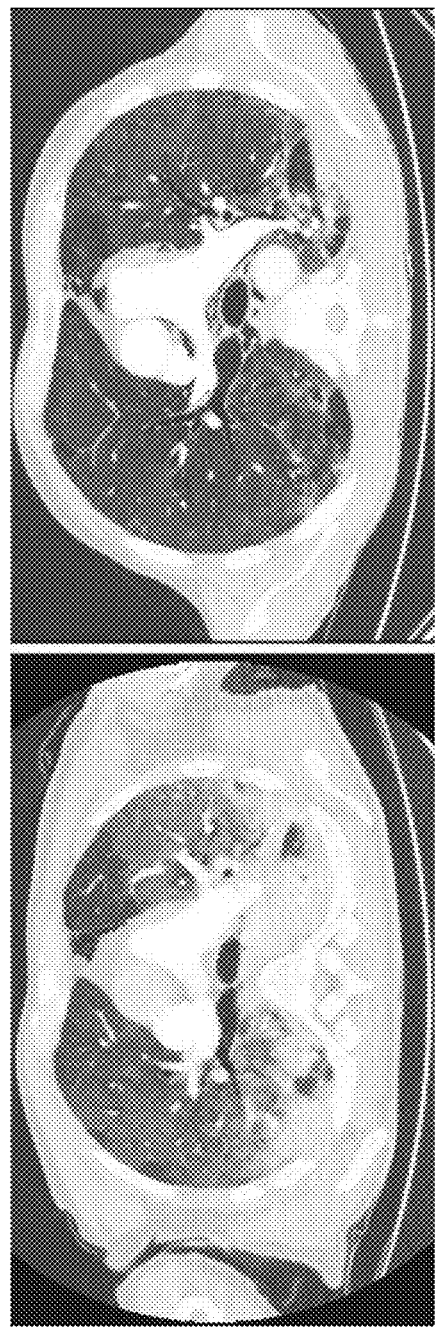

FIG. 47A shows the CT-scan of patient #4 on Day 5 since enrollment (i.e., after treatment with narsoplimab) wherein the patient is observed to have severe interstitial pneumonia with diffuse ground-glass opacity involving both the peripheral and central regions, consolidation in lower lobes, especially in the left lung, and massive bilateral pulmonary embolism with filling defects in interlobar and segmental arteries (not shown), as described in Example 21.

FIG. 47B shows the CT-scan of patient #4 on Day 16 since enrollment (i.e., after treatment with narsoplimab) in which the ground-glass opacity is significantly reduced and almost complete resolution of parenchymal consolidation, as described in Example 21.

Figure 48:
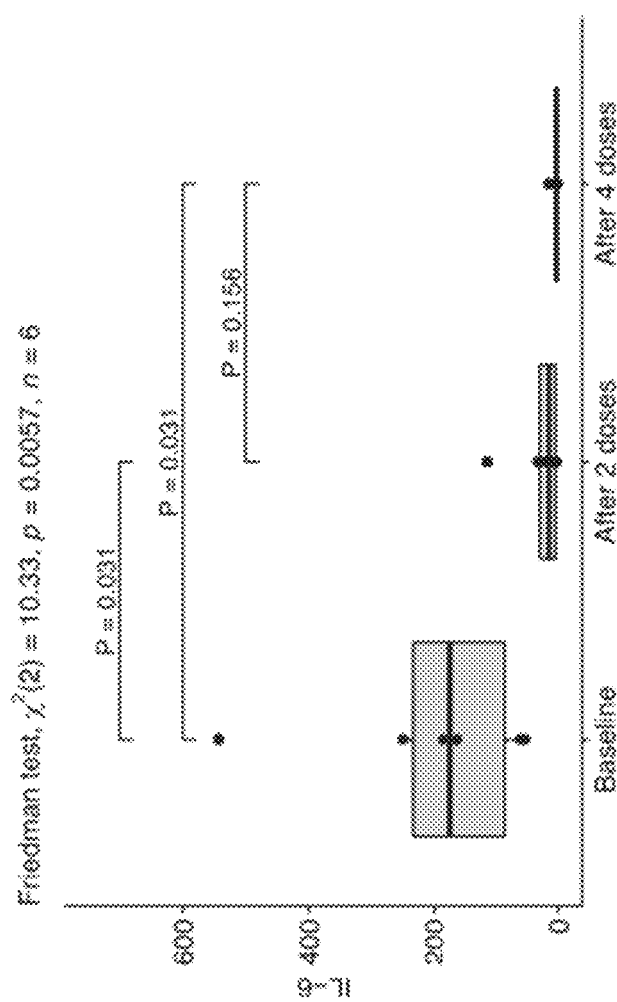

FIG. 48 graphically illustrates the serum levels of IL-6 (pg/mL) at baseline and at different time points after narsoplimab treatment (after 2 doses, after four doses) in the COVID-19 patients treated with narsoplimab, wherein boxes represent values from the first to the third quartile, horizontal line shows the median value, and dots show all patient values, as described in Example 21.

Figure 49:
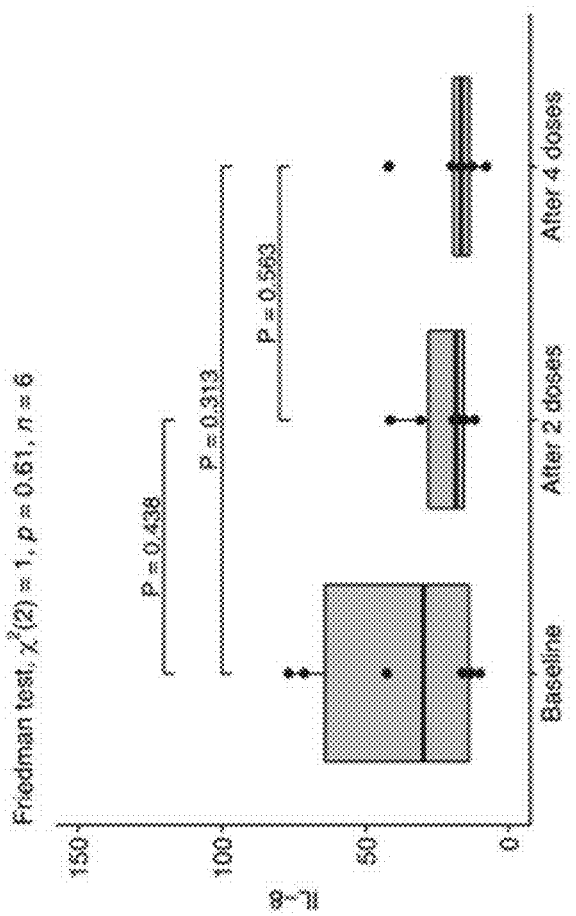

FIG. 49 graphically illustrates the serum levels of IL-8 (pg/mL) at baseline and at different time points after narsoplimab treatment (after two doses, after 4 doses) in the COVID-19 patients treated with narsoplimab, wherein boxes represent values from the first to the third quartile, horizontal line shows the median value, and dots show all patient values, as described in Example 21.

Figure 50:
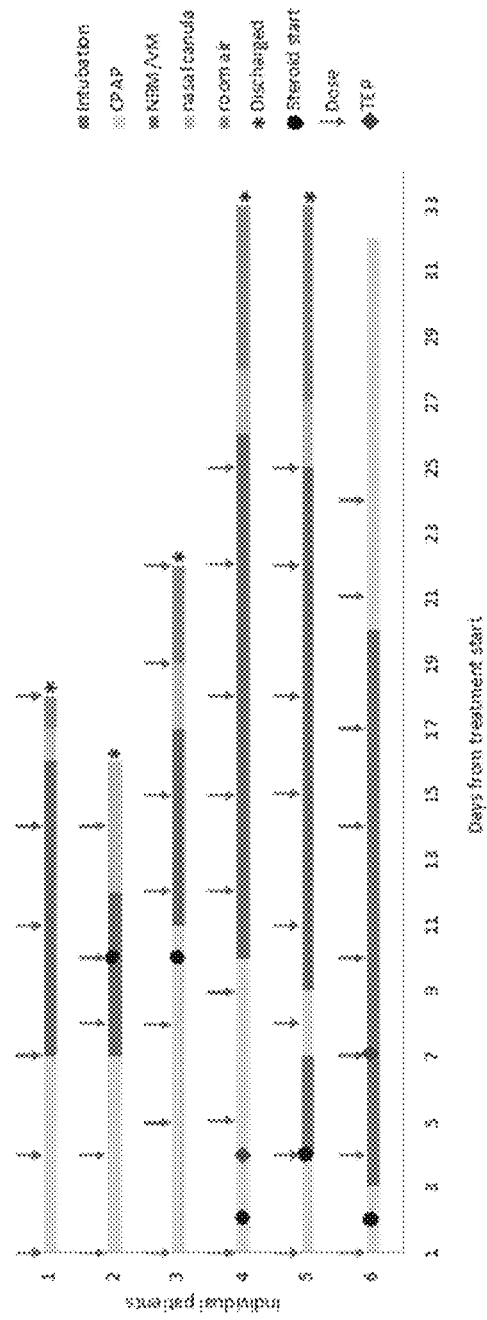

FIG. 50 graphically illustrates the clinical outcome of six COVID-19 patients treated with narsoplimab, as described in Example 21.

Figure 51A:
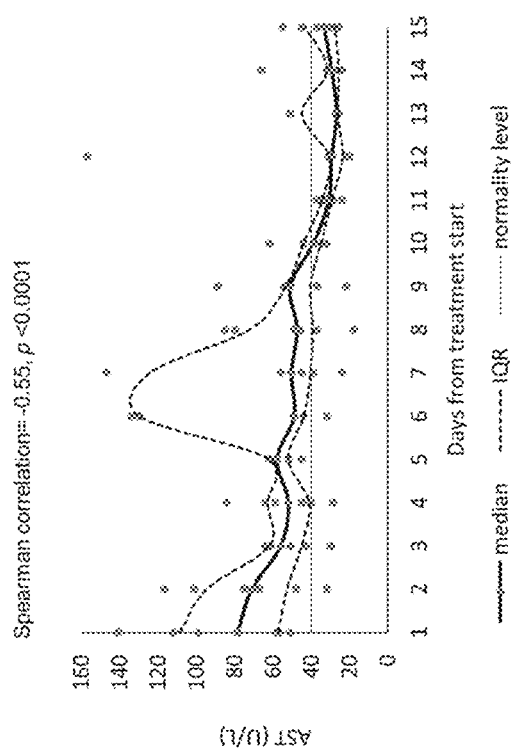

FIG. 51A graphically illustrates the serum levels of Aspartate aminotransferase (AST) (Units/Liter, U/L) values before and after narsoplimab treatment. Black lines represent median and interquartile range (IQR). The red line represents normality level and dots show all patient values, as described in Example 21.

Figure 51B:
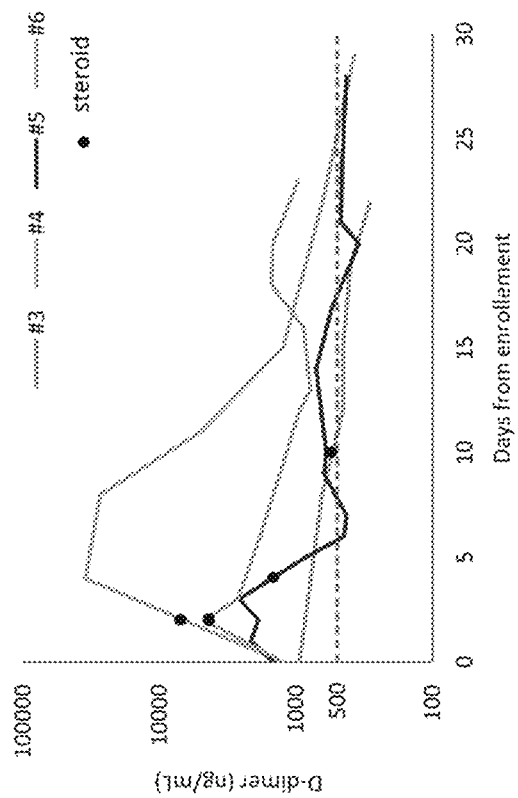

FIG. 51B graphically illustrates the serum levels of D-Dimer values (ng/ml), in the four COVID-19 patients in whom base line values were available before treatment with narsoplimab started. Black circles indicate when steroid treatment was initiated. The red line represents normality level, as described in Example 21.

Figure 52A:
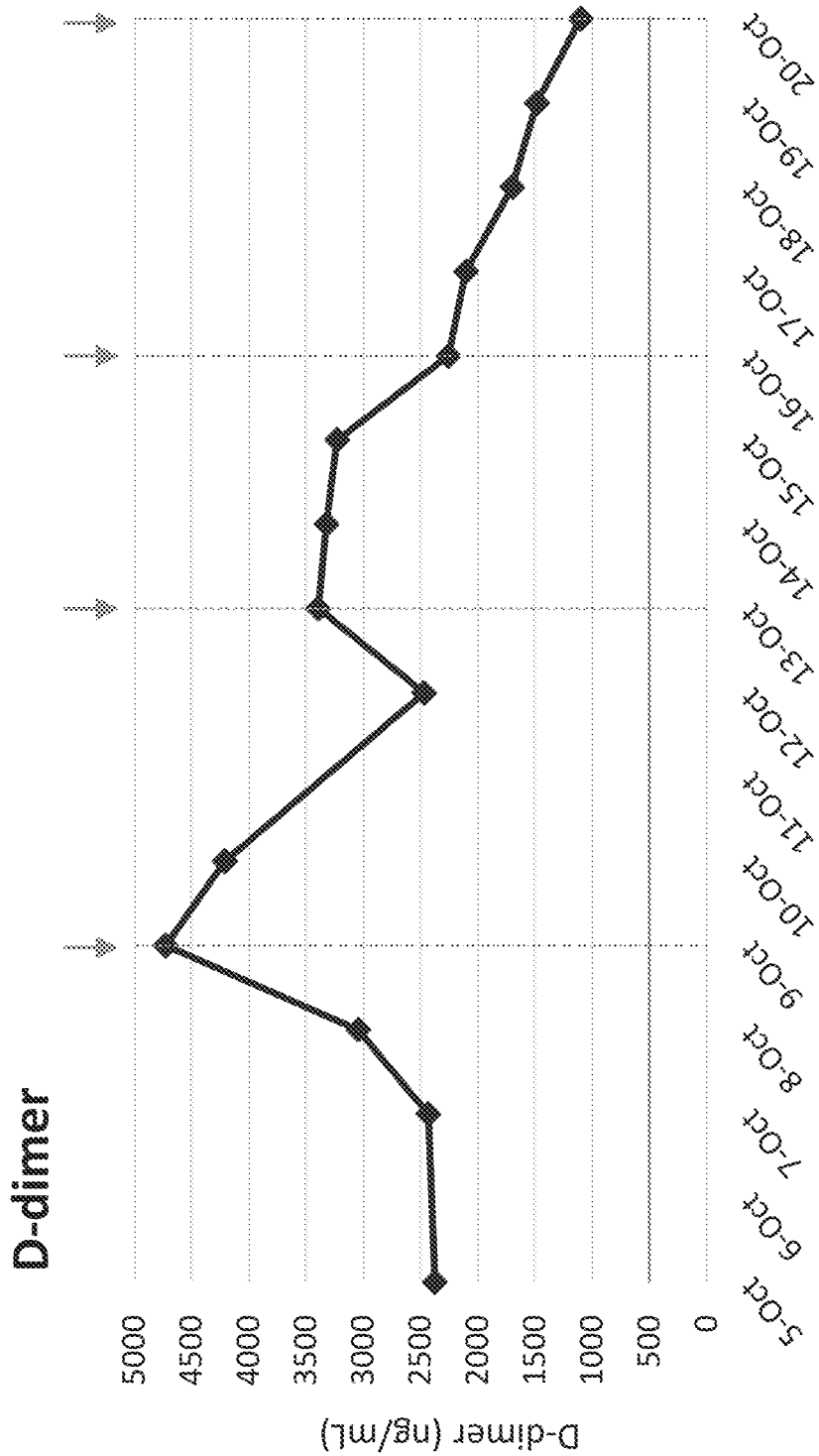

FIG. 52A graphically illustrates the serum level of D-Dimer values (ng/ml), in the seventh COVID-19 patient treated with narsoplimab (patient #7) at baseline prior to treatment (day 0) and at different time points after treatment with narsoplimab, wherein dosing with narsoplimab is indicated by the vertical arrows and wherein the horizontal line represents normality level, as described in Example 22.

Figure 52B:
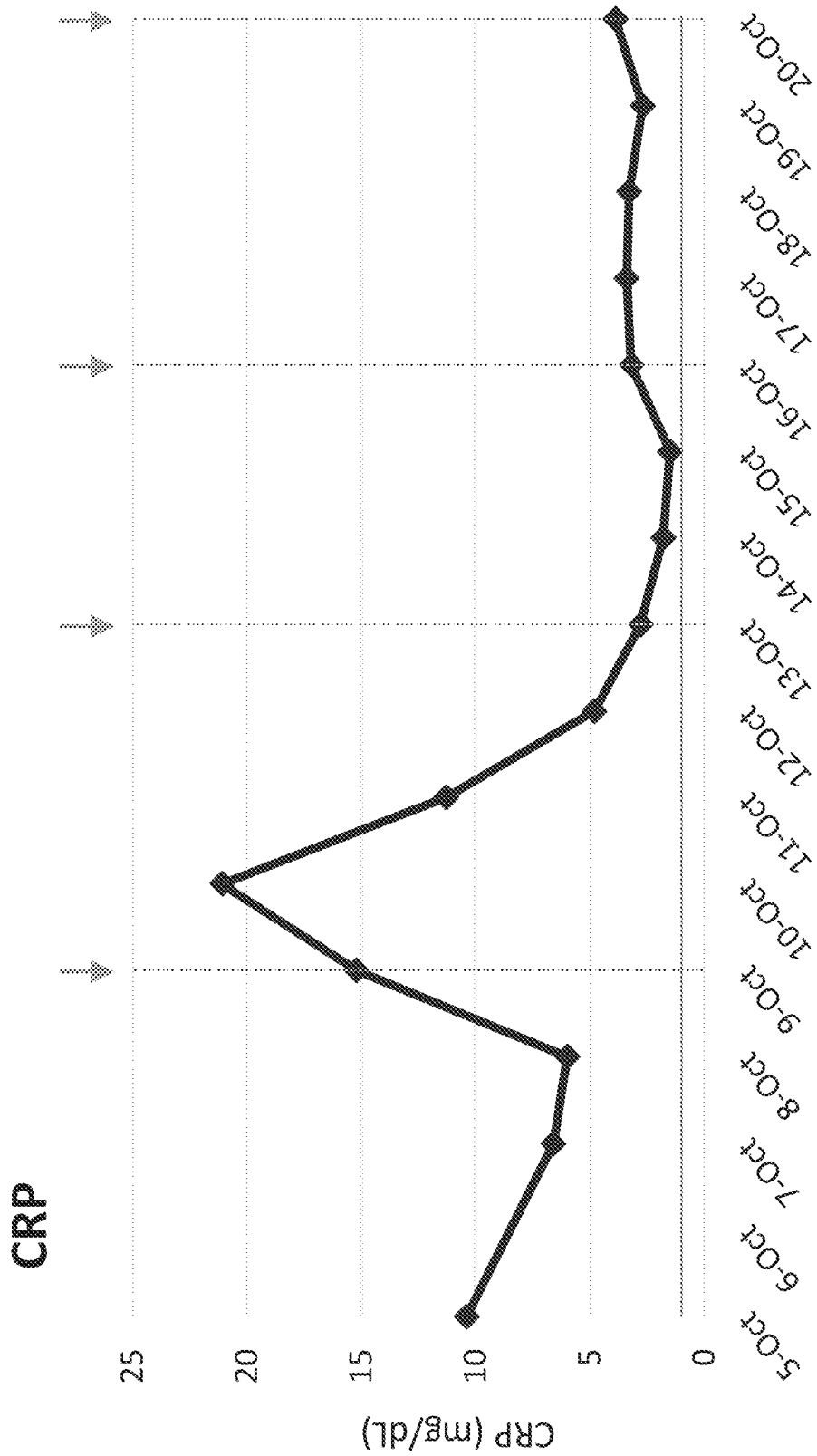

FIG. 52B graphically illustrates the serum level of C Reactive Protein (CRP) in patient #7 with COVID-19 at baseline prior to treatment (day 0) and at different time points after treatment with narsoplimab, wherein dosing with narsoplimab is indicated by the vertical arrows and wherein the horizontal line represents normality level, as described in Example 22.

Figure 52C:
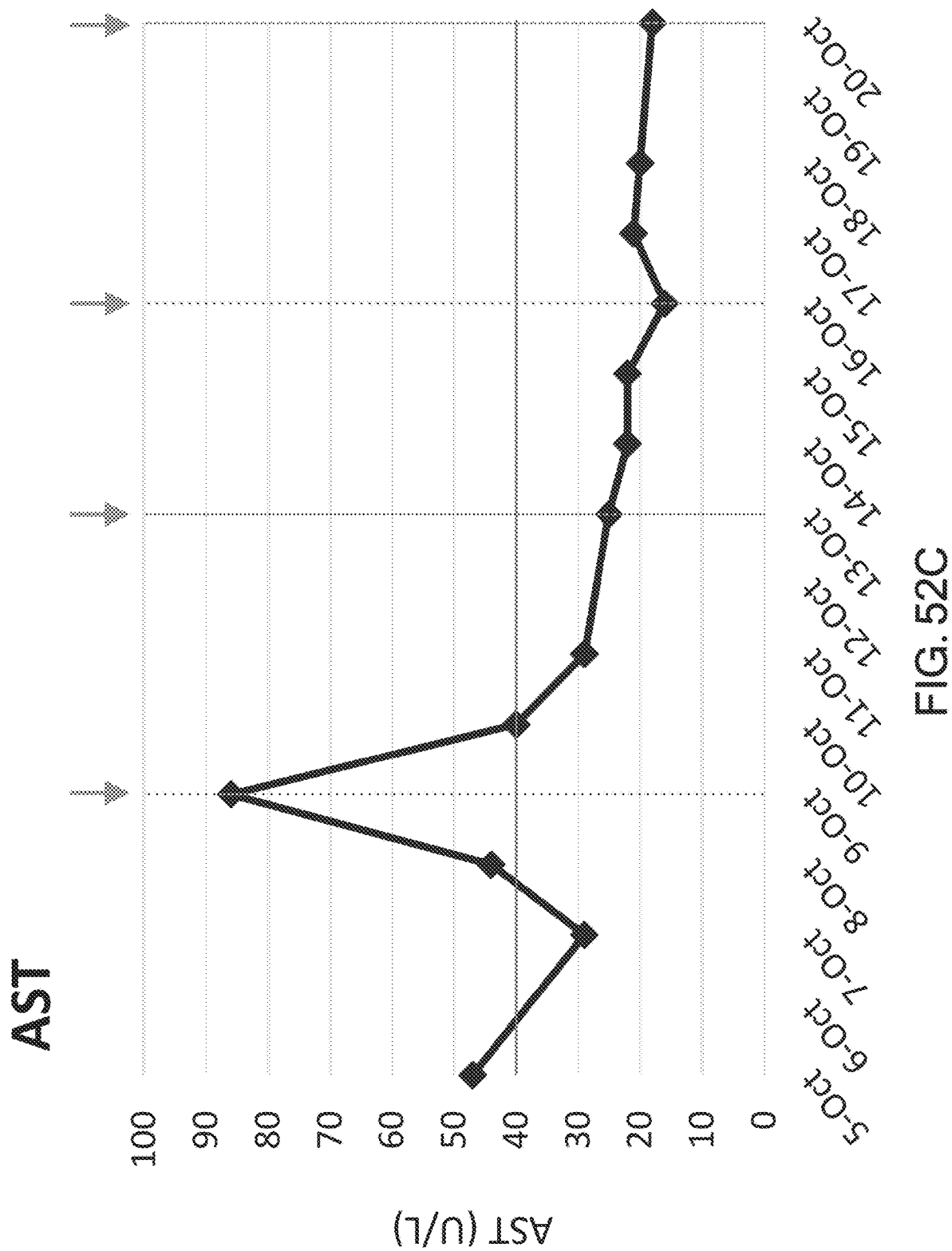

FIG. 52C graphically illustrates the serum level of Aspartate aminotransferase (AST) (Units/Liter, U/L) in patient #7 with COVID-19 at baseline prior to treatment (day 0) and at different time points after narsoplimab treatment, wherein dosing with narsoplimab is indicated by the vertical arrows and wherein the horizonal line represents normality level, as described in Example 22.

Figure 52D:
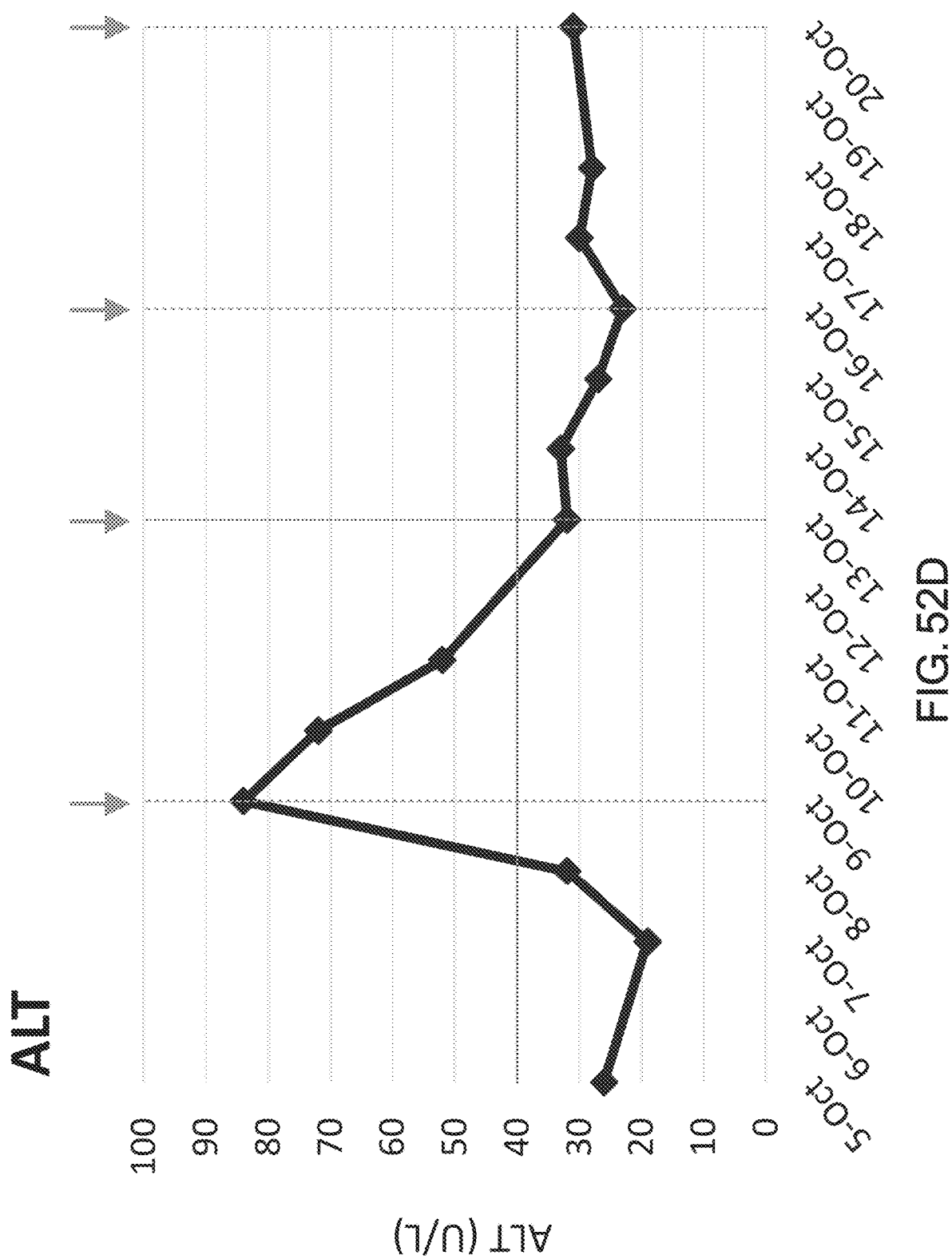

FIG. 52D graphically illustrates the serum level of Alanine transaminase (ALT) (Units/Liter, U/L) in patient #7 with COVID-19 at baseline prior to treatment (day 0) and at different time points after narsoplimab treatment, wherein dosing with narsoplimab is indicated by the vertical arrows and wherein the horizontal line represents normality level, as described in Example 22.

Figure 52E:
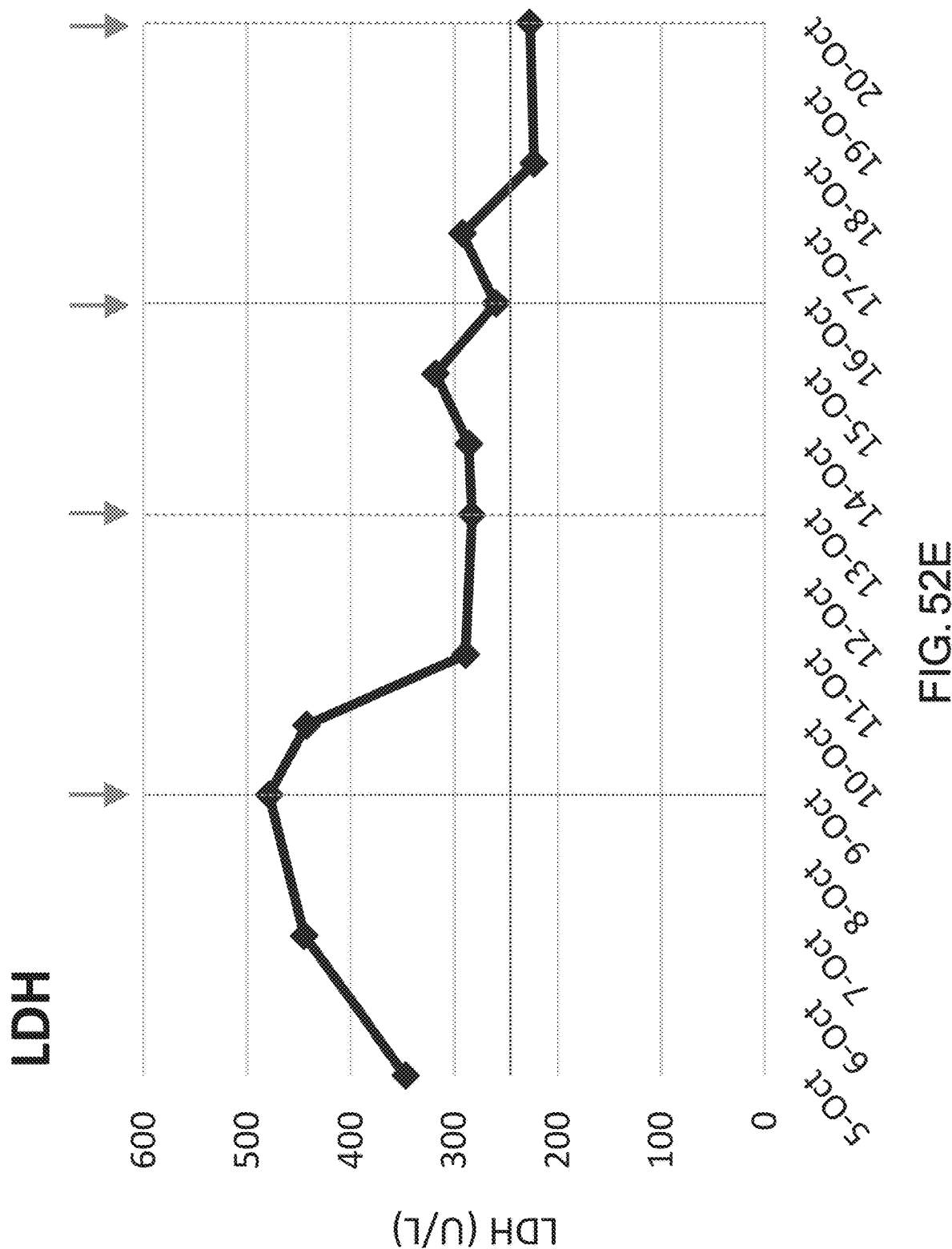

FIG. 52E graphically illustrates the serum level of Lactate Dehydrogenase (LDH) in patient #7 with COVID-19 at baseline prior to treatment (day 0) and at different time points after treatment with narsoplimab, wherein dosing with narsoplimab is indicated by the vertical arrows and wherein the horizontal line represents normality level, as described in Example 22.

Figure 53:
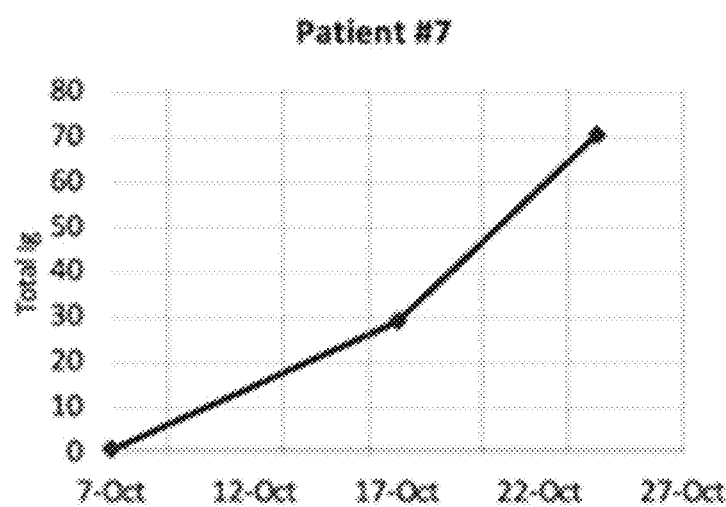

FIG. 53 graphically illustrates the titer of anti-SARS-CoV-2 antibodies in patient #7 over time, indicating that treatment with narsoplimab does not impede effector function of the adaptive immune response, as described in Example 22.

Figure 54:
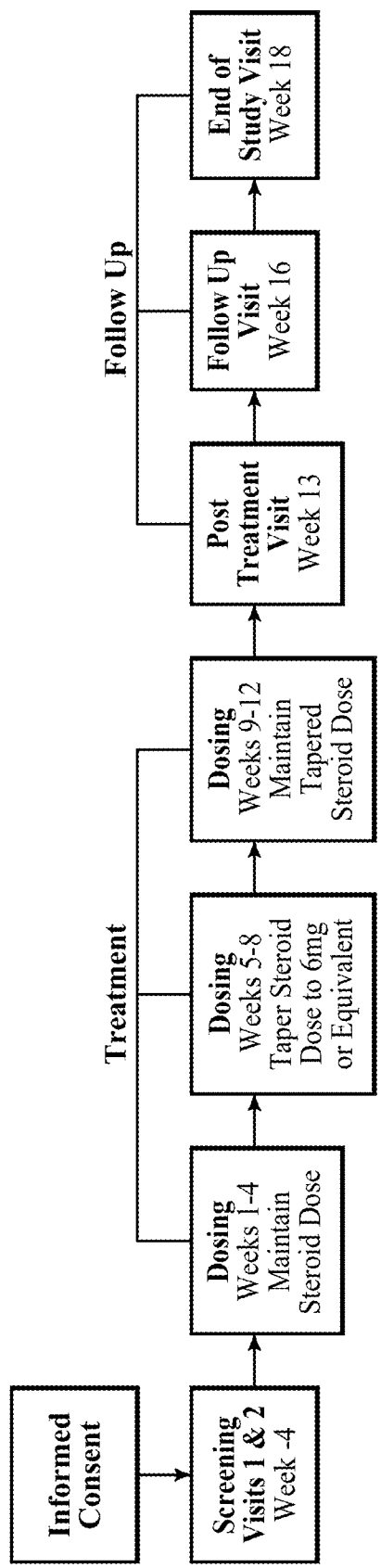

FIG. 54 is a schematic diagram showing the study plan for an ongoing Phase 2 clinical trial to evaluate the safety and clinical efficacy of a fully human monoclonal MASP-2 inhibitory antibody in adults with steroid-dependent immunoglobulin A nephropathy (IgAN) and in adults with steroid-dependent membranous nephropathy (MN), as described in Example 19.

DESCRIPTION OF THE SEQUENCE LISTING

SEQ ID NO: 1 human MAp19 cDNA

SEQ ID NO: 2 human MAp19 protein (with leader)

SEQ ID NO: 3 human MAp19 protein (mature)

SEQ ID NO: 4 human MASP-2 cDNA

SEQ ID NO: 5 human MASP-2 protein (with leader)

SEQ ID NO: 6 human MASP-2 protein (mature)

SEQ ID NO: 7 human MASP-2 gDNA (exons 1-6)

ANTIGENS: (IN REFERENCE TO THE MASP-2 MATURE PROTEIN)

SEQ ID NO: 8 CUBI sequence (aa 1-121)

SEQ ID NO: 9 CUBEGF sequence (aa 1-166)

SEQ ID NO: 10 CUBEGFCUBII (aa 1-293)

SEQ ID NO: 11 EGF region (aa 122-166)

SEQ ID NO: 12 serine protease domain (aa 429-671)

SEQ ID NO: 13 serine protease domain inactive (aa 610-625 with Ser618 to Ala mutation)

SEQ ID NO: 14
TPLGPKWPEPVFGRL (CUBI peptide)

SEQ ID NO: 15
TAPPGYRLRLYFTHFDLELSHLCEYDFVKLSSGAKVLATLCGQ (CUBI peptide)

SEQ ID NO: 16
TFRSDYSN (MBL binding region core)

-continued

SEQ ID NO: 17
FYSLGSSLDITFRSDYSNEKPFTGF (MBL binding region)

SEQ ID NO: 18
IDECQVAPG (EGF PEPTIDE)

SEQ ID NO: 19
ANMLCAGLESGGKDSCRGDSGGALV (serine protease binding core)

PEPTIDE INHIBITORS:
SEQ ID NO: 20 MBL full length cDNA

SEQ ID NO: 21 MBL full length protein

SEQ ID NO: 22
OGK-X-GP (consensus binding)

SEQ ID NO: 23
OGKLG

SEQ ID NO: 24
GLR GLQ GPO GKL GPO G

SEQ ID NO: 25
GPO GPO GLR GLQ GPO GKL GPO GPO GPO

SEQ ID NO: 26
GKDGRDGTKGEKGEPGQGLRGLQGPOGKLGPOG

SEQ ID NO: 27
GAOGSOGEKGAOGPQGPOGPOGKMGPKGEOGDO (human h-ficolin)

SEQ ID NO: 28
GCOGLOGAOGDKGEAGTNGKRGERGPOGPOGKAGPOGPNGA OGEO (human ficolin p35)

SEQ ID NO: 29
LQRALEILPNRVTIKANRPFLVFI (C4 cleavage site)

EXPRESSION INHIBITORS:
SEQ ID NO:30 cDNA of CUBI-EGF domain (nucleotides 22-680 of SEQ ID NO: 4)

SEQ ID NO:31
5'CGGGCACACCATGAGGCTGCTGACCCTCCTGGGC3'

Nucleotides 12-45 of SEQ ID NO: 4 including the MASP-2 translation start site (sense)

SEQ ID NO: 32
5'GACATTACCTTCCGCTCCGACTCCAACGAGAAG3'
Nucleotides 361-396 of SEQ ID NO:4 encoding a region comprising the MASP-2 MBL binding site (sense)

SEQ ID NO: 33
5'AGCAGCCCTGAATACCCACGGCCGTATCCCAAA3'
Nucleotides 610-642 of SEQ ID NO: 4 encoding a region comprising the CUBII domain

CLONING PRIMERS:

SEQ ID NO: 34
CGGGATCCATGAGGCTGCTGACCCTC (5' PCR for CUB)

SEQ ID NO: 35
GGAATTCCTAGGCTGCATA (3' PCR FOR CUB)

SEQ ID NO: 36
GGAATTCCTACAGGGCGCT (3' PCR FOR CUBIEGF)

SEQ ID NO: 37
GGAATTCCTAGTAGTGGAT (3' PCR FOR CUBIEGFCUBII)

SEQ ID NOS: 38-47 are cloning primers for humanized antibody

SEQ ID NO: 48 is 9 aa peptide

EXPRESSION VECTOR:
SEQ ID NO: 49 is the MASP-2 minigene insert

SEQ ID NO: 50 is the murine MASP-2 cDNA

SEQ ID NO: 51 is the murine MASP-2 protein (w/leader)

SEQ ID NO: 52 is the mature murine MASP-2 protein

SEQ ID NO: 53 the rat MASP-2 cDNA

SEQ ID NO: 54 is the rat MASP-2 protein (w/leader)

SEQ ID NO: 55 is the mature rat MASP-2 protein

SEQ ID NO: 56-59 are the oligonucleotides for site-directed mutagenesis of human MASP-2 used to generate human MASP-2A SEQ ID NO: 60-63 are the oligonucleotides for site-directed mutagenesis of murine MASP-2 used to generate murine MASP-2A SEQ ID NO: 64-65 are the oligonucleotides for site-directed mutagenesis of rat MASP-2 used to generate rat MASP-2A SEQ ID NO: 66 DNA encoding 17D20_dc35VH21N11VL (OMS646) heavy chain variable region (VH) (without signal peptide)

SEQ ID NO: 67 17D20_dc35VH21N11VL (OMS646) heavy chain variable region (VH) polypeptide SEQ ID NO: 68 17N16mc heavy chain variable region (VH) polypeptide SEQ ID NO: 69 17D20_dc35VH21N11VL (OMS646) light chain variable region (VL) polypeptide SEQ ID NO: 70 DNA encoding 17D20_dc35VH21N11VL (OMS646) light chain variable region (VL)

SEQ ID NO: 71 17N16_dc17N9 light chain variable region (VL) polypeptide

SEQ ID NO: 72: SGMI-2L(full-length)

SEQ ID NO: 73: SGMI-2M (medium truncated version)

SEQ ID NO: 74: SGMI-2S (short truncated version)

SEQ ID NO: 75: mature polypeptide comprising the VH-M2ab6-SGMI-2-N and the human IgG4 constant region with hinge mutation SEQ ID NO: 76: mature polypeptide comprising the VH-M2ab6-SGMI-2-C and the human IgG4 constant region with hinge mutation SEQ ID NO: 77: mature polypeptide comprising the VL-M2ab6-SGMI-2-N and the human Ig lambda constant region SEQ ID NO: 78: mature polypeptide comprising the VL-M2ab6-SGMI-2-C and the human Ig lambda constant region SEQ ID NO: 79: peptide linker (10aa)

SEQ ID NO: 80: peptide linker (6aa)

SEQ ID NO: 81: peptide linker (4aa)

-continued

SEQ ID NO: 82: polynucleotide encoding the
polypeptide comprising the VH-M2ab6-SGMI-2-N and
the human IgG4 constant region with hinge mutation SEQ ID NO: 83: polynucleotide encoding the
polypeptide comprising the VH-M2ab 6-SGMI-2-C and
the human IgG4 constant region with hinge mutation SEQ ID NO: 84: polynucleotide encoding the
polypeptide comprising the VL-M2ab6-SGMI-2-N and
the human Ig lambda constant region SEQ ID NO: 85: polynucleotide encoding the
polypeptide comprising the VL-M2ab6-SGMI-2-C and
the human Ig lambda constant region

DETAILED DESCRIPTION

The present invention is based upon the surprising discovery by the present inventors that inhibition of mannan-binding lectin-associated serine protease-2 (MASP-2), the key regulator of the lectin pathway of the complement system, significantly reduces inflammation and fibrosis in various animal models of fibrotic disease including the unilateral ureteral obstruction (UUO) model, the protein overload model and the adriamycin-induced nephrology model of renal fibrosis. Therefore, the inventors have demonstrated that inhibition of MASP-2-mediated lectin pathway activation provides an effective therapeutic approach to ameliorate, treat or prevent renal fibrosis, e.g., tubulointerstitial inflammation and fibrosis, regardless of the underlying cause. As further described herein, the use of a MASP-2 inhibitory antibody (OMS646) is effective to improve renal function and decrease corticosteroid needs in human subjects suffering from Immunoglobulin A Nephropathy (IgAN) and membranous nephropathy (MN). As further described herein, the use of a MASP-2 inhibitory agent is also useful to treat, inhibit, alleviate or prevent acute respiratory distress syndrome in a subject infected with coronavirus, such as SARS-CoV-2 and is also useful to treat, inhibit, alleviate, or prevent acute respiratory distress in a subject infected with influenza virus.

I. DEFINITIONS

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "MASP-2-dependent complement activation" comprises MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n, which has been determined to primarily cause opsonization.

As used herein, the term "alternative pathway" refers to complement activation that is triggered, for example, by zymosan from fungal and yeast cell walls, lipopolysaccharide (LPS) from Gram negative outer membranes, and rabbit erythrocytes, as well as from many pure polysaccharides, rabbit erythrocytes, viruses, bacteria, animal tumor cells, parasites and damaged cells, and which has traditionally been thought to arise from spontaneous proteolytic generation of C3b from complement factor C3.

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

As used herein, the term "classical pathway" refers to complement activation that is triggered by antibody bound to a foreign particle and requires binding of the recognition molecule C1q.

As used herein, the term "MASP-2 inhibitory agent" refers to any agent that binds to or directly interacts with MASP-2 and effectively inhibits MASP-2-dependent complement activation, including anti-MASP-2 antibodies and MASP-2 binding fragments thereof, natural and synthetic peptides, small molecules, soluble MASP-2 receptors, expression inhibitors and isolated natural inhibitors, and also encompasses peptides that compete with MASP-2 for binding to another recognition molecule (e.g., MBL, H-ficolin, M-ficolin, or L-ficolin) in the lectin pathway, but does not encompass antibodies that bind to such other recognition molecules. MASP-2 inhibitory agents useful in the method of the invention may reduce MASP-2-dependent complement activation by greater than 20%, such as greater than 50%, such as greater than 90%. In one embodiment, the MASP-2 inhibitory agent reduces MASP-2-dependent complement activation by greater than 90% (i.e., resulting in MASP-2 complement activation of only 10% or less).

As used herein, the term "fibrosis" refers to the formation or presence of excessive connective tissue in an organ or tissue. Fibrosis may occur as a repair or replacement response to a stimulus such as tissue injury or inflammation. A hallmark of fibrosis is the production of excessive extracellular matrix. The normal physiological response to injury results in the deposition of connective tissue as part of the healing process, but this connective tissue deposition may persist and become pathological, altering the architecture and function of the tissue. At the cellular level, epithelial cells and fibroblasts proliferate and differentiate into myofibroblasts, resulting in matrix contraction, increased rigidity, microvascular compression, and hypoxia.

As used herein, the term "treating fibrosis in a mammalian subject suffering from or at risk of developing a disease or disorder caused or exacerbated by fibrosis and/or inflammation" refers to reversing, alleviating, ameliorating, or inhibiting fibrosis in said mammalian subject.

As used herein, the term "proteinuria" refers to the presence of urinary protein in an abnormal amount, such as in amounts exceeding 0.3 g protein in a 24-hour urine collection from a human subject, or in concentrations of more than 1 g per liter in a human subject.

As used herein, the term "improving proteinuria" or "reducing proteinuria" refers to reducing the 24-hour urine protein excretion in a subject suffering from proteinuria by at least 20%, such as at least 30%, such as at least 40%, such at least 50% or more in comparison to baseline 24-hour urine protein excretion in the subject prior to treatment with a MASP-2 inhibitory agent. In one embodiment, treatment with a MASP-2 inhibitory agent in accordance with the methods of the invention is effective to reduce proteinuria in a human subject such as to achieve greater than 20 percent reduction in 24-hour urine protein excretion, or such as greater than 30 percent reduction in 24-hour urine protein excretion, or such as greater than 40 percent reduction in 24-hour urine protein excretion, or such as greater than 50 percent reduction in 24-hour urine protein excretion).

As used herein, the terms "small molecule," "small organic molecule," and "small inorganic molecule" refer to molecules (either organic, organometallic, or inorganic), organic molecules, and inorganic molecules, respectively, which are either naturally occurring or synthetic and that have a molecular weight of more than about 50 Da and less than about 2500 Da. Small organic (for example) molecules may be less than about 2000 Da, between about 100 Da to about 1000 Da, or between about 100 to about 600 Da, or between about 200 to 500 Da.

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments"), that specifically bind to a target polypeptide, such as, for example, MASP-2, polypeptides or portions thereof. It is not intended that the term "antibody" limited as regards to the source of the antibody or the manner in which it is made (e.g., by hybridoma, phage selection, recombinant expression, transgenic animal, peptide synthesis, etc). Exemplary antibodies include polyclonal, monoclonal and recombinant antibodies; pan-specific, multispecific antibodies (e.g., bispecific antibodies, trispecific antibodies); humanized antibodies; murine antibodies; chimeric, mouse-human, mouse-primate, primate-human monoclonal antibodies; and anti-idiotype antibodies, and may be any intact antibody or fragment thereof. As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific for the target antigen. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

As used herein, the term "antibody fragment" refers to a portion derived from or related to a full-length antibody, such as, for example, an anti-MASP-2 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "mannan-binding lectin" ("MBL") is equivalent to mannan-binding protein ("MBP").

As used herein, the "membrane attack complex" ("MAC") refers to a complex of the terminal five complement components (C5b combined with C6, C7, C8 and C-9) that inserts into and disrupts membranes (also referred to as C5b-9).

As used herein, "a subject" includes all mammals, including without limitation humans, non-human primates, dogs, cats, horses, sheep, goats, cows, rabbits, pigs and rodents.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; j), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein, the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "oligonucleotide," as used herein, refers to an oligomer or polymer of ribonucleic acid (RNA) or deoxyribonucleic acid (DNA) or mimetics thereof. This term also covers those oligonucleobases composed of naturally-occurring nucleotides, sugars and covalent internucleoside (backbone) linkages as well as oligonucleotides having non-naturally-occurring modifications.

As used herein, an "epitope" refers to the site on a protein (e.g., a human MASP-2 protein) that is bound by an antibody. "Overlapping epitopes" include at least one (e.g., two, three, four, five, or six) common amino acid residue(s), including linear and non-linear epitopes.

As used herein, the terms "polypeptide," "peptide," and "protein" are used interchangeably and mean any peptide-linked chain of amino acids, regardless of length or post-translational modification. The MASP-2 protein described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments, the human MASP-2 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human MASP-2 protein having the amino acid sequence set forth in SEQ ID NO: 5.

In some embodiments, peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or 600 or more) amino acid residues in length (e.g., at least 6 contiguous amino acid residues of SEQ ID NO: 5). In some embodiments, an antigenic peptide fragment of a human MASP-2 protein is fewer than 500 (e.g., fewer than 450, 400, 350, 325, 300, 275, 250, 225, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6) amino acid residues in length (e.g., fewer than 500 contiguous amino acid residues in any one of SEQ ID NOS: 5).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

II. OVERVIEW OF THE INVENTION

As described herein, the inventors have identified the central role of the lectin pathway in the initiation and disease progression of tubular renal pathology, thereby implicating a key role of the lectin pathway activation in the pathophysiology of a diverse range of renal diseases including IgA nephropathy, C3 glomerulopathy and other glomerulo-nephritides. As further described herein, the inventors discovered that inhibition of mannan-binding lectin-associated serine protease-2 (MASP-2), the key regulator of the lectin pathway of the complement system, significantly reduces inflammation and fibrosis in various animal models of fibrotic disease including the unilateral ureteral obstruction (UUO) model, the protein overload model and the adriamycin-induced nephrology model of renal fibrosis. Therefore, the inventors have demonstrated that inhibition of MASP-2-mediated lectin pathway activation provides an effective therapeutic approach to ameliorate, treat or prevent renal fibrosis, e.g., tubulointerstitial fibrosis, regardless of the underlying cause. As further described herein, the use of a MASP-2 inhibitory agent is also useful to treat, inhibit, alleviate or prevent acute respiratory distress syndrome in a subject infected with coronavirus, such as SARS-CoV-2.

Lectins (MBL, M-ficolin, H-ficolin, L-ficolin and CL-11) are the specific recognition molecules that trigger the innate complement system and the system includes the lectin initiation pathway and the associated terminal pathway amplification loop that amplifies lectin-initiated activation of terminal complement effector molecules. C1q is the specific recognition molecule that triggers the acquired complement system and the system includes the classical initiation pathway and associated terminal pathway amplification loop that amplifies C1q-initiated activation of terminal complement effector molecules. We refer to these two major complement activation systems as the lectin-dependent complement system and the C1q-dependent complement system, respectively.

In addition to its essential role in immune defense, the complement system contributes to tissue damage in many clinical conditions. Thus, there is a pressing need to develop therapeutically effective complement inhibitors to prevent these adverse effects. With the recognition that it is possible to inhibit the lectin mediated MASP-2 pathway while leaving the classical pathway intact comes the realization that it would be highly desirable to specifically inhibit only the complement activation system causing a particular pathology without completely shutting down the immune defense capabilities of complement. For example, in disease states in which complement activation is mediated predominantly by the lectin-dependent complement system, it would be advantageous to specifically inhibit only this system. This would leave the C1q-dependent complement activation system intact to handle immune complex processing and to aid in host defense against infection.

The preferred protein component to target in the development of therapeutic agents to specifically inhibit the lectin-dependent complement system is MASP-2. Of all the known protein components of the lectin-dependent complement system (MBL, H-ficolin, M-ficolin, L-ficolin, MASP-2, C2-C9, Factor B, Factor D, and properdin), only MASP-2 is both unique to the lectin-dependent complement system and required for the system to function. The lectins (MBL, H-ficolin, M-ficolin, L-ficolin and CL-11) are also unique components in the lectin-dependent complement system. However, loss of any one of the lectin components would not necessarily inhibit activation of the system due to lectin redundancy. It would be necessary to inhibit all five lectins in order to guarantee inhibition of the lectin-dependent complement activation system. Furthermore, since MBL and the ficolins are also known to have opsonic activity independent of complement, inhibition of lectin function would result in the loss of this beneficial host defense mechanism against infection. In contrast, this complement-independent lectin opsonic activity would remain intact if MASP-2 was the inhibitory target. An added benefit of MASP-2 as the therapeutic target to inhibit the lectin-dependent complement activation system is that the plasma concentration of MASP-2 is among the lowest of any complement protein (≈500 ng/ml); therefore, correspondingly low concentrations of high-affinity inhibitors of MASP-2 may be sufficient to obtain full inhibition (Moller-Kristensen, M., et al., *J. Immunol Methods* 282:159-167, 2003).

As described herein in Example 14, it was determined in an animal model of fibrotic kidney disease (unilateral ureteral obstruction UUO) that mice without the MASP-2 gene (MASP-2–/–) exhibited significantly less kidney disease compared to wild-type control animals, as shown by inflammatory cell infiltrates (75% reduction) and histological markers of fibrosis such as collagen deposition (one third reduction). As further shown in Example 15, wild-type mice systemically treated with an anti-MASP-2 monoclonal antibody that selectively blocks the lectin pathway while leaving the classical pathway intact, were protected from renal fibrosis, as compared to wild-type mice treated with an isotype control antibody. These results demonstrate that the lectin pathway is a key contributor to kidney disease and further demonstrate that a MASP-2 inhibitor that blocks the lectin pathway, such as a MASP-2 antibody, is effective as an antifibrotic agent. As further shown in Example 16, in the protein overload model, wild-type mice treated with bovine-serum albumin (BSA) developed proteinuric nephropathy, whereas MASP-2–/– mice treated with the same level of BSA had reduced renal injury. As shown in Example 17, wild-type mice systemically treated with an anti-MASP-2 monoclonal antibody that selectively blocks the lectin pathway while leaving the classical pathway intact, were protected from renal injury in the protein overload model. As described in Example 18, MASP-2–/– mice exhibited less renal inflammation and tubulointerstitial injury in an Adriamycin-induced nephrology model of renal fibrosis as compared to wild-type mice. As described in Example 19, in an ongoing Phase 2 open-label renal trial, patients with IgA nephropathy that were treated with an anti-MASP-2 antibody demonstrated a clinically meaningful and statistically significant decrease in urine albumin-to-creatinine ratios (uACRs) throughout the trial and reduction in 24-hour urine protein levels from baseline to the end of treatment. As further described in Example 19, in the same Phase 2 renal trial, patients with membranous nephropathy that were treated with an anti-MASP-2 antibody also demonstrated reductions in uACR during treatment.

In accordance with the foregoing, the present invention relates to the use of MASP-2 inhibitory agents, such as MASP-2 inhibitory antibodies, as antifibrotic agents, the use of MASP-2 inhibitory agents for the manufacture of a medicament for the treatment of a fibrotic condition, and methods of preventing, treating, alleviating or reversing a fibrotic condition in a human subject in need thereof, said method comprising administering to said patient an efficient amount of a MASP-2 inhibitory agent (e.g., an anti-MASP-2 antibody). As described in Examples 20, 21, and 22, clinical improvement was observed in patients suffering from COVID-19-related respiratory failure following treatment with narsoplimab, which inhibits MASP-2 and lectin pathway activation. As described in Example 21, all six COVID-19 patients treated with narsoplimab demonstrated clinical improvement. In each case, COVID-19 lung injury had progressed to ARDS prior to narsoplimab treatment and all patients were receiving non-invasive mechanical ventilation at the time treatment was initiated. Narsoplimab-treated COVID-19 patients for whom follow-up (5-6 month) data are available show no observed clinical or laboratory evidence of longer-term sequelae. As further described in Example 22, additional COVID-19 patients treated with narsoplimab also demonstrated clinical improvement. Similar to the first cohort, longer-term sequelae have not been observed in any of these additional COVID-19 patients treated with narsoplimab described herein. As further demonstrated in Example 22, narsoplimab-treated patients developed appropriately high titers of anti-SARS-Cov-2 antibodies, indicating that treatment with narsoplimab does not impede effector function of the adaptive immune response.

Accordingly, the methods of the invention can be used to treat, inhibit, alleviate, prevent, or reverse coronavirus-induced pneumonia or acute respiratory distress syndrome in a human subject suffering from coronavirus, such as suffering from COVID-19 due to SARS-CoV-2, SARS or MERS, as further described herein. The methods of the invention can also be used to treat, inhibit, alleviate, prevent, or reverse influenza virus-induced pneumonia or acute respiratory distress syndrome in a human subject suffering from influenza virus, such as influenza Type A virus serotypes (H1N1 (caused the "Spanish Flu" in 1918 and "Swine Flu" in 2009); H2N2 (caused the "Asian Flu" in 1957), H3N2 (caused the "Hong Kong Flu" in 1968), H5N1 (caused the "Bird Flu in 2004), H7N7, H1N2, H9N2, H7N2, H7N3, H10N7, H7N9 and H6N1); or influenza Type B virus, or influenza Type C virus.

III. THE ROLE OF MASP-2 IN DISEASES AND CONDITIONS CAUSED OR EXACERBATED BY FIBROSIS

Fibrosis is the formation or presence of excessive connective tissue in an organ or tissue, commonly in response to damage or injury. A hallmark of fibrosis is the production of excessive extracellular matrix following an injury. In the kidney, fibrosis is characterized as a progressive detrimental connective tissue deposition on the kidney parenchyma which inevitably leads to a decline in renal function independently of the primary renal disease which causes the original kidney injury. So called epithelial to mesenchymal transition (EMT), a change in cellular characteristics in which tubular epithelial cells are transformed to mesenchymal fibroblasts, constitutes the principal mechanism of renal fibrosis. Fibrosis affects nearly all tissues and organ systems and may occur as a repair or replacement response to a stimulus such as tissue injury or inflammation. The normal physiological response to injury results in the deposition of connective tissue but, if this process becomes pathological, the replacement of highly differentiated cells by scarring connective tissue alters the architecture and function of the tissue. At the cellular level, epithelial cells and fibroblasts proliferate and differentiate into myofibroblasts, resulting in matrix contraction, increased rigidity, microvascular compression, and hypoxia. Currently there are no effective treatments or therapeutics for fibrosis, but both animal studies and anecdotal human reports suggest that fibrotic tissue damage may be reversed (Tampe and Zeisberg, *Nat Rev Nephrol*, vol 10:226-237, 2014).

Many diseases result in fibrosis that causes progressive organ failure, including diseases of the kidney (e.g., chronic kidney disease, IgA nephropathy, C3 glomerulopathy and other glomerulonephritides), lung (e.g., idiopathic pulmonary fibrosis, cystic fibrosis, bronchiectasis), liver (e.g., cirrhosis, nonalcoholic fatty liver disease), heart (e.g., myocardial infarction, atrial fibrosis, valvular fibrosis, endomyocardial fibrosis), brain (e.g., stroke), skin (e.g., excessive wound healing, scleroderma, systemic sclerosis, keloids), vasculature (e.g., atherosclerotic vascular disease), intestine (e.g., Crohn's disease), eye (e.g., anterior subcapsular cataract, posterior capsule opacification), musculoskeletal soft-tissue structures (e.g., adhesive capsulitis, Dupuytren's contracture, myelofibrosis), reproductive organs (e.g., endometriosis, Peyronie's disease), and some infectious diseases (e.g., coronoavirus, alpha virus, Hepatitis C, Hepatitis B, etc.).

While fibrosis occurs in many tissues and diseases, there are common molecular and cellular mechanisms to its pathology. The deposition of extracellular matrix by fibroblasts is accompanied by immune cell infiltrates, predominately mononuclear cells (see Wynn T., *Nat Rev Immunol* 4(8):583-594, 2004, hereby incorporated herein by reference). A robust inflammatory response results in the expression of growth factors (TGF-beta, VEGF, Hepatocyte Growth Factor, connective tissue growth factor), cytokines and hormones (endothelin, IL-4, IL-6, IL-13, chemokines), degradative enzymes (elastase, matrix metaloproteinases, cathepsins), and extracellular matrix proteins (collagens, fibronectin, integrins).

In addition, the complement system becomes activated in numerous fibrotic diseases. Complement components, including the membrane attack complex, have been identified in numerous fibrotic tissue specimens. For example, components of the lectin pathway have been found in fibrotic lesions of kidney disease (Satomura et al., *Nephron.* 92(3):702-4 (2002); Sato et al., *Lupus* 20(13):1378-86 (2011); Liu et al., *Clin Exp Immunol,* 174(1):152-60 (2013)); liver disease (Rensen et al., *Hepatology* 50(6): 1809-17 (2009)); and lung disease (Olesen et al., *Clin Immunol* 121(3):324-31 (2006)).

Overshooting complement activation has been established as a key contributor to immune complex-mediated as well as antibody independent glomerulonephritides. There is, however, a strong line of evidence demonstrating that uncontrolled activation of complement in situ is intrinsically involved in the pathophysiological progression of TI fibrosis in non-glomerular disease (Quigg R. J, *J Immunol* 171:3319-3324, 2003, Naik A. et al., *Semin Nephrol* 33:575-585, 2013, Mathern D. R. et al., *Clin J Am Soc Nephrol* 10:P1636-1650, 2015). The strong proinflammatory signals that are triggered by local complement activation may be initiated by complement components filtered into the proximal tubule and subsequently entering the interstitial space, or abnormal synthesis of complement components by tubular or other resident and infiltrating cells, or by altered expression of complement regulatory proteins on kidney cells, or absence or loss or gain for function mutations in complement regulatory components (Mathern D. R. et al., *Clin J Am Soc Nephrol* 10:P1636-1650, 2015, Sheerin N. S., et al., *FASEB J* 22: 1065-1072, 2008). In mice for example, deficiency of the complement regulatory protein CR1-related gene/protein y (Crry), results in tubulointerstitial (TI) complement activation with consequent inflammation and fibrosis typical of the injury seen in human TI diseases (Naik A. et al., *Semin Nephrol* 33:575-585, 2013, Bao L. et al., *J Am Soc Nephrol* 18:811-822, 2007). Exposure of tubular epithelial cells to the anaphylatoxin C3a results in epithelial to mesenchymal transition (Tsang Z. et al., *J Am Soc Nephrol* 20:593-603, 2009). Blocking C3a signaling via the C3a receptor alone has recently been shown to lessen renal TI fibrosis in proteinuric and non-proteinuric animals (Tsang Z. et al., *J Am Soc Nephrol* 20:593-603, 2009, Bao L. et al., *Kidney Int.* 80: 524-534, 2011).

As described herein, the inventors have identified the central role of the lectin pathway in the initiation and disease progression of tubular renal pathology, thereby implicating a key role of the lectin pathway activation in the pathophysiology of a diverse range of renal diseases including IgA nephropathy, C3 glomerulopathy and other glomerulonephritides (Endo M. et al., *Nephrol Dialysis Transplant* 13: 1984-1990, 1998; Hisano S. et al., *Am J Kidney Dis* 45:295-302, 2005; Roos A. et al., *J Am Soc Nephrol* 17: 1724-1734, 2006; Liu L. L. et al., *Clin Exp. Immunol* 174:152-160, 2013; Lhotta K. et al., *Nephrol Dialysis Transplant* 14:881-886, 1999; Pickering et al., *Kidney International* 84:1079-1089, 2013), diabetic nephropathy (Hovind P. et al., *Diabetes* 54:1523-1527, 2005), ischaemic reperfusion injury (Asgari E. et al., *FASEB J* 28:3996-4003, 2014) and transplant rejection (Berger S. P. et al., *Am J Transplant* 5:1361-1366, 2005).

As further described herein, the inventors have demonstrated that MASP-2 inhibition reduces inflammation and fibrosis in mouse models of tubulointerstitial disease. Therefore, MASP-2 inhibitory agents are expected to be useful in the treatment of renal fibrosis, including tubulointerstitial inflammation and fibrosis, proteinuria, IgA nephropathy, C3 glomerulopathy and other glomerulonephritides and renal ischaemia reperfusion injury.

Lung Disease

Pulmonary fibrosis is the formation or development of excess fibrous connective tissue in the lungs, wherein normal lung tissue is replaced with fibrotic tissue. This scarring leads to stiffness of the lungs and impaired lung structure and function. In humans, pulmonary fibrosis is thought to result from repeated injury to the tissue within and between the tiny air sacs (alveoli) in the lungs. In an experimental setting, a variety of animal models have replicated aspects of the human disease. For example, a foreign agent such as bleomycin, fluorescein isothiocyanate, silica, or asbestos may be instilled into the trachea of an animal (Gharaee-Kermani et al., *Animal Models of Pulmonary Fibrosis. Methods Mol. Med.,* 2005, 117:251-259).

Accordingly, in certain embodiments, the disclosure provides a method of inhibiting pulmonary fibrosis in a subject suffering from a lung disease or disorder caused or exacerbated by fibrosis and/or inflammation such as coronaviruas-induced ARDS, comprising administering a MASP-2 inhibitory agent, such as a MASP-2 inhibitory antibody, to a subject in need thereof. This method includes administering a composition comprising an amount of a MASP-2 inhibitor effective to inhibit pulmonary fibrosis, decrease lung fibrosis, and/or improve lung function. Improvements in symptoms of lung function include improvement of lung function and/or capacity, decreased fatigue, and improvement in oxygen saturation.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying lung disease or condition.

Infectious Diseases

Infectious diseases such as coronavirus and chronic infectious diseases such as Hepatitis C and Hepatitis B cause tissue inflammation and fibrosis, and high lectin pathway activity may be detrimental. In such diseases, inhibitors of MASP-2 may be beneficial. For example, MBL and MASP-1 levels are found to be a significant predictor of the severity of liver fibrosis in hepatitis C virus (HCV) infection (Brown et al., *Clin Exp Immunol.* 147(1):90-8, 2007; Saadanay et al., *Arab J Gastroenterol.* 12(2):68-73, 2011; Saeed et al., *Clin Exp Immunol.* 174(2):265-73, 2013). MASP-1 has previously been shown to be a potent activator of MASP-2 and the lectin pathway (Megyeri et al., *J Biol Chem.* 29: 288(13):8922-34, 2013). Alphaviruses such as chikungunya virus and Ross River virus induce a strong host inflammatory response resulting in arthritis and myositis, and this pathology is mediated by MBL and the lectin pathway (Gunn et al., *PLoS Pathog.* 8(3):e1002586, 2012).

Accordingly, in certain embodiments, the disclosure provides a method of preventing, treating, reverting, inhibiting and/or reducing fibrosis and/or inflammation in a subject suffering from, or having previously suffered from, an infectious disease such as coronavirus or influenza virus that causes inflammation and/or fibrosis, comprising administering a MASP-2 inhibitory agent, such as a MASP-2 inhibitory antibody, to a subject in need thereof.

The MASP-2 inhibitory composition may be administered locally to the region of fibrosis, such as by local application of the composition during surgery or local injection, either directly or remotely, for example, by catheter. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

In certain embodiments, the MASP-2 inhibitory agents (e.g., MASP-2 inhibitory antibodies) are administered in combination with one or more agents or treatment modalities appropriate for the underlying infectious disease. For example, in some embodiments, a patient diagnosed with COVID-19 can be treated with a combination of agents which includes one or more MASP-2 inhibitory agents, such as a combination comprising an antiviral agent (e.g., remdesivir) and one or more MASP-2 inhibitory agents. The agents can be administered in any suitable sequence, e.g., sequentially or concurrently.

In some embodiments, the infectious disease that causes inflammation and/or fibrosis is selected from the group consisting of coronavirus, alpha virus, Hepatitis A, Hepatitis B, Hepatitis C, tuberculosis, HIV, and influenza.

In certain embodiments, the MASP-2 inhibitory agents (e.g., MASP-2 inhibitory antibodies or MASP-2 inhibitory small molecule compounds) are administered in combination with one or more agents or treatment modalities appropriate for the underlying disease or disorder.

In certain embodiments of any of the various methods and pharmaceutical compositions described herein, the MASP-2 inhibitory antibody or small molecule compound selectively blocks the lectin pathway while leaving intact the classical pathway.

IV. MASP-2 INHIBITORY AGENTS

In various aspects, the present invention provides methods of inhibiting the adverse effects of fibrosis and/or inflammation comprising administering a MASP-2 inhibitory agent to a subject in need thereof. MASP-2 inhibitory agents are administered in an amount effective to inhibit MASP-2-dependent complement activation in a living subject. In the practice of this aspect of the invention, representative MASP-2 inhibitory agents include: molecules that inhibit the biological activity of MASP-2 (such as small molecule inhibitors, anti-MASP-2 antibodies (e.g., MASP-2 inhibitory antibodies) or blocking peptides which interact with MASP-2 or interfere with a protein-protein interaction), and molecules that decrease the expression of MASP-2 (such as MASP-2 antisense nucleic acid molecules, MASP-2 specific RNAi molecules and MASP-2 ribozymes), thereby preventing MASP-2 from activating the lectin complement pathway. The MASP-2 inhibitory agents can be used alone as a primary therapy or in combination with other therapeutics as an adjuvant therapy to enhance the therapeutic benefits of other medical treatments.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in Example 2), the reduction of C4 cleavage and C4b deposition (measured, for example as described in Example 2), or the reduction of C3 cleavage and C3b deposition (measured, for example, as described in Example 2).

According to the present invention, MASP-2 inhibitory agents are utilized that are effective in inhibiting respiratory distress (or stated another way, improving respiratory function) in a subject infected with coronavirus such as SARS-CoV-2.

The assessment of respiratory function may be carried out periodically, e.g., each hour, each day, each week, or each month. This assessment is preferably carried out at several time points for a given subject or at one or several time points for a given subject and a healthy control. The assessment may be carried out at regular time intervals, e.g. each hour, each day, each week, or each month. When one assessment has led to the finding of a decrease of respiratory distress (i.e., an increase in respiratory function), a MASP-2 inhibitory agent, such as a MASP-2 inhibitory antibody, is said to be effective to treat a subject suffering from coronavirus-induced acute respiratory distress syndrome.

MASP-2 inhibitory agents useful in the practice of this aspect of the invention include, for example, MASP-2 antibodies and fragments thereof, MASP-2 inhibitory peptides, small molecules, MASP-2 soluble receptors and expression inhibitors. MASP-2 inhibitory agents may inhibit the MASP-2-dependent complement activation system by blocking the biological function of MASP-2. For example, an inhibitory agent may effectively block MASP-2 protein-to-protein interactions, interfere with MASP-2 dimerization or assembly, block $Ca^{2+}$ binding, interfere with the MASP-2 serine protease active site, or may reduce MASP-2 protein expression.

In some embodiments, the MASP-2 inhibitory agents selectively inhibit MASP-2 complement activation, leaving the C1q-dependent complement activation system functionally intact.

In one embodiment, a MASP-2 inhibitory agent useful in the methods of the invention is a specific MASP-2 inhibitory agent that specifically binds to a polypeptide comprising SEQ ID NO:6 with an affinity of at least ten times greater than to other antigens in the complement system. In another embodiment, a MASP-2 inhibitory agent specifically binds to a polypeptide comprising SEQ ID NO:6 with a binding affinity of at least 100 times greater than to other antigens in the complement system. In one embodiment, the MASP-2 inhibitory agent specifically binds to at least one of (i) the CCP1-CCP2 domain (aa 300-431 of SEQ ID NO:6) or the serine protease domain of MASP-2 (aa 445-682 of SEQ ID NO:6) and inhibits MASP-2-dependent complement activation. In one embodiment, the MASP-2 inhibitory agent is a MASP-2 monoclonal antibody, or fragment thereof that specifically binds to MASP-2. The binding affinity of the MASP-2 inhibitory agent can be determined using a suitable binding assay. In one embodiment, the MASP-2 inhibitory agent inhibits C3b deposition in 90% human serum with an $IC_{50}$ of 30 nM or less.

The MASP-2 polypeptide exhibits a molecular structure similar to MASP-1, MASP-3, and C1r and C1s, the proteases of the C1 complement system. The cDNA molecule set forth in SEQ ID NO:4 encodes a representative example of MASP-2 (consisting of the amino acid sequence set forth in SEQ ID NO:5) and provides the human MASP-2 polypeptide with a leader sequence (aa 1-15) that is cleaved after secretion, resulting in the mature form of human MASP-2 (SEQ ID NO:6). As shown in FIG. 2, the human MASP 2 gene encompasses twelve exons. The human MASP-2 cDNA is encoded by exons B, C, D, F, G, H, I, J, K AND L. An alternative splice results in a 20 kDa protein termed MBL-associated protein 19 ("MAp19", also referred to as "sMAP") (SEQ ID NO:2), encoded by (SEQ ID NO:1) arising from exons B, C, D and E as shown in FIG. 2. The cDNA molecule set forth in SEQ ID NO:50 encodes the murine MASP-2 (consisting of the amino acid sequence set forth in SEQ ID NO:51) and provides the murine MASP-2 polypeptide with a leader sequence that is cleaved after secretion, resulting in the mature form of murine MASP-2 (SEQ ID NO:52). The cDNA molecule set forth in SEQ ID NO:53 encodes the rat MASP-2 (consisting of the amino acid sequence set forth in SEQ ID NO:54) and provides the rat MASP-2 polypeptide with a leader sequence that is cleaved after secretion, resulting in the mature form of rat MASP-2 (SEQ ID NO:55).

Those skilled in the art will recognize that the sequences disclosed in SEQ ID NO:4, SEQ ID NO:50 and SEQ ID NO:53 represent single alleles of human, murine and rat MASP-2 respectively, and that allelic variation and alternative splicing are expected to occur. Allelic variants of the nucleotide sequences shown in SEQ ID NO:4, SEQ ID NO:50 and SEQ ID NO:53, including those containing silent mutations and those in which mutations result in amino acid sequence changes, are within the scope of the present invention. Allelic variants of the MASP-2 sequence can be cloned by probing cDNA or genomic libraries from different individuals according to standard procedures.

Figure 1:
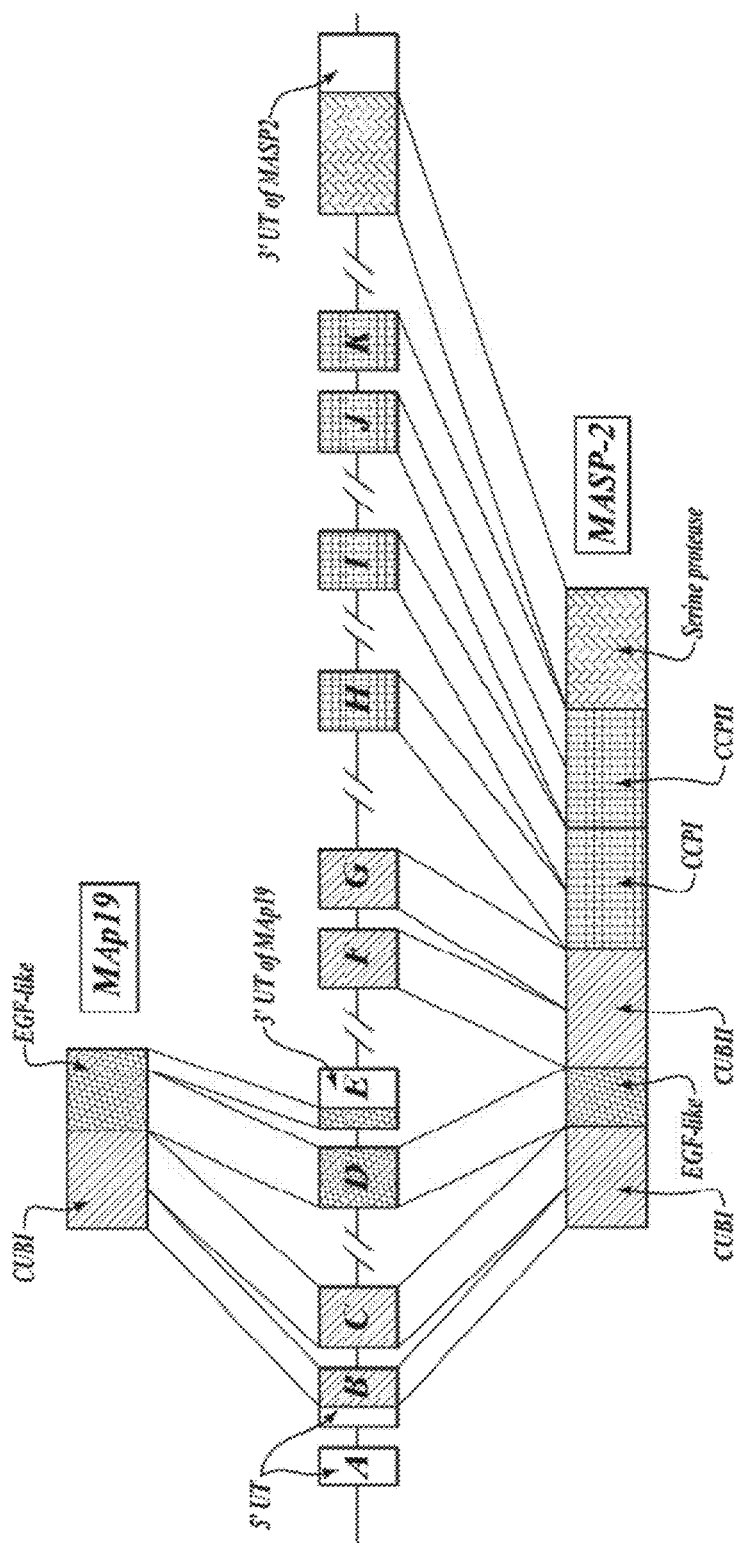
FIG. 1 is a diagram illustrating the genomic structure of human MASP-2.
Figure 2A:
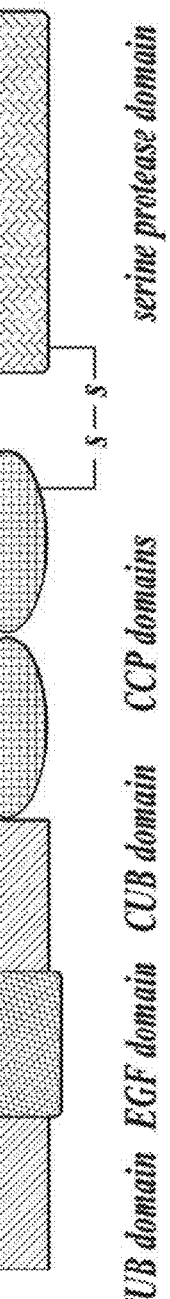
FIG. 2A is a schematic diagram illustrating the domain structure of human MASP-2 protein.
Figure 2B:
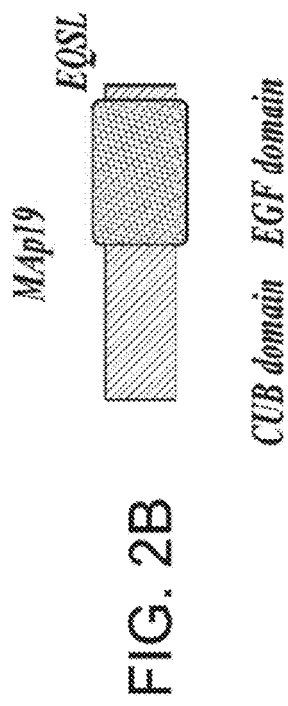
FIG. 2B is a schematic diagram illustrating the domain structure of human MAp19 protein.

The domains of the human MASP-2 protein (SEQ ID NO:6) are shown in FIGS. 1 and 2A and include an N-terminal C1r/C1s/sea urchin Vegf/bone morphogenic protein (CUBI) domain (aa 1-121 of SEQ ID NO:6), an epidermal growth factor-like domain (aa 122-166), a second CUBI domain (aa 167-293), as well as a tandem of complement control protein domains and a serine protease domain. Alternative splicing of the MASP 2 gene results in MAp19 shown in FIG. 1. MAp19 is a nonenzymatic protein containing the N-terminal CUBI-EGF region of MASP-2 with four additional residues (EQSL) derived from exon E as shown in FIG. 1.

Several proteins have been shown to bind to or interact with MASP-2 through protein-to-protein interactions. For example, MASP-2 is known to bind to, and form $Ca^{2+}$ dependent complexes with, the lectin proteins MBL, H-ficolin and L-ficolin. Each MASP-2/lectin complex has been shown to activate complement through the MASP-2-dependent cleavage of proteins C4 and C2 (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). Studies have shown that the CUBI-EGF domains of MASP-2 are essential for the association of MASP-2 with MBL (Thielens, N. M., et al., *J. Immunol.* 166:5068, 2001). It has also been shown that the CUBIEGFCUBII domains mediate dimerization of MASP-2, which is required for formation of an active MBL complex (Wallis, R., et al., *J. Biol. Chem.* 275:30962-30969, 2000). Therefore, MASP-2 inhibitory agents can be identified that bind to or interfere with MASP-2 target regions known to be important for MASP-2-dependent complement activation.

Anti-MASP-2 Antibodies

In some embodiments of this aspect of the invention, the MASP-2 inhibitory agent comprises an anti-MASP-2 antibody that inhibits the MASP-2-dependent complement activation system. The anti-MASP-2 antibodies useful in this aspect of the invention include polyclonal, monoclonal or recombinant antibodies derived from any antibody producing mammal and may be multispecific, chimeric, humanized, anti-idiotype, and antibody fragments. Antibody fragments include Fab, Fab', F(ab)$_2$, F(ab')$_2$, Fv fragments, scFv fragments and single-chain antibodies as further described herein.

MASP-2 antibodies can be screened for the ability to inhibit MASP-2-dependent complement activation system and for antifibrotic activity and/or the ability to inhibit renal damage associated with proteinuria or Adriamycin-induced nephropathy using the assays described herein. Several MASP-2 antibodies have been described in the literature and some have been newly generated, some of which are listed below in TABLE 1. For example, as described in Examples 10 and 11 herein, anti-MASP-2 Fab2 antibodies have been identified that block MASP-2-dependent complement activation. As described in Example 12, and also described in WO2012/151481, which is hereby incorporated herein by reference, fully human MASP-2 scFv antibodies (e.g., OMS646) have been identified that block MASP-2-dependent complement activation. As described in Example 13, and also described in WO2014/144542, which is hereby incorporated herein by reference, SGMI-2 peptide-bearing MASP-2 antibodies and fragments thereof with MASP-2 inhibitory activity were generated by fusing the SGMI-2 peptide amino acid sequence (SEQ ID NO:72, 73 or 74) onto the amino or carboxy termini of the heavy and/or light chains of a human MASP-2 antibody (e.g., OMS646-SGMI-2).

Accordingly, in one embodiment, the MASP-2 inhibitory agent for use in the methods of the invention comprises a human antibody such as, for example OMS646. Accordingly, in one embodiment, a MASP-2 inhibitory agent for use in the compositions and methods of the claimed invention comprises a human antibody that binds a polypeptide consisting of human MASP-2 (SEQ ID NO:6), wherein the antibody comprises: (I) (a) a heavy-chain variable region comprising: i) a heavy-chain CDR-H1 comprising the amino acid sequence from 31-35 of SEQ ID NO:67; and ii) a heavy-chain CDR-H2 comprising the amino acid sequence from 50-65 of SEQ ID NO:67; and iii) a heavy-chain CDR-H3 comprising the amino acid sequence from 95-107 of SEQ ID NO:67 and b) a light-chain variable region comprising: i) a light-chain CDR-L1 comprising the amino acid sequence from 24-34 of SEQ ID NO:69; and ii) a light-chain CDR-L2 comprising the amino acid sequence from 50-56 of SEQ ID NO:69; and iii) a light-chain CDR-L3 comprising the amino acid sequence from 89-97 of SEQ ID NO:69, or (II) a variant thereof comprising a heavy-chain variable region with at least 90% identity to SEQ ID NO:67 (e.g., at least 91%, at least 92%, at least 93%, at least 94%, at least 95%, at least 96%, at least 97%, at least 98%, at least 99% identity to SEQ ID NO:67) and a light-chain variable region with at least 90% identity (e.g., at least 91%, at least 92%, at least 93%, at least 94%, at least 95%, at least 96%, at least 97%, at least 98%, at least 99% identity to SEQ ID NO:69.

In some embodiments, the method comprises administering to the subject a composition comprising an amount of a MASP-2 inhibitory antibody, or antigen binding fragment thereof, comprising a heavy-chain variable region comprising the amino acid sequence set forth as SEQ ID NO:67 and a light-chain variable region comprising the amino acid sequence set forth as SEQ ID NO:69.

In some embodiments, the method comprises administering to the subject a composition comprising a MASP-2 inhibitory antibody, or antigen binding fragment thereof, that specifically recognizes at least part of an epitope on human MASP-2 recognized by reference antibody OMS646 comprising a heavy-chain variable region as set forth in SEQ ID NO:67 and a light-chain variable region as set forth in SEQ ID NO:69. In one embodiment, the MASP-2 inhibitory agent for use in the methods of the invention comprises the human antibody OMS646.

TABLE 1

EXEMPLARY MASP-2 SPECIFIC ANTIBODIES

| ANTIGEN | ANTIBODY TYPE | REFERENCE |
|---|---|---|
| Recombinant MASP-2 | Rat Polyclonal | Peterson, S.V., et al., Mol. Immunol. 37:803-811 2000 |
| Recombinant human CCP1/2-SP fragment (MoAb 8B5) | Rat MoAb (subclass IgG1) | Moller-Kristensen, M., et al., J. of Immunol. Methods 282:159-167, 2003 |
| Recombinant human MAp19 (MoAb 6G12) (cross reacts with MASP-2) | Rat MoAb (subclass IgG1) | Moller-Kristensen, M., et al., J. of Immunol. Methods 282:159-167, 2003 |
| hMASP-2 | Mouse MoAb (S/P) Mouse MoAb (N-term) | Peterson, S.V., et al., Mol. Immunol. 35:409, April 1998 |
| hMASP-2 (CCP1-CCP2-SP domain | rat MoAb: Nimoab 101, produced by hybridoma cell line 03050904 (ECACC) | WO 2004/106384 |
| hMASP-2 (full length-his tagged) | murine MoAbs: NimoAb104, produced by hybridoma cell line M0545YM035 (DSMZ) NimoAb108, produced by hybridoma cell line M0545YM029 (DSMZ) NimoAb109 produced by hybridoma cell line M0545YM046 (DSMZ) NimoAb110 produced by hybridoma cell line M0545YM048 (DSMZ) | WO 2004/106384 |
| Rat MASP-2 (full-length) | MASP-2 Fab2 antibody fragments | Example 10 |
| hMASP-2 (full-length) | Fully human scFv clones | Example 12 and WO2012/151481 |
| hMASP-2 (full-length) | SGMI-2 peptide bearing MASP-2 antibodies | Example 13 and WO2014/144542 |

Anti-MASP-2 Antibodies with Reduced Effector Function

In some embodiments of this aspect of the invention, the anti-MASP-2 antibodies have reduced effector function in order to reduce inflammation that may arise from the activation of the classical complement pathway. The ability of IgG molecules to trigger the classical complement pathway has been shown to reside within the Fc portion of the molecule (Duncan, A. R., et al., Nature 332:738-740 1988). IgG molecules in which the Fc portion of the molecule has been removed by enzymatic cleavage are devoid of this effector function (see Harlow, *Antibodies: A Laboratory Manual*, Cold Spring Harbor Laboratory, New York, 1988). Accordingly, antibodies with reduced effector function can be generated as the result of lacking the Fc portion of the molecule by having a genetically engineered Fc sequence that minimizes effector function or being of either the human $IgG_2$ or $IgG_4$ isotype.

Antibodies with reduced effector function can be produced by standard molecular biological manipulation of the Fc portion of the IgG heavy chains as described herein and also described in Jolliffe et al., *Int'l Rev. Immunol.* 10:241-250, 1993, and Rodrigues et al., *J. Immunol.* 151:6954-6961, 1998. Antibodies with reduced effector function also include human IgG2 and IgG4 isotypes that have a reduced ability to activate complement and/or interact with Fc receptors (Ravetch, J. V., et al., *Annu. Rev. Immunol.* 9:457-492, 1991; Isaacs, J. D., et al., *J. Immunol.* 148:3062-3071, 1992; van de Winkel, J. G., et al., *Immunol. Today* 14:215-221, 1993). Humanized or fully human antibodies specific to human MASP-2 comprised of IgG2 or IgG4 isotypes can be produced by one of several methods known to one of ordinary skilled in the art, as described in Vaughan, T. J., et al., *Nature Biotechnical* 16:535-539, 1998.

Production of Anti-MASP-2 Antibodies

Anti-MASP-2 antibodies can be produced using MASP-2 polypeptides (e.g., full length MASP-2) or using antigenic MASP-2 epitope-bearing peptides (e.g., a portion of the MASP-2 polypeptide). Immunogenic peptides may be as small as five amino acid residues. For example, the MASP-2 polypeptide including the entire amino acid sequence of SEQ ID NO:6 may be used to induce anti-MASP-2 antibodies useful in the method of the invention. Particular MASP-2 domains known to be involved in protein-protein interactions, such as the CUBI, and CUBIEGF domains, as well as the region encompassing the serine-protease active site, may be expressed as recombinant polypeptides as described in Example 3 and used as antigens. In addition, peptides comprising a portion of at least 6 amino acids of the MASP-2 polypeptide (SEQ ID NO:6) are also useful to induce MASP-2 antibodies. Additional examples of MASP-2 derived antigens useful to induce MASP-2 antibodies are provided below in TABLE 2. The MASP-2 peptides and polypeptides used to raise antibodies may be isolated as natural polypeptides, or recombinant or synthetic peptides and catalytically inactive recombinant polypeptides, such as MASP-2A, as further described herein. In some embodiments of this aspect of the invention, anti-MASP-2 antibodies are obtained using a transgenic mouse strain as described herein.

Antigens useful for producing anti-MASP-2 antibodies also include fusion polypeptides, such as fusions of MASP-2 or a portion thereof with an immunoglobulin polypeptide or with maltose-binding protein. The polypeptide immunogen may be a full-length molecule or a portion thereof. If the polypeptide portion is hapten-like, such portion may be advantageously joined or linked to a macromolecular carrier (such as keyhole limpet hemocyanin (KLH), bovine serum albumin (BSA) or tetanus toxoid) for immunization.

TABLE 2

MASP-2 DERIVED ANTIGENS

| SEQ ID NO: | Amino Acid Sequence |
|---|---|
| SEQ ID NO: 6 | Human MASP-2 protein |
| SEQ ID NO: 51 | Murine MASP-2 protein |
| SEQ ID NO: 8 | CUBI domain of human MASP-2 (aa 1-121 of SEQ ID NO: 6) |
| SEQ ID NO: 9 | CUBIEGF domains of human MASP-2 (aa 1-166 of SEQ ID NO: 6) |
| SEQ ID NO: 10 | CUBIEGFCUBII domains of human MASP-2 (aa 1-293 of SEQ ID NO: 6) |
| SEQ ID NO: 11 | EGF domain of human MASP-2 (aa 122-166 of SEQ ID NO: 6) |
| SEQ ID NO: 12 | Serine-Protease domain of human MASP-2 (aa 429-671 of SEQ ID NO: 6) |
| SEQ ID NO: 13 GKDSCRGDAGGALVFL | Serine-Protease inactivated mutant form (aa 610-625 of SEQ ID NO: 6 with mutated Ser 618) |
| SEQ ID NO: 14 TPLGPKWPEPVFGRL | Human CUBI peptide |
| SEQ ID NO: 15: TAPPGYRLRLYFTHFDLEL SHLCEYDFVKLSSGAKVL ATLCGQ | Human CUBI peptide |
| SEQ ID NO: 16: TFRSDYSN | MBL binding region in human CUBI domain |
| SEQ ID NO: 17: FYSLGSSLDITFRSDYSNEK PFTGF | MBL binding region in human CUBI domain |
| SEQ ID NO: 18 IDECQVAPG | EGF peptide |
| SEQ ID NO: 19 ANMLCAGLESGGKDSCRG DSGGALV | Peptide from serine-protease active site |

Polyclonal Antibodies

Polyclonal antibodies against MASP-2 can be prepared by immunizing an animal with MASP-2 polypeptide or an immunogenic portion thereof using methods well known to those of ordinary skill in the art. See, for example, Green et al., "Production of Polyclonal Antisera," in *Immunochemical Protocols* (Manson, ed.), page 105. The immunogenicity of a MASP-2 polypeptide can be increased through the use of an adjuvant, including mineral gels, such as aluminum hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as horses, cows, dogs, chicken, rats, mice, rabbits, guinea pigs, goats, or sheep. Alternatively, an anti-MASP-2 antibody useful in the present invention may also be derived from a subhuman primate. General techniques for raising diagnostically and therapeutically useful antibodies in baboons may be found, for example, in Goldenberg et al., International Patent Publication No. WO 91/11465, and in Losman, M. J., et al., *Int. J. Cancer* 46:310, 1990. Sera containing immunologically active antibodies are then produced from the blood of such immunized animals using standard procedures well known in the art.

Monoclonal Antibodies

In some embodiments, the MASP-2 inhibitory agent is an anti-MASP-2 monoclonal antibody. Anti-MASP-2 monoclonal antibodies are highly specific, being directed against a single MASP-2 epitope. As used herein, the modifier "monoclonal" indicates the character of the antibody as being obtained from a substantially homogenous population of antibodies and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-2 polypeptide or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-2. Examples further describing the production of anti-MASP-2 monoclonal antibodies are provided herein (see also *Current Protocols in Immunology*, Vol. 1., John Wiley & Sons, pages 2.5.1-2.6.7, 1991.)

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology as further described herein. Transgenic mice with a human immunoglobulin genome are commercially available (e.g., from Abgenix, Inc., Fremont, CA, and Medarex, Inc., Annandale, N.J.). Methods for obtaining human antibodies from transgenic mice are described, for example, by Green, L. L., et al., *Nature Genet.* 7:13, 1994; Lonberg, N., et al., *Nature* 368:856, 1994; and Taylor, L. D., et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, The Humana Press, Inc., Vol. 10, pages 79-104, 1992).

Once produced, polyclonal, monoclonal or phage-derived antibodies are first tested for specific MASP-2 binding. A variety of assays known to those skilled in the art may be utilized to detect antibodies which specifically bind to MASP-2. Exemplary assays include Western blot or immunoprecipitation analysis by standard methods (e.g., as described in Ausubel et al.), immunoelectrophoresis, enzyme-linked immuno-sorbent assays, dot blots, inhibition or competition assays and sandwich assays (as described in Harlow and Land, *Antibodies: A Laboratory Manual*, Cold Spring Harbor Laboratory Press, 1988). Once antibodies are identified that specifically bind to MASP-2, the anti-MASP-2 antibodies are tested for the ability to function as a MASP-2 inhibitory agent in one of several assays such as, for example, a lectin-specific C4 cleavage assay (described in Example 2), a C3b deposition assay (described in Example 2) or a C4b deposition assay (described in Example 2).

The affinity of anti-MASP-2 monoclonal antibodies can be readily determined by one of ordinary skill in the art (see, e.g., Scatchard, A., *NY Acad. Sci.* 51:660-672, 1949). In one embodiment, the anti-MASP-2 monoclonal antibodies useful for the methods of the invention bind to MASP-2 with a binding affinity of <100 nM, preferably <10 nM and most preferably <2 nM.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567, to Cabilly; and Morrison, S. L., et al., *Proc. Nat'l Acad. Sci. USA* 81:6851-6855, 1984).

One form of a chimeric antibody useful in the invention is a humanized monoclonal anti-MASP-2 antibody. Humanized forms of non-human (e.g., murine) antibodies are chimeric antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to further refine antibody performance. In general, the humanized antibody will comprise substantially all of at least one, and typically two variable domains, in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fc), typically that of a human immunoglobulin. For further details, see Jones, P. T., et al., *Nature* 321:522-525, 1986; Reichmann, L., et al., *Nature* 332:323-329, 1988; and Presta, *Curr. Op. Struct. Biol.* 2:593-596, 1992.

The humanized antibodies useful in the invention include human monoclonal antibodies including at least a MASP-2 binding CDRH3 region. In addition, the Fc portions may be replaced so as to produce IgA or IgM as well as human IgG antibodies. Such humanized antibodies will have particular clinical utility because they will specifically recognize human MASP-2 but will not evoke an immune response in humans against the antibody itself. Consequently, they are better suited for in vivo administration in humans, especially when repeated or long-term administration is necessary.

An example of the generation of a humanized anti-MASP-2 antibody from a murine anti-MASP-2 monoclonal antibody is provided herein in Example 6. Techniques for producing humanized monoclonal antibodies are also described, for example, by Jones, P. T., et al., *Nature* 321:522, 1986; Carter, P., et al., *Proc. Nat'l. Acad. Sci. USA* 89:4285, 1992; Sandhu, J. S., *Crit. Rev. Biotech.* 12:437, 1992; Singer, I. I., et al., *J. Immun.* 150:2844, 1993; Sudhir (ed.), *Antibody Engineering Protocols*, Humana Press, Inc., 1995; Kelley, "Engineering Therapeutic Antibodies," in *Protein Engineering: Principles and Practice*, Cleland et al. (eds.), John Wiley & Sons, Inc., pages 399-434, 1996; and by U.S. Pat. No. 5,693,762, to Queen, 1997. In addition, there are commercial entities that will synthesize humanized antibodies from specific murine antibody regions, such as Protein Design Labs (Mountain View, CA).

Recombinant Antibodies

Anti-MASP-2 antibodies can also be made using recombinant methods. For example, human antibodies can be made using human immunoglobulin expression libraries (available for example, from Stratagene, Corp., La Jolla, CA) to produce fragments of human antibodies ($V_H$, $V_L$, Fv, Fd, Fab or F(ab')$_2$). These fragments are then used to construct whole human antibodies using techniques similar to those for producing chimeric antibodies.

Anti-Idiotype Antibodies

Once anti-MASP-2 antibodies are identified with the desired inhibitory activity, these antibodies can be used to generate anti-idiotype antibodies that resemble a portion of MASP-2 using techniques that are well known in the art. See, e.g., Greenspan, N. S., et al., *FASEB J* 7:437, 1993. For example, antibodies that bind to MASP-2 and competitively inhibit a MASP-2 protein interaction required for complement activation can be used to generate anti-idiotypes that resemble the MBL binding site on MASP-2 protein and therefore bind and neutralize a binding ligand of MASP-2 such as, for example, MBL.

Immunoglobulin Fragments

The MASP-2 inhibitory agents useful in the method of the invention encompass not only intact immunoglobulin molecules but also the well known fragments including Fab, Fab', F(ab)$_2$, F(ab')$_2$ and Fv fragments, scFv fragments, diabodies, linear antibodies, single-chain antibody molecules and multispecific antibodies formed from antibody fragments.

It is well known in the art that only a small portion of an antibody molecule, the paratope, is involved in the binding of the antibody to its epitope (see, e.g., Clark, W. R., The *Experimental Foundations of Modern Immunology*, Wiley & Sons, Inc., NY, 1986). The pFc' and Fc regions of the antibody are effectors of the classical complement pathway, but are not involved in antigen binding. An antibody from which the pFc' region has been enzymatically cleaved, or which has been produced without the pFc' region, is designated an F(ab')$_2$ fragment and retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331,647 to Goldenberg; Nisonoff, A., et al., *Arch. Biochem. Biophys.* 89:230, 1960; Porter, R. R., *Biochem. J.* 73:119, 1959; Edelman, et al., in *Methods in Enzymology* 1:422, Academic Press, 1967; and by Coligan at pages 2.8.1-2.8.10 and 2.10.-2.10.4.

In some embodiments, the use of antibody fragments lacking the Fc region are preferred to avoid activation of the classical complement pathway which is initiated upon binding Fc to the Fcγ receptor. There are several methods by which one can produce a MoAb that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or F(ab)$_2$ fragments (Mariani, M., et al., *Mol. Immunol.* 28:69-71, 1991). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for MASP-2 in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described for example, by Whitlow, et al., "Methods: A Companion to Methods in Enzymology" 2:97, 1991; Bird, et al., *Science* 242:423, 1988; U.S. Pat. No. 4,946,778, to Ladner; Pack, P., et al., *Bio Technology* 11:1271, 1993.

As an illustrative example, a MASP-2 specific scFv can be obtained by exposing lymphocytes to MASP-2 polypeptide in vitro and selecting antibody display libraries in phage or similar vectors (for example, through the use of immobilized or labeled MASP-2 protein or peptide). Genes encoding polypeptides having potential MASP-2 polypeptide binding domains can be obtained by screening random peptide libraries displayed on phage or on bacteria such as *E. coli*. These random peptide display libraries can be used to screen for peptides which interact with MASP-2. Techniques for creating and screening such random peptide display libraries are well known in the art (U.S. Pat. No. 5,223,409, to Lardner; U.S. Pat. No. 4,946,778, to Ladner; U.S. Pat. No. 5,403,484, to Lardner; U.S. Pat. No. 5,571,698, to Lardner; and Kay et al., *Phage Display of Peptides and Proteins* Academic Press, Inc., 1996) and random peptide display libraries and kits for screening such libraries are available commercially, for instance from CLONTECH Laboratories, Inc. (Palo Alto, Calif), Invitrogen Inc. (San Diego, Calif), New England Biolabs, Inc. (Ipswich, Mass.), and Pharmacia LKB Biotechnology Inc. (Piscataway, N. J.).

Another form of an anti-MASP-2 antibody fragment useful in this aspect of the invention is a peptide coding for a single complementarity-determining region (CDR) that binds to an epitope on a MASP-2 antigen and inhibits MASP-2-dependent complement activation. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166, Cambridge University Press, 1995; and Ward et al., "Genetic Manipulation and Expression of Antibodies," in *Monoclonal Antibodies: Principles and Applications*, Birch et al. (eds.), page 137, Wiley-Liss, Inc., 1995).

The MASP-2 antibodies described herein are administered to a subject in need thereof to inhibit MASP-2-dependent complement activation. In some embodiments, the MASP-2 inhibitory agent is a high-affinity human or humanized monoclonal anti-MASP-2 antibody with reduced effector function.

Peptide Inhibitors

In some embodiments of this aspect of the invention, the MASP-2 inhibitory agent comprises isolated MASP-2 peptide inhibitors, including isolated natural peptide inhibitors and synthetic peptide inhibitors that inhibit the MASP-2-dependent complement activation system. As used herein, the term "isolated MASP-2 peptide inhibitors" refers to peptides that inhibit MASP-2 dependent complement activation by binding to, competing with MASP-2 for binding to another recognition molecule (e.g., MBL, H-ficolin, M-ficolin, or L-ficolin) in the lectin pathway, and/or directly interacting with MASP-2 to inhibit MASP-2-dependent complement activation that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., *European Heart J.* 16:50-55, 1995). Short linear peptides (<30 amino acids) have been described that prevent or interfere with integrin-dependent adhesion (Murayama, O., et al., *J. Biochem.* 120:445-51, 1996). Longer peptides, ranging in length from 25 to 200 amino acid residues, have also been used successfully to block integrin-dependent adhesion (Zhang, L., et al., *J. Biol. Chem.* 271(47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D. Y., et al., *J. Med. Chem.* 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592, to Larson).

Synthetic MASP-2 Peptide Inhibitors

MASP-2 inhibitory peptides useful in the methods of this aspect of the invention are exemplified by amino acid sequences that mimic the target regions important for MASP-2 function. The inhibitory peptides useful in the practice of the methods of the invention range in size from about 5 amino acids to about 300 amino acids. TABLE 3 provides a list of exemplary inhibitory peptides that may be useful in the practice of this aspect of the present invention. A candidate MASP-2 inhibitory peptide may be tested for the ability to function as a MASP-2 inhibitory agent in one of several assays including, for example, a lectin specific C4 cleavage assay (described in Example 2), and a C3b deposition assay (described in Example 2).

In some embodiments, the MASP-2 inhibitory peptides are derived from MASP-2 polypeptides and are selected from the full length mature MASP-2 protein (SEQ ID NO:6), or from a particular domain of the MASP-2 protein such as, for example, the CUBI domain (SEQ ID NO:8), the CUBIEGF domain (SEQ ID NO:9), the EGF domain (SEQ ID NO: 11), and the serine protease domain (SEQ ID NO:12). As previously described, the CUBEGFCUBII regions have been shown to be required for dimerization and binding with MBL (Thielens et al., supra). In particular, the peptide sequence TFRSDYN (SEQ ID NO:16) in the CUBI domain of MASP-2 has been shown to be involved in binding to MBL in a study that identified a human carrying a homozygous mutation at Asp105 to Gly105, resulting in the loss of MASP-2 from the MBL complex (Stengaard-Pedersen, K., et al., *New England J. Med.* 349:554-560, 2003).

In some embodiments, MASP-2 inhibitory peptides are derived from the lectin proteins that bind to MASP-2 and are involved in the lectin complement pathway. Several different lectins have been identified that are involved in this pathway, including mannan-binding lectin (MBL), L-ficolin, M-ficolin and H-ficolin. (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). These lectins are present in serum as oligomers of homotrimeric subunits, each having N-terminal collagen-like fibers with carbohydrate recognition domains. These different lectins have been shown to bind to MASP-2, and the lectin/MASP-2 complex activates complement through cleavage of proteins C4 and C2. H-ficolin has an amino-terminal region of 24 amino acids, a collagen-like domain with 11 Gly-Xaa-Yaa repeats, a neck domain of 12 amino acids, and a fibrinogen-like domain of 207 amino acids (Matsushita, M., et al., *J. Immunol.* 168:3502-3506, 2002). H-ficolin binds to GlcNAc and agglutinates human erythrocytes coated with LPS derived from *S. typhimurium*, *S. minnesota* and *E. coli*. H-ficolin has been shown to be associated with MASP-2 and MAp19 and activates the lectin pathway. Id. L-ficolin/P35 also binds to GlcNAc and has been shown to be associated with MASP-2 and MAp19 in human serum and this complex has been shown to activate the lectin pathway (Matsushita, M., et al., *J. Immunol.* 164:2281, 2000). Accordingly, MASP-2 inhibitory peptides useful in the present invention may comprise a region of at least 5 amino acids selected from the MBL protein (SEQ ID NO:21), the H-ficolin protein (Genbank accession number NM_173452), the M-ficolin protein (Genbank accession number 000602) and the L-ficolin protein (Genbank accession number NM_015838).

More specifically, scientists have identified the MASP-2 binding site on MBL to be within the 12 Gly-X-Y triplets "GKD GRD GTK GEK GEP GQG LRG LQG POG KLG POG NOG PSG SOG PKG QKG DOG KS" (SEQ ID NO:26) that lie between the hinge and the neck in the C-terminal portion of the collagen-like domain of MBP (Wallis, R., et al., *J. Biol. Chem.* 279:14065, 2004). This MASP-2 binding site region is also highly conserved in human H-ficolin and human L-ficolin. A consensus binding site has been described that is present in all three lectin proteins comprising the amino acid sequence "OGK-X-GP" (SEQ ID NO:22) where the letter "O" represents hydroxyproline and the letter "X" is a hydrophobic residue (Wallis et al., 2004, supra). Accordingly, in some embodiments, MASP-2 inhibitory peptides useful in this aspect of the invention are at least 6 amino acids in length and comprise SEQ ID NO:22. Peptides derived from MBL that include the amino acid sequence "GLR GLQ GPO GKL GPO G" (SEQ ID NO:24) have been shown to bind MASP-2 in vitro (Wallis, et al., 2004, supra). To enhance binding to MASP-2, peptides can be synthesized that are flanked by two GPO triplets at each end ("GPO GPO GLR GLQ GPO GKL GPO GGP OGP O" SEQ ID NO:25) to enhance the formation of triple helices as found in the native MBL protein (as further described in Wallis, R., et al., *J. Biol. Chem.* 279:14065, 2004).

MASP-2 inhibitory peptides may also be derived from human H-ficolin that include the sequence "GAO GSO GEK GAO GPQ GPO GPO GKM GPK GEO GDO" (SEQ ID NO:27) from the consensus MASP-2 binding region in H-ficolin. Also included are peptides derived from human L-ficolin that include the sequence "GCO GLO GAO GDK GEA GTN GKR GER GPO GPO GKA GPO GPN GAO GEO" (SEQ ID NO:28) from the consensus MASP-2 binding region in L-ficolin.

MASP-2 inhibitory peptides may also be derived from the C4 cleavage site such as "LQRALEILPNRVTIKANRP-FLVFI" (SEQ ID NO:29) which is the C4 cleavage site linked to the C-terminal portion of antithrombin III (Glover, G. I., et al., *Mol. Immunol.* 25:1261 (1988)).

TABLE 3

EXEMPLARY MASP-2 INHIBITORY PEPTIDES

| SEQ ID NO | Source |
|---|---|
| SEQ ID NO: 6 | Human MASP-2 protein |
| SEQ ID NO: 8 | CUBI domain of MASP-2 (aa 1-121 of SEQ ID NO: 6) |

TABLE 3-continued

EXEMPLARY MASP-2 INHIBITORY PEPTIDES

| SEQ ID NO | Source |
|---|---|
| SEQ ID NO: 9 | CUB1EGF domains of MASP-2 (aa 1-166 of SEQ ID NO: 6) |
| SEQ ID NO: 10 | CUB1EGFCUBII domains of MASP-2 (aa 1-293 of SEQ ID NO: 6) |
| SEQ ID NO: 11 | EGF domain of MASP-2 (aa 122-166) |
| SEQ ID NO: 12 | Serine-protease domain of MASP-2 (aa 429-671) |
| SEQ ID NO: 16 | MBL binding region in MASP-2 |
| SEQ ID NO: 3 | Human MAp19 |
| SEQ ID NO: 21 | Human MBL protein |
| SEQ ID NO: 22<br>OGK-X-GP,<br>Where "O" = hydroxyproline and "X" is a hydrophobic amino acid residue | Synthetic peptide Consensus binding site from Human MBL and Human ficolins |
| SEQ ID NO: 23<br>OGKLG | Human MBL core binding site |
| SEQ ID NO: 24<br>GLR GLQ GPO GKL GPO G | Human MBP Triplets 6-10- demonstrated binding to MASP-2 |
| SEQ ID NO: 25<br>GPOGPOGLRGLQGPO GKLGPOGGPOGPO | Human MBP Triplets with GPO added to enhance formation of triple helices |
| SEQ ID NO: 26<br>GKDGRDGTKGEKGEP GQGLRGLQGPOGKLG POGNOGPSGSOGPKG QKGDOGKS | Human MBP Triplets 1-17 |
| SEQ ID NO: 27<br>GAOGSOGEKGAOGPQ GPOGPOGKMGPKGEO GDO | Human H-Ficolin (Hataka) |
| SEQ ID NO: 28<br>GCOGLOGAOGDKGE AGTNGKRGERGPOGP OGKAGPOGPNGAOGE O | Human L-Ficolin P35 |
| SEQ ID NO: 29<br>LQRALEILPNR VTIKA NRPFL VFI | Human C4 cleavage site |
| SEQ ID NO: 72<br>LEVTCEPGTTFKDKCNT CRCGSDGKSAVCTKLW CNQ | SGMI-2L (full-length) |
| SEQ ID NO: 73<br>TCEPGTTFKDKCNTCRC GSDGKSAVCTKLWCNQ | SGMI-2M (medium truncated version) |
| SEQ ID NO: 74<br>TCRCGSDGKSAVCTKL WCNQ | SGMI-2S (short truncated version) |

Note: The letter "O" represents hydroxyproline. The letter "X" is a hydrophobic residue.

Peptides derived from the C4 cleavage site as well as other peptides that inhibit the MASP-2 serine protease site can be chemically modified so that they are irreversible protease inhibitors. For example, appropriate modifications may include, but are not necessarily limited to, halomethyl ketones (Br, Cl, I, F) at the C-terminus, Asp or Glu, or appended to functional side chains; haloacetyl (or other α-haloacetyl) groups on amino groups or other functional side chains; epoxide or imine-containing groups on the amino or carboxy termini or on functional side chains; or imidate esters on the amino or carboxy termini or on functional side chains. Such modifications would afford the advantage of permanently inhibiting the enzyme by covalent attachment of the peptide. This could result in lower effective doses and/or the need for less frequent administration of the peptide inhibitor.

In addition to the inhibitory peptides described above, MASP-2 inhibitory peptides useful in the method of the invention include peptides containing the MASP-2-binding CDRH3 region of anti-MASP-2 MoAb obtained as described herein. The sequence of the CDR regions for use in synthesizing the peptides may be determined by methods known in the art. The heavy chain variable region is a peptide that generally ranges from 100 to 150 amino acids in length. The light chain variable region is a peptide that generally ranges from 80 to 130 amino acids in length. The CDR sequences within the heavy and light chain variable regions include only approximately 3-25 amino acid sequences that may be easily sequenced by one of ordinary skill in the art.

Those skilled in the art will recognize that substantially homologous variations of the MASP-2 inhibitory peptides described above will also exhibit MASP-2 inhibitory activity. Exemplary variations include, but are not necessarily limited to, peptides having insertions, deletions, replacements, and/or additional amino acids on the carboxy-terminus or amino-terminus portions of the subject peptides and mixtures thereof. Accordingly, those homologous peptides having MASP-2 inhibitory activity are considered to be useful in the methods of this invention. The peptides described may also include duplicating motifs and other modifications with conservative substitutions. Conservative variants are described elsewhere herein, and include the exchange of an amino acid for another of like charge, size or hydrophobicity and the like.

MASP-2 inhibitory peptides may be modified to increase solubility and/or to maximize the positive or negative charge in order to more closely resemble the segment in the intact protein. The derivative may or may not have the exact primary amino acid structure of a peptide disclosed herein so long as the derivative functionally retains the desired property of MASP-2 inhibition. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer, which mimics the natural conformation, charge distribution and function of the parent peptide. Peptides may also be modified by acetylation or amidation.

The synthesis of derivative inhibitory peptides can rely on known techniques of peptide biosynthesis, carbohydrate biosynthesis and the like. As a starting point, the artisan may rely on a suitable computer program to determine the conformation of a peptide of interest. Once the conformation of peptide disclosed herein is known, then the artisan can determine in a rational design fashion what sort of substitutions can be made at one or more sites to fashion a derivative that retains the basic conformation and charge distribution of the parent peptide but which may possess characteristics which are not present or are enhanced over those found in the parent peptide. Once candidate derivative molecules are identified, the derivatives can be tested to determine if they function as MASP-2 inhibitory agents using the assays described herein.

Screening for MASP-2 Inhibitory Peptides

One may also use molecular modeling and rational molecular design to generate and screen for peptides that mimic the molecular structures of key binding regions of MASP-2 and inhibit the complement activities of MASP-2. The molecular structures used for modeling include the CDR regions of anti-MASP-2 monoclonal antibodies, as well as the target regions known to be important for MASP-2 function including the region required for dimerization, the region involved in binding to MBL, and the serine protease active site as previously described. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo synthesis of Macromolecular Binding and Catalytic Sties," *TRIP* 2(5) 1994.

As an illustrative example, one method of preparing mimics of MASP-2 binding peptides is as follows. Functional monomers of a known MASP-2 binding peptide or the binding region of an anti-MASP-2 antibody that exhibits MASP-2 inhibition (the template) are polymerized. The template is then removed, followed by polymerization of a second class of monomers in the void left by the template, to provide a new molecule that exhibits one or more desired properties that are similar to the template. In addition to preparing peptides in this manner, other MASP-2 binding molecules that are MASP-2 inhibitory agents such as polysaccharides, nucleosides, drugs, nucleoproteins, lipoproteins, carbohydrates, glycoproteins, steroid, lipids and other biologically active materials can also be prepared. This method is useful for designing a wide variety of biological mimics that are more stable than their natural counterparts because they are typically prepared by free radical polymerization of function monomers, resulting in a compound with a nonbiodegradable backbone.

Peptide Synthesis

The MASP-2 inhibitory peptides can be prepared using techniques well known in the art, such as the solid-phase synthetic technique initially described by Merrifield, in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein that can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

The MASP-2 inhibitory peptides that are useful in the method of the invention can also be produced in recombinant host cells following conventional techniques. To express a MASP-2 inhibitory peptide encoding sequence, a nucleic acid molecule encoding the peptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene, which are suitable for selection of cells that carry the expression vector.

Nucleic acid molecules that encode a MASP-2 inhibitory peptide can be synthesized with "gene machines" using protocols such as the phosphoramidite method. If chemically synthesized double-stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes, synthetic genes (double-stranded) are assembled in modular form from single-stranded fragments that are from 20 to 100 nucleotides in length. For reviews on polynucleotide synthesis, see, for example, Glick and Pasternak, "*Molecular Biotechnology, Principles and Applications of Recombinant DNA*", ASM Press, 1994; Itakura, K., et al., *Annu. Rev. Biochem.* 53:323, 1984; and Climie, S., et al., *Proc. Nat'l Acad. Sci. USA* 87:633, 1990.

Small Molecule MASP-2 Inhibitors

In some embodiments, MASP-2 inhibitory agents are small molecule inhibitors including natural, semi-synthetic, and synthetic substances that have a low molecular weight (e.g., between 50 and 1000 Da), such as for example, peptides, peptidomimetics, and non-peptide inhibitors (e.g., oligonucleotides and organic compounds). Small molecule inhibitors of MASP-2 can be generated based on the molecular structure of the variable regions of the anti-MASP-2 antibodies.

Small molecule inhibitors may also be designed and generated based on the MASP-2 crystal structure using computational drug design (Kuntz I. D., et al., *Science* 257:1078, 1992). The crystal structure of rat MASP-2 has been described (Feinberg, H., et al., *EMBO J.* 22:2348-2359, 2003). Using the method described by Kuntz et al., the MASP-2 crystal structure coordinates are used as an input for a computer program such as DOCK, which outputs a list of small molecule structures that are expected to bind to MASP-2. Use of such computer programs is well known to one of skill in the art. For example, the crystal structure of the HIV-1 protease inhibitor was used to identify unique nonpeptide ligands that are HIV-1 protease inhibitors by evaluating the fit of compounds found in the Cambridge Crystallographic database to the binding site of the enzyme using the program DOCK (Kuntz, I. D., et al., *J. Mol. Biol.* 161:269-288, 1982; DesJarlais, R. L., et al., *PNAS* 87:6644-6648, 1990).

Exemplary MASP-2 inhibitors include, but are not limited to, compounds disclosed in U.S. Patent Application Nos. 62/943,629, 62/943,622, 62/943,611, 62/943,599, 16/425,791 and PCT Application No. PCT/US19/34220, each of which are hereby incorporated by reference in their entirety.

In some embodiments, the small molecule is a compound of Formula (IA), (IB), (IIA), (IIB), (III), or (IV):

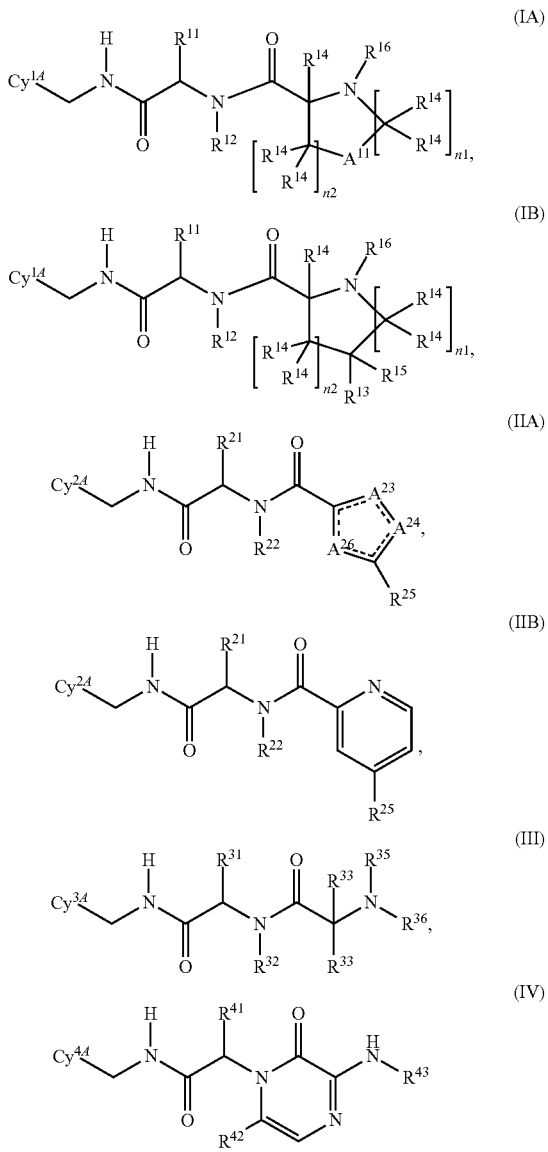

or a salt thereof, wherein:

$Cy^{1A}$ is unsubstituted or substituted $C_{6-10}$ aryl or unsubstituted or substituted 5-10 membered heteroaryl; wherein the ring atoms of the 5-10 membered heteroaryl forming $Cy^{1A}$ consist of carbon atoms and 1, 2, or 3 heteroatoms selected from O, N and S; wherein the substituted $C_{6-10}$ aryl or substituted 5-10 membered heteroaryl forming $Cy^{1A}$ are substituted with 1, 2, 3, 4 or 5 substituents each independently selected from $R^{Cy1A}$, halogen, $C_{1-6}$ haloalkyl, CN, $OR^{a11}$, $S^{Ra11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)NR$^{c11}$R$^{d11}$, NR$^{c11}$C(O)OR$^{a11}$, C(=NR$^{e11}$)NR$^{c11}$R$^{d11}$, C(=NOR$^{a11}$)NR$^{c11}$R$^{d11}$, C(=NOC(O) R$^{b11}$)NR$^{c11}$R$^{d11}$, C(=NR$^{e11}$)NR$^{c11}$C(O)R$^{a11}$, NR$^{c11}$C(=NR$^{e11}$)NR$^{c11}$R$^{d11}$, S(O)R$^{b11}$, S(O) NR$^{c11}$R$^{d11}$, S(O)$_2$R$^{b11}$, NR$^{c11}$S(O)$_2$R$^{b11}$, S(O)$_2$NR$^{c11}$R$^{d11}$ and oxo;

each R$^{Cy1A}$ is independently selected from C$_{1-6}$ alkyl, C$_{2-6}$ alkenyl, C$_{2-6}$ alkynyl, C$_{6-10}$ aryl, 5-10 membered heteroaryl, C$_{3-10}$ cycloalkyl and 4-10 membered heterocycloalkyl, wherein the ring atoms of the 5-10 membered heteroaryl or 4-10-membered heterocycloalkyl forming R$^{Cy1A}$ consist of carbon atoms and 1, 2, 3 or 4 heteroatoms selected from O, N and S, wherein each C$_{1-6}$ alkyl, C$_{2-6}$ alkenyl, or C$_{2-6}$ alkynyl forming R$^{Cy1A}$ is independently unsubstituted or substituted with 1, 2 or 3 substituents independently selected from halogen, CN, OR$^{a11}$, SR$^{a11}$, C(O)R$^{b11}$, C(O)NR$^{c11}$R$^{d11}$, C(O) OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)NR$^{c11}$R$^{d11}$, NR$^{c11}$C(O) OR$^{a11}$, C(=NR$^{e11}$)NR$^{c11}$R$^{d11}$, NR$^{c11}$C(=NR$^{e11}$) NR$^{c11}$R$^{d11}$, S(O)R$^{b11}$, S(O)NR$^{c11}$R$^{d11}$, S(O)$_2$R$^{b11}$, NR$^{c11}$S(O)$_2$R$^{b11}$, S(O)$_2$NR$^{c11}$R$^{d11}$ and oxo, and wherein each C$_{6-10}$ aryl, 5-10 membered heteroaryl, C$_{3-10}$ cycloalkyl and 4-10 membered heterocycloalkyl forming R$^{Cy1A}$ is independently unsubstituted or substituted with 1, 2 or 3 substituents independently selected from halogen, C$_{1-6}$ alkyl, C$_{2-6}$ alkenyl, C$_{2-6}$ alkynyl, C$_{1-6}$ haloalkyl, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O) NR$^{c11}$R$^{d11}$, NR$^{c11}$R$^{d11}$, NR$^{c11}$C(O)R$^{b11}$, NR$^{c11}$C(O) NR$^{c11}$R$^{d11}$, NR$^{c11}$C(O)OR$^{a11}$, C(=NR$^{e11}$)NR$^{c11}$R$^{d11}$, NR$^{c11}$C(=NR$^{e11}$)NR$^{c11}$R$^{d11}$, S(O)R$^{b11}$, S(O) NR$^{c11}$R$^{d11}$, S(O)$_2$R$^{b11}$, NR$^{c11}$S(O)$_2$R$^{b11}$, S(O)$_2$NR$^{c11}$R$^{d11}$ and oxo;

R$^{11}$ is H or C$_{1-6}$ alkyl, C$_{6-10}$ aryl-C$_{1-6}$ alkyl or 5-10 membered heteroaryl-C$_{1-6}$ alkyl, wherein the C$_{1-6}$ alkyl forming R$^{11}$ is unsubstituted or substituted by 1, 2 or 3 substituents independently selected from halogen, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O) R$^{b11}$, NR$^{c11}$C(O)NR$^{c11}$R$^{d11}$, NR$^{c11}$C(O)OR$^{a11}$, C(=NR$^{e11}$)NR$^{c11}$R$^{d11}$, NR$^{c11}$C(=NR$^{e11}$)NR$^{c11}$R$^{d11}$, S(O)R$^{b11}$, S(O)NR$^{c11}$R$^{d11}$, S(O)$_2$R$^{b11}$, NR$^{c11}$ S(O)$_2$R$^{b11}$, S(O)$_2$NR$^{c11}$R$^{d11}$ and oxo, and wherein the C$_{6-10}$ aryl-C$_{1-6}$ alkyl or 5-10 membered heteroaryl-C$_{1-6}$ alkyl forming R$^{11}$ is unsubstituted or substituted by 1, 2 or 3 substituents independently selected from C$_{1-6}$ alkyl, C$_{2-6}$ alkenyl, C$_{2-6}$ alkynyl, C$_{1-6}$ haloalkyl, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O) R$^{b11}$, NR$^{c11}$C(O)NR$^{c11}$R$^{d11}$, NR$^{c11}$C(O)OR$^{a11}$, C(=NR$^{e11}$)NR$^{c11}$R$^{d11}$, NR$^{c11}$C(=NR$^{e11}$)NR$^{c11}$R$^{d11}$, S(O)R$^{b11}$, S(O)NR$^{c11}$R$^{d11}$, S(O)$_2$R$^{b11}$, NR$^{c11}$S(O) $_2$R$^{b11}$, S(O)$_2$NR$^{c11}$R$^{d11}$ and oxo;

R$^{12}$ is H or C$_{1-6}$ alkyl; or

R$^{11}$ and R$^{12}$, together with the groups to which they are attached, form a 4-6 membered heterocycloalkyl ring;

A$^{11}$ is CR$^{13}$R$^{15}$ or N;

each R$^{13}$ is independently Cy$^{1B}$, (CR$^{13A}$R$^{13B}$)$_{n3}$Cy$^{1B}$, (C$_{1-6}$ alkylene)Cy$^{1B}$, (C$_{2-6}$ alkenylene)Cy$^{1B}$, (C$_{2-6}$ alkynylene)Cy$^{1B}$ or OCy$^{1B}$, wherein the C$_{1-6}$ alkylene, C$_{2-6}$ alkenylene, or C$_{2-6}$ alkynylene component of R$^{13}$ is unsubstituted or substituted by 1, 2, 3, 4 or 5 substituents each independently selected from the group consisting of halogen, CN, OR$^{a11}$, SR$^{a11}$, C(O)R$^{b11}$, C(O) NR$^{c11}$R$^{d11}$, C(O)OR$^{a11}$, OC(O)R$^{b11}$, OC(O) NR$^{c11}$R$^{d11}$, NR$^{c11}$R$^{d11}$, NR$^{c11}$HC(O)R$^{b11}$, NR$^{c11}$C(O) NR$^{c11}$R$^{d11}$, NR$^{c11}$C(O)OR$^{a11}$, C(=NR$^{e11}$)NR$^{c11}$R$^{d11}$, NR$^{c11}$C(=NR$^{e11}$)NR$^{c11}$R$^{d11}$, S(O)R$^{b11}$, S(O) NR$^{c11}$R$^{d11}$, S(O)$_2$R$^{b11}$, NR$^{c11}$S(O)$_2$R$^{b11}$, S(O)$_2$NR$^{c11}$R$^{d11}$ and oxo;

each R$^{14}$ is independently selected from H and C$_{1-6}$ alkyl;

R$^{15}$ is selected from H, R$^{13}$, C$_{1-6}$ alkyl and OH;

a pair of R$^{14}$ groups attached to adjacent carbon atoms, or a pairing of R$^{14}$ and R$^{15}$ groups attached to adjacent carbon atoms, may, independently of other occurrences of R$^{14}$, together be replaced a bond connecting the adjacent carbon atoms to which the pair of R$^{14}$ groups or pairing of R$^{14}$ and R$^{15}$ groups is attached, such that the adjacent carbon atoms are connected by a double bond; or a pair of R$^{14}$ groups attached to the same carbon atom, or a pairing of R$^{13}$ and R$^{15}$ groups attached to the same carbon atom, may, independently of other occurrences of R$^{14}$, and together with the carbon atom to which the pair of R$^{14}$ groups or pairing of R$^{13}$ and R$^{15}$ groups is attached together form a spiro-fused C$_{3-10}$ cycloalkyl or 4-10 membered heterocycloalkyl ring, wherein the ring atoms of the 4-10 membered heterocycloalkyl ring formed consist of carbon atoms and 1, 2, or 3 heteroatoms selected from O, N and S, wherein the spiro-fused C$_{3-10}$ cycloalkyl or 4-10 membered heterocycloalkyl ring formed is optionally further substituted with 1, 2 or 3 substituents independently selected from halogen, C$_{1-6}$ alkyl, C$_{2-6}$ alkenyl, C$_{2-6}$ alkynyl, haloalkyl, CN, OR$^{a11}$, SR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O) R$^{b11}$, NR$^{c11}$C(O)NR$^{c11}$R$^{d11}$, NR$^{c11}$C(O)OR$^{a11}$, C(=NR$^{e11}$)NR$^{c11}$R$^{d11}$, NR$^{c11}$C(=NR$^{e11}$)NR$^{c11}$R$^{d11}$, S(O)R$^{b11}$, S(O)NR$^{c11}$R$^{d11}$, S(O)$_2$R$^{b11}$, NR$^{c11}$ S(O)$_2$R$^{b11}$, S(O)$_2$NR$^{c11}$R$^{d11}$ and oxo; or pairs of R$^{14}$ groups attached to adjacent carbon atoms, or a pairing of R$^{14}$ and R$^{15}$ groups attached to adjacent carbon atoms, may, independently of other occurrences of R$^{14}$, together with the adjacent carbon atoms to which the pair of R$^{14}$ groups or pairing of R$^{14}$ and R$^{5}$ groups is attached, form a fused C$_{3-10}$ cycloalkyl or 4-10 membered heterocycloalkyl ring, wherein the ring atoms of the 4-10 membered heterocycloalkyl ring formed consist of carbon atoms and 1, 2, or 3 heteroatoms selected from O, N and S, wherein the fused C$_{3-10}$ cycloalkyl or 4-10 membered heterocycloalkyl ring formed is optionally further substituted with 1, 2 or 3 substituents independently selected from halogen, C$_{1-6}$ alkyl, C$_{2-6}$ alkenyl, C$_{2-6}$ alkynyl, haloalkyl, CN, OR$^{a11}$, SR$^{a11}$, C(O)R$^{b11}$, C(O)NR$^{c11}$R$^{d11}$, C(O)OR$^{a11}$, OC(O) R$^{b11}$, OC(O)NR$^{c11}$R$^{d11}$, NR$^{c11}$R$^{d11}$, NR$^{c11}$C(O)R$^{b11}$, NR$^{c11}$C(O)NR$^{c11}$R$^{d11}$, NR$^{c11}$C(O)OR$^{a11}$, C(=NR$^{e11}$) NR$^{c11}$R$^{d11}$, NR$^{c11}$C(=NR$^{e11}$)NR$^{c11}$R$^{d11}$, S(O)R$^{b11}$, S(O)NR$^{c11}$R$^{d11}$, S(O)$_2$R$^{b11}$, NR$^{c11}$S(O)$_2$R$^{b11}$, S(O)$_2$NR$^{c11}$R$^{d11}$ and oxo; or a grouping of four R$^{14}$ groups attached to two adjacent carbon atoms, or a grouping of two R$^{14}$, one R$^{13}$ and one R$^{5}$ groups attached to two adjacent carbon atoms, may, independently of other occurrences of R$^{14}$, together with the two adjacent carbon atoms to which the grouping of four R$^{14}$ groups or grouping of two R$^{14}$, one R$^{13}$ and one R$^{5}$ groups are attached, form a fused C$_{6-10}$ aryl or 5-10 membered heteroaryl, C$_{3-10}$ cycloalkyl or 4-10 membered heterocycloalkyl ring, wherein the ring atoms of the 5-10 membered heteroaryl or 4-10 membered heterocycloalkyl ring formed consist of carbon atoms and 1, 2, or 3 heteroatoms selected from O, N and S, and wherein the fused $C_{6-10}$ aryl or 5-10 membered heteroaryl, $C_{3-10}$ cycloalkyl or 4-10 membered heterocycloalkyl ring formed is optionally further substituted with 1, 2 or 3 substituents independently selected from halogen, $C_{1-6}$ alkyl, $C_{2-6}$ alkenyl, $C_{2-6}$ alkynyl, haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NRC(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

n1 is 1 or 2;

n2 is 0, 1 or 2;

provided that the sum of n1 and n2 is 1, 2 or 3;

provided that if n1 is 1 or n2 is 0, then $A^{11}$ is $CR^{13}R^{15}$;

n3 is 0, 1 or 2;

each $R^{13A}$ is independently H or $C_{1-6}$ alkyl;

each $R^{13B}$ is independently H or $C_{1-6}$ alkyl; or or $R^{13A}$ and $R^{13B}$ attached to the same carbon atom, independently of any other $R^{13A}$ and $R^{13B}$ groups, together may form —$(CH_2)_{2-5}$—, thereby forming a 3-6 membered cycloalkyl ring;

$Cy^{1B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{1B}$ are substituted with 1, 2, 3, 4 or 5 substituents each independently selected from $R^{Cy1B}$, halogen, $C_{1-6}$ haloalkyl, CN, $OR^{a11}$, $S^{Ra11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

wherein each $R^{Cy1B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy1B}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)^{Rb11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; and wherein each $C_{6-10}$ aryl, 5-10 membered heteroaryl, $C_{3-10}$ cycloalkyl and 4-10 membered heterocycloalkyl forming $R^{Cy1B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $S(O)R^{b11}$, $S(O)NR^{c11}R^{d11}$, $S(O)_2R^{b11}$, $NR^{c11}$ $S(O)_2R^{b11}$, $S(O)_2NR^{c11}R^{d11}$ and oxo;

$R^{16}$ is H, $Cy^{1C}$, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl forming $R^{16}$ is unsubstituted or substituted by 1, 2, 3, 4 or 5 substituents selected from the group consisting of $Cy^{1C}$, halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo, provided that no more than one of the substituents of $R^{16}$ is $Cy^{1C}$;

$Cy^{1C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{1C}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{1C}$ are substituted with 1, 2, 3, 4 or 5 substituents each independently selected from $R^{Cy1C}$, halogen, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)NR^{c11}R^{d11}$, $NR^{c11}C(O)OR^{a11}$, $C(=NR^{e11})NR^{c11}R^{d11}$, $C(=NOR^{a11})NR^{c11}R^{d11}$, $C(=NOC(O)R^{b11})NR^{c11}R^{d11}$, $C(=NR^{e11})NR^{c11}C(O)OR^{a11}$, $NR^{c11}C(=NR^{e11})NR^{c11}R^{d11}$, $S(O)NR^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

wherein each $R^{Cy1C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy1C}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy1C}$ is independently unsubstituted or substituted with 1, 2 or 3 substituents independently selected from halogen, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)^{Rb11}$, $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo; and wherein each $C_{6-10}$ aryl, 5-10 membered heteroaryl, $C_{3-10}$ cycloalkyl and 4-10 membered heterocycloalkyl forming $R^{Cy1C}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$ $NR^{c11}C(O)NR^{c11}R^{d11}$, $NR^{c11}C(O)OR^{a11}$, $C(=NR^{e11})NR^{c11}R^{d11}$, $NR^{c11}C(=NR^{e11})NR^{c11}R^{d11}$, $S(O)R^{b11}$, $S(O)NR^{c11}R^{d11}$, $S(O)_2R^{b11}$, $NR^{c11}S(O)_2R^{b11}$, $S(O)_2NR^{c11}R^{d11}$ and oxo;

$R^{a11}$, $R^{b11}$, $R^{c11}$ and $R^{d11}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a11}$, $R^{b11}$, $R^{c11}$ and $R^{d11}$ are each optionally substituted with 1, 2, 3, 4 or 5 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

or $R^{c11}$ and $R^{d11}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)NR^{c12}R^{d12}$, $NR^{c12}C(O)OR^{a12}$, $C(=NR^{e12})NR^{c12}R^{d12}$, $NR^{c12}C(=NR^{e12})NR^{c12}R^{d12}$, $S(O)R^{b12}$, $S(O)NR^{c12}R^{d12}$, $S(O)_2R^{b12}$, $NR^{c12}S(O)_2R^{b12}$, $S(O)_2NR^{c12}R^{d12}$ and oxo;

$R^{a12}$, $R^{b12}$, $R^{c12}$ and $R^{d12}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a12}$, $R^{b12}$, $R^{c12}$ and $R^{d12}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

or $R^{c12}$ and $R^{d12}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

$R^{e11}$ and $R^{e12}$ are each, independently, H, CN or $NO_2$;

$Cy^{2A}$ is unsubstituted or substituted $C_{6-10}$ aryl or unsubstituted or substituted 5-10 membered heteroaryl; wherein the ring atoms of the 5-10 membered heteroaryl forming $Cy^{2A}$ consist of carbon atoms and 1, 2, or 3 heteroatoms selected from O, N and S; wherein the substituted $C_{6-10}$ aryl or substituted 5-10 membered heteroaryl forming $Cy^{2A}$ are substituted with 1, 2, 3, 4 or 5 substituents each independently selected from $R^{Cy2A}$, halogen, $C_{1-6}$ haloalkyl, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $C(=NOR^{a21})NR^{c21}R^{d21}$, $C(=NOC(O)R^{b21})NR^{c21}R^{d21}$, $C(=NR^{e21})NR^{c21}C(O)OR^{a21}$, $NR^{c21}C(=NR^{e21})NR^{c21}R^{d21}$ $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

each $R^{Cy2A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy2A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy2A}$ is independently unsubstituted or substituted with 1, 2 or 3 substituents independently selected from halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo, and wherein each $C_{6-10}$ aryl, 5-10 membered heteroaryl, $C_{3-10}$ cycloalkyl and 4-10 membered heterocycloalkyl forming $R^{Cy2A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{21}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{21}$ is unsubstituted or substituted by 1, 2 or 3 substituents independently selected from halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$ $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo, and wherein the $C_{6-10}$ aryl-$C_{1-6}$ alkyl or 5-10 membered heteroaryl-$C_{1-6}$ alkyl forming $R^{21}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{22}$ is H or $C_{1-6}$ alkyl; or $R^{21}$ and $R^{22}$, together with the groups to which they are attached, form a 4-6 membered heterocycloalkyl ring;

$A^{23}$ is N or $NR^{23}$;

$A^{24}$ is $CR^{24}$; N or $NR^{24}$, $A^{26}$ is $CR^{26}$ or S;

provided that $A^{23}$, $A^{24}$ and $A^{26}$ in Formula (IIA) are selected such that the ring comprising $A^{23}$, $A^{24}$ and $A^{26}$ is a heteroaryl ring and the symbol $\rightleftharpoons$ represents an aromatic ring (normalized) bond;

$R^{23}$ is H or $C_{1-6}$ alkyl;

$R^{24}$ is H; $C_{1-6}$ alkyl or phenyl;

$R^{25}$ is $Cy^{2B}$, $(CR^{25A}R^{25B})_{n25}Cy^{2B}$, $(C_{1-6}$ alkylene) $Cy^{2B}$, $(C_{2-6}$ alkenylene) $Cy^{2B}$, or $(C_{2-6}$ alkynylene) $Cy^{2B}$, wherein the $C_{1-6}$ alkylene, $C_{2-6}$ alkenylene, or $C_{2-6}$ alkynylene component of $R^{25}$ is unsubstituted or substituted by 1, 2, 3, 4 or 5 substituents each independently selected from the group consisting of halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{26}$ is H or $C_{1-6}$ alkyl;

each $R^{25A}$ is H or $C_{1-6}$ alkyl;

each $R^{25B}$ is H or $C_{1-6}$ alkyl;

n25 is 0, 1 or 2;

$Cy^{2B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{2B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{2B}$ are substituted with 1, 2, 3, 4 or 5 substituents each independently selected from $R^{Cy2B}$, halogen, $C_{1-6}$ haloalkyl, CN, $OR^{a21}$, $SR^{a21}$, $C(O)R^{b21}$, $C(O)NR^{c21}R^{421}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $C(=NOR^{a21})NR^{c21}R^{d21}$, $C(=NOC(O)R^{b21})NR^{c21}R^{d21}$, $C(=NR^{e21})NR^{c21}C(O)OR^{a21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

wherein each $R^{Cy2B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy2B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy2B}$ is independently unsubstituted or substituted with 1, 2 or 3 substituents independently selected from halogen, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo; and wherein each $C_{6-10}$ aryl, 5-10 membered heteroaryl, $C_{3-10}$ cycloalkyl and 4-10 membered heterocycloalkyl forming $R^{Cy2B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)NR^{c21}R^{d21}$, $NR^{c21}C(O)OR^{a21}$, $C(=NR^{e21})NR^{c21}R^{d21}$, $NR^{c21}C(=NR^{e21})NR^{c21}R^{d21}$, $S(O)R^{b21}$, $S(O)NR^{c21}R^{d21}$, $S(O)_2R^{b21}$, $NR^{c21}S(O)_2R^{b21}$, $S(O)_2NR^{c21}R^{d21}$ and oxo;

$R^{a21}$, $R^{b21}$, $R^{c21}$ and $R^{d21}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a21}$, $R^{b21}$, $R^{c21}$ and $R^{d21}$ are each optionally substituted with 1, 2, 3, 4 or 5 substituents independently selected from $C_{1-6}$ alkyl, halo, CN, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)NR^{c22}R^{d22}$, $NR^{c22}C(O)OR^{a22}$, $C(=NR^{e22})NR^{c22}R^{d22}$, $NR^{c22}C(=NR^{e22})NR^{c22}R^{d22}$, $S(O)R^{b22}$, $S(O)NR^{c22}R^{d22}$, $S(O)_2R^{b22}$, $NR^{c22}S(O)_2R^{b22}$, $S(O)_2NR^{c22}R^{d22}$ and oxo;

or $R^{c21}$ and $R^{d21}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)NR^{c22}R^{422}$, $NR^{c22}C(O)OR^{a22}$, $C(=NR^{e22})NR^{c22}R^{d22}$, $NR^{c22}C(=NR^{e22})NR^{c22}R^{d22}$, $S(O)R^{b22}$, $S(O)NR^{c22}R^{d22}$, $S(O)_2R^{b22}$, $NR^{22}S(O)_2R^{b22}$, $S(O)_2NR^{c22}R^{d22}$ and oxo;

$R^{a22}$, $R^{b22}$, $R^{c22}$ and $R^{d22}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a22}$, $R^{b22}$, $R^{c22}$ and $R^{d22}$ are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

or $R^{c22}$ and $R^{d22}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

$R^{e21}$ and $R^{e22}$ are each, independently, H, CN or $NO_2$;

$Cy^{3A}$ is unsubstituted or substituted $C_{6-10}$ aryl or unsubstituted or substituted 5-10 membered heteroaryl; wherein the ring atoms of the 5-10 membered heteroaryl forming $Cy^{3A}$ consist of carbon atoms and 1, 2, or 3 heteroatoms selected from O, N and S; wherein the substituted $C_{6-10}$ aryl or substituted 5-10 membered heteroaryl forming $Cy^{3A}$ are substituted with 1, 2, 3, 4 or 5 substituents each independently selected from $R^{Cy3A}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})$ $NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

each $R^{Cy3A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy3A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy3A}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$ $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$ $NR^{c31}C(=NR^{c31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo, and wherein each $C_{6-10}$ aryl, 5-10 membered heteroaryl, $C_{3-10}$ cycloalkyl and 4-10 membered heterocycloalkyl forming $R^{Cy3A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$ $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{31}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{31}$ is unsubstituted or substituted by 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$ $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo, and wherein the $C_{6-10}$ aryl-$C_{1-6}$ alkyl or 5-10 membered heteroaryl-$C_{1-6}$ alkyl forming $R^{31}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{32}$ is H or $C_{1-6}$ alkyl; or $R^{31}$ and $R^{32}$, together with the groups to which they are attached, form a 4-6 membered heterocycloalkyl ring;

$R^{33}$ is $Cy^{3B}$, $(CR^{33A}R^{33B})_{n33}Cy^{3B}$, $(C_{1-6}$ alkylene$)Cy^{3B}$, $(C_{2-6}$ alkenylene$)Cy^{3B}$, or $(C_{2-6}$ alkynylene$)Cy^{3B}$, wherein the $C_{1-6}$ alkylene, $C_{2-6}$ alkenylene, or $C_{2-6}$ alkynylene component of $R^{35}$ is unsubstituted or substituted by 1, 2, 3, 4 or 5 substituents each independently selected from the group consisting of halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $NR^{c31}C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

each $R^{33A}$ is independently H or $C_{1-6}$ alkyl;

each $R^{33B}$ is independently H or $C_{1-6}$ alkyl; or or $R^{33A}$ and $R^{33B}$ attached to the same carbon atom, independently of any other $R^{33A}$ and $R^{33B}$ groups, together may form —$(CH_2)_{2-5}$—, thereby forming a 3-6 membered cycloalkyl ring;

n33 is 0, 1, 2 or 3;

$Cy^{3B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{3B}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{3B}$ are substituted with 1, 2, 3, 4 or 5 substituents each independently selected from $R^{Cy3B}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$ $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

wherein each $R^{Cy3B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy3B}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy3B}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; and wherein each $C_{6-10}$ aryl, 5-10 membered heteroaryl, $C_{3-10}$ cycloalkyl and 4-10 membered heterocycloalkyl forming $R^{Cy3B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}R^{d31}$, $NR^{c31}C(O)OR^{a31}$, $C(=NR^{e31})NR^{c31}R^{d31}$ $NR^{c31}C(=NR^{e31})NR^{c31}R^{d31}$ $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{34}$ is selected from H and $C_{1-6}$ alkyl;

$R^{35}$ is selected from H, unsubstituted or substituted $C_{1-6}$ alkyl and $Cy^{3C}$, wherein the substituted $C_{1-6}$ alkyl forming $R^{35}$ is substituted by 1, 2, 3, 4 or 5 substituents selected from the group consisting of $Cy^{3C}$, halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})$ $NR^{c31}R^{d31}$ $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; provided that no more than one of the substituents of $R^{35}$ is $Cy^{3C}$;

$Cy^{3C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or 4-10 membered heterocycloalkyl forming $Cy^{3C}$ consist of carbon atoms and 1, 2 or 3 heteroatoms selected from O, N and S; and wherein the substituted $C_{6-10}$ aryl, substituted 5-10 membered heteroaryl, substituted $C_{3-10}$ cycloalkyl or substituted 4-10 membered heterocycloalkyl forming $Cy^{3C}$ are substituted with 1, 2, 3, 4 or 5 substituents each independently selected from $R^{Cy3C}$, halogen, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $C(=NOR^{a31})NR^{c31}R^{d31}$, $C(=NOC(O)R^{b31})NR^{c31}R^{d31}$, $C(=NR^{e31})NR^{c31}C(O)OR^{a31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

wherein each $R^{Cy3C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10 membered heterocycloalkyl forming $R^{Cy3C}$ consist of carbon atoms and 1, 2 or 3 heteroatoms selected from O, N and S; wherein each $C_{1-6}$ alkyl, $C_{2-6}$ alkenyl, or $C_{2-6}$ alkynyl forming $R^{Cy3C}$ is independently unsubstituted or substituted with 1, 2 or 3 substituents independently selected from halogen, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo; and wherein each $C_{6-10}$ aryl, 5-10 membered heteroaryl, $C_{3-10}$ cycloalkyl and 4-10 membered heterocycloalkyl forming $R^{Cy3C}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a31}$, $SR^{a31}$, $C(O)R^{b31}$, $C(O)NR^{c31}R^{d31}$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)NR^{c31}R^{d31}$, $NR^{c31}C(O)OR^{a31}$, $C(=NR^{e31})NR^{c31}R^{d31}$, $NR^{c31}C(=NR^{e31})NR^{c31}R^{d31}$, $S(O)R^{b31}$, $S(O)NR^{c31}R^{d31}$, $S(O)_2R^{b31}$, $NR^{c31}S(O)_2R^{b31}$, $S(O)_2NR^{c31}R^{d31}$ and oxo;

$R^{36}$ is selected from H and $C_{1-6}$ alkyl;

$R^{a31}$, $R^{b31}$, $R^{c31}$ and $R^{d31}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a31}$, $R^{b31}$, $R^{c31}$ and $R^{d31}$ are each optionally substituted with 1, 2, 3, 4 or 5 substituents independently selected from $C_{1-6}$ alkyl, halo, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)NR^{c32}R^{d32}$, $NR^{c32}C(O)OR^{a32}$, $C(=NR^{e32})NR^{c32}R^{d32}$, $NR^{c32}C(=NR^{e32})NR^{c32}R^{d32}$, $S(O)R^{b32}$, $S(O)NR^{c32}R^{d32}$, $S(O)_2R^{b32}$, $NR^{c32}S(O)_2R^{b32}$, $S(O)_2NR^{c32}R^{d32}$ and oxo;

or $R^{c31}$ and $R^{d31}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a32}$, $SR^{a32}$, $C(O)R^{b32}$, $C(O)NR^{c32}R^{d32}$, $C(O)OR^{a32}$, $OC(O)R^{b32}$, $OC(O)NR^{c32}R^{d32}$, $NR^{c32}R^{d32}$ $NR^{c32}C(O)R^{b32}$, $NR^{c32}C(O)NR^{c32}R^{d32}$, $NR^{c32}C(O)OR^{a32}$, $C(=NR^{e32})NR^{c32}R^{d32}$, $NR^{c32}C(=NR^{e32})NR^{c32}R^{d32}$, $S(O)R^{b32}$, $S(O)NR^{c32}R^{d32}$, $S(O)_2R^{b32}$, $NR^{c32}S(O)_2R^{b32}$, $S(O)_2NR^{c32}R^{d32}$ and oxo;

$R^{a32}$, $R^{b32}$, $R^{c32}$ and $R^{d32}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a32}$, $R^{b32}$, $R^{c32}$ and $R^{d32}$ are each optionally substituted with 1, 2 or 3 substituents independently selected from OH, CN, amino, $NH(C_{1-6}$ alkyl), $N(C_{1-6}$ alkyl$)_2$, halo, $C_{1-6}$ alkyl, $C_{1-6}$ alkoxy, $C_{1-6}$ haloalkyl, $C_{1-6}$ haloalkoxy and oxo;

or $R^{c32}$ and $R^{d32}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, $NH(C_{1-6}$ alkyl), $N(C_{1-6}$ alkyl$)_2$, halo, $C_{1-6}$ alkyl, $C_{1-6}$ alkoxy, $C_{1-6}$ haloalkyl, $C_{1-6}$ haloalkoxy and oxo; and $R^{e31}$ and $R^{e32}$ are each, independently, H, CN or $NO_2$;

$Cy^{4A}$ is unsubstituted or substituted $C_{6-10}$ aryl or unsubstituted or substituted 5-10 membered heteroaryl; wherein the ring atoms of the 5-10 membered heteroaryl forming $Cy^{4A}$ consist of carbon atoms and 1, 2, or 3 heteroatoms selected from O, N and S; wherein the substituted $C_{6-10}$ aryl or substituted 5-10 membered heteroaryl forming $Cy^{4A}$ are substituted with 1, 2, 3, 4 or 5 substituents each independently selected from $R^{Cy4A}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

each $R^{Cy4A}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4A}$ consist of carbon atoms and 1, 2, 3 or 4 heteroatoms selected from O, N and S, wherein each $C_{1-6}$ alkyl, $C_{2-6}$ alkenyl, or $C_{2-6}$ alkynyl forming $R^{Cy4A}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, and wherein each $C_{6-10}$ aryl, 5-10 membered heteroaryl, $C_{3-10}$ cycloalkyl and 4-10 membered heterocycloalkyl forming $R^{Cy4A}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{41}$ is H or $C_{1-6}$ alkyl, $C_{6-10}$ aryl-$C_{1-6}$ alkyl or 5-10 membered heteroaryl-$C_{1-6}$ alkyl, wherein the $C_{1-6}$ alkyl forming $R^{41}$ is unsubstituted or substituted by 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$ $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, and wherein the $C_{6-10}$ aryl-$C_{1-6}$ alkyl or 5-10 membered heteroaryl-$C_{1-6}$ alkyl forming $R^{41}$ is unsubstituted or substituted by 1, 2 or 3 substituents independently selected from $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{42}$ is H, $C_{1-6}$ alkyl, $C_{2-6}$ alkenyl, $C_{2-6}$ alkynyl, or $Cy^{4B}$; wherein each of the $C_{1-6}$ alkyl, $C_{2-6}$ alkenyl, or $C_{2-6}$ alkynyl, forming $R^{42}$ is unsubstituted or substituted by 1, 2, 3, 4 or 5 substituents selected from the group consisting of $Cy^{4B}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$ $NR^{c41}C(O)R^{b41}$ $NR^{c41}C(O)NR^{c41}R^{d41}$, $NR^{c41}C(O)OR^{a41}$, $C(=NR^{e41})NR^{c41}R^{d41}$ $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo; provided that no more than one of the substituents is $Cy^{4B}$;

$Cy^{4B}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl; wherein the ring atoms of the 5-10 membered heteroaryl or unsubstituted or substituted 4-10 membered heterocycloalkyl forming $Cy^{4B}$ consist of carbon atoms and 1, 2 or 3 heteroatoms selected from O, N and S; and wherein the substituted $C_{6-10}$ aryl, substituted 5-10 membered heteroaryl substituted $C_{3-10}$ cycloalkyl, or 4-10 membered heterocycloalkyl forming $Cy^{4B}$ is substituted with 1, 2, 3, 4 or 5 substituents each independently selected from $R^{Cy4B}$, halogen, $C_{1-6}$ haloalkyl, CN, $OR^{a41}$, $SR^{a41}$, $C(O)R^{b41}$, $C(O)NR^{c41}R^{d41}$, $C(O)$ $OR^{a41}$, $OC(O)R^{b41}$, $OC(O)NR^{c41}R^{d41}$, $NR^{c41}R^{d41}$, $NR^{c41}C(O)R^{b41}$ $NR^{c41}C(O)NR^{c41}R^{d41}$, $NR^{c41}C(O)$ $OR^{a41}$, $C(=NR^{e41})NR^{c41}R^{d41}$, $C(=NOR^{a41})$ $NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})$ $NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

wherein each $R^{Cy4B}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4B}$ consist of carbon atoms and 1, 2, or 3 heteroatoms selected from O, N and S, and wherein each $C_{1-6}$ alkyl, $C_{2-6}$ alkenyl, or $C_{2-6}$ alkynyl forming $R^{Cy4B}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)$ $NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)$ $NR^{c41}R^{d41}$, $S(O)_2R^{b41}$, $NR^{c41}S(O)_2R^{b41}$, $S(O)_2NR^{c41}R^{d41}$ and oxo; and leach $C_{6-10}$ aryl, 5-10 membered heteroaryl, $C_{3-10}$ cycloalkyl and 4-10 membered heterocycloalkyl forming each $R^{Cy4B}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)$ $R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}$ $S(O)_2R^{b41}$, $S(O)_2NR^{c41}R^{d41}$ and oxo;

or $R^{41}$ and $R^{42}$, together with the atoms to which they are attached and the nitrogen atom linking the atoms to which $R^{41}$ and $R^{42}$ are attached, form a 4-7 membered heterocycloalkyl ring; which is optionally further substituted by 1, 2, 3, 4 or 5 substituents each independently selected from $R^{Cy4B}$, halogen, $C_{1-6}$ haloalkyl, CN, $OR^{a41}$, $SR^{a41}$, $C(O)R^{b41}$, $C(O)NR^{c41}R^{d41}$, $C(O)$ $OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)$ $OR^{a41}$, $C(=NR^{e41})NR^{c41}R^{d41}$, $C(=NOR^{a41})$ $NR^{c41}R^{d41}$, $C(=NOC(O)R^{b41})NR^{c41}R^{d41}$, $C(=NR^{e41})NR^{c41}C(O)OR^{a41}$, $S(O)R^{b41}$, $S(O)$ $NR^{c41}R^{d41}$, $S(O)_2R^{b41}$, $NR^{c41}S(O)_2R^{b41}$, $S(O)_2NR^{c41}R^{d41}$ and oxo;

$R^{43}$ is H, $C_{1-6}$ alkyl, $C_{2-6}$ alkenyl, $C_{2-6}$ alkynyl, or $Cy^{4C}$; wherein each of the $C_{1-6}$ alkyl, $C_{2-6}$ alkenyl, or $C_{2-6}$ alkynyl forming $R^{43}$ is unsubstituted or substituted by 1, 2, 3, 4 or 5 substituents each independently selected from: 0, 1, 2, 3, 4 or 5 substituents selected from the group consisting of $Cy^{4C}$, halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})$ $NR^{c41}R^{d41}$, $NR^{c41}C(=NR^{e41})NR^{c41}R^{d41}$ $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo, provided that no more than one substituent of the $C_{1-6}$ alkyl, $C_{2-6}$ alkenyl, or $C_{2-6}$ alkynyl forming $R^{43}$ is $Cy^{4C}$;

$Cy^{4C}$ is unsubstituted or substituted $C_{6-10}$ aryl, unsubstituted or substituted 5-10 membered heteroaryl, unsubstituted or substituted $C_{3-10}$ cycloalkyl, or unsubstituted or substituted 4-10 membered heterocycloalkyl;

wherein the ring atoms of the 5-10 membered heteroaryl or unsubstituted or substituted 4-10 membered heterocycloalkyl forming $Cy^{4B}$ consist of carbon atoms and 1, 2 or 3 heteroatoms selected from O, N and S; and wherein the substituted $C_{6-10}$ aryl, substituted 5-10 membered heteroaryl substituted $C_{3-10}$ cycloalkyl, or 4-10 membered heterocycloalkyl forming $Cy^{4C}$ is substituted with 1, 2, 3, 4 or 5 substituents each independently selected from $R^{Cy4C}$, halogen, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{41}R^{441}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $C(=NOR^{a41})NR^{c41}R^{d41}$, $C(=NOC(O)R^{b41})NR^{c41}R^{d41}$, $C(=NR^{e41})NR^{c41}C(O)OR^{a41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

each $R^{Cy4C}$ is independently selected from $C_{1-6}$ alkyl, $C_{2-6}$ alkenyl, $C_{2-6}$ alkynyl, $C_{6-10}$ aryl, 5-10 membered heteroaryl, $C_{3-10}$ cycloalkyl and 4-10 membered heterocycloalkyl, wherein the ring atoms of the 5-10 membered heteroaryl or 4-10-membered heterocycloalkyl forming $R^{Cy4C}$ consist of carbon atoms and 1, 2, or 3 heteroatoms selected from O, N and S, wherein the $C_{1-6}$ alkyl, $C_{2-6}$ alkenyl, or $C_{2-6}$ alkynyl forming $R^{Cy4C}$ is independently unsubstituted or substituted with 1, 2 or 3 substituents independently selected from halogen, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo; and wherein each $C_{6-10}$ aryl, 5-10 membered heteroaryl, $C_{3-10}$ cycloalkyl and 4-10 membered heterocycloalkyl forming each $R^{Cy4.4}$ is independently unsubstituted or substituted with 1, 2 or 3 substituents independently selected from halogen, $C_{1-6}$ alkyl, $C_{2-6}$ alkenyl, $C_{2-6}$ alkynyl, $C_{1-6}$ haloalkyl, CN, $OR^{a41}$, $SR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{41}C(O)NR^{c41}R^{d41}$, $NR^{c41}C(O)OR^{a41}$, $C(=NR^{e41})NR^{c41}R^{d41}$, $NR^{c41}C(=NR^{e41})NR^{c41}R^{d41}$, $S(O)R^{b41}$, $S(O)NR^{c41}R^{d41}$, $S(O)_2R^{b41}$, $NR^{c41}S(O)_2R^{b41}$, $S(O)_2NR^{c41}R^{d41}$ and oxo;

$R^{a41}$, $R^{b41}$, $R^{c41}$ and $R^{d41}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming $R^{a41}$, $R^{b41}$, $R^{c41}$ and $R^{d41}$ are each optionally substituted with 1, 2, 3, 4 or 5 substituents independently selected from $C_{1-6}$ alkyl, halo, CN, $OR^{a42}$, $SR^{a42}$, $C(O)R^{b42}$, $C(O)NR^{c42}R^{d42}$, $C(O)OR^{a42}$, $OC(O)R^{b42}$ $OC(O)NR^{c42}R^{d42}$, $NR^{c42}R^{d42}$, $NR^{c42}C(O)R^{b42}$, $NR^{c42}C(O)NR^{c42}R^{d42}$, $NR^{c42}C(O)OR^{a42}$, $C(=NR^{e42})NR^{c42}R^{d42}$, $S(O)R^{b42}$, $S(O)NR^{c42}R^{d42}$, $S(O)_2R^{b42}$, $NR^{c42}S(O)_2R^{b42}$, $S(O)_2NR^{c42}R^{d42}$ and oxo;

or $R^{c41}$ and $R^{d41}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)NR^{c42}R^{d42}$, $NR^{c42}C(O)OR^{a42}$, $C(=NR^{e42})NR^{c42}R^{d42}$, $NR^{c42}C(=NR^{e42})NR^{c42}R^{d42}$ $S(O)R^{b42}$, $S(O)NR^{c42}R^{d42}$, $S(O)_2R^{b42}$, $NR^{c42}S(O)_2R^{b42}$, $S(O)_2NR^{c42}R^{d42}$ and oxo;

$R^{a42}$, $R^{b42}$, $R^{c42}$ and $R^{d42}$ are each independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-3}$ alkyl, 5-6 membered heteroaryl-$C_{1-3}$ alkyl, $C_{3-7}$ cycloalkyl-$C_{1-3}$ alkyl and 4-7 membered heterocycloalkyl-$C_{1-3}$ alkyl forming $R^{a42}$, $R^{b42}$, $R^{c42}$ and $R^{d42}$ are each optionally substituted with 1, 2 or 3 substituents independently selected from OH, CN, amino, $NH(C_{1-6}$ alkyl), $N(C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo;

or $R^{c42}$ and $R^{d42}$ attached to the same N atom, together with the N atom to which they are both attached, form a 4-, 5-, 6- or 7-membered heterocycloalkyl group or 5-membered heteroaryl group, each of which is unsubstituted or substituted with 1, 2 or 3 substituents independently selected from OH, CN, amino, $NH(C_{1-6}$ alkyl), $N(C_{1-6}$ alkyl)$_2$, halo, $C_{1-6}$ alkyl, $C_{1-6}$ alkoxy, $C_{1-6}$ haloalkyl, $C_{1-6}$ haloalkoxy and oxo; and $R^{e41}$ and $R^{e42}$ are each, independently, H, CN or $NO_2$.

In some embodiments, the small molecule is a compound Formula (VA) or (VB):

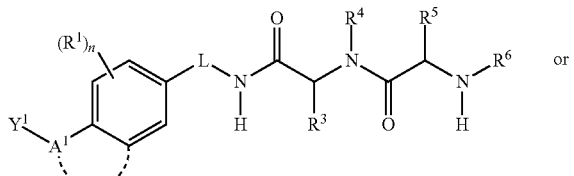

(VA)

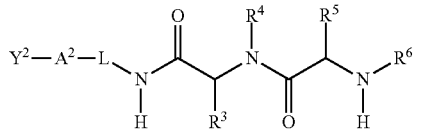

(VB)

a stereoisomer, tautomer, or pharmaceutically acceptable salt thereof;

wherein:

$A^1$ is a member selected from the group consisting of —(C=NH)—, —(C=NOR$^a$)—, —[C=NO(C=O)R$^a$]—, —[C=N[O(C=O)ZR$^b$]}—, a fused 5- or 6-member heterocyclyl, and a fused 5- or 6-member heteroaryl;

when $A^1$ is —(C=NH)—, $Y^1$ is selected from the group consisting of —NH$_2$, —NH(C=O)R$^a$, and —NH(C=O)ZR$^b$;

when $A^1$ is —(C=NOR$^a$)—, —[C=NO(C=O)R$^a$]—, or —{C=N[O(C=O)ZR$^b$]}—, $Y^1$ is —NH$_2$;

when $A^1$ is fused heterocyclyl or heteroaryl, $Y^1$ is —NH$_2$ or halo, and $A^1$ is substituted with m additional $R^1$ groups;

each $R^a$ and $R^b$ is independently selected from the group consisting of $C_1$-$C_6$ alkyl, $C_3$-$C_{10}$ cycloalkyl, $C_6$-$C_{10}$ aryl, and $C_7$-$C_{12}$ arylalkyl; wherein $R^a$ has m substituents selected from the group consisting of $C_1$-$C_6$ alkyl, hydroxyl, hydroxyl ($C_1$-$C_6$ alkyl), $C_1$-$C_6$ alkoxy, $C_2$-$C_9$ alkoxyalkyl, amino, $C_1$-$C_6$ alkylamino, and halo; or, alternatively, $R^a$ and $R^b$ join to form an heterocyclyl ring with m substituents selected from the group consisting of $C_1$-$C_6$ alkyl, hydroxyl, $C_1$-$C_6$ alkoxy, and halo;

each Z is independently selected from the group consisting of O and S;

$A^2$ is a member selected from the group consisting of $C_3$-$C_6$ heteroaryl, $C_6$ aryl, and $C_2$-$C_6$ alkyl;

when $A^2$ is $C_3$-$C_6$ heteroaryl, $Y^2$ is selected from the group consisting of —NH$_2$, —CH$_2$NH$_2$, chloro, —(C=NH)NH$_2$, —(C=NH)NH(C=O)R$^a$, —(C=NH)NH(C=O)ZR$^b$, (C=NOR$^a$)NH$_2$, —[C=NO(C=O)R$^a$]NH$_2$, and —{C=N[O(C=O)ZR$^b$]}NH$_2$; and $A^2$ is substituted with m additional $R^1$ groups;

when $A^2$ is $C_6$ aryl, $Y^2$ is selected from the group consisting of aminomethyl, hydroxy, and halo, and $A^2$ is substituted with m additional $R^1$ groups;

when $A^2$ is $C_2$-$C_6$ alkyl, $Y^2$ is selected from the group consisting of —NH(C=NH)NH$_2$, —NH(C=NH)NH(C=O)R$^a$, and —NH(C=NH)NH(C=O)ZR$^b$;

each $R^1$ is a member independently selected from the group consisting of $C_1$-$C_6$ alkyl, hydroxyl, $C_1$-$C_6$ alkoxy, amino, $C_1$-$C_6$ alkylamino, and halo;

each m and n is an integer independently selected from 0 to 3;

L is —(O)$_p$—(C(R$^{2a}$)(R$^{2b}$))$_q$—, each $R^{2a}$ or $R^{2b}$ is a member independently selected from the group consisting of hydrogen and fluoro;

p is an integer from 0 to 1;

q is an integer from 1 to 2;

$R^3$ is a member selected from the group consisting of hydrogen, $C_1$-$C_6$ alkyl, $C_1$-$C_6$ fluoroalkyl, and carboxy ($C_1$-$C_6$ alkyl); or, alternatively, $R^3$ and $R^4$ join to form an azetidine, pyrrolidine, or piperidine ring;

$R^4$ is a member selected from the group consisting of hydrogen and $C_1$-$C_6$ alkyl; or, alternatively, $R^4$ and $R^3$ join to form an azetidine, pyrrolidine, or piperidine ring;

$R^5$ is a member selected from the group consisting of $C_3$-$C_7$ cycloalkyl, $C_4$-$C_8$ cycloalkylalkyl, heteroaryl, and $C_7$-$C_{12}$ arylalkyl or heteroarylalkyl with from 0 to 3 $R^{13}$ substituents; or, alternatively, $R^5$ and $R^6$ join to form a heterocyclic ring with from 0 to 3 $R^{13}$ substituents;

$R^6$ is a member selected from the group consisting of hydrogen, $C_1$-$C_6$ alkyl, $C_3$-$C_7$ cycloalkyl, carboxy ($C_1$-$C_6$ alkyl), $C_7$-$C_{12}$ arylalkyl or heteroarylalkyl with from 0 to 3 $R^{13}$ substituents, amino ($C_1$-$C_8$ alkyl); and amido ($C_1$-$C_8$ alkyl); or, alternatively, $R^6$ and $R^5$ join to form a heterocyclic ring with from 0 to 3 $R^{13}$ substituents; and each $R^{13}$ is a member independently selected from the group consisting of $C_1$-$C_6$ alkyl, $C_6$-$C_{10}$ aryl, ($C_6$-$C_{10}$ aryl) $C_1$-$C_6$ alkyl, carboxy ($C_1$-$C_6$ alkyloxy), heteroaryl, ($C_6$-$C_{10}$ heteroaryl) $C_1$-$C_6$ alkyl, heterocyclyl, hydroxyl, hydroxyl ($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two $R^{13}$ groups join to form a fused $C_6$-$C_{10}$ aryl, $C_6$-$C_{10}$ heteroaryl, or $C_5$-$C_7$ cycloalkyl ring.

In some embodiments, the small molecule is a compound of Formula (VIA) or (VIB):

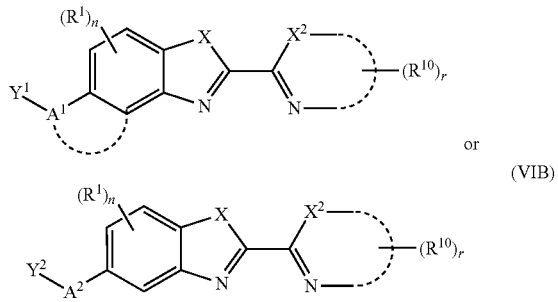

a stereoisomer, tautomer, or pharmaceutically acceptable salt thereof;

wherein:

$A^1$ is a member selected from the group consisting of —(C=NH)—, —(C=NOR$^a$)—, —[C=NO(C=O)R$^a$]—, —[C=N[O(C=O)ZR$^b$]—, a fused 5- or 6-member heterocyclyl, and a fused 5- or 6-member heteroaryl;

when $A^1$ is —(C=NH)—, $Y^1$ is selected from the group consisting of —NH$_2$, —NH(C=O)R$^a$, and —NH(C=O)ZR$^b$;

when $A^1$ is —(C=NOR$^a$)—, —[C=NO(C=O)R$^a$]—, or —{C=N[O(C=O)ZR$^b$]}—, $Y^1$ is —NH$_2$;

when $A^1$ is fused heterocyclyl or heteroaryl, $Y^1$ is —NH$_2$ or halo, and $A^1$ is substituted with m additional $R^1$ groups;

each $R^a$ and $R^b$ is independently selected from the group consisting of $C_1$-$C_6$ alkyl, $C_3$-$C_{10}$ cycloalkyl, $C_6$-$C_{10}$ aryl, and $C_7$-$C_{12}$ arylalkyl; wherein $R^a$ has m substituents selected from the group consisting of $C_1$-$C_6$ alkyl, hydroxyl, hydroxyl ($C_1$-$C_6$ alkyl), $C_1$-$C_6$ alkoxy, $C_2$-$C_9$ alkoxyalkyl, amino, $C_1$-$C_6$ alkylamino, and halo; or, alternatively, $R^a$ and $R^b$ join to form an heterocyclyl ring with m substituents selected from the group consisting of $C_1$-$C_6$ alkyl, hydroxyl, $C_1$-$C_6$ alkoxy, and halo;

each Z is independently selected from the group consisting of O and S;

$A^2$ is a member selected from the group consisting of $C_3$-$C_6$ heteroaryl and $C_2$-$C_6$ alkyl;

when $A^2$ is $C_3$-$C_6$ heteroaryl, $Y^2$ is selected from the group consisting of —NH$_2$, —CH$_2$NH$_2$, chloro, —(C=NH)NH$_2$, —(C=NH)NH(C=O)R$^a$, (C=NH)NH(C=O)ZR$^b$, (C=NOR$^a$)NH$_2$, —[C=NO(C=O)R$^a$]NH$_2$, and {C=N[O(C=O)ZR$^b$]}NH$_2$; and $A^2$ is substituted with m additional $R^1$ groups;

when $A^2$ is $C_2$-$C_6$ alkyl, $Y^2$ is selected from the group consisting of —NH(C=NH)NH$_2$, —NH(C=NH)NH(C=O)R$^a$, and —NH(C=NH)NH(C=O)ZR$^b$;

each $R^1$ is a member independently selected from the group consisting of $C_1$-$C_6$ alkyl, hydroxyl, $C_1$-$C_6$ alkoxy, amino, $C_1$-$C_6$ alkylamino, and halo;

each m and n is an independently selected integer from 0 to 3;

X and X² are each a member selected from the group consisting of NR⁸, CH, and CR¹⁰;

each R⁸ is a member independently selected from the group consisting of hydrogen and $C_1$-$C_6$ alkyl;

each R¹⁰ is a member independently selected from the group consisting of $C_1$-$C_6$ alkyl, heteroaryl or $C_6$-$C_{10}$ aryl with from 0 to 3 R¹³ substituents, hydroxyl, hydroxyl ($C_1$-$C_6$ alkyl), $C_1$-$C_6$ alkoxy, $C_2$-$C_9$ alkoxyalkyl, amino, $C_1$-$C_6$ alkylamino, and halo; or, alternatively, two R¹⁰ groups join to form a fused $C_6$ aryl, heteroaryl, or $C_5$-$C_7$ cycloalkyl ring with from 0 to 3 R¹³ substituents;

r is an integer from 0 to 4; and each R¹³ is a member independently selected from the group consisting of $C_1$-$C_6$ alkyl, $C_6$-$C_{10}$ aryl, carboxy ($C_1$-$C_6$ alkyloxy), heteroaryl, heterocyclyl, hydroxyl, hydroxyl ($C_1$-$C_6$ alkyl), $C_1$-$C_6$ alkoxy, $C_2$-$C_9$ alkoxyalkyl, amino, $C_1$-$C_6$ amido, $C_1$-$C_6$ alkylamino, and halo; or, alternatively, two R¹³ groups join to form a fused $C_6$-$C_{10}$ aryl, $C_6$-$C_{10}$ heteroaryl, or $C_5$-$C_7$ cycloalkyl ring.

In certain specific embodiments, the small molecule is a compound of Formula (VIIA) or (VIIB):

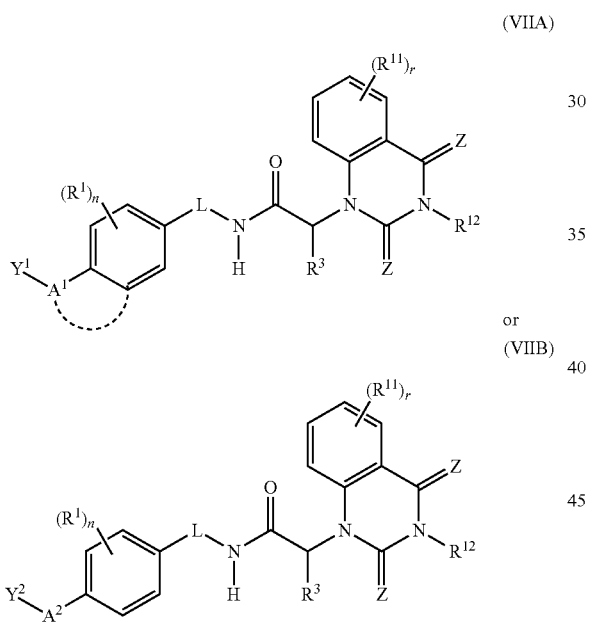

a stereoisomer, tautomer, or pharmaceutically acceptable salt thereof;
wherein:

A¹ is a member selected from the group consisting of —(C═NH)—, —(C═NOR$^a$)—, —[C═NO(C═O)R$^a$]—, —[C═N[O(C═O)ZR$^b$]]—, a fused 5- or 6-member heterocyclyl, and a fused 5- or 6-member heteroaryl;

when A¹ is —(C═NH)—, Y¹ is selected from the group consisting of —NH₂, —NH(C═O)R$^a$, and —NH(C═O)ZR$^b$;

when A¹ is —(C═NOR$^a$)—, —[C═NO(C═O)R$^a$]—, or —{C═N[O(C═O)ZR$^b$]}—, Y¹ is —NH₂;

when A¹ is fused heterocyclyl or heteroaryl, Y¹ is —NH₂ or halo, and A¹ is substituted with m additional R¹ groups;

each R$^a$ and R$^b$ is independently selected from the group consisting of $C_1$-$C_6$ alkyl, $C_3$-$C_{10}$ cycloalkyl, $C_6$-$C_{10}$ aryl, and $C_7$-$C_{12}$ arylalkyl; wherein R$^a$ has m substituents selected from the group consisting of $C_1$-$C_6$ alkyl, hydroxyl, hydroxyl ($C_1$-$C_6$ alkyl), $C_1$-$C_6$ alkoxy, $C_2$-$C_9$ alkoxyalkyl, amino, $C_1$-$C_6$ alkylamino, and halo; or, alternatively, R$^a$ and R$^b$ join to form an heterocyclyl ring with m substituents selected from the group consisting of $C_1$-$C_6$ alkyl, hydroxyl, $C_1$-$C_6$ alkoxy, and halo;

each Z is independently selected from the group consisting of O and S;

A² is a member selected from the group consisting of $C_3$-$C_6$ heteroaryl and $C_2$-$C_6$ alkyl;

when A² is $C_3$-$C_6$ heteroaryl, Y² is selected from the group consisting of —NH₂, —CH₂NH₂, chloro, —(C═NH)NH₂, —(C═NH)NH(C═O)R$^a$, —(C═NH)NH(C═O)ZR$^b$, —(C═NOR$^a$)NH₂, —[C═NO(C═O)R$^a$]NH₂, and —{C═N[O(C═O)ZR$^b$]}NH₂; and A² is substituted with m additional R¹ groups;

when A² is $C_2$-$C_6$ alkyl, Y² is selected from the group consisting of —NH(C═NH)NH₂, —NH(C═NH)NH(C═O)R$^a$, and —NH(C═NH)NH(C═O)ZR$^b$;

each R¹ is a member independently selected from the group consisting of $C_1$-$C_6$ alkyl, hydroxyl, $C_1$-$C_6$ alkoxy, amino, $C_1$-$C_6$ alkylamino, and halo;

each m and n is an independently selected integer from 0 to 3;

L is —(O)$_p$—(C(R$^{2a}$)(R$^{2b}$))$_q$—, each R$^{2a}$ or R$^{2b}$ is a member independently selected from the group consisting of hydrogen and fluoro;

p is an integer from 0 to 1;

q is an integer from 1 to 2;

R³ is a member selected from the group consisting of hydrogen, $C_1$-$C_6$ alkyl, and carboxy ($C_1$-$C_6$ alkyl);

each R¹¹ is a member independently selected from the group consisting of $C_1$-$C_6$ alkyl, hydroxyl, $C_1$-$C_6$ alkoxy, amino, $C_1$-$C_6$ alkylamino, halo, and (R¹⁴)(R¹⁴)N(CO)—; or, alternatively, two R¹¹ groups join to form a fused $C_6$ aryl, heteroaryl, or $C_5$-$C_7$ cycloalkyl ring with from 0 to 3 R¹³ substituents;

r is an integer from 0 to 4; and each Z is a member independently selected from the group consisting of O and NR⁸;

each R⁸ is a member independently selected from the group consisting of hydrogen and $C_1$-$C_6$ alkyl;

each R¹² is a member independently selected from the group consisting of hydrogen, $C_1$-$C_6$ alkyl, and $C_7$-$C_{14}$ arylalkyl with from 0 to 3 R¹³ substituents;

each R¹³ is a member independently selected from the group consisting of $C_1$-$C_6$ alkyl, hydroxyl, hydroxyl ($C_1$-$C_6$ alkyl), $C_1$-$C_6$ alkoxy, $C_2$-$C_9$ alkoxyalkyl, amino, $C_1$-$C_6$ alkylamino, and halo; or, alternatively, two R¹³ groups join to form a fused $C_6$ aryl, heteroaryl, or $C_5$-$C_7$ cycloalkyl ring; and each R¹⁴ is a member independently selected from the group consisting of hydrogen, $C_1$-$C_6$ alkyl, $C_3$-$C_7$ cycloalkyl, $C_4$-$C_8$ cycloalkylalkyl, $C_7$-$C_{14}$ arylalkyl, and heteroaryl ($C_1$-$C_6$ alkyl); or, alternatively, two R¹³ groups join to form a fused heterocyclyl ring.

In some embodiments, the small molecule is a compound having the following structure:

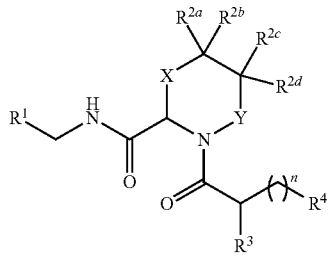

or a stereoisomer, tautomer, or pharmaceutically acceptable salt thereof, wherein:
- $R^1$ is a substituted or unsubstituted aryl, substituted or unsubstituted heteroaryl, substituted or unsubstituted cycloalkyl, or a substituted or unsubstituted heterocyclyl;
- $R^{2a}$, $R^{2b}$, $R^{2c}$, and $R^{2d}$, are independently selected from the group consisting of hydrogen, halo, C(=O)OR$^5$, OC(=O)R$^5$, hydroxyalkyl, alkoxy, alkoxyalkyl, haloalkoxy, cyano, aminylalkyl, carboxyalkyl, NR$^5$R$^6$, C(=O)NR$^5$R$^6$, N(R$^5$)C(=O)R$^6$, NR$^5$C(=O)NR$^6$, S(O)$_t$, SR$^5$, nitro, N(R$^5$)C(O)OR$^6$, C(=NR$^5$)NR$^6$R$^7$, N(R$^5$)C(=NR$^6$)NR$^7$R$^8$, S(O)R$^5$, S(O)NR$^5$R$^6$, S(O)$_2$R$^5$, N(R$^5$) S(O)$_2$R$^6$, S(O)$_2$NR$^5$R$^6$, aryl, heteroaryl, heterocyclyl, cycloalkyl, and oxo provided that at least one occurrence of $R^{2a}$, $R^{2b}$, $R^{2c}$, or $R^{2d}$ is not hydrogen;
- $R^3$ is NR$^{3a}$R$^{3b}$,
- $R^{3a}$ and $R^{3b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, (CH$_2$)$_n$C(=O)OR$^6$, or (CH$_2$)$_n$P(=O)(OR$^6$)$_2$;
- or $R^{3a}$ and $R^{3b}$, together with the nitrogen to which they are attached, form an optionally substituted 4-7 membered heteroaryl or an optionally substituted 4-7 membered heterocyclyl;
- or $R^{3a}$ and $R^4$ together with the nitrogen can carbon to which they are attached, respectively, form an optionally substituted 4-7 membered heterocyclyl;
- $R^4$ is a substituted or unsubstituted aryl, a substituted or unsubstituted heteroaryl, a substituted or unsubstituted cycloalkyl, or a substituted or unsubstituted heterocyclyl when n is 2, 3, 4, 5, or 6; or
- $R^4$ is a substituted or unsubstituted monocyclic heteroaryl, or a substituted or unsubstituted heterocyclyl when n is 0 or 1;
- $R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;
- X is a direct bond, —CR$^{2e}$R$^{2f}$—, or —CR$^{2e}$R$^{2f}$—CR$^{2g}$R$^{2h}$—;
- Y is a direct bond or —CR$^{2i}$R$^{2j}$—;
- n is an integer from 0-6; and
- t is 1-3.

In some embodiments, the small molecule is a compound having the following structure:

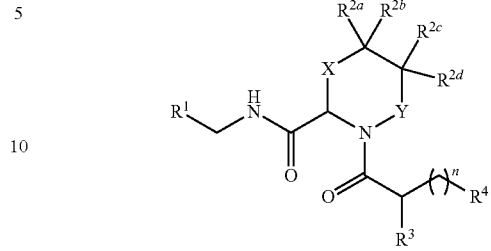

or a stereoisomer, tautomer, or pharmaceutically acceptable salt thereof, wherein:
- $R^1$ is a substituted or unsubstituted aryl, substituted or unsubstituted heteroaryl, substituted or unsubstituted cycloalkyl, or a substituted or unsubstituted heterocyclyl;
- $R^{2a}$, $R^{2b}$, $R^{2c}$, $R^{2d}$ are independently selected from the group consisting of hydrogen, halo, OR$^5$, C(=O)OR$^5$, OC(=O)R$^5$, hydroxyalkyl, alkoxy, alkoxyalkyl, haloalkoxy, cyano, aminylalkyl, carboxyalkyl, NR$^5$R$^6$, C(=O)NR$^5$R$^6$, N(R$^5$)C(=O)R$^6$, NR$^5$C(=O)NR$^6$, S(O)$_t$, SR$^5$, nitro, N(R$^5$)C(O)OR$^6$, C(=NR$^5$)NR$^6$R$^7$, N(R$^5$)C(=NR$^6$)NR$^7$R$^8$, S(O)R$^5$, S(O)NR$^5$R$^6$, S(O)$_2$R$^5$, N(R$^5$) S(O)$_2$R$^6$, S(O)$_2$NR$^5$R$^6$, aryl, heteroaryl, heterocyclyl, cycloalkyl, and oxo provided that at least one occurrence of $R^{2a}$, $R^{2b}$, $R^{2c}$, $R^{2d}$ is not hydrogen;
- $R^3$ is NR$^{3a}$R$^{3b}$,
- $R^{3a}$ and $R^{3b}$ are each independently hydrogen, alkyl, hydroxyalkyl, haloalkyl, alkoxyalkyl, —CH$_2$C(C=O) OH, —CH$_2$C(=O) Oalkyl, heterocyclyl, heteroaryl, heterocyclylalkyl, heteroarylalkyl, or cycloalkyl;
- or $R^{3a}$ and $R^{3b}$, together with the nitrogen to which they are attached, form an optionally substituted 4-7 membered heteroaryl or an optionally substituted 4-7 membered heterocyclyl;
- $R^4$ is a substituted or unsubstituted aryl, a substituted or unsubstituted heteroaryl, a substituted or unsubstituted cycloalkyl, or a substituted or unsubstituted heterocyclyl when n is 2, 3, 4, 5, or 6; or
- $R^4$ is a substituted or unsubstituted monocyclic heteroaryl, or a substituted or unsubstituted heterocyclyl when n is 0 or 1;
- $R^5$, $R^6$, $R^7$, and $R^8$ are, at each occurrence, independently hydrogen, alkyl, hydroxyalkyl, haloalkyl, alkoxyalkyl, carboxyalkyl, heterocyclyl, heteroaryl, or cycloalkyl;
- X is a direct bond, —[C(R$^{2e}$)R$^{2f}$]—, or —[C(R$^{2e}$)R$^{2f}$]—[C(R$^{2g}$)R$^{2h}$]—;
- Y is a direct bond or —[C(R$^{2i}$)R$^{2j}$]—;
- n is an integer from 0-6; and
- t is 1-3, provided that:
a) when one occurrence of $R^{2a}$, $R^{2b}$, $R^{2c}$, $R^{2d}$ is OH, $R^1$ does not have the following structure:

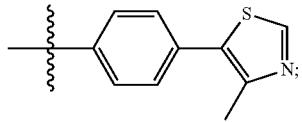 [SMILES: *c1ccc(-c2scnc2C)cc1]

b) when one occurrence of $R^{2a}$, $R^{2b}$, $R^{2c}$, $R^{2d}$ is —OH, n is an integer from 2-6; and c) when one occurrence of $R^{2a}$, $R^{2b}$, $R^{2c}$, $R^{2d}$ is an unsubstituted phenyl, neither $R^{3a}$ nor $R^{3b}$ has the following structure:

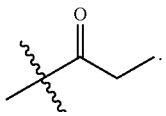 [SMILES: *C(=O)CC]

In some embodiments, the small molecule is a compound having the following structure:

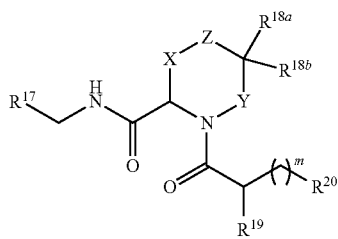

or a stereoisomer, tautomer, or pharmaceutically acceptable salt thereof, wherein:

$R^{17}$ is a substituted or unsubstituted aryl, substituted or unsubstituted heteroaryl, substituted or unsubstituted cycloalkyl, or a substituted or unsubstituted heterocyclyl;

$R^{18a}$, $R^{18b}$ are independently selected from the group consisting of hydrogen, halo, —$OR^{21}$, $C(=O)OR^{21}$, $OC(=O)R^{21}$, hydroxyalkyl, alkoxy, alkoxyalkyl, haloalkoxy, cyano, aminylalkyl, carboxyalkyl, $NR^{21}R^{22}$, $C(=O)NR^{21}R^{22}$, $N(R^{21})C(=O)R^{22}$, $NR^{21}C(=O)NR^{22}$, $S(O)_p$, $SR^{21}$, nitro, $N(R^{21})C(O)OR^{22}$, $C(=NR^{21})NR^{22}R^{23}$, $N(R^{21})C(=NR^{22})NR^{23}R^{24}$, $S(O)R^{21}$, $S(O)NR^{21}R^{22}$, $S(O)_2R^{21}$, $N(R^{21})S(O)_2R^{22}$, $S(O)_2NR^{21}R^{22}$, aryl, heteroaryl, heterocyclyl, cycloalkyl, and oxo provided that at least one occurrence of $R^{18a}$, $R^{18b}$ is not hydrogen;

$R^{19}$ is $NR^{19a}R^{19b}$;

$R^{19a}$ and $R^{19b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^5$, or $(CH_2)_nP(=O)(OR^5)_2$;

or $R^{19a}$ and $R^{19b}$, together with the nitrogen to which they are attached, form an optionally substituted 4-7 membered heteroaryl or an optionally substituted 4-7 membered heterocyclyl;

$R^{20}$ is a substituted or unsubstituted aryl, a substituted or unsubstituted heteroaryl, a substituted or unsubstituted cycloalkyl, or a substituted or unsubstituted heterocyclyl;

$R^{21}$, $R^{22}$, $R^{23}$, and $R^{24}$ are, at each occurrence, independently hydrogen, alkyl, hydroxyalkyl, haloalkyl, alkoxyalkyl, carboxyalkyl, heterocyclyl, heteroaryl, or cycloalkyl; X is a direct bond, —$CR^{2e}R^{2f}$—, or —$CR^{2e}R^{2f}$—$CR^{2g}R^{2h}$—;

Y is a direct bond or —$CR^{2i}R^{2j}$—;

Z is O or S;

m is an integer from 0-6; and t is 1-3.

In some embodiments, the small molecule is a compound having the following structure:

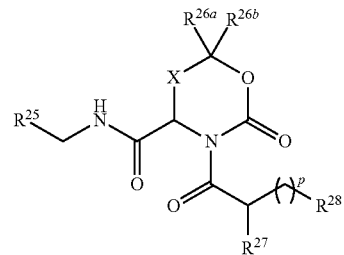

or a stereoisomer, tautomer, or pharmaceutically acceptable salt thereof, wherein:

$R^{25}$ is a substituted or unsubstituted aryl, substituted or unsubstituted heteroaryl, substituted or unsubstituted cycloalkyl, or a substituted or unsubstituted heterocyclyl;

$R^{26a}$, $R^{26b}$ are independently selected from the group consisting of hydrogen, halo, —$OR^{29}$, $C(=O)OR^{29}$, $OC(=O)R^{29}$, hydroxyalkyl, alkoxy, alkoxyalkyl, haloalkoxy, cyano, aminylalkyl, carboxyalkyl, $NR^{29}R^{30}$, $C(=O)NR^{29}R^{30}$, $N(R^{29})C(=O)R^{30}$, $NR^{29}C(=O)NR^{30}$, $S(O)_p$, $SR^{29}$, nitro, $N(R^{29})C(O)OR^{30}$, $C(=NR^{29})NR^{30}R^{31}$, $N(R^{29})C(=NR^{30})NR^{31}R^{32}$, $S(O)R^{29}$, $S(O)NR^{29}R^{30}$, $S(O)_2R^{30}$, $N(R^{29})S(O)_2R^{30}$, $S(O)_2NR^{29}R^{30}$, aryl, heteroaryl, heterocyclyl, cycloalkyl, and oxo provided that at least one occurrence of $R^{26a}$, $R^{26b}$ is not hydrogen;

$R^{27}$ is $NR^{27a}R^{27b}$;

$R^{27a}$ and $R^{27b}$ are each independently hydrogen, alkyl, hydroxyalkyl, haloalkyl, alkoxyalkyl, heterocyclyl, heteroaryl, heterocyclylalkyl, heteroarylalkyl, cycloalkyl, $(CH_2)_nC(=O)OR^{29}$, or $(CH_2)_nP(=O)(OR^{29})_2$;

or $R^{27a}$ and $R^{27b}$, together with the nitrogen to which they are attached, form an optionally substituted 4-7 membered heteroaryl or an optionally substituted 4-7 membered heterocyclyl;

$R^{28}$ is a substituted or unsubstituted aryl, a substituted or unsubstituted heteroaryl, a substituted or unsubstituted cycloalkyl, or a substituted or unsubstituted heterocyclyl;

$R^{29}$, $R^{30}$, $R^{31}$, and $R^{32}$ are, at each occurrence, independently hydrogen, alkyl, hydroxyalkyl, haloalkyl, alkoxyalkyl, carboxyalkyl, heterocyclyl, heteroaryl, or cycloalkyl;

X is a direct bond or —$CR^{26c}R^{26d}$—;

p is an integer from 0-6; and t is 1-3.

In some embodiments, the small molecule is a compound having the following structure:

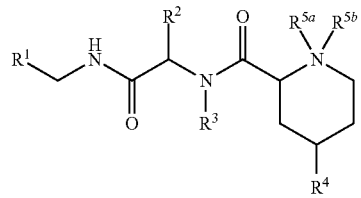

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ is hydrogen, alkyl, haloalkyl, cycloalkyl, phosphonalkyl, $(CH_2)_nC(=O)OR^6$, $C(=O)R^6$, $C(=O)OR^6$, or $C(=O)NR^6R^7$;

$R^{5b}$ is an electron pair or alkyl;

$R^6$ and $R^7$ are, at each occurrence, independently hydrogen, alkyl, haloalkyl, cycloalkyl, or arylalkyl;

$R^8$ is alkyl, haloalkyl, aminylalkyl, substituted or unsubstituted arylalkyl; and n is 1, 2, 3, 4, 5, 6, 7, or 8, provided that A) $R^{5a}$ is alkyl, haloalkyl, cycloalkyl, phosphonalkyl, $(CH_2)_nC(=O)OR^6$, $C(=O)R^6$, $C(=O)OR^6$, or $C(=O)NR^6R^7$ or $R^1$ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$; and B) when $R^{5a}$ is alkyl or $(CH_2)_nC(=O)OR^6$, $R^1$ does not have the following structure:

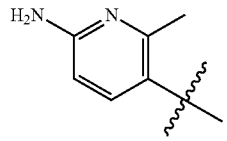 [SMILES: *c1ccc(N)nc1C]

unless $R^2$ and $R^3$, together with the carbon and nitrogen to which they are attached, respectively, form an optionally substituted 4-7 membered heterocyclyl.

In some embodiments, the small molecule is a compound having the following structure:

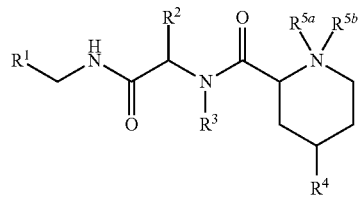

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ is hydrogen, alkyl, haloalkyl, cycloalkyl, phosphonalkyl, $(CH_2)_nC(=O)OR^6$, $C(=O)R^6$, $C(=O)OR^6$, or $C(=O)NR^6R^7$;

$R^{5b}$ is an electron pair or alkyl;

$R^6$ and $R^7$ are, at each occurrence, independently hydrogen, alkyl, haloalkyl, cycloalkyl, or arylalkyl;

$R^8$ is alkyl, haloalkyl, aminylalkyl, substituted or unsubstituted arylalkyl; and n is 1, 2, 3, 4, 5, 6, 7, or 8, provided that A) $R^{5a}$ is alkyl, haloalkyl, cycloalkyl, phosphonalkyl, $(CH_2)_nC(=O)OR^6$, $C(=O)R^6$, $C(=O)OR^6$, or $C(=O)NR^6R^7$ or $R^1$ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$; and B) the compound does not have one of the following structures:

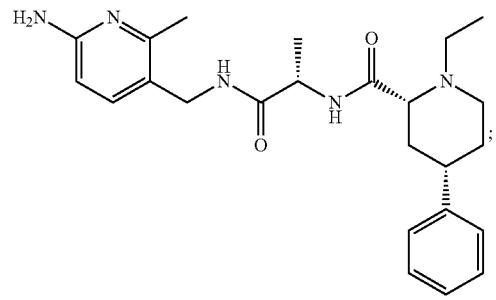

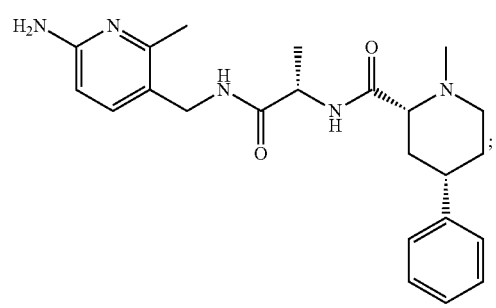

-continued

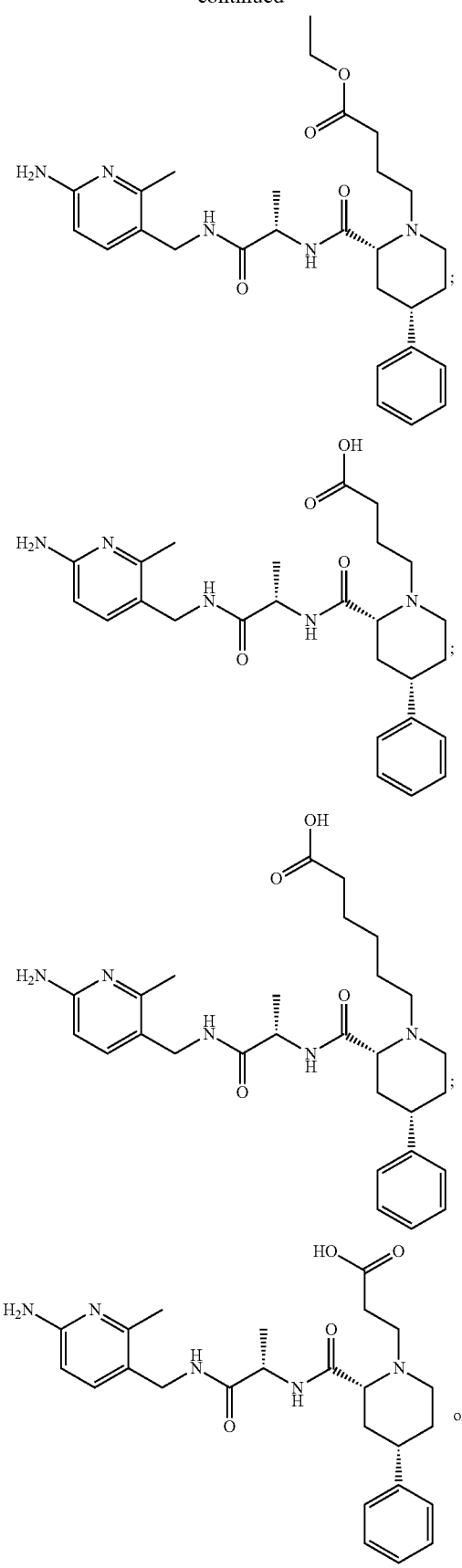

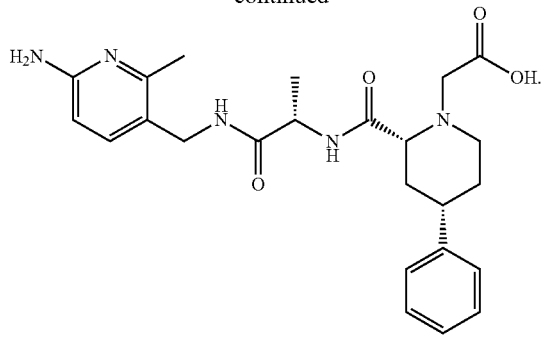

In some embodiments, the small molecule is a compound having the following structure:

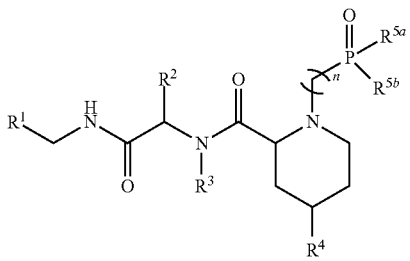

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ and $R^{5b}$ at each occurrence, independently have one of the following structures:

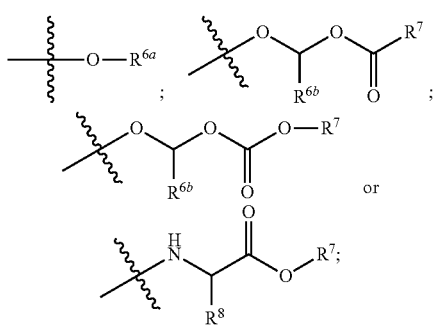

or $R^{5a}$ and $R^{5b}$, together with the phosphorus atom to which they are attached form an optionally substituted 4-7 membered heterocyclyl;

R$^{6a}$ is alkyl, haloalkyl, aryl, heteroaryl, cycloalkyl, or heterocyclyl;

R$^{6b}$ is, at each occurrence, independently hydrogen or alkyl;

R$^7$ is, at each occurrence, independently alkyl, haloalkyl, heteroaryl, cycloalkyl, heterocyclyl, arylalkyl, heteroarylalkyl, cycloalkylalkyl, or heterocyclylalkyl;

R$^8$ is an amino acid side chain; and n is 1, 2, 3, 4, 5, 6, 7, or 8.

In some embodiments, the small molecule is a compound having the following structure:

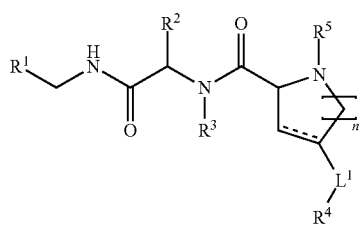

or a stereoisomer, tautomer, or pharmaceutically acceptable salt thereof, wherein:

==== represents a double or single bond;

R$^1$ is a substituted or unsubstituted aryl or a substituted or unsubstituted heteroaryl;

R$^2$ is hydrogen, alkyl, alkoxy, haloalkyl, hydroxyalkyl, haloalkoxy, or cycloalkyl;

R$^3$ is hydrogen, alkyl, haloalkyl, or cycloalkyl, or R$^2$ and R$^3$, together with the carbon and nitrogen to which they are attached, respectively, form an optionally substituted 4-7 membered heterocyclyl;

R$^4$ is a substituted or unsubstituted aryl, substituted or unsubstituted heteroaryl, substituted or unsubstituted cycloalkyl, or substituted or unsubstituted heterocyclyl;

R$^5$ is hydrogen, alkyl, haloalkyl, cycloalkyl, phosphonalkyl, (CH$_2$)$_m$C(=O)OR$^6$, C(=O)R$^6$, C(=O)OR$^6$, (CH$_2$)$_m$NR$^6$S(O)$_2$R$^7$, or C(=O)NR$^6$R$^7$;

R$^6$ and R$^7$ are, at each occurrence, independently hydrogen, alkyl, haloalkyl, cycloalkyl, or arylalkyl;

L$^1$ is a direct bond, —CR$^{8a}$R$^{8b}$—, —S(O)$_t$—, NR$^{8c}$, or —O—;

R$^{8a}$ and R$^{8b}$ are each independently hydrogen, alkyl, or R$^{8a}$ and R$^{8b}$, together with the carbon to which they are attached form an optionally substituted 3-6 membered cycloalkyl;

R$^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C—O)heterocyclyl, (C—O)O heterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;

n is 1 or 2;

m is 1, 2, 3, 4, 5, or 6; and t is 0, 1, or 2.

In some embodiments, the small molecule is a compound having the following structure:

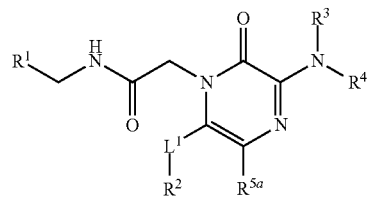

or a stereoisomer, tautomer, or pharmaceutically acceptable salt thereof, wherein:

R$^1$ is a substituted or unsubstituted heteroaryl;

R$^2$ is a substituted or unsubstituted aryl or a substituted or unsubstituted heteroaryl;

R$^3$ is hydrogen or alkyl;

R$^4$ is alkyl, a substituted or unsubstituted arylalkyl, a heterocyclyl substituted with substituents selected from the group consisting of a substituted or unsubstituted phenyl or a substituted or unsubstituted pyridinyl, or R$^3$ and R$^4$, together with the nitrogen and carbon to which they are attached, respectively, form an optionally substituted 4-10 membered heterocyclyl;

R$^{5a}$ is hydrogen or halo;

R$^{5b}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C—O)Oheteroaryl, (C—O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;

L$^1$ is a direct bond, —CH$_2$—, —S(O)$_t$—, NR$^{5b}$, —O—, —C=C—, or —C≡C—; and t is 0, 1, or 2, provided that:

A) R$^2$ does not have one of the following structures:

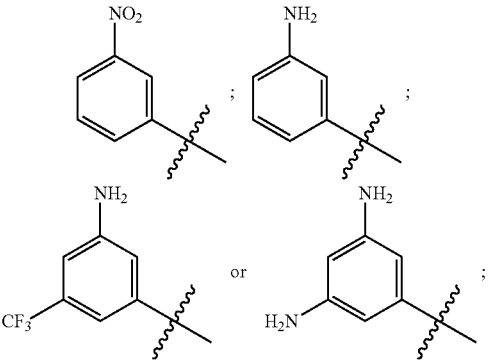

B) R$^1$ does not have one of the following structures:

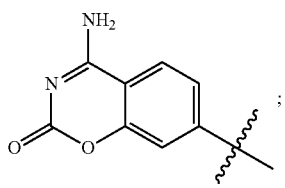

-continued

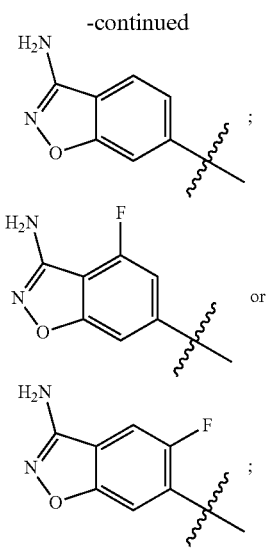

and

C) when $R^2$ is unsubstituted phenyl, $R^1$ does not have one of the following structures:

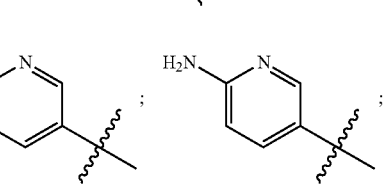

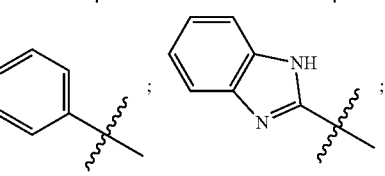

In some embodiments, the small molecule is a compound having the following structure:

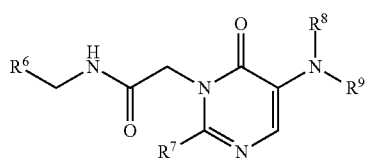

or a stereoisomer, tautomer, or pharmaceutically acceptable salt thereof, wherein:

$R^6$ is a substituted or unsubstituted aryl or a substituted or unsubstituted heteroaryl;

$R^7$ is alkyl, —$SR^{10}$ a substituted or unsubstituted aryl, or a substituted or unsubstituted heteroaryl;

$R^8$ is hydrogen, alkyl, haloalkyl, or cycloalkyl;

$R^9$ is a substituted or unsubstituted arylalkyl, a substituted or unsubstituted heteroarylalkyl, or $R^8$ and $R^9$, together with the nitrogen to which they are attached, form an optionally substituted 4-10 membered heterocyclyl;

$R^{10}$ is hydrogen, alkyl, haloalkyl, or cycloalkyl;

provided that:

A) when $R^7$ is unsubstituted phenyl, 3-((methylsulfonyl)amino)phenyl, 2-methylphenyl, 3-(dimethylamino)phenyl, 3-(methylamino)phenyl, 3-methylphenyl, 3-aminomethylphenyl, 3-aminophenyl, unsubstituted pyridinyl, 3-(methylamino)-2-thienyl, 3,4-diamino-2-thienyl, 3-((methylsulfonyl)amino)-2-thienyl, 3-amino-2-thienyl, 3-amino-5-5(aminocarbonyl)phenyl, or has one of the following structures:

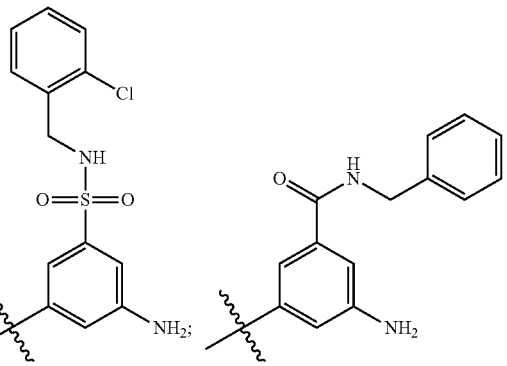

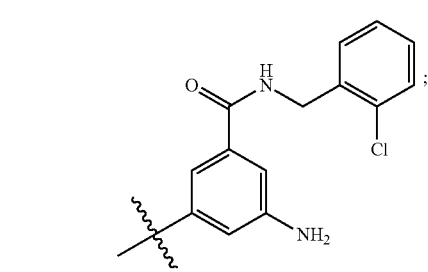

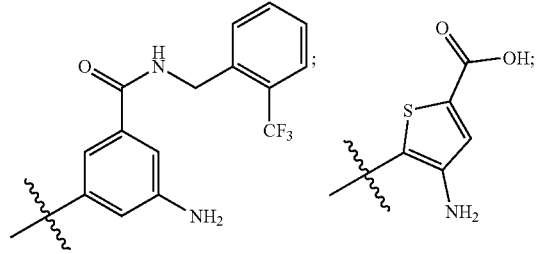

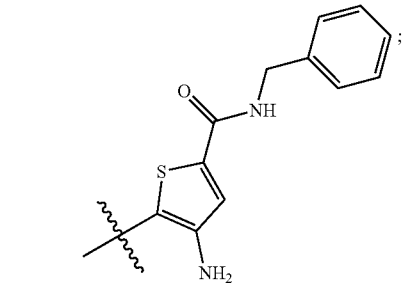

-continued

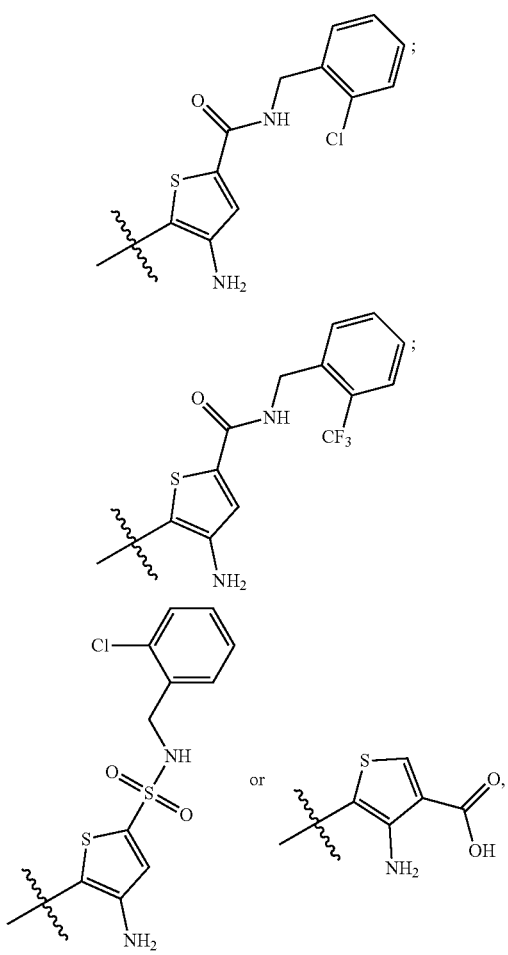

R⁶ does not have the following structure:

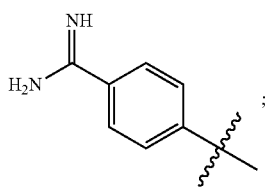 [SMILES: *c1ccc(C(=N)N)cc1]

and

B) when R⁷ is unsubstituted phenyl, R⁶ does not have the following structure:

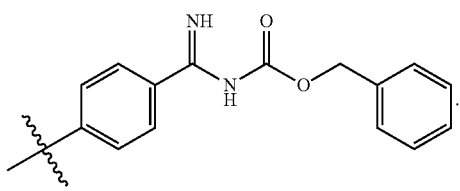 [SMILES: *c1ccc(C(=N)NC(=O)OCc2ccccc2)cc1]

In some embodiments, the small molecule is a compound having the following structure:

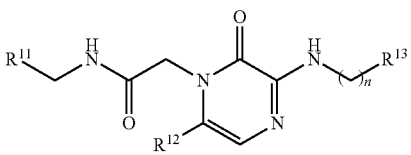

or a stereoisomer, tautomer, or pharmaceutically acceptable salt thereof, wherein:

R¹¹ has one of the following structures:

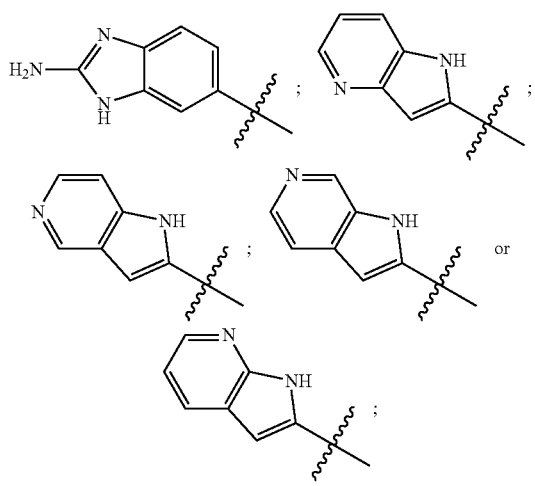

R¹² is methyl or halo;
R¹³ is a substituted or unsubstituted aryl; and
n is 1 or 2
provided that:
the compound does not have the following structure:

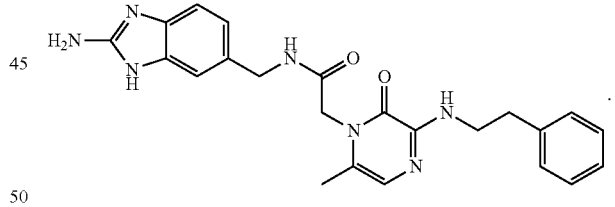

In some embodiments, the small molecule is a compound having the following Structure:

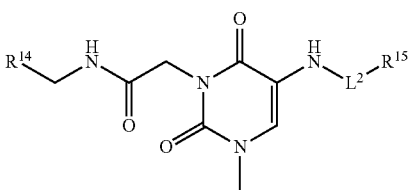

or a stereoisomer, tautomer, or pharmaceutically acceptable salt thereof, wherein:
R¹⁴ is a substituted or unsubstituted aryl or a substituted or unsubstituted heteroaryl;

$R^{15}$ is a substituted or unsubstituted arylalkyl, or a substituted or unsubstituted heteroarylalkyl;

$L^2$ is a direct bond, —C(=O), or —S(=O)$_t$—; and t is 0, 1, or 2.

In some embodiments, certain features of the compounds and/or formulae are disclosed in groups or in ranges. It is specifically intended that such a disclosure include each and every individual subcombination of the members of such groups and ranges. For example, the terms "$C_{1-6}$ alkyl" and "$C_1$-$C_6$ alkyl" are specifically intended to individually disclose (without limitation) methyl, ethyl, $C_3$ alkyl, $C_4$ alkyl, $C_5$ alkyl and $C_6$ alkyl.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means substituted or unsubstituted. The term "substituted" means that a hydrogen atom is formally removed and replaced by a substituent. A single divalent substituent, e.g., oxo, can replace two hydrogen atoms.

The terms "$C_{n-m}$" and "$C_n$-$C_m$" where n and m are integers indicates a group that contains from n to m carbon atoms. Examples include $C_{1-4}$, $C_{1-6}$, and the like. The term is intended to expressly disclose every member in the range, i.e., $C_n$, $C_{n+1}$, $C_{n+2}$ .... $C_{m-2}$, $C_{m-1}$, $C_m$. For example, $C_{1-6}$ is intended to disclose $C_1$, $C_2$, $C_3$, $C_4$, $C_5$, and $C_6$. "$C_{n-m}$" means the same as "$C_n$-$C_m$".

The term "alkyl" employed alone or in combination with other terms, refers to a saturated hydrocarbon group that may be straight-chain or branched. The terms "$C_{n-m}$ alkyl" and "$C_n$-$C_m$ alkyl" refer to an alkyl group having n to m carbon atoms. For example, $C_1$-$C_{12}$ indicates that the group may have from 1 to 12 (inclusive) carbon atoms in it. If not otherwise indicated, an alkyl group about 1 to about 20 carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, 1,1-dimethylpropyl, n-pentyl, 3-pentyl, n-hexyl, 1,2,2-trimethylpropyl, hexyl, heptyl, octyl, nonyl, decyl, dodecyl, and the like. The term "lower alkyl" refers to alkyl groups having from 1 to 6 carbon atoms in the chain. A "substituted alkyl" group is an alkyl group that is substituted with one or more substituents.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The terms "$C_{n-m}$ alkenyl" and "$C_n$-$C_m$ alkenyl" refer to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" and "$C_n$-$C_m$ alkynyl" refer to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bonds replaced by points of attachment of the alkylene group to the remainder of the compound. The term "$C_{n-m}$ alkylene" refers to an alkylene group having n to m carbon atoms. Examples of alkylene groups include, but are not limited to, methylene, ethan-1,2-diyl, propan-1,3-diyl, propan-1,2-diyl, butan-1,4-diyl, butan-1,3-diyl, butan-1,2-diyl, 2-methyl-propan-1,3-diyl and the like. In some embodiments, "$C_{n-m}$ alkylene" can refer to chain of from n to m methylene ($CH_2$) groups, —($CH_2$)$_{n-m}$—, such as —$CH_2$—, —$CH_2CH_2$—, —$CH_2CH_2CH_2$—, etc.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "alkoxyalkyl" refers to an alkyl group in which one or more of the hydrogen atoms has been replaced by an alkoxy group. The term "$C_{n-m}$ alkoxy-$C_{p-q}$ alkyl" refers to a $C_{p-q}$ alkyl group substituted by a $C_{n-m}$ alkoxy group. In some embodiments, the hydroxyalkyl group has one alkoxy group. In some embodiments, the alkoxyalkyl group has one or two alkoxy groups, each on a different carbon atom. Examples may include, but are not limited to, methoxymethyl, ethoxymethyl, 3-ethoxyethyl, and 1-methoxyethyl.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom 10 selected from F, Cl, or Br. In some embodiments, halo is F.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "hydroxyalkyl" refers to an alkyl group in which one or more of the hydrogen atoms has been replaced by a hydroxy. The term "$C_{n-m}$ hydroxyalkyl" refers to a $C_{n-m}$ alkyl group having n to m carbon atoms and from at least one hydroxy group. In some embodiments, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "n-membered," where n is an integer, typically describes the number of ring-forming atoms in a moiety where the number of ring-forming atoms is n. The term "n-m membered" wherein n and m are integers describes a range where the number of ring forming atoms is from n to m. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, tetracenyl, and the like. In some embodiments, aryl groups have from 6 to about 20 carbon atoms, from 6 to about 18 carbon atoms, from 6 to about 15 carbon atoms, or from 6 to about 10 carbon atoms. In some embodiments, the aryl group is phenyl.

The term "arylalkyl" or "aralkyl" or "alkylaryl" employed alone or in combination with other terms, refers to a group of formula -alkylene-aryl, and refers to an alkyl group as defined herein wherein at least one hydrogen has been replaced by an aryl group as defined herein. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is $C_{6-10}$ aryl-$C_{1-3}$ alkyl. In some embodiments, arylalkyl is phenyl-$C_{1-3}$ alkyl. Examples include, but are not limited to, benzyl, 1-phenylethyl, 4-methylbenzyl, and 1,1,-dimethyl-1-phenylmethyl. In some embodiments, arylalkyl is benzyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. An "n-membered heteroaryl" or "n-membered heteroaromatic", wherein n is an integer, refers to a heteroaryl having n ring-forming atoms. An "n-m membered heteroaryl" or "n-m membered heteroaromatic", wherein n and m are integers, refers to a heteroaryl having from n to m ring-forming atoms. The number of carbon atoms in the ring is fewer than the number of ring forming atoms by the number of heteroatoms. Thus, in some embodiments, an n-membered heteroaryl may have n-1, n-2, n-3 or n-4 ring carbon atoms and an n-m membered heteroaryl may have from n-1, n-2, n-3 or n-4 ring carbon atoms to m-1, m-2, m-3 or m-4 ring carbon atoms. In some embodiments, an n-m membered heteroaryl may have from 1 to m-1 ring carbon atoms. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, quinoline, isoquinoline, naphthyridine (including 1,2-, 1,3-, 1,4-, 1,5-, 1,6-, 1,7-, 1,8-, 2,3- and 2,6-naphthyridine), indole, azaindole, benzothiophene, benzofuran, benzisoxazole, benzimidazole, imidazo[1,2-b]thiazole, purine, furazane, triazole, tetrazole, 1,2,4-thiadiazole, quinazoline, phthalazine, imidazo[1,2-a]pyridine, imidazo[2,1-b]thiazolyl, or the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkyl," employed alone or in combination with other terms, refers to a group of formula -alkylene-heteroaryl. The term "n-membered heteroarylalkyl" wherein n is an integer refers to a heteroarylalkyl group in which the heteroaryl is n-membered. The term "n-m membered-$C_{p-q}$-alkyl" wherein n, m, p and q are integers refers to heteroarylalkyl group in which the heteroaryl is n to m membered and the alkyl has from p to q carbon atoms. In some embodiments, heteroarylalkyl is 5-10 membered heteroaryl-$C_{1-3}$ alkyl or $C_{1-9}$ heteroaryl-$C_{1-3}$ alkyl, wherein the heteroaryl portion is monocyclic or bicyclic and has 1, 2, 3, 4 or 5 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen. Examples include pyridylmethyl, such as 2-pyridylmethyl, 3-pyridylmethyl, or 4-pyridylmethyl.

The term "cycloalkyl", employed alone or in combination with other terms, refers to a non-aromatic, saturated, monocyclic, bicyclic or polycyclic hydrocarbon ring system. The term includes cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, 4,4-dimethylcyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "cycloalkylalkyl," employed alone or in combination with other terms, refers to a group of formula -alkylene-cycloalkyl. The term $C_{n-m}$ cycloalkyl-$C_{p-q}$ alkyl wherein n, m, p and q are integers, refers to a cycloalkyl group having from n to m carbon atoms attached to an alkyl group having from p to q carbon atoms. In some embodiments, cycloalkylalkyl is $C_{3-7}$ cycloalkyl-$C_{1-3}$ alkyl, wherein the cycloalkyl portion is monocyclic or bicyclic. Examples include cyclopropylmethyl, cyclobutylmethyl, cyclopentanemethyl, and cyclohexylmethyl.

The term "heterocycloalkyl", employed alone or in combination with other terms, refers to a non-aromatic ring or ring system, which may optionally contain one or more alkenylene groups as part of the ring structure, which has at least one heteroatom ring member independently selected from nitrogen, sulfur, and oxygen. An "n-membered heterocycloalkyl" wherein n is an integer, refers to a heteroaryl having n ring-forming atoms. An "n-m membered heterocycloalkyl" wherein n and m are integers, refers to a heterocycloalkyl having from n to m ring-forming atoms. The number of carbon atoms in the ring is fewer than the number of ring forming atoms by the number of heteroatoms. Thus, in some embodiments, an n-membered heterocycloalkyl may have n-1, n-2, n-3 or n-4 ring carbon atoms and an n-m membered heterocycloalkyl may have from n-1, n-2, n-3 or n-4 ring carbon atoms to m-1, m-2, m-3 or m-4 ring carbon atoms. In some embodiments, an n-m membered heterocycloalkyl may have from 1 to m-1 ring carbon atoms. In some embodiments, a heterocycloalkyl has 4-12 ring members, 4-10 ring members, 4-7 ring members or 4-6 ring members. Included in heterocycloalkyl groups are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfide group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidine, azepane, dihydrobenzofuran, dihydrofuran, dihydropyran, morpholine, 3-oxa-9-azaspiro[5.5]undecane, 1-oxa-8-azaspiro[4.5]decane, piperidine, piperazine, pyran, pyrrolidine, quinuclidine, tetrahydrofuran, tetrahydropyran, 1,2,3,4-tetrahydroquinoline, tropane, and thiomorpholine.

As used herein, the term "heterocycloalkylalkyl," employed alone or in combination with other terms, refers to a group of formula -alkylene-heterocycloalkyl. The term "n-membered heterocycloalkylalkyl" wherein n is an integer refers to a hereoarylalkylalkyl group in which the heterocycloalkyl is n-membered. The term "n-m membered-$C_{p-q}$-alkyl wherein n, m, p and q are integers refers to heterocycloalkylalkyl group in which the heterocycloalkyl is n to m membered and the alkyl has from p to q carbon atoms. In some embodiments, heterocycloalkylalkyl is 4-10 membered heterocycloalkyl-$C_{1-3}$ alkyl or $C_{1-9}$ heterocycloalkyl-$C_{1-3}$ alkyl, wherein the heterocycloalkyl portion is monocyclic or bicyclic and has 1, 2, 3, 4 or 5 heteroatom ring members independently selected from nitrogen, sulfur and oxygen. In some embodiments, heterocycloalkylalkyl is $C_{2-9}$ heterocycloalkyl-$C_{1-4}$ alkyl or $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

At certain places, the definitions or embodiments may refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

When any two groups or two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). Unless otherwise indicated, if two or more groups having the same definition are present, but the definition provides for alternatives, it should be understood that each occurrence of the same group is independently selected from the possible alternatives. For example, if two or more $R^a$ groups are present in a compound, and the definition of $R^a$ provides that $R^a$ can be A, B or C, then it should be understood that each $R^a$ group present in the compound is independently chosen from A, B and C, so that the $R^a$ groups present in the compound can be the same or different.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or(S), unless otherwise indicated.

Compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution. The disclosure is intended to encompass all such tautomers of the compounds described.

Compounds described herein can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

Compounds described herein may include acidic and/or basic groups and be capable of forming salts. It should be understood that the present disclosure is intended to include all salts of compounds that are capable of forming salts, whether or not the possible existence of salts is expressly described, including both acid and base salts of a compound. Furthermore, when a compound is described that is a salt, it is understood that the disclosure of the compound is intended to include all forms of the compound, including the free base or free acid, as well as alternative salt forms thereof. The term "salt" refers to derivatives of the disclosed compounds wherein the parent compound is modified by converting an existing acid or base moiety to its salt form. Examples of salts include, but are not limited to, mineral or organic acid salts of basic residues such as amines; alkali or organic salts of acidic residues such as carboxylic acids; and the like. The terms "a salt thereof," "salt thereof," or "salts thereof" can be applied to any preceding member of an associated Markush group. For example, a group consisting of A, B, C, and salts thereof would include within its scope embodiments that were a salt of A, embodiments that were a salt of B, and embodiments that were a salt of C.

Salts of the compounds disclosed herein include pharmaceutically acceptable salts. The term "pharmaceutically acceptable salts" refers to non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms. Additional information on suitable pharmaceutically acceptable salts can be found in Remington's, Pharmaceutical Sciences (current edition), Mack Publishing Co., Easton, PA, which is incorporated herein by reference.

Compounds and salts thereof, including pharmaceutically acceptable salts, can be found together with other substances such as water and solvents (e.g., hydrates and solvates) or can be isolated. When in the solid state, the compounds described herein, and salts thereof may occur in various forms and may, e.g., take the form of solvates, including hydrates. The compounds may be in any solid-state form, such as a polymorph or solvate, so unless clearly indicated otherwise, reference to compounds and salts thereof should be understood as encompassing any solid-state form of the compound.

In some embodiments, the compounds described herein or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

Compounds described herein, including salts, hydrates, and/or solvates thereof, can be prepared by any suitable known organic synthesis techniques and can be synthesized according to any of numerous possible synthetic routes, such as those described in U.S. Patent Application Nos. 62/943,629, 62/943,622, 62/943,611, 62/943,599, 16/425,791 and PCT Application No. PCT/US19/34220, each of which are hereby incorporated by reference in their entirety.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March's Advanced Organic Chemistry: Reactions, Mechanisms, and Structure, 6th Ed. (Wiley, 2007); Peturssion et al., "Protecting Groups in Carbohydrate Chemistry," *J. Chem. Educ.,* 1997, 74(11), 1297; and Wuts et al., Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

One skilled in the art would understand that the preparations can be modified or optimized using general knowledge of organic chemistry to prepare various compounds within the scope of the present disclosure.

Starting materials, reagents and intermediates whose synthesis is not described herein are either commercially available, known in the literature, or can be prepared by methods known to one skilled in the art.

It will be appreciated by one skilled in the art that the processes described are not the exclusive means by which compounds of the disclosure may be synthesized and that a broad repertoire of synthetic organic reactions is available to be potentially employed in synthesizing compounds of the disclosure. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry*, Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II* (Pergamon Press, 1996); Smith et al., *March's Advanced Organic Chemistry: Reactions, Mechanisms, and Structure,* 6th Ed. (Wiley, 2007); Trost et al. (Ed.), *Comprehensive Organic Synthesis* (Pergamon Press, 1991).

In some embodiments, the compounds of the disclosure are selectively inhibiting MASP-2 over thrombin. In some embodiments, the selectivity ratio of MASP-2: thrombin inhibition is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1. In some embodiments, the the compounds of the disclosure can inhibit one or more coagulation proteases such as thrombin, in addition to inhibiting MASP-2.

MASP-2 inhibitory acivity of the small molecule compounds of the disclosure can be determined by methods known in the art, for example, enzymatic MASP-2 assay utilizing a fluorogenic substrate as disclosed in PCT Application No. PCT/US19/34220, which is hereby incorporated by reference in their entirety. Likewise, thrombin inhibitory activity of the compounds of the diaclosure can be determined using methods known in the art. Exemplary assay methods and MASP-2 inhibitory activity of representative small molecule compounds are described in Examples 23 to 25 herein.

In some embodiments, the compounds disclosed herein inhibit activation of lectin pathway. Lectin pathway inhibitory activity of the compounds of the disclosure can be determined by methods known in the art, for example, using lectin pathway activation (LPA) assay in human serum described in in PCT Application No. PCT/US19/34220, which is hereby incorporated by reference in their entirety.

In some embodiments, the compound has a MASP-2 inhibition Ki values, as determined, for example, by enzymatic MASP-2 assay described above, of less than about 25 μM, less than about 10 μM, less than about 2.5 μM, less than about 1 µM, less than about 0.5 µM, or less than about 0.1 µM. In some embodiments, the compound a Lectin Pathway Inhibition $IC_{50}$, as determined, for example, by lectin pathway activation (LPA) assay described above, of less than about 50 µM, less than about 5 µM, less than about 0.5 µM, or less than about 0.05 µM. In some embodiments, the compound has a selectivity of for MASP-2 inhibition versus thrombin (as determined, for example, by the ratio of the respective Ki) of greater than about 5.0-fold, greater than about 25-fold, greater than about 50-fold, or greater than about 100-fold.

In some embodiments, the compound is a compound of Tables 4A-4E below.

TABLE 4A

Exemplary compounds

| Compound No. | Structure | Salt |
|---|---|---|
| 1000 | 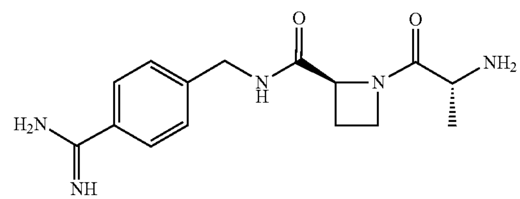 [SMILES: C[C@@H](N)C(=O)N1CC[C@H]1C(=O)NCc1ccc(C(=N)N)cc1] | NA |
| 1001 | 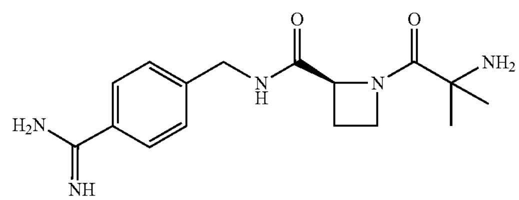 [SMILES: CC(C)(N)C(=O)N1CC[C@H]1C(=O)NCc1ccc(C(=N)N)cc1] | NA |
| 1002 | 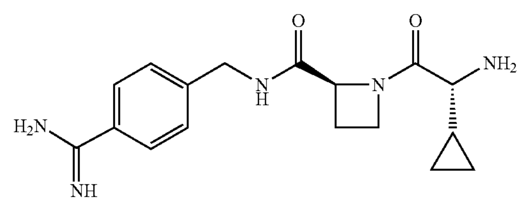 [SMILES: N=C(N)c1ccc(CNC(=O)[C@@H]2CCN2C(=O)[C@H](N)C2CC2)cc1] | NA |
| 1003 | 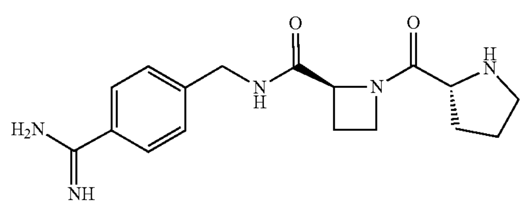 [SMILES: N=C(N)c1ccc(CNC(=O)[C@@H]2CCN2C(=O)[C@H]2CCCN2)cc1] | NA |
| 1004 | 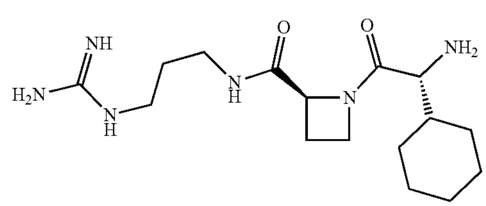 [SMILES: N=C(N)NCCCNC(=O)[C@@H]1CCN1C(=O)[C@H](N)C1CCCCC1] | 2HCl |
| 1005 | 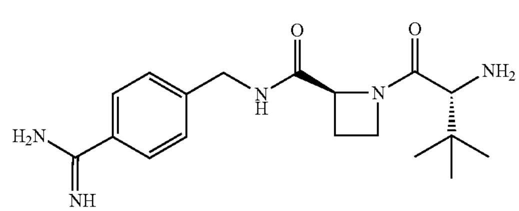 [SMILES: CC(C)(C)[C@@H](N)C(=O)N1CC[C@H]1C(=O)NCc1ccc(C(=N)N)cc1] | NA |

TABLE 4A-continued

| Compound No. | Structure | Salt |
|---|---|---|
| 1006 | 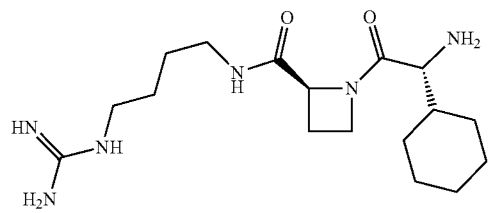 [SMILES: N=C(N)NCCCCNC(=O)[C@@H]1CCN1C(=O)[C@H](N)C1CCCCC1] | 2HCl |
| 1007 | 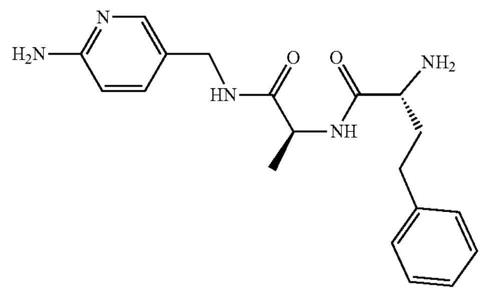 [SMILES: C[C@H](NC(=O)[C@H](N)CCc1ccccc1)C(=O)NCc1ccc(N)nc1] | 2HCl |
| 1008 | 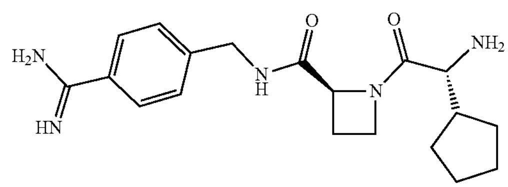 [SMILES: N=C(N)c1ccc(CNC(=O)[C@@H]2CCN2C(=O)[C@H](N)C2CCCC2)cc1] | NA |
| 1009 | 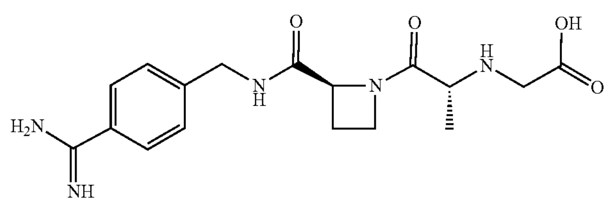 [SMILES: C[C@@H](NCC(=O)O)C(=O)N1CC[C@H]1C(=O)NCc1ccc(C(=N)N)cc1] | NA |
| 1010 | 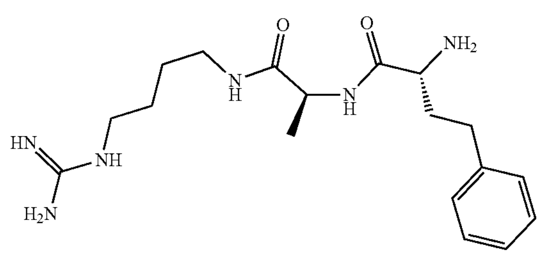 [SMILES: C[C@H](NC(=O)[C@H](N)CCc1ccccc1)C(=O)NCCCCNC(=N)N] | 2HCl |
| 1011 | 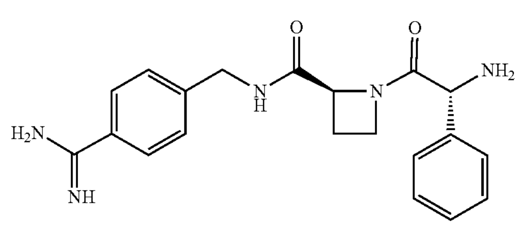 [SMILES: N=C(N)c1ccc(CNC(=O)[C@@H]2CCN2C(=O)[C@H](N)c2ccccc2)cc1] | NA |

TABLE 4A-continued

Exemplary compounds

| Compound No. | Structure | Salt |
|---|---|---|
| 1012 | 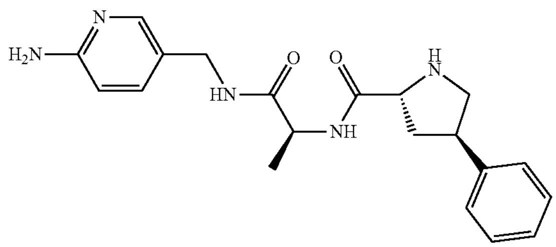 [SMILES: C[C@H](NC(=O)[C@H]1C[C@H](c2ccccc2)CN1)C(=O)NCc1ccc(N)nc1] | 2HCl |
| 1013 | 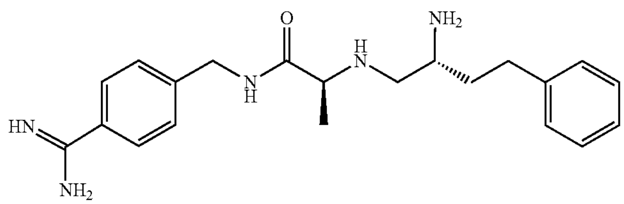 [SMILES: C[C@H](NC[C@H](N)CCc1ccccc1)C(=O)NCc1ccc(C(=N)N)cc1] | 2HCl |
| 1014 | 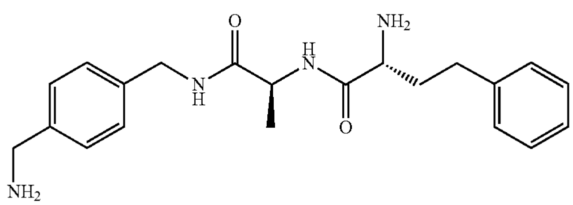 [SMILES: C[C@H](NC(=O)[C@H](N)CCc1ccccc1)C(=O)NCc1ccc(CN)cc1] | 2HCl |
| 1015 | 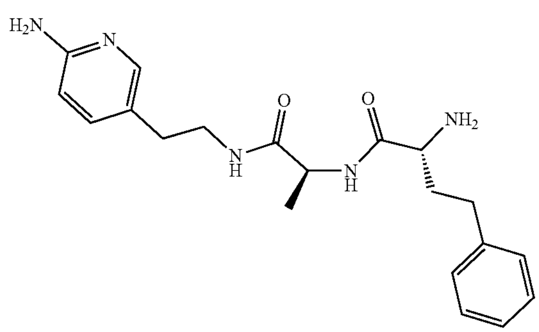 [SMILES: C[C@H](NC(=O)[C@H](N)CCc1ccccc1)C(=O)NCCc1ccc(N)nc1] | 2HCl |
| 1016 | 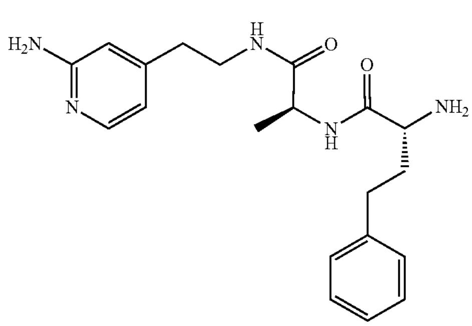 [SMILES: C[C@H](NC(=O)[C@H](N)CCc1ccccc1)C(=O)NCCc1ccnc(N)c1] | 2HCl |

TABLE 4A-continued

| Compound No. | Structure | Salt |
|---|---|---|
| 1017 | 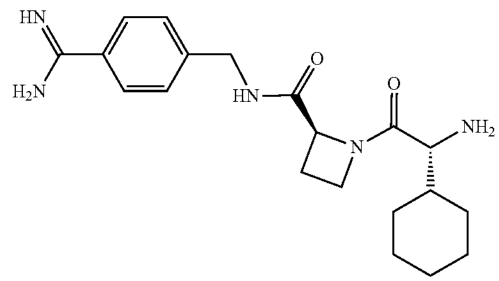 [SMILES: N=C(N)c1ccc(CNC(=O)[C@@H]2CCN2C(=O)[C@H](N)C2CCCCC2)cc1] | NA |
| 1018 | 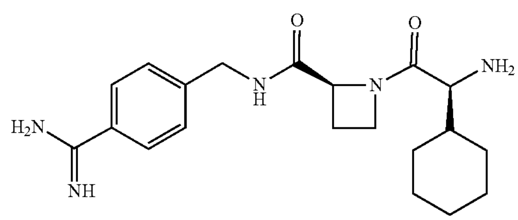 [SMILES: N=C(N)c1ccc(CNC(=O)[C@@H]2CCN2C(=O)[C@@H](N)C2CCCCC2)cc1] | NA |
| 1019 | 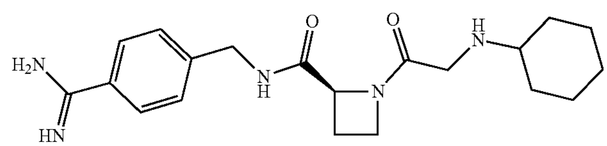 [SMILES: N=C(N)c1ccc(CNC(=O)[C@@H]2CCN2C(=O)CNC2CCCCC2)cc1] | NA |
| 1020 | 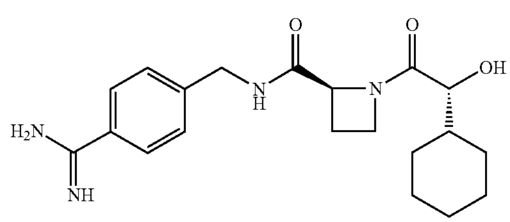 [SMILES: N=C(N)c1ccc(CNC(=O)[C@@H]2CCN2C(=O)[C@H](O)C2CCCCC2)cc1] | NA |
| 1021 | 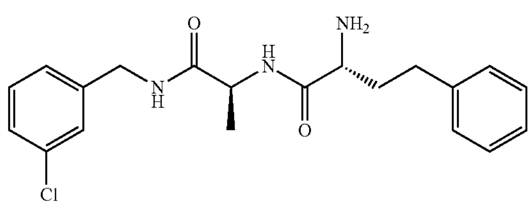 [SMILES: C[C@H](NC(=O)[C@H](N)CCc1ccccc1)C(=O)NCc1cccc(Cl)c1] | HCl |
| 1022 | 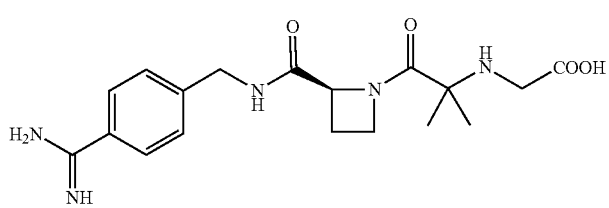 [SMILES: CC(C)(NCC(=O)O)C(=O)N1CC[C@H]1C(=O)NCc1ccc(C(=N)N)cc1] | NA |
| 1023 | 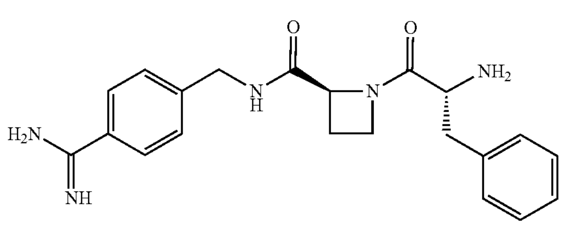 [SMILES: N=C(N)c1ccc(CNC(=O)[C@@H]2CCN2C(=O)[C@H](N)Cc2ccccc2)cc1] | NA |

TABLE 4A-continued

Exemplary compounds

| Compound No. | Structure | Salt |
|---|---|---|
| 1024 | 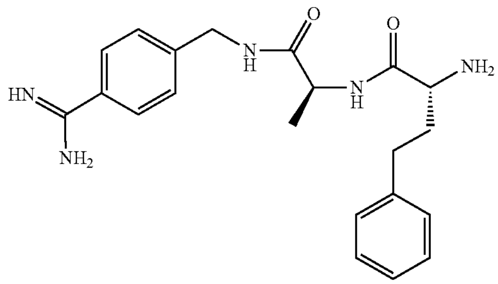 [SMILES: C[C@H](NC(=O)[C@H](N)CCc1ccccc1)C(=O)NCc1ccc(C(=N)N)cc1] | 2HCl |
| 1025 | isomer 3 | 2HCl |
| 1026 | 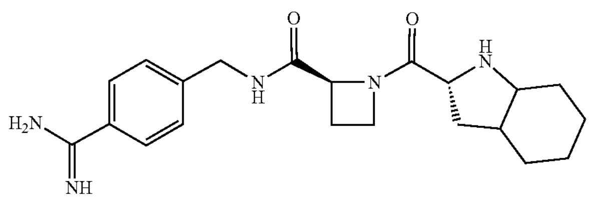 | NA |
| 1027 | 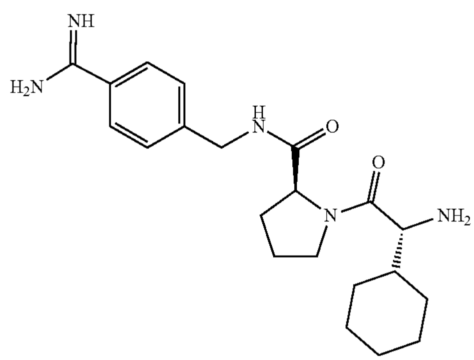 [SMILES: N=C(N)c1ccc(CNC(=O)[C@@H]2CCCN2C(=O)[C@H](N)C2CCCCC2)cc1] | 2HCl |
| 1028 | 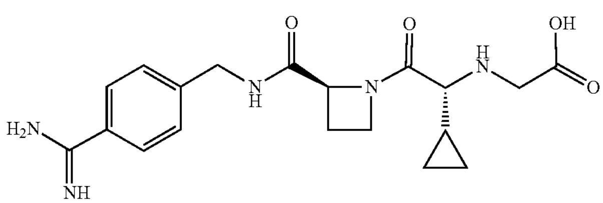 [SMILES: N=C(N)c1ccc(CNC(=O)[C@@H]2CCN2C(=O)[C@H](NCC(=O)O)C2CC2)cc1] | NA |
| 1029 | 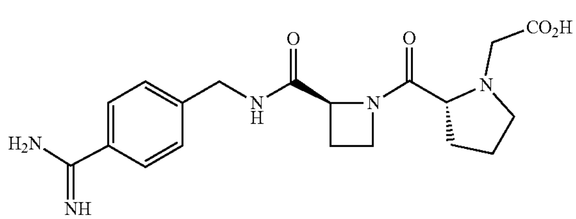 [SMILES: N=C(N)c1ccc(CNC(=O)[C@@H]2CCN2C(=O)[C@H]2CCCN2CC(=O)O)cc1] | NA |

TABLE 4A-continued

| Compound No. | Structure | Salt |
|---|---|---|
| 1030 | 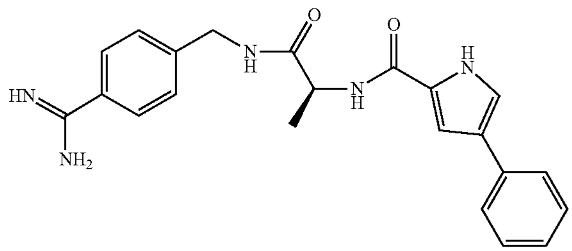 [SMILES: C[C@H](NC(=O)c1cc(-c2ccccc2)c[nH]1)C(=O)NCc1ccc(C(=N)N)cc1] | NA |
| 1031 | 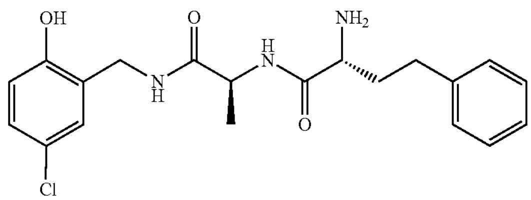 [SMILES: C[C@H](NC(=O)[C@H](N)CCc1ccccc1)C(=O)NCc1cc(Cl)ccc1O] | HCl |
| 1032 | 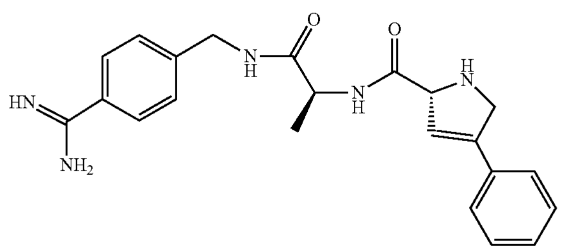 [SMILES: C[C@H](NC(=O)[C@H]1C=C(c2ccccc2)CN1)C(=O)NCc1ccc(C(=N)N)cc1] | 2HCl |
| 1033 | 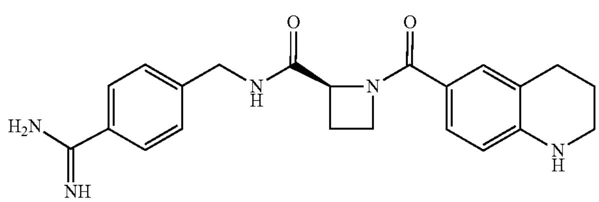 [SMILES: N=C(N)c1ccc(CNC(=O)[C@@H]2CCN2C(=O)c2ccc3c(c2)CCCN3)cc1] | NA |
| 1034 | 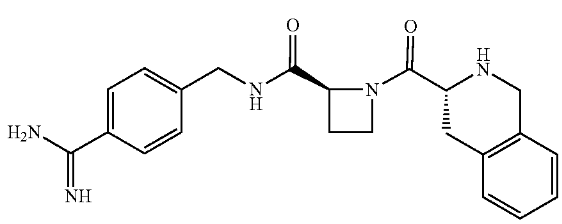 [SMILES: N=C(N)c1ccc(CNC(=O)[C@@H]2CCN2C(=O)[C@H]2Cc3ccccc3CN2)cc1] | NA |
| 1035 | 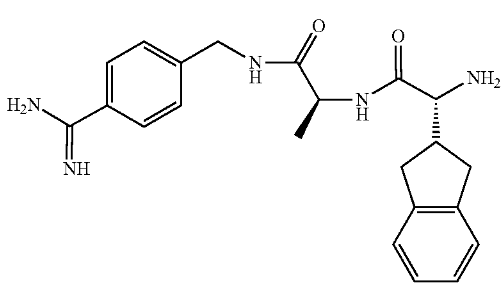 [SMILES: C[C@H](NC(=O)[C@H](N)C1Cc2ccccc2C1)C(=O)NCc1ccc(C(=N)N)cc1] | 2HCl |

TABLE 4A-continued

| Compound No. | Structure | Salt |
|---|---|---|
| 1036 | 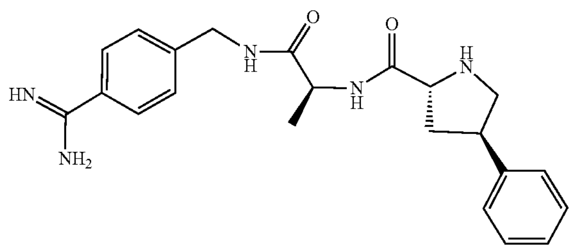 [SMILES: C[C@H](NC(=O)[C@H]1C[C@H](c2ccccc2)CN1)C(=O)NCc1ccc(C(=N)N)cc1] | 2HCl |
| 1037 | 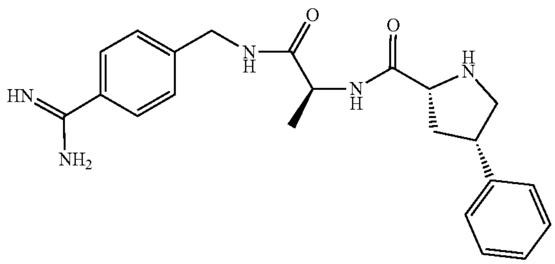 [SMILES: C[C@H](NC(=O)[C@H]1C[C@@H](c2ccccc2)CN1)C(=O)NCc1ccc(C(=N)N)cc1] | 2HCl |
| 1038 | 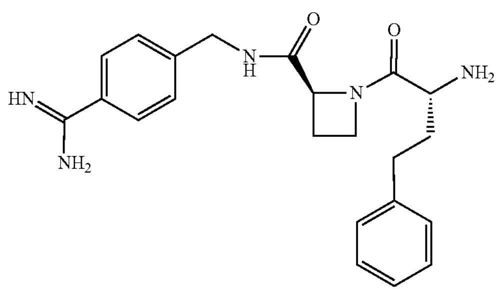 [SMILES: N=C(N)c1ccc(CNC(=O)[C@@H]2CCN2C(=O)[C@H](N)CCc2ccccc2)cc1] | 2HCl |
| 1039 | 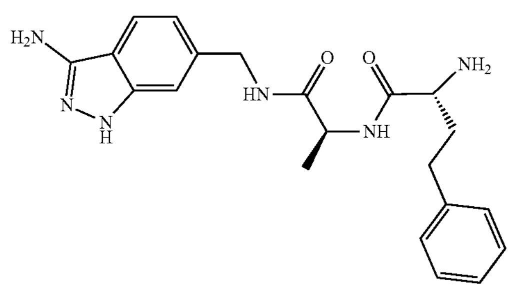 [SMILES: C[C@H](NC(=O)[C@H](N)CCc1ccccc1)C(=O)NCc1ccc2c(N)n[nH]c2c1] | 2HCl |
| 1040 | 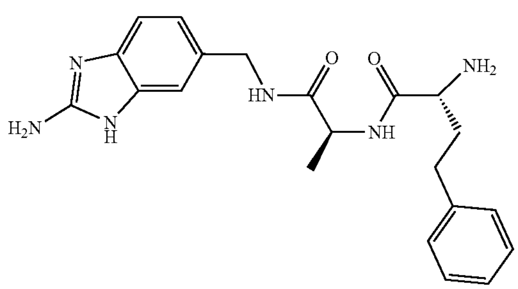 [SMILES: C[C@H](NC(=O)[C@H](N)CCc1ccccc1)C(=O)NCc1ccc2nc(N)[nH]c2c1] | 2HCl |

TABLE 4A-continued

Exemplary compounds

| Compound No. | Structure | Salt |
|---|---|---|
| 1041 | 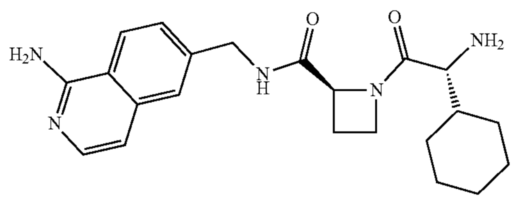 [SMILES: Nc1nccc2cc(CNC(=O)[C@@H]3CCN3C(=O)[C@H](N)C3CCCCC3)ccc12] | 2HCl |
| 1042 | 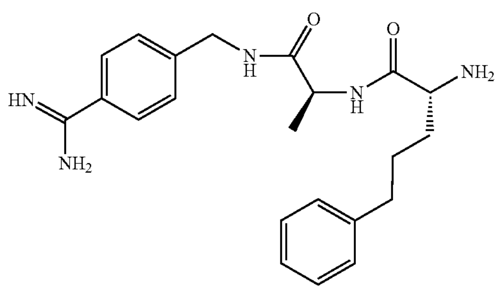 [SMILES: C[C@H](NC(=O)[C@H](N)CCCc1ccccc1)C(=O)NCc1ccc(C(=N)N)cc1] | 2HCl |
| 1043 | 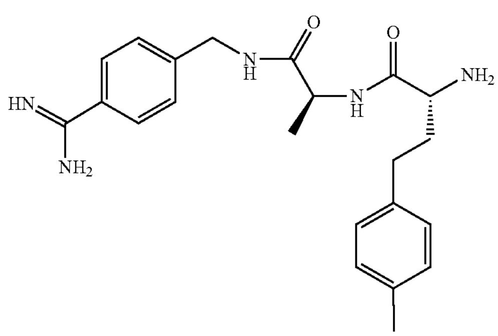 [SMILES: Cc1ccc(CC[C@@H](N)C(=O)N[C@@H](C)C(=O)NCc2ccc(C(=N)N)cc2)cc1] | 2HCl |
| 1044 | 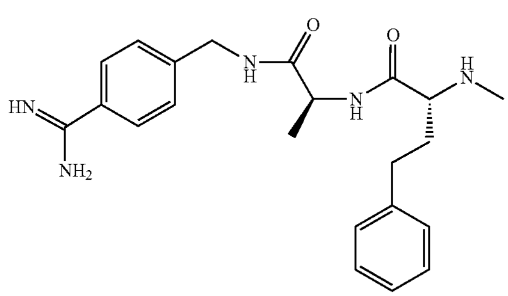 [SMILES: CN[C@H](CCc1ccccc1)C(=O)N[C@@H](C)C(=O)NCc1ccc(C(=N)N)cc1] | 2HCl |
| 1045 | 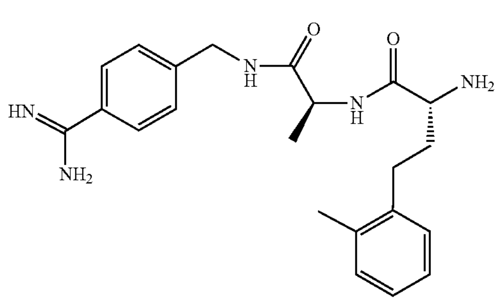 [SMILES: Cc1ccccc1CC[C@@H](N)C(=O)N[C@@H](C)C(=O)NCc1ccc(C(=N)N)cc1] | 2HCl |

TABLE 4A-continued

| Compound No. | Structure | Salt |
|---|---|---|
| 1046 | 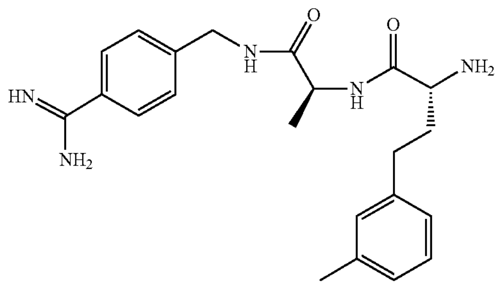 [SMILES: Cc1cccc(CC[C@@H](N)C(=O)N[C@@H](C)C(=O)NCc2ccc(C(=N)N)cc2)c1] | 2HCl |
| 1047 | 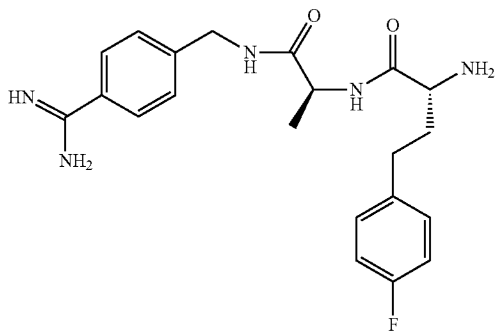 | 2HCl |
| 1048 | 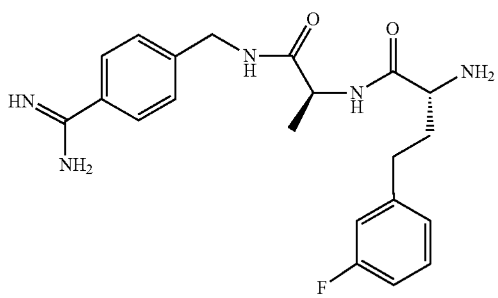 [SMILES: C[C@H](NC(=O)[C@H](N)CCc1cccc(F)c1)C(=O)NCc1ccc(C(=N)N)cc1] | 2HCl |
| 1049 | 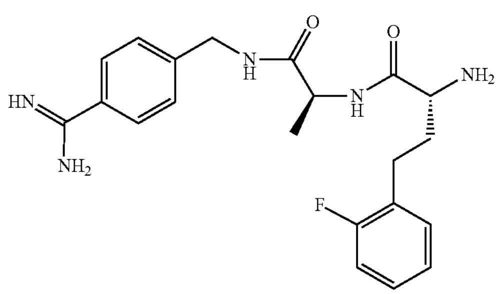 [SMILES: C[C@H](NC(=O)[C@H](N)CCc1ccccc1F)C(=O)NCc1ccc(C(=N)N)cc1] | 2HCl |
| 1050 | 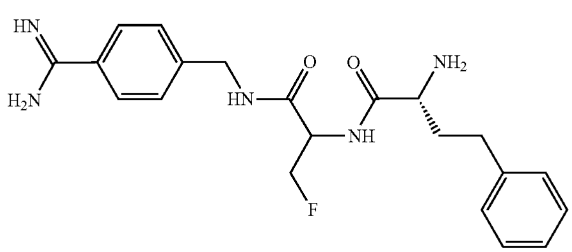 [SMILES: N=C(N)c1ccc(CNC(=O)C(CF)NC(=O)[C@H](N)CCc2ccccc2)cc1] | 2HCl |

TABLE 4A-continued

Exemplary compounds

| Compound No. | Structure | Salt |
|---|---|---|
| 1051 | 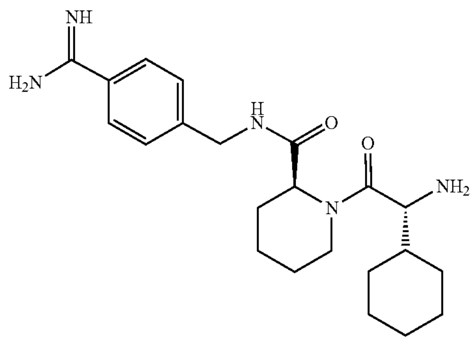 [SMILES: N=C(N)c1ccc(CNC(=O)[C@@H]2CCCCN2C(=O)[C@H](N)C2CCCCC2)cc1] | 2HCl |
| 1052 | 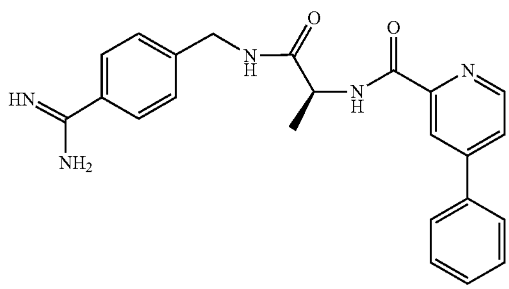 [SMILES: C[C@H](NC(=O)c1cc(-c2ccccc2)ccn1)C(=O)NCc1ccc(C(=N)N)cc1] | 2HCl |
| 1053 | 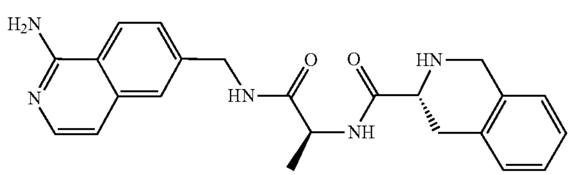 [SMILES: C[C@H](NC(=O)[C@H]1Cc2ccccc2CN1)C(=O)NCc1ccc2c(N)nccc2c1] | 2 TFA |
| 1054 | 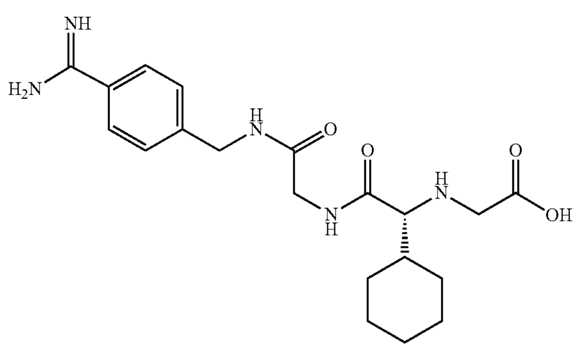 | 2HCl |
| 1055 | 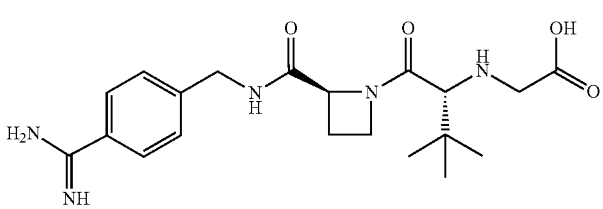 [SMILES: CC(C)(C)[C@@H](NCC(=O)O)C(=O)N1CC[C@H]1C(=O)NCc1ccc(C(=N)N)cc1] | NA |

TABLE 4A-continued

Exemplary compounds

| Compound No. | Structure | Salt |
|---|---|---|
| 1056 | 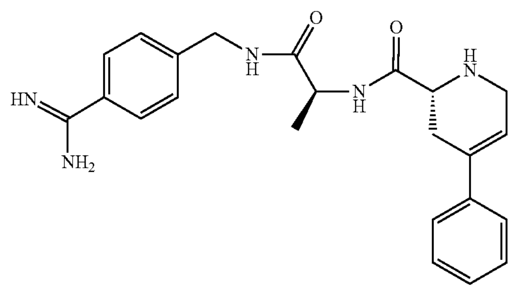 [SMILES: C[C@H](NC(=O)[C@H]1CC(c2ccccc2)=CCN1)C(=O)NCc1ccc(C(=N)N)cc1] | 2HCl |
| 1057 | 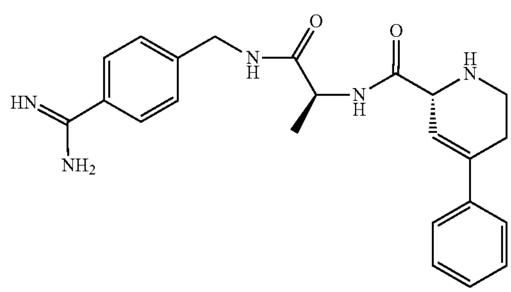 [SMILES: C[C@H](NC(=O)[C@H]1C=C(c2ccccc2)CCN1)C(=O)NCc1ccc(C(=N)N)cc1] | 2HCl |
| 1058 | 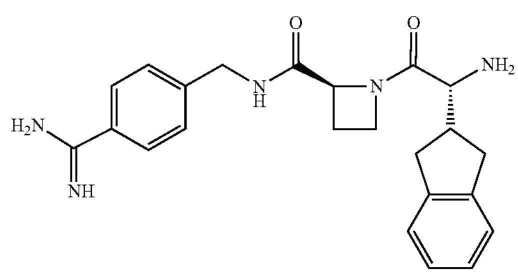 [SMILES: N=C(N)c1ccc(CNC(=O)[C@@H]2CCN2C(=O)[C@H](N)C2Cc3ccccc3C2)cc1] | NA |
| 1059 | 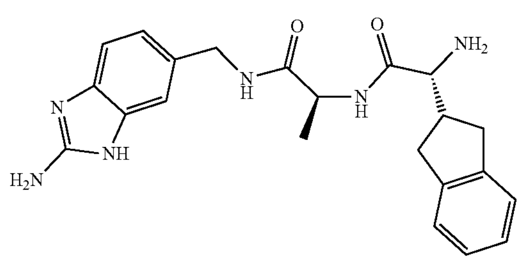 [SMILES: C[C@H](NC(=O)[C@H](N)C1Cc2ccccc2C1)C(=O)NCc1ccc2nc(N)[nH]c2c1] | 2HCl |
| 1060 | 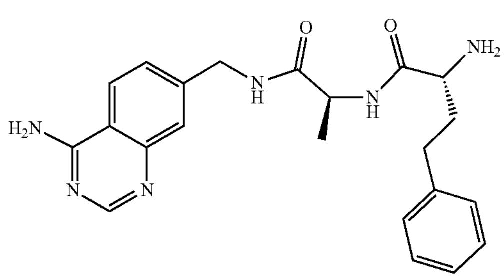 [SMILES: C[C@H](NC(=O)[C@H](N)CCc1ccccc1)C(=O)NCc1ccc2c(N)ncnc2c1] | 2HCl |

TABLE 4A-continued

| Compound No. | Structure | Salt |
|---|---|---|
| 1061 | 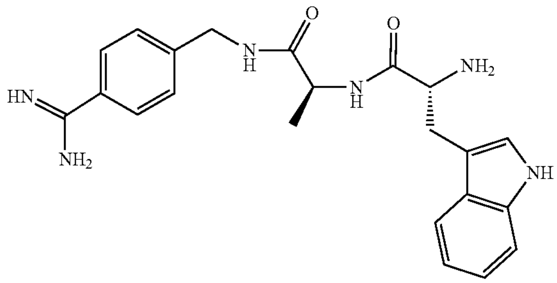 [SMILES: C[C@H](NC(=O)[C@H](N)Cc1c[nH]c2ccccc12)C(=O)NCc1ccc(C(=N)N)cc1] | 2HCl |
| 1062 | 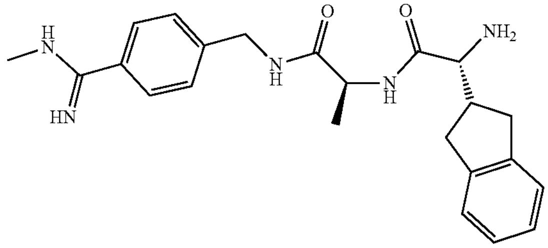 [SMILES: CNC(=N)c1ccc(CNC(=O)[C@H](C)NC(=O)[C@H](N)C2Cc3ccccc3C2)cc1] | 2HCl |
| 1063 | isomer 1 | 2HCl |
| 1064 | isomer 2 | 2HCl |
| 1065 | isomer 3 | 2HCl |

TABLE 4A-continued
Exemplary compounds
| Compound No. | Structure | Salt |
|---|---|---|
| 1066 | 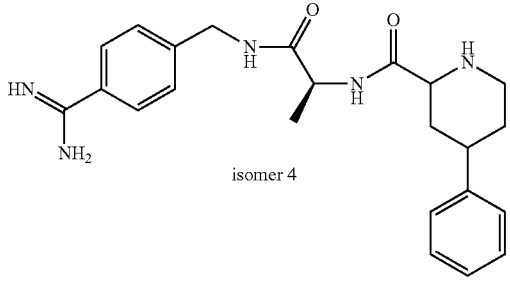 [SMILES: C[C@H](NC(=O)C1CC(c2ccccc2)CCN1)C(=O)NCc1ccc(C(=N)N)cc1] isomer 4 | 2HCl |
| 1067 | 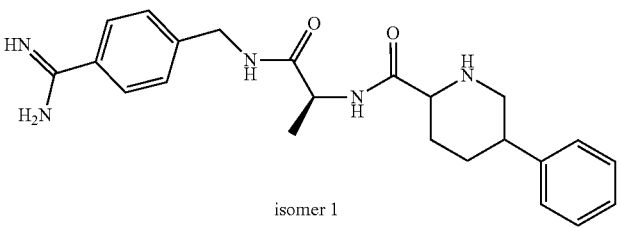 [SMILES: C[C@H](NC(=O)C1CCC(c2ccccc2)CN1)C(=O)NCc1ccc(C(=N)N)cc1] isomer 1 | 2HCl |
| 1068 | 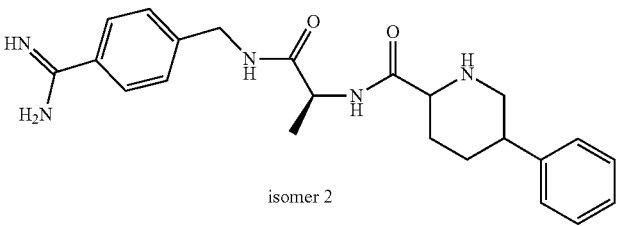 [SMILES: C[C@H](NC(=O)C1CCC(c2ccccc2)CN1)C(=O)NCc1ccc(C(=N)N)cc1] isomer 2 | 2HCl |
| 1069 | 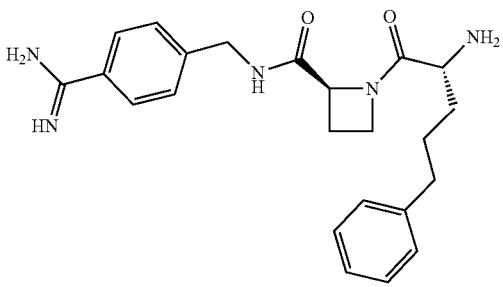 [SMILES: N=C(N)c1ccc(CNC(=O)[C@@H]2CCN2C(=O)[C@H](N)CCCc2ccccc2)cc1] | NA |
| 1070 | 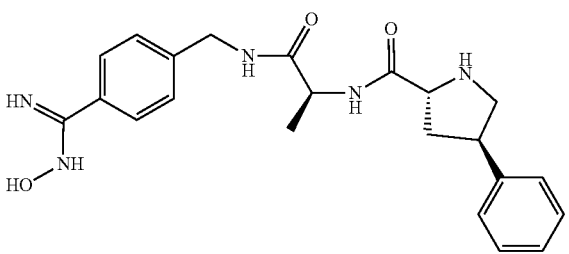 [SMILES: C[C@H](NC(=O)[C@H]1C[C@H](c2ccccc2)CN1)C(=O)NCc1ccc(C(=N)NO)cc1] | 2HCl |
| 1071 | 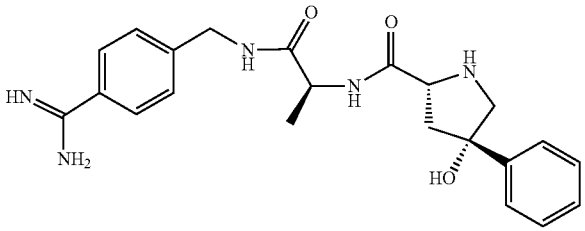 [SMILES: C[C@H](NC(=O)[C@H]1C[C@](O)(c2ccccc2)CN1)C(=O)NCc1ccc(C(=N)N)cc1] | 2HCl |

TABLE 4A-continued

| Compound No. | Structure | Salt |
|---|---|---|
| 1072 | 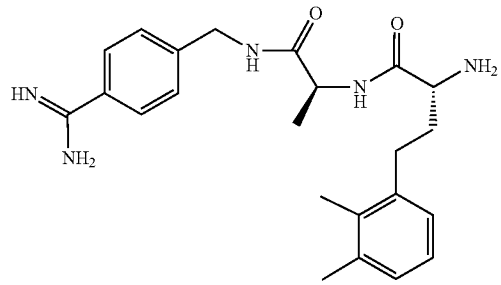 [SMILES: Cc1cccc(CC[C@@H](N)C(=O)N[C@@H](C)C(=O)NCc2ccc(C(=N)N)cc2)c1C] | 2HCl |
| 1073 | 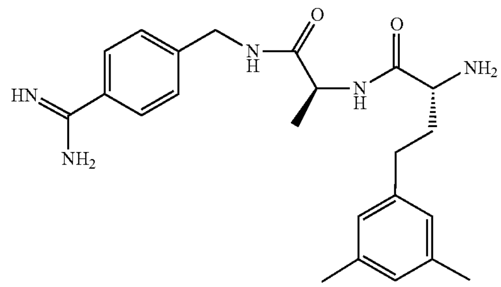 [SMILES: Cc1cc(C)cc(CC[C@@H](N)C(=O)N[C@@H](C)C(=O)NCc2ccc(C(=N)N)cc2)c1] | 2HCl |
| 1074 | 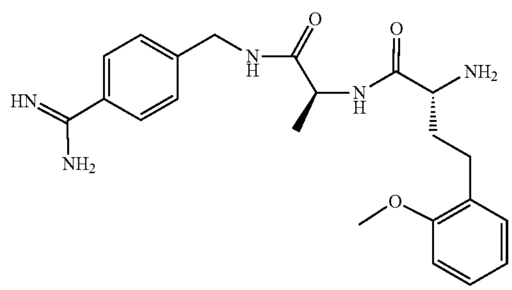 [SMILES: COc1ccccc1CC[C@@H](N)C(=O)N[C@@H](C)C(=O)NCc1ccc(C(=N)N)cc1] | 2HCl |
| 1075 | 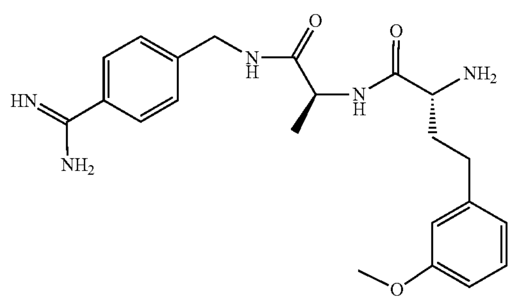 [SMILES: COc1cccc(CC[C@@H](N)C(=O)N[C@@H](C)C(=O)NCc2ccc(C(=N)N)cc2)c1] | 2HCl |
| 1076 | 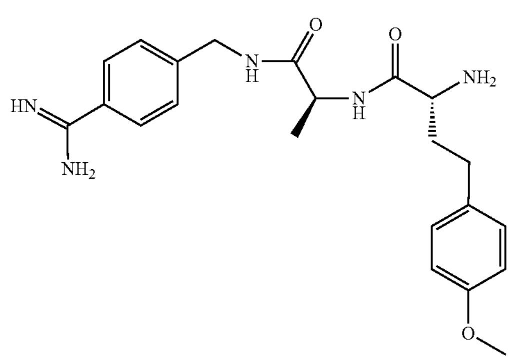 [SMILES: COc1ccc(CC[C@@H](N)C(=O)N[C@@H](C)C(=O)NCc2ccc(C(=N)N)cc2)cc1] | 2HCl |

TABLE 4A-continued

Exemplary compounds

| Compound No. | Structure | Salt |
|---|---|---|
| 1077 | 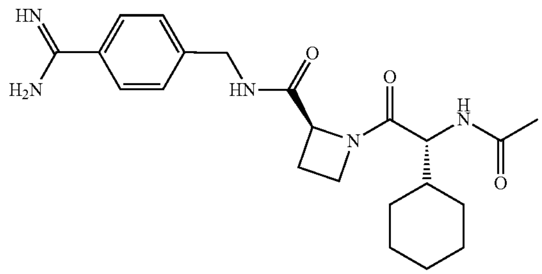 [SMILES: CC(=O)N[C@@H](C(=O)N1CC[C@H]1C(=O)NCc1ccc(C(=N)N)cc1)C1CCCCC1] | NA |
| 1078 | 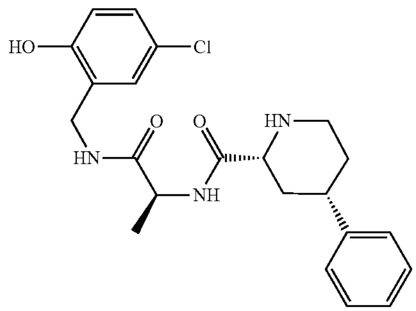 [SMILES: C[C@H](NC(=O)[C@H]1C[C@@H](c2ccccc2)CCN1)C(=O)NCc1cc(Cl)ccc1O] | HCl |
| 1079 | 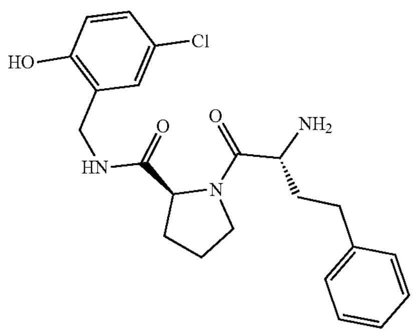 [SMILES: N[C@H](CCc1ccccc1)C(=O)N1CCC[C@H]1C(=O)NCc1cc(Cl)ccc1O] | HCl |
| 1080 | 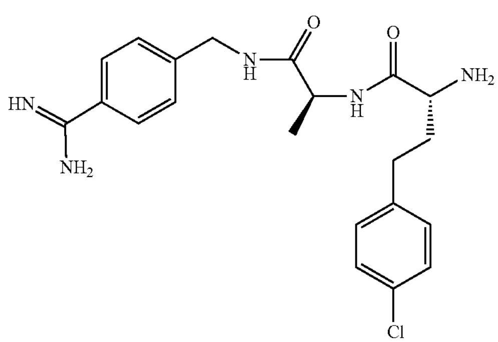 [SMILES: C[C@H](NC(=O)[C@H](N)CCc1ccc(Cl)cc1)C(=O)NCc1ccc(C(=N)N)cc1] | 2HCl |
| 1081 | 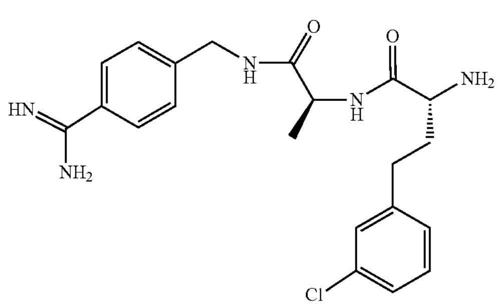 [SMILES: C[C@H](NC(=O)[C@H](N)CCc1cccc(Cl)c1)C(=O)NCc1ccc(C(=N)N)cc1] | 2HCl |

TABLE 4A-continued

Exemplary compounds

| Compound No. | Structure | Salt |
|---|---|---|
| 1082 | 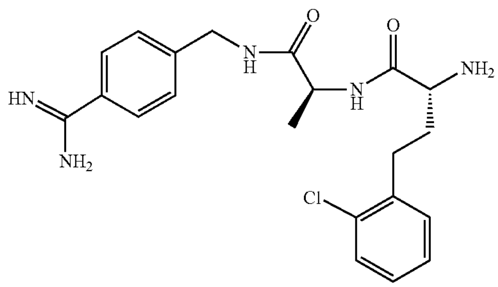 [SMILES: C[C@H](NC(=O)[C@H](N)CCc1ccccc1Cl)C(=O)NCc1ccc(C(=N)N)cc1] | 2HCl |
| 1083 | 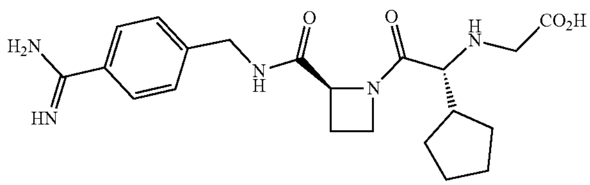 [SMILES: N=C(N)c1ccc(CNC(=O)[C@@H]2CCN2C(=O)[C@H](NCC(=O)O)C2CCCC2)cc1] | NA |
| 1084 | 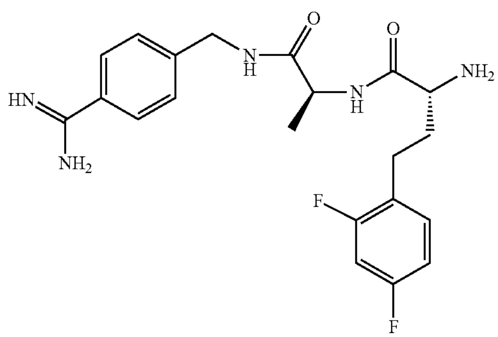 [SMILES: C[C@H](NC(=O)[C@H](N)CCc1ccc(F)cc1F)C(=O)NCc1ccc(C(=N)N)cc1] | 2HCl |
| 1085 | 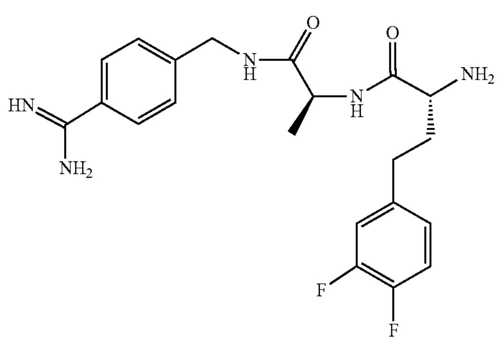 [SMILES: C[C@H](NC(=O)[C@H](N)CCc1ccc(F)c(F)c1)C(=O)NCc1ccc(C(=N)N)cc1] | 2HCl |
| 1086 | 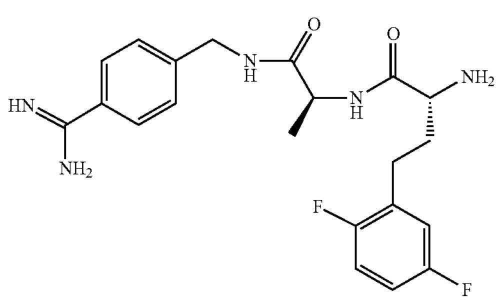 [SMILES: C[C@H](NC(=O)[C@H](N)CCc1cc(F)ccc1F)C(=O)NCc1ccc(C(=N)N)cc1] | 2HCl |

TABLE 4A-continued

Exemplary compounds

| Compound No. | Structure | Salt |
|---|---|---|
| 1087 | 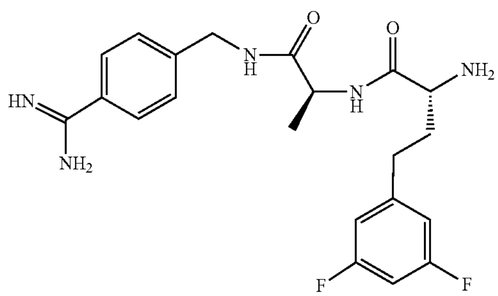 [SMILES: C[C@H](NC(=O)[C@H](N)CCc1cc(F)cc(F)c1)C(=O)NCc1ccc(C(=N)N)cc1] | 2HCl |
| 1088 | 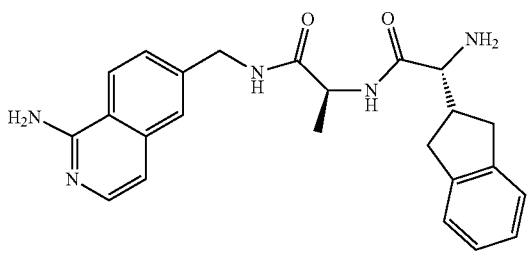 [SMILES: C[C@H](NC(=O)[C@H](N)C1Cc2ccccc2C1)C(=O)NCc1ccc2c(N)nccc2c1] | 2HCl |
| 1089 | 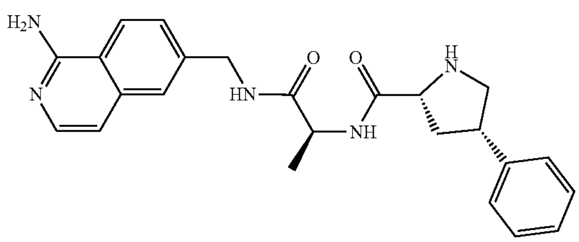 [SMILES: C[C@H](NC(=O)[C@H]1C[C@@H](c2ccccc2)CN1)C(=O)NCc1ccc2c(N)nccc2c1] | 2HCl |
| 1090 | 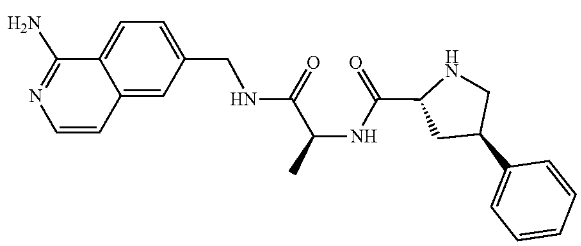 [SMILES: C[C@H](NC(=O)[C@H]1C[C@H](c2ccccc2)CN1)C(=O)NCc1ccc2c(N)nccc2c1] | 2HCl |
| 1091 | 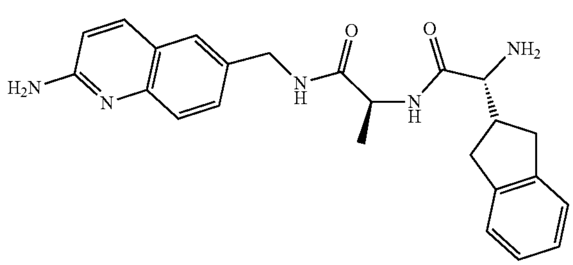 [SMILES: C[C@H](NC(=O)[C@H](N)C1Cc2ccccc2C1)C(=O)NCc1ccc2nc(N)ccc2c1] | 2HCl |

TABLE 4A-continued

Exemplary compounds

| Compound No. | Structure | Salt |
|---|---|---|
| 1092 | 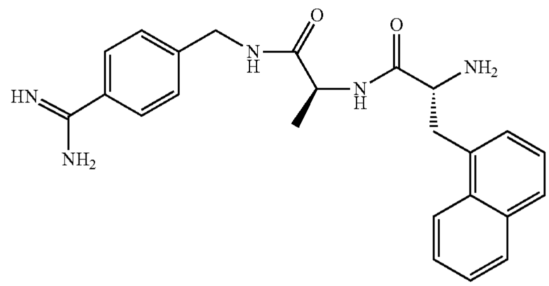 [SMILES: C[C@H](NC(=O)[C@H](N)Cc1cccc2ccccc12)C(=O)NCc1ccc(C(=N)N)cc1] | 2HCl |
| 1093 | 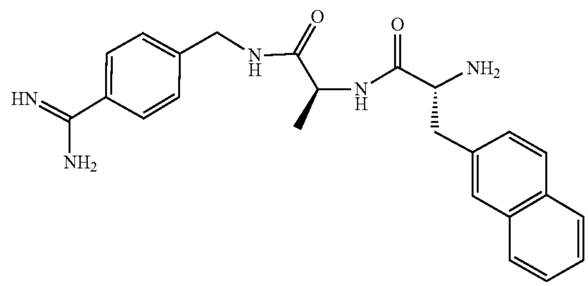 [SMILES: C[C@H](NC(=O)[C@H](N)Cc1ccc2ccccc2c1)C(=O)NCc1ccc(C(=N)N)cc1] | 2HCl |
| 1094 | 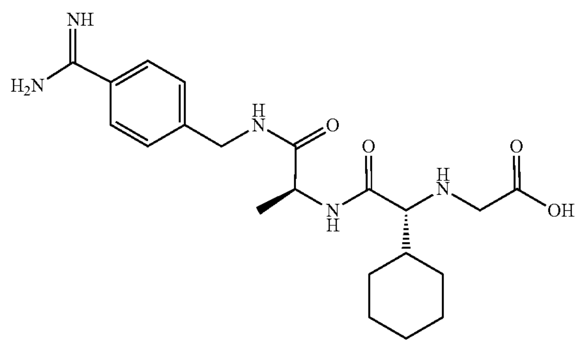 [SMILES: C[C@H](NC(=O)[C@H](NCC(=O)O)C1CCCCC1)C(=O)NCc1ccc(C(=N)N)cc1] | 2HCl |
| 1095 | 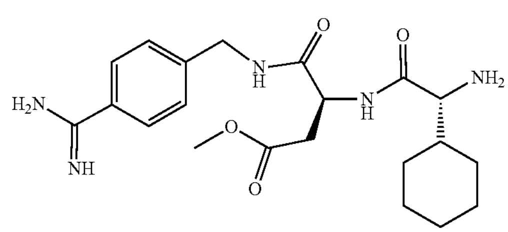 [SMILES: COC(=O)C[C@H](NC(=O)[C@H](N)C1CCCCC1)C(=O)NCc1ccc(C(=N)N)cc1] | 2HCl |
| 1096 | 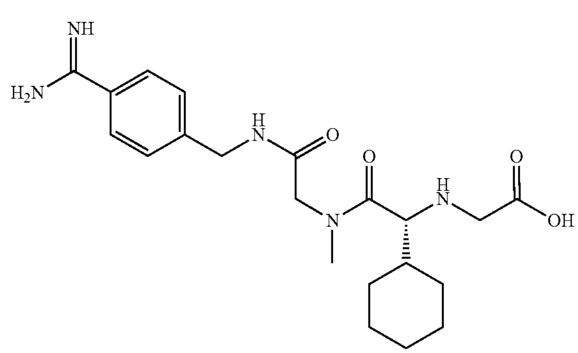 [SMILES: CN(CC(=O)NCc1ccc(C(=N)N)cc1)C(=O)[C@H](NCC(=O)O)C1CCCCC1] | NA |

TABLE 4A-continued

Exemplary compounds

| Compound No. | Structure | Salt |
|---|---|---|
| 1097 | 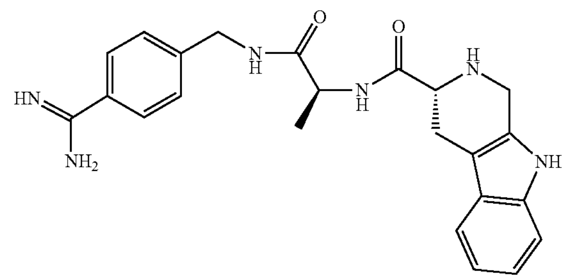 [SMILES: C[C@H](NC(=O)[C@H]1Cc2c([nH]c3ccccc23)CN1)C(=O)NCc1ccc(C(=N)N)cc1] | 2HCl |
| 1098 | isomer 3 | 2HCl |
| 1099 | 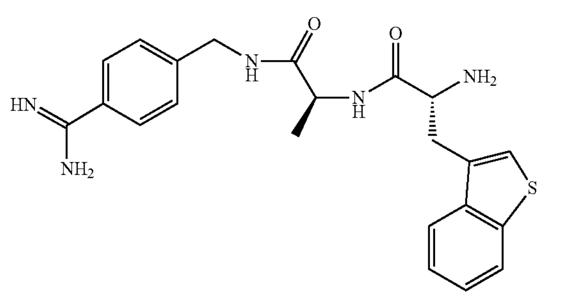 [SMILES: C[C@H](NC(=O)[C@H](N)Cc1csc2ccccc12)C(=O)NCc1ccc(C(=N)N)cc1] | 2HCl |
| 1100 | 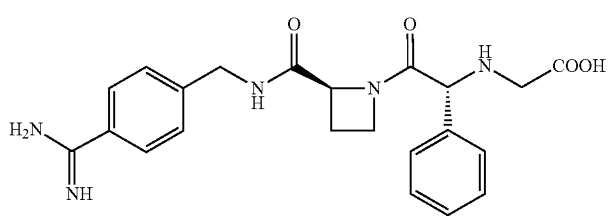 [SMILES: N=C(N)c1ccc(CNC(=O)[C@@H]2CCN2C(=O)[C@H](NCC(=O)O)c2ccccc2)cc1] | NA |
| 1101 | 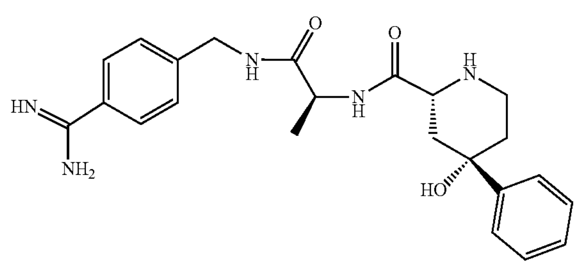 [SMILES: C[C@H](NC(=O)[C@H]1C[C@](O)(c2ccccc2)CCN1)C(=O)NCc1ccc(C(=N)N)cc1] | 2HCl |

TABLE 4A-continued

Exemplary compounds

| Compound No. | Structure | Salt |
|---|---|---|
| 1102 | 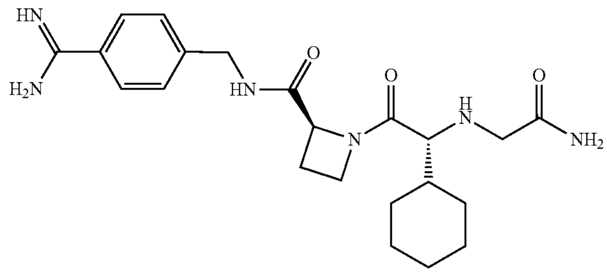 [SMILES: N=C(N)c1ccc(CNC(=O)[C@@H]2CCN2C(=O)[C@H](NCC(N)=O)C2CCCCC2)cc1] | NA |
| 1103 | 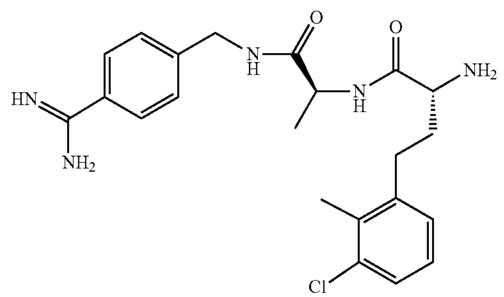 [SMILES: Cc1c(Cl)cccc1CC[C@@H](N)C(=O)N[C@@H](C)C(=O)NCc1ccc(C(=N)N)cc1] | 2HCl |
| 1104 | 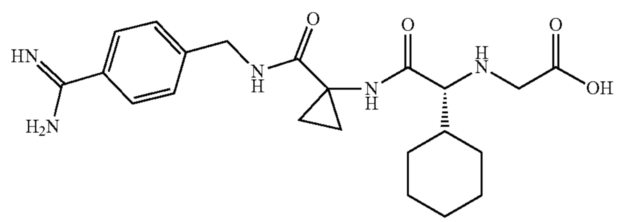 [SMILES: N=C(N)c1ccc(CNC(=O)C2(NC(=O)[C@H](NCC(=O)O)C3CCCCC3)CC2)cc1] | 2HCl |
| 1105 | 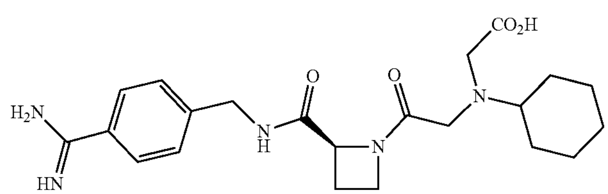 [SMILES: N=C(N)c1ccc(CNC(=O)[C@@H]2CCN2C(=O)CN(CC(=O)O)C2CCCCC2)cc1] | NA |
| 1106 | 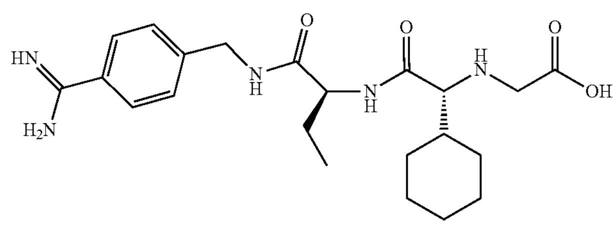 [SMILES: CC[C@H](NC(=O)[C@H](NCC(=O)O)C1CCCCC1)C(=O)NCc1ccc(C(=N)N)cc1] | 2HCl |
| 1107 | 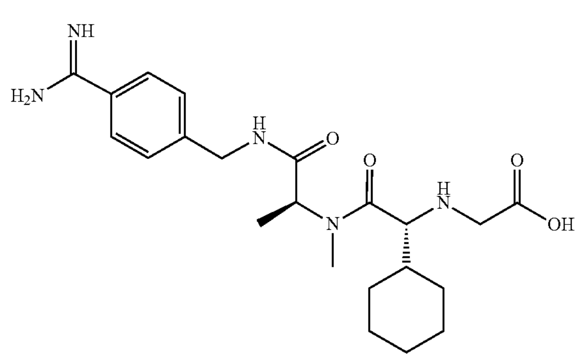 [SMILES: C[C@@H](C(=O)NCc1ccc(C(=N)N)cc1)N(C)C(=O)[C@H](NCC(=O)O)C1CCCCC1] | NA |

TABLE 4A-continued

Exemplary compounds

| Compound No. | Structure | Salt |
|---|---|---|
| 1108 | 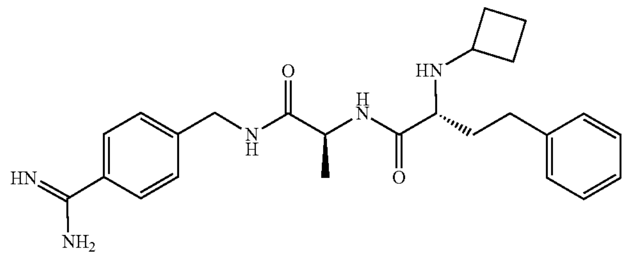 [SMILES: C[C@H](NC(=O)[C@@H](CCc1ccccc1)NC1CCC1)C(=O)NCc1ccc(C(=N)N)cc1] | 2HCl |
| 1109 | 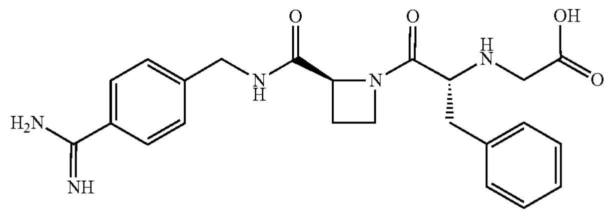 [SMILES: N=C(N)c1ccc(CNC(=O)[C@@H]2CCN2C(=O)[C@@H](Cc2ccccc2)NCC(=O)O)cc1] | NA |
| 1110 | 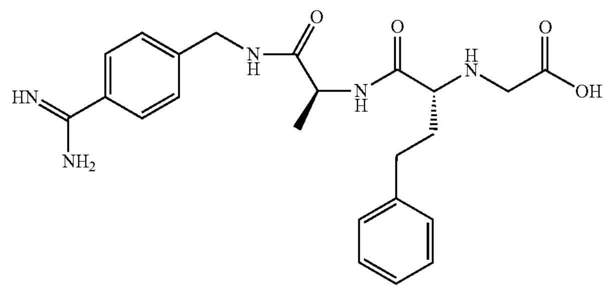 [SMILES: C[C@H](NC(=O)[C@@H](CCc1ccccc1)NCC(=O)O)C(=O)NCc1ccc(C(=N)N)cc1] | 2HCl |
| 1111 | 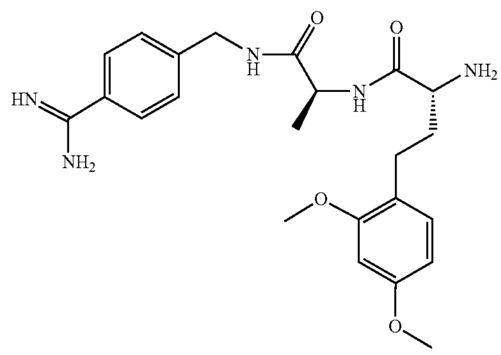 [SMILES: COc1ccc(CC[C@@H](N)C(=O)N[C@@H](C)C(=O)NCc2ccc(C(=N)N)cc2)c(OC)c1] | 2HCl |
| 1112 | 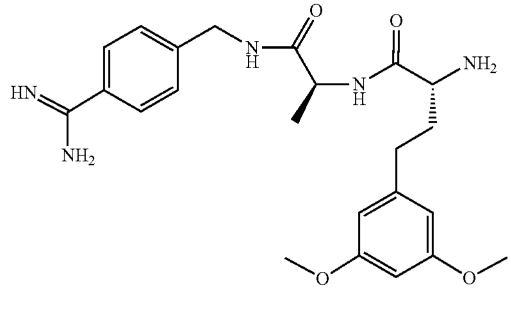 [SMILES: COc1cc(CC[C@@H](N)C(=O)N[C@@H](C)C(=O)NCc2ccc(C(=N)N)cc2)cc(OC)c1] | 2HCl |

TABLE 4A-continued

Exemplary compounds

| Compound No. | Structure | Salt |
|---|---|---|
| 1113 | 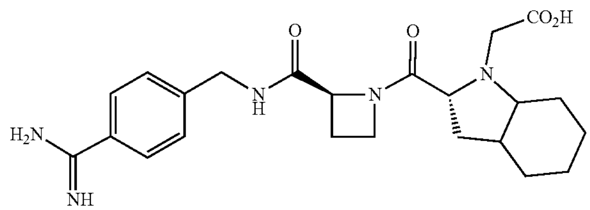 | NA |
| 1114 | 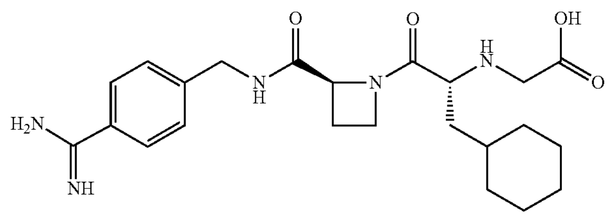 [SMILES: N=C(N)c1ccc(CNC(=O)[C@@H]2CCN2C(=O)[C@@H](CC2CCCCC2)NCC(=O)O)cc1] | NA |
| 1115 | 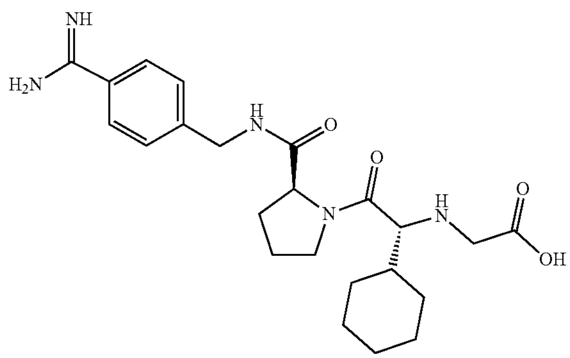 [SMILES: N=C(N)c1ccc(CNC(=O)[C@@H]2CCCN2C(=O)[C@H](NCC(=O)O)C2CCCCC2)cc1] | NA |
| 1116 | 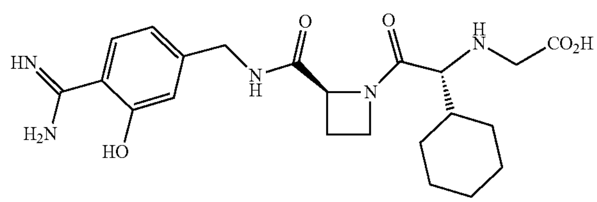 [SMILES: N=C(N)c1ccc(CNC(=O)[C@@H]2CCN2C(=O)[C@H](NCC(=O)O)C2CCCCC2)cc1O] | NA |
| 1117 | 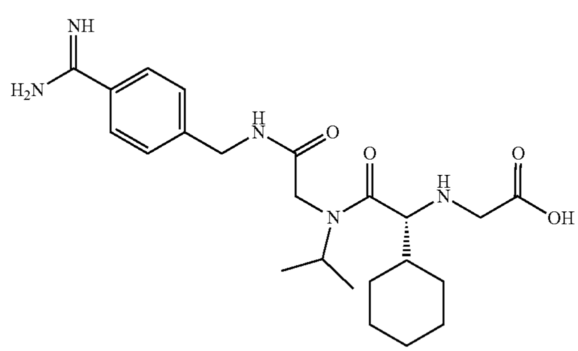 [SMILES: CC(C)N(CC(=O)NCc1ccc(C(=N)N)cc1)C(=O)[C@H](NCC(=O)O)C1CCCCC1] | NA |

TABLE 4A-continued

| Compound No. | Structure | Salt |
|---|---|---|
| 1118 | 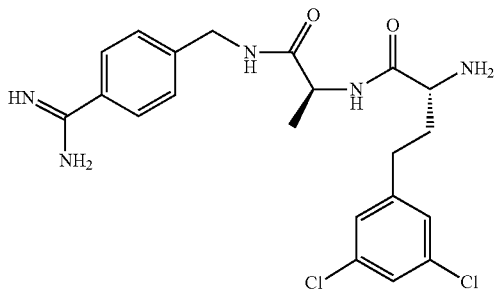 [SMILES: C[C@H](NC(=O)[C@H](N)CCc1cc(Cl)cc(Cl)c1)C(=O)NCc1ccc(C(=N)N)cc1] | 2HCl |
| 1119 | 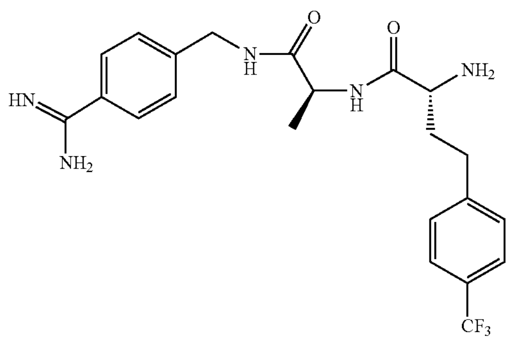 [SMILES: C[C@H](NC(=O)[C@H](N)CCc1ccc(C(F)(F)F)cc1)C(=O)NCc1ccc(C(=N)N)cc1] | 2HCl |
| 1120 | 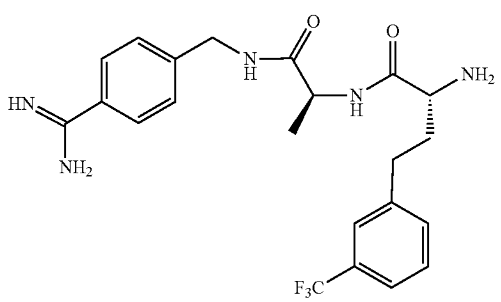 [SMILES: C[C@H](NC(=O)[C@H](N)CCc1cccc(C(F)(F)F)c1)C(=O)NCc1ccc(C(=N)N)cc1] | 2HCl |
| 1121 | 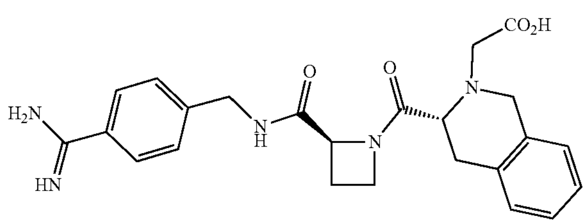 [SMILES: N=C(N)c1ccc(CNC(=O)[C@@H]2CCN2C(=O)[C@H]2Cc3ccccc3CN2CC(=O)O)cc1] | NA |
| 1122 | 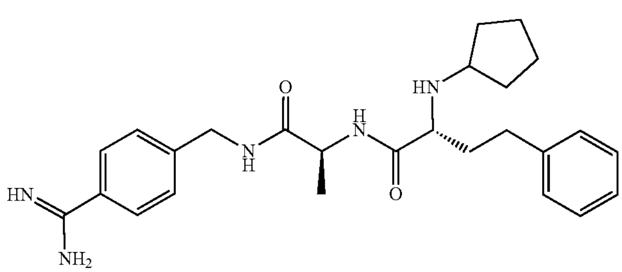 [SMILES: C[C@H](NC(=O)[C@@H](CCc1ccccc1)NC1CCCC1)C(=O)NCc1ccc(C(=N)N)cc1] | 2HCl |

TABLE 4A-continued

Exemplary compounds

| Compound No. | Structure | Salt |
|---|---|---|
| 1123 | 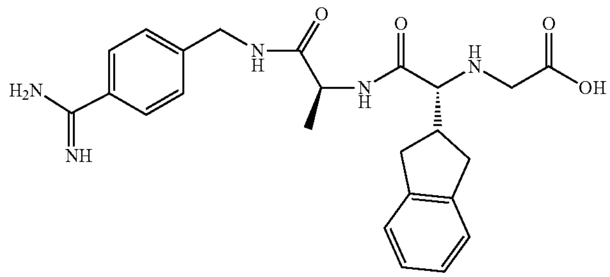 [SMILES: C[C@H](NC(=O)[C@H](NCC(=O)O)C1Cc2ccccc2C1)C(=O)NCc1ccc(C(=N)N)cc1] | 2HCl |
| 1124 | 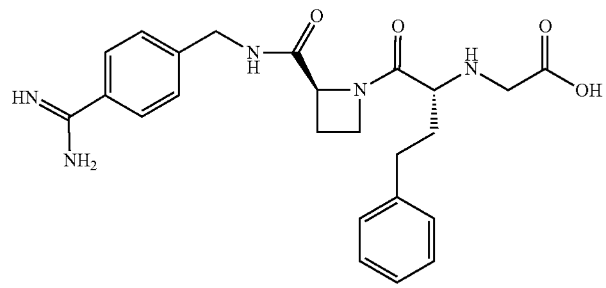 [SMILES: N=C(N)c1ccc(CNC(=O)[C@@H]2CCN2C(=O)[C@@H](CCc2ccccc2)NCC(=O)O)cc1] | 2HCl |
| 1125 | 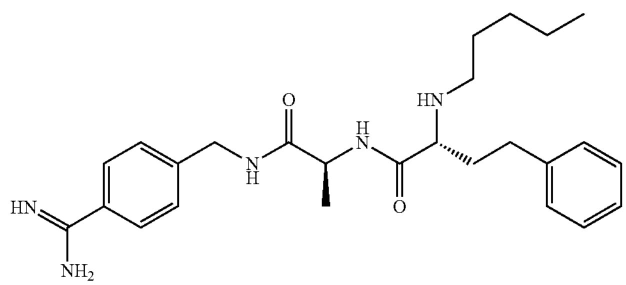 [SMILES: CCCCCN[C@H](CCc1ccccc1)C(=O)N[C@@H](C)C(=O)NCc1ccc(C(=N)N)cc1] | 2HCl |
| 1126 | 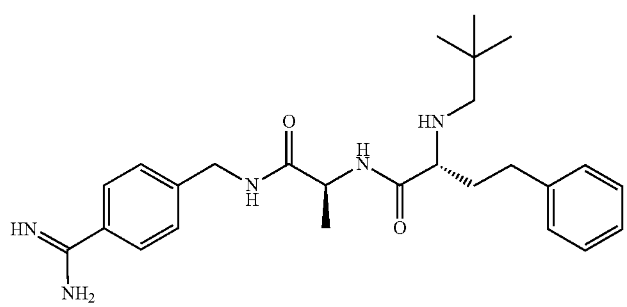 [SMILES: C[C@H](NC(=O)[C@@H](CCc1ccccc1)NCC(C)(C)C)C(=O)NCc1ccc(C(=N)N)cc1] | 2HCl |
| 1127 | 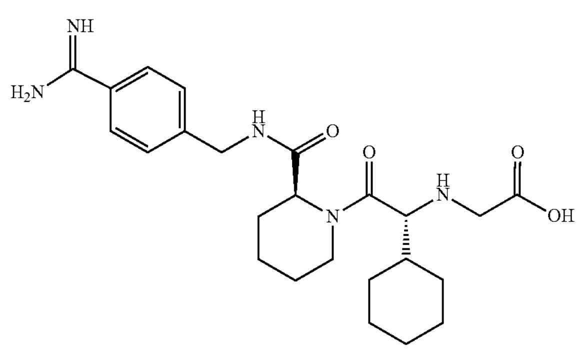 [SMILES: N=C(N)c1ccc(CNC(=O)[C@@H]2CCCCN2C(=O)[C@H](NCC(=O)O)C2CCCCC2)cc1] | NA |

TABLE 4A-continued

| Exemplary compounds | | |
|---|---|---|
| Compound No. | Structure | Salt |
| 1128 | | 2HCl |
| 1129 | | NA |
| 1130 | | 2 HCl |
| 1131 | | NA |
| 1132 | | 3HCl |

TABLE 4A-continued
Exemplary compounds
| Compound No. | Structure | Salt |
|---|---|---|
| 1133 | 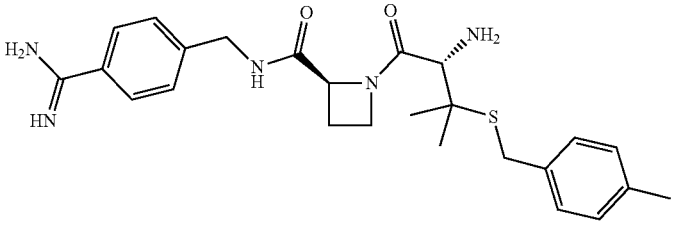 [SMILES: Cc1ccc(CSC(C)(C)[C@@H](N)C(=O)N2CC[C@H]2C(=O)NCc2ccc(C(=N)N)cc2)cc1] | NA |
| 1134 | 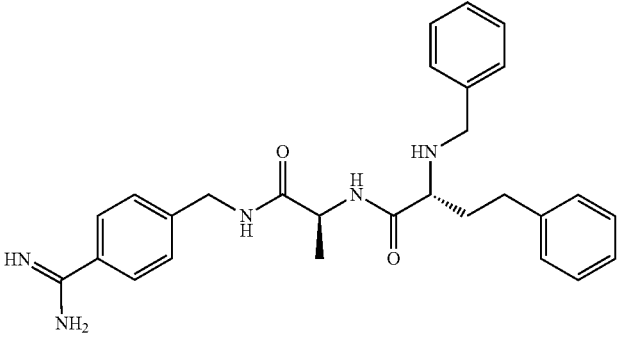 [SMILES: C[C@H](NC(=O)[C@@H](CCc1ccccc1)NCc1ccccc1)C(=O)NCc1ccc(C(=N)N)cc1] | 2HCl |
| 1135 | 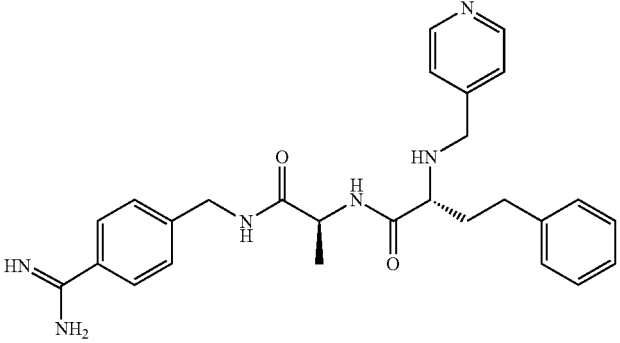 [SMILES: C[C@H](NC(=O)[C@@H](CCc1ccccc1)NCc1ccncc1)C(=O)NCc1ccc(C(=N)N)cc1] | 3HCl |
| 1136 | 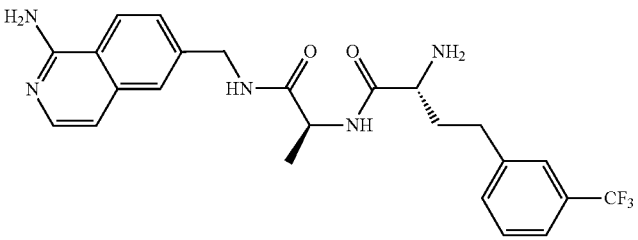 [SMILES: C[C@H](NC(=O)[C@H](N)CCc1cccc(C(F)(F)F)c1)C(=O)NCc1ccc2c(N)nccc2c1] | 2HCl |
| 1137 | 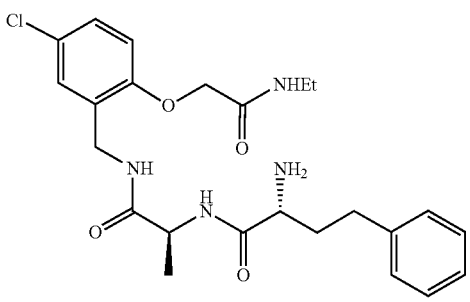 | TFA |

TABLE 4A-continued

| Compound No. | Structure | Salt |
|---|---|---|
| 1138 | 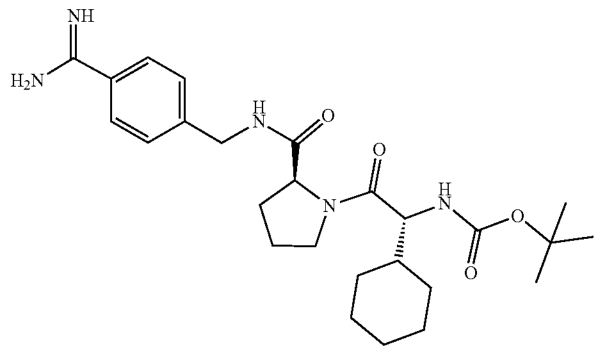 [SMILES: CC(C)(C)OC(=O)N[C@@H](C(=O)N1CCC[C@H]1C(=O)NCc1ccc(C(=N)N)cc1)C1CCCCC1] | NA |
| 1139 | 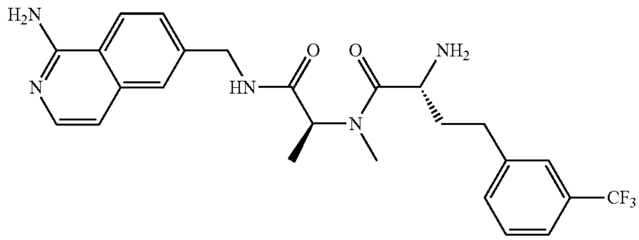 [SMILES: C[C@@H](C(=O)NCc1ccc2c(N)nccc2c1)N(C)C(=O)[C@H](N)CCc1cccc(C(F)(F)F)c1] | 2HCl |
| 1140 | 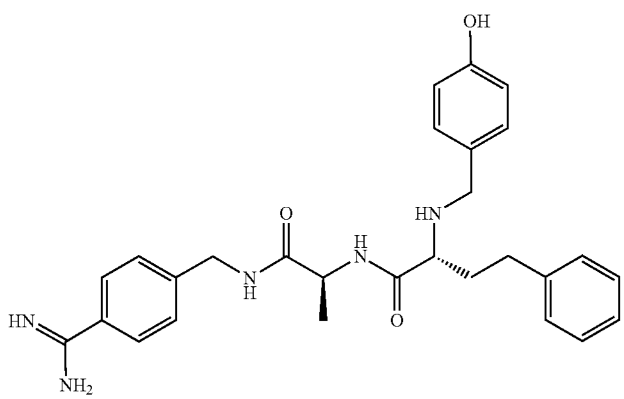 [SMILES: C[C@H](NC(=O)[C@@H](CCc1ccccc1)NCc1ccc(O)cc1)C(=O)NCc1ccc(C(=N)N)cc1] | 2HCl |
| 1141 | 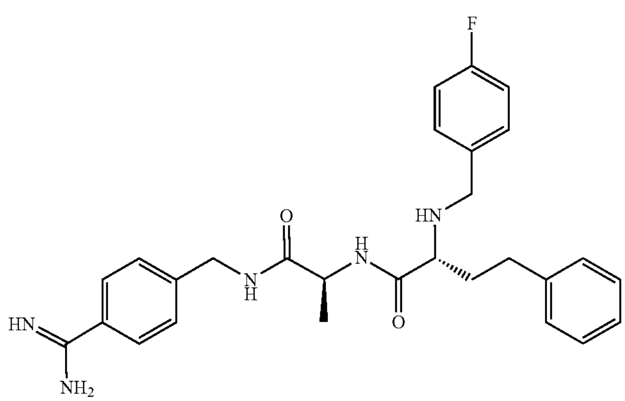 [SMILES: C[C@H](NC(=O)[C@@H](CCc1ccccc1)NCc1ccc(F)cc1)C(=O)NCc1ccc(C(=N)N)cc1] | 2HCl |

TABLE 4A-continued

| Exemplary compounds | | |
|---|---|---|
| Compound No. | Structure | Salt |
| 1142 | | 2HCl |
| 1143 | | 2HCl |
| 1144 | | 3TFA |

TABLE 4A-continued

| Exemplary compounds | | |
|---|---|---|
| Compound No. | Structure | Salt |
| 1145 | | 2HCl |
| 1146 | | NA |
| 1147 | | 2HCl |

TABLE 4A-continued

| | Exemplary compounds | |
|---|---|---|
| Compound No. | Structure | Salt |
| 1148 | | 3TFA |
| 1149 | | 2HCl |
| 1150 | | 2HCl |

TABLE 4A-continued

| Exemplary compounds | | |
|---|---|---|
| Compound No. | Structure | Salt |
| 1151 | | 2HCl |
| 1152 | | 2HCl |
| 1153 | | 2HCl |

TABLE 4A-continued

Exemplary compounds

| Compound No. | Structure | Salt |
|---|---|---|
| 1154 | 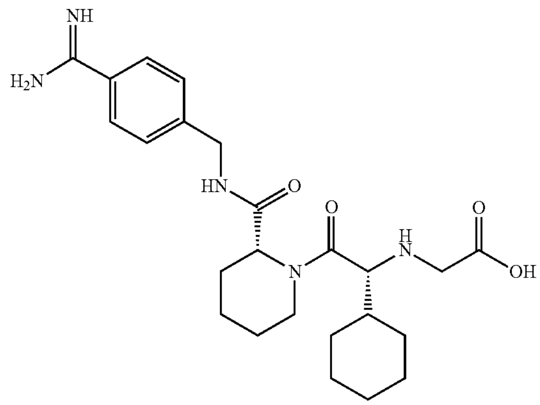 [SMILES: N=C(N)c1ccc(CNC(=O)[C@H]2CCCCN2C(=O)[C@H](NCC(=O)O)C2CCCCC2)cc1] | NA |
| 1156 | 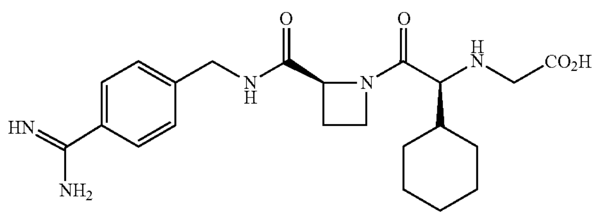 [SMILES: N=C(N)c1ccc(CNC(=O)[C@@H]2CCN2C(=O)[C@@H](NCC(=O)O)C2CCCCC2)cc1] | NA |
| 1157 | 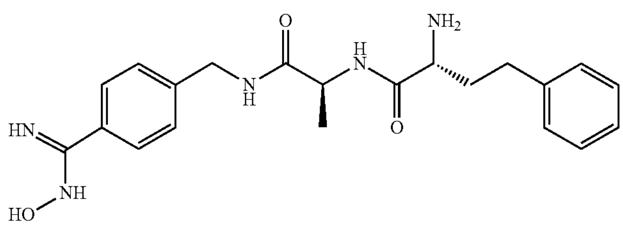 [SMILES: C[C@H](NC(=O)[C@H](N)CCc1ccccc1)C(=O)NCc1ccc(C(=N)NO)cc1] | 2HCl |
| 1158 | 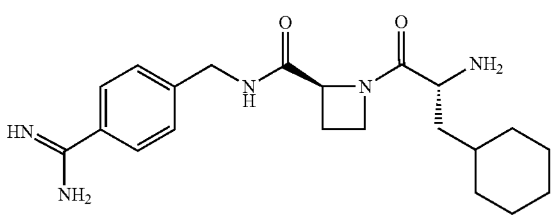 [SMILES: N=C(N)c1ccc(CNC(=O)[C@@H]2CCN2C(=O)[C@H](N)CC2CCCCC2)cc1] | 2HCl |
| 1170 | 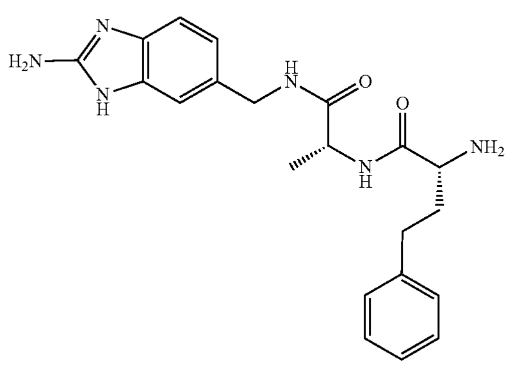 [SMILES: C[C@@H](NC(=O)[C@H](N)CCc1ccccc1)C(=O)NCc1ccc2nc(N)[nH]c2c1] | |

TABLE 4A-continued

Exemplary compounds

| Compound No. | Structure | Salt |
|---|---|---|
| 1171 | 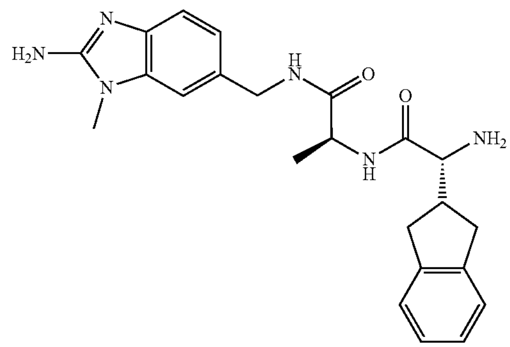 [SMILES: C[C@H](NC(=O)[C@H](N)C1Cc2ccccc2C1)C(=O)NCc1ccc2nc(N)n(C)c2c1] | 2HCl |
| 1192 | 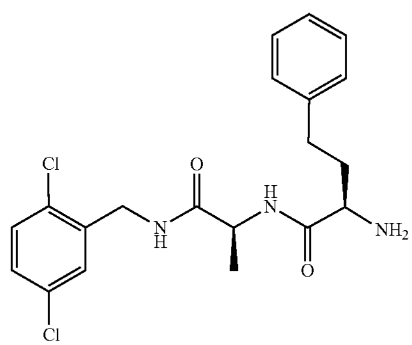 [SMILES: C[C@H](NC(=O)[C@H](N)CCc1ccccc1)C(=O)NCc1cc(Cl)ccc1Cl] | 1HCl |
| 1194 | 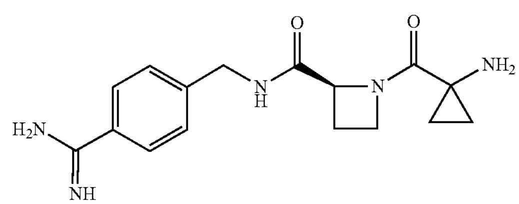 [SMILES: N=C(N)c1ccc(CNC(=O)[C@@H]2CCN2C(=O)C2(N)CC2)cc1] | NA |
| 1195 | 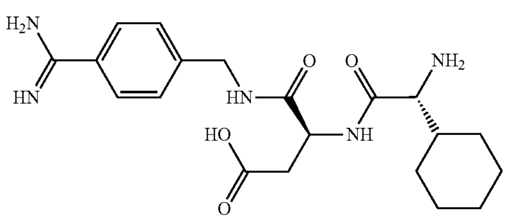 [SMILES: N=C(N)c1ccc(CNC(=O)[C@H](CC(=O)O)NC(=O)[C@H](N)C2CCCCC2)cc1] | 2HCl |
| 1207 | 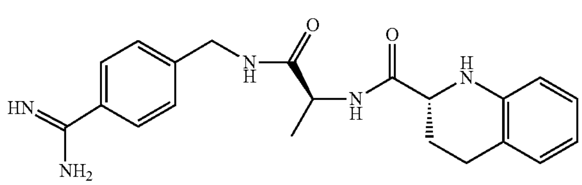 [SMILES: C[C@H](NC(=O)[C@H]1CCc2ccccc2N1)C(=O)NCc1ccc(C(=N)N)cc1] | 2HCl |
| 1211 | 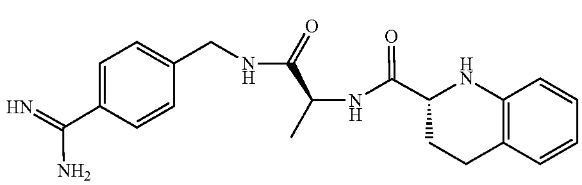 [SMILES: C[C@H](NC(=O)[C@H]1CCc2ccccc2N1)C(=O)NCc1ccc(C(=N)N)cc1] | 2HCl |

TABLE 4A-continued

Exemplary compounds

| Compound No. | Structure | Salt |
|---|---|---|
| 1213 | 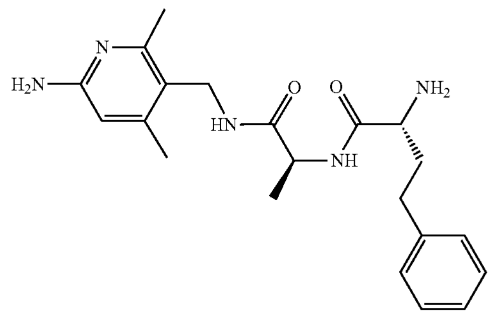 [SMILES: Cc1cc(N)nc(C)c1CNC(=O)[C@H](C)NC(=O)[C@H](N)CCc1ccccc1] | 2HCl |
| 1215 | 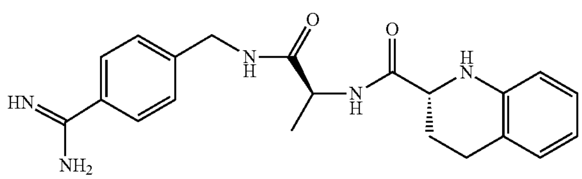 [SMILES: C[C@H](NC(=O)[C@H]1CCc2ccccc2N1)C(=O)NCc1ccc(C(=N)N)cc1] | 2HCl |
| 1218 | 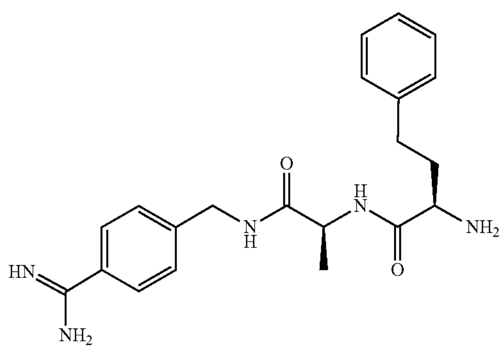 [SMILES: C[C@H](NC(=O)[C@H](N)CCc1ccccc1)C(=O)NCc1ccc(C(=N)N)cc1] | 2HCl |
| 1223 | 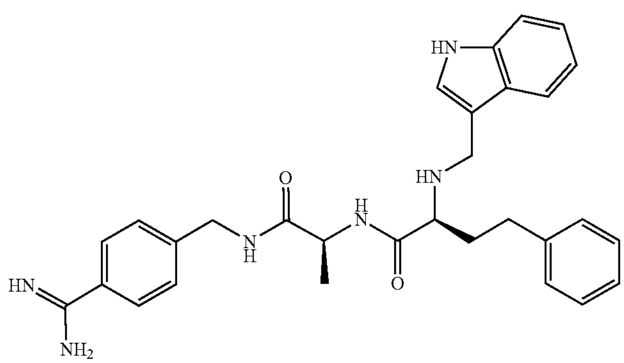 [SMILES: C[C@H](NC(=O)[C@H](CCc1ccccc1)NCc1c[nH]c2ccccc12)C(=O)NCc1ccc(C(=N)N)cc1] | 2HCl |
| 1229 | 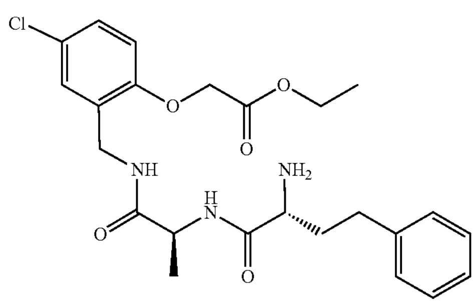 [SMILES: CCOC(=O)COc1ccc(Cl)cc1CNC(=O)[C@H](C)NC(=O)[C@H](N)CCc1ccccc1] | 1HCl |

TABLE 4A-continued

| Exemplary compounds | | |
|---|---|---|
| Compound No. | Structure | Salt |
| 999 | | |
| 1230 | | 2 HCl |
| 1231 | | 2 HCl |
| 1232 | | 2TFA |

TABLE 4A-continued
| Compound No. | Structure | Salt |
|---|---|---|
| 1233 | 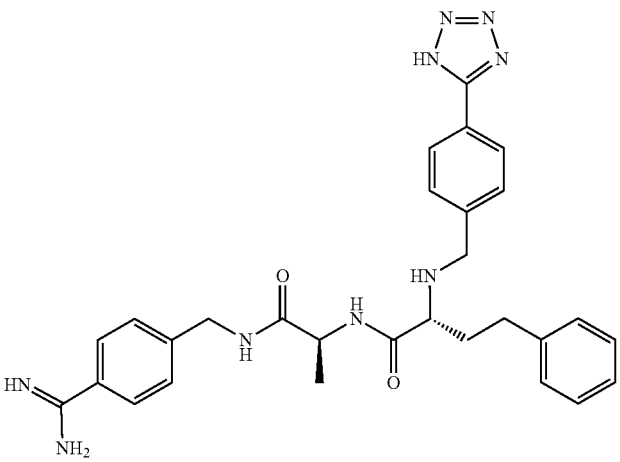 [SMILES: C[C@H](NC(=O)[C@@H](CCc1ccccc1)NCc1ccc(-c2nnn[nH]2)cc1)C(=O)NCc1ccc(C(=N)N)cc1] | 2TFA |
| 1234 | 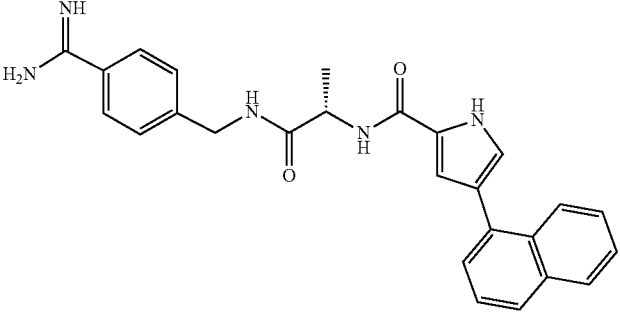 [SMILES: C[C@H](NC(=O)c1cc(-c2cccc3ccccc23)c[nH]1)C(=O)NCc1ccc(C(=N)N)cc1] | NA |
| 1235 | 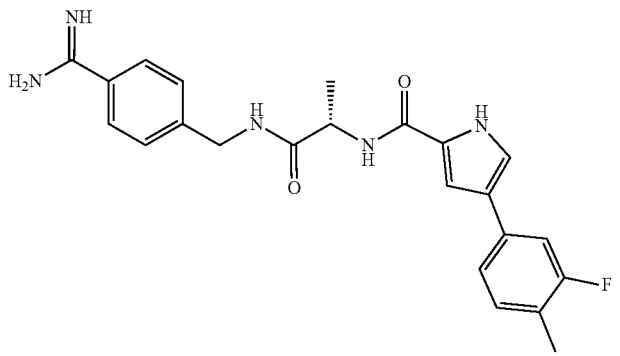 [SMILES: Cc1ccc(-c2c[nH]c(C(=O)N[C@@H](C)C(=O)NCc3ccc(C(=N)N)cc3)c2)cc1F] | NA |

TABLE 4A-continued
Exemplary compounds
| Compound No. | Structure | Salt |
|---|---|---|
| 1236 | 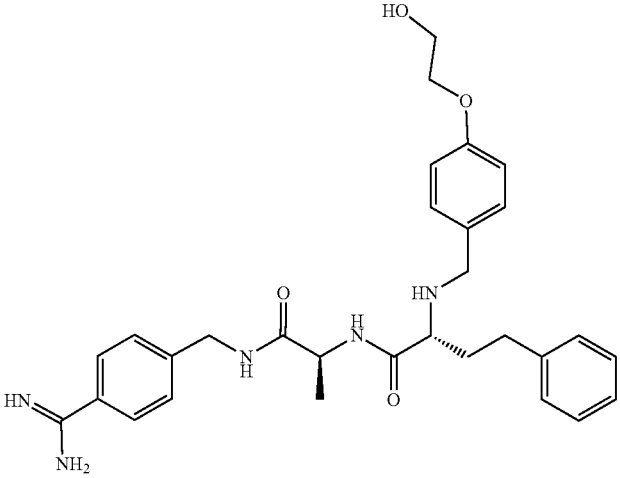 [SMILES: C[C@H](NC(=O)[C@@H](CCc1ccccc1)NCc1ccc(OCCO)cc1)C(=O)NCc1ccc(C(=N)N)cc1] | 2TFA |
| 1237 | 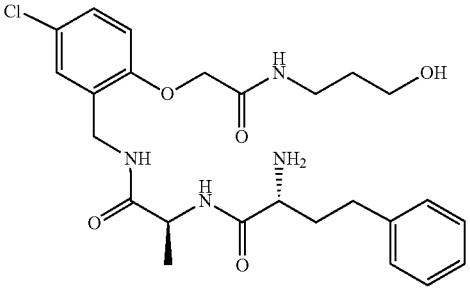 [SMILES: C[C@H](NC(=O)[C@H](N)CCc1ccccc1)C(=O)NCc1cc(Cl)ccc1OCC(=O)NCCCO] | HCl |
| 1238 | 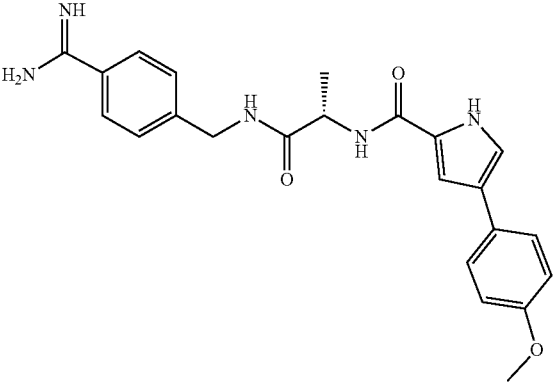 [SMILES: COc1ccc(-c2c[nH]c(C(=O)N[C@@H](C)C(=O)NCc3ccc(C(=N)N)cc3)c2)cc1] | TFA |
| 1239 | 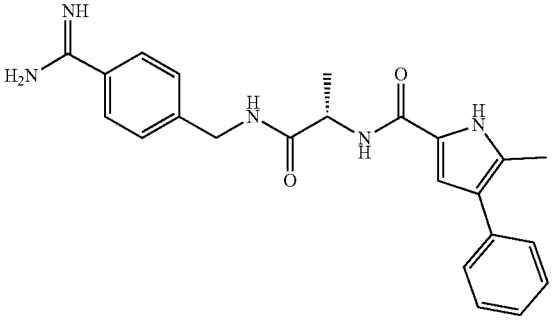 [SMILES: Cc1[nH]c(C(=O)N[C@@H](C)C(=O)NCc2ccc(C(=N)N)cc2)cc1-c1ccccc1] | TFA |

TABLE 4A-continued

Exemplary compounds

| Compound No. | Structure | Salt |
|---|---|---|
| 1240 | 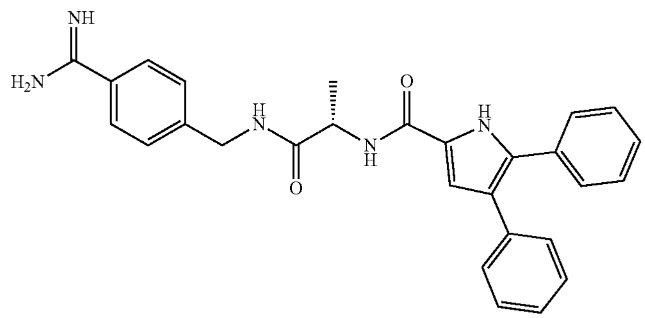 [SMILES: C[C@H](NC(=O)c1cc(-c2ccccc2)c(-c2ccccc2)[nH]1)C(=O)NCc1ccc(C(=N)N)cc1] | NA |
| 1241 | 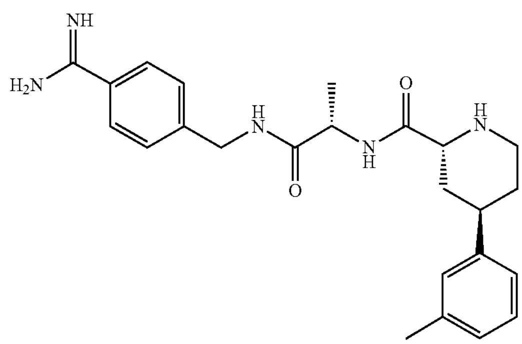 [SMILES: Cc1cccc([C@@H]2CCN[C@@H](C(=O)N[C@@H](C)C(=O)NCc3ccc(C(=N)N)cc3)C2)c1] | HCl |
| 1242 | 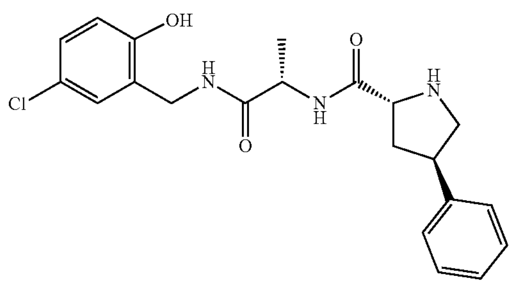 [SMILES: C[C@H](NC(=O)[C@H]1C[C@H](c2ccccc2)CN1)C(=O)NCc1cc(Cl)ccc1O] | N/A |
| 1243 | 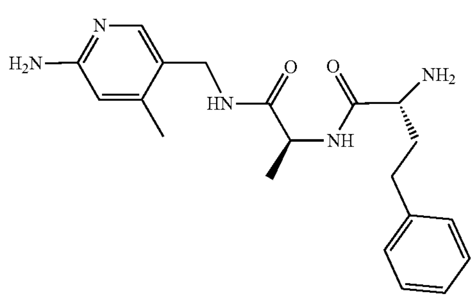 [SMILES: Cc1cc(N)ncc1CNC(=O)[C@H](C)NC(=O)[C@H](N)CCc1ccccc1] | 2HCl |
| 1244 | 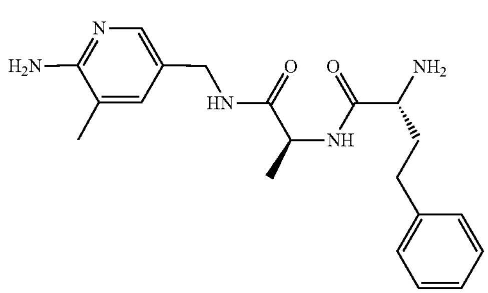 [SMILES: Cc1cc(CNC(=O)[C@H](C)NC(=O)[C@H](N)CCc2ccccc2)cnc1N] | 2HCl |

TABLE 4A-continued

| Compound No. | Structure | Salt |
|---|---|---|
| 1245 | 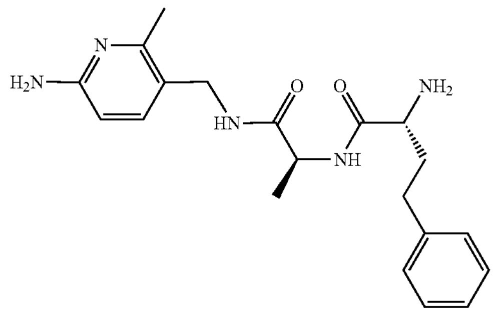 [SMILES: Cc1nc(N)ccc1CNC(=O)[C@H](C)NC(=O)[C@H](N)CCc1ccccc1] | 2HCl |
| 1246 | 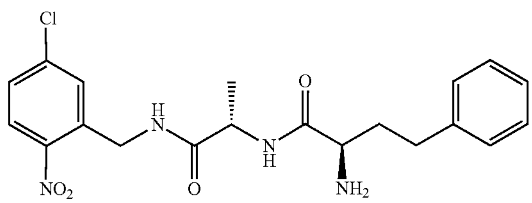 [SMILES: C[C@H](NC(=O)[C@H](N)CCc1ccccc1)C(=O)NCc1cc(Cl)ccc1[N+](=O)[O-]] | HCl |
| 1247 | 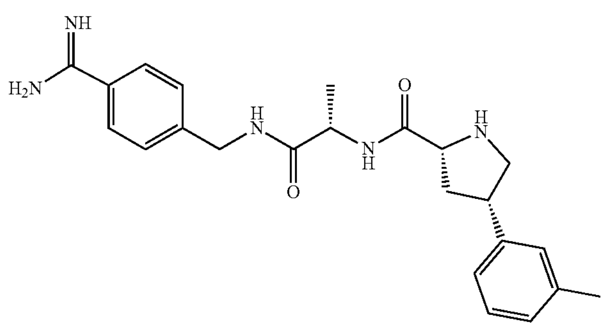 [SMILES: Cc1cccc([C@H]2CN[C@@H](C(=O)N[C@@H](C)C(=O)NCc3ccc(C(=N)N)cc3)C2)c1] | 2HCl |
| 1248 | 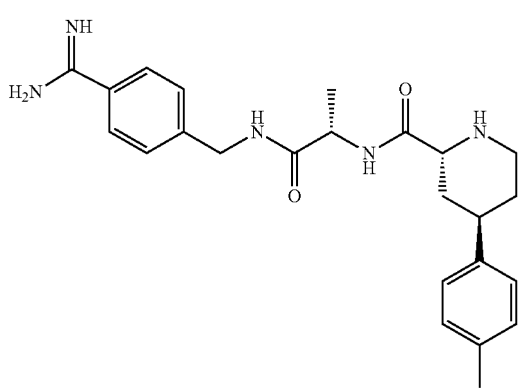 [SMILES: Cc1ccc([C@@H]2CCN[C@@H](C(=O)N[C@@H](C)C(=O)NCc3ccc(C(=N)N)cc3)C2)cc1] | 2 HCl |

TABLE 4A-continued

Exemplary compounds

| Compound No. | Structure | Salt |
|---|---|---|
| 1249 | 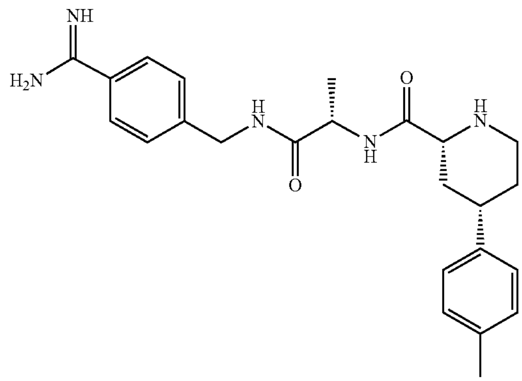 [SMILES: Cc1ccc([C@H]2CCN[C@@H](C(=O)N[C@@H](C)C(=O)NCc3ccc(C(=N)N)cc3)C2)cc1] | 2 HCl |
| 1250 | 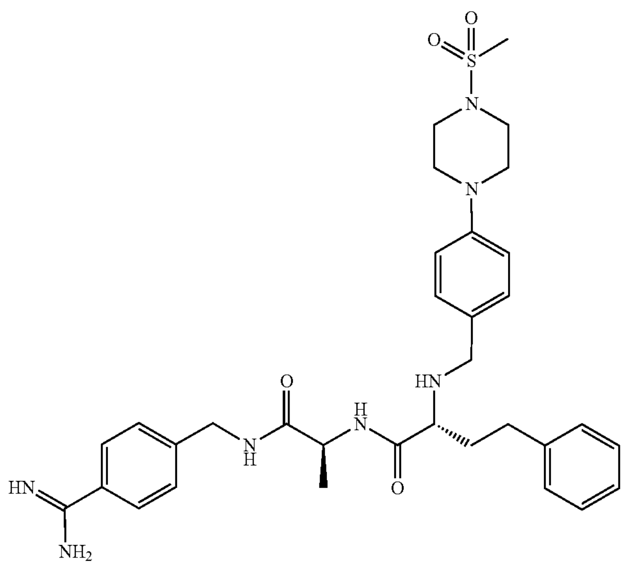 [SMILES: C[C@H](NC(=O)[C@@H](CCc1ccccc1)NCc1ccc(N2CCN(S(C)(=O)=O)CC2)cc1)C(=O)NCc1ccc(C(=N)N)cc1] | 2TFA |
| 1251 | 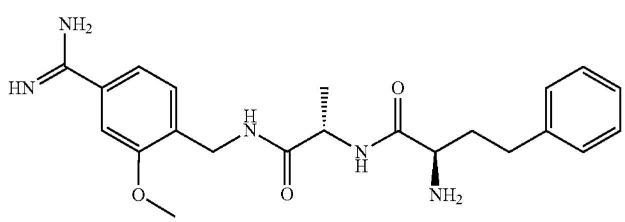 [SMILES: COc1cc(C(=N)N)ccc1CNC(=O)[C@H](C)NC(=O)[C@H](N)CCc1ccccc1] | TFA |
| 1252 | 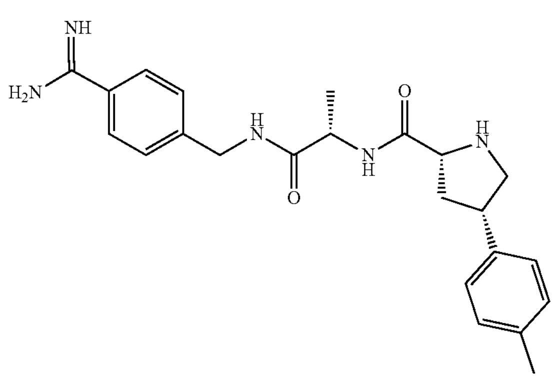 [SMILES: Cc1ccc([C@H]2CN[C@@H](C(=O)N[C@@H](C)C(=O)NCc3ccc(C(=N)N)cc3)C2)cc1] | 2HCl |

TABLE 4A-continued

| Compound No. | Structure | Salt |
|---|---|---|
| 1253 | 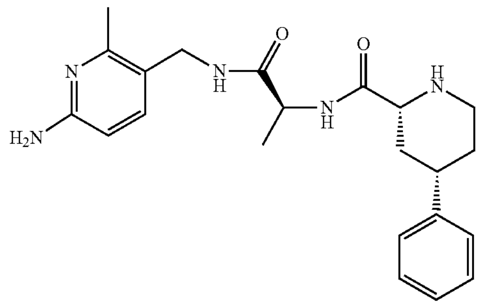 [SMILES: Cc1nc(N)ccc1CNC(=O)[C@H](C)NC(=O)[C@H]1C[C@@H](c2ccccc2)CCN1] | HCl |
| 1254 | 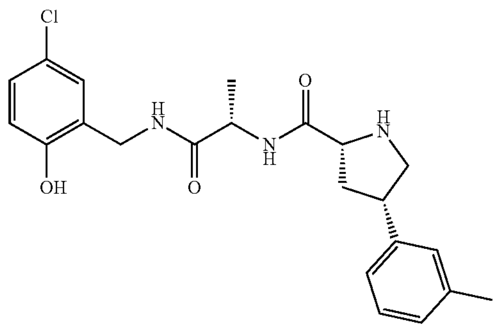 [SMILES: Cc1cccc([C@H]2CN[C@@H](C(=O)N[C@@H](C)C(=O)NCc3cc(Cl)ccc3O)C2)c1] | HCl |
| 1255 | 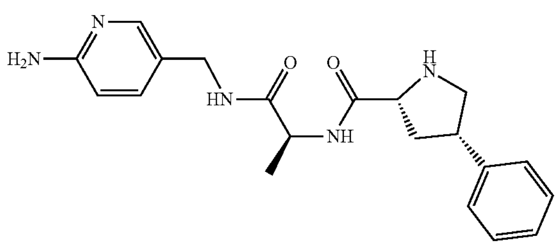 [SMILES: C[C@H](NC(=O)[C@H]1C[C@@H](c2ccccc2)CN1)C(=O)NCc1ccc(N)nc1] | 2HCl |
| 1256 | 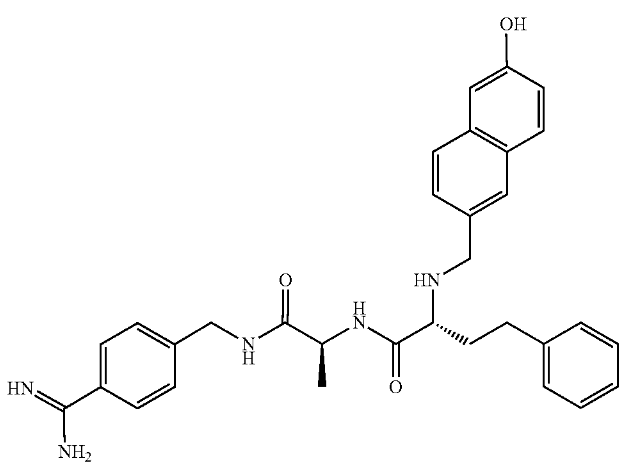 [SMILES: C[C@H](NC(=O)[C@@H](CCc1ccccc1)NCc1ccc2cc(O)ccc2c1)C(=O)NCc1ccc(C(=N)N)cc1] | 2TFA |

TABLE 4A-continued

Exemplary compounds

| Compound No. | Structure | Salt |
|---|---|---|
| 1257 | 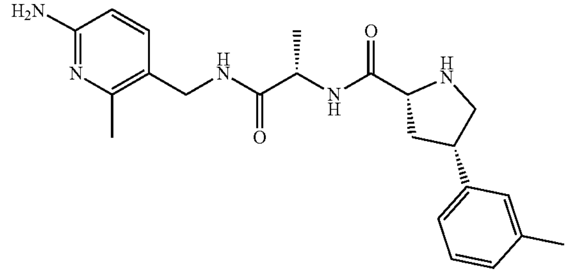 [SMILES: Cc1cccc([C@H]2CN[C@@H](C(=O)N[C@@H](C)C(=O)NCc3ccc(N)nc3C)C2)c1] | 2HCl |
| 1258 | 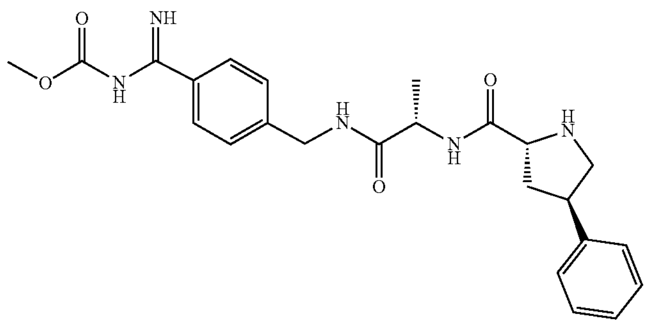 [SMILES: COC(=O)NC(=N)c1ccc(CNC(=O)[C@H](C)NC(=O)[C@H]2C[C@H](c3ccccc3)CN2)cc1] | NA |
| 1259 | 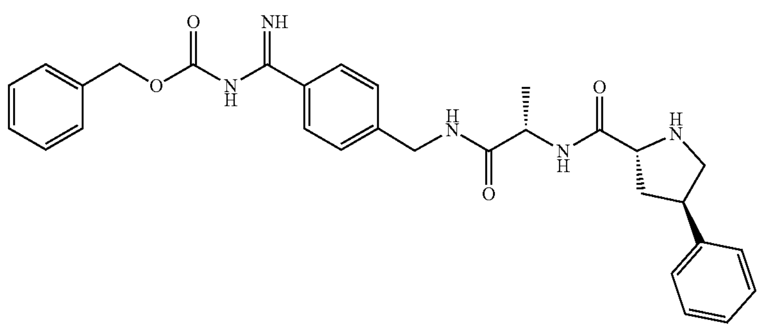 [SMILES: C[C@H](NC(=O)[C@H]1C[C@H](c2ccccc2)CN1)C(=O)NCc1ccc(C(=N)NC(=O)OCc2ccccc2)cc1] | NA |
| 1260 | (n = 3) | NA |

TABLE 4A-continued

| Compound No. | Structure | Salt |
|---|---|---|
| 1261 | 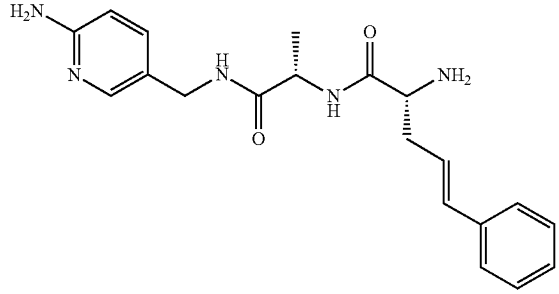 [SMILES: C[C@H](NC(=O)[C@H](N)C/C=C/c1ccccc1)C(=O)NCc1ccc(N)nc1] | 2HCl |
| 1262 | 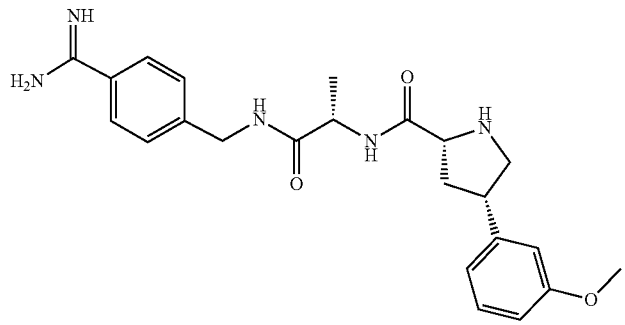 [SMILES: COc1cccc([C@H]2CN[C@@H](C(=O)N[C@@H](C)C(=O)NCc3ccc(C(=N)N)cc3)C2)c1] | 2HCl |
| 1263 | 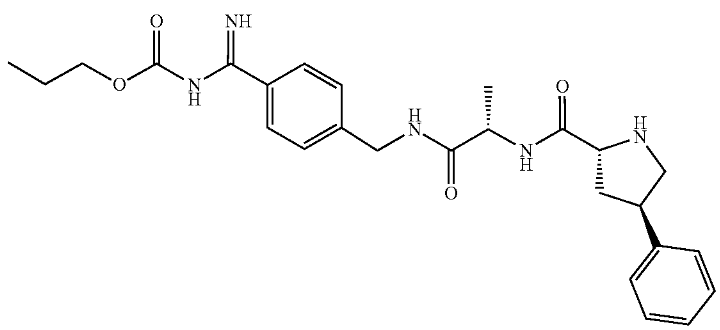 [SMILES: CCCOC(=O)NC(=N)c1ccc(CNC(=O)[C@H](C)NC(=O)[C@H]2C[C@H](c3ccccc3)CN2)cc1] | NA |
| 1264 | 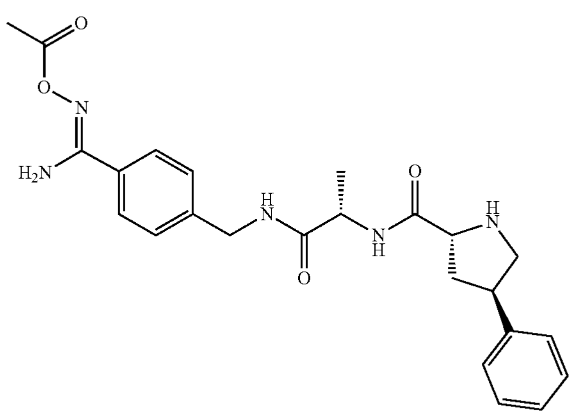 [SMILES: CC(=O)O/N=C(\N)c1ccc(CNC(=O)[C@H](C)NC(=O)[C@H]2C[C@H](c3ccccc3)CN2)cc1] | NA |

TABLE 4A-continued

| Compound No. | Structure | Salt |
|---|---|---|
| 1265 | 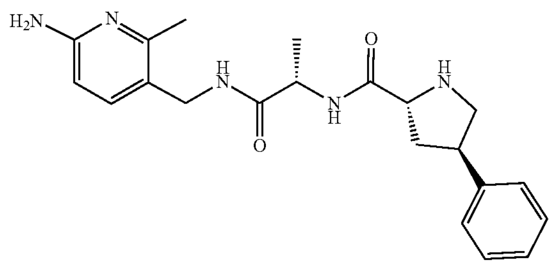 [SMILES: Cc1nc(N)ccc1CNC(=O)[C@H](C)NC(=O)[C@H]1C[C@H](c2ccccc2)CN1] | N/A |
| 1266 | 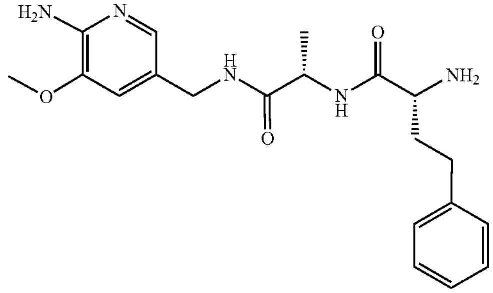 [SMILES: COc1cc(CNC(=O)[C@H](C)NC(=O)[C@H](N)CCc2ccccc2)cnc1N] | 2HCl |
| 1267 | 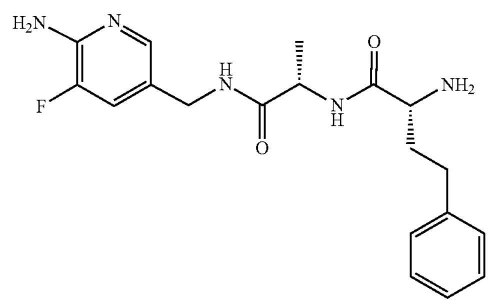 [SMILES: C[C@H](NC(=O)[C@H](N)CCc1ccccc1)C(=O)NCc1cnc(N)c(F)c1] | 2HCl |
| 1268 | 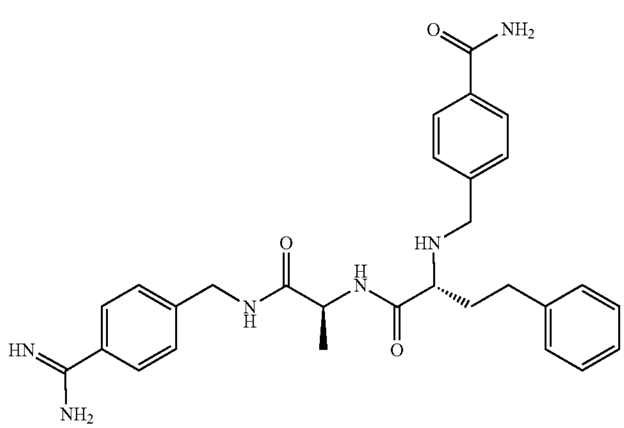 [SMILES: C[C@H](NC(=O)[C@@H](CCc1ccccc1)NCc1ccc(C(N)=O)cc1)C(=O)NCc1ccc(C(=N)N)cc1] | 2TFA |

TABLE 4A-continued

| Compound No. | Structure | Salt |
|---|---|---|
| 1269 | 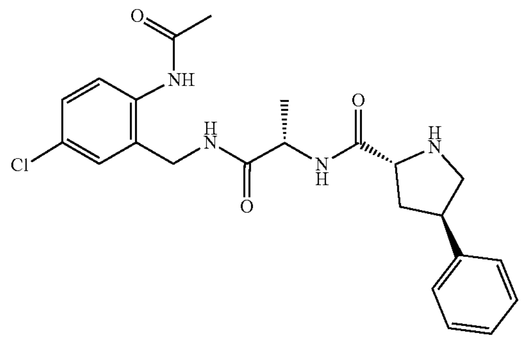 [SMILES: CC(=O)Nc1ccc(Cl)cc1CNC(=O)[C@H](C)NC(=O)[C@H]1C[C@H](c2ccccc2)CN1] | HCl |
| 1270 | 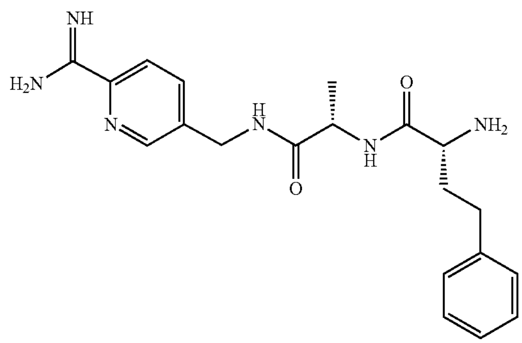 [SMILES: C[C@H](NC(=O)[C@H](N)CCc1ccccc1)C(=O)NCc1ccc(C(=N)N)nc1] | 2 HCl |
| 1271 | 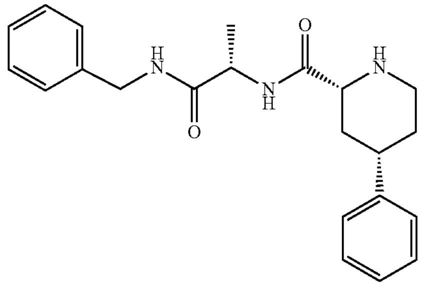 [SMILES: C[C@H](NC(=O)[C@H]1C[C@@H](c2ccccc2)CCN1)C(=O)NCc1ccccc1] | HCl |
| 1272 | 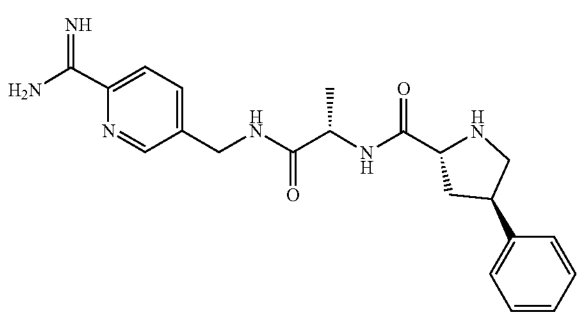 [SMILES: C[C@H](NC(=O)[C@H]1C[C@H](c2ccccc2)CN1)C(=O)NCc1ccc(C(=N)N)nc1] | 2 HCl |

TABLE 4A-continued

Exemplary compounds

| Compound No. | Structure | Salt |
|---|---|---|
| 1273 | 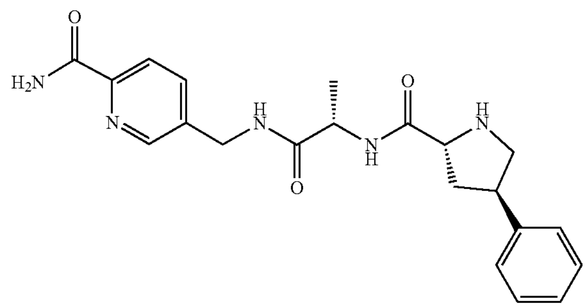 [SMILES: C[C@H](NC(=O)[C@H]1C[C@H](c2ccccc2)CN1)C(=O)NCc1ccc(C(N)=O)nc1] | HCl |
| 1274 | 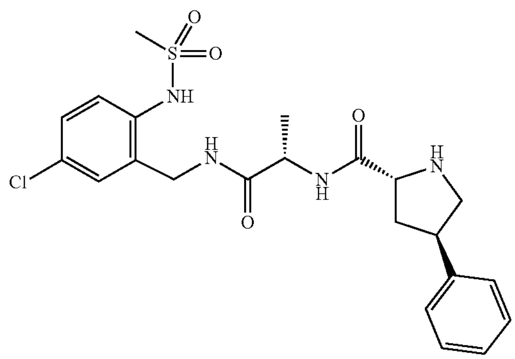 [SMILES: C[C@H](NC(=O)[C@H]1C[C@H](c2ccccc2)CN1)C(=O)NCc1cc(Cl)ccc1NS(C)(=O)=O] | HCl |
| 1275 | 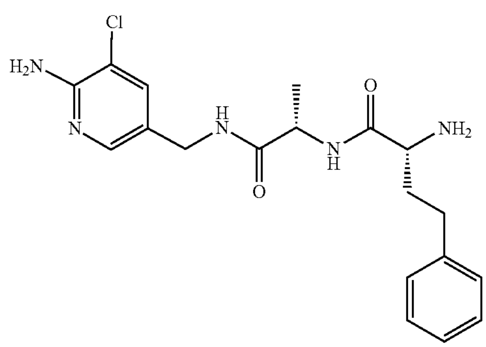 [SMILES: C[C@H](NC(=O)[C@H](N)CCc1ccccc1)C(=O)NCc1cnc(N)c(Cl)c1] | 2HCl |
| 1276 | 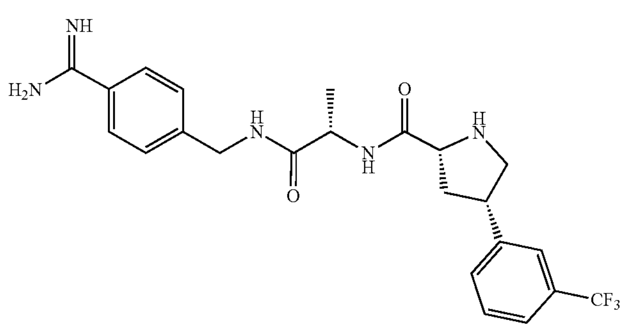 [SMILES: C[C@H](NC(=O)[C@H]1C[C@@H](c2cccc(C(F)(F)F)c2)CN1)C(=O)NCc1ccc(C(=N)N)cc1] | 2HCl |

TABLE 4A-continued

Exemplary compounds

| Compound No. | Structure | Salt |
|---|---|---|
| 1277 | 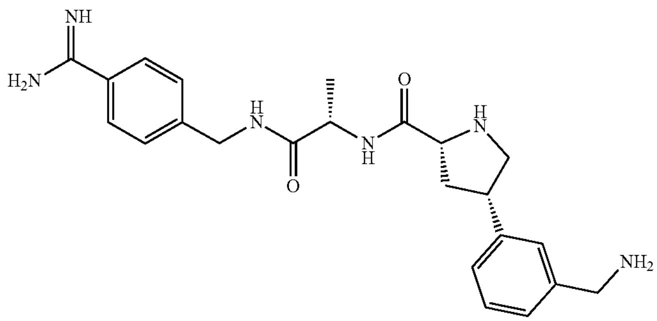 [SMILES: C[C@H](NC(=O)[C@H]1C[C@@H](c2cccc(CN)c2)CN1)C(=O)NCc1ccc(C(=N)N)cc1] | 3HCl |
| 1278 | 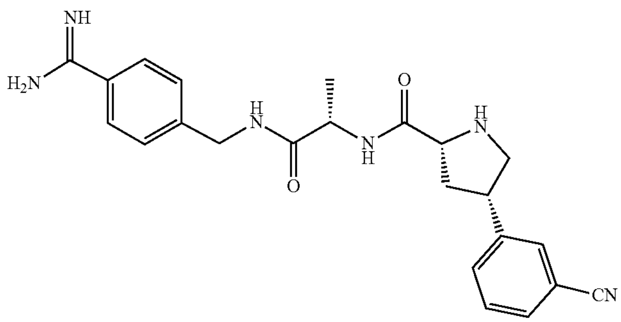 [SMILES: C[C@H](NC(=O)[C@H]1C[C@@H](c2cccc(C#N)c2)CN1)C(=O)NCc1ccc(C(=N)N)cc1] | 2HCl |
| 1279 | 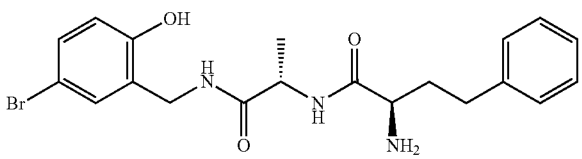 [SMILES: C[C@H](NC(=O)[C@H](N)CCc1ccccc1)C(=O)NCc1cc(Br)ccc1O] | HCl |
| 1280 | 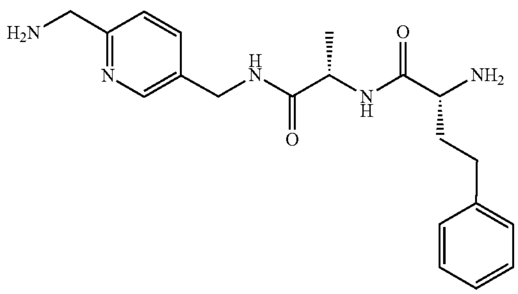 [SMILES: C[C@H](NC(=O)[C@H](N)CCc1ccccc1)C(=O)NCc1ccc(CN)nc1] | 2HCl |
| 1281 | 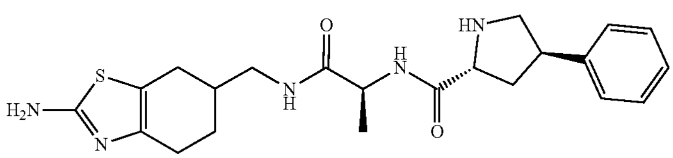 [SMILES: C[C@H](NC(=O)[C@H]1C[C@H](c2ccccc2)CN1)C(=O)NCC1CCc2nc(N)sc2C1] | 2TFA |
| 1282 | 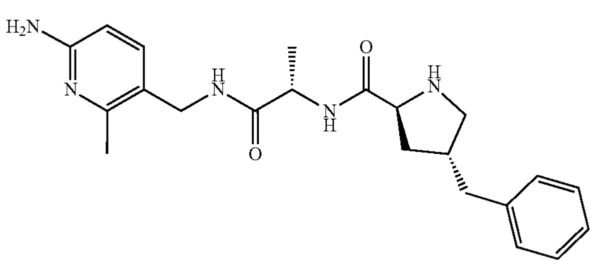 [SMILES: Cc1nc(N)ccc1CNC(=O)[C@H](C)NC(=O)[C@@H]1C[C@@H](Cc2ccccc2)CN1] | 2HCl |

TABLE 4A-continued

| Compound No. | Structure | Salt |
|---|---|---|
| 1283 | 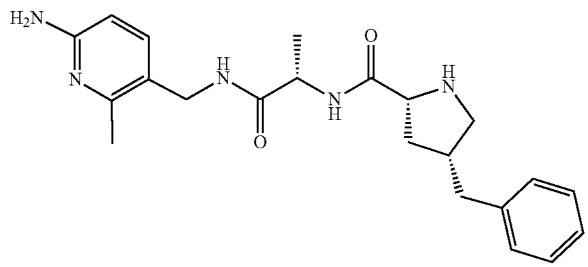 [SMILES: Cc1nc(N)ccc1CNC(=O)[C@H](C)NC(=O)[C@H]1C[C@@H](Cc2ccccc2)CN1] | 2HCl |
| 1284 | 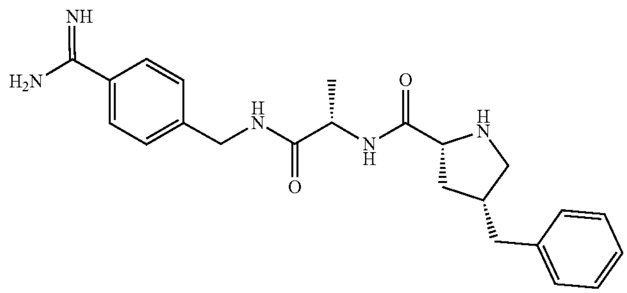 [SMILES: C[C@H](NC(=O)[C@H]1C[C@@H](Cc2ccccc2)CN1)C(=O)NCc1ccc(C(=N)N)cc1] | 2TFA |
| 1285 | 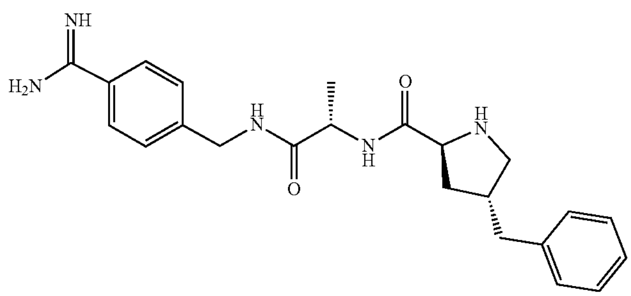 [SMILES: C[C@H](NC(=O)[C@@H]1C[C@@H](Cc2ccccc2)CN1)C(=O)NCc1ccc(C(=N)N)cc1] | 2HCl |
| 1286 | 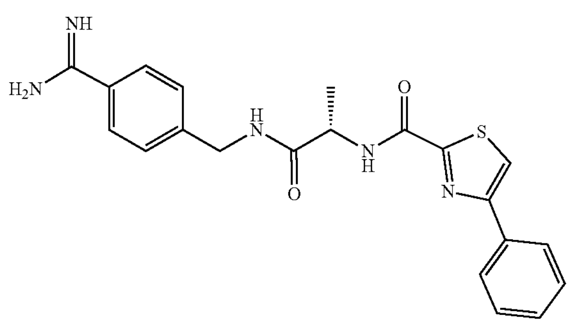 [SMILES: C[C@H](NC(=O)c1nc(-c2ccccc2)cs1)C(=O)NCc1ccc(C(=N)N)cc1] | HCl |
| 1287 | 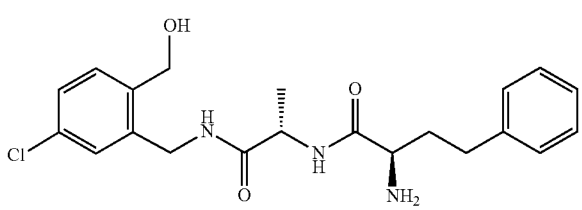 [SMILES: C[C@H](NC(=O)[C@H](N)CCc1ccccc1)C(=O)NCc1cc(Cl)ccc1CO] | HCl |

TABLE 4A-continued

| Compound No. | Structure | Salt |
|---|---|---|
| 1288 | 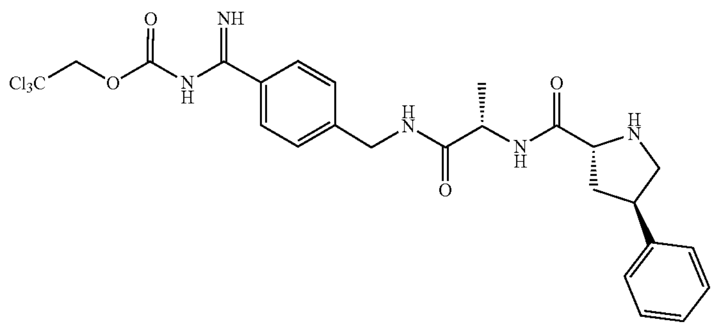 | NA |
| 1289 | 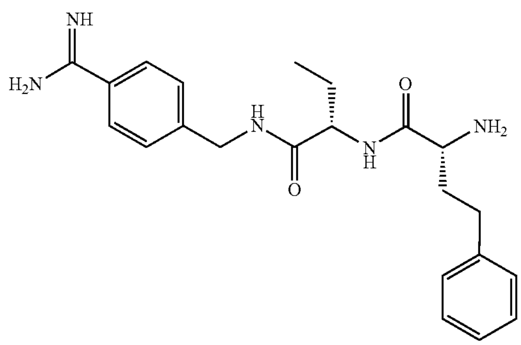 [SMILES: CC[C@H](NC(=O)[C@H](N)CCc1ccccc1)C(=O)NCc1ccc(C(=N)N)cc1] | HCl |
| 1290 | 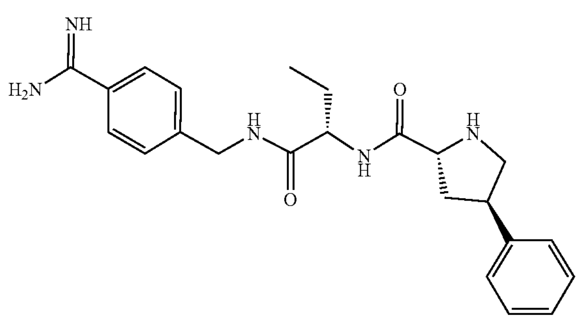 [SMILES: CC[C@H](NC(=O)[C@H]1C[C@H](c2ccccc2)CN1)C(=O)NCc1ccc(C(=N)N)cc1] | HCl |
| 1291 | 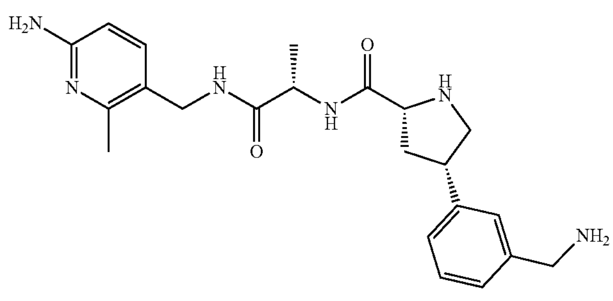 [SMILES: Cc1nc(N)ccc1CNC(=O)[C@H](C)NC(=O)[C@H]1C[C@@H](c2cccc(CN)c2)CN1] | 2HCl |

TABLE 4A-continued
Exemplary compounds
| Compound No. | Structure | Salt |
|---|---|---|
| 1292 | 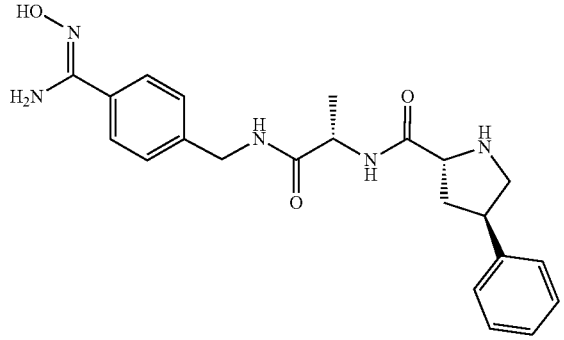 [SMILES: C[C@H](NC(=O)[C@H]1C[C@H](c2ccccc2)CN1)C(=O)NCc1ccc(/C(N)=N/O)cc1] | NA |
| 1293 | 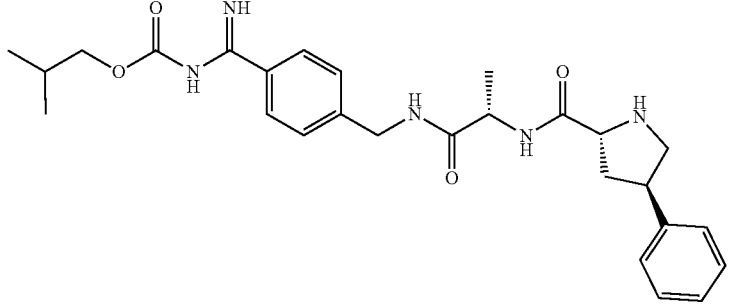 [SMILES: CC(C)COC(=O)NC(=N)c1ccc(CNC(=O)[C@H](C)NC(=O)[C@H]2C[C@H](c3ccccc3)CN2)cc1] | NA |
| 1294 | 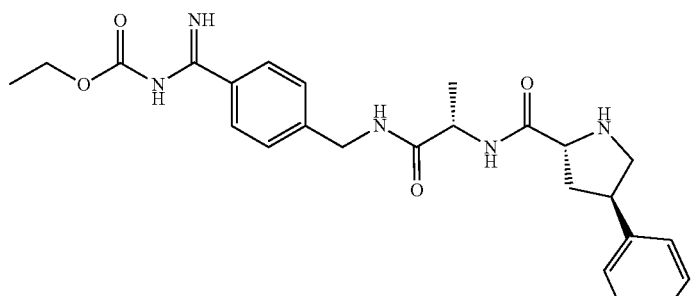 | NA |
| 1295 | 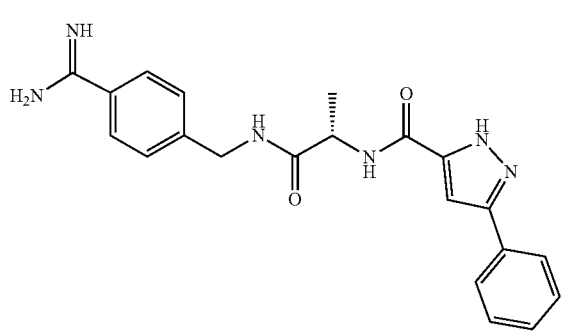 [SMILES: C[C@H](NC(=O)c1cc(-c2ccccc2)n[nH]1)C(=O)NCc1ccc(C(=N)N)cc1] | NA |

TABLE 4A-continued

| Compound No. | Structure | Salt |
|---|---|---|
| 1296 | 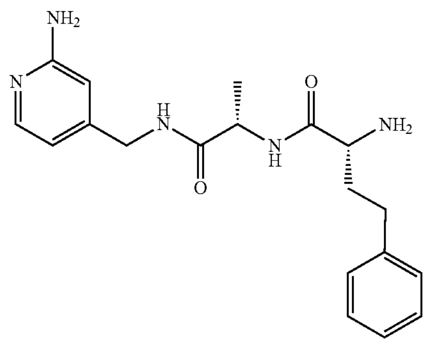 [SMILES: C[C@H](NC(=O)[C@H](N)CCc1ccccc1)C(=O)NCc1ccnc(N)c1] | 2HCl |
| 1297 | 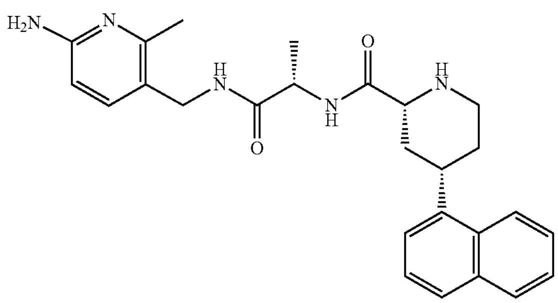 [SMILES: Cc1nc(N)ccc1CNC(=O)[C@H](C)NC(=O)[C@H]1C[C@@H](c2cccc3ccccc23)CCN1] | 2 HCl |
| 1298 | 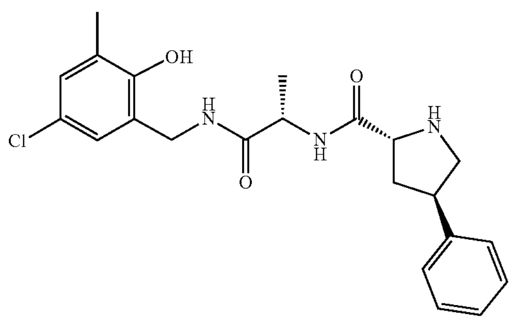 [SMILES: Cc1cc(Cl)cc(CNC(=O)[C@H](C)NC(=O)[C@H]2C[C@H](c3ccccc3)CN2)c1O] | HCl |
| 1299 | 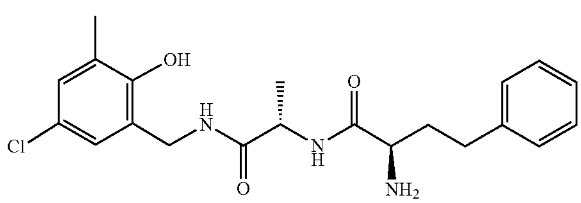 [SMILES: Cc1cc(Cl)cc(CNC(=O)[C@H](C)NC(=O)[C@H](N)CCc2ccccc2)c1O] | HCl |
| 1300 | 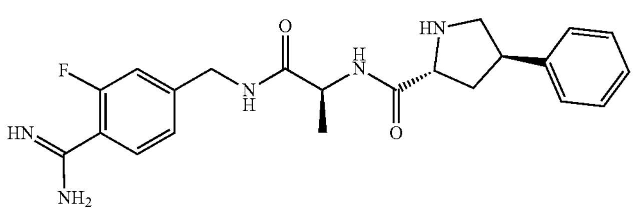 [SMILES: C[C@H](NC(=O)[C@H]1C[C@H](c2ccccc2)CN1)C(=O)NCc1ccc(C(=N)N)c(F)c1] | 2TFA |

TABLE 4A-continued

Exemplary compounds

| Compound No. | Structure | Salt |
|---|---|---|
| 1301 | 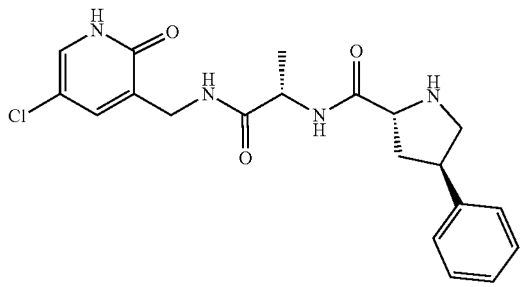 [SMILES: C[C@H](NC(=O)[C@H]1C[C@H](c2ccccc2)CN1)C(=O)NCc1cc(Cl)c[nH]c1=O] | N/A |
| 1302 | 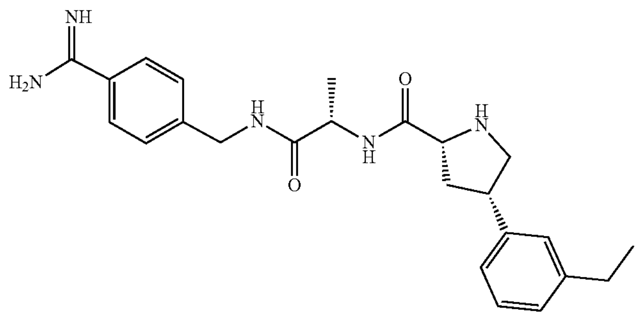 [SMILES: CCc1cccc([C@H]2CN[C@@H](C(=O)N[C@@H](C)C(=O)NCc3ccc(C(=N)N)cc3)C2)c1] | 2HCl |
| 1303 | 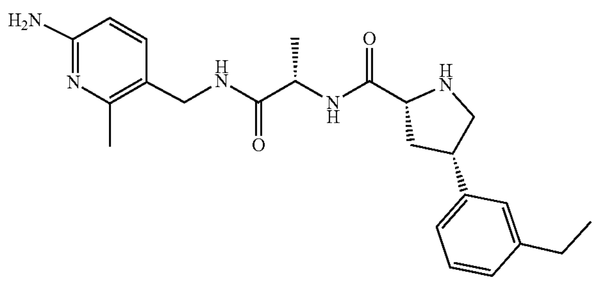 [SMILES: CCc1cccc([C@H]2CN[C@@H](C(=O)N[C@@H](C)C(=O)NCc3ccc(N)nc3C)C2)c1] | 2HCl |
| 1304 | 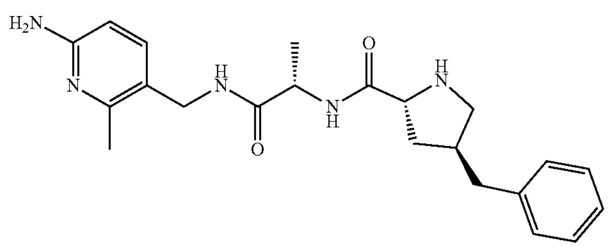 [SMILES: Cc1nc(N)ccc1CNC(=O)[C@H](C)NC(=O)[C@H]1C[C@H](Cc2ccccc2)CN1] | 2HCl |
| 1305 | 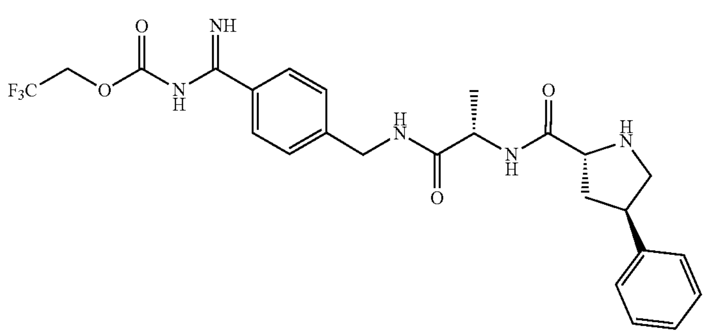 [SMILES: C[C@H](NC(=O)[C@H]1C[C@H](c2ccccc2)CN1)C(=O)NCc1ccc(C(=N)NC(=O)OCC(F)(F)F)cc1] | NA |

TABLE 4A-continued

Exemplary compounds

| Compound No. | Structure | Salt |
|---|---|---|
| 1306 | 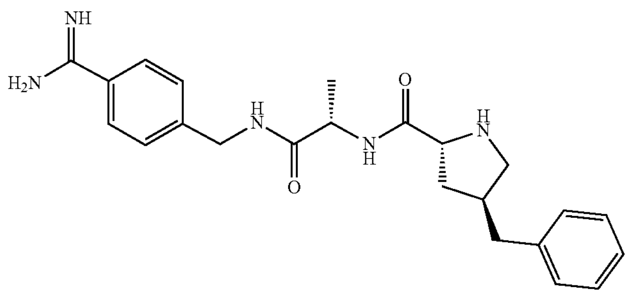 [SMILES: C[C@H](NC(=O)[C@H]1C[C@H](Cc2ccccc2)CN1)C(=O)NCc1ccc(C(=N)N)cc1] | 2HCl |
| 1307 | 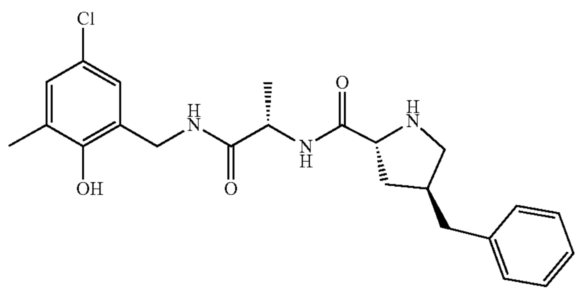 [SMILES: Cc1cc(Cl)cc(CNC(=O)[C@H](C)NC(=O)[C@H]2C[C@H](Cc3ccccc3)CN2)c1O] | HCl |
| 1308 | 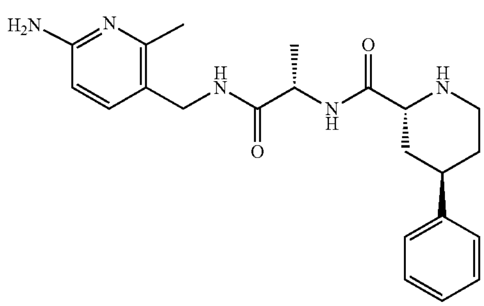 [SMILES: Cc1nc(N)ccc1CNC(=O)[C@H](C)NC(=O)[C@H]1C[C@H](c2ccccc2)CCN1] | 2 HCl |
| 1309 | 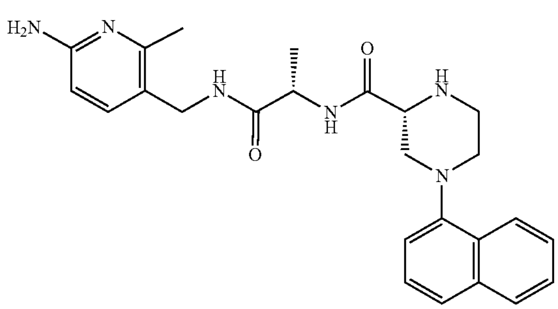 [SMILES: Cc1nc(N)ccc1CNC(=O)[C@H](C)NC(=O)[C@H]1CN(c2cccc3ccccc23)CCN1] | 2 HCl |
| 1310 | 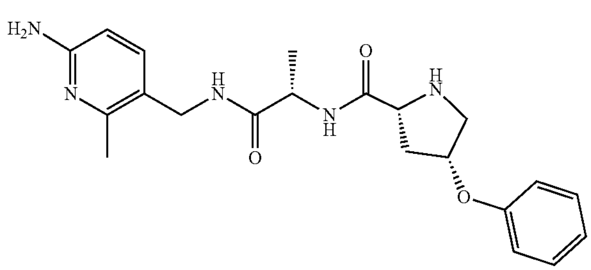 [SMILES: Cc1nc(N)ccc1CNC(=O)[C@H](C)NC(=O)[C@H]1C[C@@H](Oc2ccccc2)CN1] | 2HCl |

TABLE 4A-continued

| Compound No. | Structure | Salt |
|---|---|---|
| 1311 | 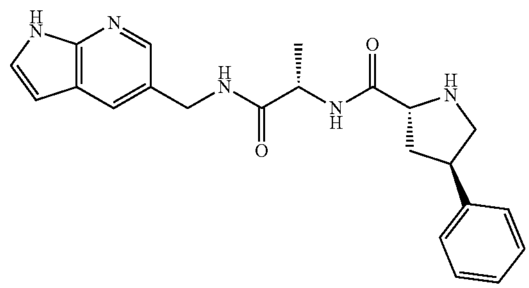 [SMILES: C[C@H](NC(=O)[C@H]1C[C@H](c2ccccc2)CN1)C(=O)NCc1cnc2[nH]ccc2c1] | 2HCl |
| 1312 | 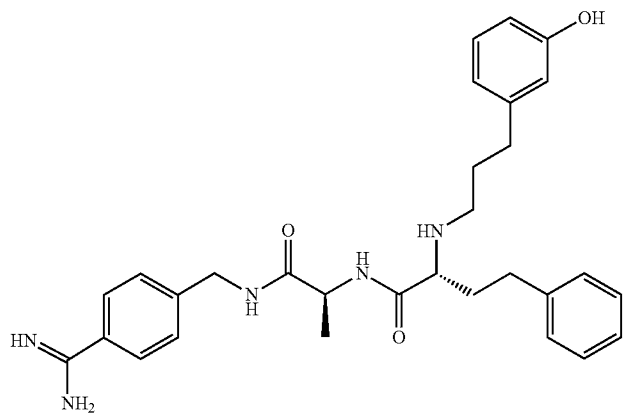 [SMILES: C[C@H](NC(=O)[C@@H](CCc1ccccc1)NCCCc1cccc(O)c1)C(=O)NCc1ccc(C(=N)N)cc1] | 2TFA |
| 1313 | 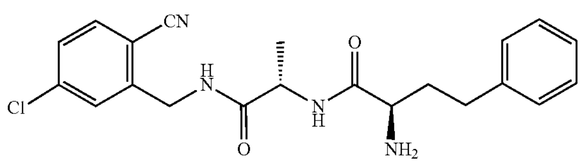 [SMILES: C[C@H](NC(=O)[C@H](N)CCc1ccccc1)C(=O)NCc1cc(Cl)ccc1C#N] | TFA |
| 1314 | 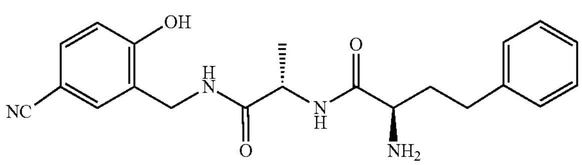 [SMILES: C[C@H](NC(=O)[C@H](N)CCc1ccccc1)C(=O)NCc1cc(C#N)ccc1O] | TFA |
| 1315 | 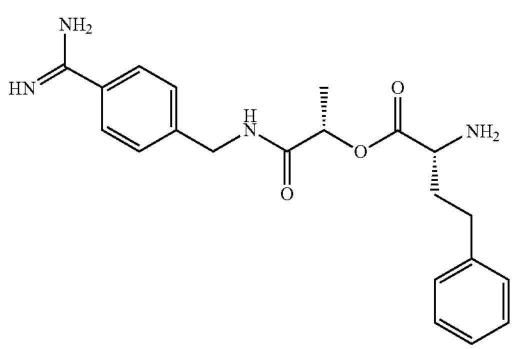 [SMILES: C[C@H](OC(=O)[C@H](N)CCc1ccccc1)C(=O)NCc1ccc(C(=N)N)cc1] | HCl |

TABLE 4A-continued

Exemplary compounds

| Compound No. | Structure | Salt |
|---|---|---|
| 1316 | 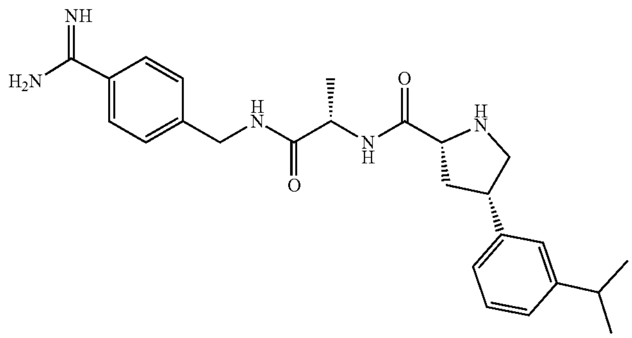 [SMILES: CC(C)c1cccc([C@H]2CN[C@@H](C(=O)N[C@@H](C)C(=O)NCc3ccc(C(=N)N)cc3)C2)c1] | 2HCl |
| 1317 | 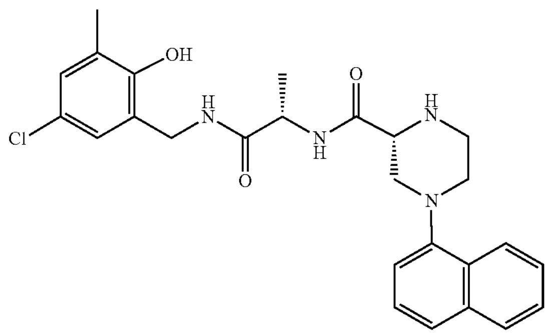 [SMILES: Cc1cc(Cl)cc(CNC(=O)[C@H](C)NC(=O)[C@H]2CN(c3cccc4ccccc34)CCN2)c1O] | HCl |
| 1318 | 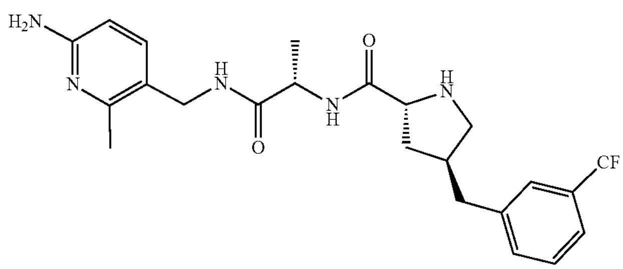 | 2HCl |
| 1319 | 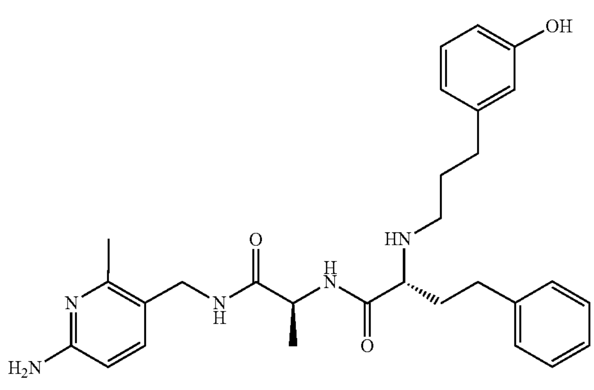 [SMILES: Cc1nc(N)ccc1CNC(=O)[C@H](C)NC(=O)[C@@H](CCc1ccccc1)NCCCc1cccc(O)c1] | 2HCl |
| 1320 | 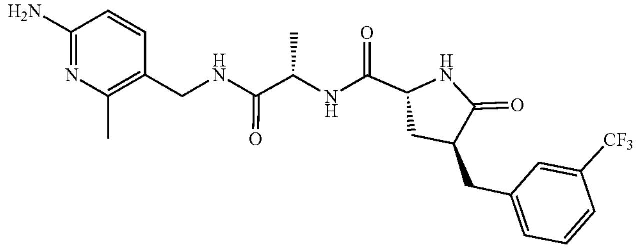 [SMILES: Cc1nc(N)ccc1CNC(=O)[C@H](C)NC(=O)[C@H]1C[C@H](Cc2cccc(C(F)(F)F)c2)C(=O)N1] | 2TFA |

TABLE 4A-continued

Exemplary compounds

| Compound No. | Structure | Salt |
|---|---|---|
| 1321 | 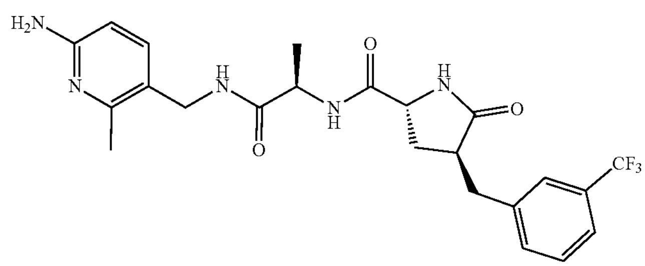 [SMILES: Cc1nc(N)ccc1CNC(=O)[C@@H](C)NC(=O)[C@H]1C[C@H](Cc2cccc(C(F)(F)F)c2)C(=O)N1] | 2TFA |
| 1322 | 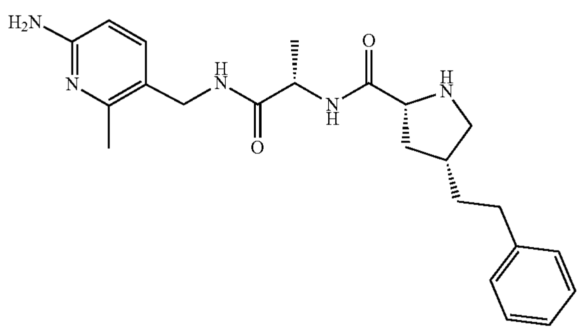 [SMILES: Cc1nc(N)ccc1CNC(=O)[C@H](C)NC(=O)[C@H]1C[C@@H](CCc2ccccc2)CN1] | 2HCl |
| 1323 | 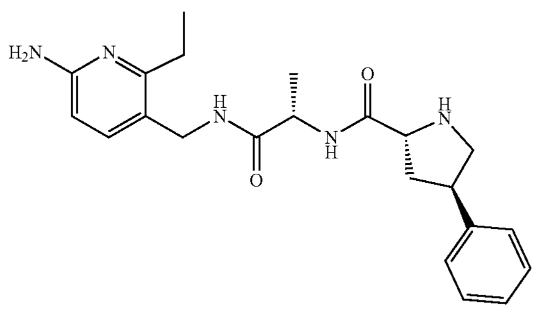 [SMILES: CCc1nc(N)ccc1CNC(=O)[C@H](C)NC(=O)[C@H]1C[C@H](c2ccccc2)CN1] | 2HCl |
| 1324 | 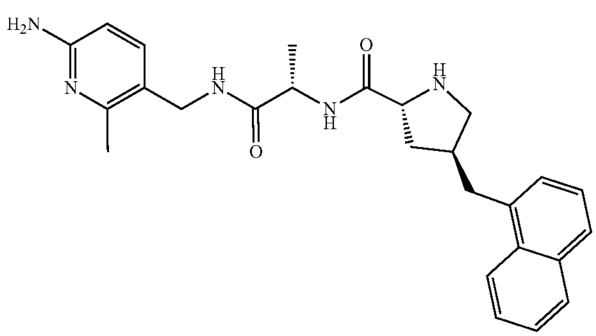 [SMILES: Cc1nc(N)ccc1CNC(=O)[C@H](C)NC(=O)[C@H]1C[C@H](Cc2cccc3ccccc23)CN1] | 2TFA |
| 1325 | 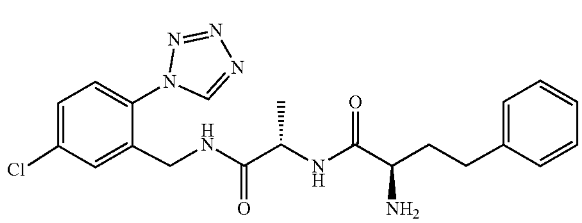 [SMILES: C[C@H](NC(=O)[C@H](N)CCc1ccccc1)C(=O)NCc1cc(Cl)ccc1-n1cnnn1] | TFA |

TABLE 4A-continued
| Exemplary compounds | | |
|---|---|---|
| Compound No. | Structure | Salt |
| 1326 |  | 2TFA |
| 1327 | 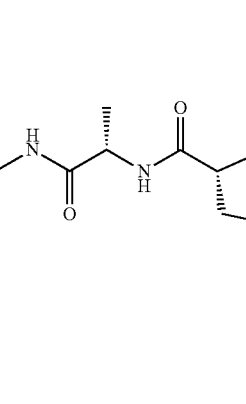 | 2HCl |
| 1328 |  | 2HCl |
| 1329 | 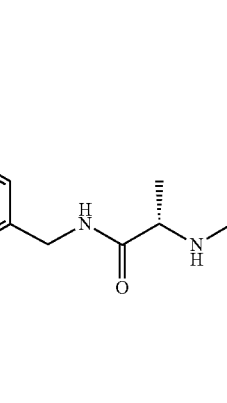 | 2HCl |

TABLE 4A-continued
Exemplary compounds
| Compound No. | Structure | Salt |
|---|---|---|
| 1330 | 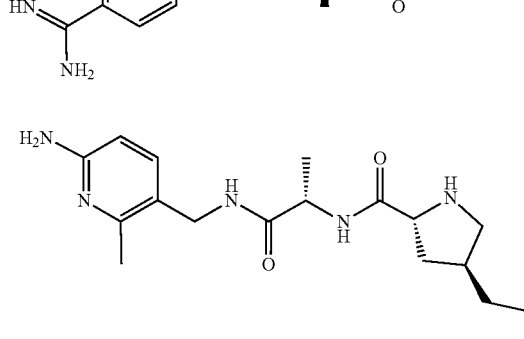 | 2TFA |
| 1331 | 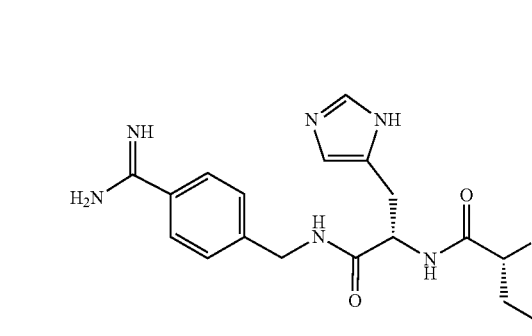 | 2HCl |
| 1332 | 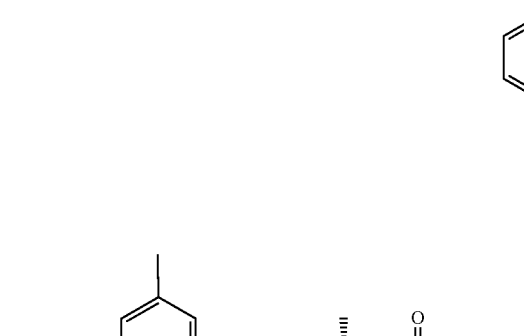 | 2TFA |
| 1333 | 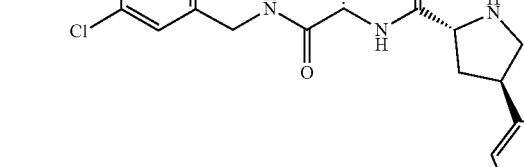 | HCl |

TABLE 4A-continued

| Compound No. | Structure | Salt |
|---|---|---|
| 1334 | 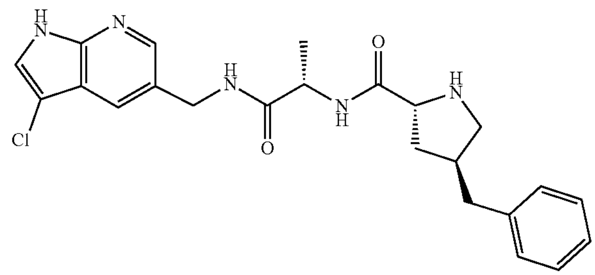 [SMILES: C[C@H](NC(=O)[C@H]1C[C@H](Cc2ccccc2)CN1)C(=O)NCc1cnc2[nH]cc(Cl)c2c1] | 2HCl |
| 1335 | 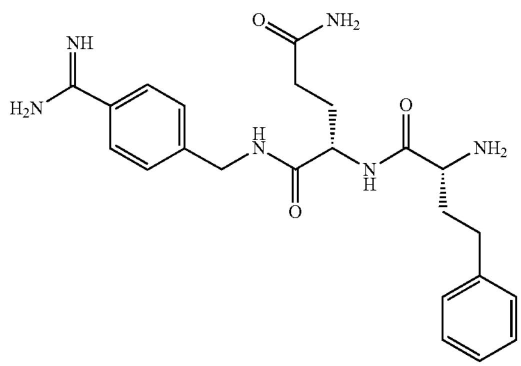 [SMILES: N=C(N)c1ccc(CNC(=O)[C@H](CCC(N)=O)NC(=O)[C@H](N)CCc2ccccc2)cc1] | 2TFA |
| 1336 | 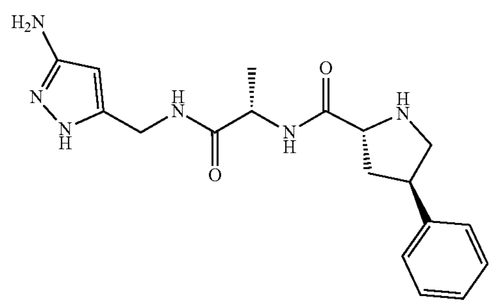 [SMILES: C[C@H](NC(=O)[C@H]1C[C@H](c2ccccc2)CN1)C(=O)NCc1cc(N)n[nH]1] | 2HCl |
| 1337 | 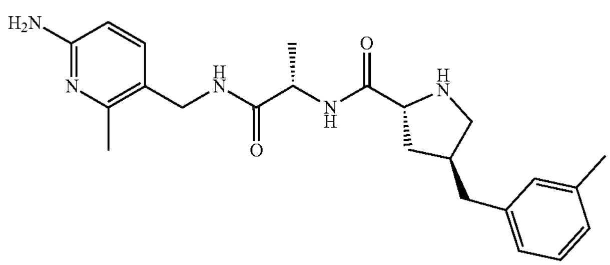 [SMILES: Cc1cccc(C[C@@H]2CN[C@@H](C(=O)N[C@@H](C)C(=O)NCc3ccc(N)nc3C)C2)c1] | 2HCl |
| 1338 | 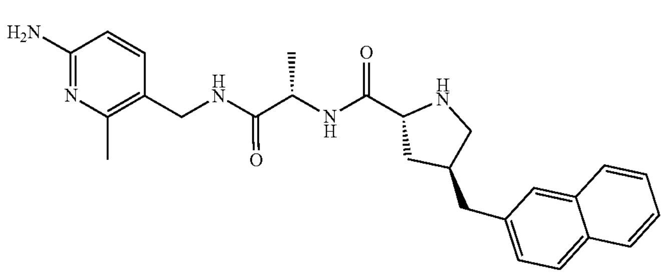 [SMILES: Cc1nc(N)ccc1CNC(=O)[C@H](C)NC(=O)[C@H]1C[C@H](Cc2ccc3ccccc3c2)CN1] | 2HCl |

TABLE 4A-continued

Exemplary compounds

| Compound No. | Structure | Salt |
|---|---|---|
| 1339 | 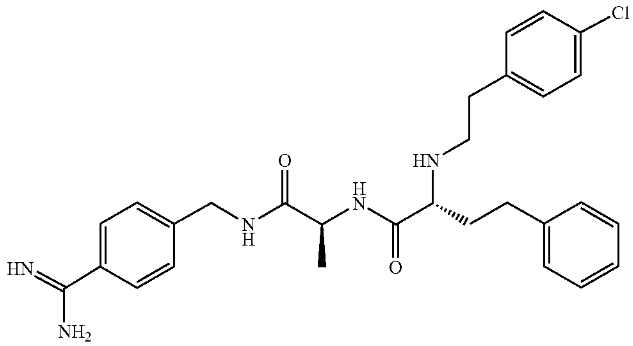 [SMILES: C[C@H](NC(=O)[C@@H](CCc1ccccc1)NCCc1ccc(Cl)cc1)C(=O)NCc1ccc(C(=N)N)cc1] | 2TFA |
| 1340 | 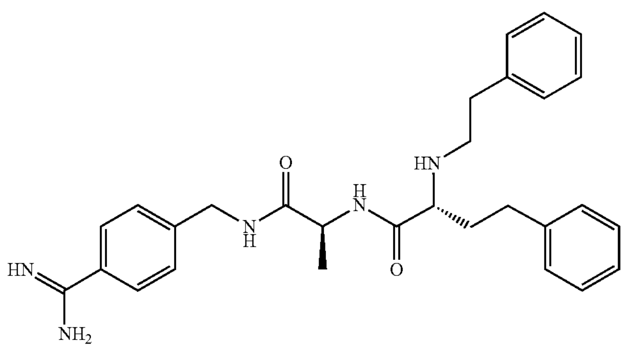 [SMILES: C[C@H](NC(=O)[C@@H](CCc1ccccc1)NCCc1ccccc1)C(=O)NCc1ccc(C(=N)N)cc1] | 2HCl |
| 1341 | 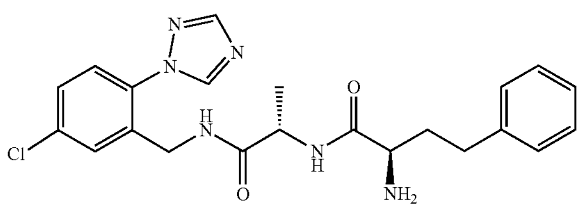 [SMILES: C[C@H](NC(=O)[C@H](N)CCc1ccccc1)C(=O)NCc1cc(Cl)ccc1-n1cncn1] | TFA |
| 1342 | 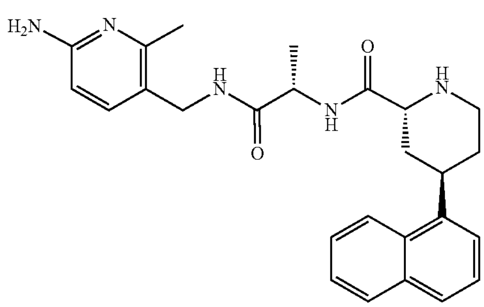 [SMILES: Cc1nc(N)ccc1CNC(=O)[C@H](C)NC(=O)[C@H]1C[C@H](c2cccc3ccccc23)CCN1] | 2 HCl |
| 1343 | 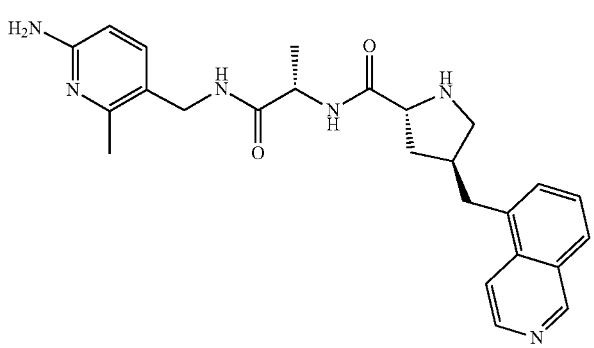 [SMILES: Cc1nc(N)ccc1CNC(=O)[C@H](C)NC(=O)[C@H]1C[C@H](Cc2cccc3cnccc23)CN1] | 2TFA |

TABLE 4A-continued

Exemplary compounds

| Compound No. | Structure | Salt |
|---|---|---|
| 1344 | 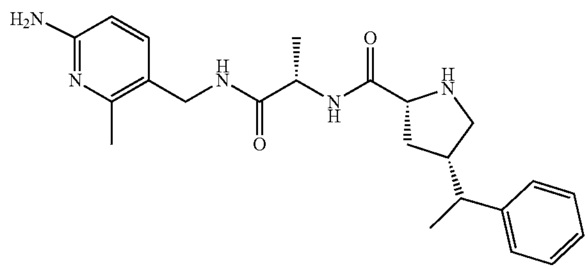 [SMILES: Cc1nc(N)ccc1CNC(=O)[C@H](C)NC(=O)[C@H]1C[C@@H](C(C)c2ccccc2)CN1] | 2HCl |
| 1345 | 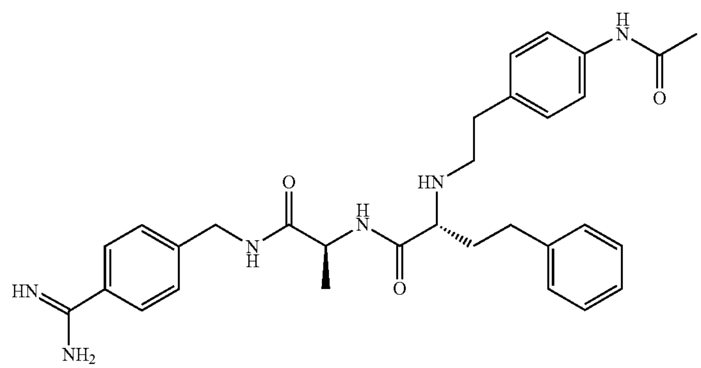 [SMILES: CC(=O)Nc1ccc(CCN[C@H](CCc2ccccc2)C(=O)N[C@@H](C)C(=O)NCc2ccc(C(=N)N)cc2)cc1] | 2HCl |
| 1346 | 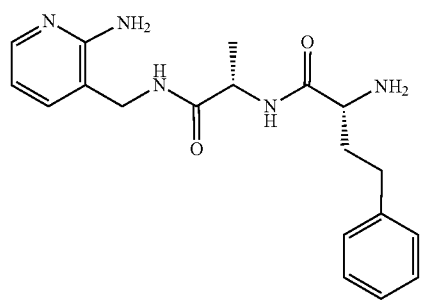 [SMILES: C[C@H](NC(=O)[C@H](N)CCc1ccccc1)C(=O)NCc1cccnc1N] | 2HCl |
| 1347 | 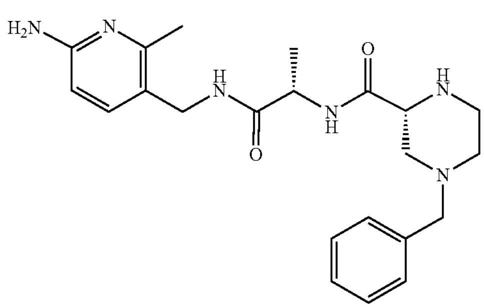 [SMILES: Cc1nc(N)ccc1CNC(=O)[C@H](C)NC(=O)[C@H]1CN(Cc2ccccc2)CCN1] | 2 HCl |
| 1348 | 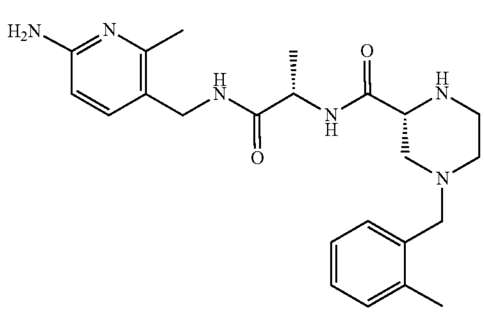 [SMILES: Cc1ccccc1CN1CCN[C@@H](C(=O)N[C@@H](C)C(=O)NCc2ccc(N)nc2C)C1] | 2 HCl |

TABLE 4A-continued

Exemplary compounds

| Compound No. | Structure | Salt |
|---|---|---|
| 1349 | 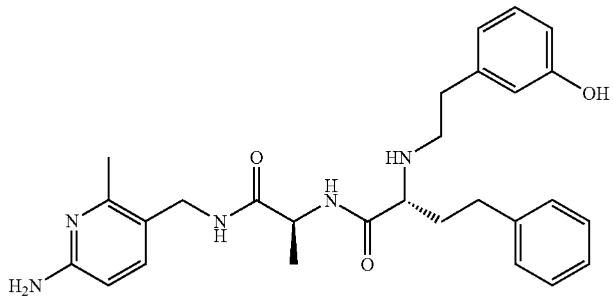 [SMILES: Cc1nc(N)ccc1CNC(=O)[C@H](C)NC(=O)[C@@H](CCc1ccccc1)NCCc1cccc(O)c1] | 2HCl |
| 1350 | 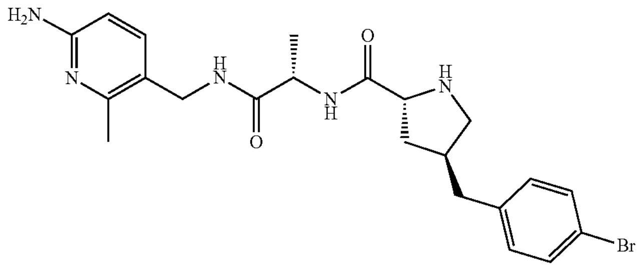 [SMILES: Cc1nc(N)ccc1CNC(=O)[C@H](C)NC(=O)[C@H]1C[C@H](Cc2ccc(Br)cc2)CN1] | 2HCl |
| 1351 | 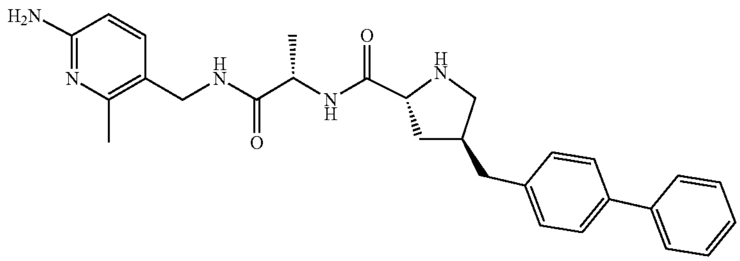 [SMILES: Cc1nc(N)ccc1CNC(=O)[C@H](C)NC(=O)[C@H]1C[C@H](Cc2ccc(-c3ccccc3)cc2)CN1] | 2HCl |
| 1352 | 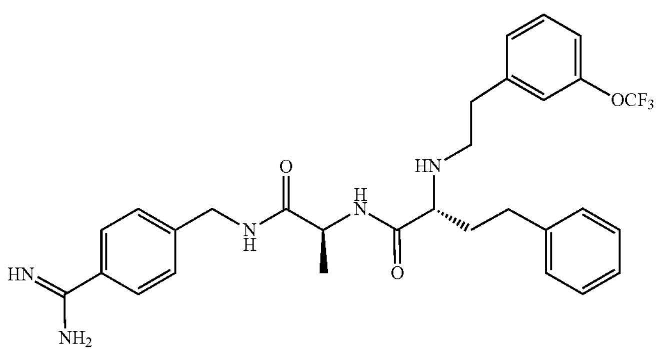 [SMILES: C[C@H](NC(=O)[C@@H](CCc1ccccc1)NCCc1cccc(OC(F)(F)F)c1)C(=O)NCc1ccc(C(=N)N)cc1] | 2TFA |
| 1353 | 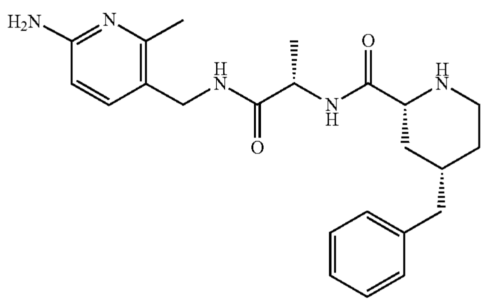 [SMILES: Cc1nc(N)ccc1CNC(=O)[C@H](C)NC(=O)[C@H]1C[C@@H](Cc2ccccc2)CCN1] | 2 HCl |

TABLE 4A-continued

Exemplary compounds

| Compound No. | Structure | Salt |
|---|---|---|
| 1354 | 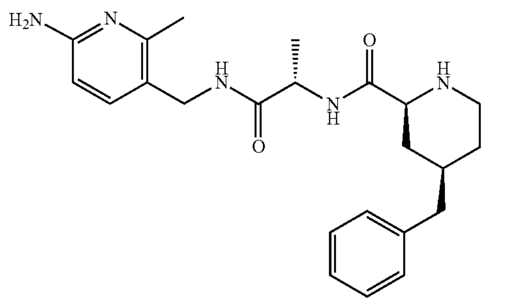 [SMILES: Cc1nc(N)ccc1CNC(=O)[C@H](C)NC(=O)[C@@H]1C[C@H](Cc2ccccc2)CCN1] | 2 HCl |
| 1355 | 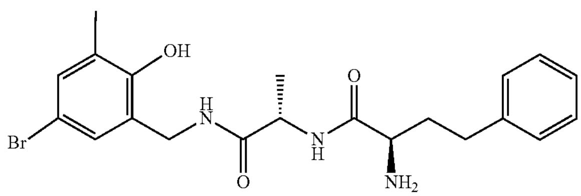 [SMILES: Cc1cc(Br)cc(CNC(=O)[C@H](C)NC(=O)[C@H](N)CCc2ccccc2)c1O] | TFA |
| 1356 | 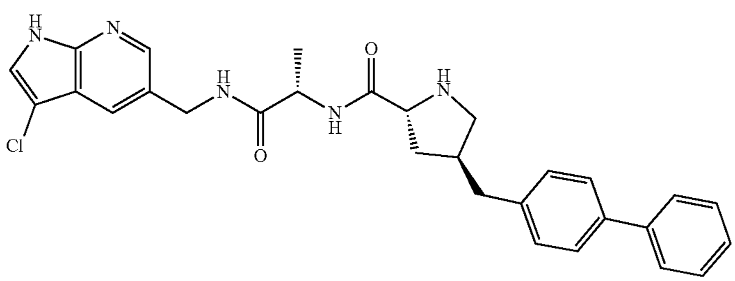 [SMILES: C[C@H](NC(=O)[C@H]1C[C@H](Cc2ccc(-c3ccccc3)cc2)CN1)C(=O)NCc1cnc2[nH]cc(Cl)c2c1] | TFA |
| 1357 | 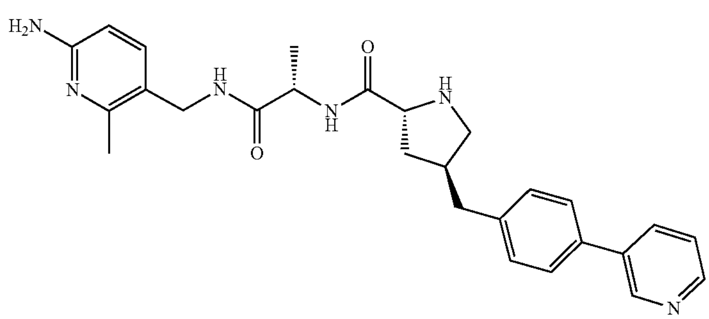 [SMILES: Cc1nc(N)ccc1CNC(=O)[C@H](C)NC(=O)[C@H]1C[C@H](Cc2ccc(-c3cccnc3)cc2)CN1] | 2TFA |
| 1358 | 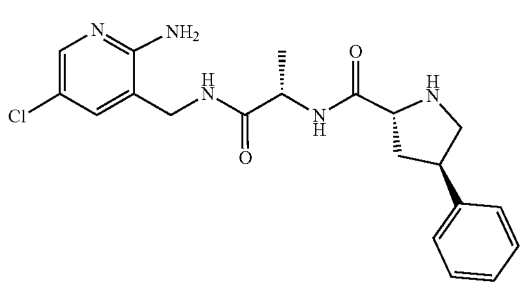 [SMILES: C[C@H](NC(=O)[C@H]1C[C@H](c2ccccc2)CN1)C(=O)NCc1cc(Cl)cnc1N] | 2TFA |

TABLE 4A-continued

Exemplary compounds

| Compound No. | Structure | Salt |
|---|---|---|
| 1359 | 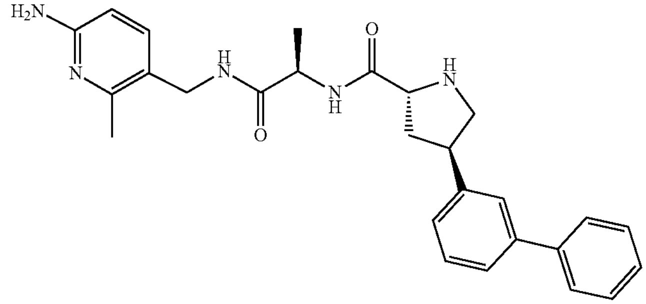 [SMILES: Cc1nc(N)ccc1CNC(=O)[C@@H](C)NC(=O)[C@H]1C[C@H](c2cccc(-c3ccccc3)c2)CN1] | 2TFA |
| 1360 | 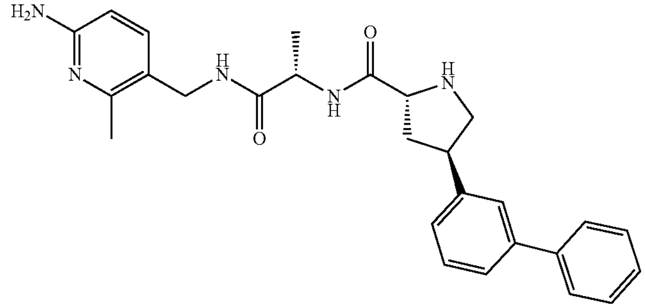 [SMILES: Cc1nc(N)ccc1CNC(=O)[C@H](C)NC(=O)[C@H]1C[C@H](c2cccc(-c3ccccc3)c2)CN1] | 2TFA |
| 1361 | 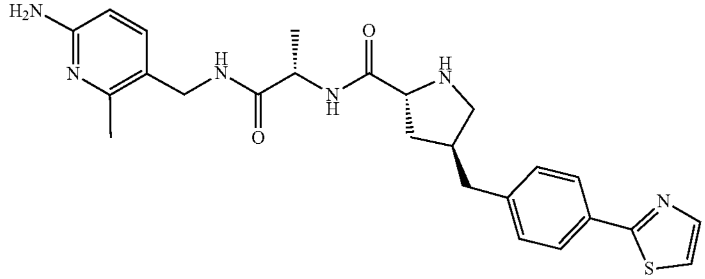 [SMILES: Cc1nc(N)ccc1CNC(=O)[C@H](C)NC(=O)[C@H]1C[C@H](Cc2ccc(-c3nccs3)cc2)CN1] | 2TFA |
| 1362 | 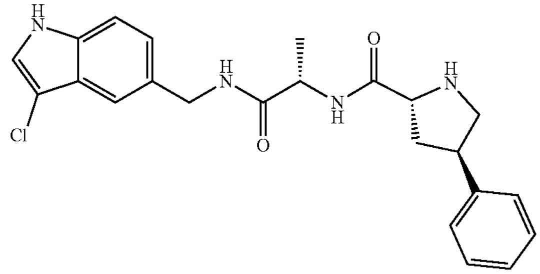 [SMILES: C[C@H](NC(=O)[C@H]1C[C@H](c2ccccc2)CN1)C(=O)NCc1ccc2[nH]cc(Cl)c2c1] | N/A |
| 1363 | 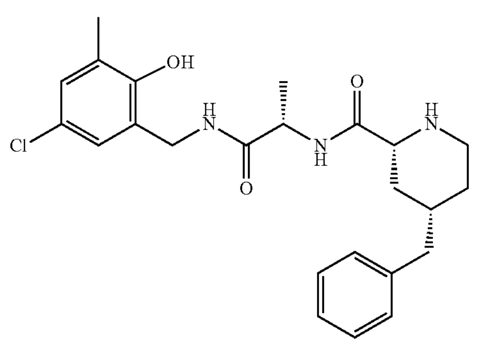 [SMILES: Cc1cc(Cl)cc(CNC(=O)[C@H](C)NC(=O)[C@H]2C[C@@H](Cc3ccccc3)CCN2)c1O] | HCl |

TABLE 4A-continued

Exemplary compounds

| Compound No. | Structure | Salt |
|---|---|---|
| 1364 | 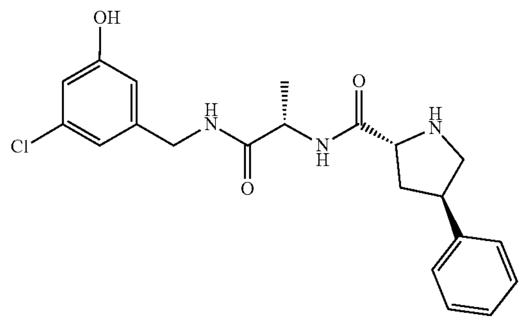 [SMILES: C[C@H](NC(=O)[C@H]1C[C@H](c2ccccc2)CN1)C(=O)NCc1cc(O)cc(Cl)c1] | HCl |
| 1365 | 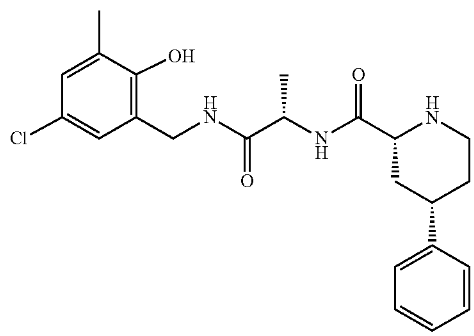 [SMILES: Cc1cc(Cl)cc(CNC(=O)[C@H](C)NC(=O)[C@H]2C[C@@H](c3ccccc3)CCN2)c1O] | HCl |
| 1366 | 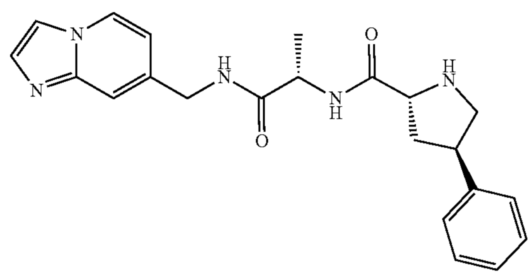 [SMILES: C[C@H](NC(=O)[C@H]1C[C@H](c2ccccc2)CN1)C(=O)NCc1ccn2ccnc2c1] | 2HCl |
| 1367 | 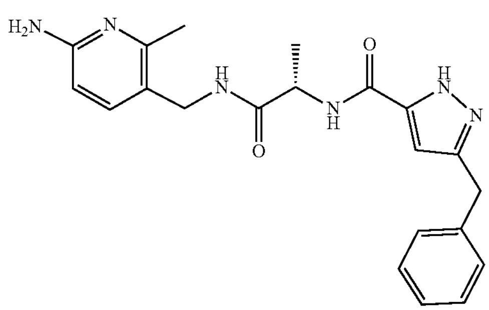 [SMILES: Cc1nc(N)ccc1CNC(=O)[C@H](C)NC(=O)c1cc(Cc2ccccc2)n[nH]1] | NA |
| 1368 | 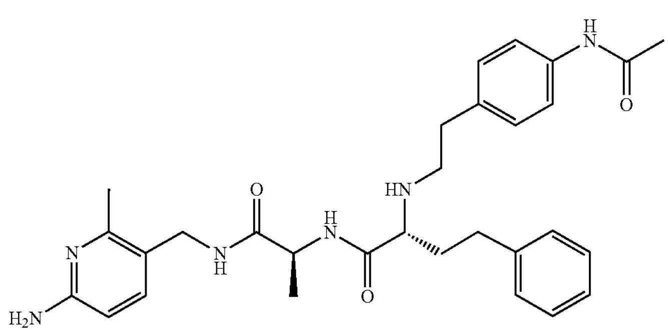 [SMILES: CC(=O)Nc1ccc(CCN[C@H](CCc2ccccc2)C(=O)N[C@@H](C)C(=O)NCc2ccc(N)nc2C)cc1] | 2HCl |

TABLE 4A-continued

Exemplary compounds

| Compound No. | Structure | Salt |
|---|---|---|
| 1369 | 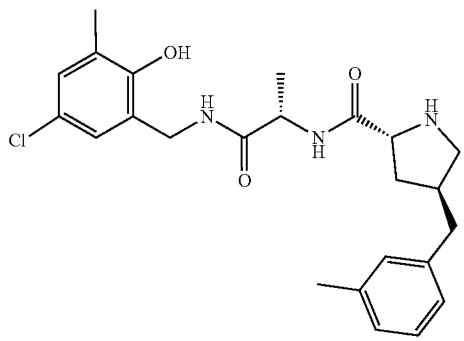 [SMILES: Cc1cccc(C[C@@H]2CN[C@@H](C(=O)N[C@@H](C)C(=O)NCc3cc(Cl)cc(C)c3O)C2)c1] | HCl |
| 1370 | 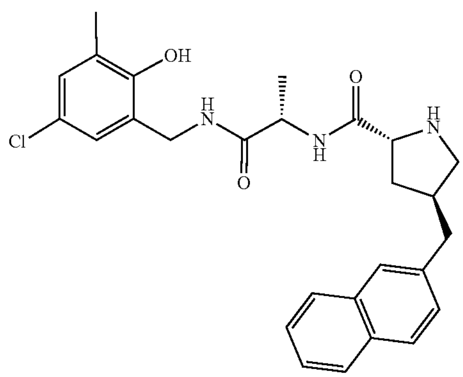 [SMILES: Cc1cc(Cl)cc(CNC(=O)[C@H](C)NC(=O)[C@H]2C[C@H](Cc3ccc4ccccc4c3)CN2)c1O] | TFA |
| 1371 | 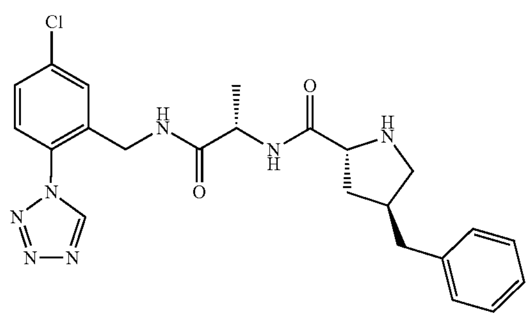 [SMILES: C[C@H](NC(=O)[C@H]1C[C@H](Cc2ccccc2)CN1)C(=O)NCc1cc(Cl)ccc1-n1cnnn1] | HCl |
| 1372 | 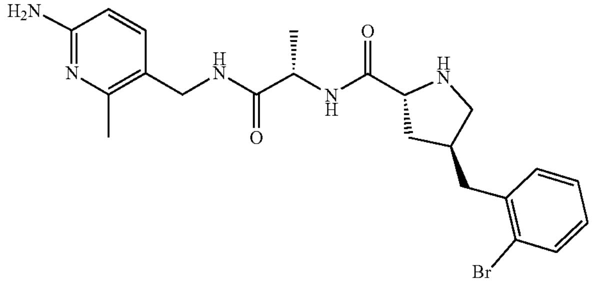 [SMILES: Cc1nc(N)ccc1CNC(=O)[C@H](C)NC(=O)[C@H]1C[C@H](Cc2ccccc2Br)CN1] | 2TFA |

TABLE 4A-continued

| Compound No. | Structure | Salt |
|---|---|---|
| 1373 | 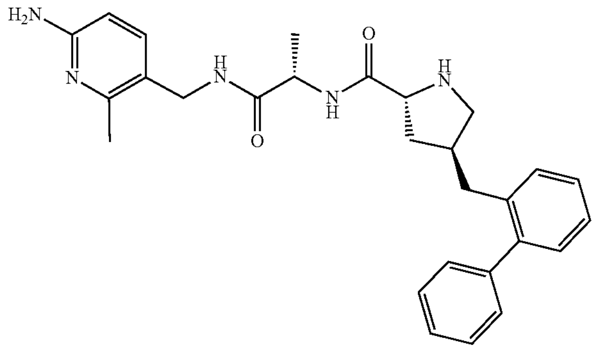 [SMILES: Cc1nc(N)ccc1CNC(=O)[C@H](C)NC(=O)[C@H]1C[C@H](Cc2ccccc2-c2ccccc2)CN1] | 2TFA |
| 1374 | 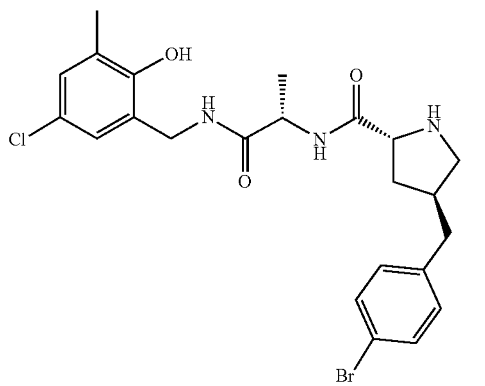 [SMILES: Cc1cc(Cl)cc(CNC(=O)[C@H](C)NC(=O)[C@H]2C[C@H](Cc3ccc(Br)cc3)CN2)c1O] | HCl |
| 1375 | 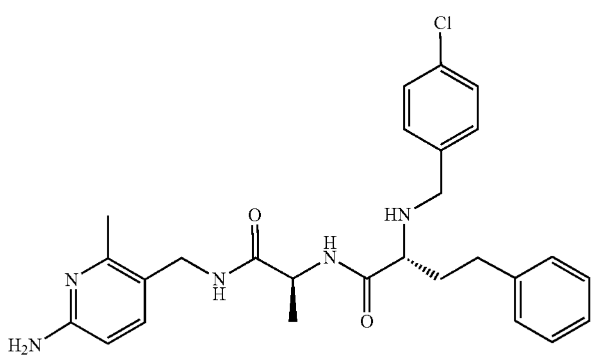 [SMILES: Cc1nc(N)ccc1CNC(=O)[C@H](C)NC(=O)[C@@H](CCc1ccccc1)NCc1ccc(Cl)cc1] | NA |
| 1376 | 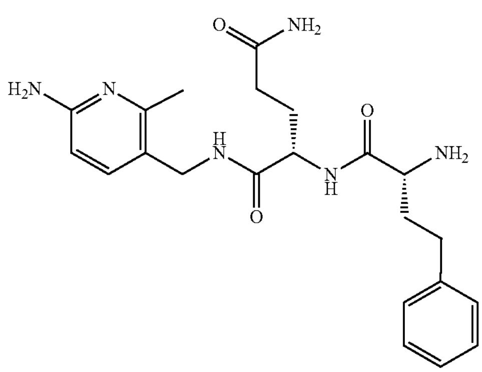 [SMILES: Cc1nc(N)ccc1CNC(=O)[C@H](CCC(N)=O)NC(=O)[C@H](N)CCc1ccccc1] | 2TFA |

TABLE 4A-continued

Exemplary compounds

| Compound No. | Structure | Salt |
|---|---|---|
| 1377 | 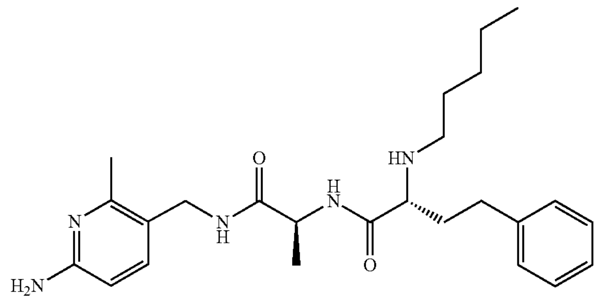 [SMILES: CCCCCN[C@H](CCc1ccccc1)C(=O)N[C@@H](C)C(=O)NCc1ccc(N)nc1C] | 2TFA |
| 1378 | 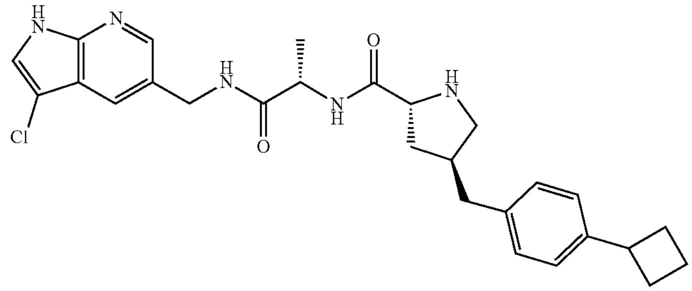 [SMILES: C[C@H](NC(=O)[C@H]1C[C@H](Cc2ccc(C3CCC3)cc2)CN1)C(=O)NCc1cnc2[nH]cc(Cl)c2c1] | 2TFA |
| 1379 | 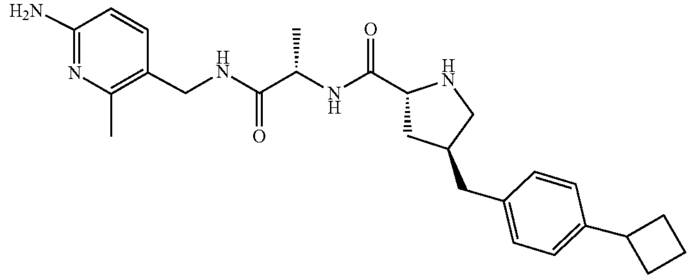 [SMILES: Cc1nc(N)ccc1CNC(=O)[C@H](C)NC(=O)[C@H]1C[C@H](Cc2ccc(C3CCC3)cc2)CN1] | 2TFA |
| 1380 | 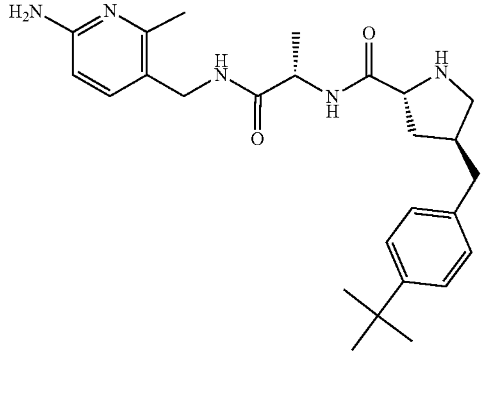 [SMILES: Cc1nc(N)ccc1CNC(=O)[C@H](C)NC(=O)[C@H]1C[C@H](Cc2ccc(C(C)(C)C)cc2)CN1] | 2 HCl |

TABLE 4A-continued

Exemplary compounds

| Compound No. | Structure | Salt |
|---|---|---|
| 1381 | 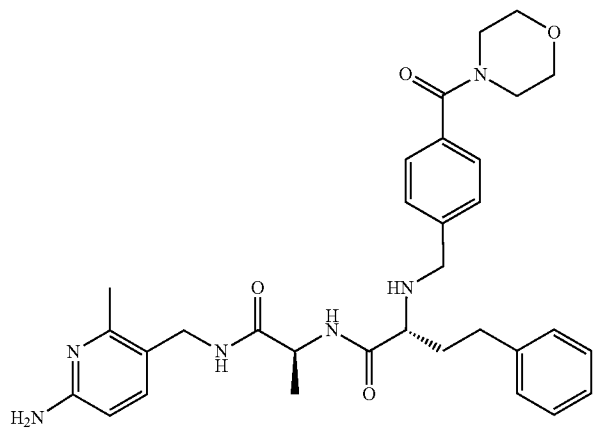 [SMILES: Cc1nc(N)ccc1CNC(=O)[C@H](C)NC(=O)[C@@H](CCc1ccccc1)NCc1ccc(C(=O)N2CCOCC2)cc1] | 2TFA |
| 1382 | 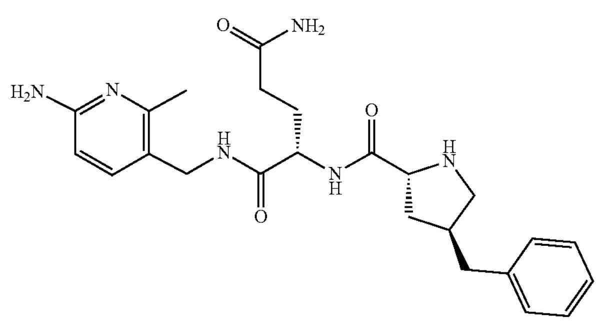 [SMILES: Cc1nc(N)ccc1CNC(=O)[C@H](CCC(N)=O)NC(=O)[C@H]1C[C@H](Cc2ccccc2)CN1] | 2TFA |
| 1383 | 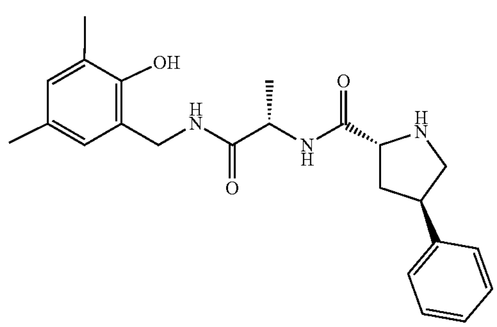 [SMILES: Cc1cc(C)c(O)c(CNC(=O)[C@H](C)NC(=O)[C@H]2C[C@H](c3ccccc3)CN2)c1] | TFA |
| 1384 | 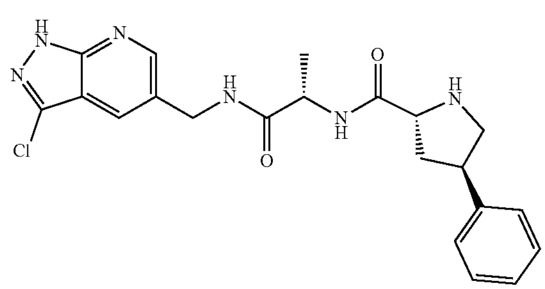 [SMILES: C[C@H](NC(=O)[C@H]1C[C@H](c2ccccc2)CN1)C(=O)NCc1cnc2[nH]nc(Cl)c2c1] | 2HCl |

TABLE 4A-continued

Exemplary compounds

| Compound No. | Structure | Salt |
|---|---|---|
| 1385 | 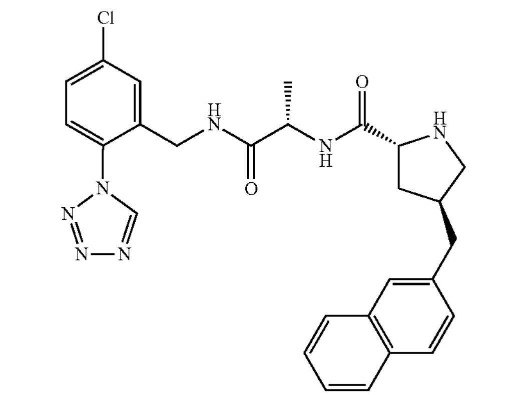 [SMILES: C[C@H](NC(=O)[C@H]1C[C@H](Cc2ccc3ccccc3c2)CN1)C(=O)NCc1cc(Cl)ccc1-n1cnnn1] | TFA |
| 1386 | 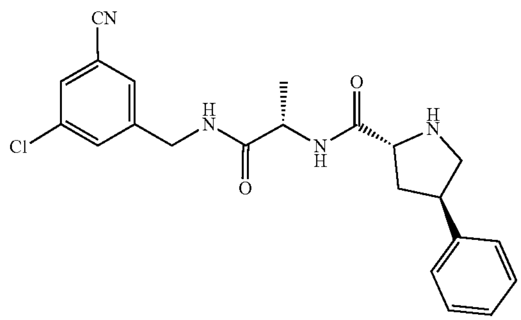 [SMILES: C[C@H](NC(=O)[C@H]1C[C@H](c2ccccc2)CN1)C(=O)NCc1cc(Cl)cc(C#N)c1] | TFA |
| 1387 | 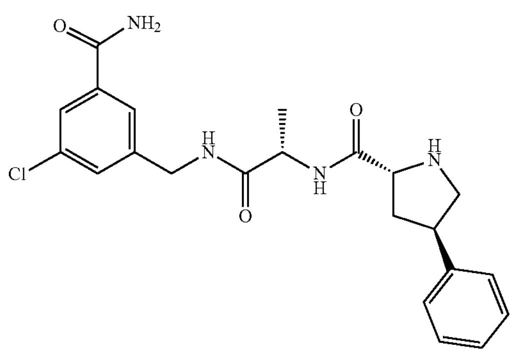 [SMILES: C[C@H](NC(=O)[C@H]1C[C@H](c2ccccc2)CN1)C(=O)NCc1cc(Cl)cc(C(N)=O)c1] | TFA |
| 1388 | 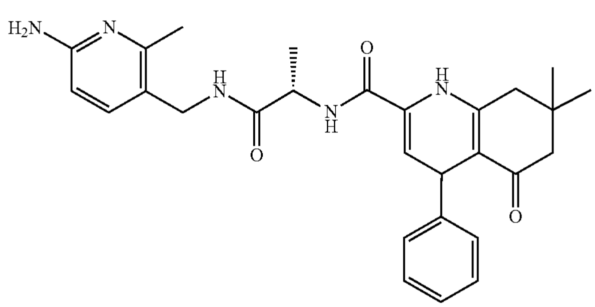 [SMILES: Cc1nc(N)ccc1CNC(=O)[C@H](C)NC(=O)C1=CC(c2ccccc2)C2=C(CC(C)(C)CC2=O)N1] | NA |

TABLE 4A-continued

Exemplary compounds

| Compound No. | Structure | Salt |
|---|---|---|
| 1389 | 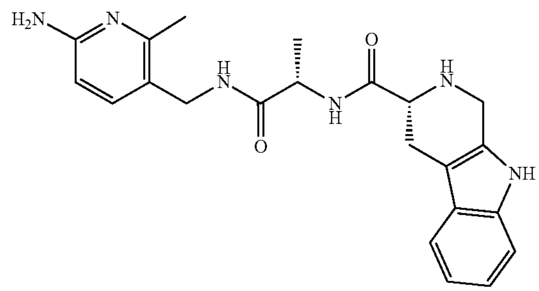 [SMILES: Cc1nc(N)ccc1CNC(=O)[C@H](C)NC(=O)[C@H]1Cc2c([nH]c3ccccc23)CN1] | 2 HCl |
| 1390 | 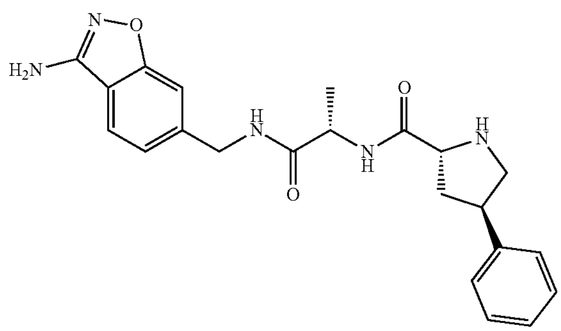 [SMILES: C[C@H](NC(=O)[C@H]1C[C@H](c2ccccc2)CN1)C(=O)NCc1ccc2c(N)noc2c1] | 2TFA |
| 1391 | 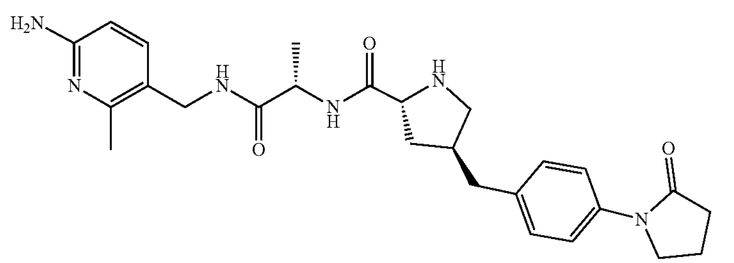 [SMILES: Cc1nc(N)ccc1CNC(=O)[C@H](C)NC(=O)[C@H]1C[C@H](Cc2ccc(N3CCCC3=O)cc2)CN1] | 2TFA |
| 1392 | 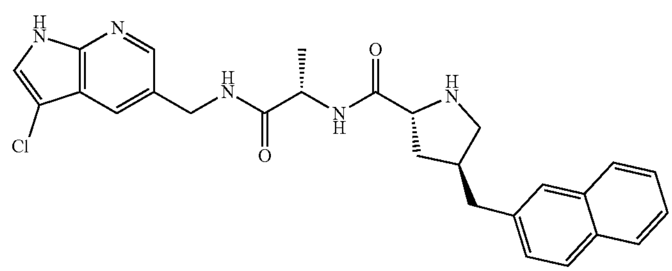 [SMILES: C[C@H](NC(=O)[C@H]1C[C@H](Cc2ccc3ccccc3c2)CN1)C(=O)NCc1cnc2[nH]cc(Cl)c2c1] | 2TFA |
| 1393 | 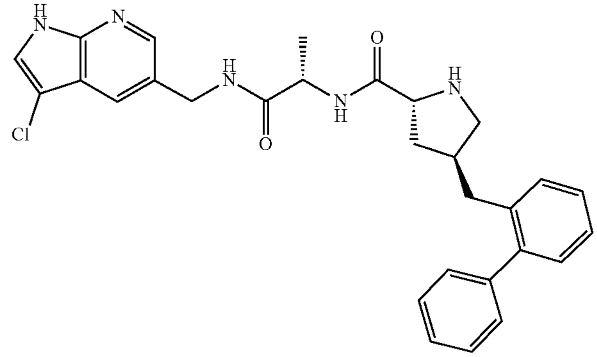 [SMILES: C[C@H](NC(=O)[C@H]1C[C@H](Cc2ccccc2-c2ccccc2)CN1)C(=O)NCc1cnc2[nH]cc(Cl)c2c1] | 2TFA |

TABLE 4A-continued

| Compound No. | Structure | Salt |
|---|---|---|
| 1394 | 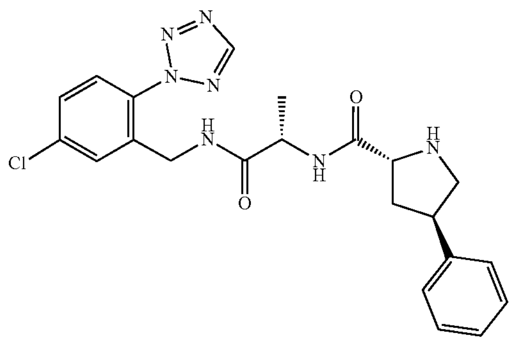 [SMILES: C[C@H](NC(=O)[C@H]1C[C@H](c2ccccc2)CN1)C(=O)NCc1cc(Cl)ccc1-n1ncnn1] | TFA |
| 1395 | 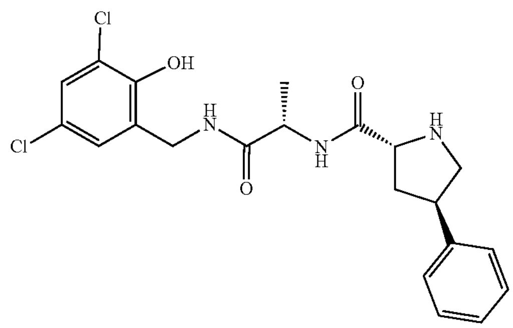 [SMILES: C[C@H](NC(=O)[C@H]1C[C@H](c2ccccc2)CN1)C(=O)NCc1cc(Cl)cc(Cl)c1O] | TFA |
| 1396 | 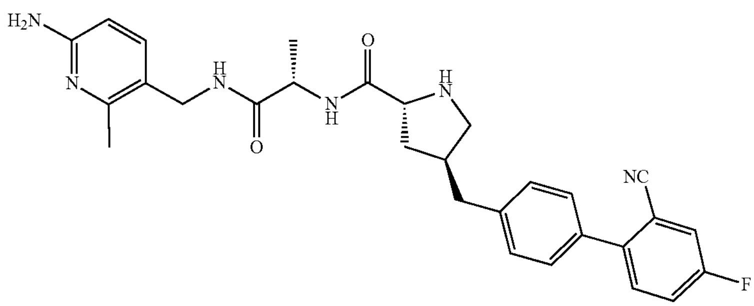 [SMILES: Cc1nc(N)ccc1CNC(=O)[C@H](C)NC(=O)[C@H]1C[C@H](Cc2ccc(-c3ccc(F)cc3C#N)cc2)CN1] | NA |
| 1397 | 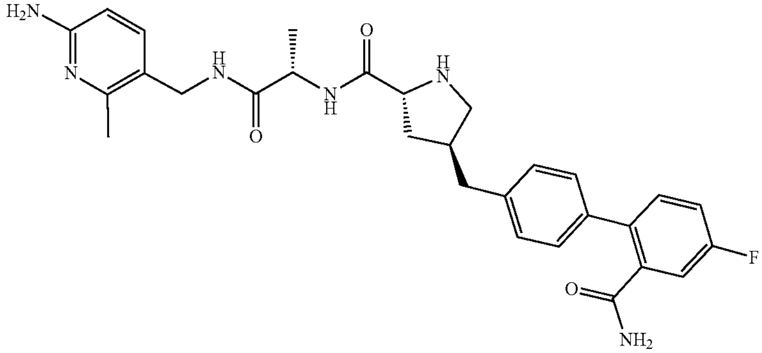 [SMILES: Cc1nc(N)ccc1CNC(=O)[C@H](C)NC(=O)[C@H]1C[C@H](Cc2ccc(-c3ccc(F)cc3C(N)=O)cc2)CN1] | 2TFA |

TABLE 4A-continued

Exemplary compounds

| Compound No. | Structure | Salt |
|---|---|---|
| 1398 | 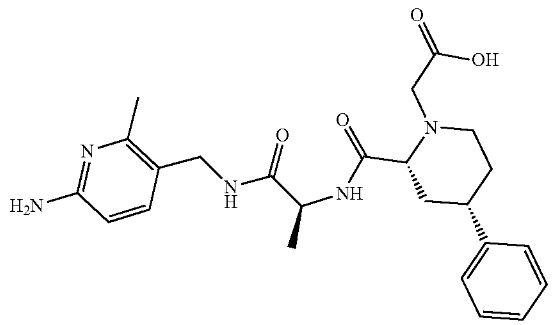 [SMILES: Cc1nc(N)ccc1CNC(=O)[C@H](C)NC(=O)[C@H]1C[C@@H](c2ccccc2)CCN1CC(=O)O] | TFA |
| 1399 | 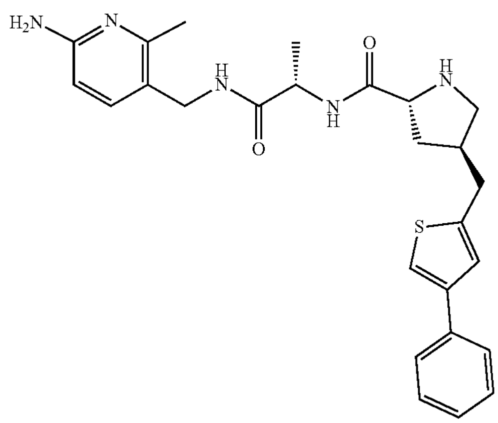 [SMILES: Cc1nc(N)ccc1CNC(=O)[C@H](C)NC(=O)[C@H]1C[C@H](Cc2cc(-c3ccccc3)cs2)CN1] | 2 HCl |
| 1400 | 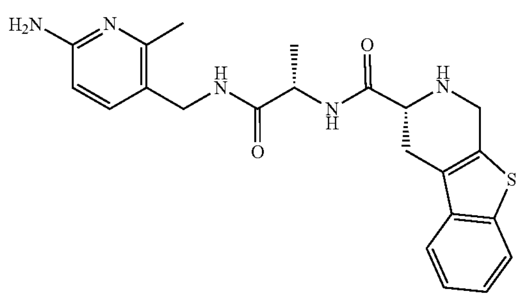 [SMILES: Cc1nc(N)ccc1CNC(=O)[C@H](C)NC(=O)[C@H]1Cc2c(sc3ccccc23)CN1] | 2 HCl |
| 1401 | 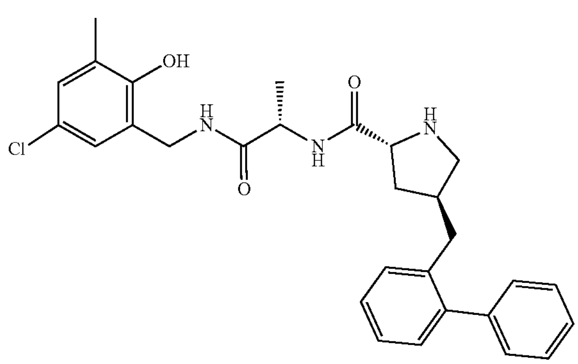 [SMILES: Cc1cc(Cl)cc(CNC(=O)[C@H](C)NC(=O)[C@H]2C[C@H](Cc3ccccc3-c3ccccc3)CN2)c1O] | HCl |

TABLE 4A-continued

Exemplary compounds

| Compound No. | Structure | Salt |
|---|---|---|
| 1402 | 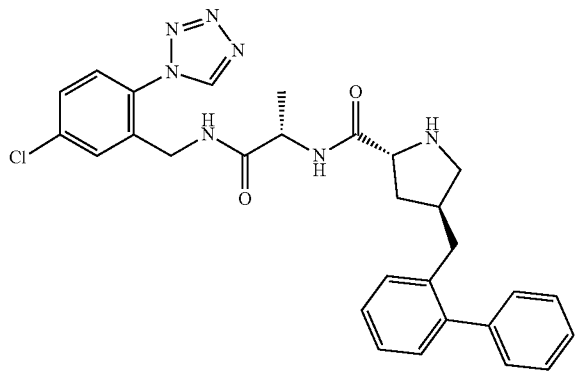 [SMILES: C[C@H](NC(=O)[C@H]1C[C@H](Cc2ccccc2-c2ccccc2)CN1)C(=O)NCc1cc(Cl)ccc1-n1cnnn1] | TFA |
| 1403 | 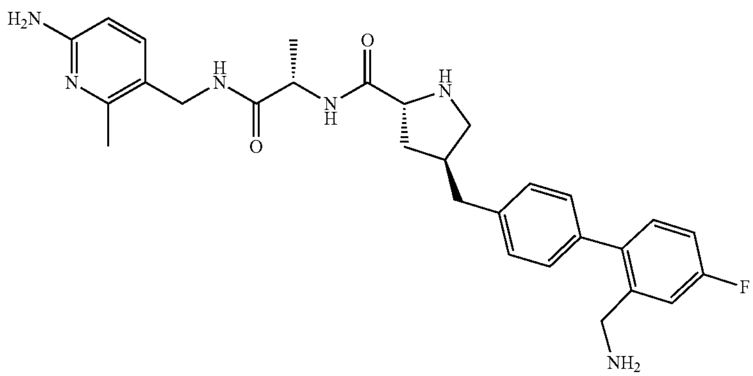 [SMILES: Cc1nc(N)ccc1CNC(=O)[C@H](C)NC(=O)[C@H]1C[C@H](Cc2ccc(-c3ccc(F)cc3CN)cc2)CN1] | NA |
| 1404 | 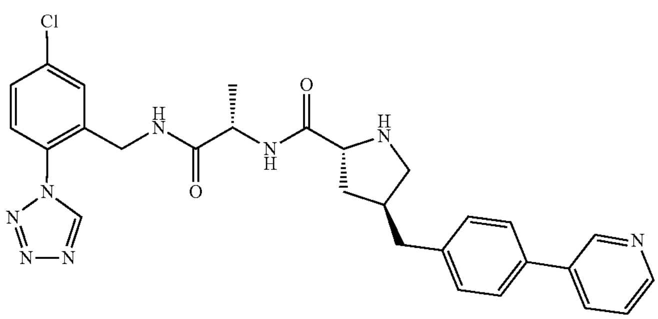 [SMILES: C[C@H](NC(=O)[C@H]1C[C@H](Cc2ccc(-c3cccnc3)cc2)CN1)C(=O)NCc1cc(Cl)ccc1-n1cnnn1] | HCl |
| 1405 | 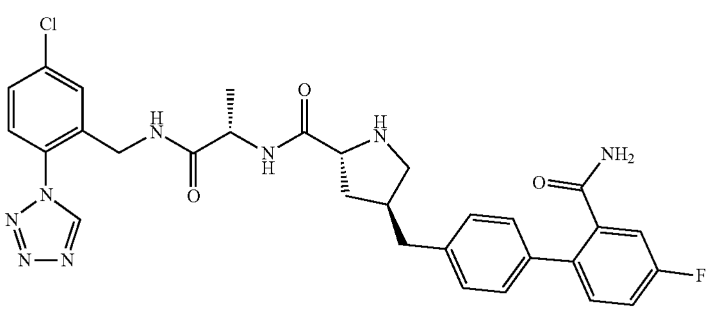 [SMILES: C[C@H](NC(=O)[C@H]1C[C@H](Cc2ccc(-c3ccc(F)cc3C(N)=O)cc2)CN1)C(=O)NCc1cc(Cl)ccc1-n1cnnn1] | HCl |

TABLE 4A-continued

| Compound No. | Structure | Salt |
|---|---|---|
| 1406 | 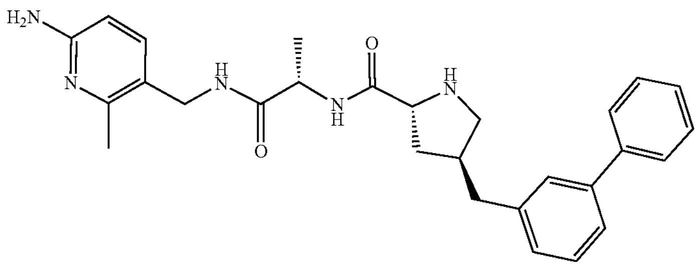 [SMILES: Cc1nc(N)ccc1CNC(=O)[C@H](C)NC(=O)[C@H]1C[C@H](Cc2cccc(-c3ccccc3)c2)CN1] | 2HCl |
| 1407 | 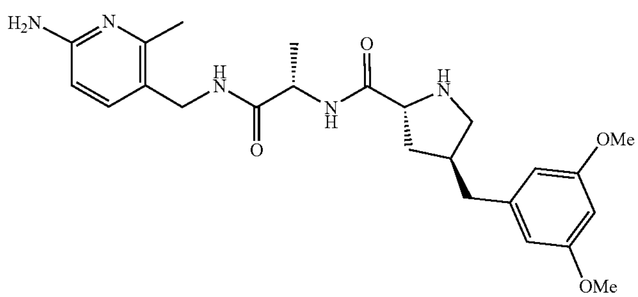 [SMILES: COc1cc(C[C@@H]2CN[C@@H](C(=O)N[C@@H](C)C(=O)NCc3ccc(N)nc3C)C2)cc(OC)c1] | 2TFA |
| 1408 | 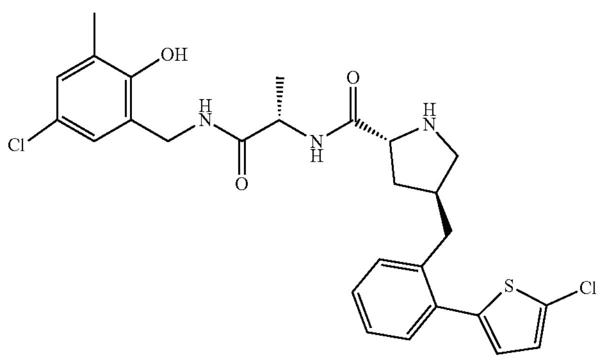 [SMILES: Cc1cc(Cl)cc(CNC(=O)[C@H](C)NC(=O)[C@H]2C[C@H](Cc3ccccc3-c3ccc(Cl)s3)CN2)c1O] | HCl |
| 1409 | 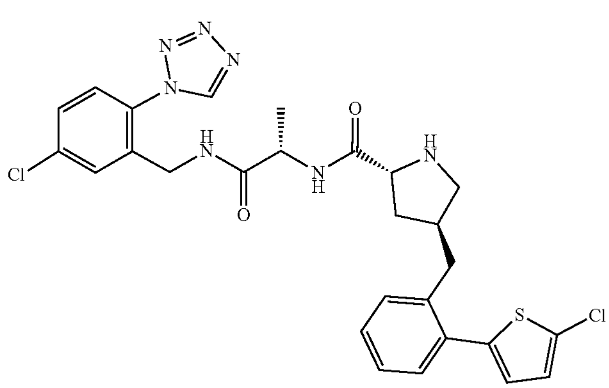 [SMILES: C[C@H](NC(=O)[C@H]1C[C@H](Cc2ccccc2-c2ccc(Cl)s2)CN1)C(=O)NCc1cc(Cl)ccc1-n1cnnn1] | TFA |

TABLE 4A-continued

Exemplary compounds

| Compound No. | Structure | Salt |
|---|---|---|
| 1410 | 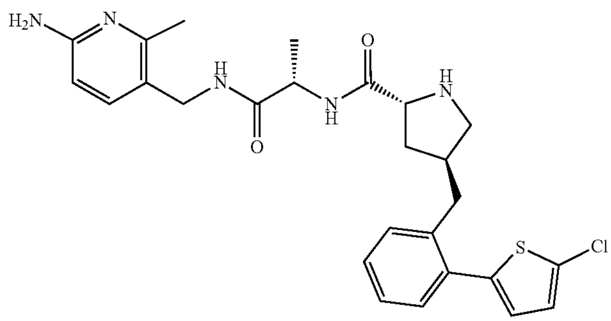 [SMILES: Cc1nc(N)ccc1CNC(=O)[C@H](C)NC(=O)[C@H]1C[C@H](Cc2ccccc2-c2ccc(Cl)s2)CN1] | TFA |
| 1411 | 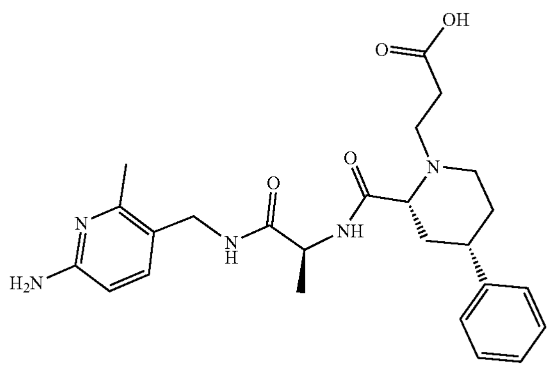 [SMILES: Cc1nc(N)ccc1CNC(=O)[C@H](C)NC(=O)[C@H]1C[C@@H](c2ccccc2)CCN1CCC(=O)O] | TFA |
| 1412 | 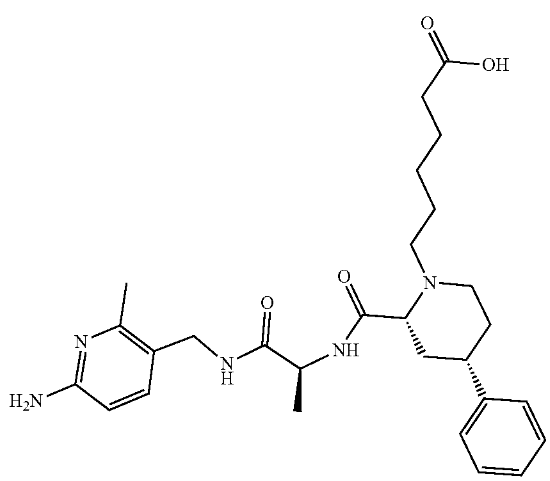 [SMILES: Cc1nc(N)ccc1CNC(=O)[C@H](C)NC(=O)[C@H]1C[C@@H](c2ccccc2)CCN1CCCCCC(=O)O] | TFA |
| 1413 | 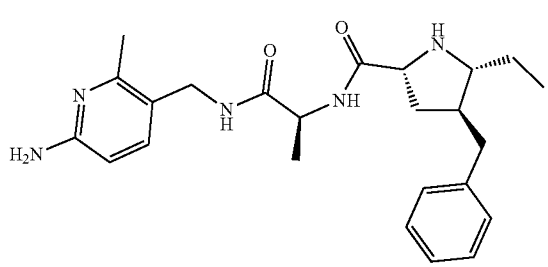 [SMILES: CC[C@H]1N[C@@H](C(=O)N[C@@H](C)C(=O)NCc2ccc(N)nc2C)C[C@@H]1Cc1ccccc1] | 2TFA |

TABLE 4A-continued

Exemplary compounds

| Compound No. | Structure | Salt |
|---|---|---|
| 1414 | 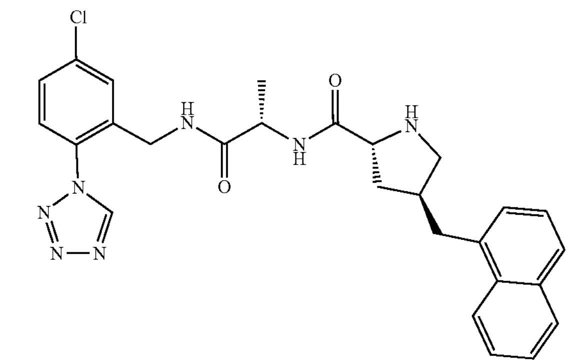 [SMILES: C[C@H](NC(=O)[C@H]1C[C@H](Cc2cccc3ccccc23)CN1)C(=O)NCc1cc(Cl)ccc1-n1cnnn1] | HCl |
| 1415 | 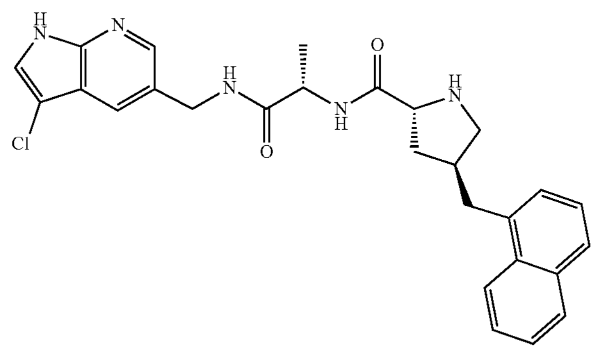 [SMILES: C[C@H](NC(=O)[C@H]1C[C@H](Cc2cccc3ccccc23)CN1)C(=O)NCc1cnc2[nH]cc(Cl)c2c1] | HCl |
| 1416 | 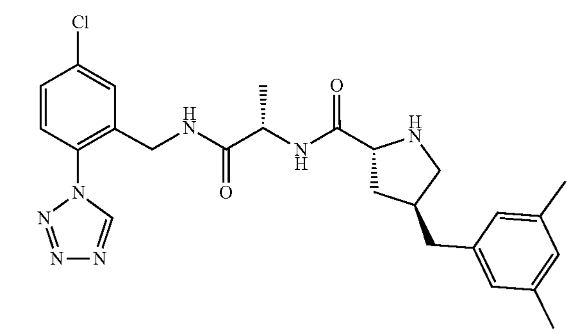 [SMILES: Cc1cc(C)cc(C[C@@H]2CN[C@@H](C(=O)N[C@@H](C)C(=O)NCc3cc(Cl)ccc3-n3cnnn3)C2)c1] | HCl |
| 1417 | 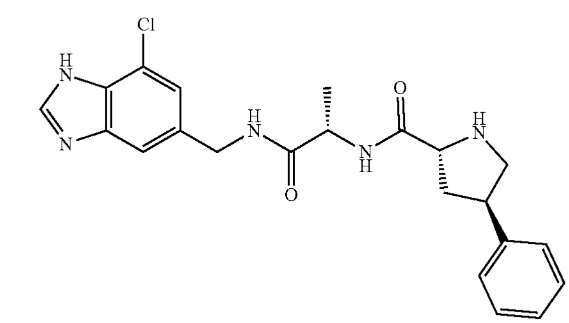 [SMILES: C[C@H](NC(=O)[C@H]1C[C@H](c2ccccc2)CN1)C(=O)NCc1cc(Cl)c2[nH]cnc2c1] | TFA |

TABLE 4A-continued

Exemplary compounds

| Compound No. | Structure | Salt |
|---|---|---|
| 1418 | 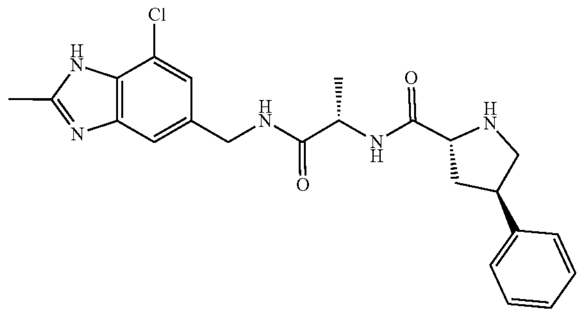 [SMILES: Cc1nc2cc(CNC(=O)[C@H](C)NC(=O)[C@H]3C[C@H](c4ccccc4)CN3)cc(Cl)c2[nH]1] | TFA |
| 1419 | 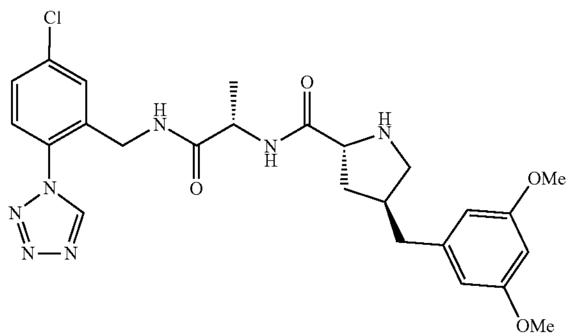 [SMILES: COc1cc(C[C@@H]2CN[C@@H](C(=O)N[C@@H](C)C(=O)NCc3cc(Cl)ccc3-n3cnnn3)C2)cc(OC)c1] | TFA |
| 1420 | 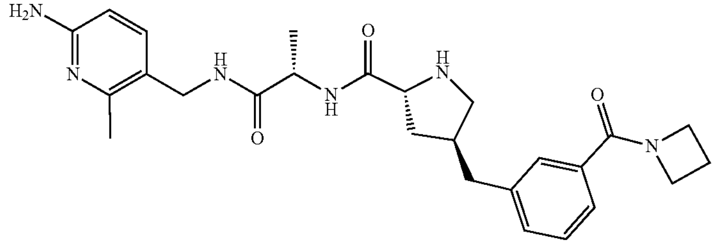 [SMILES: Cc1nc(N)ccc1CNC(=O)[C@H](C)NC(=O)[C@H]1C[C@H](Cc2cccc(C(=O)N3CCC3)c2)CN1] | 2TFA |
| 1421 | 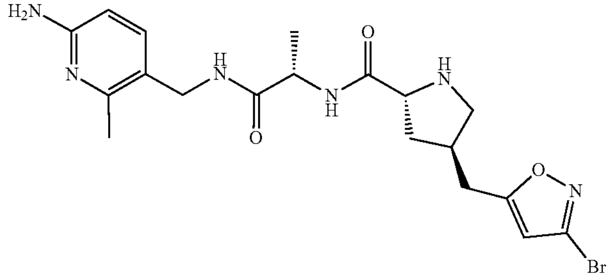 [SMILES: Cc1nc(N)ccc1CNC(=O)[C@H](C)NC(=O)[C@H]1C[C@H](Cc2cc(Br)no2)CN1] | 2TFA |
| 1422 | 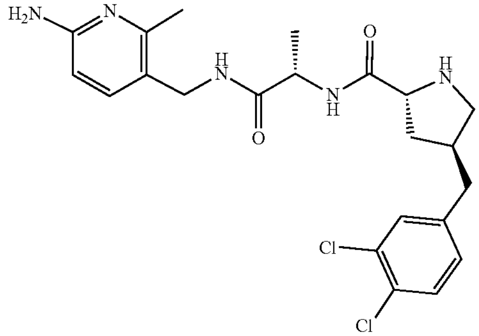 [SMILES: Cc1nc(N)ccc1CNC(=O)[C@H](C)NC(=O)[C@H]1C[C@H](Cc2ccc(Cl)c(Cl)c2)CN1] | HCl |

TABLE 4A-continued

Exemplary compounds

| Compound No. | Structure | Salt |
|---|---|---|
| 1423 | 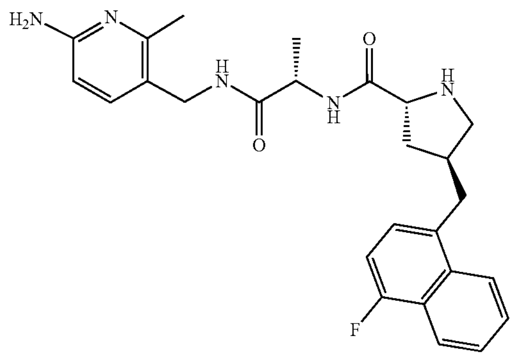 [SMILES: Cc1nc(N)ccc1CNC(=O)[C@H](C)NC(=O)[C@H]1C[C@H](Cc2ccc(F)c3ccccc23)CN1] | HCl |
| 1424 | 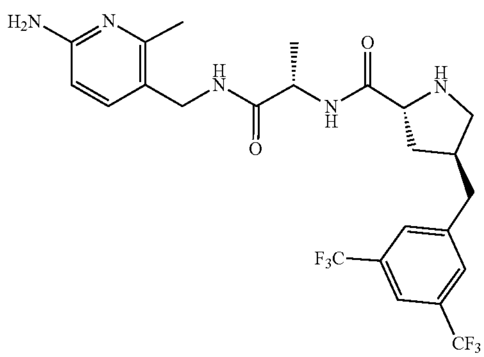 [SMILES: Cc1nc(N)ccc1CNC(=O)[C@H](C)NC(=O)[C@H]1C[C@H](Cc2cc(C(F)(F)F)cc(C(F)(F)F)c2)CN1] | 2TFA |
| 1425 | 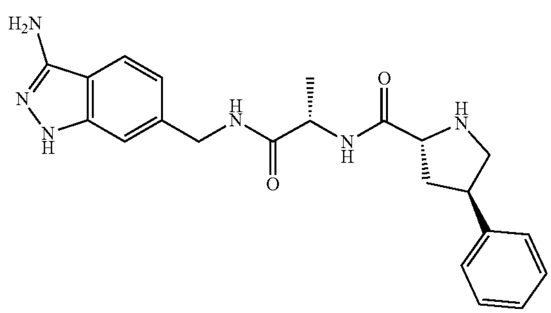 [SMILES: C[C@H](NC(=O)[C@H]1C[C@H](c2ccccc2)CN1)C(=O)NCc1ccc2c(N)n[nH]c2c1] | TFA |
| 1426 | 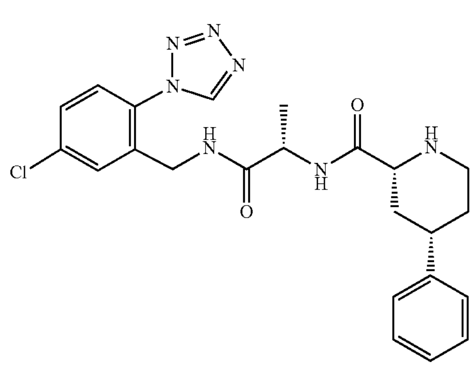 [SMILES: C[C@H](NC(=O)[C@H]1C[C@@H](c2ccccc2)CCN1)C(=O)NCc1cc(Cl)ccc1-n1cnnn1] | TFA |

TABLE 4A-continued

Exemplary compounds

| Compound No. | Structure | Salt |
|---|---|---|
| 1427 | 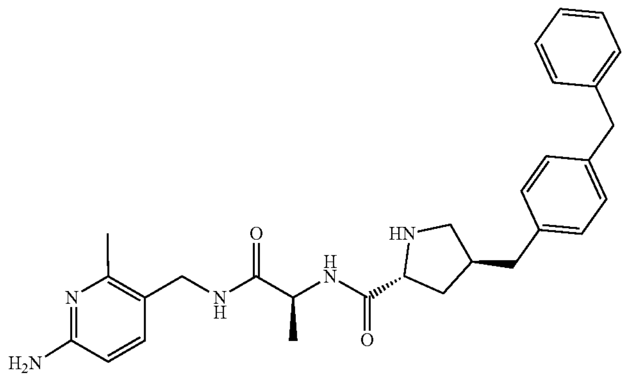 [SMILES: Cc1nc(N)ccc1CNC(=O)[C@H](C)NC(=O)[C@H]1C[C@H](Cc2ccc(Cc3ccccc3)cc2)CN1] | 2TFA |
| 1428 | 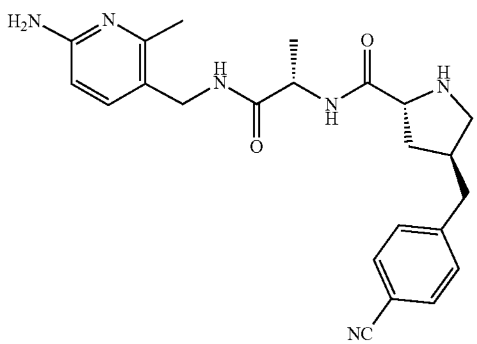 [SMILES: Cc1nc(N)ccc1CNC(=O)[C@H](C)NC(=O)[C@H]1C[C@H](Cc2ccc(C#N)cc2)CN1] | 2TFA |
| 1429 | 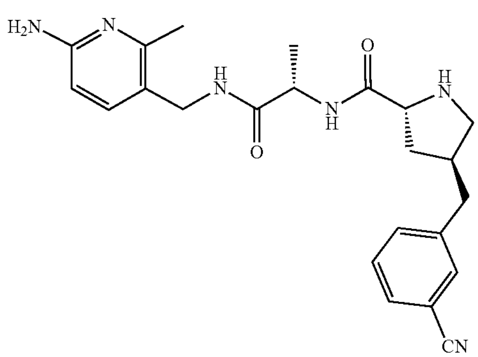 [SMILES: Cc1nc(N)ccc1CNC(=O)[C@H](C)NC(=O)[C@H]1C[C@H](Cc2cccc(C#N)c2)CN1] | 2TFA |
| 1430 | 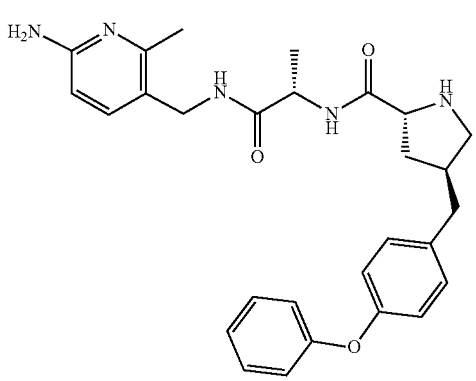 [SMILES: Cc1nc(N)ccc1CNC(=O)[C@H](C)NC(=O)[C@H]1C[C@H](Cc2ccc(Oc3ccccc3)cc2)CN1] | 2TFA |

TABLE 4A-continued

Exemplary compounds

| Compound No. | Structure | Salt |
|---|---|---|
| 1431 | 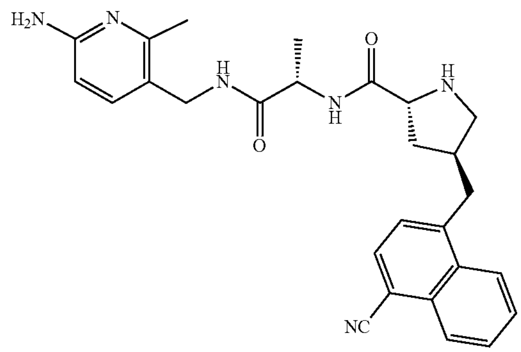 [SMILES: Cc1nc(N)ccc1CNC(=O)[C@H](C)NC(=O)[C@H]1C[C@H](Cc2ccc(C#N)c3ccccc23)CN1] | HCl |
| 1432 | 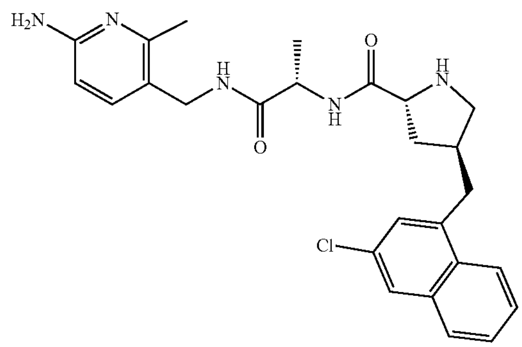 [SMILES: Cc1nc(N)ccc1CNC(=O)[C@H](C)NC(=O)[C@H]1C[C@H](Cc2cc(Cl)cc3ccccc23)CN1] | HCl |
| 1433 | 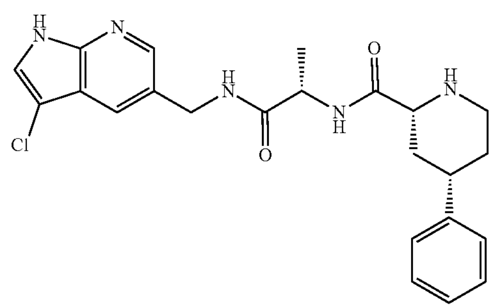 [SMILES: C[C@H](NC(=O)[C@H]1C[C@@H](c2ccccc2)CCN1)C(=O)NCc1cnc2[nH]cc(Cl)c2c1] | TFA |
| 1434 | 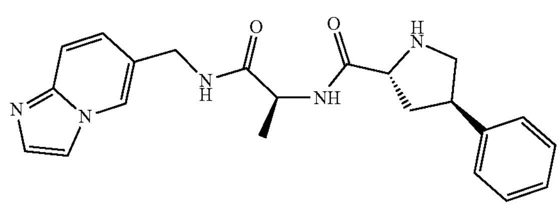 [SMILES: C[C@H](NC(=O)[C@H]1C[C@H](c2ccccc2)CN1)C(=O)NCc1ccc2nccn2c1] | 2HCl |
| 1435 | 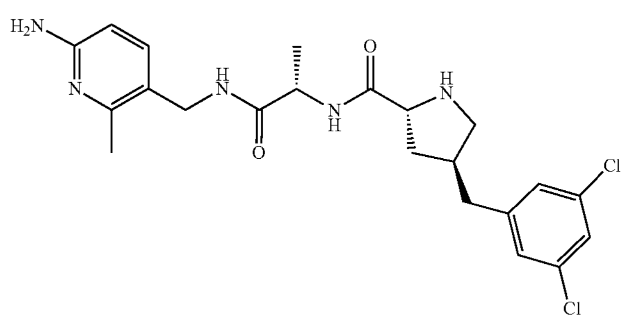 [SMILES: Cc1nc(N)ccc1CNC(=O)[C@H](C)NC(=O)[C@H]1C[C@H](Cc2cc(Cl)cc(Cl)c2)CN1] | 2HCl |

TABLE 4A-continued

Exemplary compounds

| Compound No. | Structure | Salt |
|---|---|---|
| 1436 | 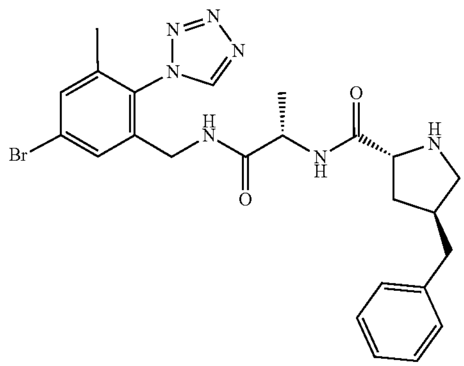 [SMILES: Cc1cc(Br)cc(CNC(=O)[C@H](C)NC(=O)[C@H]2C[C@H](Cc3ccccc3)CN2)c1-n1cnnn1] | TFA |
| 1437 | 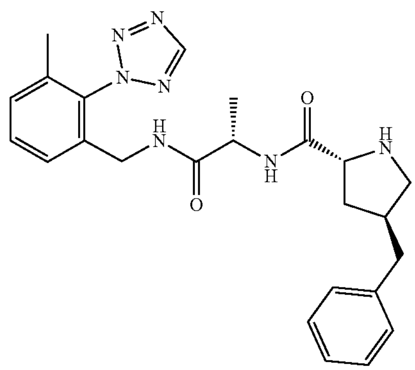 [SMILES: Cc1cccc(CNC(=O)[C@H](C)NC(=O)[C@H]2C[C@H](Cc3ccccc3)CN2)c1-n1ncnn1] | TFA |
| 1438 | 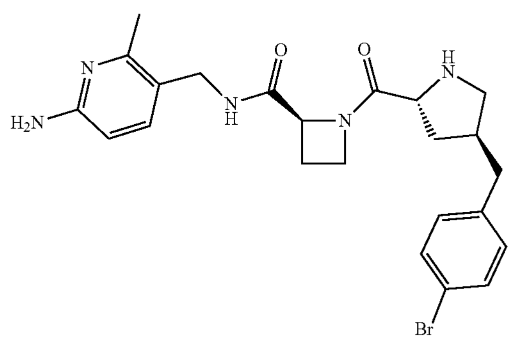 [SMILES: Cc1nc(N)ccc1CNC(=O)[C@@H]1CCN1C(=O)[C@H]1C[C@H](Cc2ccc(Br)cc2)CN1] | 2TFA |
| 1439 | 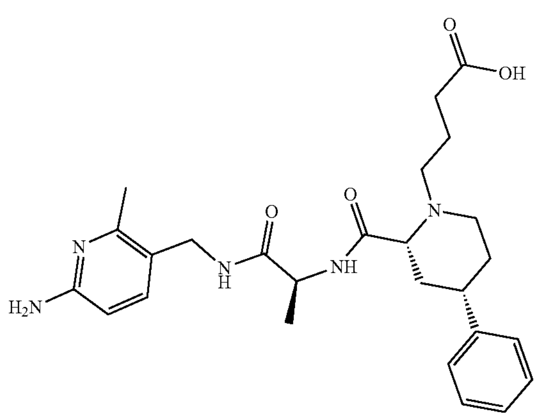 [SMILES: Cc1nc(N)ccc1CNC(=O)[C@H](C)NC(=O)[C@H]1C[C@@H](c2ccccc2)CCN1CCCC(=O)O] | TFA |

TABLE 4A-continued
Exemplary compounds
| Compound No. | Structure | Salt |
|---|---|---|
| 1440 | 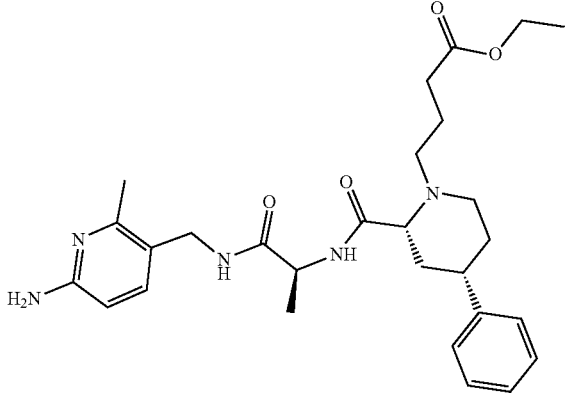 [SMILES: CCOC(=O)CCCN1CC[C@H](c2ccccc2)C[C@@H]1C(=O)N[C@@H](C)C(=O)NCc1ccc(N)nc1C] | NA |
| 1441 | 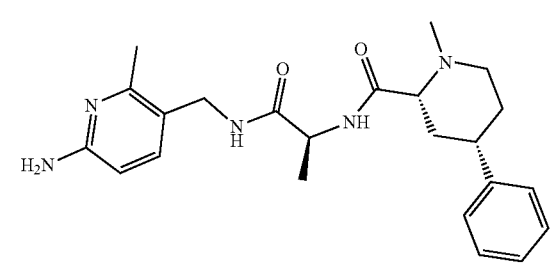 [SMILES: Cc1nc(N)ccc1CNC(=O)[C@H](C)NC(=O)[C@H]1C[C@@H](c2ccccc2)CCN1C] | NA |
| 1442 | 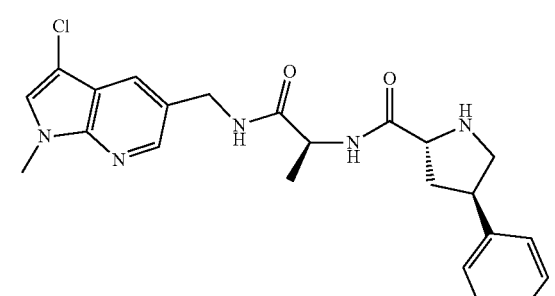 | 2HCl |
| 1443 | 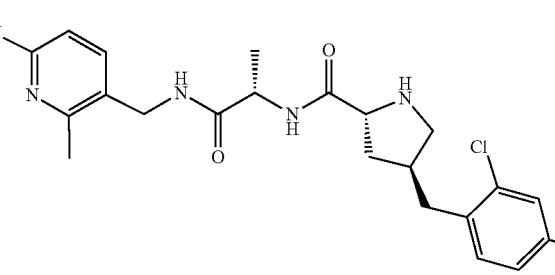 | 2HCl |
| 1444 | 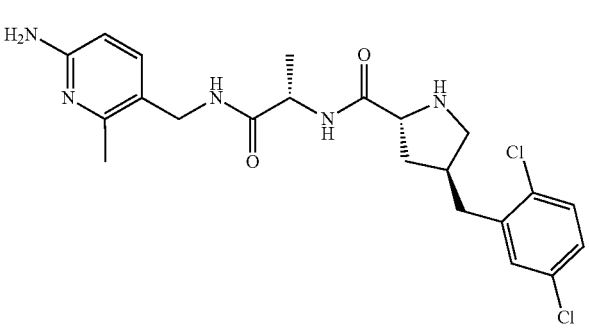 [SMILES: Cc1nc(N)ccc1CNC(=O)[C@H](C)NC(=O)[C@H]1C[C@H](Cc2cc(Cl)ccc2Cl)CN1] | 2HCl |

TABLE 4A-continued

| Compound No. | Structure | Salt |
|---|---|---|
| 1445 | 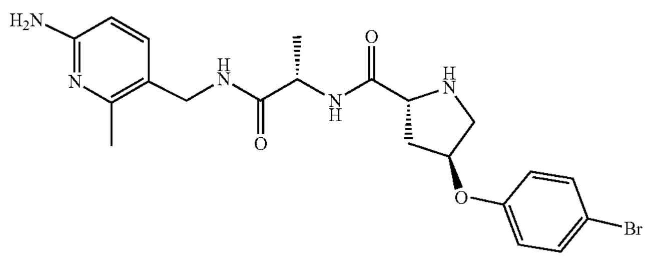 [SMILES: Cc1nc(N)ccc1CNC(=O)[C@H](C)NC(=O)[C@H]1C[C@H](Oc2ccc(Br)cc2)CN1] | 2HCl |
| 1446 | 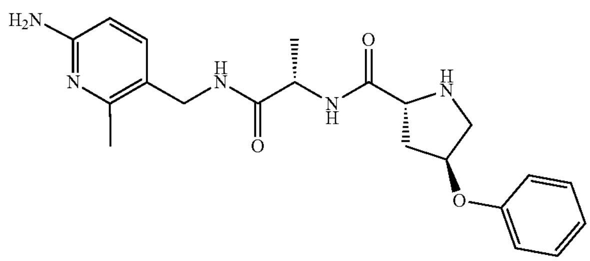 [SMILES: Cc1nc(N)ccc1CNC(=O)[C@H](C)NC(=O)[C@H]1C[C@H](Oc2ccccc2)CN1] | 2HCl |
| 1447 | 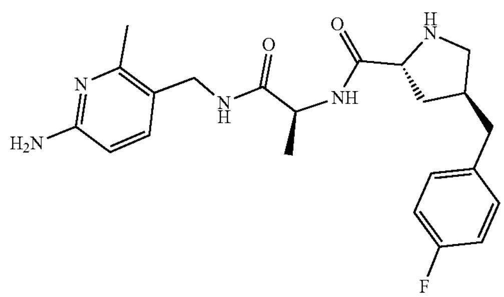 [SMILES: Cc1nc(N)ccc1CNC(=O)[C@H](C)NC(=O)[C@H]1C[C@H](Cc2ccc(F)cc2)CN1] | 2TFA |
| 1448 | 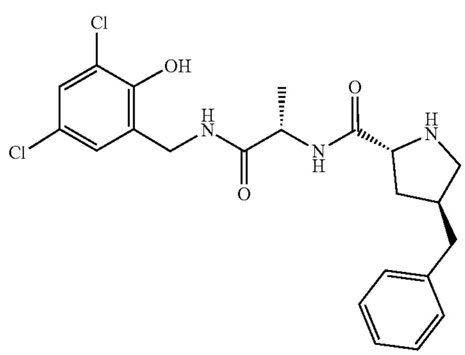 [SMILES: C[C@H](NC(=O)[C@H]1C[C@H](Cc2ccccc2)CN1)C(=O)NCc1cc(Cl)cc(Cl)c1O] | HCl |
| 1449 | 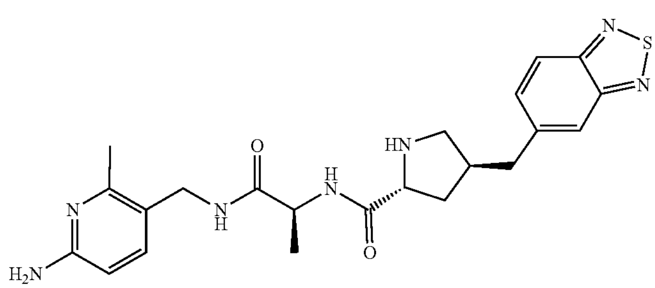 [SMILES: Cc1nc(N)ccc1CNC(=O)[C@H](C)NC(=O)[C@H]1C[C@H](Cc2ccc3nsnc3c2)CN1] | 2TFA |

TABLE 4A-continued

| Exemplary compounds | | |
|---|---|---|
| Compound No. | Structure | Salt |
| 1450 | | 2HCl |
| 1451 | | 2TFA |
| 1452 | | 2HCl |
| 1453 | | HCl |

TABLE 4A-continued

Exemplary compounds

| Compound No. | Structure | Salt |
|---|---|---|
| 1454 | 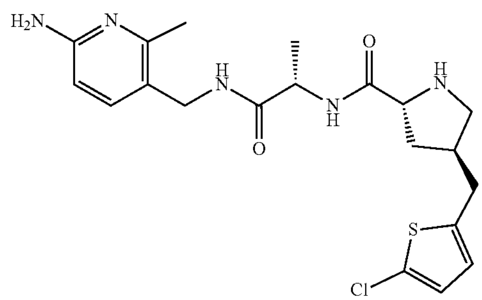 [SMILES: Cc1nc(N)ccc1CNC(=O)[C@H](C)NC(=O)[C@H]1C[C@H](Cc2ccc(Cl)s2)CN1] | HCl |
| 1455 | 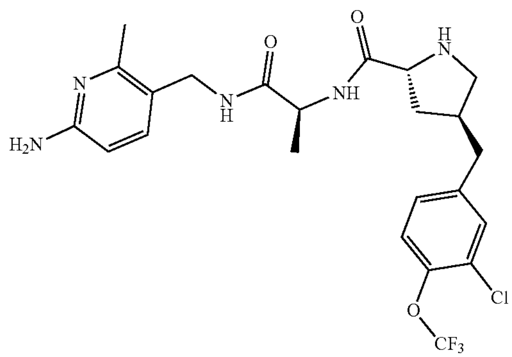 [SMILES: Cc1nc(N)ccc1CNC(=O)[C@H](C)NC(=O)[C@H]1C[C@H](Cc2ccc(OC(F)(F)F)c(Cl)c2)CN1] | 2TFA |
| 1456 | 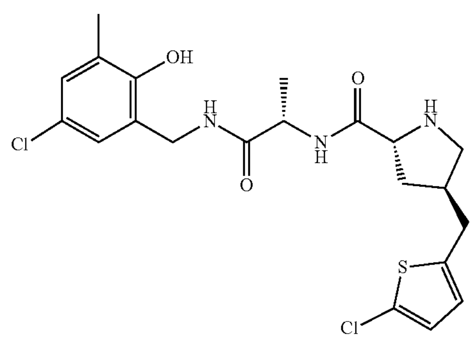 [SMILES: Cc1cc(Cl)cc(CNC(=O)[C@H](C)NC(=O)[C@H]2C[C@H](Cc3ccc(Cl)s3)CN2)c1O] | HCl |
| 1457 | 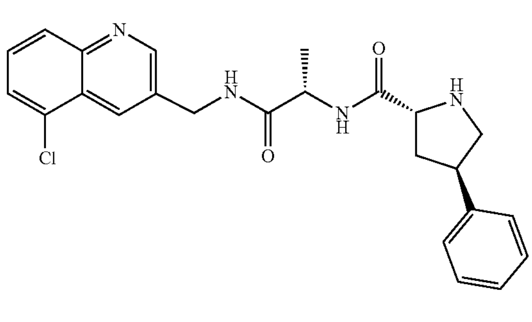 [SMILES: C[C@H](NC(=O)[C@H]1C[C@H](c2ccccc2)CN1)C(=O)NCc1cnc2cccc(Cl)c2c1] | HCl |

TABLE 4A-continued

Exemplary compounds

| Compound No. | Structure | Salt |
|---|---|---|
| 1458 | 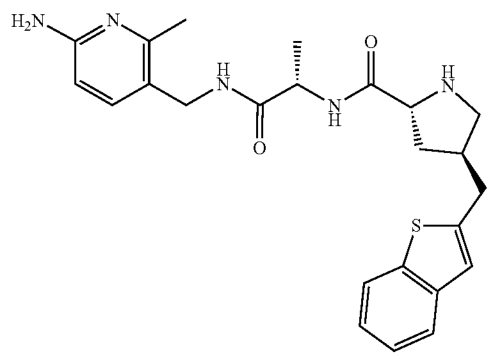 [SMILES: Cc1nc(N)ccc1CNC(=O)[C@H](C)NC(=O)[C@H]1C[C@H](Cc2cc3ccccc3s2)CN1] | 2TFA |
| 1459 | 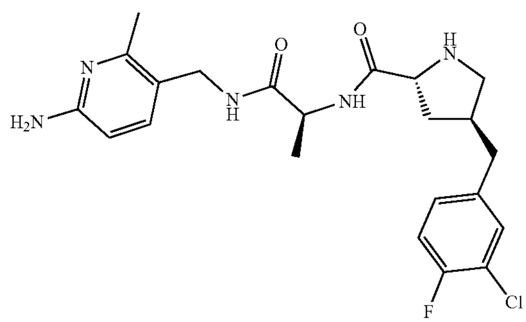 [SMILES: Cc1nc(N)ccc1CNC(=O)[C@H](C)NC(=O)[C@H]1C[C@H](Cc2ccc(F)c(Cl)c2)CN1] | 2TFA |
| 1460 | 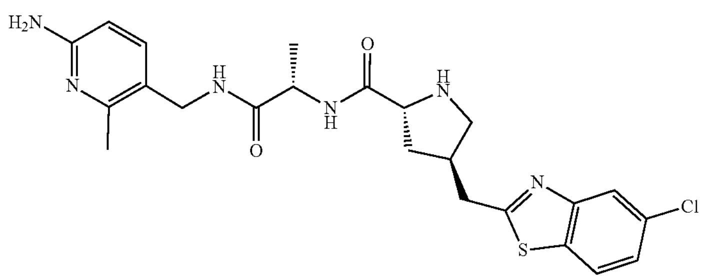 [SMILES: Cc1nc(N)ccc1CNC(=O)[C@H](C)NC(=O)[C@H]1C[C@H](Cc2nc3cc(Cl)ccc3s2)CN1] | 2TFA |
| 1461 | 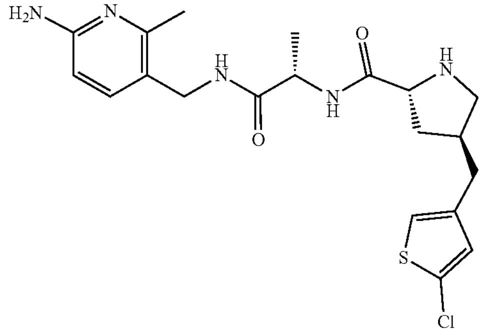 [SMILES: Cc1nc(N)ccc1CNC(=O)[C@H](C)NC(=O)[C@H]1C[C@H](Cc2csc(Cl)c2)CN1] | HCl |

TABLE 4A-continued

Exemplary compounds

| Compound No. | Structure | Salt |
|---|---|---|
| 1462 | 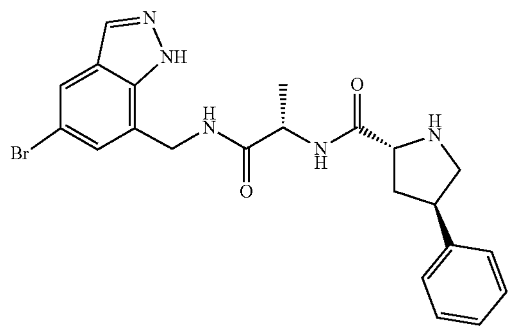 [SMILES: C[C@H](NC(=O)[C@H]1C[C@H](c2ccccc2)CN1)C(=O)NCc1cc(Br)cc2cn[nH]c12] | TFA |
| 1463 | 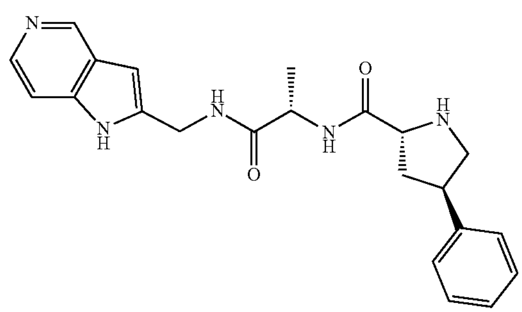 [SMILES: C[C@H](NC(=O)[C@H]1C[C@H](c2ccccc2)CN1)C(=O)NCc1cc2cnccc2[nH]1] | 2TFA |
| 1464 | 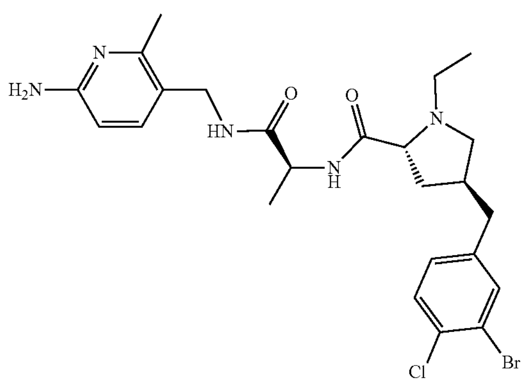 [SMILES: CCN1C[C@@H](Cc2ccc(Cl)c(Br)c2)C[C@@H]1C(=O)N[C@@H](C)C(=O)NCc1ccc(N)nc1C] | NA |
| 1465 | 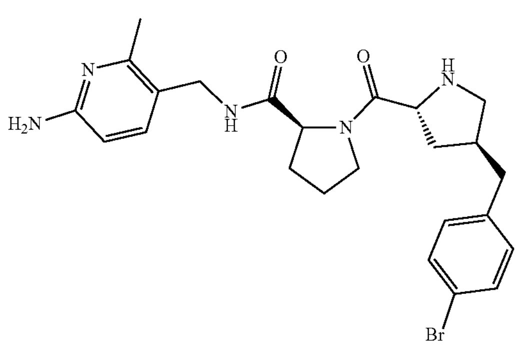 [SMILES: Cc1nc(N)ccc1CNC(=O)[C@@H]1CCCN1C(=O)[C@H]1C[C@H](Cc2ccc(Br)cc2)CN1] | 2TFA |

TABLE 4A-continued

Exemplary compounds

| Compound No. | Structure | Salt |
|---|---|---|
| 1466 | 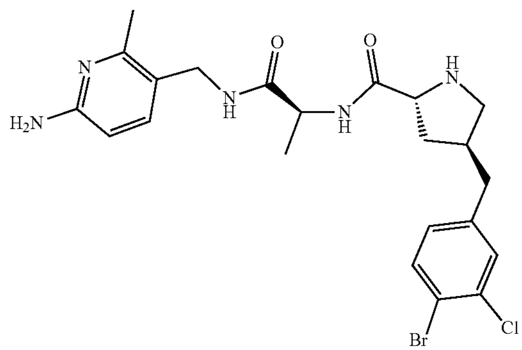 [SMILES: Cc1nc(N)ccc1CNC(=O)[C@H](C)NC(=O)[C@H]1C[C@H](Cc2ccc(Br)c(Cl)c2)CN1] | 2TFA |
| 1467 | 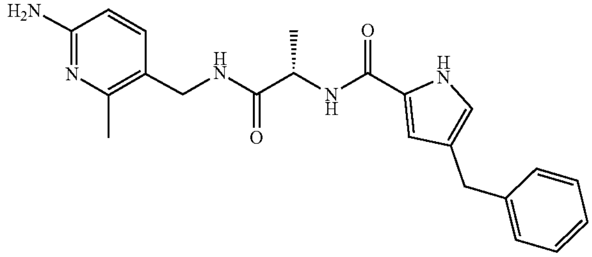 [SMILES: Cc1nc(N)ccc1CNC(=O)[C@H](C)NC(=O)c1cc(Cc2ccccc2)c[nH]1] | TFA |
| 1468 | 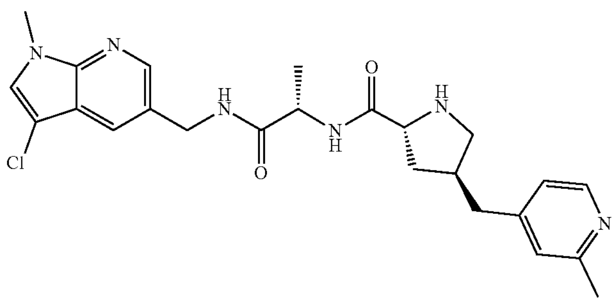 [SMILES: Cc1cc(C[C@@H]2CN[C@@H](C(=O)N[C@@H](C)C(=O)NCc3cnc4c(c3)c(Cl)cn4C)C2)ccn1] | TFA |
| 1469 | 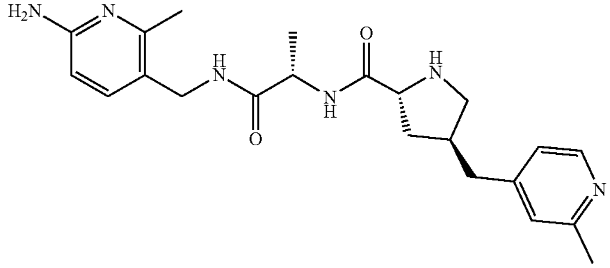 [SMILES: Cc1cc(C[C@@H]2CN[C@@H](C(=O)N[C@@H](C)C(=O)NCc3ccc(N)nc3C)C2)ccn1] | HCl |
| 1470 | 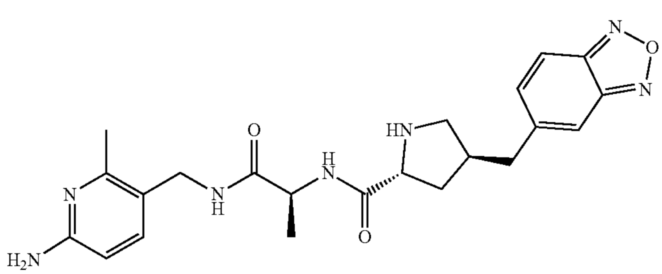 [SMILES: Cc1nc(N)ccc1CNC(=O)[C@H](C)NC(=O)[C@H]1C[C@H](Cc2ccc3nonc3c2)CN1] | 2TFA |

TABLE 4A-continued
| Exemplary compounds | | |
|---|---|---|
| Compound No. | Structure | Salt |
| 1471 | 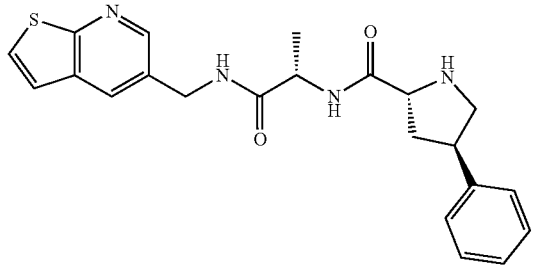 [SMILES: C[C@H](NC(=O)[C@H]1C[C@H](c2ccccc2)CN1)C(=O)NCc1cnc2sccc2c1] | 1TFA |
| 1472 | 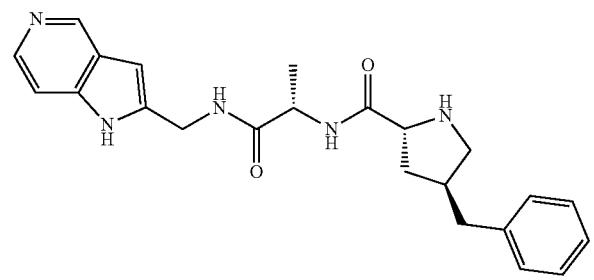 [SMILES: C[C@H](NC(=O)[C@H]1C[C@H](Cc2ccccc2)CN1)C(=O)NCc1cc2cnccc2[nH]1] | 2TFA |
| 1473 | 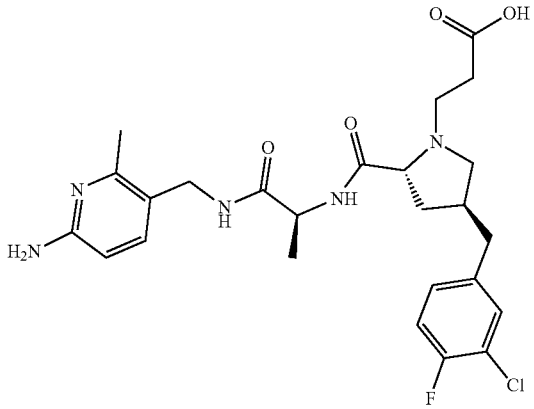 [SMILES: Cc1nc(N)ccc1CNC(=O)[C@H](C)NC(=O)[C@H]1C[C@H](Cc2ccc(F)c(Cl)c2)CN1CCC(=O)O] | 1TFA |
| 1474 | 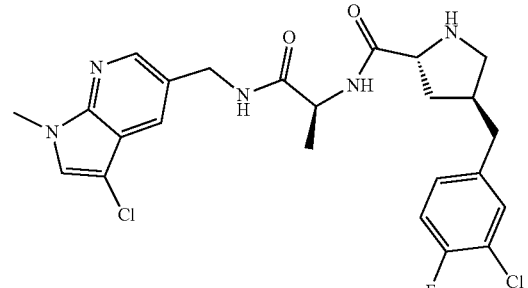 | TFA |

TABLE 4A-continued

| Exemplary compounds | | |
|---|---|---|
| Compound No. | Structure | Salt |
| 1475 | | 2TFA |
| 1476 | | HCl |
| 1477 | | TFA |
| 1478 | | HCl |

TABLE 4A-continued

Exemplary compounds

| Compound No. | Structure | Salt |
|---|---|---|
| 1479 | 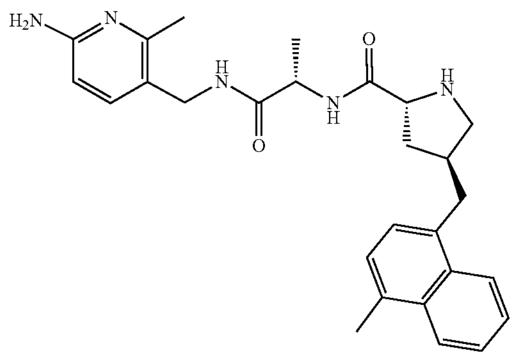 [SMILES: Cc1nc(N)ccc1CNC(=O)[C@H](C)NC(=O)[C@H]1C[C@H](Cc2ccc(C)c3ccccc23)CN1] | HCl |
| 1480 | 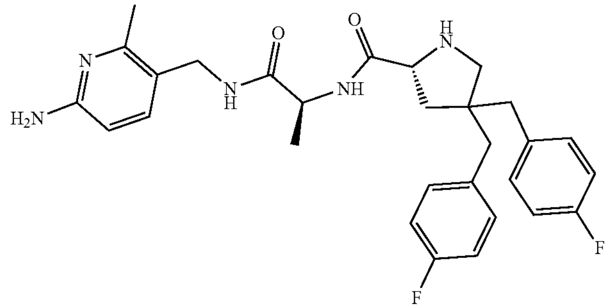 [SMILES: Cc1nc(N)ccc1CNC(=O)[C@H](C)NC(=O)[C@H]1CC(Cc2ccc(F)cc2)(Cc2ccc(F)cc2)CN1] | 2TFA |
| 1481 | 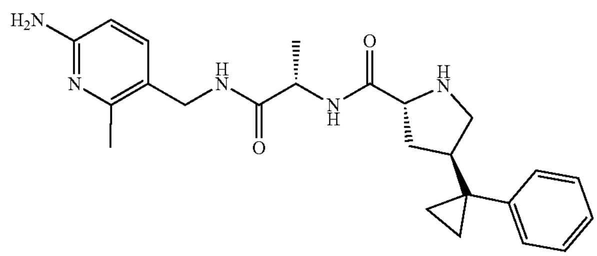 [SMILES: Cc1nc(N)ccc1CNC(=O)[C@H](C)NC(=O)[C@H]1C[C@H](C2(c3ccccc3)CC2)CN1] | 2TFA |
| 1482 | 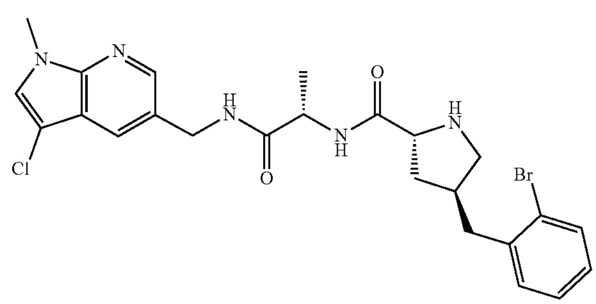 [SMILES: C[C@H](NC(=O)[C@H]1C[C@H](Cc2ccccc2Br)CN1)C(=O)NCc1cnc2c(c1)c(Cl)cn2C] | HCl |
| 1483 | 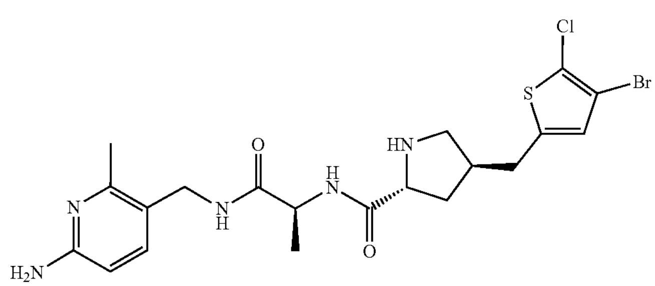 [SMILES: Cc1nc(N)ccc1CNC(=O)[C@H](C)NC(=O)[C@H]1C[C@H](Cc2cc(Br)c(Cl)s2)CN1] | 2TFA |

TABLE 4A-continued

Exemplary compounds

| Compound No. | Structure | Salt |
|---|---|---|
| 1484 | 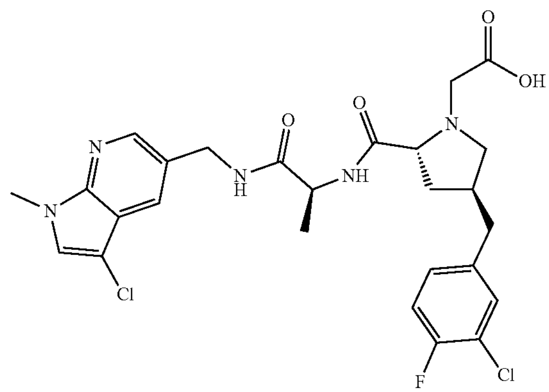 [SMILES: C[C@H](NC(=O)[C@H]1C[C@H](Cc2ccc(F)c(Cl)c2)CN1CC(=O)O)C(=O)NCc1cnc2c(c1)c(Cl)cn2C] | 1TFA |
| 1485 | 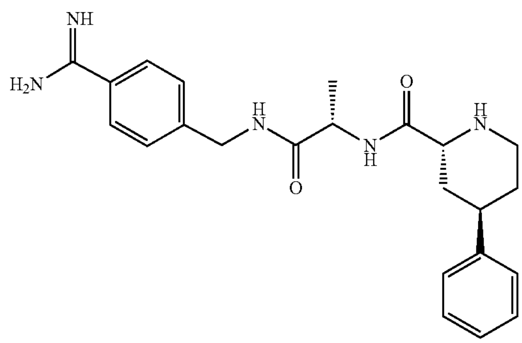 [SMILES: C[C@H](NC(=O)[C@H]1C[C@H](c2ccccc2)CCN1)C(=O)NCc1ccc(C(=N)N)cc1] | 2 HCl |
| 1486 | 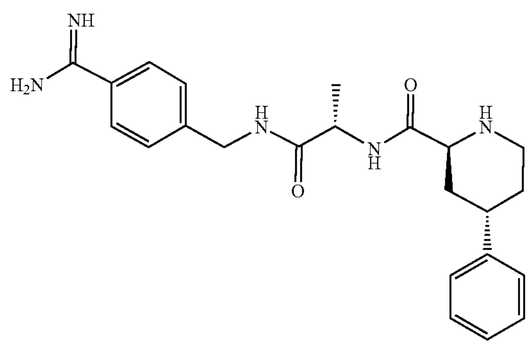 [SMILES: C[C@H](NC(=O)[C@@H]1C[C@@H](c2ccccc2)CCN1)C(=O)NCc1ccc(C(=N)N)cc1] | 2 HCl |
| 1487 | 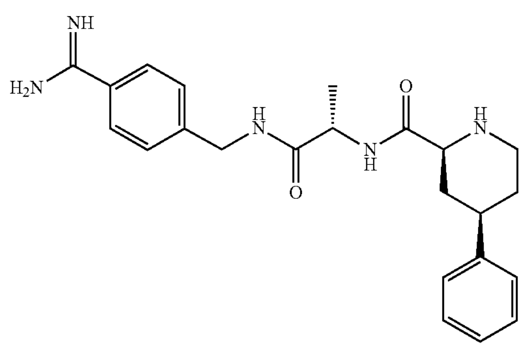 [SMILES: C[C@H](NC(=O)[C@@H]1C[C@H](c2ccccc2)CCN1)C(=O)NCc1ccc(C(=N)N)cc1] | 2HCl |

TABLE 4A-continued

Exemplary compounds

| Compound No. | Structure | Salt |
|---|---|---|
| 1488 | 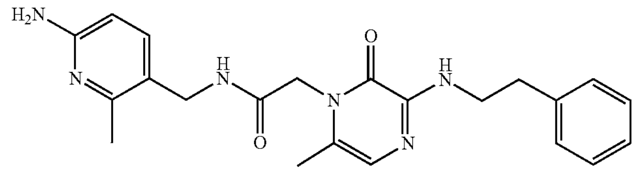 [SMILES: Cc1nc(N)ccc1CNC(=O)Cn1c(C)cnc(NCCc2ccccc2)c1=O] | NA |
| 1489 | 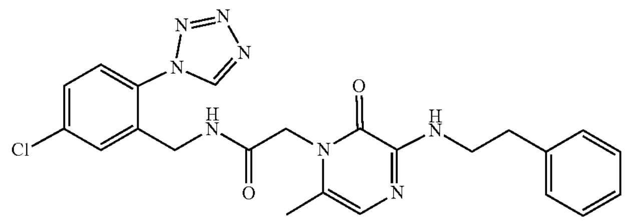 [SMILES: Cc1cnc(NCCc2ccccc2)c(=O)n1CC(=O)NCc1cc(Cl)ccc1-n1cnnn1] | NA |
| 1490 | 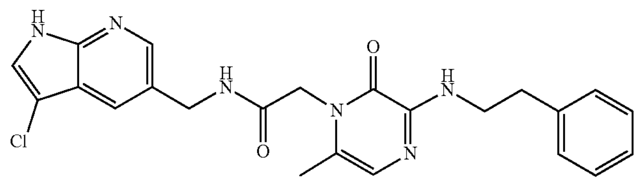 [SMILES: Cc1cnc(NCCc2ccccc2)c(=O)n1CC(=O)NCc1cnc2[nH]cc(Cl)c2c1] | AcOH |
| 1491 | 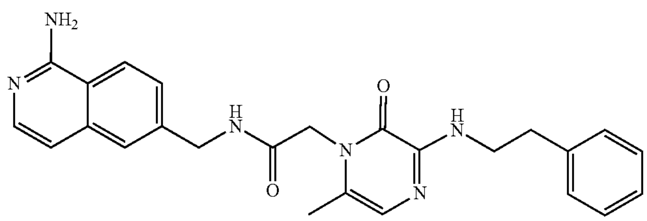 [SMILES: Cc1cnc(NCCc2ccccc2)c(=O)n1CC(=O)NCc1ccc2c(N)nccc2c1] | TFA |
| 1492 | 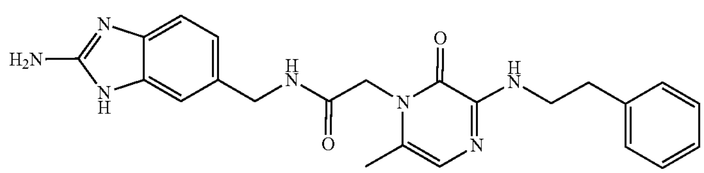 [SMILES: Cc1cnc(NCCc2ccccc2)c(=O)n1CC(=O)NCc1ccc2nc(N)[nH]c2c1] | TFA |
| 1493 | 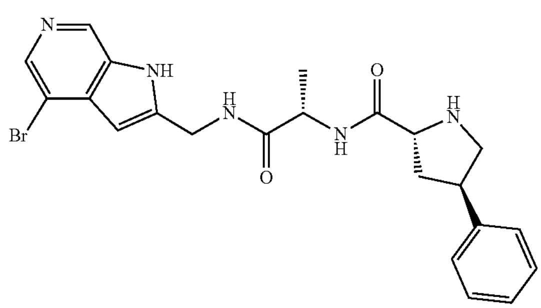 [SMILES: C[C@H](NC(=O)[C@H]1C[C@H](c2ccccc2)CN1)C(=O)NCc1cc2c(Br)cncc2[nH]1] | 2TFA |
| 1494 | 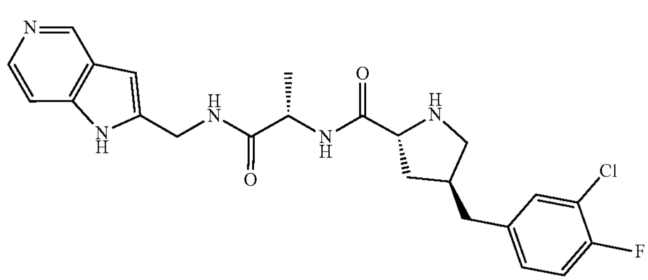 [SMILES: C[C@H](NC(=O)[C@H]1C[C@H](Cc2ccc(F)c(Cl)c2)CN1)C(=O)NCc1cc2cnccc2[nH]1] | 2TFA |

TABLE 4A-continued

| Compound No. | Structure | Salt |
|---|---|---|
| 1495 | 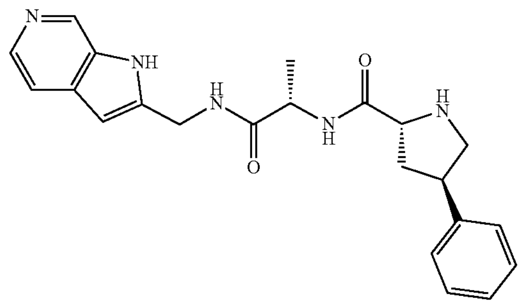 [SMILES: C[C@H](NC(=O)[C@H]1C[C@H](c2ccccc2)CN1)C(=O)NCc1cc2ccncc2[nH]1] | 2TFA |
| 1496 | 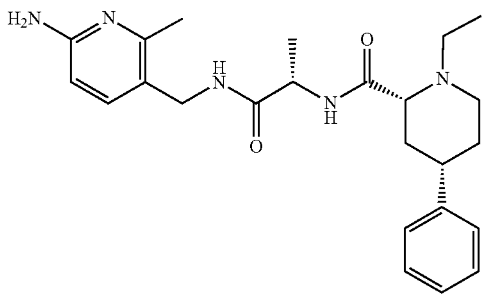 [SMILES: CCN1CC[C@H](c2ccccc2)C[C@@H]1C(=O)N[C@@H](C)C(=O)NCc1ccc(N)nc1C] | NA |
| 1497 | 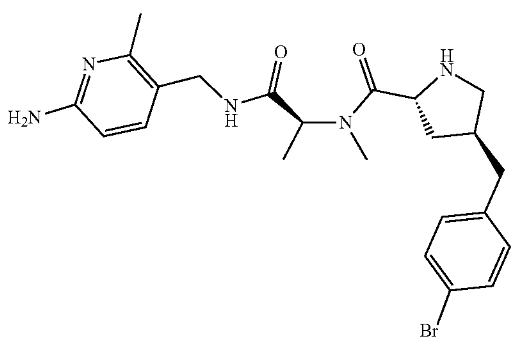 [SMILES: Cc1nc(N)ccc1CNC(=O)[C@H](C)N(C)C(=O)[C@H]1C[C@H](Cc2ccc(Br)cc2)CN1] | 2TFA |
| 2000 | 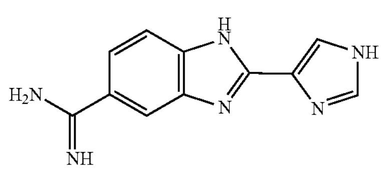 [SMILES: N=C(N)c1ccc2[nH]c(-c3c[nH]cn3)nc2c1] | 2 HCl |
| 2001 | 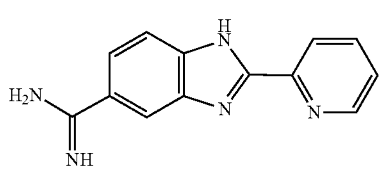 [SMILES: N=C(N)c1ccc2[nH]c(-c3ccccn3)nc2c1] | 2 HCl |
| 2002 | 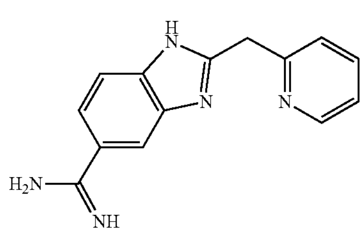 [SMILES: N=C(N)c1ccc2[nH]c(Cc3ccccn3)nc2c1] | 2 HCl |

TABLE 4A-continued
| Compound No. | Structure | Salt |
|---|---|---|
| 2003 | 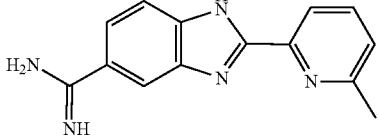 | 2 HCl |
| 2004 | 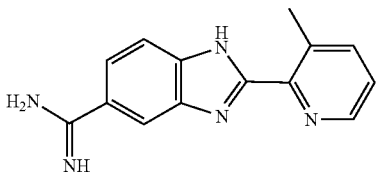 [SMILES: Cc1cccnc1-c1nc2cc(C(=N)N)ccc2[nH]1] | 2 HCl |
| 2005 | 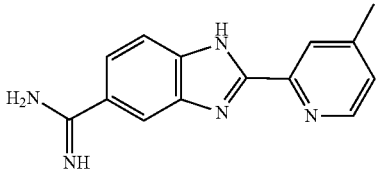 [SMILES: Cc1ccnc(-c2nc3cc(C(=N)N)ccc3[nH]2)c1] | 2 HCl |
| 2006 | 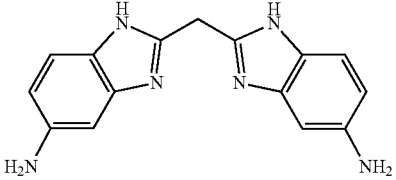 [SMILES: Nc1ccc2[nH]c(Cc3nc4cc(N)ccc4[nH]3)nc2c1] | |
| 2007 | 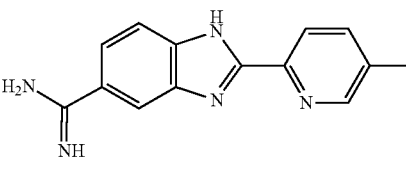 | 2 HCl |
| 2008 | 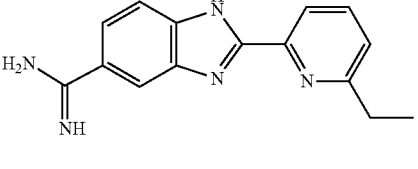 | 2 HCl |
| 2009 | 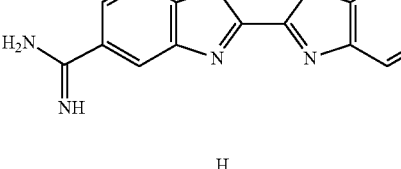 | 2 HCl |
| 2010 | 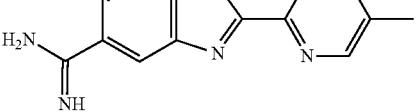 | 2 HCl |

TABLE 4A-continued

| Compound No. | Structure | Salt |
|---|---|---|
| 2011 | 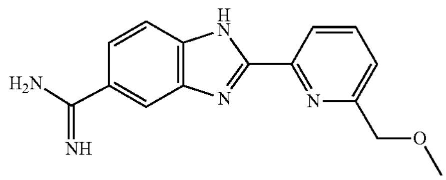 [SMILES: COCc1cccc(-c2nc3cc(C(=N)N)ccc3[nH]2)n1] | 2 HCl |
| 2012 | 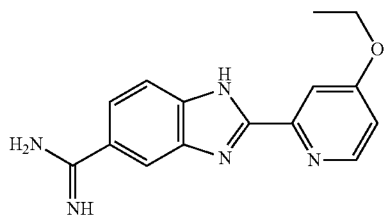 [SMILES: CCOc1ccnc(-c2nc3cc(C(=N)N)ccc3[nH]2)c1] | 2 HCl |
| 2013 | 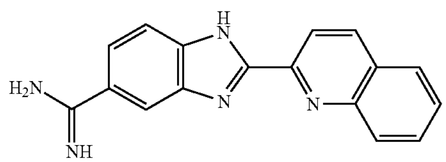 [SMILES: N=C(N)c1ccc2[nH]c(-c3ccc4ccccc4n3)nc2c1] | 2 HCl |
| 2014 | 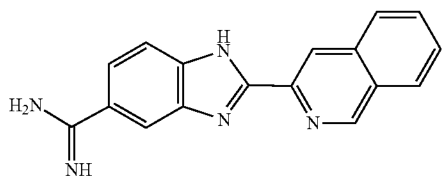 [SMILES: N=C(N)c1ccc2[nH]c(-c3cc4ccccc4cn3)nc2c1] | 2 HCl |
| 2015 | 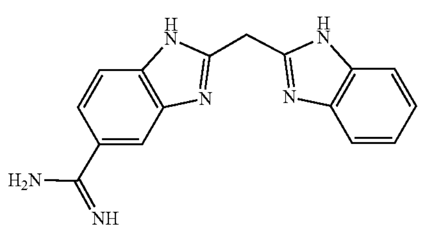 [SMILES: N=C(N)c1ccc2[nH]c(Cc3nc4ccccc4[nH]3)nc2c1] | 2 HCl |
| 2016 | 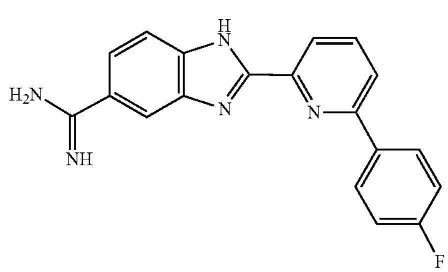 [SMILES: N=C(N)c1ccc2[nH]c(-c3cccc(-c4ccc(F)cc4)n3)nc2c1] | 2 HCl |

TABLE 4A-continued

Exemplary compounds

| Compound No. | Structure | Salt |
|---|---|---|
| 2017 | 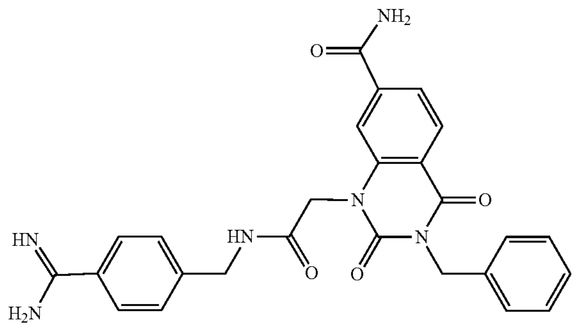 [SMILES: N=C(N)c1ccc(CNC(=O)Cn2c(=O)n(Cc3ccccc3)c(=O)c3ccc(C(N)=O)cc32)cc1] | HOAc |
| 2018 | 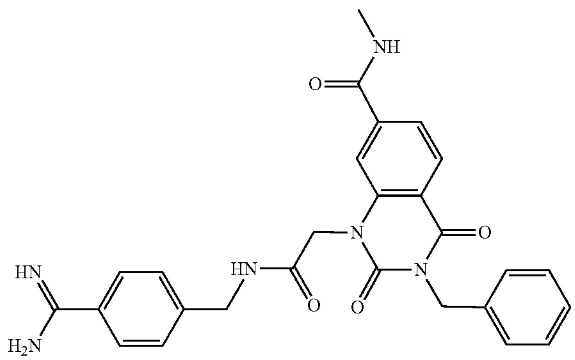 [SMILES: CNC(=O)c1ccc2c(=O)n(Cc3ccccc3)c(=O)n(CC(=O)NCc3ccc(C(=N)N)cc3)c2c1] | HOAc |
| 2019 | 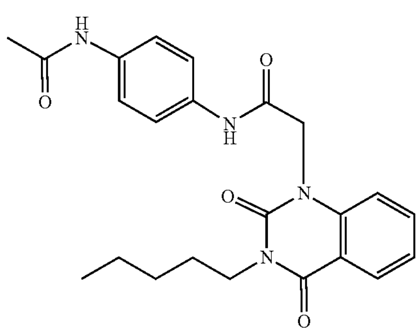 [SMILES: CCCCCn1c(=O)c2ccccc2n(CC(=O)Nc2ccc(NC(C)=O)cc2)c1=O] | N/A |
| 2020 | 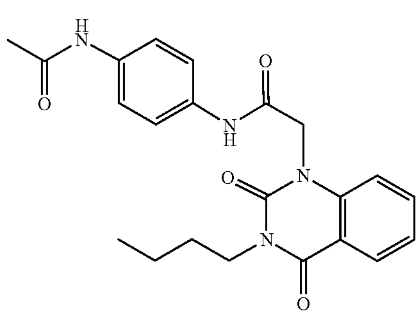 [SMILES: CCCCn1c(=O)c2ccccc2n(CC(=O)Nc2ccc(NC(C)=O)cc2)c1=O] | N/A |

TABLE 4A-continued
Exemplary compounds
| Compound No. | Structure | Salt |
|---|---|---|
| 2021 | 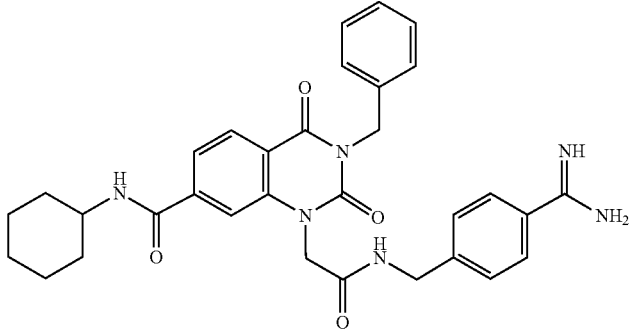 [SMILES: N=C(N)c1ccc(CNC(=O)Cn2c(=O)n(Cc3ccccc3)c(=O)c3ccc(C(=O)NC4CCCCC4)cc32)cc1] | N/A |
TABLE 4B
Exemplary MASP-2 inhibitory compounds
| Comp No. | Structure | Salt |
|---|---|---|
| I-1 | 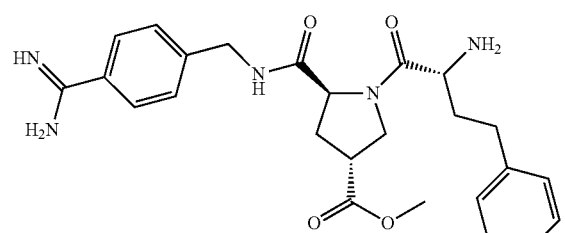 | 2TFA |
| I-2 | 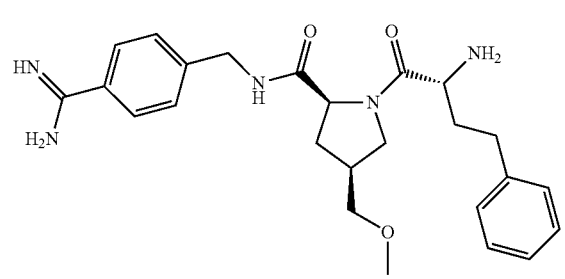 [SMILES: COC[C@H]1C[C@@H](C(=O)NCc2ccc(C(=N)N)cc2)N(C(=O)[C@H](N)CCc2ccccc2)C1] | 2HCl |
| I-3 | 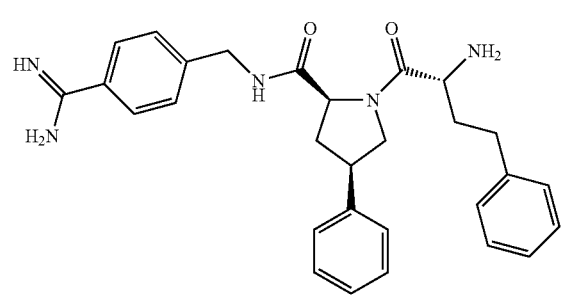 [SMILES: N=C(N)c1ccc(CNC(=O)[C@@H]2C[C@H](c3ccccc3)CN2C(=O)[C@H](N)CCc2ccccc2)cc1] | 2HCl |

TABLE 4B-continued

Exemplary MASP-2 inhibitory compounds

| Comp No. | Structure | Salt |
|---|---|---|
| I-4 | 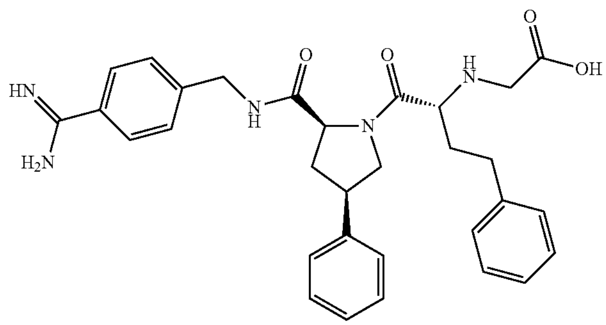 [SMILES: N=C(N)c1ccc(CNC(=O)[C@@H]2C[C@H](c3ccccc3)CN2C(=O)[C@@H](CCc2ccccc2)NCC(=O)O)cc1] | — |
| I-5 | 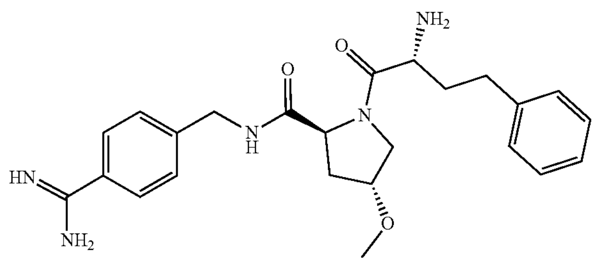 [SMILES: CO[C@@H]1C[C@@H](C(=O)NCc2ccc(C(=N)N)cc2)N(C(=O)[C@H](N)CCc2ccccc2)C1] | — |
| I-6 | 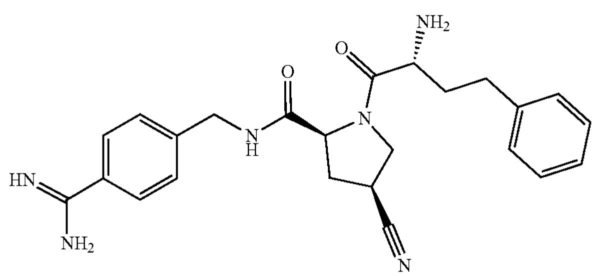 [SMILES: N#C[C@H]1C[C@@H](C(=O)NCc2ccc(C(=N)N)cc2)N(C(=O)[C@H](N)CCc2ccccc2)C1] | 2TFA |
| I-7 | 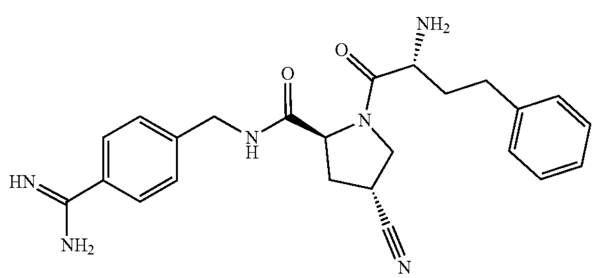 [SMILES: N#C[C@@H]1C[C@@H](C(=O)NCc2ccc(C(=N)N)cc2)N(C(=O)[C@H](N)CCc2ccccc2)C1] | — |
| I-8 | 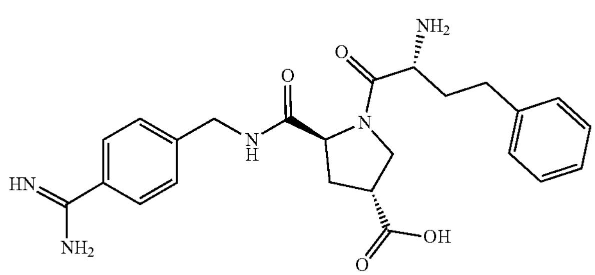 [SMILES: N=C(N)c1ccc(CNC(=O)[C@@H]2C[C@@H](C(=O)O)CN2C(=O)[C@H](N)CCc2ccccc2)cc1] | — |

TABLE 4B-continued

Exemplary MASP-2 inhibitory compounds

| Comp No. | Structure | Salt |
|---|---|---|
| I-9 | 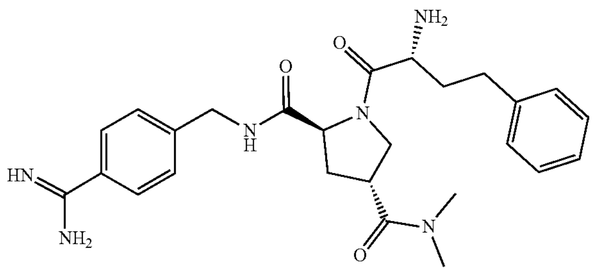 [SMILES: CN(C)C(=O)[C@@H]1C[C@@H](C(=O)NCc2ccc(C(=N)N)cc2)N(C(=O)[C@H](N)CCc2ccccc2)C1] | — |
| I-10 | 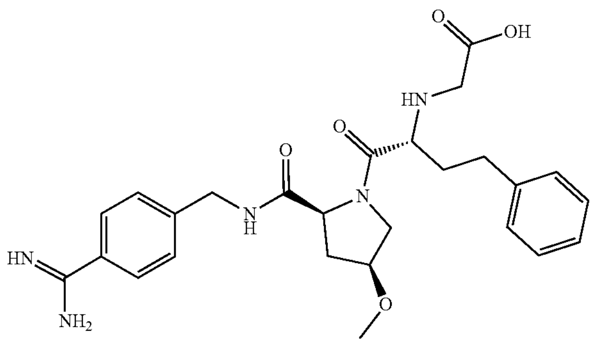 [SMILES: CO[C@H]1C[C@@H](C(=O)NCc2ccc(C(=N)N)cc2)N(C(=O)[C@@H](CCc2ccccc2)NCC(=O)O)C1] | — |
| I-11 | 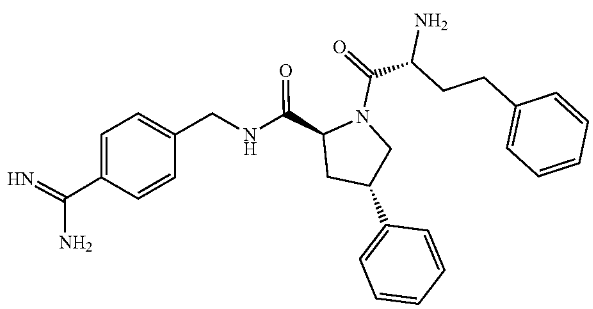 [SMILES: N=C(N)c1ccc(CNC(=O)[C@@H]2C[C@@H](c3ccccc3)CN2C(=O)[C@H](N)CCc2ccccc2)cc1] | 2HCl |
| I-12 | 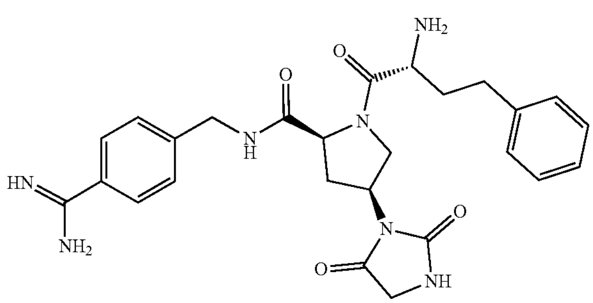 [SMILES: N=C(N)c1ccc(CNC(=O)[C@@H]2C[C@H](N3C(=O)CNC3=O)CN2C(=O)[C@H](N)CCc2ccccc2)cc1] | — |
| I-13 | 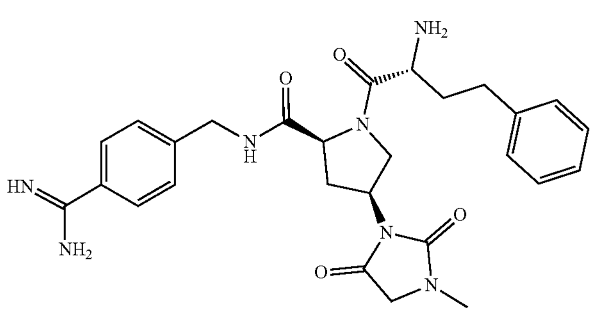 [SMILES: CN1CC(=O)N([C@H]2C[C@@H](C(=O)NCc3ccc(C(=N)N)cc3)N(C(=O)[C@H](N)CCc3ccccc3)C2)C1=O] | — |

TABLE 4B-continued

Exemplary MASP-2 inhibitory compounds

| Comp No. | Structure | Salt |
|---|---|---|
| I-14 | 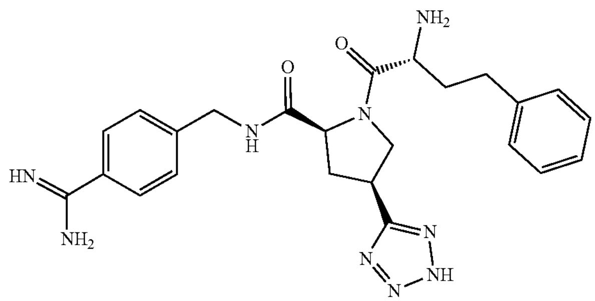 [SMILES: N=C(N)c1ccc(CNC(=O)[C@@H]2C[C@H](c3nn[nH]n3)CN2C(=O)[C@H](N)CCc2ccccc2)cc1] | — |
| I-15 | 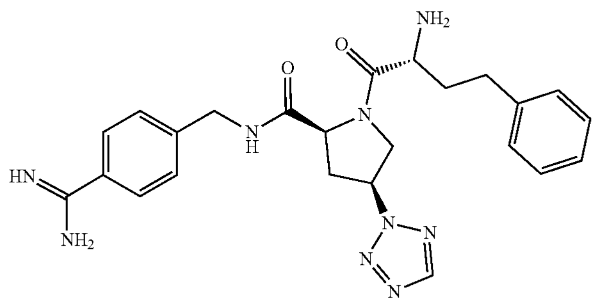 [SMILES: N=C(N)c1ccc(CNC(=O)[C@@H]2C[C@H](n3ncnn3)CN2C(=O)[C@H](N)CCc2ccccc2)cc1] | — |
| I-16 | 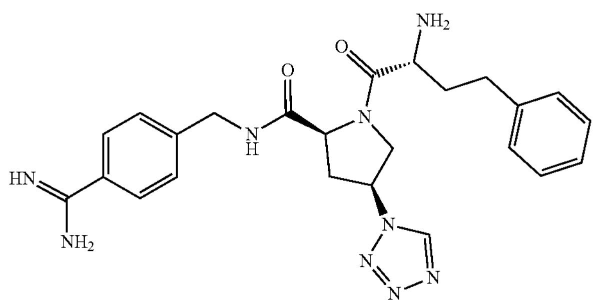 [SMILES: N=C(N)c1ccc(CNC(=O)[C@@H]2C[C@H](n3cnnn3)CN2C(=O)[C@H](N)CCc2ccccc2)cc1] | — |
| I-17 | 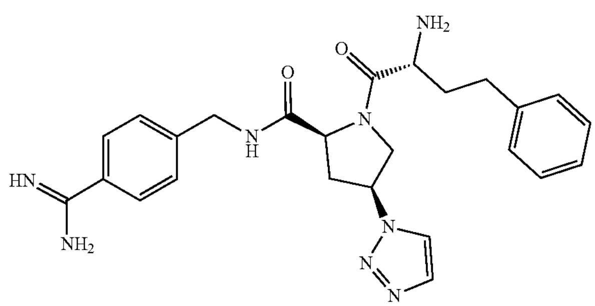 [SMILES: N=C(N)c1ccc(CNC(=O)[C@@H]2C[C@H](n3ccnn3)CN2C(=O)[C@H](N)CCc2ccccc2)cc1] | — |
| I-18 | 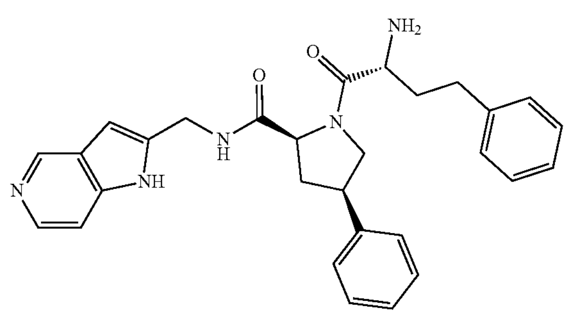 [SMILES: N[C@H](CCc1ccccc1)C(=O)N1C[C@@H](c2ccccc2)C[C@H]1C(=O)NCc1cc2cnccc2[nH]1] | — |

TABLE 4B-continued

Exemplary MASP-2 inhibitory compounds

| Comp No. | Structure | Salt |
|---|---|---|
| I-19 | 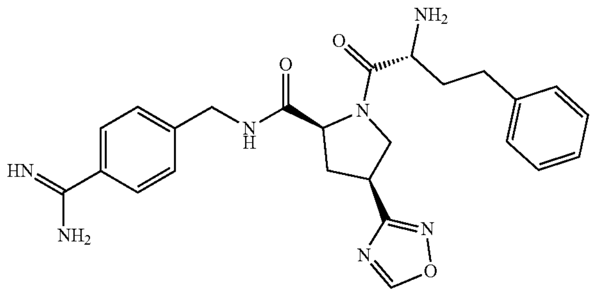 [SMILES: N=C(N)c1ccc(CNC(=O)[C@@H]2C[C@H](c3ncon3)CN2C(=O)[C@H](N)CCc2ccccc2)cc1] | — |
| I-20 | 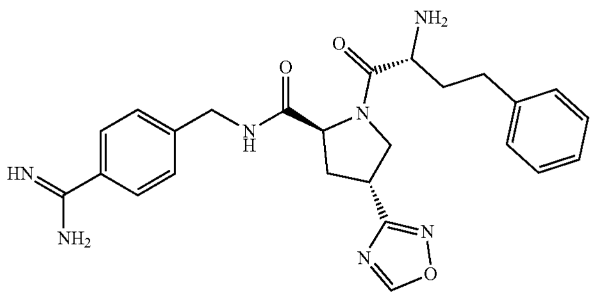 [SMILES: N=C(N)c1ccc(CNC(=O)[C@@H]2C[C@@H](c3ncon3)CN2C(=O)[C@H](N)CCc2ccccc2)cc1] | — |
| I-21 | 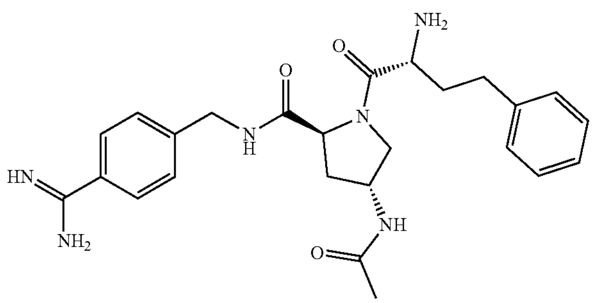 [SMILES: CC(=O)N[C@@H]1C[C@@H](C(=O)NCc2ccc(C(=N)N)cc2)N(C(=O)[C@H](N)CCc2ccccc2)C1] | — |
| I-22 | 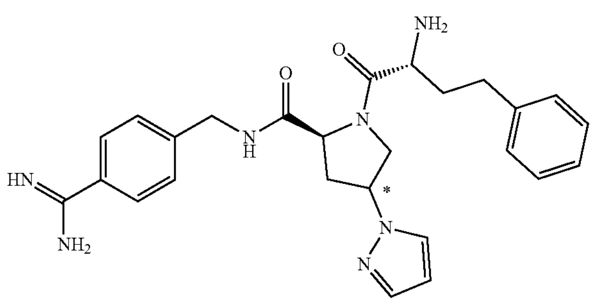 [SMILES: N=C(N)c1ccc(CNC(=O)[C@@H]2CC(n3cccn3)CN2C(=O)[C@H](N)CCc2ccccc2)cc1] | 2HCl |
| I-23 | 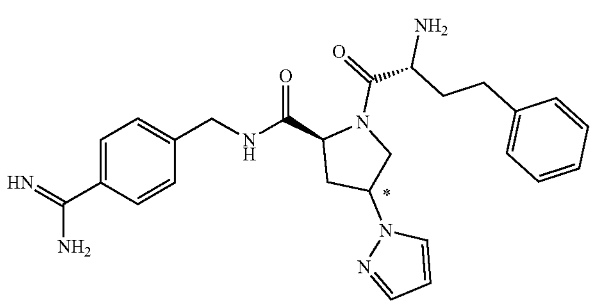 [SMILES: N=C(N)c1ccc(CNC(=O)[C@@H]2CC(n3cccn3)CN2C(=O)[C@H](N)CCc2ccccc2)cc1] | 2HCl |

TABLE 4B-continued
Exemplary MASP-2 inhibitory compounds
| Comp No. | Structure | Salt |
|---|---|---|
| I-24 | 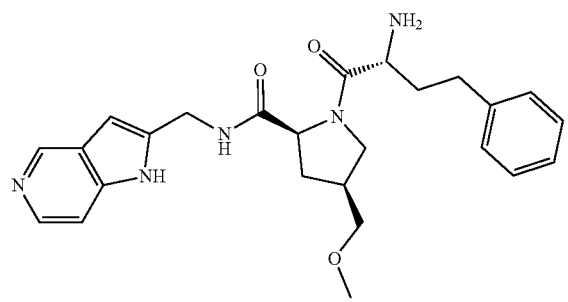 [SMILES: COC[C@H]1C[C@@H](C(=O)NCc2cc3cnccc3[nH]2)N(C(=O)[C@H](N)CCc2ccccc2)C1] | 2TFA |
| I-25 | 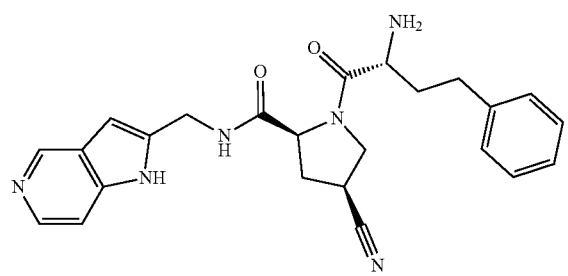 [SMILES: N#C[C@H]1C[C@@H](C(=O)NCc2cc3cnccc3[nH]2)N(C(=O)[C@H](N)CCc2ccccc2)C1] | 2TFA |
TABLE 4C
Exemplary MASP-2 inhibitory compounds
| Comp No. | Structure | Salt |
|---|---|---|
| II-1 | 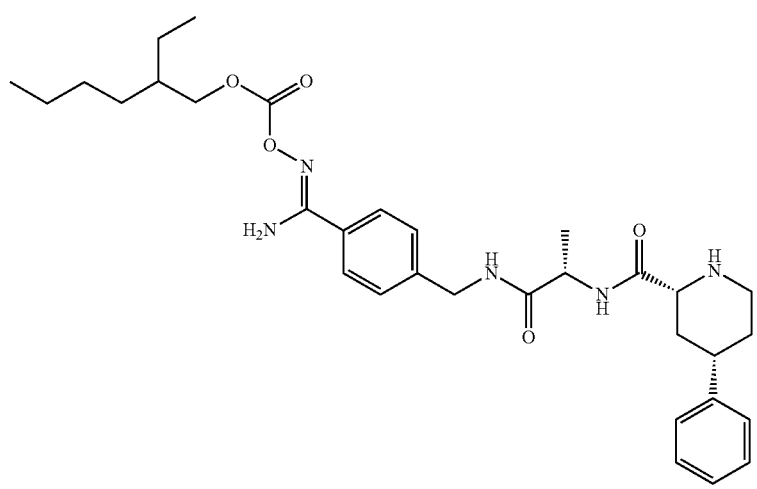 [SMILES: CCCCC(CC)COC(=O)O/N=C(\N)c1ccc(CNC(=O)[C@H](C)NC(=O)[C@H]2C[C@@H](c3ccccc3)CCN2)cc1] | 2TFA |

TABLE 4C-continued
Exemplary MASP-2 inhibitory compounds
| Comp No. | Structure | Salt |
|---|---|---|
| II-2 | 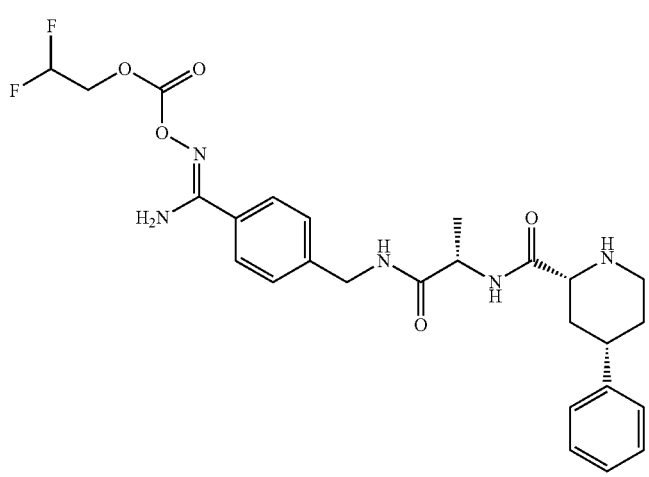 [SMILES: C[C@H](NC(=O)[C@H]1C[C@@H](c2ccccc2)CCN1)C(=O)NCc1ccc(/C(N)=N/OC(=O)OCC(F)F)cc1] | 2TFA |
| II-3 | 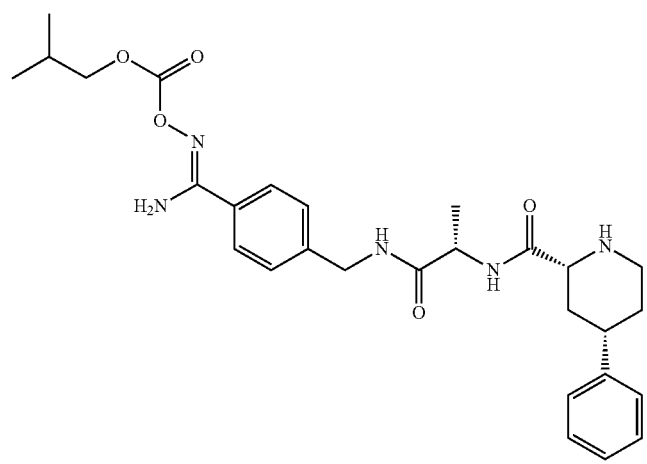 [SMILES: CC(C)COC(=O)O/N=C(\N)c1ccc(CNC(=O)[C@H](C)NC(=O)[C@H]2C[C@@H](c3ccccc3)CCN2)cc1] | 2TFA |
| II-4 | 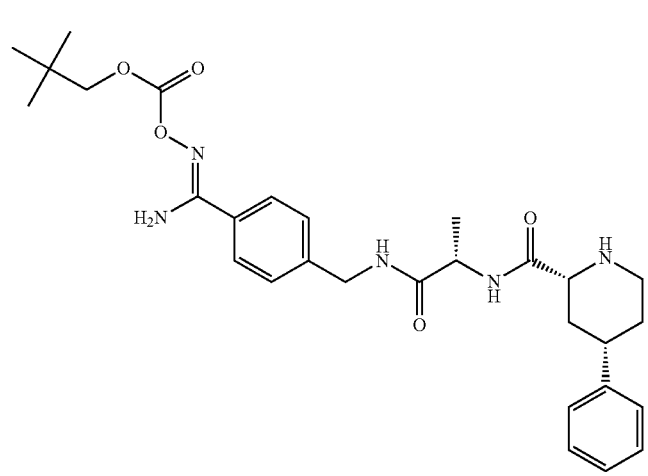 [SMILES: C[C@H](NC(=O)[C@H]1C[C@@H](c2ccccc2)CCN1)C(=O)NCc1ccc(/C(N)=N/OC(=O)OCC(C)(C)C)cc1] | 2TFA |

TABLE 4C-continued

Exemplary MASP-2 inhibitory compounds

| Comp No. | Structure | Salt |
|---|---|---|
| II-5 | 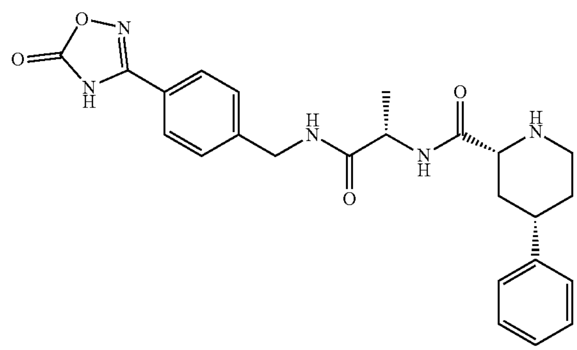 [SMILES: C[C@H](NC(=O)[C@H]1C[C@@H](c2ccccc2)CCN1)C(=O)NCc1ccc(-c2noc(=O)[nH]2)cc1] | 1TFA |
| II-6 | 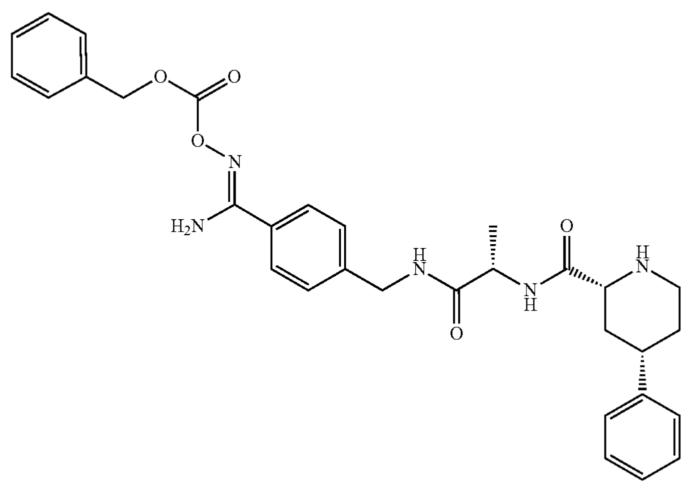 [SMILES: C[C@H](NC(=O)[C@H]1C[C@@H](c2ccccc2)CCN1)C(=O)NCc1ccc(/C(N)=N/OC(=O)OCc2ccccc2)cc1] | 2TFA |
| II-7 | 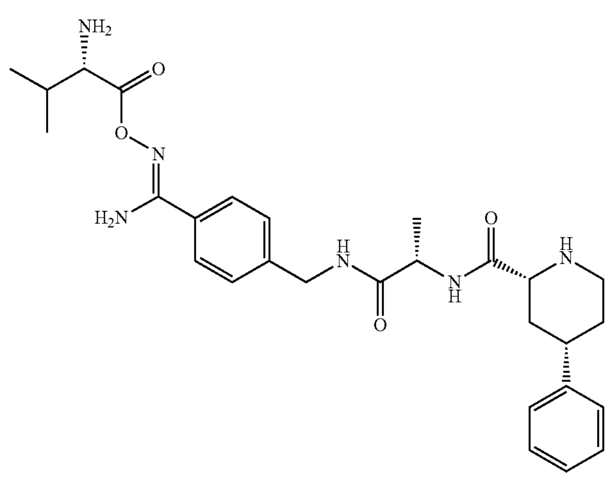 [SMILES: CC(C)[C@H](N)C(=O)O/N=C(\N)c1ccc(CNC(=O)[C@H](C)NC(=O)[C@H]2C[C@@H](c3ccccc3)CCN2)cc1] | 2HCl |

TABLE 4C-continued

Exemplary MASP-2 inhibitory compounds

| Comp No. | Structure | Salt |
|---|---|---|
| II-8 | 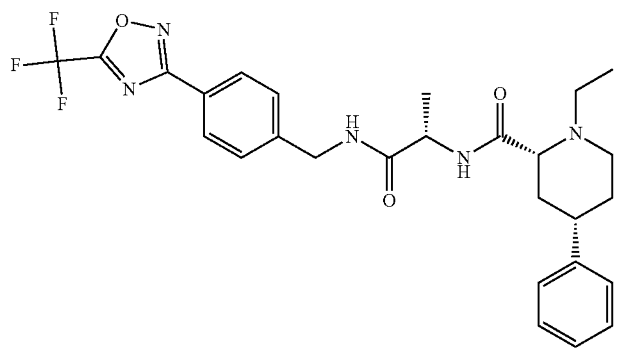 [SMILES: CCN1CC[C@H](c2ccccc2)C[C@@H]1C(=O)N[C@@H](C)C(=O)NCc1ccc(-c2noc(C(F)(F)F)n2)cc1] | 1TFA |
| II-9 | 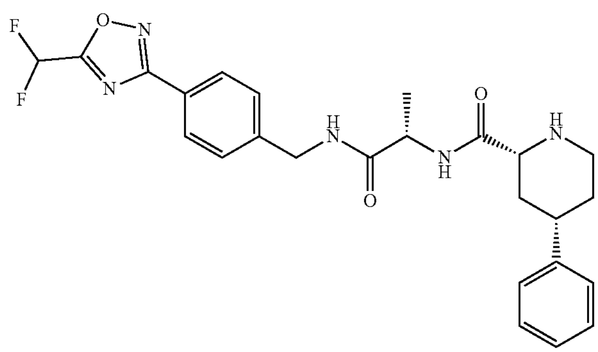 [SMILES: C[C@H](NC(=O)[C@H]1C[C@@H](c2ccccc2)CCN1)C(=O)NCc1ccc(-c2noc(C(F)F)n2)cc1] | 1TFA |
| II-10 | 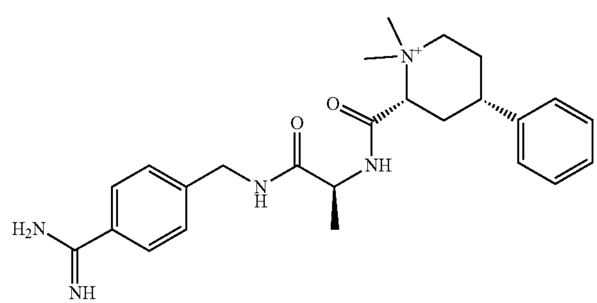 [SMILES: C[C@H](NC(=O)[C@H]1C[C@@H](c2ccccc2)CC[N+]1(C)C)C(=O)NCc1ccc(C(=N)N)cc1] | 2TFA |
| II-11 | 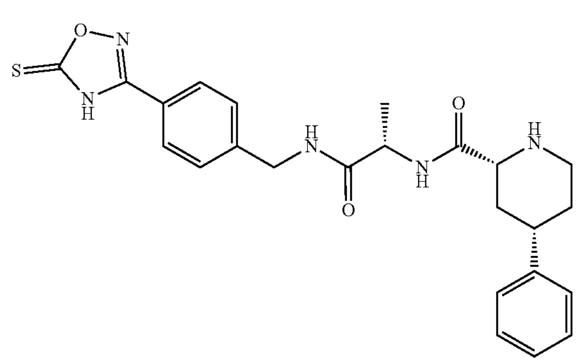 [SMILES: C[C@H](NC(=O)[C@H]1C[C@@H](c2ccccc2)CCN1)C(=O)NCc1ccc(-c2noc(=S)[nH]2)cc1] | 1TFA |

TABLE 4C-continued

Exemplary MASP-2 inhibitory compounds

| Comp No. | Structure | Salt |
|---|---|---|
| II-12 | 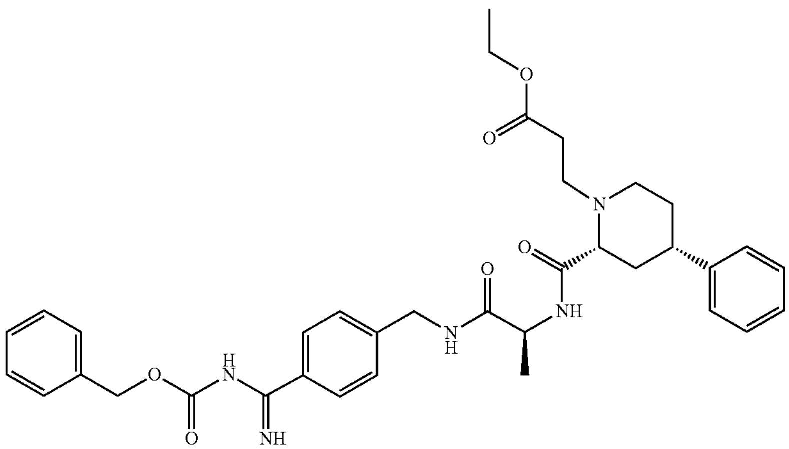 [SMILES: CCOC(=O)CCN1CC[C@H](c2ccccc2)C[C@@H]1C(=O)N[C@@H](C)C(=O)NCc1ccc(C(=N)NC(=O)OCc2ccccc2)cc1] | — |
| II-13 | 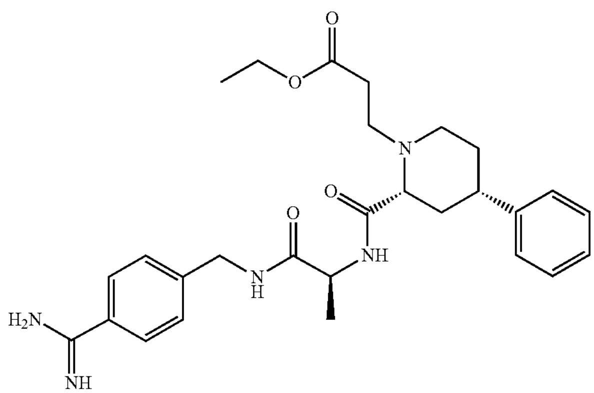 [SMILES: CCOC(=O)CCN1CC[C@H](c2ccccc2)C[C@@H]1C(=O)N[C@@H](C)C(=O)NCc1ccc(C(=N)N)cc1] | — |
| II-14 | 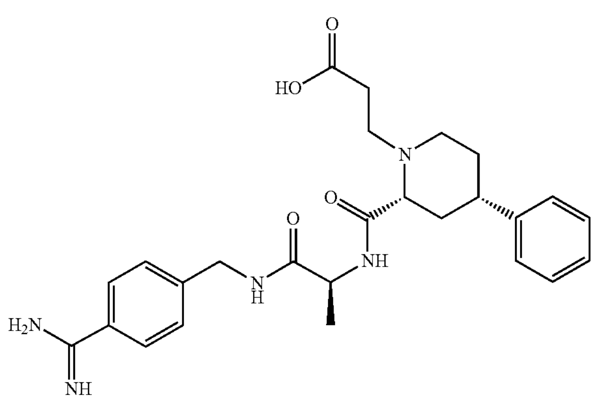 [SMILES: C[C@H](NC(=O)[C@H]1C[C@@H](c2ccccc2)CCN1CCC(=O)O)C(=O)NCc1ccc(C(=N)N)cc1] | 2TFA |

TABLE 4C-continued

Exemplary MASP-2 inhibitory compounds

| Comp No. | Structure | Salt |
|---|---|---|
| II-15 | 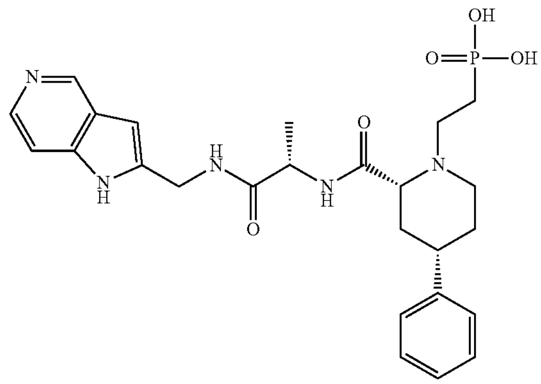 [SMILES: C[C@H](NC(=O)[C@H]1C[C@@H](c2ccccc2)CCN1CCP(=O)(O)O)C(=O)NCc1cc2cnccc2[nH]1] | 2TFA |
| II-16 | 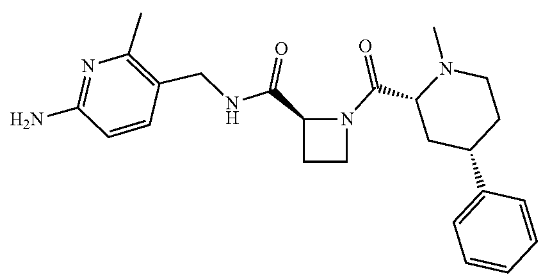 [SMILES: Cc1nc(N)ccc1CNC(=O)[C@@H]1CCN1C(=O)[C@H]1C[C@@H](c2ccccc2)CCN1C] | 2TFA |
| II-17 | 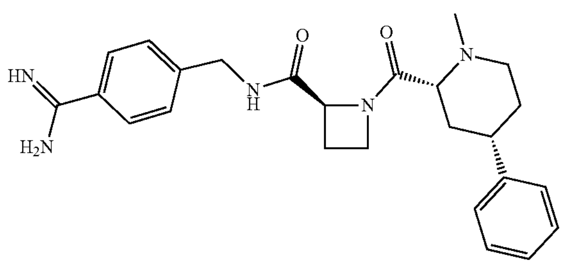 [SMILES: CN1CC[C@H](c2ccccc2)C[C@@H]1C(=O)N1CC[C@H]1C(=O)NCc1ccc(C(=N)N)cc1] | 2TFA |
| II-18 | 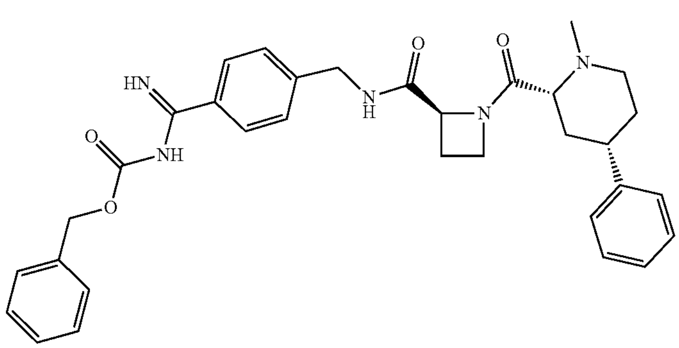 [SMILES: CN1CC[C@H](c2ccccc2)C[C@@H]1C(=O)N1CC[C@H]1C(=O)NCc1ccc(C(=N)NC(=O)OCc2ccccc2)cc1] | 2TFA |

TABLE 4C-continued

Exemplary MASP-2 inhibitory compounds

| Comp No. | Structure | Salt |
|---|---|---|
| II-19 | 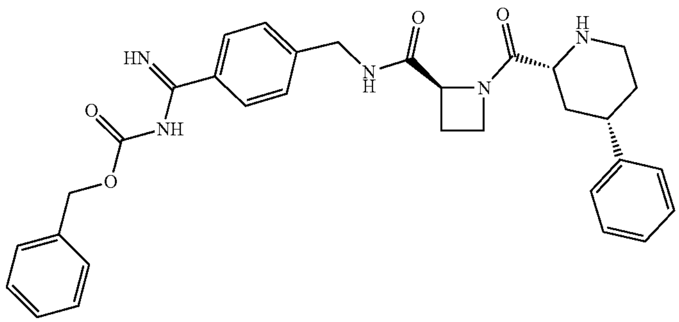 [SMILES: N=C(NC(=O)OCc1ccccc1)c1ccc(CNC(=O)[C@@H]2CCN2C(=O)[C@H]2C[C@@H](c3ccccc3)CCN2)cc1] | 2TFA |
| II-20 | 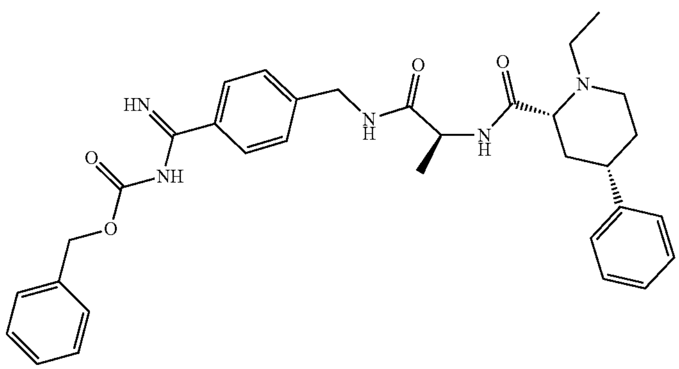 [SMILES: CCN1CC[C@H](c2ccccc2)C[C@@H]1C(=O)N[C@@H](C)C(=O)NCc1ccc(C(=N)NC(=O)OCc2ccccc2)cc1] | — |
| II-21 | 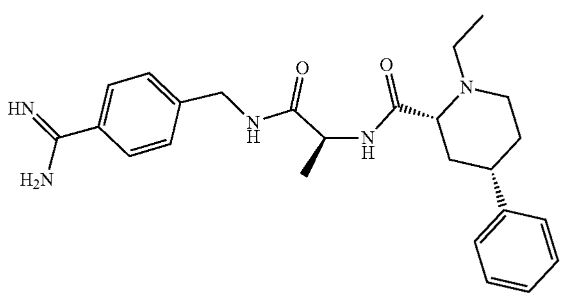 [SMILES: CCN1CC[C@H](c2ccccc2)C[C@@H]1C(=O)N[C@@H](C)C(=O)NCc1ccc(C(=N)N)cc1] | — |
| II-22 | 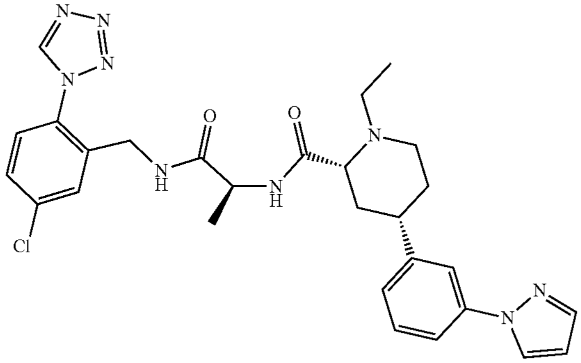 [SMILES: CCN1CC[C@H](c2cccc(-n3cccn3)c2)C[C@@H]1C(=O)N[C@@H](C)C(=O)NCc1cc(Cl)ccc1-n1cnnn1] | — |

TABLE 4C-continued

Exemplary MASP-2 inhibitory compounds

| Comp No. | Structure | Salt |
|---|---|---|
| II-23 | 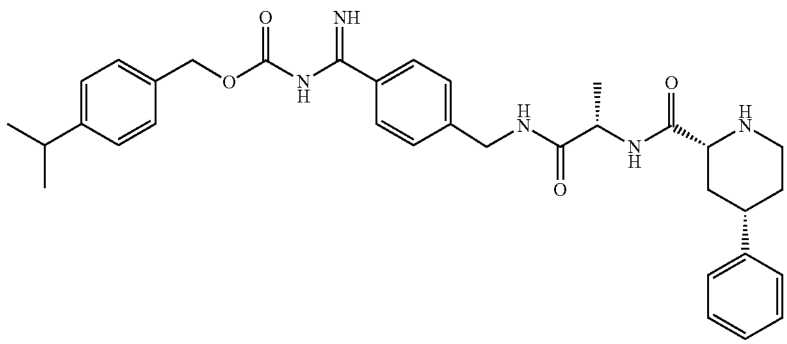 [SMILES: CC(C)c1ccc(COC(=O)NC(=N)c2ccc(CNC(=O)[C@H](C)NC(=O)[C@H]3C[C@@H](c4ccccc4)CCN3)cc2)cc1] | 1HCl |
| II-24 | 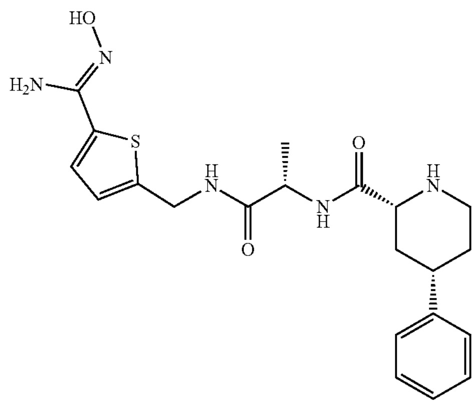 [SMILES: C[C@H](NC(=O)[C@H]1C[C@@H](c2ccccc2)CCN1)C(=O)NCc1ccc(/C(N)=N/O)s1] | 1HCl |
| II-25 | 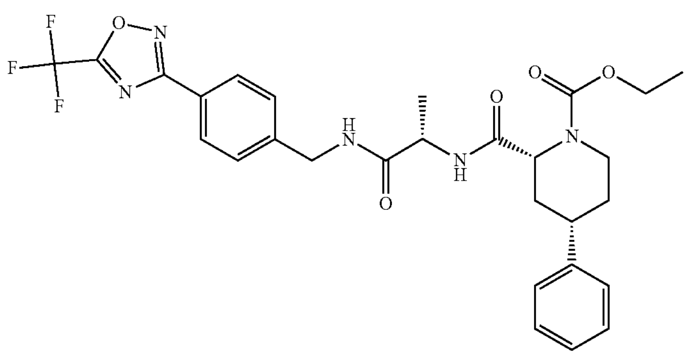 [SMILES: CCOC(=O)N1CC[C@H](c2ccccc2)C[C@@H]1C(=O)N[C@@H](C)C(=O)NCc1ccc(-c2noc(C(F)(F)F)n2)cc1] | — |
| II-26 | 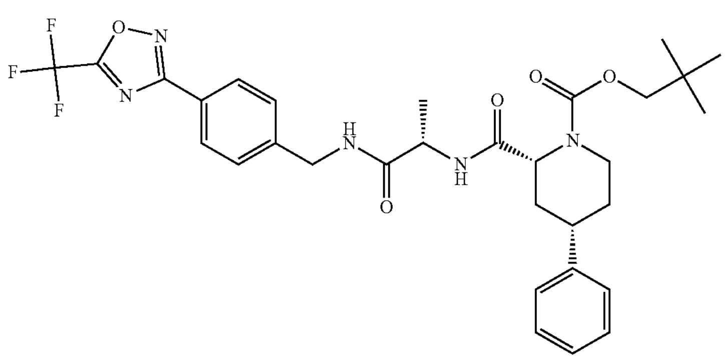 [SMILES: C[C@H](NC(=O)[C@H]1C[C@@H](c2ccccc2)CCN1C(=O)OCC(C)(C)C)C(=O)NCc1ccc(-c2noc(C(F)(F)F)n2)cc1] | — |

TABLE 4C-continued

Exemplary MASP-2 inhibitory compounds

| Comp No. | Structure | Salt |
|---|---|---|
| II-27 | 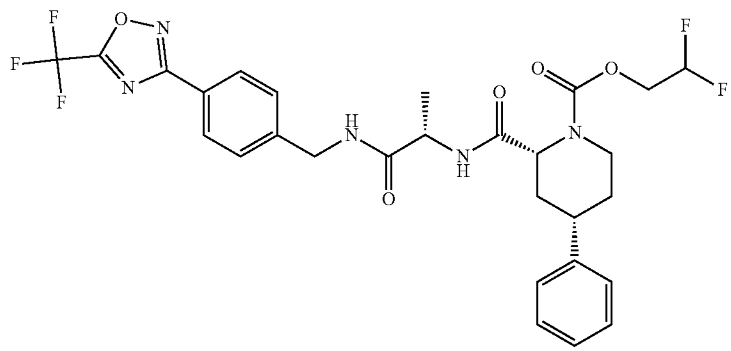 [SMILES: C[C@H](NC(=O)[C@H]1C[C@@H](c2ccccc2)CCN1C(=O)OCC(F)F)C(=O)NCc1ccc(-c2noc(C(F)(F)F)n2)cc1] | — |
| II-28 | 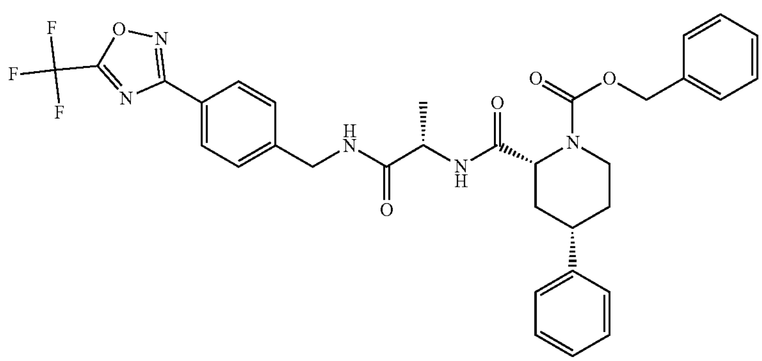 [SMILES: C[C@H](NC(=O)[C@H]1C[C@@H](c2ccccc2)CCN1C(=O)OCc1ccccc1)C(=O)NCc1ccc(-c2noc(C(F)(F)F)n2)cc1] | — |
| II-29 | 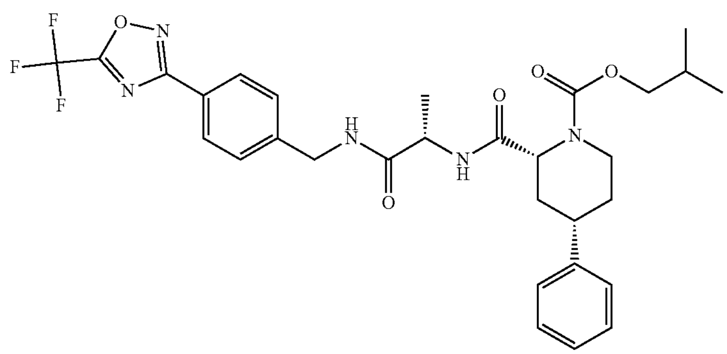 [SMILES: CC(C)COC(=O)N1CC[C@H](c2ccccc2)C[C@@H]1C(=O)N[C@@H](C)C(=O)NCc1ccc(-c2noc(C(F)(F)F)n2)cc1] | — |
| II-30 | 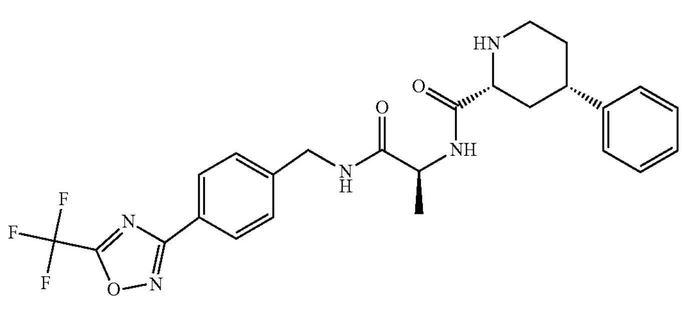 [SMILES: C[C@H](NC(=O)[C@H]1C[C@@H](c2ccccc2)CCN1)C(=O)NCc1ccc(-c2noc(C(F)(F)F)n2)cc1] | 1TFA |

TABLE 4C-continued

Exemplary MASP-2 inhibitory compounds

| Comp No. | Structure | Salt |
|---|---|---|
| II-31 | 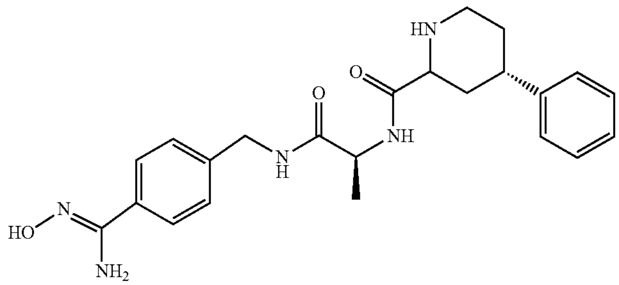 [SMILES: C[C@H](NC(=O)C1C[C@@H](c2ccccc2)CCN1)C(=O)NCc1ccc(/C(N)=N/O)cc1] | 2TFA |
| II-32 | 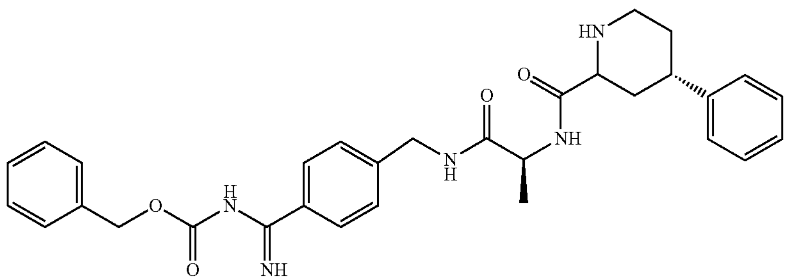 [SMILES: C[C@H](NC(=O)C1C[C@@H](c2ccccc2)CCN1)C(=O)NCc1ccc(C(=N)NC(=O)OCc2ccccc2)cc1] | 2TFA |
| II-33 | 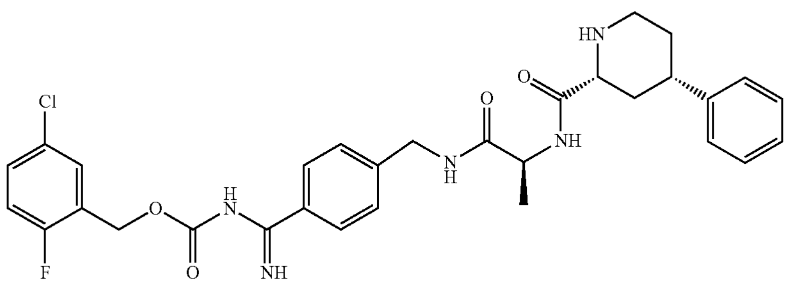 [SMILES: C[C@H](NC(=O)[C@H]1C[C@@H](c2ccccc2)CCN1)C(=O)NCc1ccc(C(=N)NC(=O)OCc2cc(Cl)ccc2F)cc1] | 2TFA |
| II-34 | 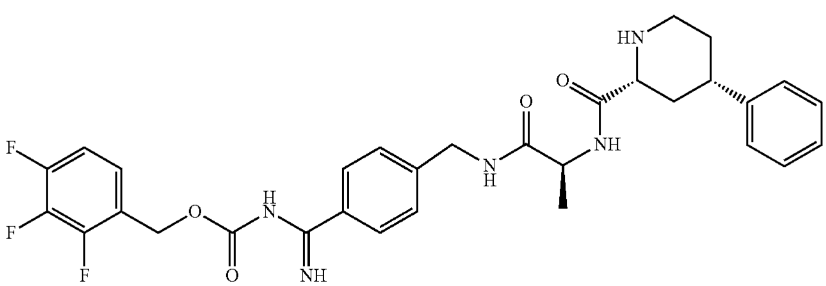 | 2TFA |
| II-35 | 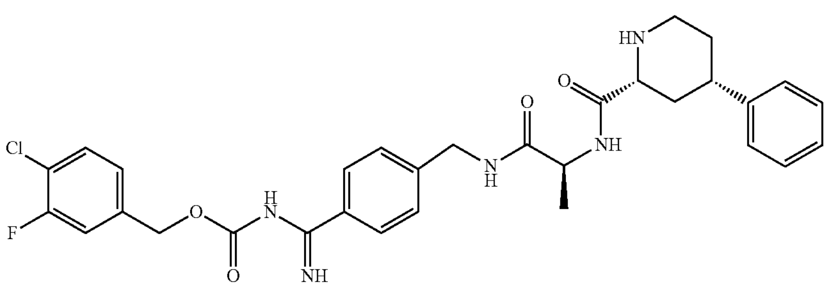 [SMILES: C[C@H](NC(=O)[C@H]1C[C@@H](c2ccccc2)CCN1)C(=O)NCc1ccc(C(=N)NC(=O)OCc2ccc(F)c(F)c2F)cc1] | 2TFA |

TABLE 4C-continued

Exemplary MASP-2 inhibitory compounds

| Comp No. | Structure | Salt |
|---|---|---|
| II-36 | 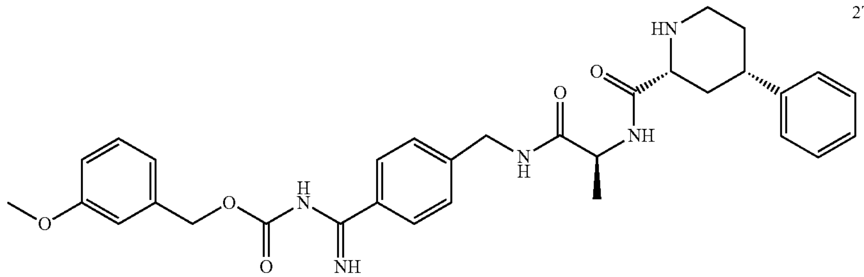 | 2TFA |

TABLE 4D

Exemplary MASP-2 inhibitory compounds

| Comp No. | Structure | Salt |
|---|---|---|
| III-1 | 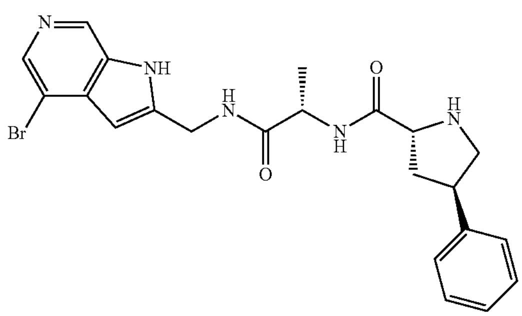 [SMILES: C[C@H](NC(=O)[C@H]1C[C@H](c2ccccc2)CN1)C(=O)NCc1cc2c(Br)cncc2[nH]1] | 2TFA |
| III-2 | 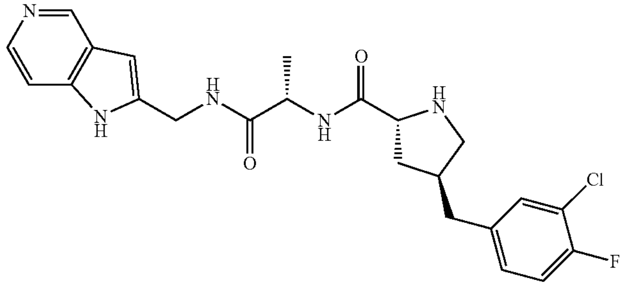 [SMILES: C[C@H](NC(=O)[C@H]1C[C@H](Cc2ccc(F)c(Cl)c2)CN1)C(=O)NCc1cc2cnccc2[nH]1] | 2TFA |
| III-3 | 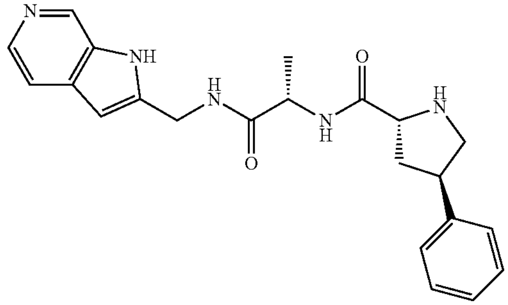 [SMILES: C[C@H](NC(=O)[C@H]1C[C@H](c2ccccc2)CN1)C(=O)NCc1cc2ccncc2[nH]1] | 2TFA |

TABLE 4D-continued

Exemplary MASP-2 inhibitory compounds

| Comp No. | Structure | Salt |
|---|---|---|
| III-4 | 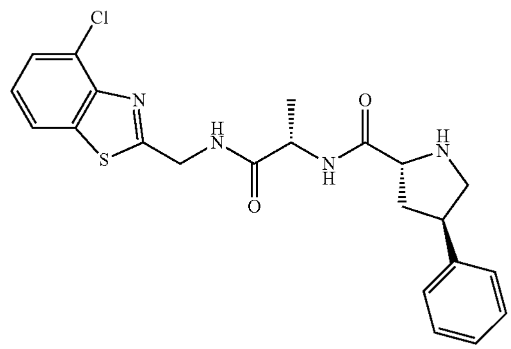 [SMILES: C[C@H](NC(=O)[C@H]1C[C@H](c2ccccc2)CN1)C(=O)NCc1nc2c(Cl)cccc2s1] | TFA |
| III-5 | 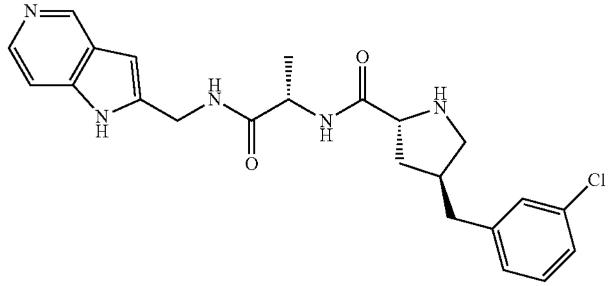 [SMILES: C[C@H](NC(=O)[C@H]1C[C@H](Cc2cccc(Cl)c2)CN1)C(=O)NCc1cc2cnccc2[nH]1] | 2TFA |
| III-6 | 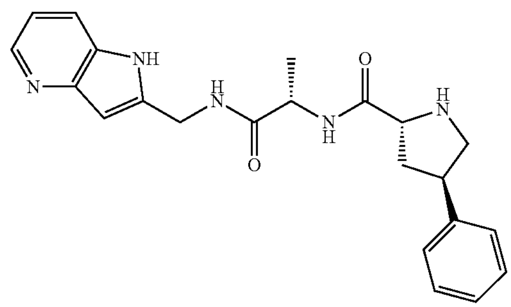 [SMILES: C[C@H](NC(=O)[C@H]1C[C@H](c2ccccc2)CN1)C(=O)NCc1cc2ncccc2[nH]1] | 2TFA |
| III-7 | 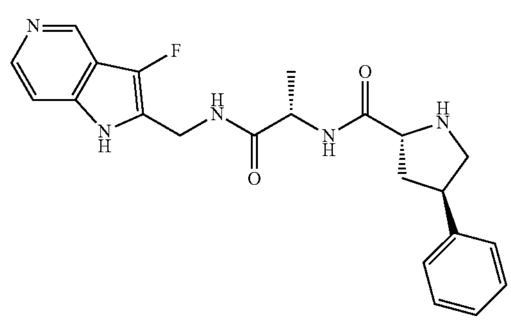 [SMILES: C[C@H](NC(=O)[C@H]1C[C@H](c2ccccc2)CN1)C(=O)NCc1[nH]c2ccncc2c1F] | 2TFA |
| III-8 | 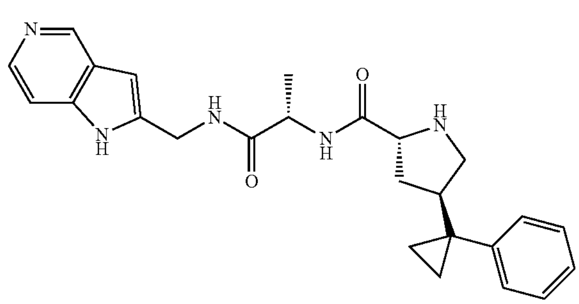 [SMILES: C[C@H](NC(=O)[C@H]1C[C@H](C2(c3ccccc3)CC2)CN1)C(=O)NCc1cc2cnccc2[nH]1] | 2TFA |

TABLE 4D-continued
Exemplary MASP-2 inhibitory compounds
| Comp No. | Structure | Salt |
|---|---|---|
| III-9 | 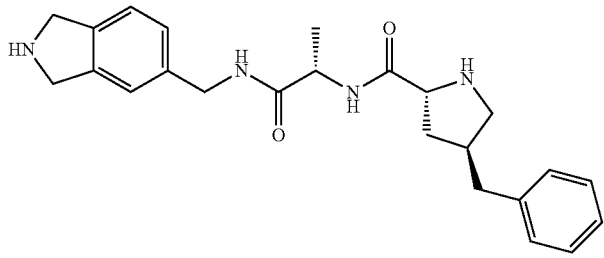 [SMILES: C[C@H](NC(=O)[C@H]1C[C@H](Cc2ccccc2)CN1)C(=O)NCc1ccc2c(c1)CNC2] | 2TFA |
| III-10 | 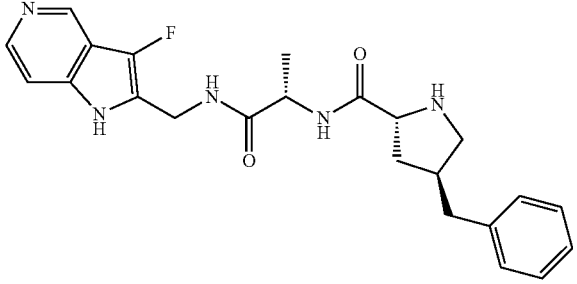 [SMILES: C[C@H](NC(=O)[C@H]1C[C@H](Cc2ccccc2)CN1)C(=O)NCc1[nH]c2ccncc2c1F] | 2TFA |
| III-11 | 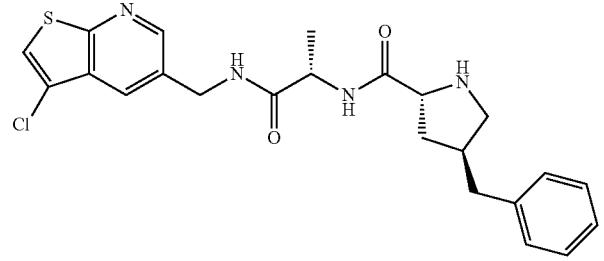 [SMILES: C[C@H](NC(=O)[C@H]1C[C@H](Cc2ccccc2)CN1)C(=O)NCc1cnc2scc(Cl)c2c1] | TFA |
| III-12 | 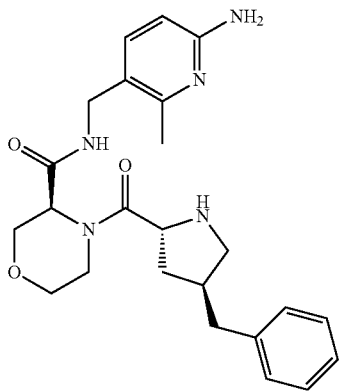 [SMILES: Cc1nc(N)ccc1CNC(=O)[C@@H]1COCCN1C(=O)[C@H]1C[C@H](Cc2ccccc2)CN1] | 2TFA |
| III-13 | 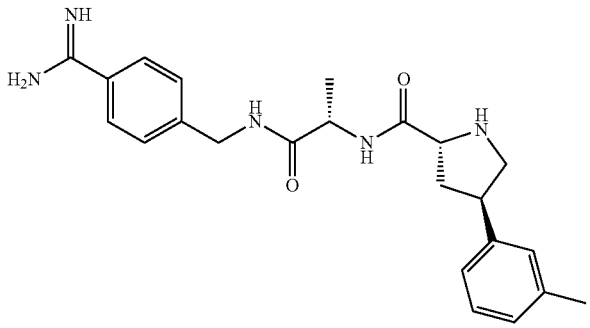 [SMILES: Cc1cccc([C@@H]2CN[C@@H](C(=O)N[C@@H](C)C(=O)NCc3ccc(C(=N)N)cc3)C2)c1] | — |

TABLE 4D-continued

| Comp No. | Structure | Salt |
|---|---|---|
| III-14 | 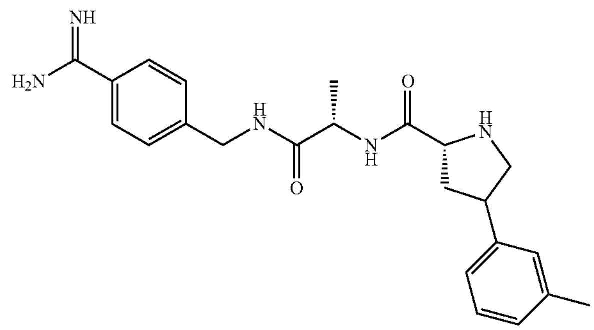 | — |
| III-15 | 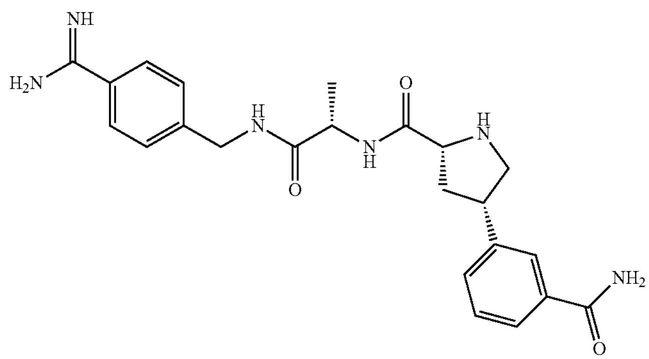 [SMILES: C[C@H](NC(=O)[C@H]1C[C@@H](c2cccc(C(N)=O)c2)CN1)C(=O)NCc1ccc(C(=N)N)cc1] | 2TFA |
| III-16 | 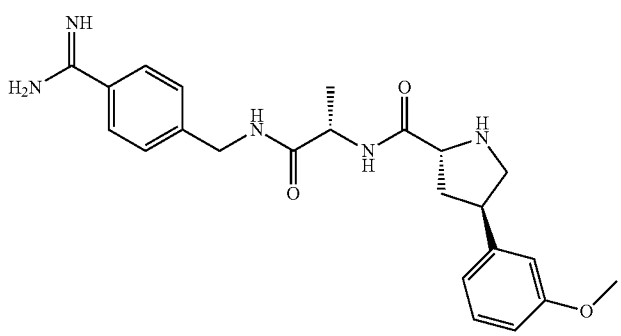 [SMILES: COc1cccc([C@@H]2CN[C@@H](C(=O)N[C@@H](C)C(=O)NCc3ccc(C(=N)N)cc3)C2)c1] | 2HCl |
| III-17 | 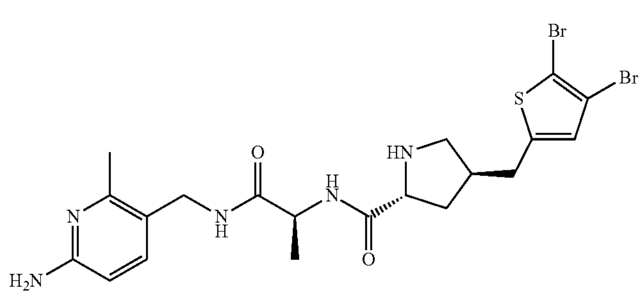 [SMILES: Cc1nc(N)ccc1CNC(=O)[C@H](C)NC(=O)[C@H]1C[C@H](Cc2cc(Br)c(Br)s2)CN1] | 2TFA |

TABLE 4D-continued

Exemplary MASP-2 inhibitory compounds

| Comp No. | Structure | Salt |
|---|---|---|
| III-18 | 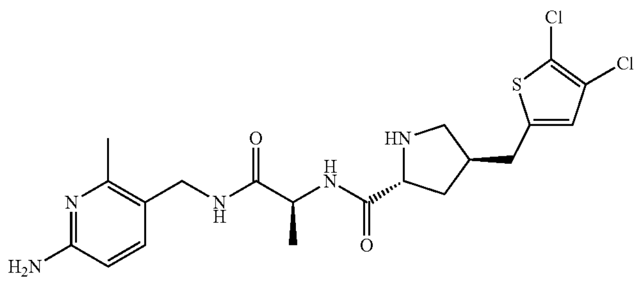 [SMILES: Cc1nc(N)ccc1CNC(=O)[C@H](C)NC(=O)[C@H]1C[C@H](Cc2cc(Cl)c(Cl)s2)CN1] | 2TFA |
| III-19 | 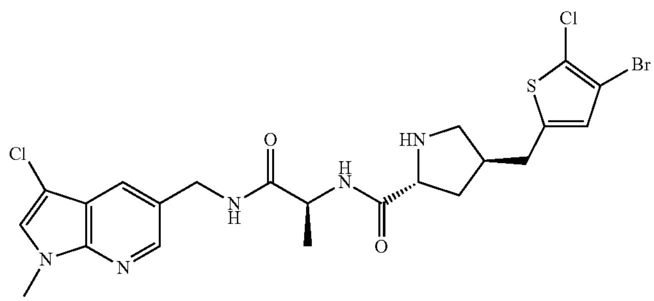 [SMILES: C[C@H](NC(=O)[C@H]1C[C@H](Cc2cc(Br)c(Cl)s2)CN1)C(=O)NCc1cnc2c(c1)c(Cl)cn2C] | TFA |
| III-20 | 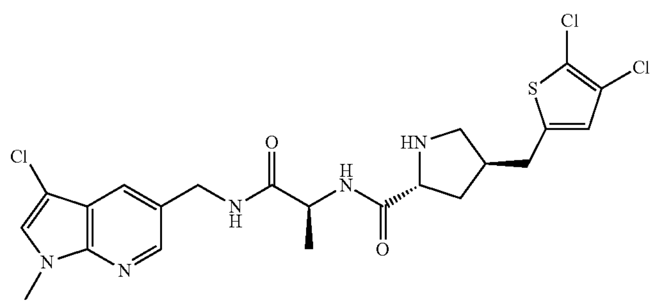 [SMILES: C[C@H](NC(=O)[C@H]1C[C@H](Cc2cc(Cl)c(Cl)s2)CN1)C(=O)NCc1cnc2c(c1)c(Cl)cn2C] | TFA |
| III-21 | 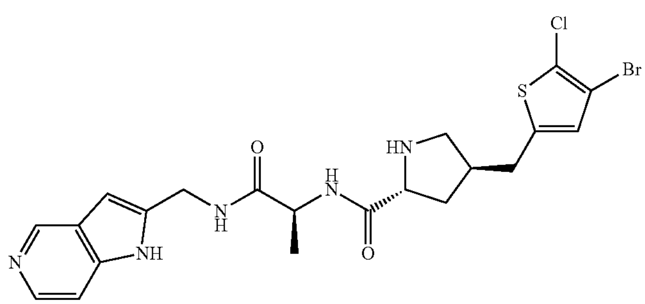 [SMILES: C[C@H](NC(=O)[C@H]1C[C@H](Cc2cc(Br)c(Cl)s2)CN1)C(=O)NCc1cc2cnccc2[nH]1] | 2TFA |
| III-22 | 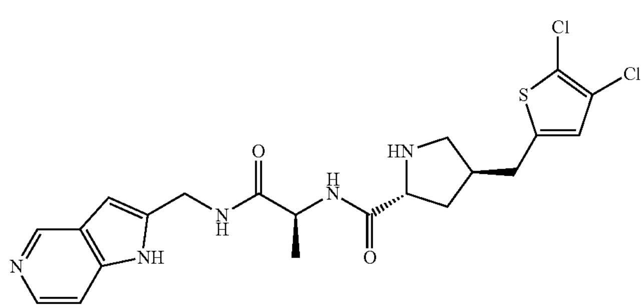 [SMILES: C[C@H](NC(=O)[C@H]1C[C@H](Cc2cc(Cl)c(Cl)s2)CN1)C(=O)NCc1cc2cnccc2[nH]1] | 2TFA |

TABLE 4D-continued

Exemplary MASP-2 inhibitory compounds

| Comp No. | Structure | Salt |
|---|---|---|
| III-23 | 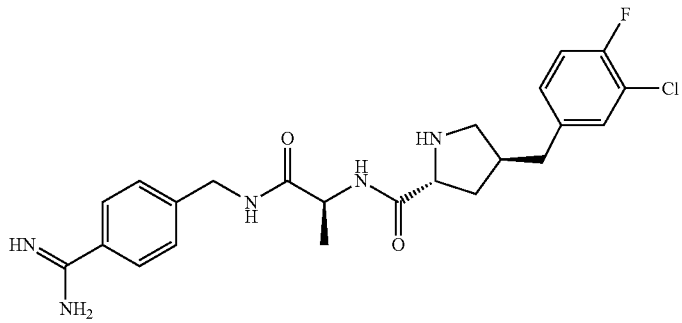 [SMILES: C[C@H](NC(=O)[C@H]1C[C@H](Cc2ccc(F)c(Cl)c2)CN1)C(=O)NCc1ccc(C(=N)N)cc1] | 2TFA |
| III-24 | 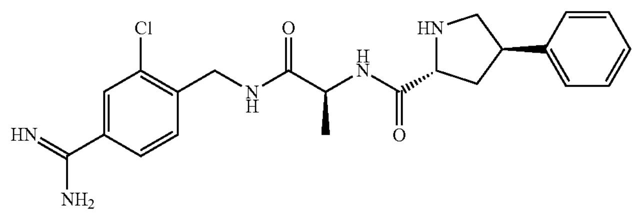 [SMILES: C[C@H](NC(=O)[C@H]1C[C@H](c2ccccc2)CN1)C(=O)NCc1ccc(C(=N)N)cc1Cl] | 2TFA |
| III-25 | 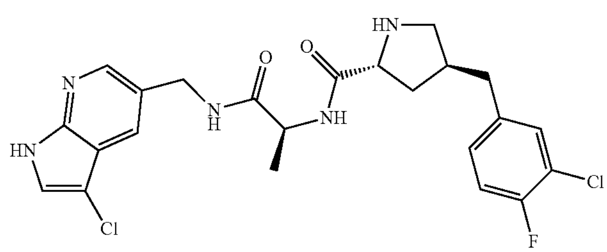 [SMILES: C[C@H](NC(=O)[C@H]1C[C@H](Cc2ccc(F)c(Cl)c2)CN1)C(=O)NCc1cnc2[nH]cc(Cl)c2c1] | 2TFA |
| III-26 | 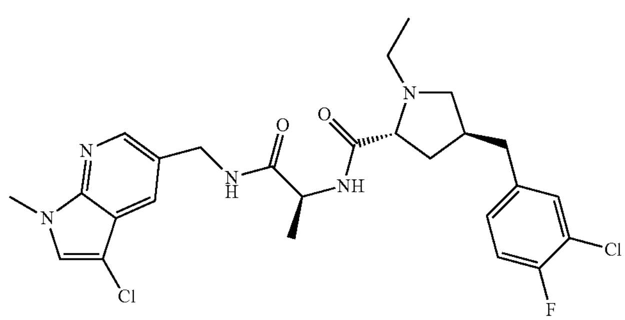 [SMILES: CCN1C[C@@H](Cc2ccc(F)c(Cl)c2)C[C@@H]1C(=O)N[C@@H](C)C(=O)NCc1cnc2c(c1)c(Cl)cn2C] | — |
| III-27 | 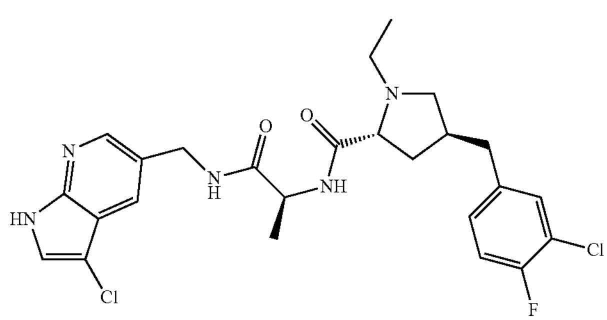 [SMILES: CCN1C[C@@H](Cc2ccc(F)c(Cl)c2)C[C@@H]1C(=O)N[C@@H](C)C(=O)NCc1cnc2[nH]cc(Cl)c2c1] | — |

TABLE 4D-continued

Exemplary MASP-2 inhibitory compounds

| Comp No. | Structure | Salt |
|---|---|---|
| III-28 | 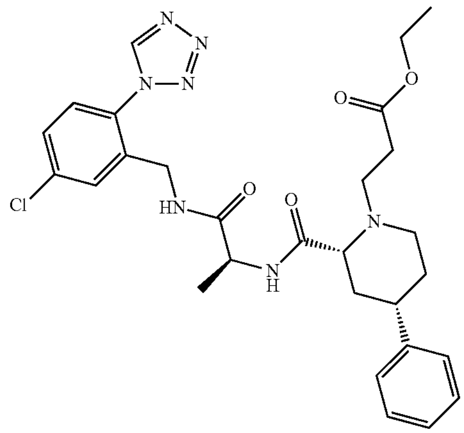 [SMILES: CCOC(=O)CCN1CC[C@H](c2ccccc2)C[C@@H]1C(=O)N[C@@H](C)C(=O)NCc1cc(Cl)ccc1-n1cnnn1] | — |
| III-29 | 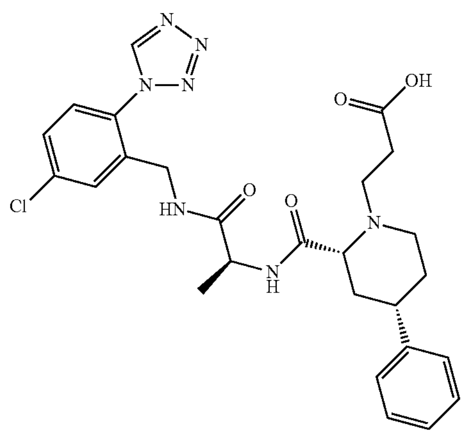 [SMILES: C[C@H](NC(=O)[C@H]1C[C@@H](c2ccccc2)CCN1CCC(=O)O)C(=O)NCc1cc(Cl)ccc1-n1cnnn1] | TFA |
| III-30 | 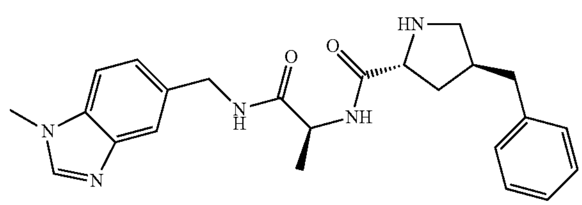 [SMILES: C[C@H](NC(=O)[C@H]1C[C@H](Cc2ccccc2)CN1)C(=O)NCc1ccc2c(c1)ncn2C] | TFA |
| III-31 | 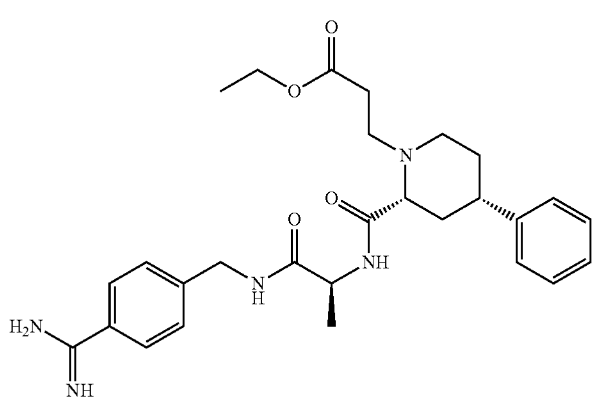 [SMILES: CCOC(=O)CCN1CC[C@H](c2ccccc2)C[C@@H]1C(=O)N[C@@H](C)C(=O)NCc1ccc(C(=N)N)cc1] | — |

TABLE 4D-continued

Exemplary MASP-2 inhibitory compounds

| Comp No. | Structure | Salt |
|---|---|---|
| III-32 | 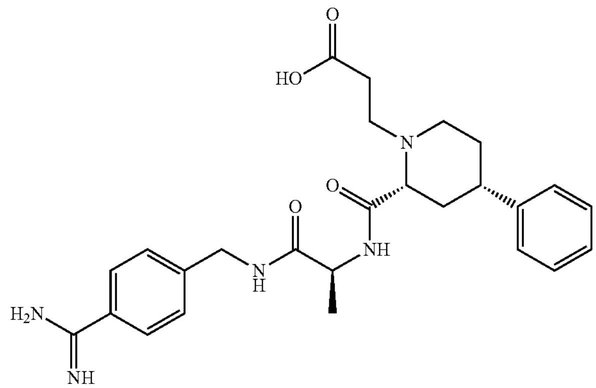 [SMILES: C[C@H](NC(=O)[C@H]1C[C@@H](c2ccccc2)CCN1CCC(=O)O)C(=O)NCc1ccc(C(=N)N)cc1] | 2TFA |
| III-33 | 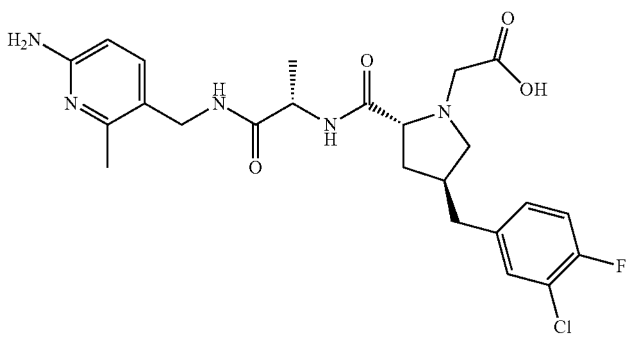 [SMILES: Cc1nc(N)ccc1CNC(=O)[C@H](C)NC(=O)[C@H]1C[C@H](Cc2ccc(F)c(Cl)c2)CN1CC(=O)O] | 2TFA |
| III-34 | 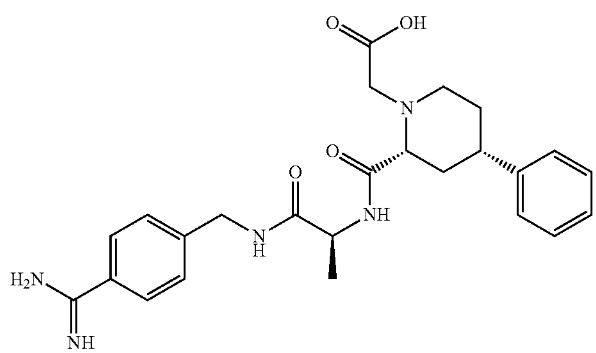 [SMILES: C[C@H](NC(=O)[C@H]1C[C@@H](c2ccccc2)CCN1CC(=O)O)C(=O)NCc1ccc(C(=N)N)cc1] | 2TFA |
| III-35 | 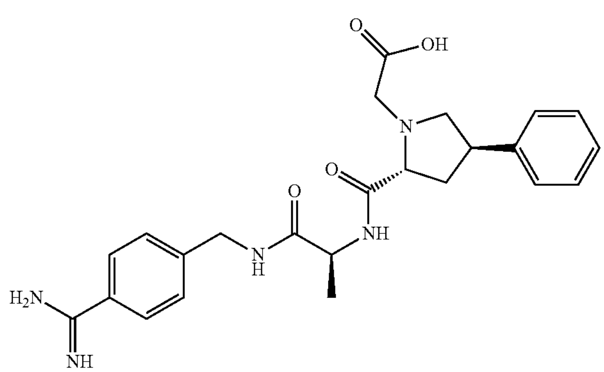 [SMILES: C[C@H](NC(=O)[C@H]1C[C@H](c2ccccc2)CN1CC(=O)O)C(=O)NCc1ccc(C(=N)N)cc1] | 2TFA |

TABLE 4D-continued

Exemplary MASP-2 inhibitory compounds

| Comp No. | Structure | Salt |
|---|---|---|
| III-36 | 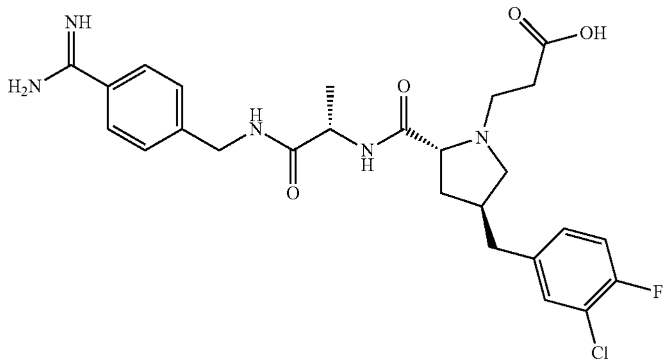 [SMILES: C[C@H](NC(=O)[C@H]1C[C@H](Cc2ccc(F)c(Cl)c2)CN1CCC(=O)O)C(=O)NCc1ccc(C(=N)N)cc1] | 2TFA |
| III-37 | 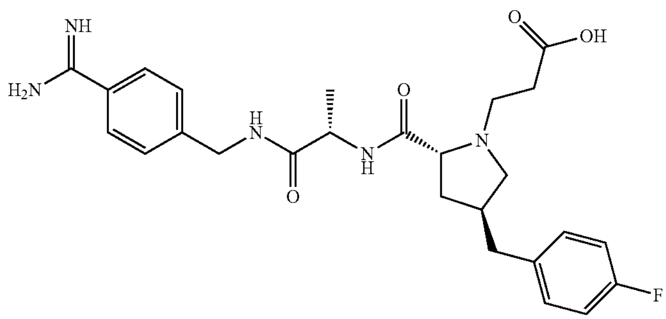 [SMILES: C[C@H](NC(=O)[C@H]1C[C@H](Cc2ccc(F)cc2)CN1CCC(=O)O)C(=O)NCc1ccc(C(=N)N)cc1] | 2TFA |
| III-38 | 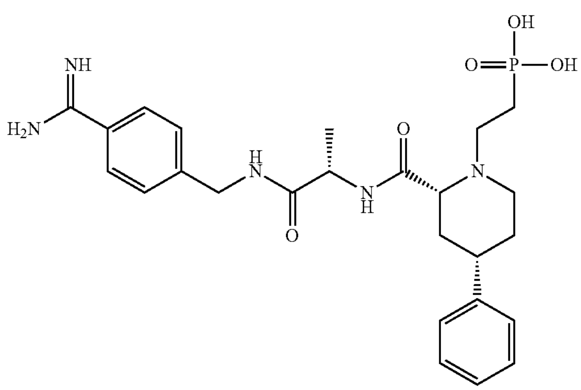 [SMILES: C[C@H](NC(=O)[C@H]1C[C@@H](c2ccccc2)CCN1CCP(=O)(O)O)C(=O)NCc1ccc(C(=N)N)cc1] | 2TFA |
| III-39 | 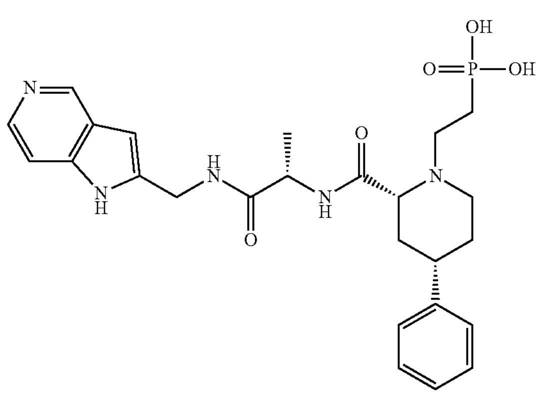 [SMILES: C[C@H](NC(=O)[C@H]1C[C@@H](c2ccccc2)CCN1CCP(=O)(O)O)C(=O)NCc1cc2cnccc2[nH]1] | 2TFA |

TABLE 4D-continued

Exemplary MASP-2 inhibitory compounds

| Comp No. | Structure | Salt |
|---|---|---|
| III-40 | 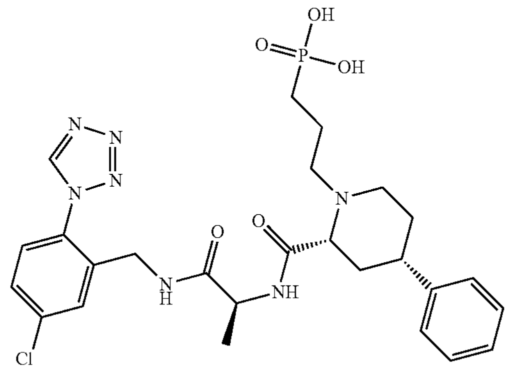 [SMILES: C[C@H](NC(=O)[C@H]1C[C@@H](c2ccccc2)CCN1CCCP(=O)(O)O)C(=O)NCc1cc(Cl)ccc1-n1cnnn1] | 2TFA |
| III-41 | 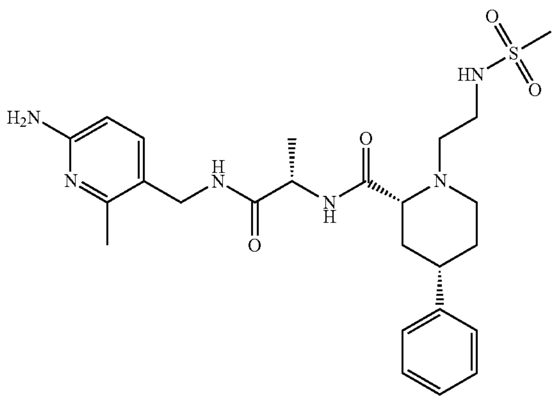 [SMILES: Cc1nc(N)ccc1CNC(=O)[C@H](C)NC(=O)[C@H]1C[C@@H](c2ccccc2)CCN1CCNS(C)(=O)=O] | 2TFA |
| III-42 | 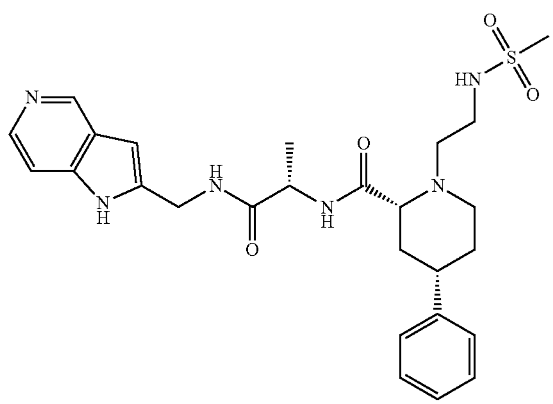 [SMILES: C[C@H](NC(=O)[C@H]1C[C@@H](c2ccccc2)CCN1CCNS(C)(=O)=O)C(=O)NCc1cc2cnccc2[nH]1] | 2TFA |
| III-43 | 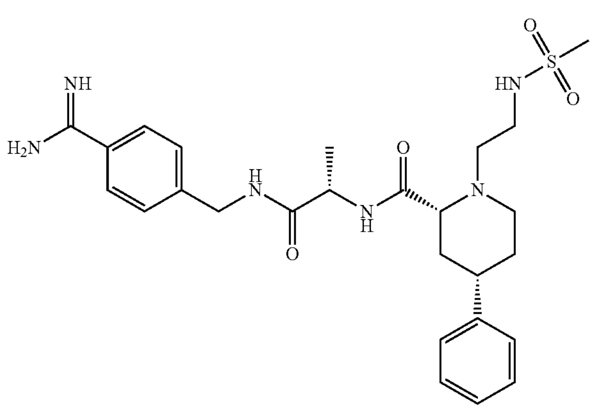 [SMILES: C[C@H](NC(=O)[C@H]1C[C@@H](c2ccccc2)CCN1CCNS(C)(=O)=O)C(=O)NCc1ccc(C(=N)N)cc1] | 2TFA |

TABLE 4D-continued

| Exemplary MASP-2 inhibitory compounds | | |
|---|---|---|
| Comp No. | Structure | Salt |
| III-44 | | 2TFA |
| III-45 | | HCl |
| III-46 | | TFA |
| III-47 | | 2HCl |
| III-48 | | 2TFA |

TABLE 4D-continued

Exemplary MASP-2 inhibitory compounds

| Comp No. | Structure | Salt |
|---|---|---|
| III-49 | 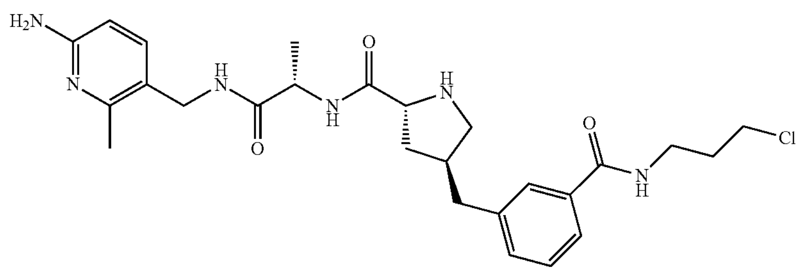 [SMILES: Cc1nc(N)ccc1CNC(=O)[C@H](C)NC(=O)[C@H]1C[C@H](Cc2cccc(C(=O)NCCCCl)c2)CN1] | 2TFA |
| III-50 | 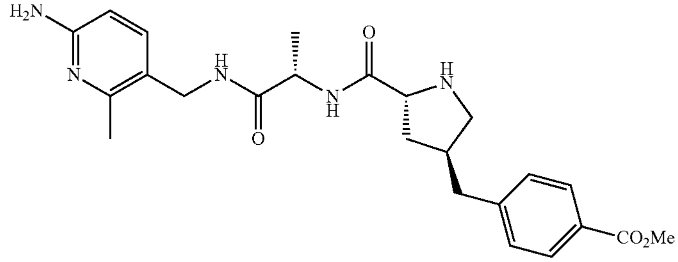 [SMILES: COC(=O)c1ccc(C[C@@H]2CN[C@@H](C(=O)N[C@@H](C)C(=O)NCc3ccc(N)nc3C)C2)cc1] | 2HCl |
| III-51 | 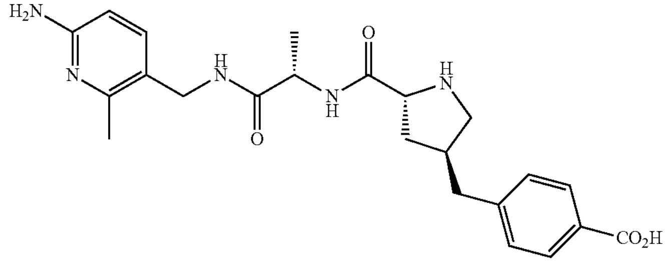 [SMILES: Cc1nc(N)ccc1CNC(=O)[C@H](C)NC(=O)[C@H]1C[C@H](Cc2ccc(C(=O)O)cc2)CN1] | 2TFA |
| III-52 | 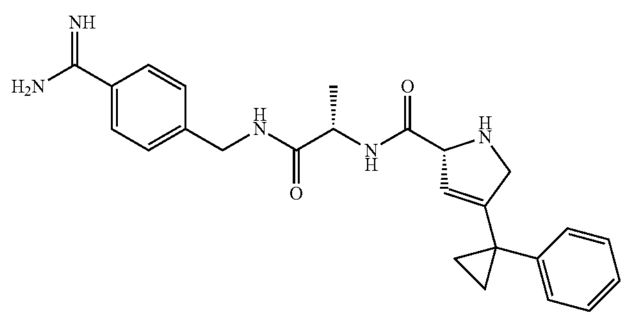 [SMILES: C[C@H](NC(=O)[C@H]1C=C(C2(c3ccccc3)CC2)CN1)C(=O)NCc1ccc(C(=N)N)cc1] | 2HCl |
| III-53 | 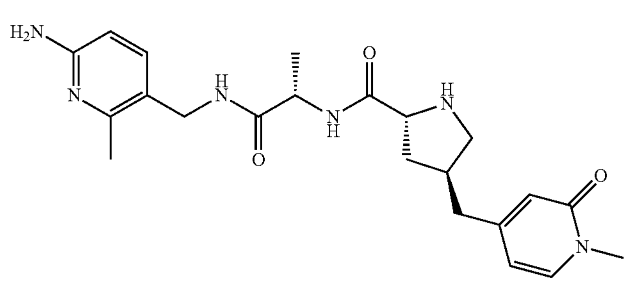 [SMILES: Cc1nc(N)ccc1CNC(=O)[C@H](C)NC(=O)[C@H]1C[C@H](Cc2ccn(C)c(=O)c2)CN1] | 2TFA |

TABLE 4D-continued

Exemplary MASP-2 inhibitory compounds

| Comp No. | Structure | Salt |
|---|---|---|
| III-54 | 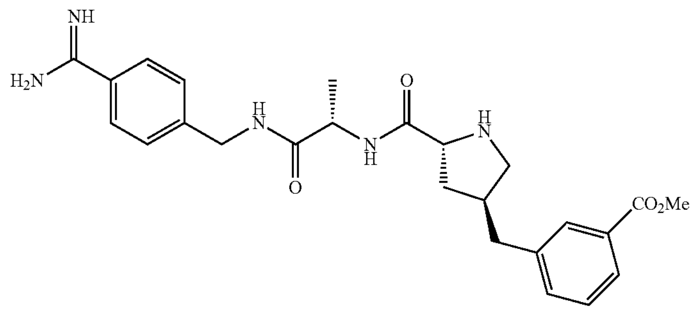 [SMILES: COC(=O)c1cccc(C[C@@H]2CN[C@@H](C(=O)N[C@@H](C)C(=O)NCc3ccc(C(=N)N)cc3)C2)c1] | 2TFA |
| III-55 | 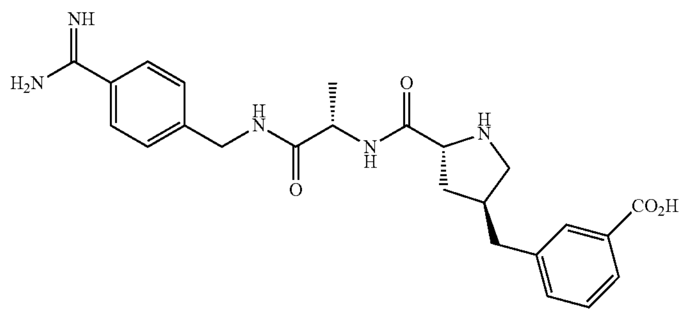 [SMILES: C[C@H](NC(=O)[C@H]1C[C@H](Cc2cccc(C(=O)O)c2)CN1)C(=O)NCc1ccc(C(=N)N)cc1] | 2TFA |
| III-56 | 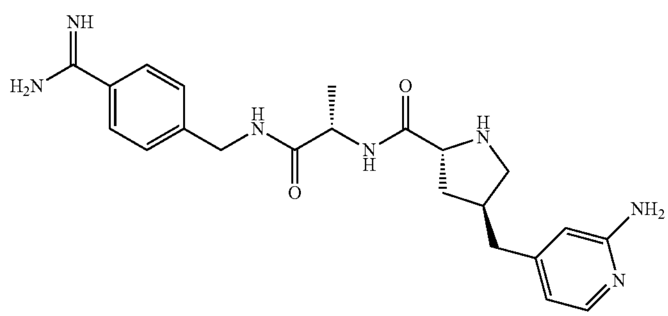 [SMILES: C[C@H](NC(=O)[C@H]1C[C@H](Cc2ccnc(N)c2)CN1)C(=O)NCc1ccc(C(=N)N)cc1] | 2TFA |
| III-57 | 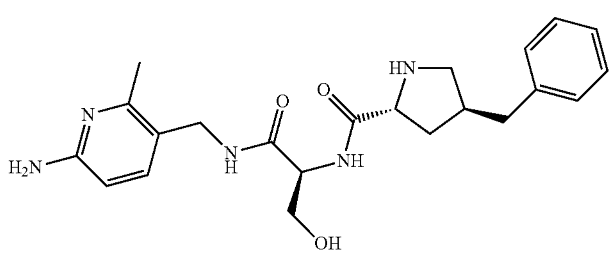 [SMILES: Cc1nc(N)ccc1CNC(=O)[C@H](CO)NC(=O)[C@H]1C[C@H](Cc2ccccc2)CN1] | 2HCl |
| III-58 | 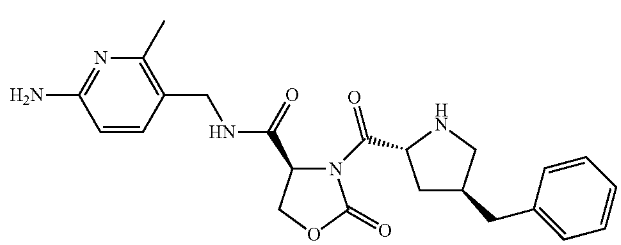 [SMILES: Cc1nc(N)ccc1CNC(=O)[C@@H]1COC(=O)N1C(=O)[C@H]1C[C@H](Cc2ccccc2)CN1] | 2TFA |

TABLE 4D-continued

| Comp No. | Structure | Salt |
|---|---|---|
| III-59 | 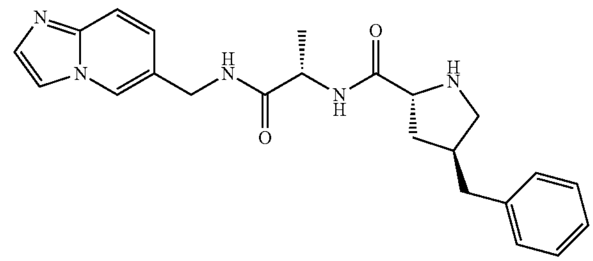 [SMILES: C[C@H](NC(=O)[C@H]1C[C@H](Cc2ccccc2)CN1)C(=O)NCc1ccc2nccn2c1] | TFA |
| III-60 | 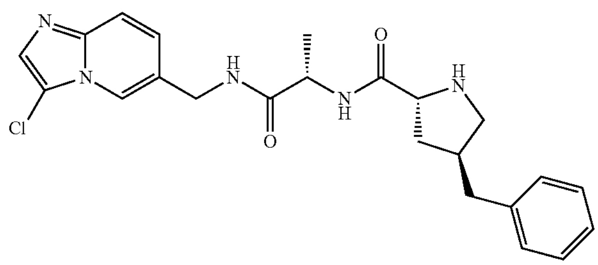 [SMILES: C[C@H](NC(=O)[C@H]1C[C@H](Cc2ccccc2)CN1)C(=O)NCc1ccc2ncc(Cl)n2c1] | HCl |
| III-61 | 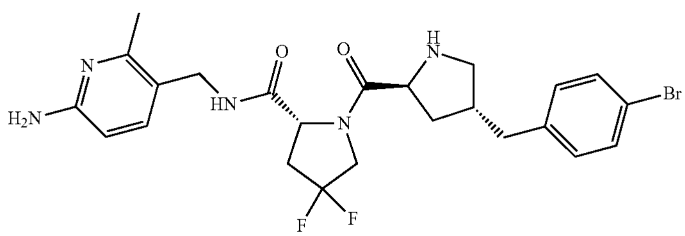 [SMILES: Cc1nc(N)ccc1CNC(=O)[C@H]1CC(F)(F)CN1C(=O)[C@@H]1C[C@@H](Cc2ccc(Br)cc2)CN1] | 2HCl |
| III-62 | 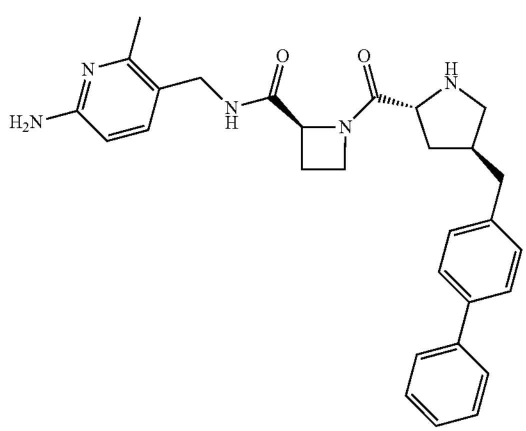 [SMILES: Cc1nc(N)ccc1CNC(=O)[C@@H]1CCN1C(=O)[C@H]1C[C@H](Cc2ccc(-c3ccccc3)cc2)CN1] | 2TFA |
| III-63 | 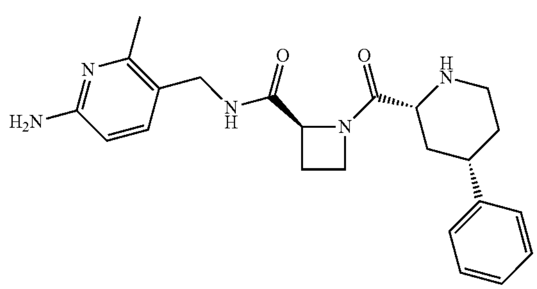 [SMILES: Cc1nc(N)ccc1CNC(=O)[C@@H]1CCN1C(=O)[C@H]1C[C@@H](c2ccccc2)CCN1] | 2TFA |

TABLE 4D-continued

Exemplary MASP-2 inhibitory compounds

| Comp No. | Structure | Salt |
|---|---|---|
| III-64 | 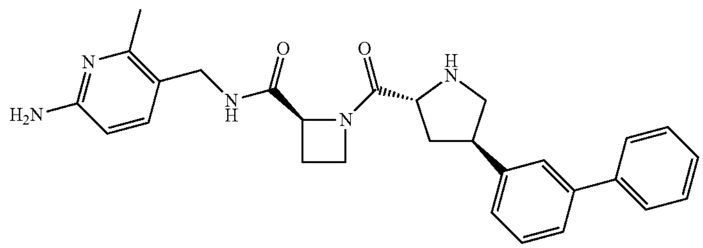 [SMILES: Cc1nc(N)ccc1CNC(=O)[C@@H]1CCN1C(=O)[C@H]1C[C@H](c2cccc(-c3ccccc3)c2)CN1] | 2TFA |
| III-65 | 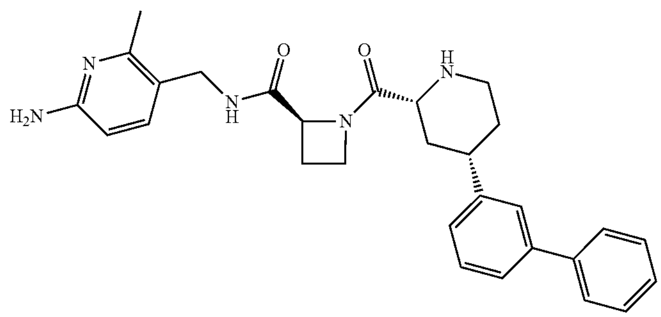 [SMILES: Cc1nc(N)ccc1CNC(=O)[C@@H]1CCN1C(=O)[C@H]1C[C@@H](c2cccc(-c3ccccc3)c2)CCN1] | 2TFA |
| III-66 | 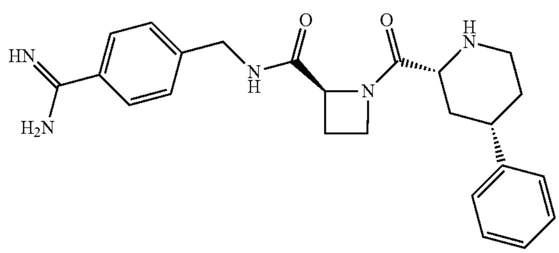 [SMILES: N=C(N)c1ccc(CNC(=O)[C@@H]2CCN2C(=O)[C@H]2C[C@@H](c3ccccc3)CCN2)cc1] | 2TFA |
| III-67 | 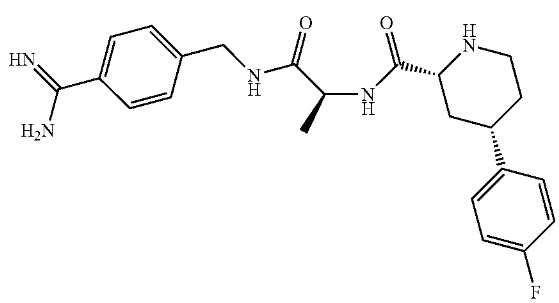 [SMILES: C[C@H](NC(=O)[C@H]1C[C@@H](c2ccc(F)cc2)CCN1)C(=O)NCc1ccc(C(=N)N)cc1] | 2TFA |
| III-68 | 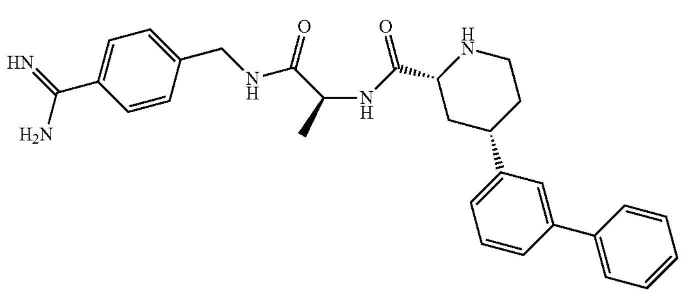 [SMILES: C[C@H](NC(=O)[C@H]1C[C@@H](c2cccc(-c3ccccc3)c2)CCN1)C(=O)NCc1ccc(C(=N)N)cc1] | 2TFA |

TABLE 4D-continued

Exemplary MASP-2 inhibitory compounds

| Comp No. | Structure | Salt |
|---|---|---|
| III-69 | 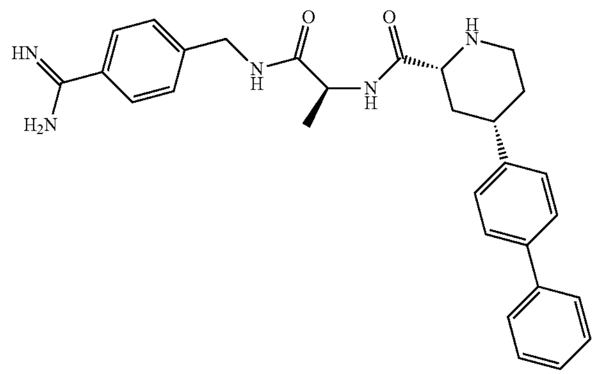 [SMILES: C[C@H](NC(=O)[C@H]1C[C@@H](c2ccc(-c3ccccc3)cc2)CCN1)C(=O)NCc1ccc(C(=N)N)cc1] | 2TFA |
| III-70 | 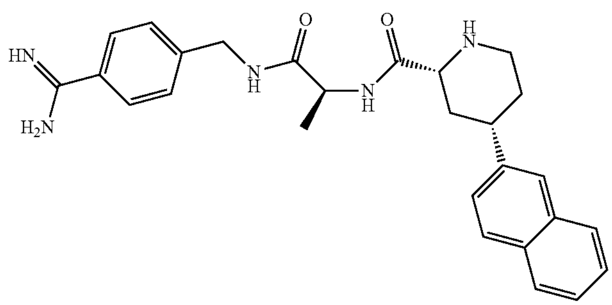 [SMILES: C[C@H](NC(=O)[C@H]1C[C@@H](c2ccc3ccccc3c2)CCN1)C(=O)NCc1ccc(C(=N)N)cc1] | 2TFA |
| III-71 | 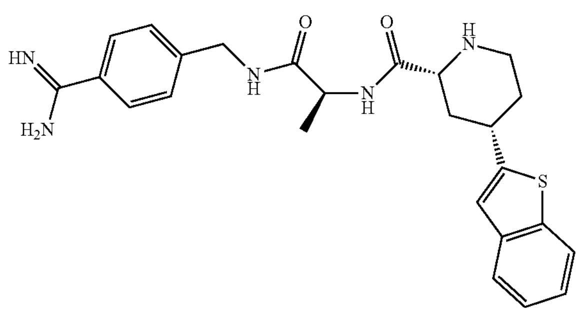 [SMILES: C[C@H](NC(=O)[C@H]1C[C@@H](c2cc3ccccc3s2)CCN1)C(=O)NCc1ccc(C(=N)N)cc1] | 2TFA |
| III-72 | 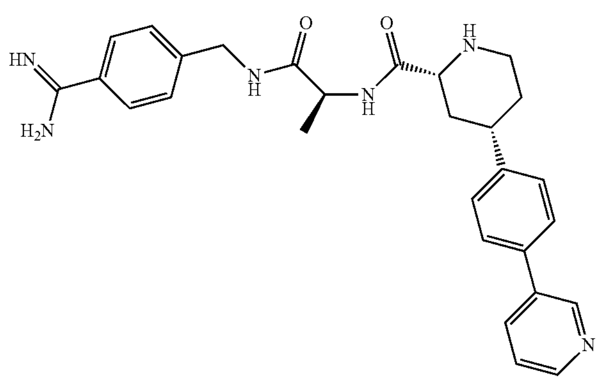 [SMILES: C[C@H](NC(=O)[C@H]1C[C@@H](c2ccc(-c3cccnc3)cc2)CCN1)C(=O)NCc1ccc(C(=N)N)cc1] | 2TFA |

TABLE 4D-continued
Exemplary MASP-2 inhibitory compounds
| Comp No. | Structure | Salt |
|---|---|---|
| III-73 | 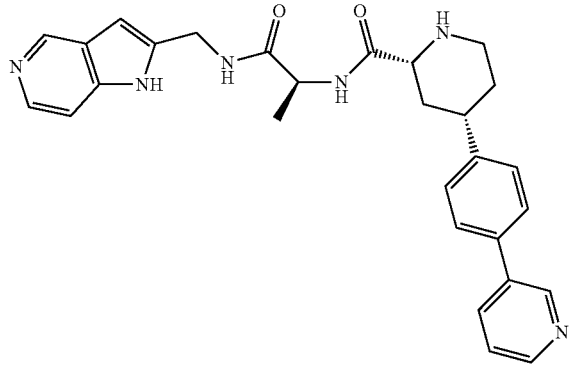 [SMILES: C[C@H](NC(=O)[C@H]1C[C@@H](c2ccc(-c3cccnc3)cc2)CCN1)C(=O)NCc1cc2cnccc2[nH]1] | 2TFA |
| III-74 | 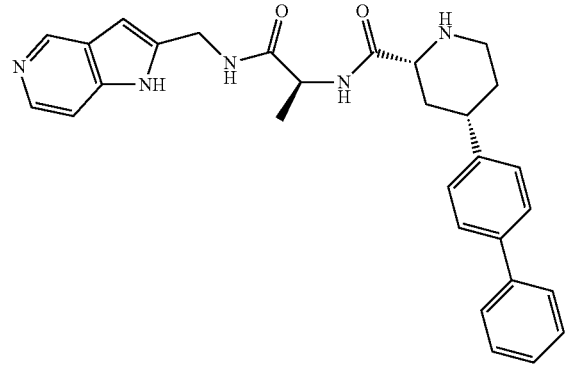 [SMILES: C[C@H](NC(=O)[C@H]1C[C@@H](c2ccc(-c3ccccc3)cc2)CCN1)C(=O)NCc1cc2cnccc2[nH]1] | 2TFA |
| III-75 | 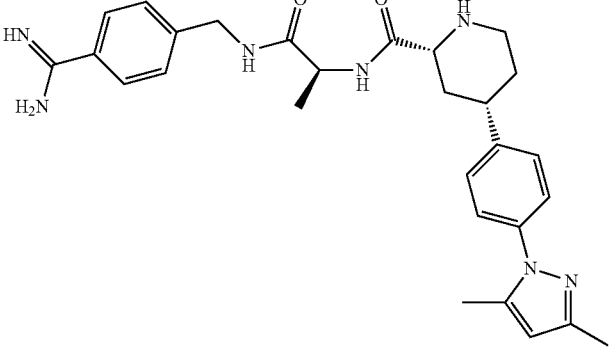 | 2HCl |
| III-76 | 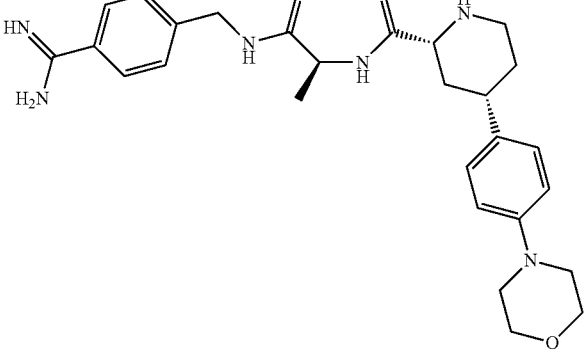 | 2HCl |

TABLE 4D-continued

Exemplary MASP-2 inhibitory compounds

| Comp No. | Structure | Salt |
|---|---|---|
| III-77 | 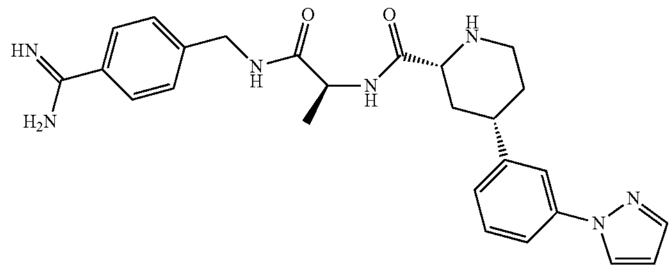 [SMILES: C[C@H](NC(=O)[C@H]1C[C@@H](c2cccc(-n3cccn3)c2)CCN1)C(=O)NCc1ccc(C(=N)N)cc1] | 2HCl |
| III-78 | 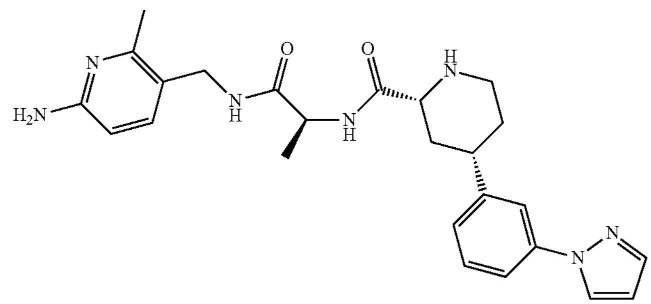 [SMILES: Cc1nc(N)ccc1CNC(=O)[C@H](C)NC(=O)[C@H]1C[C@@H](c2cccc(-n3cccn3)c2)CCN1] | 2HCl |
| III-79 | 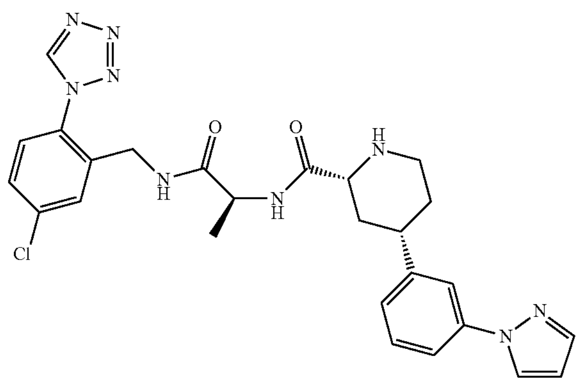 [SMILES: C[C@H](NC(=O)[C@H]1C[C@@H](c2cccc(-n3cccn3)c2)CCN1)C(=O)NCc1cc(Cl)ccc1-n1cnnn1] | HCl |
| III-80 | 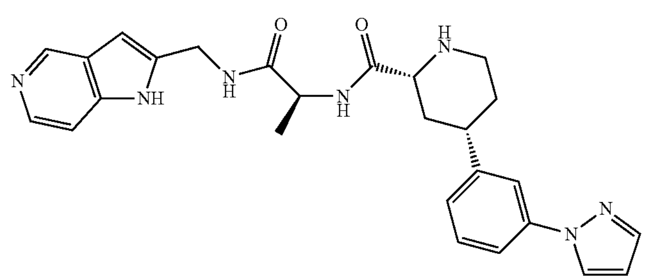 [SMILES: C[C@H](NC(=O)[C@H]1C[C@@H](c2cccc(-n3cccn3)c2)CCN1)C(=O)NCc1cc2cnccc2[nH]1] | 2HCl |
| III-81 | 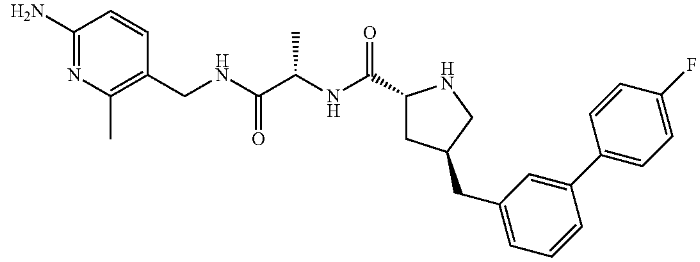 [SMILES: Cc1nc(N)ccc1CNC(=O)[C@H](C)NC(=O)[C@H]1C[C@H](Cc2cccc(-c3ccc(F)cc3)c2)CN1] | 2TFA |

TABLE 4D-continued

Exemplary MASP-2 inhibitory compounds

| Comp No. | Structure | Salt |
|---|---|---|
| III-82 | 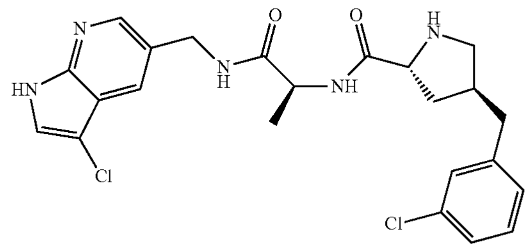 [SMILES: C[C@H](NC(=O)[C@H]1C[C@H](Cc2cccc(Cl)c2)CN1)C(=O)NCc1cnc2[nH]cc(Cl)c2c1] | 2HCl |
| III-83 | 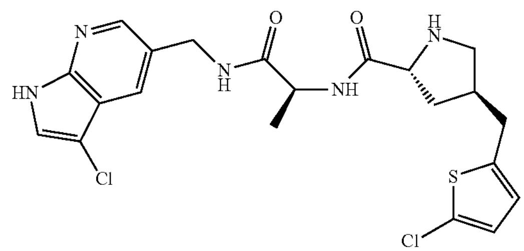 [SMILES: C[C@H](NC(=O)[C@H]1C[C@H](Cc2ccc(Cl)s2)CN1)C(=O)NCc1cnc2[nH]cc(Cl)c2c1] | 2HCl |
| III-84 | 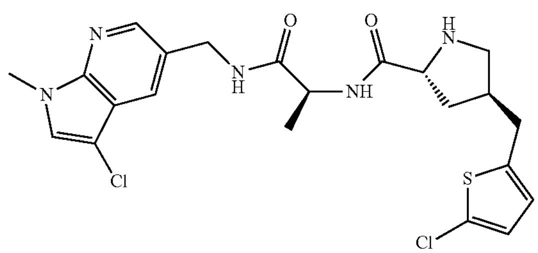 [SMILES: C[C@H](NC(=O)[C@H]1C[C@H](Cc2ccc(Cl)s2)CN1)C(=O)NCc1cnc2c(c1)c(Cl)cn2C] | 2HCl |
| III-85 | 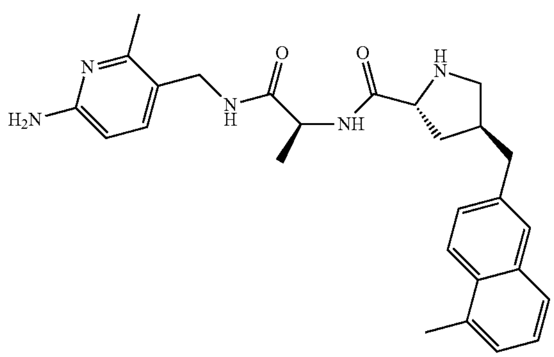 [SMILES: Cc1nc(N)ccc1CNC(=O)[C@H](C)NC(=O)[C@H]1C[C@H](Cc2ccc3c(C)cccc3c2)CN1] | 2HCl |
| III-86 | 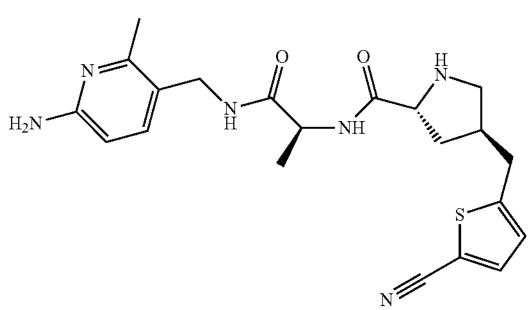 [SMILES: Cc1nc(N)ccc1CNC(=O)[C@H](C)NC(=O)[C@H]1C[C@H](Cc2ccc(C#N)s2)CN1] | 2HCl |

TABLE 4D-continued

Exemplary MASP-2 inhibitory compounds

| Comp No. | Structure | Salt |
|---|---|---|
| III-87 | 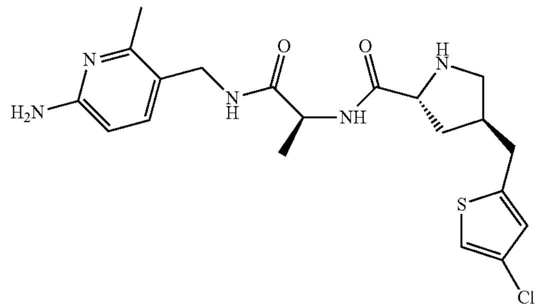 [SMILES: Cc1nc(N)ccc1CNC(=O)[C@H](C)NC(=O)[C@H]1C[C@H](Cc2cc(Cl)cs2)CN1] | 2HCl |
| III-88 | 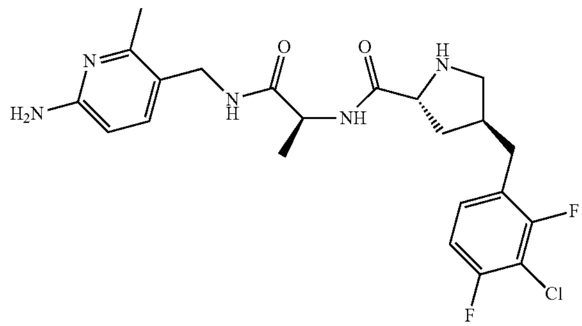 [SMILES: Cc1nc(N)ccc1CNC(=O)[C@H](C)NC(=O)[C@H]1C[C@H](Cc2ccc(F)c(Cl)c2F)CN1] | 2HCl |
| III-89 | 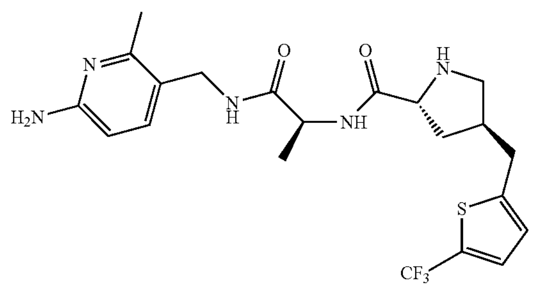 [SMILES: Cc1nc(N)ccc1CNC(=O)[C@H](C)NC(=O)[C@H]1C[C@H](Cc2ccc(C(F)(F)F)s2)CN1] | 2HCl |
| III-90 | 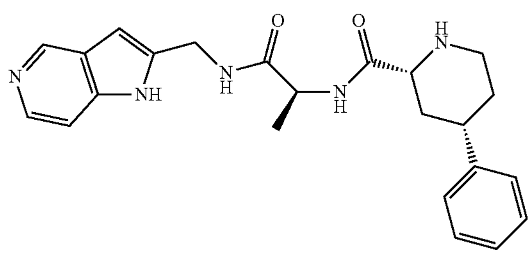 [SMILES: C[C@H](NC(=O)[C@H]1C[C@@H](c2ccccc2)CCN1)C(=O)NCc1cc2cnccc2[nH]1] | 2TFA |
| III-91 | 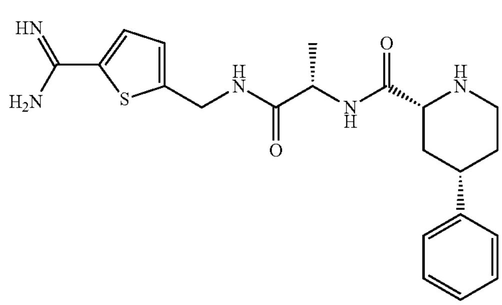 [SMILES: C[C@H](NC(=O)[C@H]1C[C@@H](c2ccccc2)CCN1)C(=O)NCc1ccc(C(=N)N)s1] | 2TFA |

TABLE 4D-continued

Exemplary MASP-2 inhibitory compounds

| Comp No. | Structure | Salt |
|---|---|---|
| III-92 | 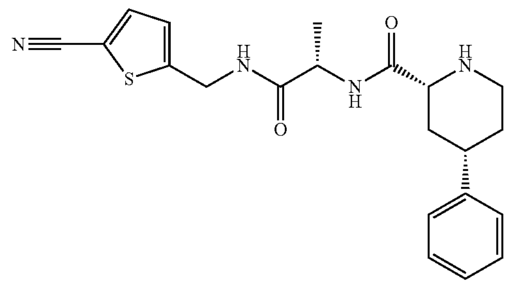 [SMILES: C[C@H](NC(=O)[C@H]1C[C@@H](c2ccccc2)CCN1)C(=O)NCc1ccc(C#N)s1] | HCl |
| III-93 | 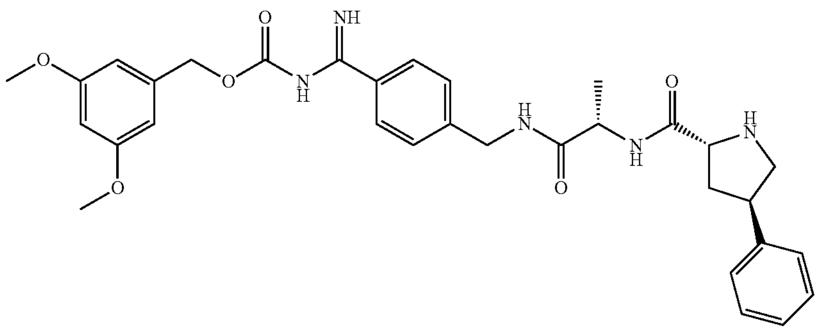 [SMILES: COc1cc(COC(=O)NC(=N)c2ccc(CNC(=O)[C@H](C)NC(=O)[C@H]3C[C@H](c4ccccc4)CN3)cc2)cc(OC)c1] | — |
| III-94 | 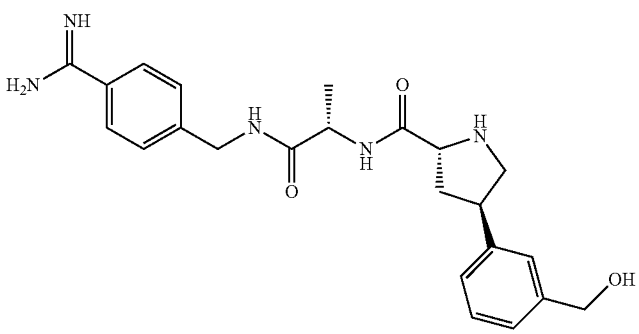 [SMILES: C[C@H](NC(=O)[C@H]1C[C@H](c2cccc(CO)c2)CN1)C(=O)NCc1ccc(C(=N)N)cc1] | 2TFA |
| III-95 | 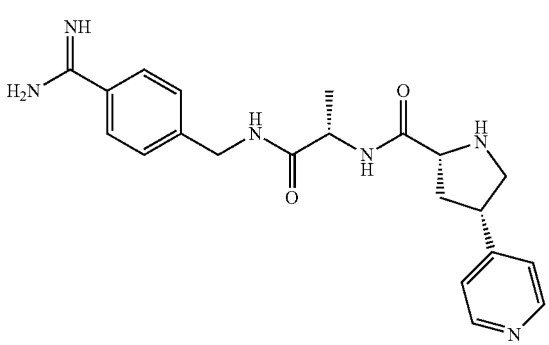 [SMILES: C[C@H](NC(=O)[C@H]1C[C@@H](c2ccncc2)CN1)C(=O)NCc1ccc(C(=N)N)cc1] | 2TFA |

TABLE 4D-continued
Exemplary MASP-2 inhibitory compounds
| Comp No. | Structure | Salt |
|---|---|---|
| III-96 | 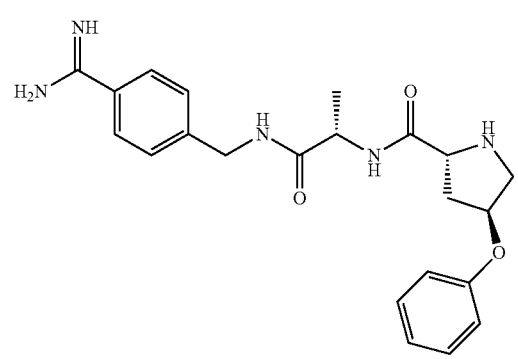 [SMILES: C[C@H](NC(=O)[C@H]1C[C@H](Oc2ccccc2)CN1)C(=O)NCc1ccc(C(=N)N)cc1] | 2TFA |
| III-97 | 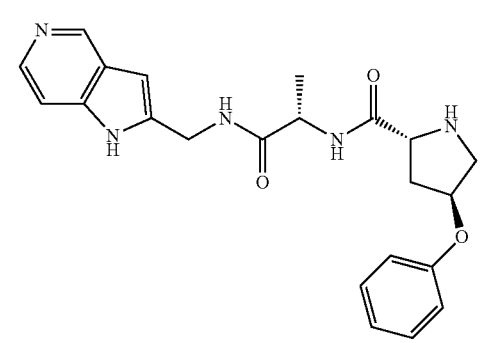 [SMILES: C[C@H](NC(=O)[C@H]1C[C@H](Oc2ccccc2)CN1)C(=O)NCc1cc2cnccc2[nH]1] | 2TFA |
| III-98 | 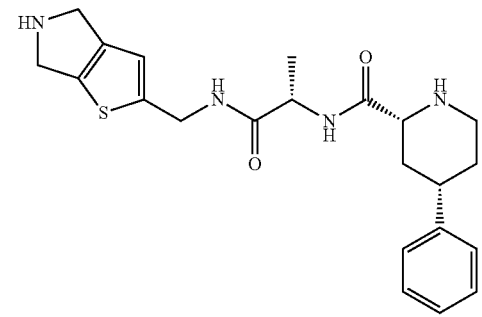 [SMILES: C[C@H](NC(=O)[C@H]1C[C@@H](c2ccccc2)CCN1)C(=O)NCc1cc2c(s1)CNC2] | 2TFA |
| III-99 | 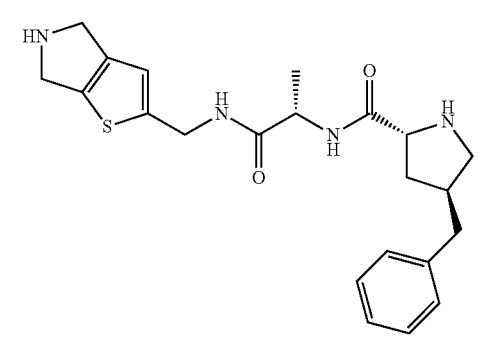 [SMILES: C[C@H](NC(=O)[C@H]1C[C@H](Cc2ccccc2)CN1)C(=O)NCc1cc2c(s1)CNC2] | 2TFA |

TABLE 4D-continued

Exemplary MASP-2 inhibitory compounds

| Comp No. | Structure | Salt |
|---|---|---|
| III-100 | 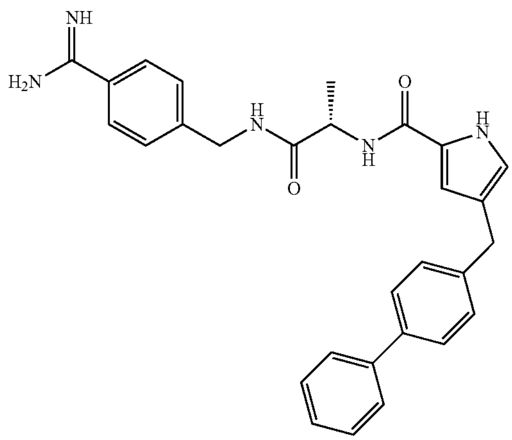 [SMILES: C[C@H](NC(=O)c1cc(Cc2ccc(-c3ccccc3)cc2)c[nH]1)C(=O)NCc1ccc(C(=N)N)cc1] | TFA |
| III-101 | 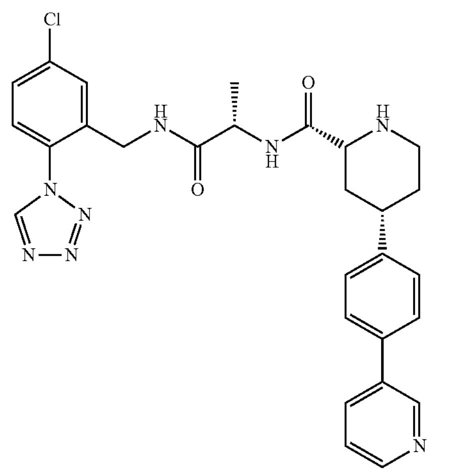 | TFA |
| III-102 | 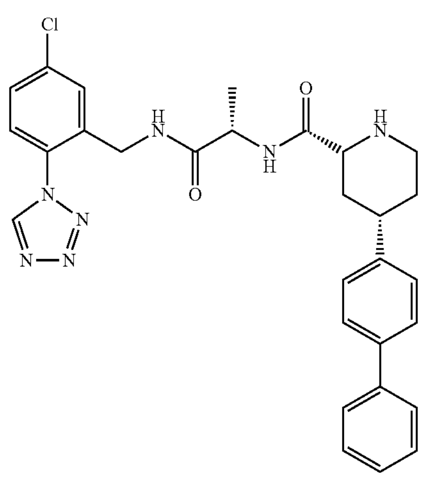 | TFA |

TABLE 4D-continued

Exemplary MASP-2 inhibitory compounds

| Comp No. | Structure | Salt |
|---|---|---|
| III-103 | 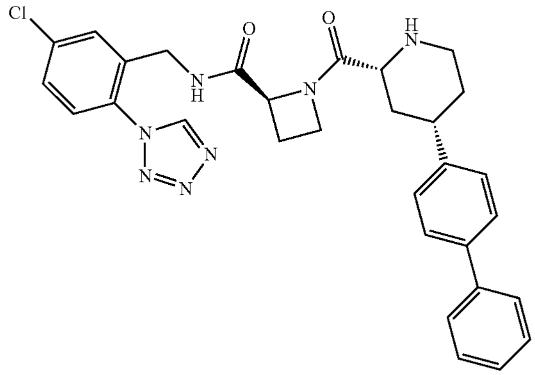 [SMILES: O=C(NCc1cc(Cl)ccc1-n1cnnn1)[C@@H]1CCN1C(=O)[C@H]1C[C@@H](c2ccc(-c3ccccc3)cc2)CCN1] | TFA |
| III-104 | 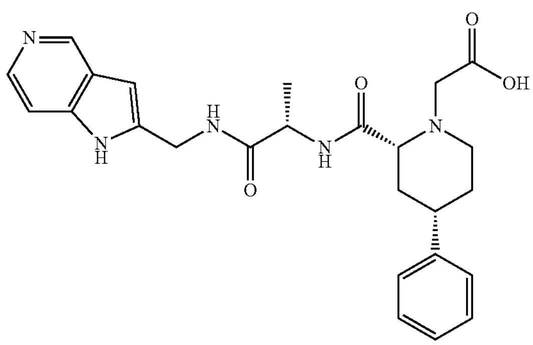 [SMILES: C[C@H](NC(=O)[C@H]1C[C@@H](c2ccccc2)CCN1CC(=O)O)C(=O)NCc1cc2cnccc2[nH]1] | 2TFA |
| III-105 | 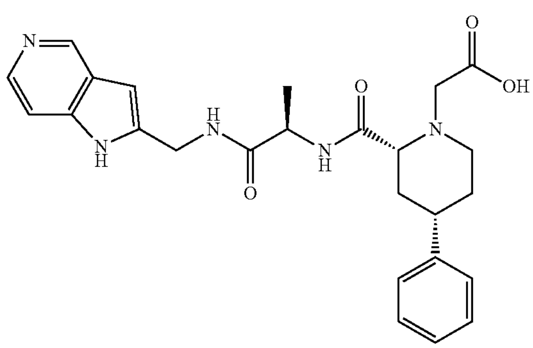 [SMILES: C[C@@H](NC(=O)[C@H]1C[C@@H](c2ccccc2)CCN1CC(=O)O)C(=O)NCc1cc2cnccc2[nH]1] | 2TFA |
| III-106 | 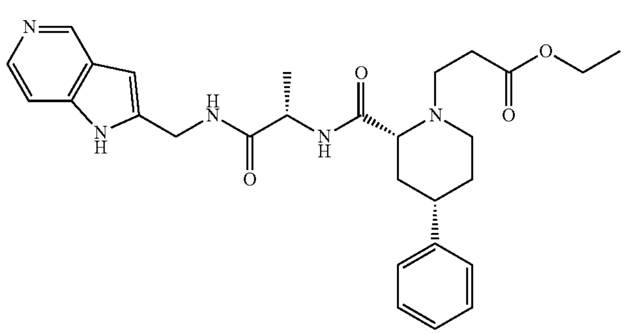 [SMILES: CCOC(=O)CCN1CC[C@H](c2ccccc2)C[C@@H]1C(=O)N[C@@H](C)C(=O)NCc1cc2cnccc2[nH]1] | — |

TABLE 4D-continued

Exemplary MASP-2 inhibitory compounds

| Comp No. | Structure | Salt |
|---|---|---|
| III-107 | 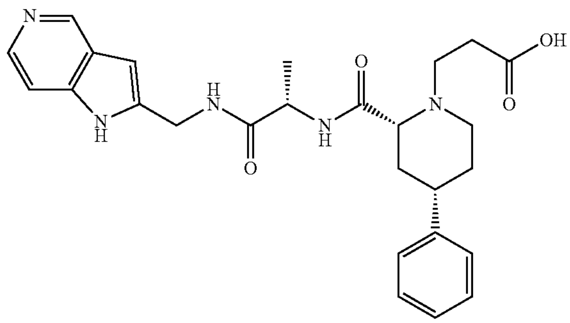 [SMILES: C[C@H](NC(=O)[C@H]1C[C@@H](c2ccccc2)CCN1CCC(=O)O)C(=O)NCc1cc2cnccc2[nH]1] | 2TFA |

TABLE 4E

Exemplary MASP-2 inhibitory compounds

| Comp No. | Structure | Salt |
|---|---|---|
| IV-1 | 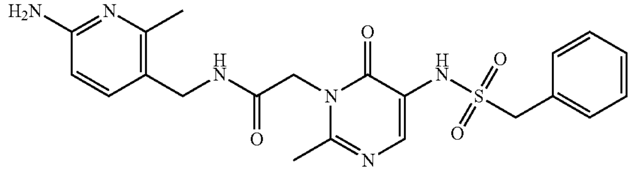 [SMILES: Cc1nc(N)ccc1CNC(=O)Cn1c(C)ncc(NS(=O)(=O)Cc2ccccc2)c1=O] | TFA |
| IV-2 | 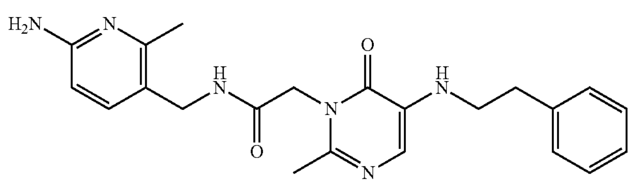 [SMILES: Cc1nc(N)ccc1CNC(=O)Cn1c(C)ncc(NCCc2ccccc2)c1=O] | TFA |
| IV-3 | 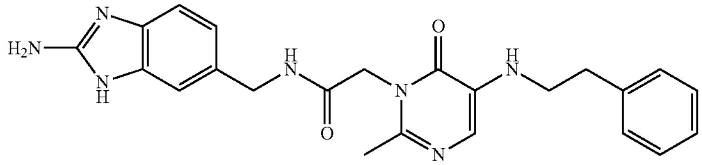 [SMILES: Cc1ncc(NCCc2ccccc2)c(=O)n1CC(=O)NCc1ccc2nc(N)[nH]c2c1] | TFA |
| IV-4 | 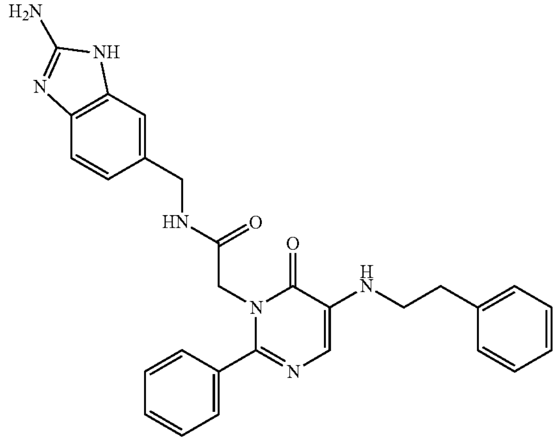 [SMILES: Nc1nc2ccc(CNC(=O)Cn3c(-c4ccccc4)ncc(NCCc4ccccc4)c3=O)cc2[nH]1] | TFA |

TABLE 4E-continued
Exemplary MASP-2 inhibitory compounds
| Comp No. | Structure | Salt |
|---|---|---|
| IV-5 | 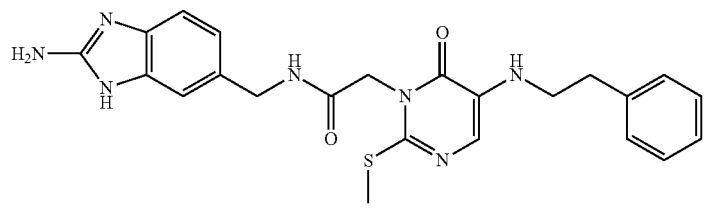 [SMILES: CSc1ncc(NCCc2ccccc2)c(=O)n1CC(=O)NCc1ccc2nc(N)[nH]c2c1] | — |
| IV-6 | 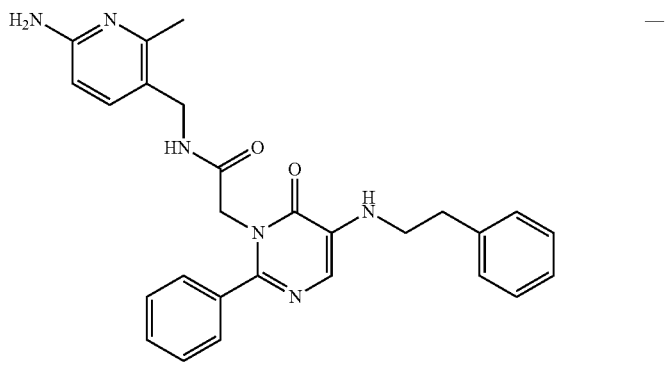 | — |
| IV-7 | 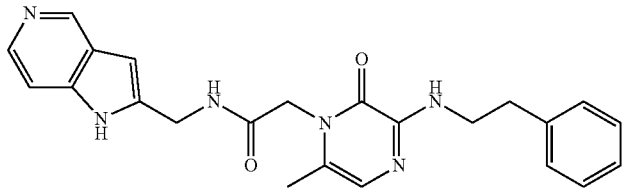 [SMILES: Cc1cnc(NCCc2ccccc2)c(=O)n1CC(=O)NCc1cc2cnccc2[nH]1] | — |
| IV-8 | 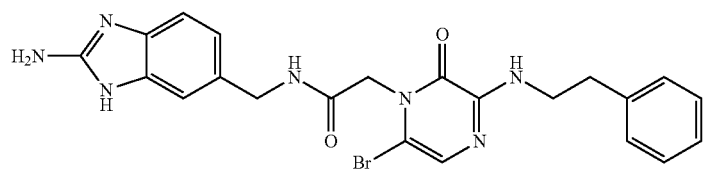 [SMILES: Nc1nc2ccc(CNC(=O)Cn3c(Br)cnc(NCCc4ccccc4)c3=O)cc2[nH]1] | — |
| IV-9 | 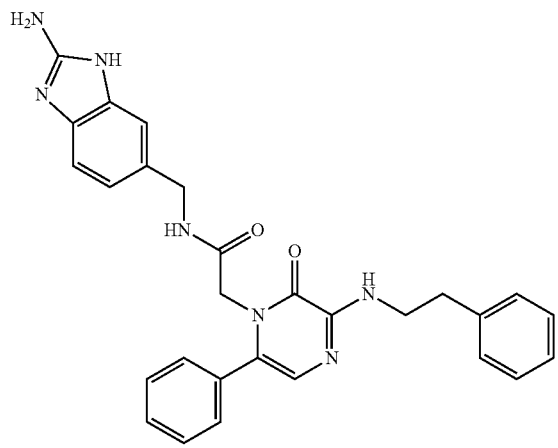 [SMILES: Nc1nc2ccc(CNC(=O)Cn3c(-c4ccccc4)cnc(NCCc4ccccc4)c3=O)cc2[nH]1] | — |

TABLE 4E-continued
Exemplary MASP-2 inhibitory compounds
| Comp No. | Structure | Salt |
|---|---|---|
| IV-10 | 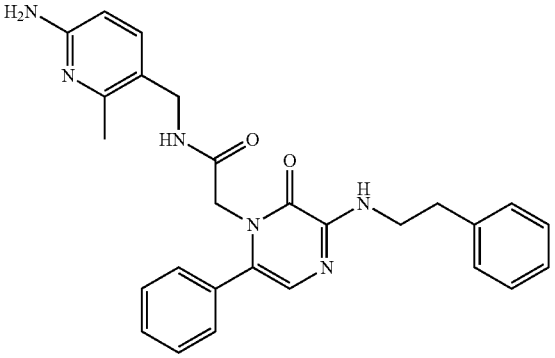 [SMILES: Cc1nc(N)ccc1CNC(=O)Cn1c(-c2ccccc2)cnc(NCCc2ccccc2)c1=O] | — |
| IV-11 | 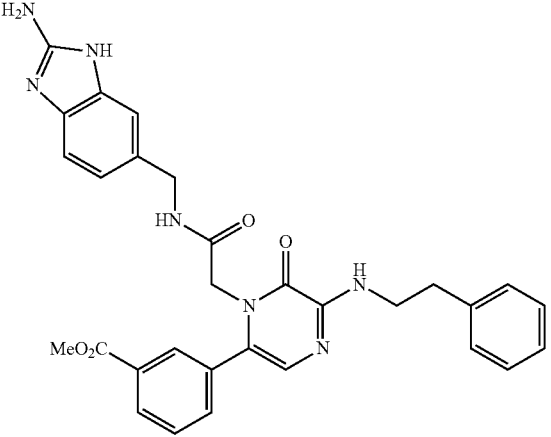 [SMILES: COC(=O)c1cccc(-c2cnc(NCCc3ccccc3)c(=O)n2CC(=O)NCc2ccc3nc(N)[nH]c3c2)c1] | — |
| IV-12 | 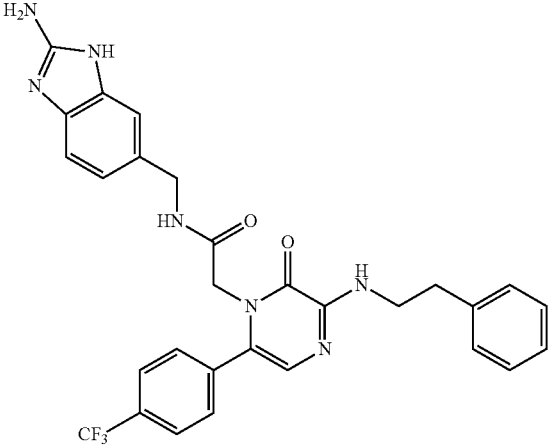 [SMILES: Nc1nc2ccc(CNC(=O)Cn3c(-c4ccc(C(F)(F)F)cc4)cnc(NCCc4ccccc4)c3=O)cc2[nH]1] | TFA |

TABLE 4E-continued

Exemplary MASP-2 inhibitory compounds

| Comp No. | Structure | Salt |
|---|---|---|
| IV-13 | 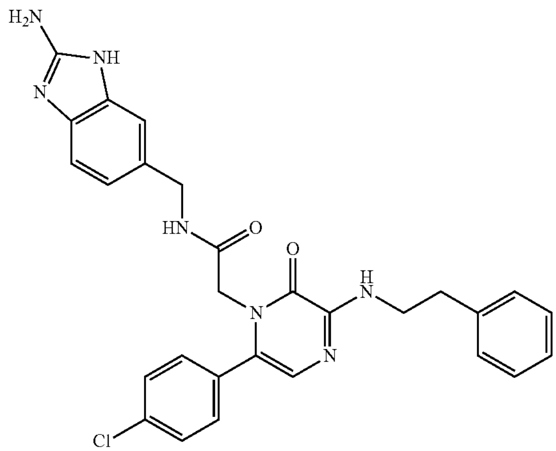 [SMILES: Nc1nc2ccc(CNC(=O)Cn3c(-c4ccc(Cl)cc4)cnc(NCCc4ccccc4)c3=O)cc2[nH]1] | TFA |
| IV-14 | 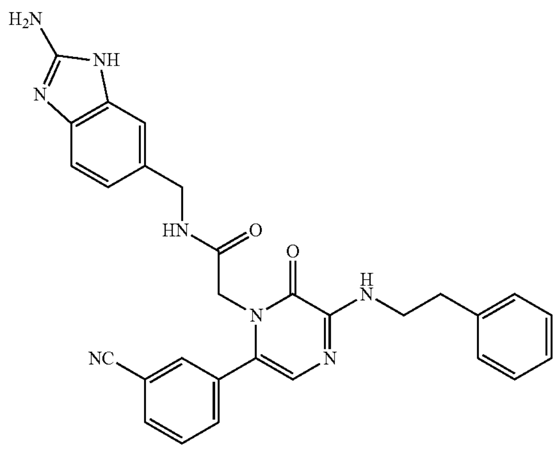 [SMILES: N#Cc1cccc(-c2cnc(NCCc3ccccc3)c(=O)n2CC(=O)NCc2ccc3nc(N)[nH]c3c2)c1] | — |
| IV-15 | 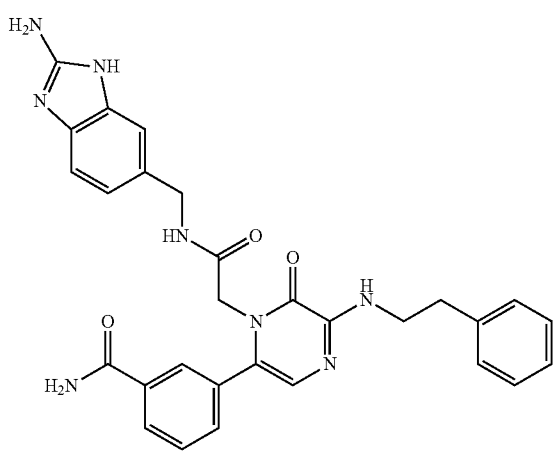 [SMILES: NC(=O)c1cccc(-c2cnc(NCCc3ccccc3)c(=O)n2CC(=O)NCc2ccc3nc(N)[nH]c3c2)c1] | TFA |

TABLE 4E-continued

Exemplary MASP-2 inhibitory compounds

| Comp No. | Structure | Salt |
|---|---|---|
| IV-16 | 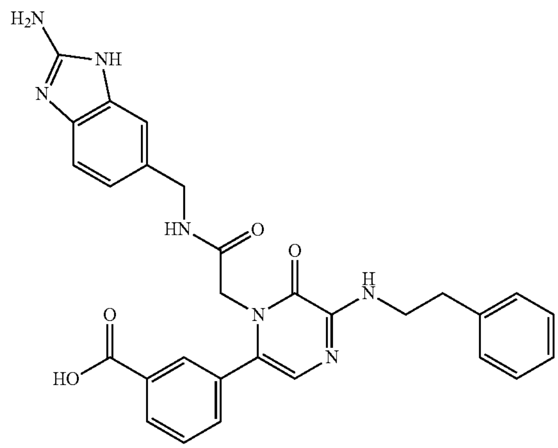 [SMILES: Nc1nc2ccc(CNC(=O)Cn3c(-c4cccc(C(=O)O)c4)cnc(NCCc4ccccc4)c3=O)cc2[nH]1] | TFA |
| IV-17 | 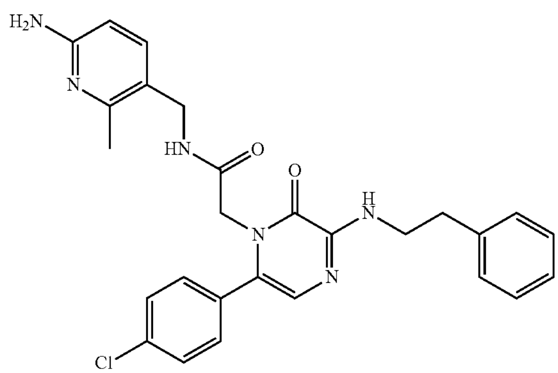 [SMILES: Cc1nc(N)ccc1CNC(=O)Cn1c(-c2ccc(Cl)cc2)cnc(NCCc2ccccc2)c1=O] | TFA |
| IV-18 | 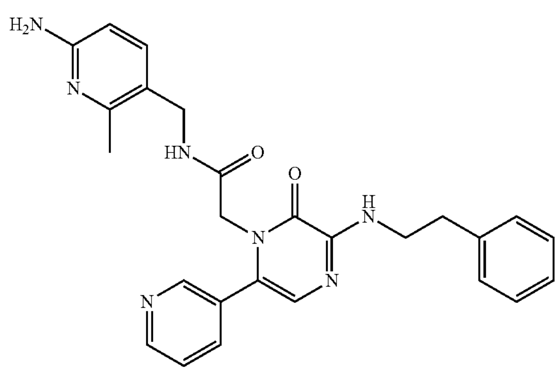 [SMILES: Cc1nc(N)ccc1CNC(=O)Cn1c(-c2cccnc2)cnc(NCCc2ccccc2)c1=O] | 2TFA |
| IV-19 | 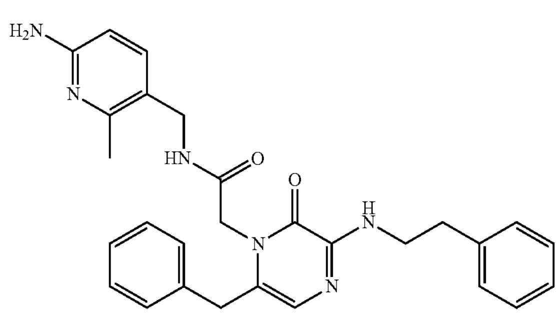 [SMILES: Cc1nc(N)ccc1CNC(=O)Cn1c(Cc2ccccc2)cnc(NCCc2ccccc2)c1=O] | TFA |

TABLE 4E-continued

Exemplary MASP-2 inhibitory compounds

| Comp No. | Structure | Salt |
|---|---|---|
| IV-20 | 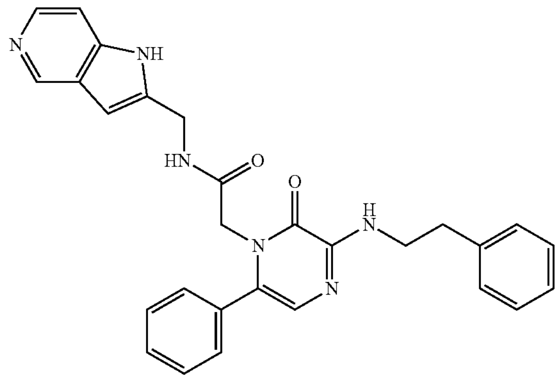 [SMILES: O=C(Cn1c(-c2ccccc2)cnc(NCCc2ccccc2)c1=O)NCc1cc2cnccc2[nH]1] | TFA |
| IV-21 | 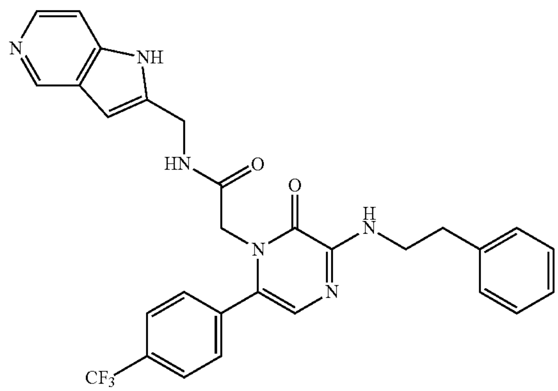 [SMILES: O=C(Cn1c(-c2ccc(C(F)(F)F)cc2)cnc(NCCc2ccccc2)c1=O)NCc1cc2cnccc2[nH]1] | TFA |
| IV-22 | 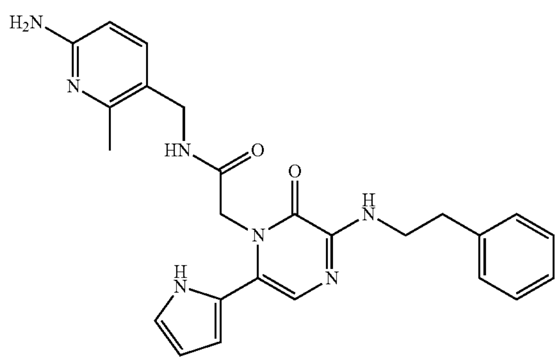 [SMILES: Cc1nc(N)ccc1CNC(=O)Cn1c(-c2ccc[nH]2)cnc(NCCc2ccccc2)c1=O] | — |
| IV-23 | 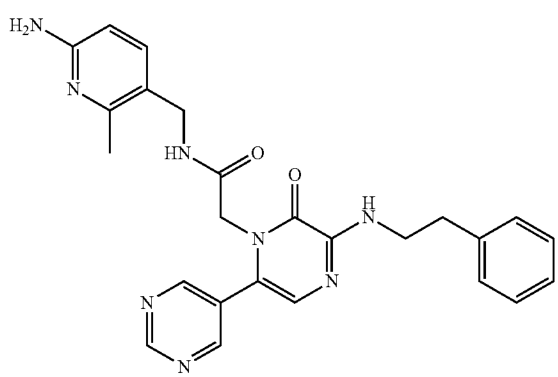 [SMILES: Cc1nc(N)ccc1CNC(=O)Cn1c(-c2cncnc2)cnc(NCCc2ccccc2)c1=O] | — |

TABLE 4E-continued
Exemplary MASP-2 inhibitory compounds
| Comp No. | Structure | Salt |
|---|---|---|
| IV-24 | 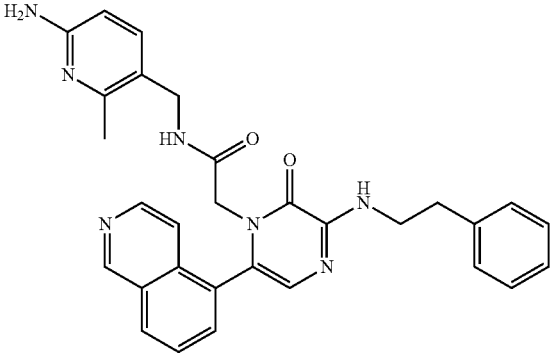 [SMILES: Cc1nc(N)ccc1CNC(=O)Cn1c(-c2cccc3cnccc23)cnc(NCCc2ccccc2)c1=O] | — |
| IV-25 | 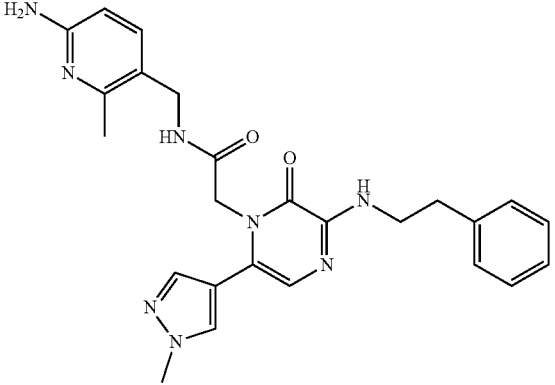 [SMILES: Cc1nc(N)ccc1CNC(=O)Cn1c(-c2cnn(C)c2)cnc(NCCc2ccccc2)c1=O] | — |
| IV-26 | 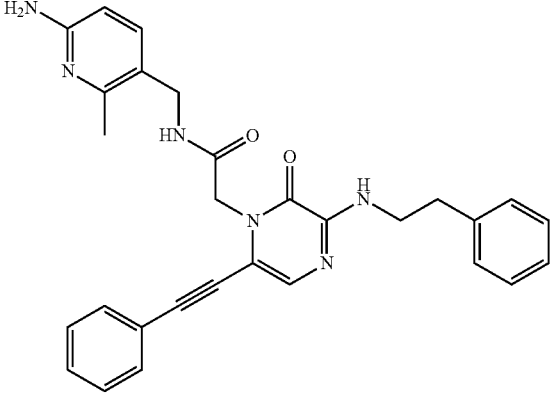 [SMILES: Cc1nc(N)ccc1CNC(=O)Cn1c(C#Cc2ccccc2)cnc(NCCc2ccccc2)c1=O] | — |
| IV-27 | 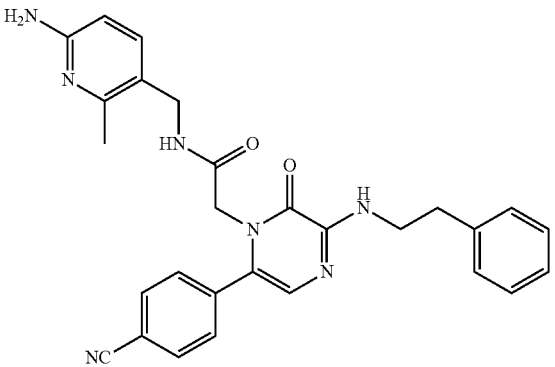 | — |

TABLE 4E-continued

Exemplary MASP-2 inhibitory compounds

| Comp No. | Structure | Salt |
|---|---|---|
| IV-28 | 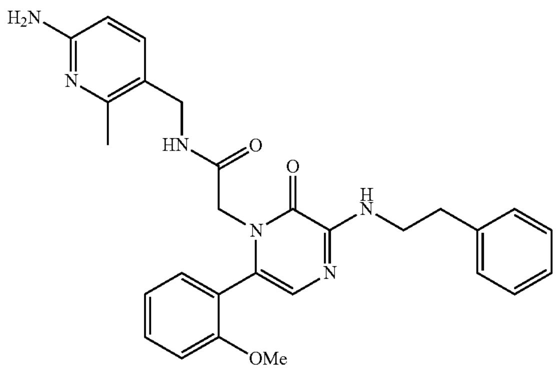 [SMILES: COc1ccccc1-c1cnc(NCCc2ccccc2)c(=O)n1CC(=O)NCc1ccc(N)nc1C] | HCl |
| IV-29 | 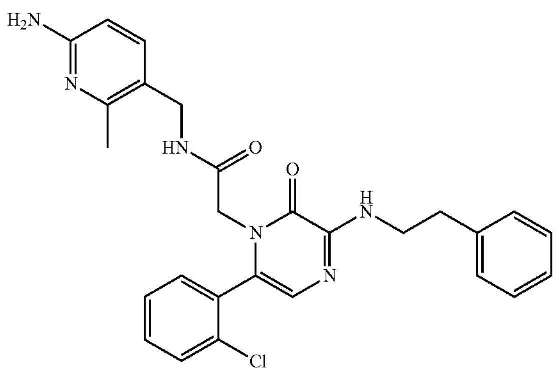 [SMILES: Cc1nc(N)ccc1CNC(=O)Cn1c(-c2ccccc2Cl)cnc(NCCc2ccccc2)c1=O] | — |
| IV-30 | 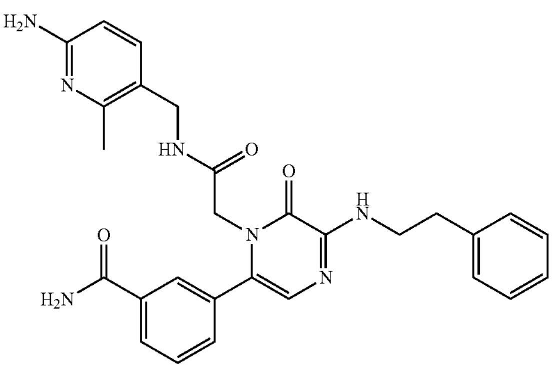 [SMILES: Cc1nc(N)ccc1CNC(=O)Cn1c(-c2cccc(C(N)=O)c2)cnc(NCCc2ccccc2)c1=O] | HCl |
| IV-31 | 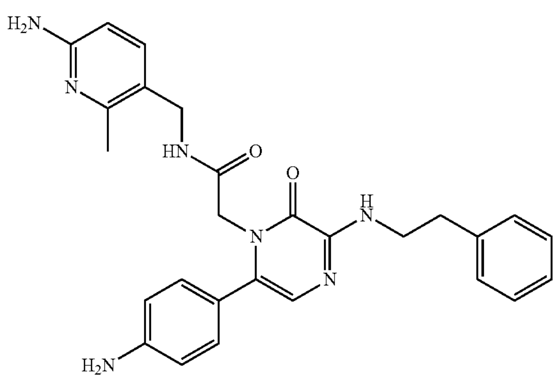 [SMILES: Cc1nc(N)ccc1CNC(=O)Cn1c(-c2ccc(N)cc2)cnc(NCCc2ccccc2)c1=O] | — |

TABLE 4E-continued

Exemplary MASP-2 inhibitory compounds

| Comp No. | Structure | Salt |
|---|---|---|
| IV-32 | 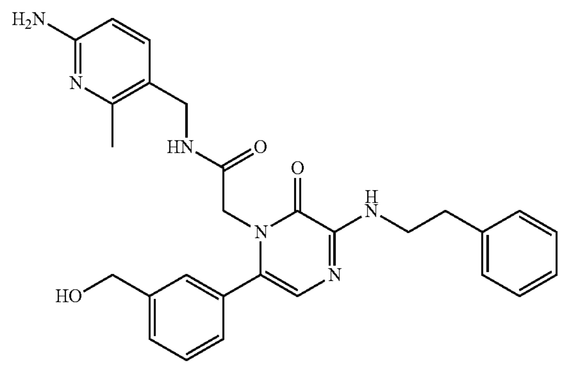 [SMILES: Cc1nc(N)ccc1CNC(=O)Cn1c(-c2cccc(CO)c2)cnc(NCCc2ccccc2)c1=O] | — |
| IV-33 | 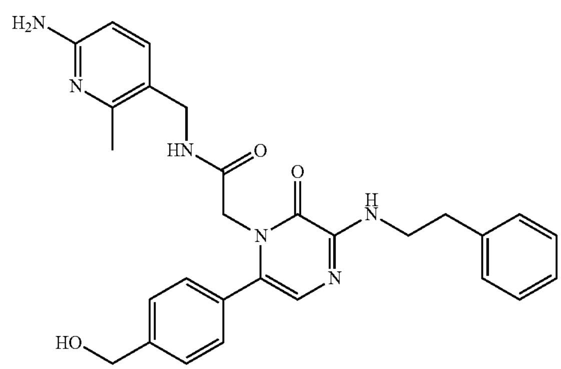 [SMILES: Cc1nc(N)ccc1CNC(=O)Cn1c(-c2ccc(CO)cc2)cnc(NCCc2ccccc2)c1=O] | — |
| IV-34 | 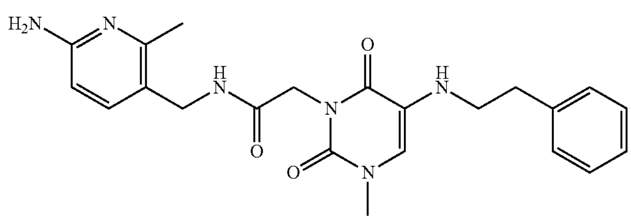 [SMILES: Cc1nc(N)ccc1CNC(=O)Cn1c(=O)c(NCCc2ccccc2)cn(C)c1=O] | — |
| IV-35 | 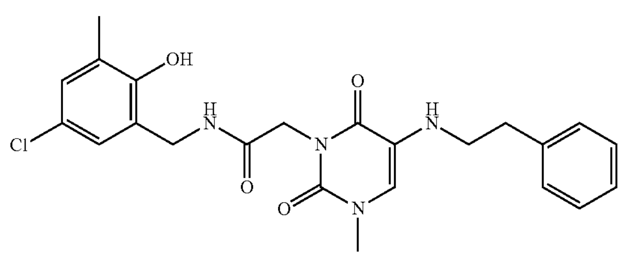 [SMILES: Cc1cc(Cl)cc(CNC(=O)Cn2c(=O)c(NCCc3ccccc3)cn(C)c2=O)c1O] | TFA |
| IV-36 | 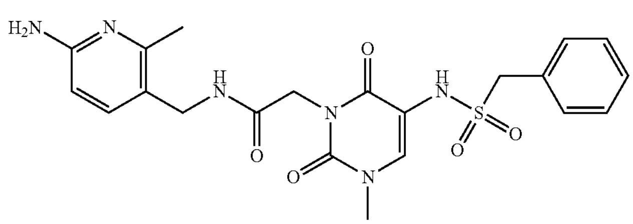 [SMILES: Cc1nc(N)ccc1CNC(=O)Cn1c(=O)c(NS(=O)(=O)Cc2ccccc2)cn(C)c1=O] | TFA |

TABLE 4E-continued

Exemplary MASP-2 inhibitory compounds

| Comp No. | Structure | Salt |
|---|---|---|
| IV-37 | 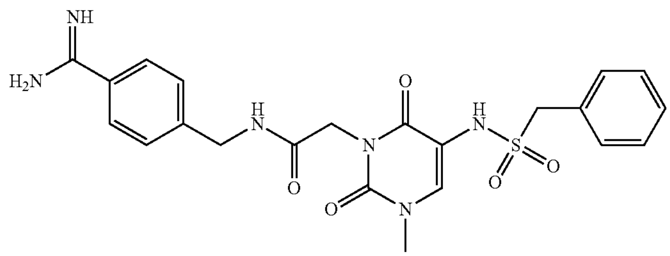 [SMILES: Cn1cc(NS(=O)(=O)Cc2ccccc2)c(=O)n(CC(=O)NCc2ccc(C(=N)N)cc2)c1=O] | TFA |
| IV-38 | 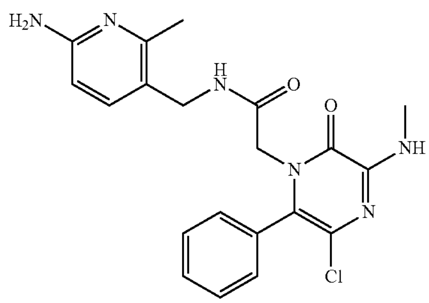 [SMILES: CNc1nc(Cl)c(-c2ccccc2)n(CC(=O)NCc2ccc(N)nc2C)c1=O] | — |
| IV-39 | 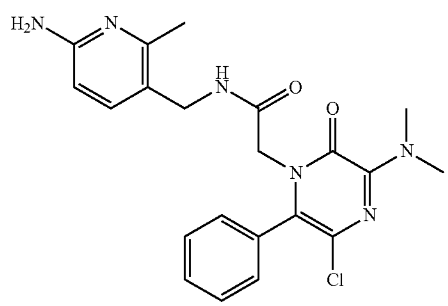 [SMILES: Cc1nc(N)ccc1CNC(=O)Cn1c(-c2ccccc2)c(Cl)nc(N(C)C)c1=O] | — |
| IV-40 | 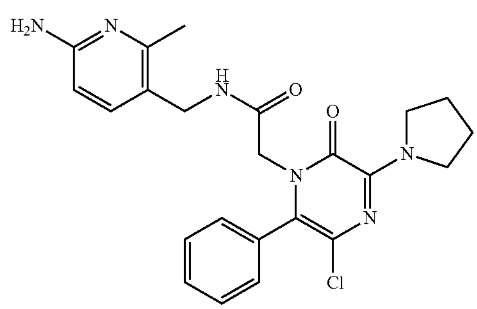 [SMILES: Cc1nc(N)ccc1CNC(=O)Cn1c(-c2ccccc2)c(Cl)nc(N2CCCC2)c1=O] | — |
| IV-41 | 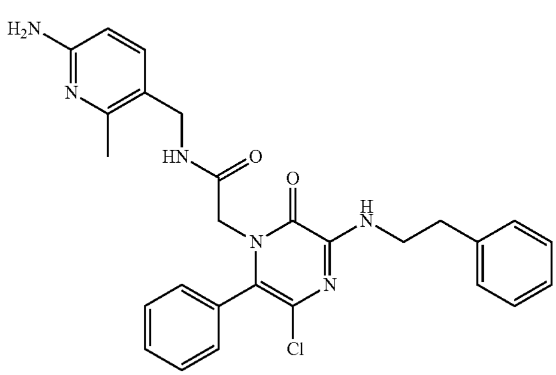 [SMILES: Cc1nc(N)ccc1CNC(=O)Cn1c(-c2ccccc2)c(Cl)nc(NCCc2ccccc2)c1=O] | — |

TABLE 4E-continued
Exemplary MASP-2 inhibitory compounds
| Comp No. | Structure | Salt |
|---|---|---|
| IV-42 | 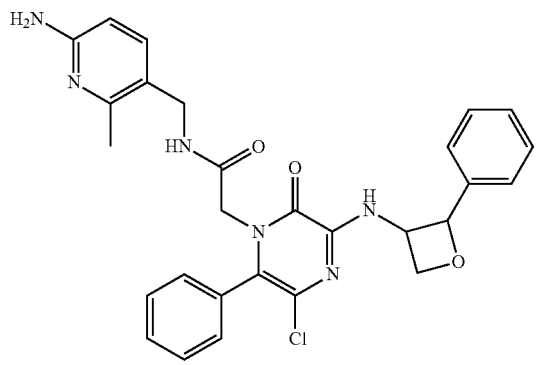 [SMILES: Cc1nc(N)ccc1CNC(=O)Cn1c(-c2ccccc2)c(Cl)nc(NC2COC2c2ccccc2)c1=O] | — |
| 43 | 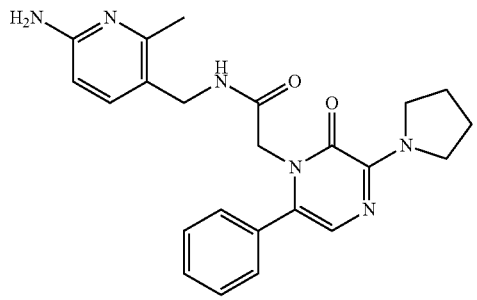 [SMILES: Cc1nc(N)ccc1CNC(=O)Cn1c(-c2ccccc2)cnc(N2CCCC2)c1=O] | — |
| IV-44 | 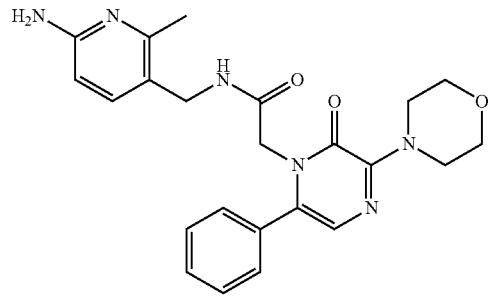 [SMILES: Cc1nc(N)ccc1CNC(=O)Cn1c(-c2ccccc2)cnc(N2CCOCC2)c1=O] | — |
| IV-45 | 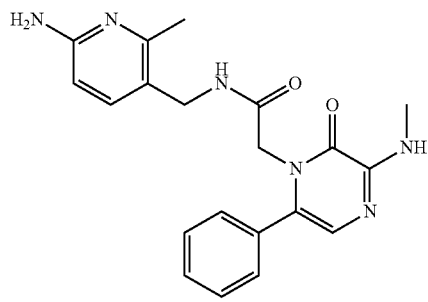 [SMILES: CNc1ncc(-c2ccccc2)n(CC(=O)NCc2ccc(N)nc2C)c1=O] | — |

TABLE 4E-continued
Exemplary MASP-2 inhibitory compounds
| Comp No. | Structure | Salt |
|---|---|---|
| IV-46 | 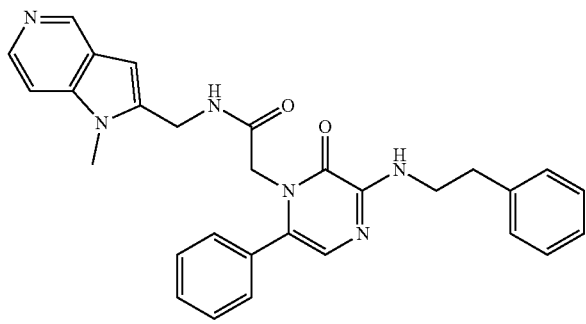 [SMILES: Cn1c(CNC(=O)Cn2c(-c3ccccc3)cnc(NCCc3ccccc3)c2=O)cc2cnccc21] | TFA |
| IV-47 | 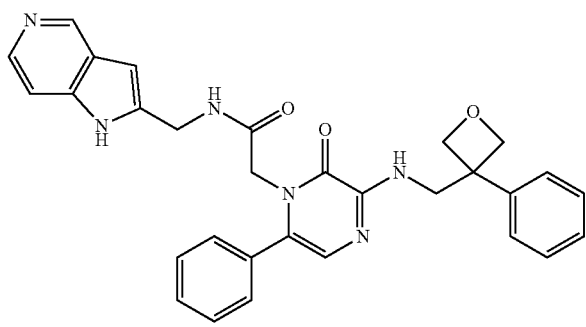 [SMILES: O=C(Cn1c(-c2ccccc2)cnc(NCC2(c3ccccc3)COC2)c1=O)NCc1cc2cnccc2[nH]1] | TFA |
| IV-48 | 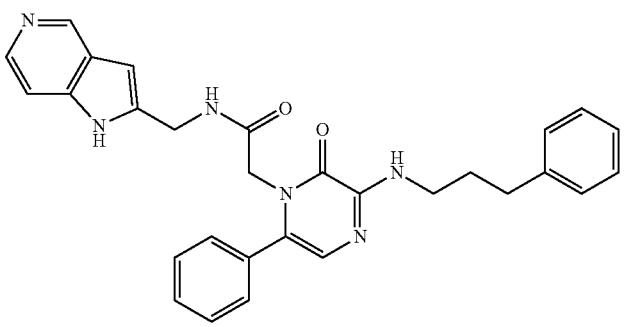 [SMILES: O=C(Cn1c(-c2ccccc2)cnc(NCCCc2ccccc2)c1=O)NCc1cc2cnccc2[nH]1] | TFA |
| IV-49 | 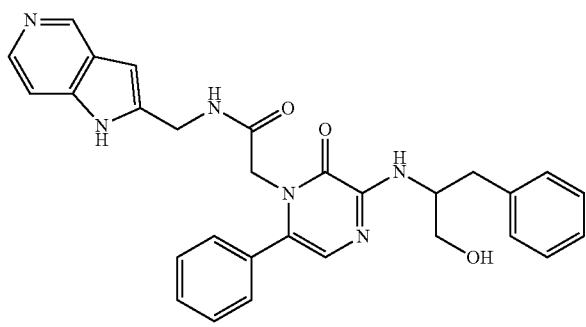 [SMILES: O=C(Cn1c(-c2ccccc2)cnc(NC(CO)Cc2ccccc2)c1=O)NCc1cc2cnccc2[nH]1] | TFA |

TABLE 4E-continued
Exemplary MASP-2 inhibitory compounds
| Comp No. | Structure | Salt |
|---|---|---|
| IV-50 | 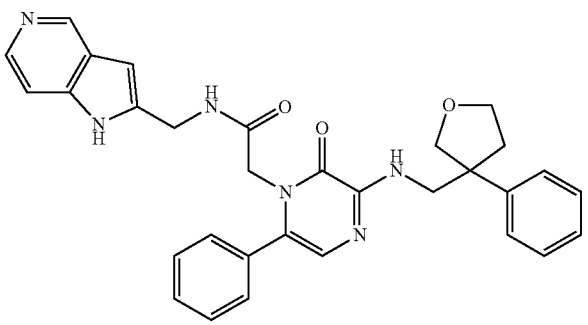 [SMILES: O=C(Cn1c(-c2ccccc2)cnc(NCC2(c3ccccc3)CCOC2)c1=O)NCc1cc2cnccc2[nH]1] | TFA |
| IV-51 | 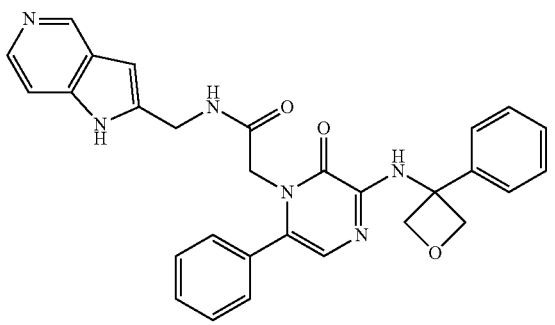 [SMILES: O=C(Cn1c(-c2ccccc2)cnc(NC2(c3ccccc3)COC2)c1=O)NCc1cc2cnccc2[nH]1] | TFA |
| IV-52 | 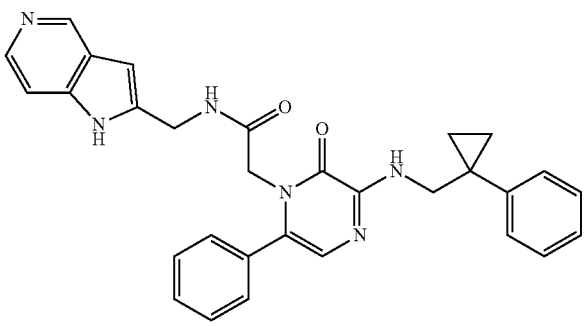 | TFA |
| IV-53 | 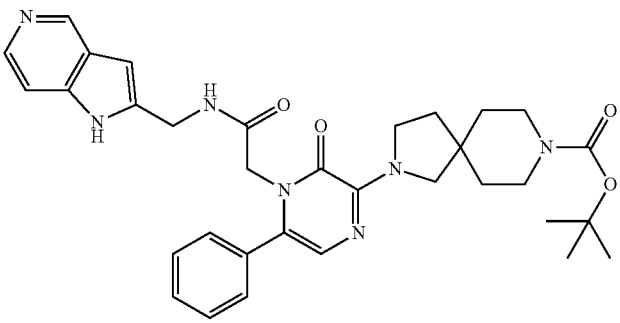 [SMILES: CC(C)(C)OC(=O)N1CCC2(CC1)CCN(c1ncc(-c3ccccc3)n(CC(=O)NCc3cc4cnccc4[nH]3)c1=O)C2] | — |

TABLE 4E-continued

Exemplary MASP-2 inhibitory compounds

| Comp No. | Structure | Salt |
|---|---|---|
| IV-54 | 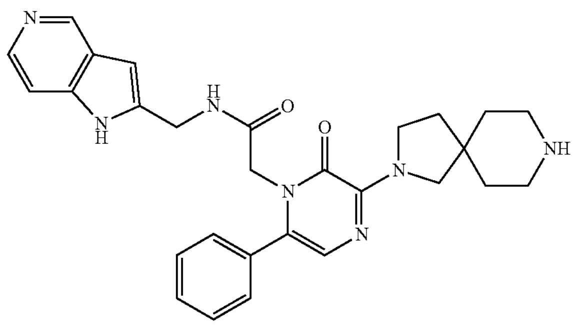 [SMILES: O=C(Cn1c(-c2ccccc2)cnc(N2CCC3(CCNCC3)C2)c1=O)NCc1cc2cnccc2[nH]1] | 2TFA |
| IV-55 | 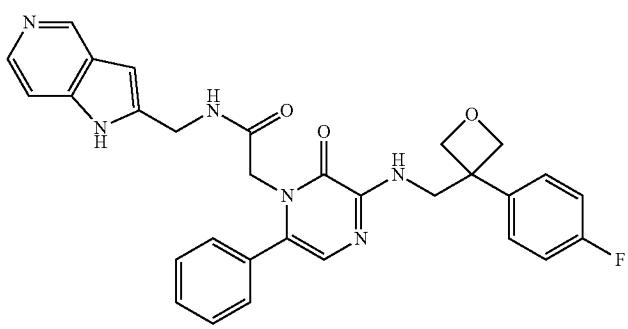 [SMILES: O=C(Cn1c(-c2ccccc2)cnc(NCC2(c3ccc(F)cc3)COC2)c1=O)NCc1cc2cnccc2[nH]1] | TFA |
| IV-56 | 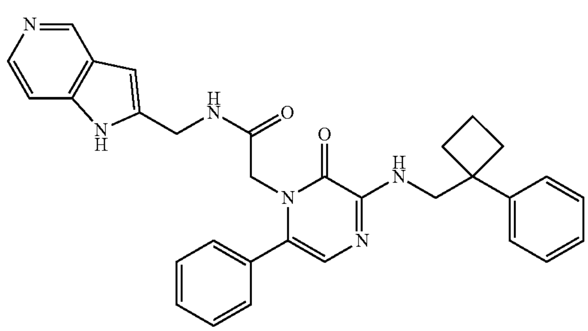 [SMILES: O=C(Cn1c(-c2ccccc2)cnc(NCC2(c3ccccc3)CCC2)c1=O)NCc1cc2cnccc2[nH]1] | TFA |
| IV-57 | 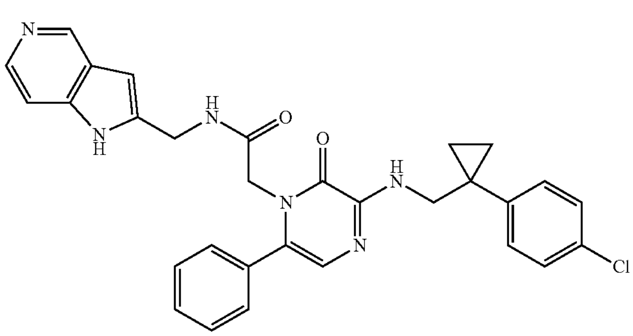 [SMILES: O=C(Cn1c(-c2ccccc2)cnc(NCC2(c3ccc(Cl)cc3)CC2)c1=O)NCc1cc2cnccc2[nH]1] | TFA |

TABLE 4E-continued

Exemplary MASP-2 inhibitory compounds

| Comp No. | Structure | Salt |
|---|---|---|
| IV-58 | 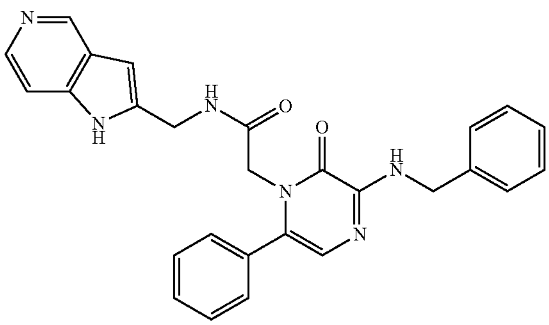 [SMILES: O=C(Cn1c(-c2ccccc2)cnc(NCc2ccccc2)c1=O)NCc1cc2cnccc2[nH]1] | TFA |
| IV-59 | 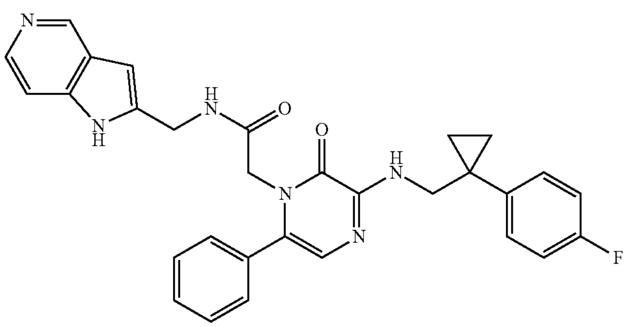 [SMILES: O=C(Cn1c(-c2ccccc2)cnc(NCC2(c3ccc(F)cc3)CC2)c1=O)NCc1cc2cnccc2[nH]1] | TFA |
| IV-60 | 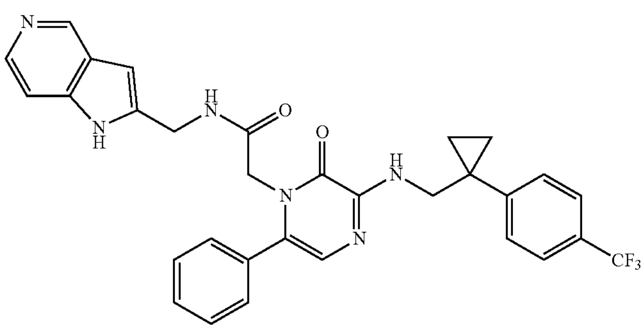 [SMILES: O=C(Cn1c(-c2ccccc2)cnc(NCC2(c3ccc(C(F)(F)F)cc3)CC2)c1=O)NCc1cc2cnccc2[nH]1] | TFA |
| IV-61 | 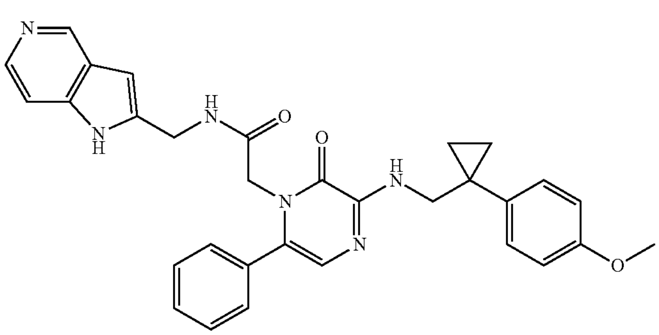 [SMILES: COc1ccc(C2(CNc3ncc(-c4ccccc4)n(CC(=O)NCc4cc5cnccc5[nH]4)c3=O)CC2)cc1] | TFA |

TABLE 4E-continued
Exemplary MASP-2 inhibitory compounds
| Comp No. | Structure | Salt |
|---|---|---|
| IV-62 | 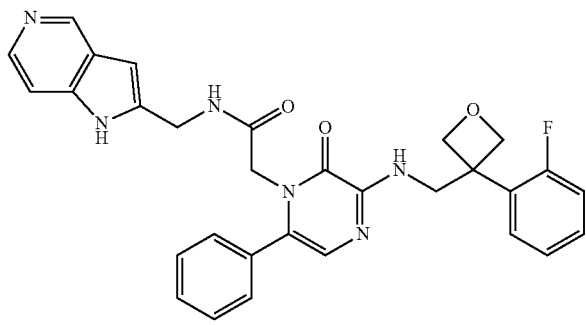 [SMILES: O=C(Cn1c(-c2ccccc2)cnc(NCC2(c3ccccc3F)COC2)c1=O)NCc1cc2cnccc2[nH]1] | TFA |
| IV-63 | 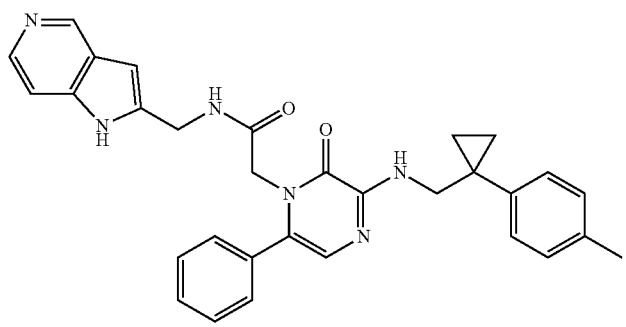 [SMILES: Cc1ccc(C2(CNc3ncc(-c4ccccc4)n(CC(=O)NCc4cc5cnccc5[nH]4)c3=O)CC2)cc1] | TFA |
| IV-64 | 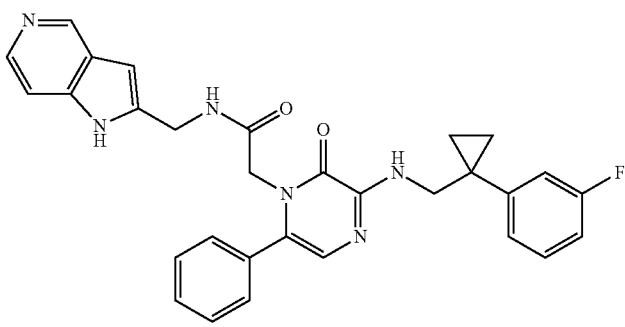 [SMILES: O=C(Cn1c(-c2ccccc2)cnc(NCC2(c3cccc(F)c3)CC2)c1=O)NCc1cc2cnccc2[nH]1] | — |
| IV-65 | 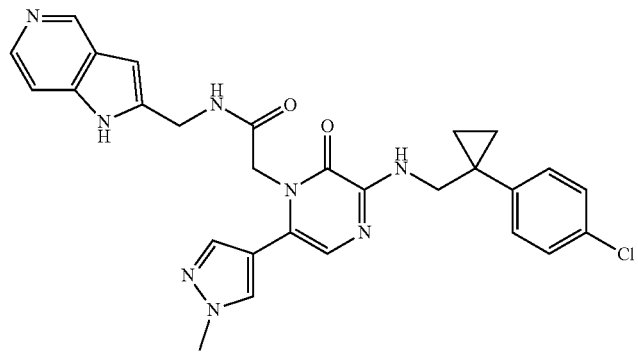 [SMILES: Cn1cc(-c2cnc(NCC3(c4ccc(Cl)cc4)CC3)c(=O)n2CC(=O)NCc2cc3cnccc3[nH]2)cn1] | TFA |

TABLE 4E-continued

Exemplary MASP-2 inhibitory compounds

| Comp No. | Structure | Salt |
|---|---|---|
| IV-66 | 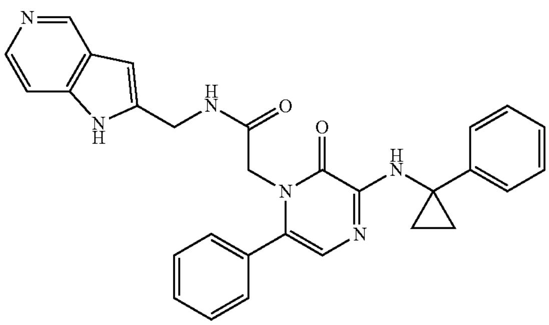 [SMILES: O=C(Cn1c(-c2ccccc2)cnc(NC2(c3ccccc3)CC2)c1=O)NCc1cc2cnccc2[nH]1] | TFA |
| IV-67 | 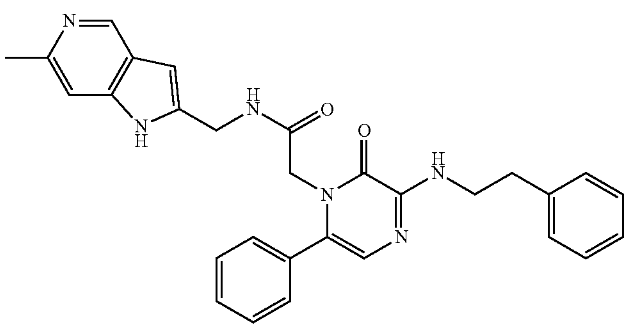 [SMILES: Cc1cc2[nH]c(CNC(=O)Cn3c(-c4ccccc4)cnc(NCCc4ccccc4)c3=O)cc2cn1] | TFA |
| IV-68 | 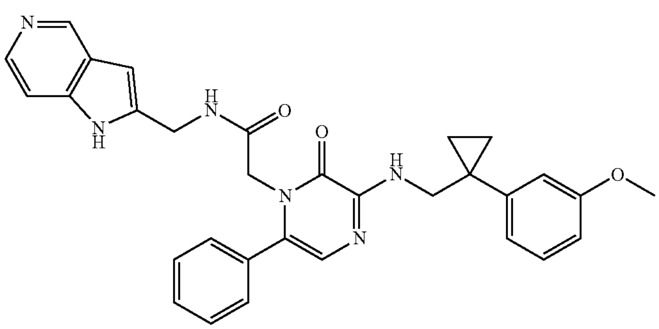 [SMILES: COc1cccc(C2(CNc3ncc(-c4ccccc4)n(CC(=O)NCc4cc5cnccc5[nH]4)c3=O)CC2)c1] | TFA |
| IV-69 | 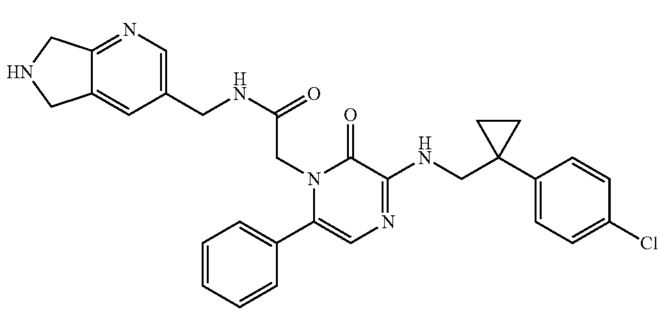 [SMILES: O=C(Cn1c(-c2ccccc2)cnc(NCC2(c3ccc(Cl)cc3)CC2)c1=O)NCc1cnc2c(c1)CNC2] | TFA |

TABLE 4E-continued
Exemplary MASP-2 inhibitory compounds
| Comp No. | Structure | Salt |
|---|---|---|
| IV-70 | 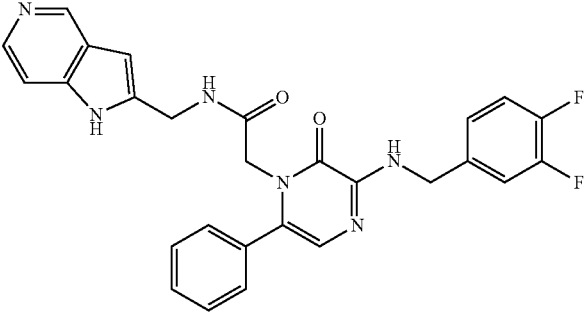 [SMILES: O=C(Cn1c(-c2ccccc2)cnc(NCc2ccc(F)c(F)c2)c1=O)NCc1cc2cnccc2[nH]1] | TFA |
| IV-71 | 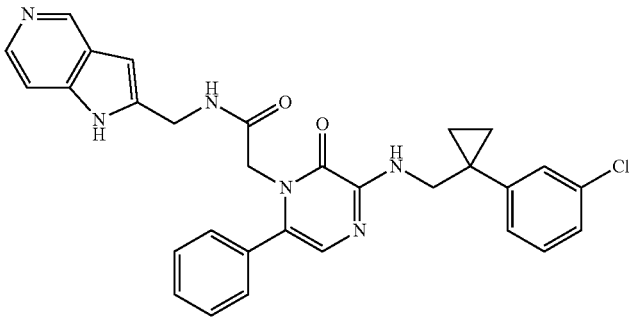 [SMILES: O=C(Cn1c(-c2ccccc2)cnc(NCC2(c3cccc(Cl)c3)CC2)c1=O)NCc1cc2cnccc2[nH]1] | TFA |
| IV-72 | 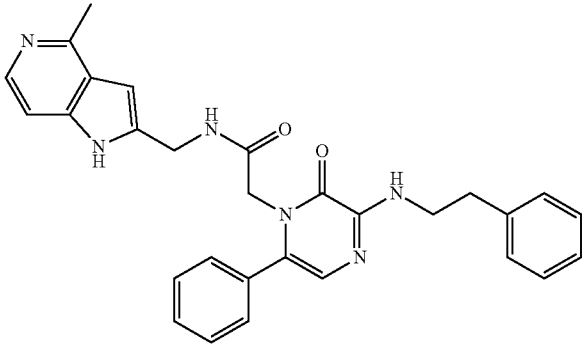 [SMILES: Cc1nccc2[nH]c(CNC(=O)Cn3c(-c4ccccc4)cnc(NCCc4ccccc4)c3=O)cc12] | TFA |
| IV-73 | 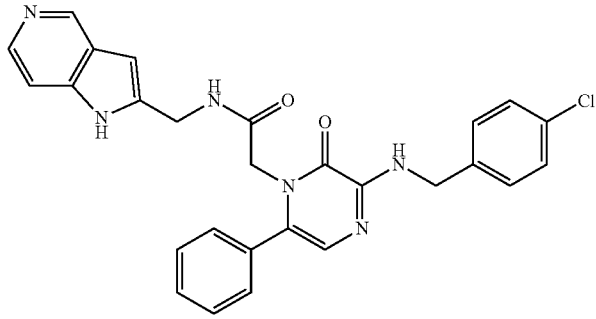 [SMILES: O=C(Cn1c(-c2ccccc2)cnc(NCc2ccc(Cl)cc2)c1=O)NCc1cc2cnccc2[nH]1] | TFA |

TABLE 4E-continued
Exemplary MASP-2 inhibitory compounds
| Comp No. | Structure | Salt |
|---|---|---|
| IV-74 | 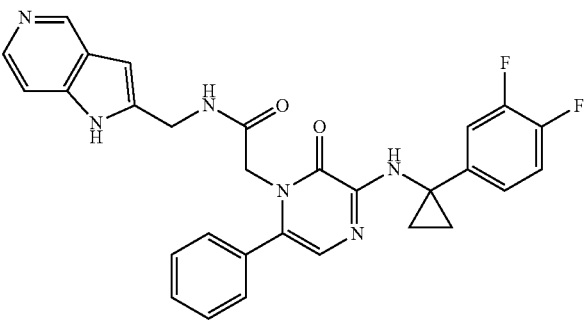 [SMILES: O=C(Cn1c(-c2ccccc2)cnc(NC2(c3ccc(F)c(F)c3)CC2)c1=O)NCc1cc2cnccc2[nH]1] | TFA |
| IV-75 | 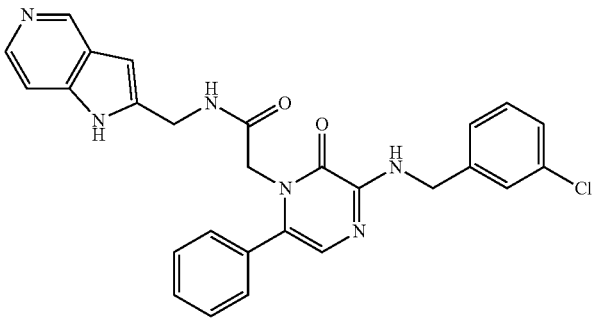 [SMILES: O=C(Cn1c(-c2ccccc2)cnc(NCc2cccc(Cl)c2)c1=O)NCc1cc2cnccc2[nH]1] | TFA |
| IV-76 | 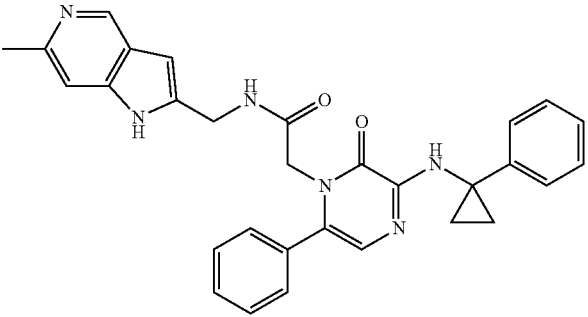 [SMILES: Cc1cc2[nH]c(CNC(=O)Cn3c(-c4ccccc4)cnc(NC4(c5ccccc5)CC4)c3=O)cc2cn1] | TFA |
| IV-77 | 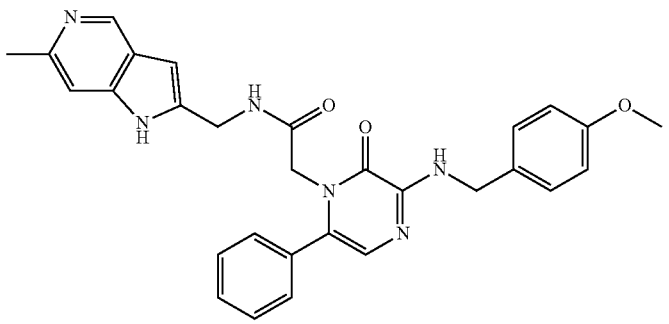 | TFA |

TABLE 4E-continued

Exemplary MASP-2 inhibitory compounds

| Comp No. | Structure | Salt |
|---|---|---|
| IV-78 | 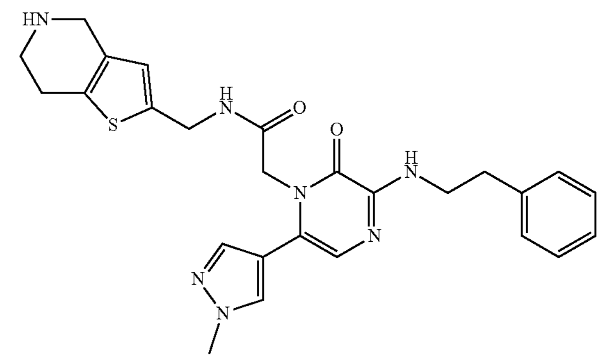 [SMILES: Cn1cc(-c2cnc(NCCc3ccccc3)c(=O)n2CC(=O)NCc2cc3c(s2)CCNC3)cn1] | — |
| IV-79 | 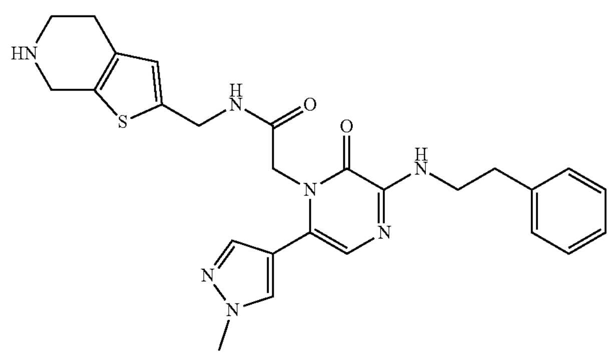 [SMILES: Cn1cc(-c2cnc(NCCc3ccccc3)c(=O)n2CC(=O)NCc2cc3c(s2)CNCC3)cn1] | — |
| IV-80 | 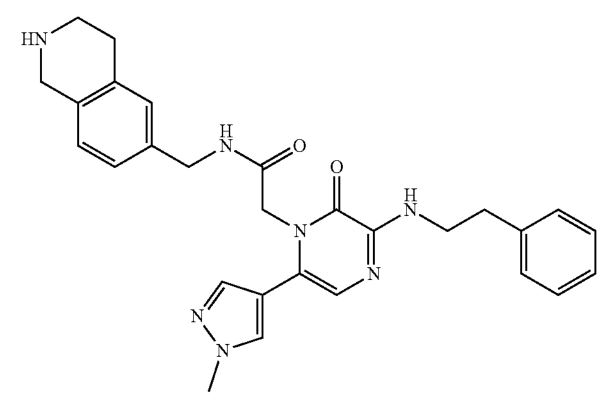 [SMILES: Cn1cc(-c2cnc(NCCc3ccccc3)c(=O)n2CC(=O)NCc2ccc3c(c2)CCNC3)cn1] | — |
| IV-81 | 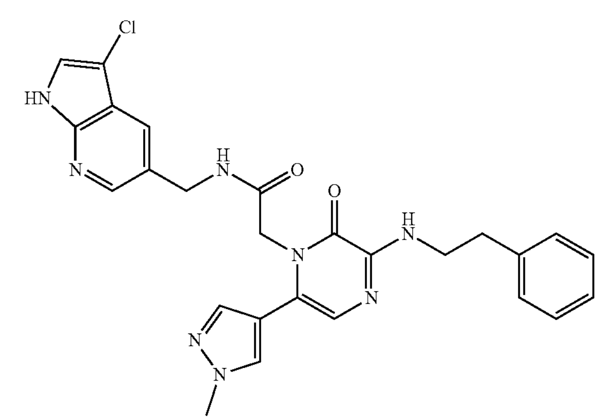 [SMILES: Cn1cc(-c2cnc(NCCc3ccccc3)c(=O)n2CC(=O)NCc2cnc3[nH]cc(Cl)c3c2)cn1] | — |

TABLE 4E-continued
Exemplary MASP-2 inhibitory compounds
| Comp No. | Structure | Salt |
|---|---|---|
| IV-82 | 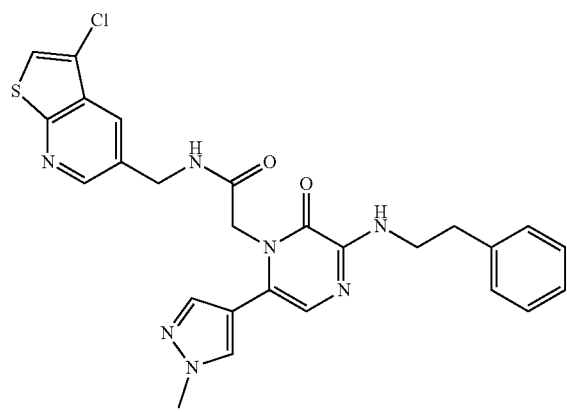 [SMILES: Cn1cc(-c2cnc(NCCc3ccccc3)c(=O)n2CC(=O)NCc2cnc3scc(Cl)c3c2)cn1] | — |
| IV-83 | 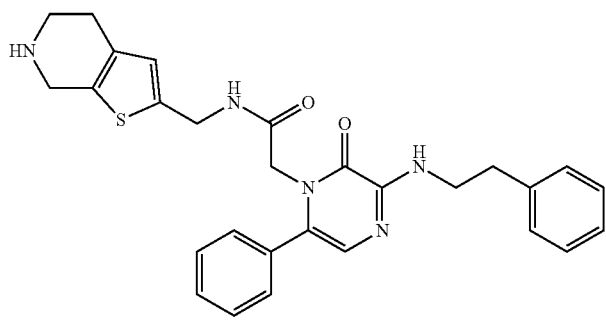 [SMILES: O=C(Cn1c(-c2ccccc2)cnc(NCCc2ccccc2)c1=O)NCc1cc2c(s1)CNCC2] | — |
| IV-84 | 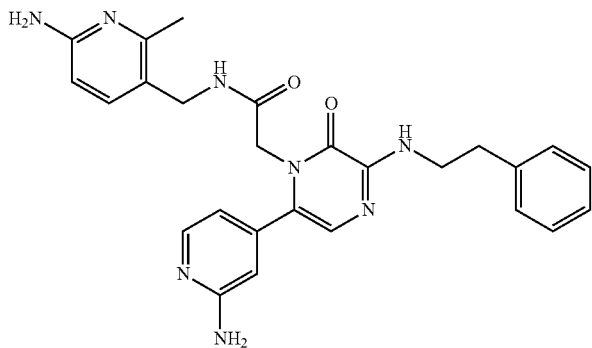 [SMILES: Cc1nc(N)ccc1CNC(=O)Cn1c(-c2ccnc(N)c2)cnc(NCCc2ccccc2)c1=O] | — |
| IV-85 | 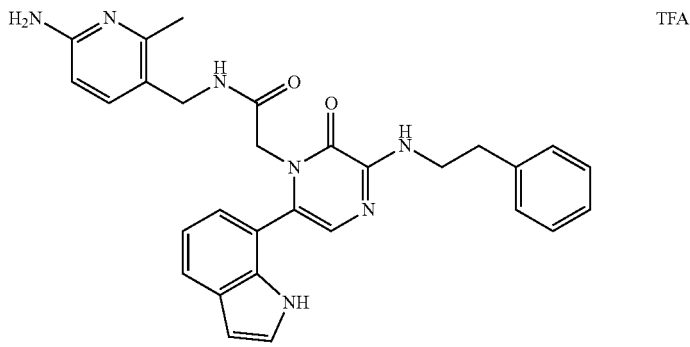 | TFA |

TABLE 4E-continued

Exemplary MASP-2 inhibitory compounds

| Comp No. | Structure | Salt |
|---|---|---|
| IV-86 | 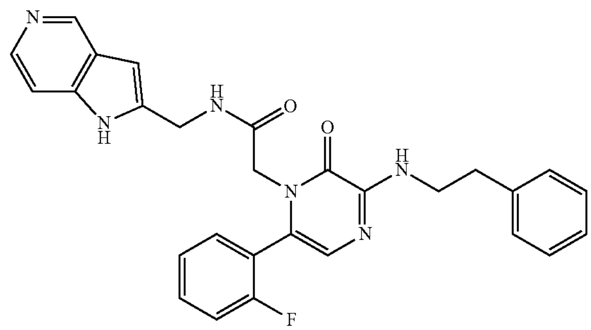 [SMILES: O=C(Cn1c(-c2ccccc2F)cnc(NCCc2ccccc2)c1=O)NCc1cc2cnccc2[nH]1] | TFA |
| IV-87 | 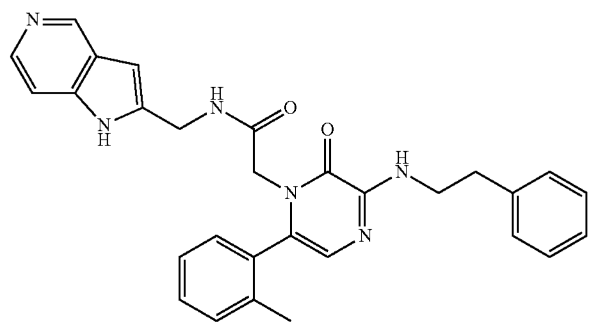 [SMILES: Cc1ccccc1-c1cnc(NCCc2ccccc2)c(=O)n1CC(=O)NCc1cc2cnccc2[nH]1] | TFA |
| IV-88 | 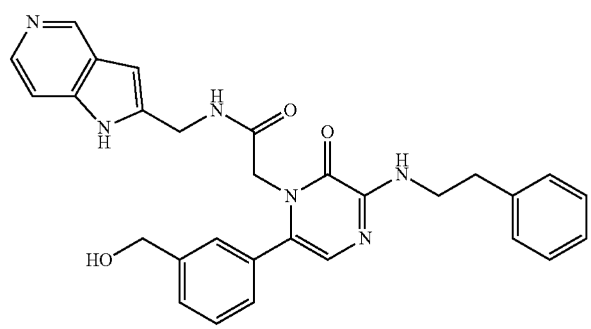 [SMILES: O=C(Cn1c(-c2cccc(CO)c2)cnc(NCCc2ccccc2)c1=O)NCc1cc2cnccc2[nH]1] | TFA |
| IV-89 | 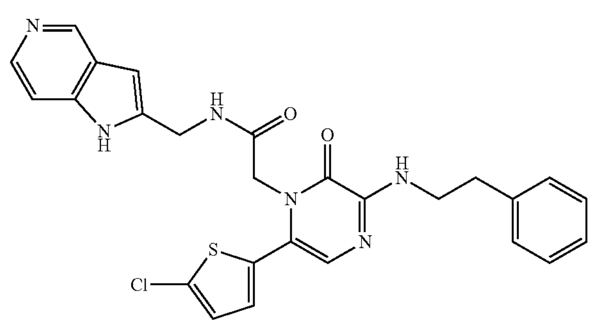 [SMILES: O=C(Cn1c(-c2ccc(Cl)s2)cnc(NCCc2ccccc2)c1=O)NCc1cc2cnccc2[nH]1] | — |

TABLE 4E-continued

Exemplary MASP-2 inhibitory compounds

| Comp No. | Structure | Salt |
| --- | --- | --- |
| IV-90 | 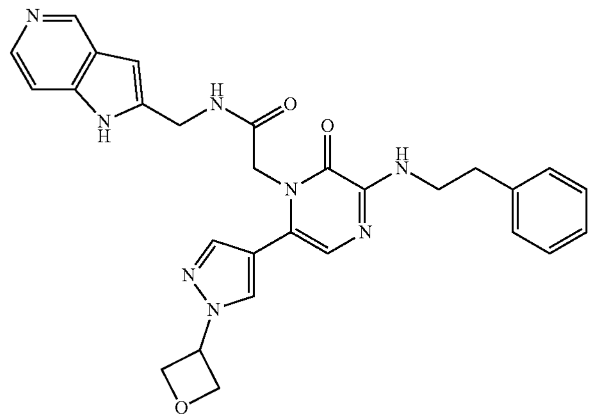 [SMILES: O=C(Cn1c(-c2cnn(C3COC3)c2)cnc(NCCc2ccccc2)c1=O)NCc1cc2cnccc2[nH]1] | TFA |
| IV-91 | 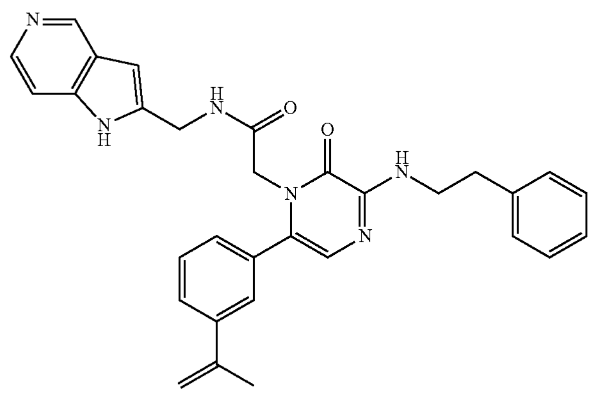 [SMILES: C=C(C)c1cccc(-c2cnc(NCCc3ccccc3)c(=O)n2CC(=O)NCc2cc3cnccc3[nH]2)c1] | — |
| IV-92 | 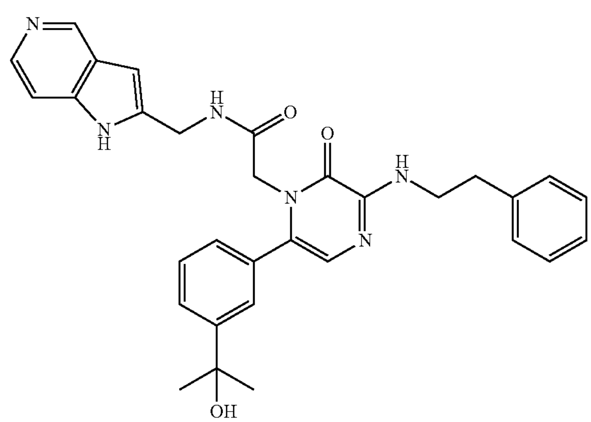 [SMILES: CC(C)(O)c1cccc(-c2cnc(NCCc3ccccc3)c(=O)n2CC(=O)NCc2cc3cnccc3[nH]2)c1] | — |
| IV-93 | 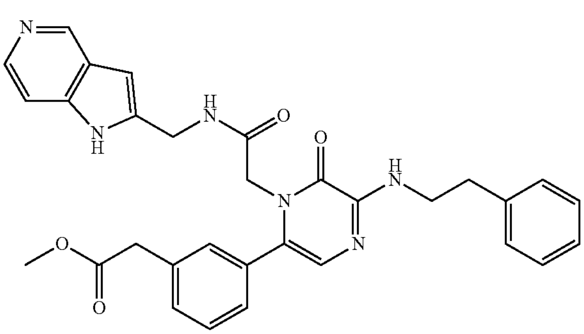 [SMILES: COC(=O)Cc1cccc(-c2cnc(NCCc3ccccc3)c(=O)n2CC(=O)NCc2cc3cnccc3[nH]2)c1] | TFA |

TABLE 4E-continued

Exemplary MASP-2 inhibitory compounds

| Comp No. | Structure | Salt |
|---|---|---|
| IV-94 | 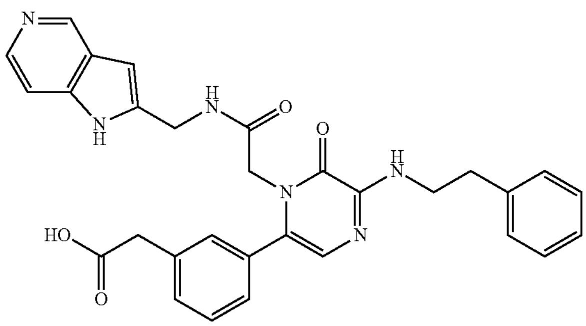 [SMILES: O=C(O)Cc1cccc(-c2cnc(NCCc3ccccc3)c(=O)n2CC(=O)NCc2cc3cnccc3[nH]2)c1] | TFA |
| IV-95 | 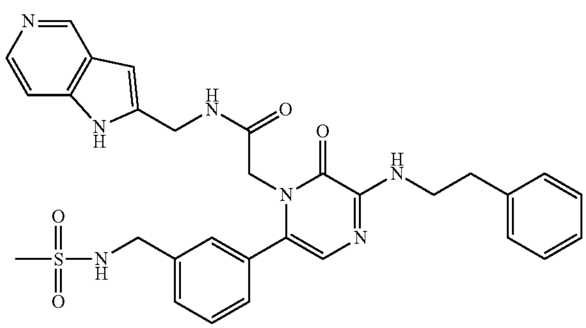 [SMILES: CS(=O)(=O)NCc1cccc(-c2cnc(NCCc3ccccc3)c(=O)n2CC(=O)NCc2cc3cnccc3[nH]2)c1] | — |
| IV-96 | 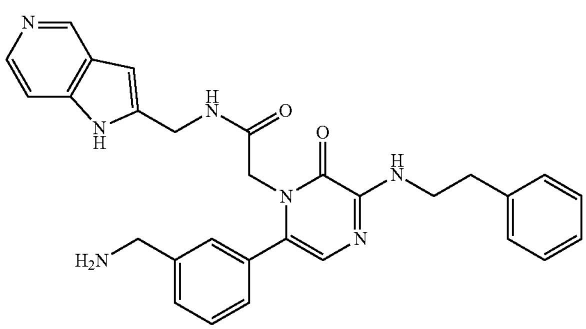 | — |
| IV-97 | 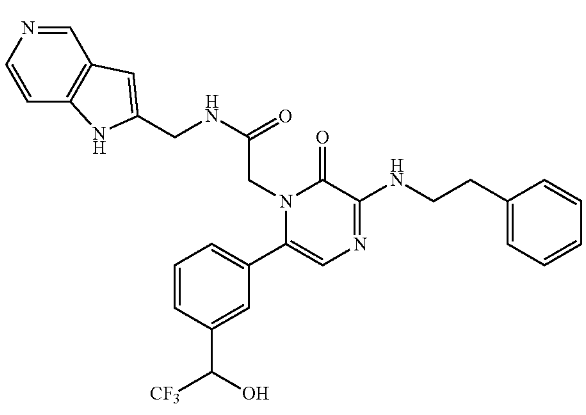 [SMILES: O=C(Cn1c(-c2cccc(C(O)C(F)(F)F)c2)cnc(NCCc2ccccc2)c1=O)NCc1cc2cnccc2[nH]1] | — |

TABLE 4E-continued
Exemplary MASP-2 inhibitory compounds
| Comp No. | Structure | Salt |
|---|---|---|
| IV-98 | 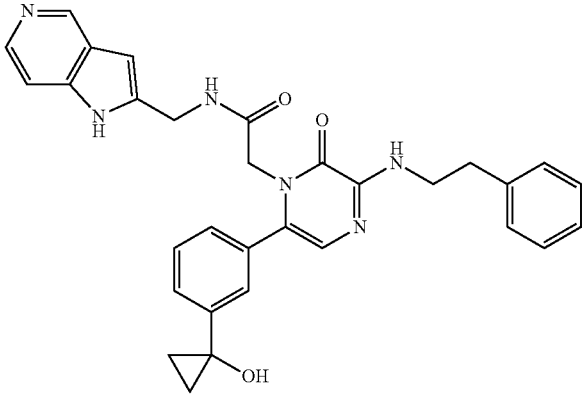 [SMILES: O=C(Cn1c(-c2cccc(C3(O)CC3)c2)cnc(NCCc2ccccc2)c1=O)NCc1cc2cnccc2[nH]1] | — |
| IV-99 | 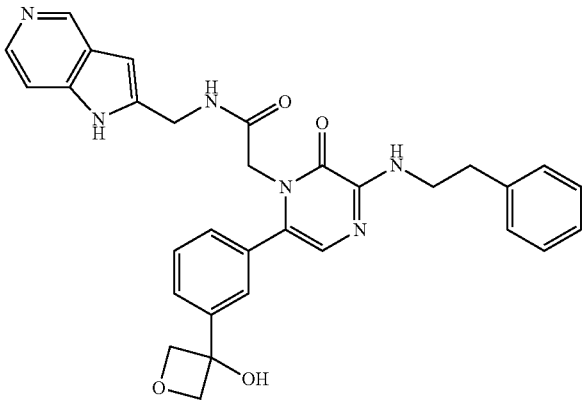 [SMILES: O=C(Cn1c(-c2cccc(C3(O)COC3)c2)cnc(NCCc2ccccc2)c1=O)NCc1cc2cnccc2[nH]1] | — |
| IV-100 | 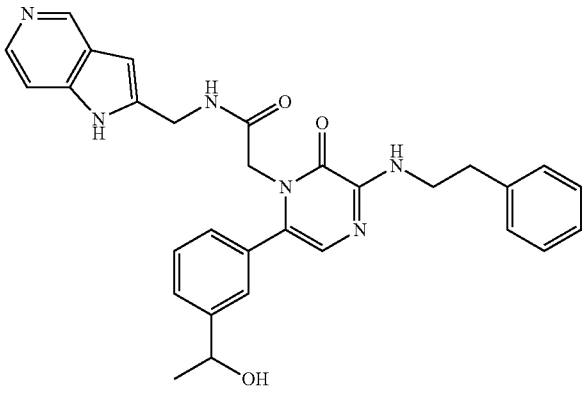 [SMILES: CC(O)c1cccc(-c2cnc(NCCc3ccccc3)c(=O)n2CC(=O)NCc2cc3cnccc3[nH]2)c1] | — |
| IV-101 | 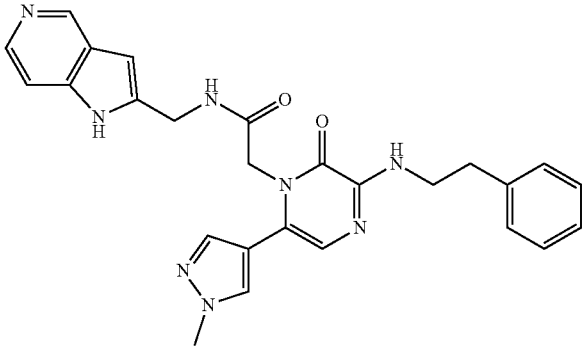 [SMILES: Cn1cc(-c2cnc(NCCc3ccccc3)c(=O)n2CC(=O)NCc2cc3cnccc3[nH]2)cn1] | — |

TABLE 4E-continued
Exemplary MASP-2 inhibitory compounds
| Comp No. | Structure | Salt |
|---|---|---|
| IV-102 | 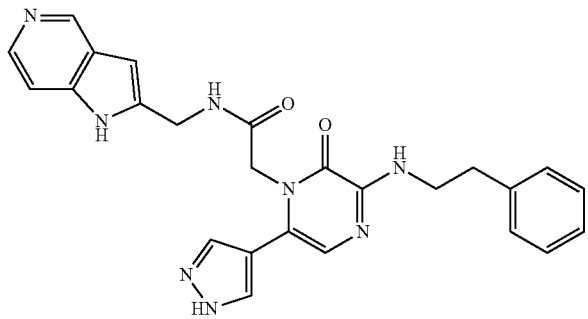 [SMILES: O=C(Cn1c(-c2cn[nH]c2)cnc(NCCc2ccccc2)c1=O)NCc1cc2cnccc2[nH]1] | — |
| IV-103 | 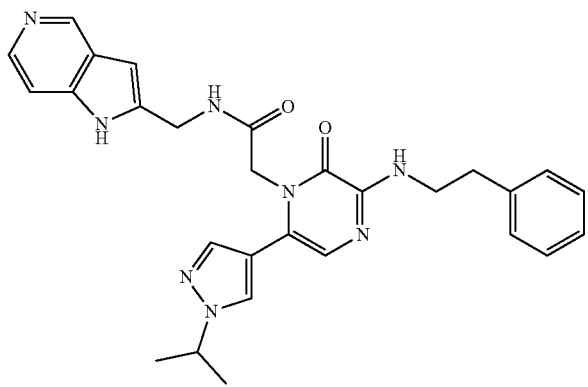 [SMILES: CC(C)n1cc(-c2cnc(NCCc3ccccc3)c(=O)n2CC(=O)NCc2cc3cnccc3[nH]2)cn1] | — |
| IV-104 | 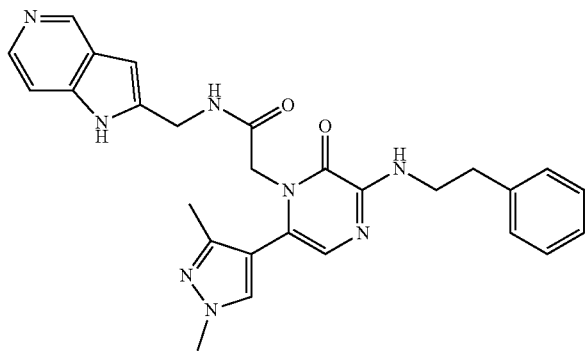 [SMILES: Cc1nn(C)cc1-c1cnc(NCCc2ccccc2)c(=O)n1CC(=O)NCc1cc2cnccc2[nH]1] | — |
| IV-105 | 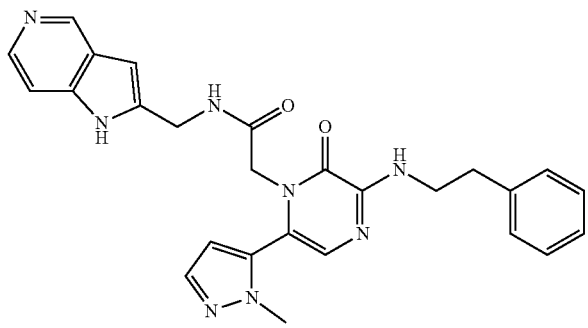 [SMILES: Cn1nccc1-c1cnc(NCCc2ccccc2)c(=O)n1CC(=O)NCc1cc2cnccc2[nH]1] | — |

TABLE 4E-continued

| Exemplary MASP-2 inhibitory compounds | | |
|---|---|---|
| Comp No. | Structure | Salt |
| IV-106 | | — |
| IV-107 | | — |
| IV-108 | | — |
| IV-109 | | — |

TABLE 4E-continued

Exemplary MASP-2 inhibitory compounds

| Comp No. | Structure | Salt |
|---|---|---|
| IV-110 | 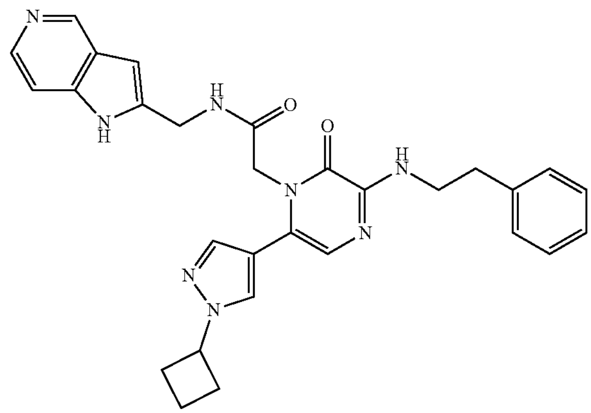 [SMILES: O=C(Cn1c(-c2cnn(C3CCC3)c2)cnc(NCCc2ccccc2)c1=O)NCc1cc2cnccc2[nH]1] | — |
| IV-111 | 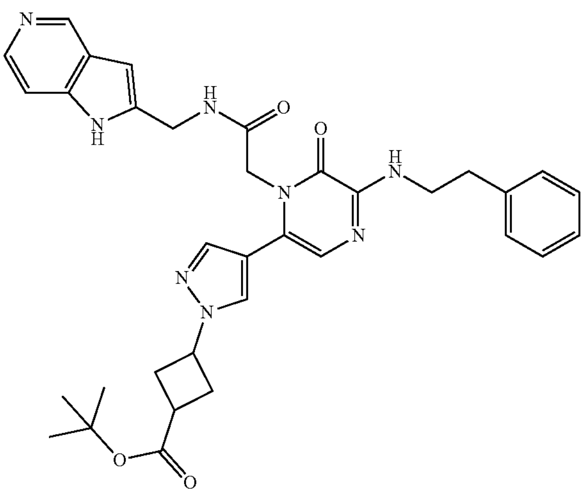 [SMILES: CC(C)(C)OC(=O)C1CC(n2cc(-c3cnc(NCCc4ccccc4)c(=O)n3CC(=O)NCc3cc4cnccc4[nH]3)cn2)C1] | — |
| IV-112 | 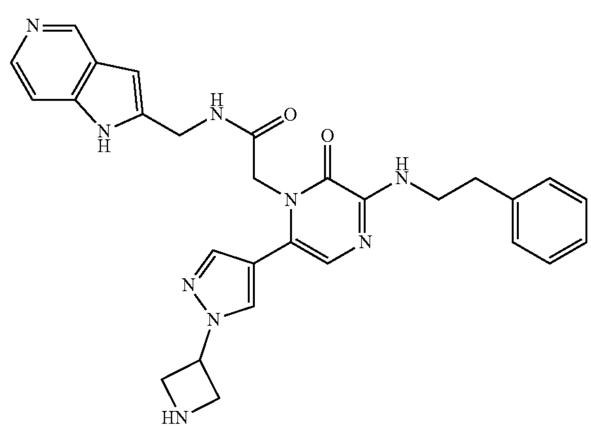 [SMILES: O=C(Cn1c(-c2cnn(C3CNC3)c2)cnc(NCCc2ccccc2)c1=O)NCc1cc2cnccc2[nH]1] | HCl |

TABLE 4E-continued
| Comp No. | Structure | Salt |
|---|---|---|
| IV-113 | 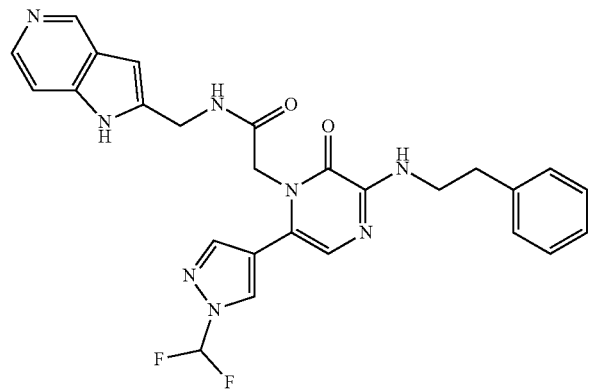 [SMILES: O=C(Cn1c(-c2cnn(C(F)F)c2)cnc(NCCc2ccccc2)c1=O)NCc1cc2cnccc2[nH]1] | — |
| IV-114 | 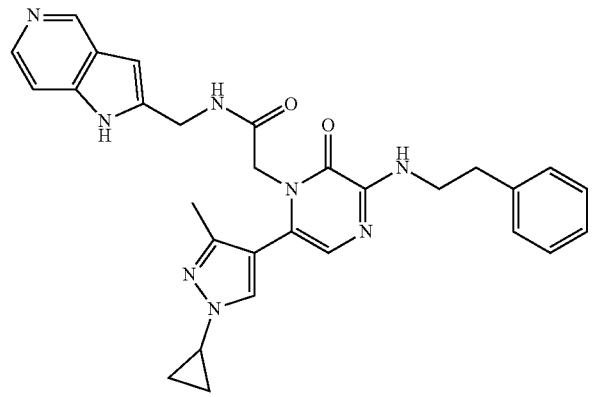 [SMILES: Cc1nn(C2CC2)cc1-c1cnc(NCCc2ccccc2)c(=O)n1CC(=O)NCc1cc2cnccc2[nH]1] | — |
| IV-115 | 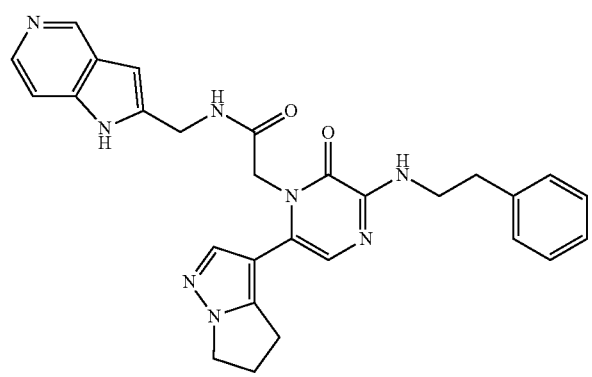 [SMILES: O=C(Cn1c(-c2cnn3c2CCC3)cnc(NCCc2ccccc2)c1=O)NCc1cc2cnccc2[nH]1] | — |
| IV-116 | 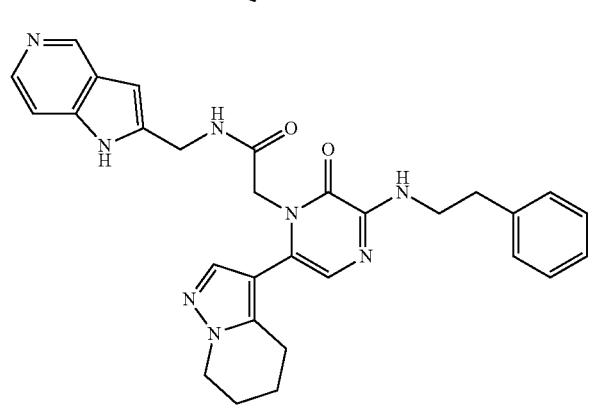 | — |

TABLE 4E-continued

Exemplary MASP-2 inhibitory compounds

| Comp No. | Structure | Salt |
|---|---|---|
| IV-117 | 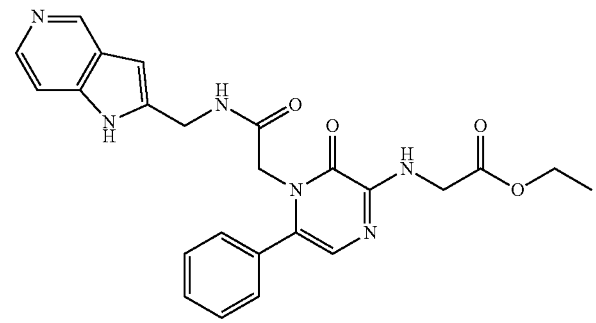 [SMILES: CCOC(=O)CNc1ncc(-c2ccccc2)n(CC(=O)NCc2cc3cnccc3[nH]2)c1=O] | — |
| IV-118 | 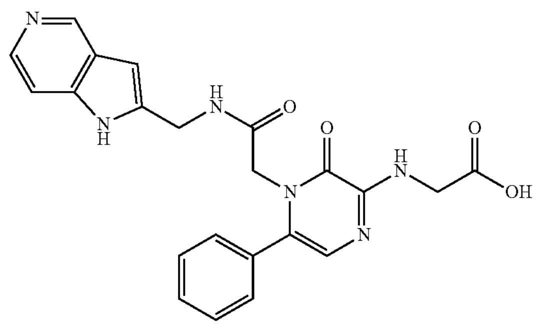 [SMILES: O=C(O)CNc1ncc(-c2ccccc2)n(CC(=O)NCc2cc3cnccc3[nH]2)c1=O] | TFA |
| IV-119 | 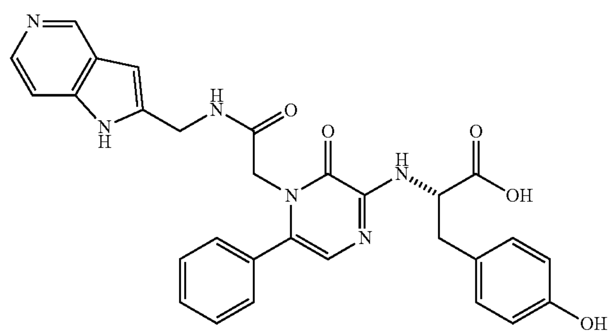 | TFA |
| IV-120 | 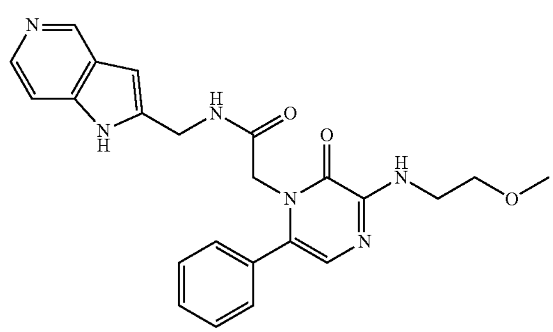 [SMILES: COCCNc1ncc(-c2ccccc2)n(CC(=O)NCc2cc3cnccc3[nH]2)c1=O] | TFA |

TABLE 4E-continued
Exemplary MASP-2 inhibitory compounds
| Comp No. | Structure | Salt |
|---|---|---|
| IV-121 | 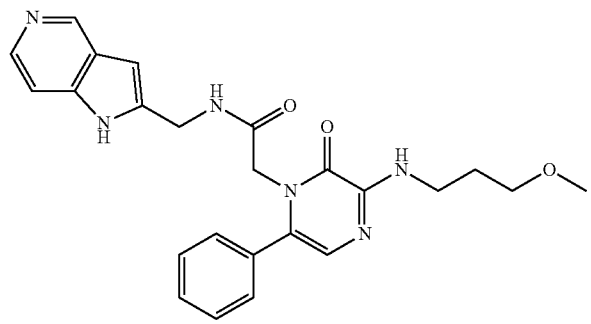 [SMILES: COCCCNc1ncc(-c2ccccc2)n(CC(=O)NCc2cc3cnccc3[nH]2)c1=O] | TFA |
| IV-122 | 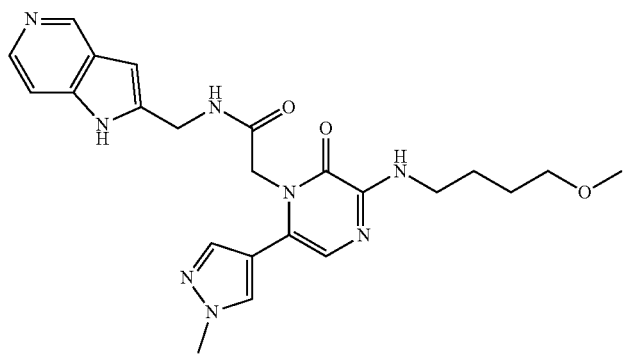 [SMILES: COCCCCNc1ncc(-c2cnn(C)c2)n(CC(=O)NCc2cc3cnccc3[nH]2)c1=O] | TFA |
| IV-123 | 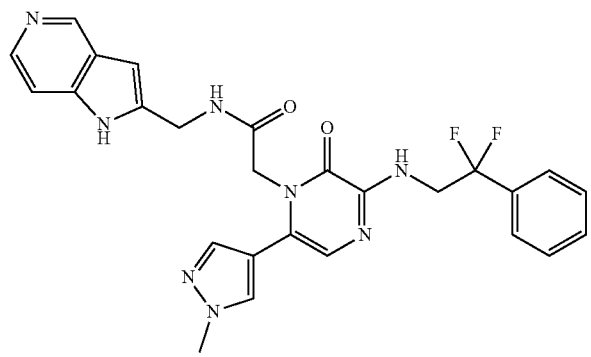 [SMILES: Cn1cc(-c2cnc(NCC(F)(F)c3ccccc3)c(=O)n2CC(=O)NCc2cc3cnccc3[nH]2)cn1] | TFA |
| IV-124 | 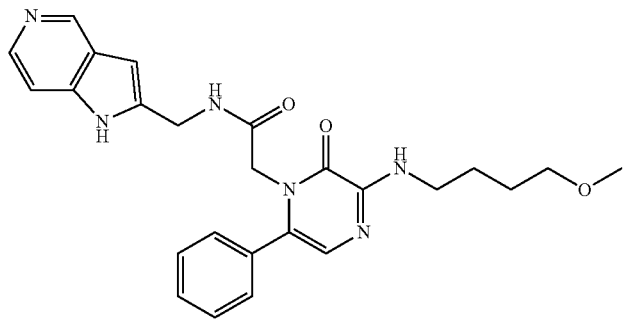 [SMILES: COCCCCNc1ncc(-c2ccccc2)n(CC(=O)NCc2cc3cnccc3[nH]2)c1=O] | TFA |

TABLE 4E-continued

Exemplary MASP-2 inhibitory compounds

| Comp No. | Structure | Salt |
|---|---|---|
| IV-125 | 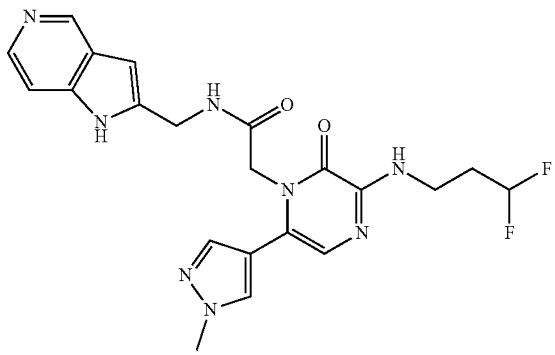 [SMILES: Cn1cc(-c2cnc(NCCC(F)F)c(=O)n2CC(=O)NCc2cc3cnccc3[nH]2)cn1] | TFA |
| IV-126 | 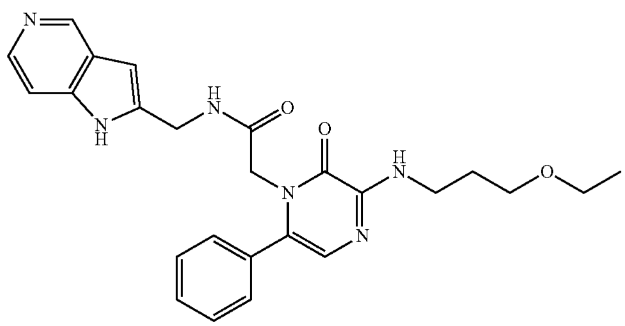 [SMILES: CCOCCCNc1ncc(-c2ccccc2)n(CC(=O)NCc2cc3cnccc3[nH]2)c1=O] | TFA |
| IV-127 | 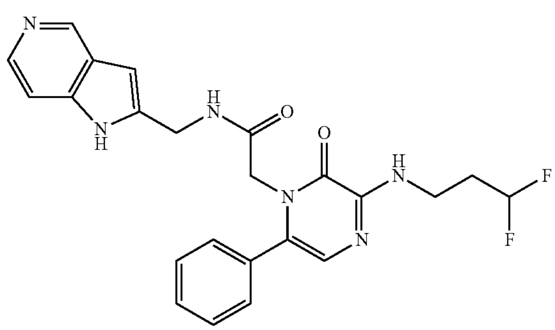 [SMILES: O=C(Cn1c(-c2ccccc2)cnc(NCCC(F)F)c1=O)NCc1cc2cnccc2[nH]1] | TFA |
| IV-128 | 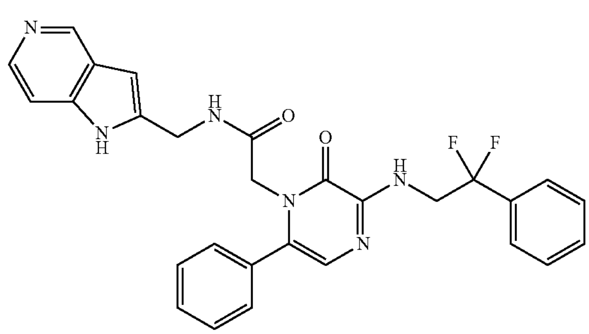 [SMILES: O=C(Cn1c(-c2ccccc2)cnc(NCC(F)(F)c2ccccc2)c1=O)NCc1cc2cnccc2[nH]1] | TFA |

TABLE 4E-continued
Exemplary MASP-2 inhibitory compounds
| Comp No. | Structure | Salt |
|---|---|---|
| IV-129 | 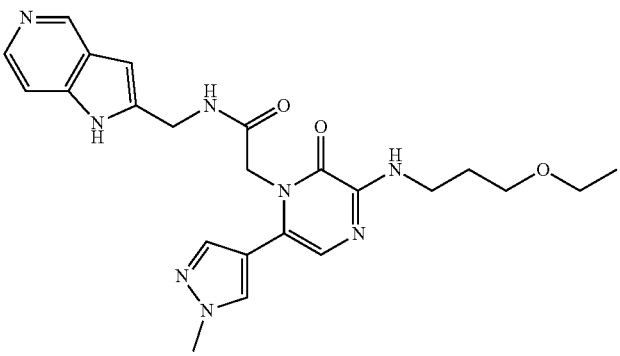 [SMILES: CCOCCCNc1ncc(-c2cnn(C)c2)n(CC(=O)NCc2cc3cnccc3[nH]2)c1=O] | TFA |
| IV-130 | 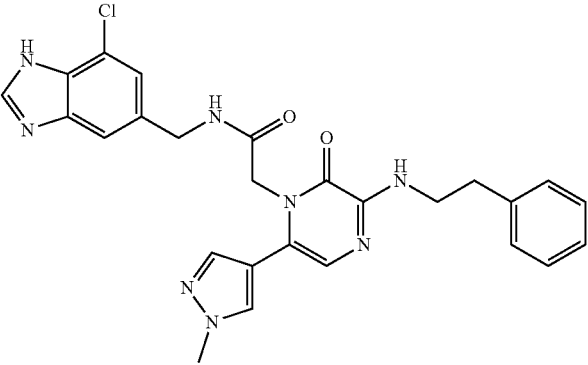 [SMILES: Cn1cc(-c2cnc(NCCc3ccccc3)c(=O)n2CC(=O)NCc2cc(Cl)c3[nH]cnc3c2)cn1] | — |
| IV-131 | 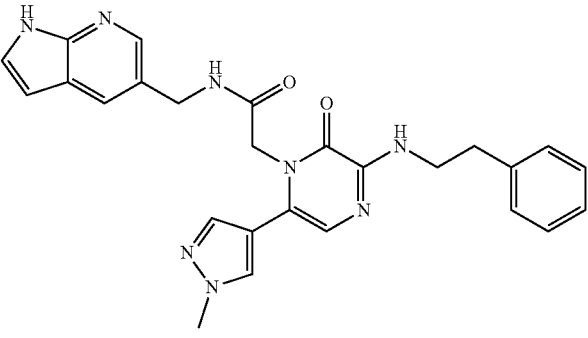 [SMILES: Cn1cc(-c2cnc(NCCc3ccccc3)c(=O)n2CC(=O)NCc2cnc3[nH]ccc3c2)cn1] | — |
| IV-132 | 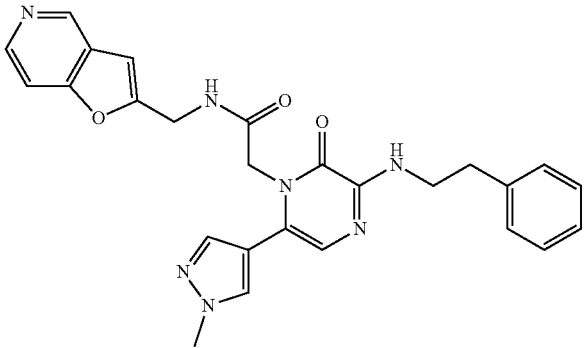 [SMILES: Cn1cc(-c2cnc(NCCc3ccccc3)c(=O)n2CC(=O)NCc2cc3cnccc3o2)cn1] | — |

TABLE 4E-continued

Exemplary MASP-2 inhibitory compounds

| Comp No. | Structure | Salt |
|---|---|---|
| IV-133 | 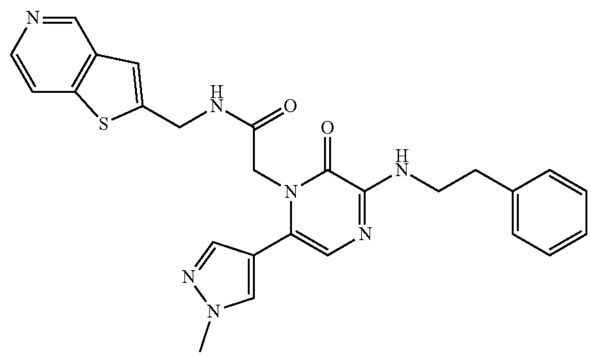 [SMILES: Cn1cc(-c2cnc(NCCc3ccccc3)c(=O)n2CC(=O)NCc2cc3cnccc3s2)cn1] | — |
| IV-134 | 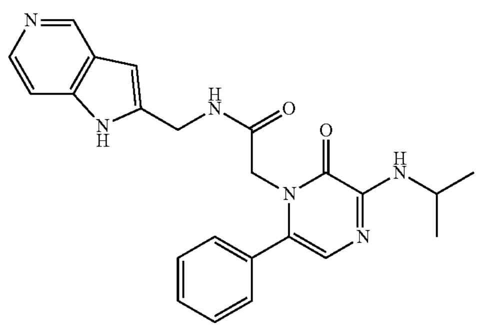 [SMILES: CC(C)Nc1ncc(-c2ccccc2)n(CC(=O)NCc2cc3cnccc3[nH]2)c1=O] | — |
| IV-135 | 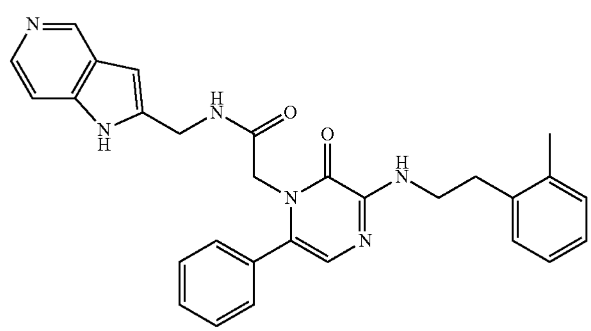 [SMILES: Cc1ccccc1CCNc1ncc(-c2ccccc2)n(CC(=O)NCc2cc3cnccc3[nH]2)c1=O] | — |
| IV-136 | 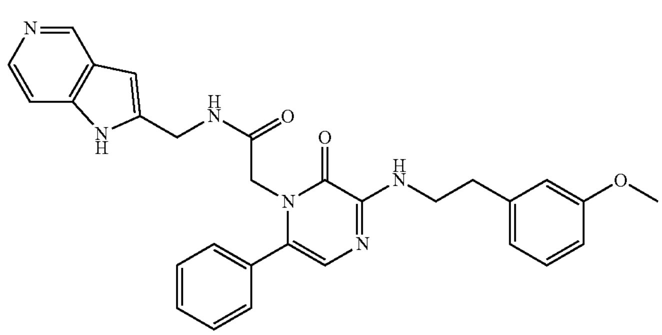 [SMILES: COc1cccc(CCNc2ncc(-c3ccccc3)n(CC(=O)NCc3cc4cnccc4[nH]3)c2=O)c1] | — |

TABLE 4E-continued

Exemplary MASP-2 inhibitory compounds

| Comp No. | Structure | Salt |
|---|---|---|
| IV-137 | 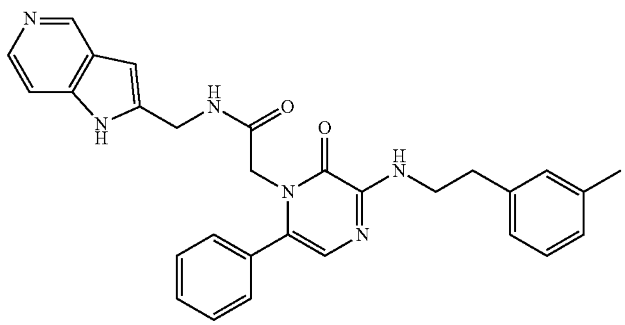 [SMILES: Cc1cccc(CCNc2ncc(-c3ccccc3)n(CC(=O)NCc3cc4cnccc4[nH]3)c2=O)c1] | — |
| IV-138 | 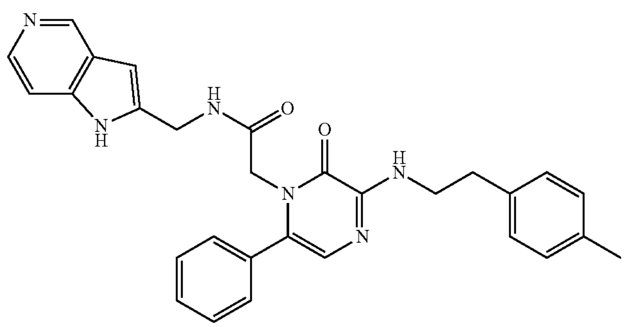 [SMILES: Cc1ccc(CCNc2ncc(-c3ccccc3)n(CC(=O)NCc3cc4cnccc4[nH]3)c2=O)cc1] | — |
| IV-139 | 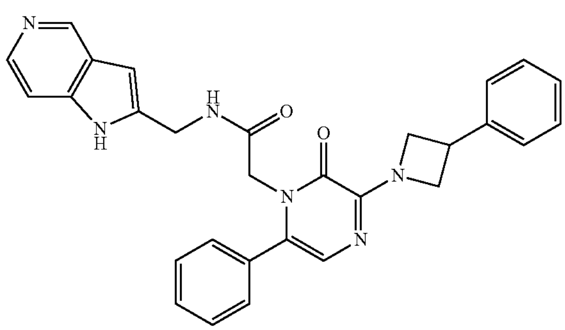 [SMILES: O=C(Cn1c(-c2ccccc2)cnc(N2CC(c3ccccc3)C2)c1=O)NCc1cc2cnccc2[nH]1] | — |
| IV-140 | 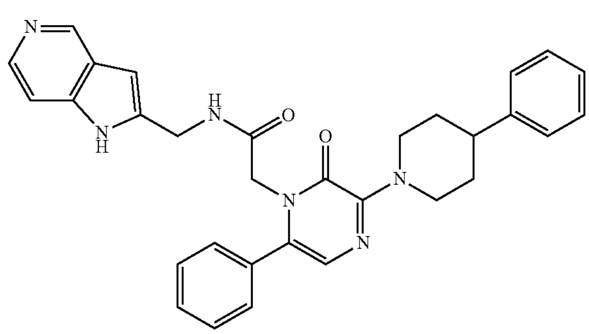 [SMILES: O=C(Cn1c(-c2ccccc2)cnc(N2CCC(c3ccccc3)CC2)c1=O)NCc1cc2cnccc2[nH]1] | — |

TABLE 4E-continued
Exemplary MASP-2 inhibitory compounds
| Comp No. | Structure | Salt |
|---|---|---|
| IV-141 | 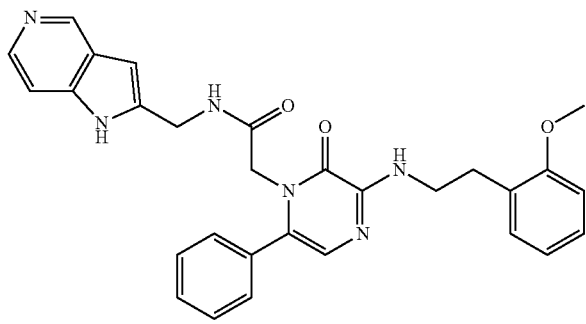 [SMILES: COc1ccccc1CCNc1ncc(-c2ccccc2)n(CC(=O)NCc2cc3cnccc3[nH]2)c1=O] | — |
| IV-142 | 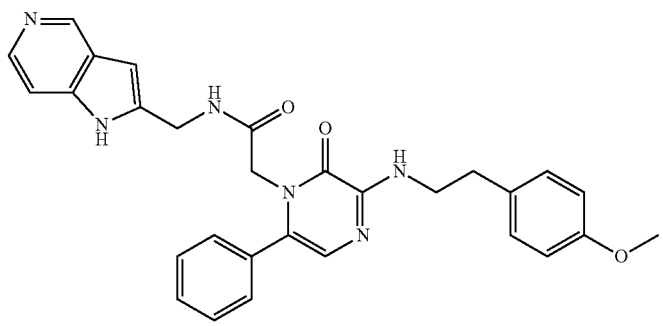 [SMILES: COc1ccc(CCNc2ncc(-c3ccccc3)n(CC(=O)NCc3cc4cnccc4[nH]3)c2=O)cc1] | — |
| IV-143 | 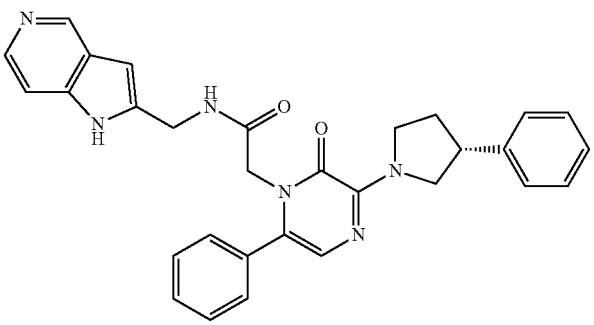 [SMILES: O=C(Cn1c(-c2ccccc2)cnc(N2CC[C@H](c3ccccc3)C2)c1=O)NCc1cc2cnccc2[nH]1] | — |
| IV-144 | 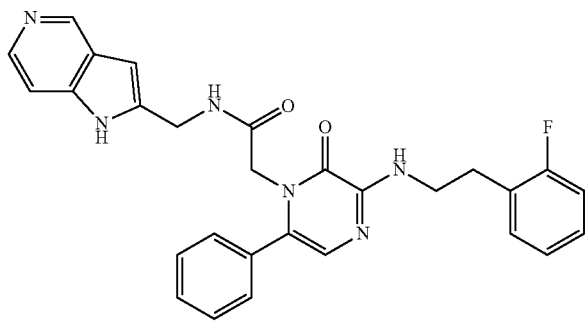 [SMILES: O=C(Cn1c(-c2ccccc2)cnc(NCCc2ccccc2F)c1=O)NCc1cc2cnccc2[nH]1] | — |

TABLE 4E-continued
Exemplary MASP-2 inhibitory compounds
| Comp No. | Structure | Salt |
|---|---|---|
| IV-145 | 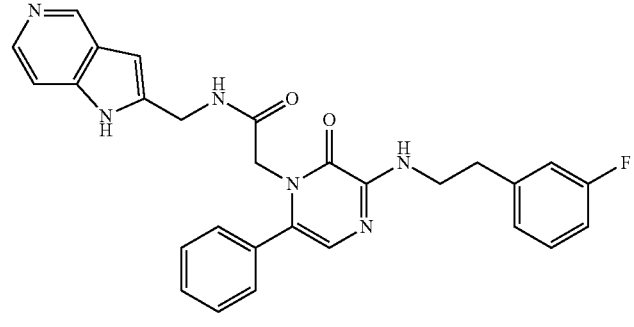 [SMILES: O=C(Cn1c(-c2ccccc2)cnc(NCCc2cccc(F)c2)c1=O)NCc1cc2cnccc2[nH]1] | — |
| IV-146 | 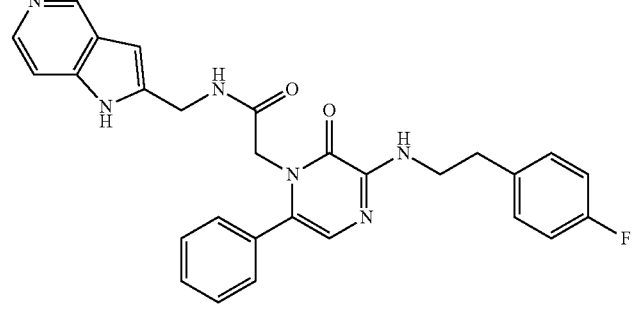 | — |
| IV-147 | 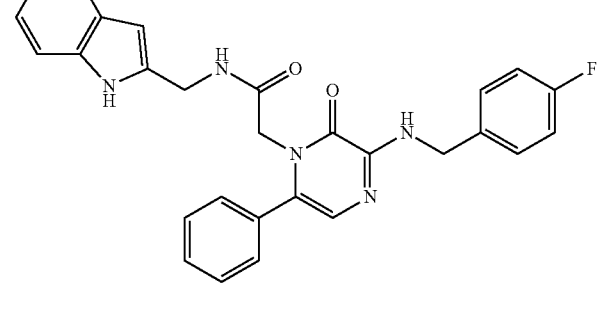 | — |
| IV-148 | 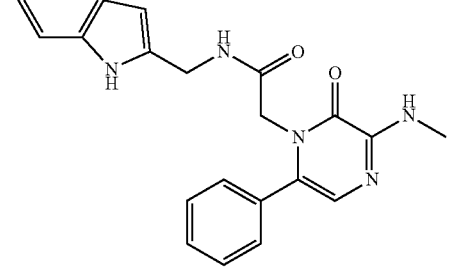 | — |

TABLE 4E-continued
Exemplary MASP-2 inhibitory compounds
| Comp No. | Structure | Salt |
|---|---|---|
| IV-149 | 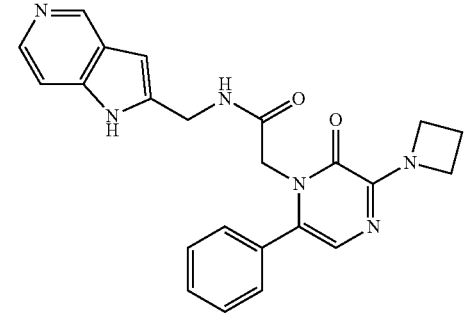 [SMILES: O=C(Cn1c(-c2ccccc2)cnc(N2CCC2)c1=O)NCc1cc2cnccc2[nH]1] | — |
| IV-150 | 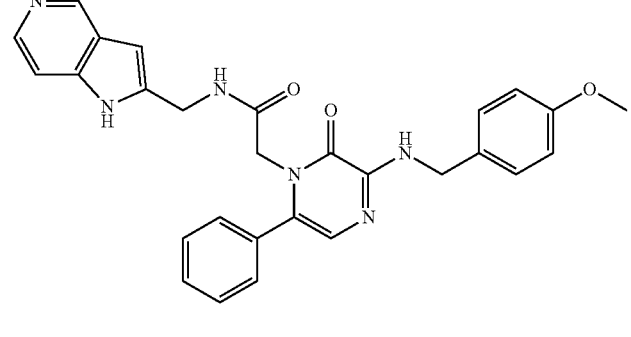 | — |
| IV-151 | 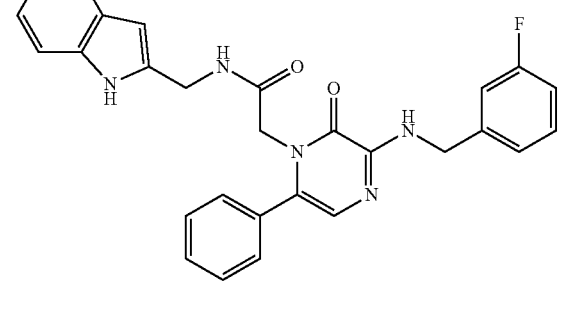 | — |
| IV-152 | 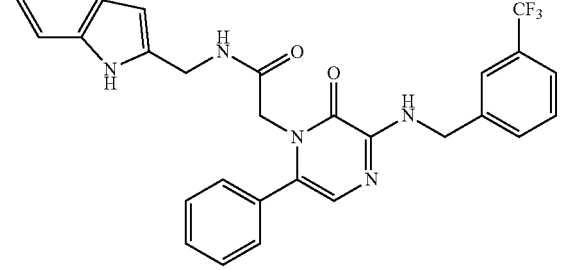 | — |

TABLE 4E-continued
Exemplary MASP-2 inhibitory compounds
| Comp No. | Structure | Salt |
|---|---|---|
| IV-153 | 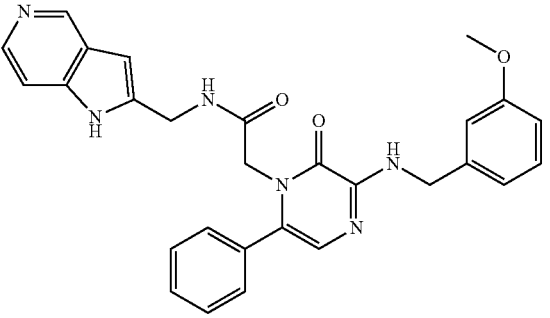 [SMILES: COc1cccc(CNc2ncc(-c3ccccc3)n(CC(=O)NCc3cc4cnccc4[nH]3)c2=O)c1] | — |
| IV-154 | 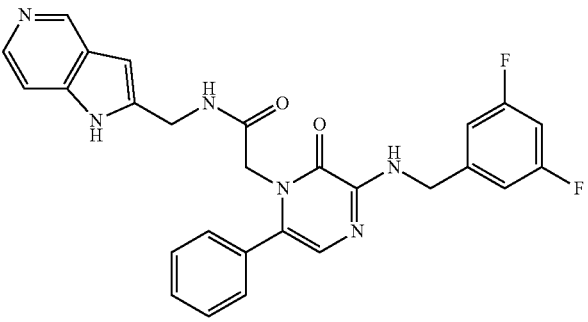 [SMILES: O=C(Cn1c(-c2ccccc2)cnc(NCc2cc(F)cc(F)c2)c1=O)NCc1cc2cnccc2[nH]1] | — |
| IV-155 | 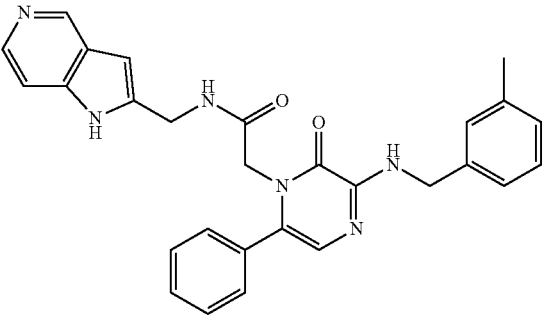 [SMILES: Cc1cccc(CNc2ncc(-c3ccccc3)n(CC(=O)NCc3cc4cnccc4[nH]3)c2=O)c1] | — |
| IV-156 | 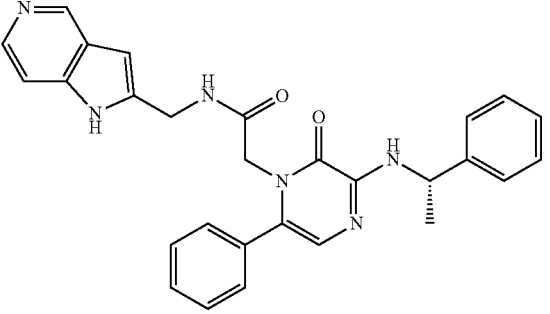 [SMILES: C[C@H](Nc1ncc(-c2ccccc2)n(CC(=O)NCc2cc3cnccc3[nH]2)c1=O)c1ccccc1] | — |

TABLE 4E-continued

Exemplary MASP-2 inhibitory compounds

| Comp No. | Structure | Salt |
|---|---|---|
| IV-157 | 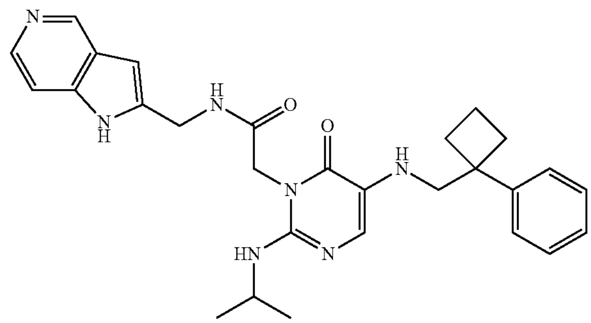 [SMILES: CC(C)Nc1ncc(NCC2(c3ccccc3)CCC2)c(=O)n1CC(=O)NCc1cc2cnccc2[nH]1] | 2TFA |
| IV-158 | 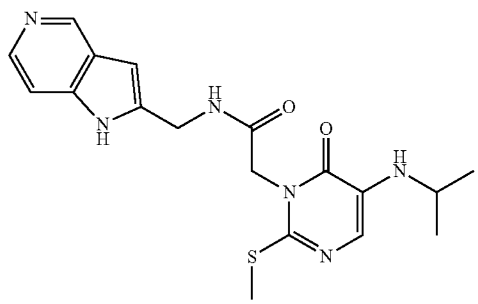 [SMILES: CSc1ncc(NC(C)C)c(=O)n1CC(=O)NCc1cc2cnccc2[nH]1] | — |
| IV-159 | 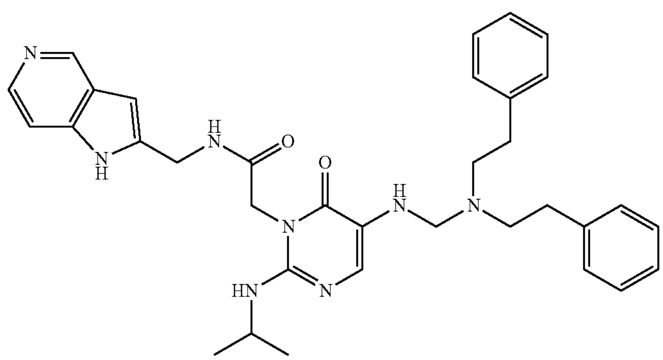 [SMILES: CC(C)Nc1ncc(NCN(CCc2ccccc2)CCc2ccccc2)c(=O)n1CC(=O)NCc1cc2cnccc2[nH]1] | — |
| IV-160 | 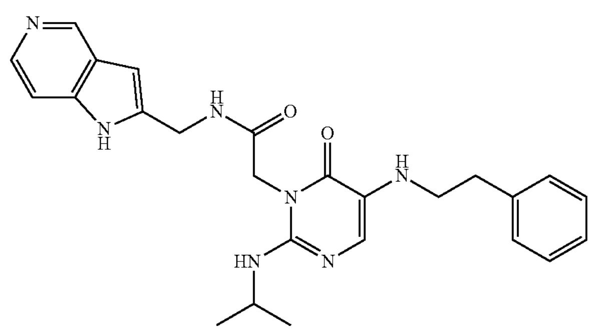 [SMILES: CC(C)Nc1ncc(NCCc2ccccc2)c(=O)n1CC(=O)NCc1cc2cnccc2[nH]1] | — |

TABLE 4E-continued

Exemplary MASP-2 inhibitory compounds

| Comp No. | Structure | Salt |
|---|---|---|
| IV-161 | 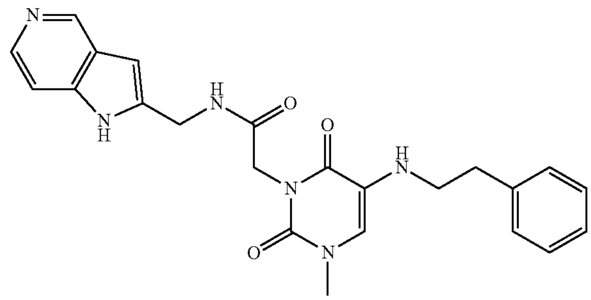 [SMILES: Cn1cc(NCCc2ccccc2)c(=O)n(CC(=O)NCc2cc3cnccc3[nH]2)c1=O] | — |
| IV-162 | 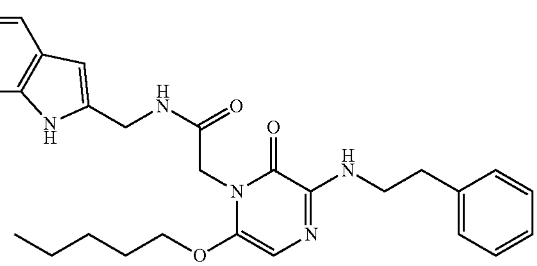 | — |
| IV-163 | 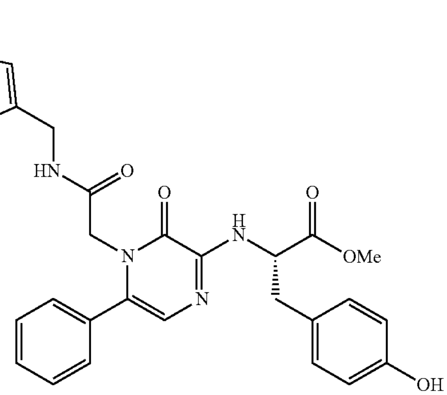 | TFA |

In some embodiments, the MASP-2 inhibitory agent is a compound of any one of Tables 4A, 4B, 4C, 4D, and 4E. In some embodiments, the MASP-2 inhibitory agent is compound 1230, 1231, III-91, or I-89. In some embodiments, the MASP-2 inhibitory agent is a small molecule with a molecular weight from 200 Da to 2,000 Da. In some embodiments, the MASP-2 inhibitory agent is a small molecule with a molecular weight from 250 Da to 2,000 Da. In some embodiments, the MASP-2 inhibitory agent is a small molecule with a molecular weight from 350 Da to 2,000 Da. In some embodiments, the MASP-2 inhibitory agent is a small molecule with a molecular weight from 350 Da to 1,500 Da. In some embodiments, the MASP-2 inhibitory agent is a small molecule with a molecular weight from 350 Da to 1,200 Da.

In some embodiments, the MASP-2 inhibitory agent is a small molecule that has only one basic group selected from guanidine and benzamidine groups. In some embodiments, the MASP-2 inhibitory agent is a small molecule that does not include a basic group selected from guanidine and benzamidine groups.

Expression Inhibitors of MASP-2

In another embodiment of this aspect of the invention, the MASP-2 inhibitory agent is a MASP-2 expression inhibitor capable of inhibiting MASP-2-dependent complement activation. In the practice of this aspect of the invention, representative MASP-2 expression inhibitors include MASP-2 antisense nucleic acid molecules (such as antisense mRNA, antisense DNA or antisense oligonucleotides), MASP-2 ribozymes and MASP-2 RNAi molecules.

Anti-sense RNA and DNA molecules act to directly block the translation of MASP-2 mRNA by hybridizing to MASP-2 mRNA and preventing translation of MASP-2 protein. An antisense nucleic acid molecule may be constructed in a number of different ways provided that it is capable of interfering with the expression of MASP-2. For example, an antisense nucleic acid molecule can be constructed by inverting the coding region (or a portion thereof) of MASP-2 cDNA (SEQ ID NO:4) relative to its normal orientation for transcription to allow for the transcription of its complement.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of MASP-2 is an antisense MASP-2 nucleic acid molecule which is at least ninety percent identical to the complement of the MASP-2 cDNA consisting of the nucleic acid sequence set forth in SEQ ID NO:4. The nucleic acid sequence set forth in SEQ ID NO:4 encodes the MASP-2 protein consisting of the amino acid sequence set forth in SEQ ID NO:5.

The targeting of antisense oligonucleotides to bind MASP-2 mRNA is another mechanism that may be used to reduce the level of MASP-2 protein synthesis. For example, the synthesis of polygalacturonase and the muscarine type 2 acetylcholine receptor is inhibited by antisense oligonucleotides directed to their respective mRNA sequences (U.S. Pat. No. 5,739,119, to Cheng, and U.S. Pat. No. 5,759,829, to Shewmaker). Furthermore, examples of antisense inhibition have been demonstrated with the nuclear protein cyclin, the multiple drug resistance gene (MDG1), ICAM-1, E-se-lectin, STK-1, striatal GABAA receptor and human EGF (see, e.g., U.S. Pat. No. 5,801,154, to Baracchini; U.S. Pat. No. 5,789,573, to Baker; U.S. Pat. No. 5,718,709, to Consi-dine; and U.S. Pat. No. 5,610,288, to Reubenstein).

A system has been described that allows one of ordinary skill to determine which oligonucleotides are useful in the invention, which involves probing for suitable sites in the target mRNA using RNAse H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the MASP-2 transcript is added to cell extracts expressing MASP-2, such as hepatocytes, and hybridized in order to create an RNAse H vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, I., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the MASP-2 mRNA are those that are at or near the AUG translation initiation codon, and those sequences that are substantially complementary to 5' regions of the mRNA, e.g., between the −10 and +10 regions of the MASP-2 gene nucleotide sequence (SEQ ID NO:4). Exemplary MASP-2 expression inhibitors are provided below: SEQ ID NO:30 (nucleotides 22-680 of SEQ ID NO:4): Nucleic acid sequence of MASP-2 cDNA (SEQ ID NO:4) encoding CUBIEGF.

SEQ ID NO:31 (5'CGGGCACACCAT-GAGGCTGCTGACCCTCCTGGGC3'): Nucleotides 12-45 of SEQ ID NO:4 including the MASP-2 translation start site (sense).

SEQ ID NO:32 (5'GACATTACCTTCCGCTCCGACTC-CAACGAGAAG3'): Nucleotides 361-396 of SEQ ID NO:4 encoding a region comprising the MASP-2 MBL binding site (sense).

SEQ ID NO:33 (5'AGCAGCCCTGAATACC-CACGGCCGTATCCCAAA3'): Nucleotides 610-642 of SEQ ID NO:4 encoding a region comprising the CUBII domain As noted above, the term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illustrative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent base-pairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a sequence and its complement listed herein. (e.g., SEQ ID NO:30 to SEQ ID NO:33). Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:4 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods. Such methods are taught in Ausubel et al., *Current Protocols in Molecular Biology*, John Wiley & Sons, Inc., 1993.

Ribozymes can also be utilized to decrease the amount and/or biological activity of MASP-2, such as ribozymes that target MASP-2 mRNA. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target MASP-2 mRNA, and a catalytic region that is adapted to cleave the target MASP-2 mRNA (see generally, EPA No. 0 321 201; WO88/04300; Haseloff, J., et al., *Nature* 334:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

V. PHARMACEUTICAL COMPOSITIONS AND DELIVERY METHODS DOSING

In another aspect, the invention provides compositions for inhibiting the adverse effects of MASP-2-dependent complement activation in a subject suffering from a disease or condition as disclosed herein, comprising administering to the subject a composition comprising a therapeutically effective amount of a MASP-2 inhibitory agent and a pharmaceutically acceptable carrier. The MASP-2 inhibitory agents can be administered to a subject in need thereof, at therapeutically effective doses to treat or ameliorate conditions associated with MASP-2-dependent complement activation. A therapeutically effective dose refers to the amount of the MASP-2 inhibitory agent sufficient to result in amelioration of symptoms associated with the disease or condition.

Toxicity and therapeutic efficacy of MASP-2 inhibitory agents can be determined by standard pharmaceutical procedures employing experimental animal models, such as the murine MASP-2−/− mouse model expressing the human MASP-2 transgene described in Example 1. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-2 inhibitory agents that exhibit large therapeutic ratios or indices are most preferred. The data obtained from the cell culture assays and animal studies can be used in formulating a range of dosages for use in humans. The dosage of the MASP-2 inhibitory agent preferably lies within a range of circulating concentrations that include the MED with little or no toxicity. The dosage may vary within this range depending upon the dosage form employed and the route of administration utilized.

In some embodiments, therapeutic efficacy of the MASP-2 inhibitory agents for treating, inhibiting, alleviating or preventing fibrosis in a mammalian subject suffering, or at risk of developing a disease or disorder caused or exacerbated by fibrosis and/or inflammation is determined by one or more of the following: a reduction in one of more markers of inflammation and scarring (e.g., TGFβ-1, CTFF, IL-6, apoptosis, fibronectin, laminin, collagens, EMT, infiltrating macrophages) in renal tissue; a reduction in the release of soluble markers of inflammation and fibrotic renal disease into urine and plasma (e.g., by the measurement of renal excretory functions).

For any compound formulation, the therapeutically effective dose can be estimated using animal models. For example, a dose may be formulated in an animal model to achieve a circulating plasma concentration range that includes the MED. Quantitative levels of the MASP-2 inhibitory agent in plasma may also be measured, for example, by high performance liquid chromatography.

In addition to toxicity studies, effective dosage may also be estimated based on the amount of MASP-2 protein present in a living subject and the binding affinity of the MASP-2 inhibitory agent. It has been shown that MASP-2 levels in normal human subjects is present in serum in low levels in the range of 500 ng/ml, and MASP-2 levels in a particular subject can be determined using a quantitative assay for MASP-2 described in Moller-Kristensen M., et al., *J. Immunol. Methods* 282:159-167, 2003.

Generally, the dosage of administered compositions comprising MASP-2 inhibitory agents varies depending on such factors as the subject's age, weight, height, sex, general medical condition, and previous medical history. As an illustration, MASP-2 inhibitory agents, such as anti-MASP-2 antibodies, can be administered in dosage ranges from about 0.010 to 10.0 mg/kg, preferably 0.010 to 1.0 mg/kg, more preferably 0.010 to 0.1 mg/kg of the subject body weight. In some embodiments the composition comprises a combination of anti-MASP-2 antibodies and MASP-2 inhibitory peptides.

Therapeutic efficacy of MASP-2 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize monoclonal antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in measured, for example, as described in Example 2, the reduction of C4 cleavage and C4b deposition (measured, for example as described in Example 10), or the reduction of C3 cleavage and C3b deposition (measured, for example, as described in Example 10).

Additional Agents

In certain embodiments, methods of preventing, treating, reverting and/or inhibiting fibrosis and/or inflammation include administering an MASP-2 inhibitory agent (e.g., a MASP-2 inhibitory antibody) as part of a therapeutic regimen along with one or more other drugs, biologics, or therapeutic interventions appropriate for inhibiting fibrosis and/or inflammation. In certain embodiments, the additional drug, biologic, or therapeutic intervention is appropriate for particular symptoms associated with a disease or disorder caused or exacerbated by fibrosis and/or inflammation. By way of example, MASP-2 inhibitory antibodies may be administered as part of a therapeutic regimen along with one or more immunosuppressive agents, such as methotrexate, cyclophosphamide, azathioprine, and mycophenolate mofetil. By way of further example, MASP-2 inhibitory antibodies may be administered as part of a therapeutic regimen along with one or more agents designed to increase blood flow (e.g., nifedipine, amlodipine, diltiazem, felodipine, or nicardipine). By way of further example, MASP-2 inhibitory antibodies may be administered as part of a therapeutic regimen along with one or more agents intended to decrease fibrosis, such as d-penicillamine, colchicine, PUVA, Relaxin, cyclosporine, TGF beta blockers and/or p38 MAPK blockers. By way of further example, MASP-2 inhibitory antibodies may be administered as part of a therapeutic regimen along with steroids or broncho-dilators.

The compositions and methods comprising MASP-2 inhibitory agents (e.g., MASP-2 inhibitory antibodies) may optionally comprise one or more additional therapeutic agents, which may augment the activity of the MASP-2 inhibitory agent or that provide related therapeutic functions in an additive or synergistic fashion. For example, in the context of treating a subject suffering from a disease or disorder caused or exacerbated by fibrosis and/or inflammation one or more MASP-2 inhibitory agents may be administered in combination (including co-administration) with one or more additional antifibrotic agents and/or one or more anti-viral and/or anti-inflammatory and/or immunosuppressive agents.

MASP-2 inhibitory agents (e.g., MASP-2 inhibitory antibodies) can be used in combination with other therapeutic agents such as general antiviral drugs, or immunosuppressive drugs such as corticosteroids, immunosuppressive or cytotoxic agents, and/or antifibrotic agents.

In some embodiments of the methods described herein, MASP-2 inhibitory agents (e.g., MASP-2 inhibitory antibodies or small molecule inhibitors of MASP-2) are used as a monotherapy for the treatment of a subject suffering from coronavirus such as suffering from COVID-19 or influenza virus. In some embodiments of the methods described herein, MASP-2 inhibitory agents (e.g., MASP-2 inhibitory antibodies or small molecule inhibitors of MASP-2) are used in combination with other therapeutic agents, such as antiviral agents, therapeutic antibodies, corticosteroids and/or other agents that are shown to be efficacious for the treatment of a subject suffering from coronavirus or influenza virus. In some embodiments, a pharmaceutical composition comprises a MASP-2 inhibitory agent (e.g., MASP-2 inhibitory antibodies or small molecule inhibitors of MASP-2) and at least one additional therapeutic agent such as an antiviral agent (e.g., remdesivir), a therapeutic antibody to a target other than MASP-2, a corticosteroid, an anticoagulant, such as low molecular weight herparin (e.g., enoxaparin) and an antibiotic (e.g., azithromycin).

In such combination therapies, a MASP-2 inhibitory agent may be formulated with or administered concurrently with, prior to, or subsequent to, one or more other desired COVID-19 therapeutic agent such as an antiviral agent (e.g., remdesivir), a therapeutic antibody to a target other than MASP-2, a corticosteroid, or an anticoagulant. Each component of a combination therapy may be formulated in a variety of ways that are known in the art. For example, the MASP-2 inhibitory agent and second agent of the combination therapy may be formulated together or separately. The MASP-2 inhibitory agent and additional agent may be suitably administered to the COVID-19 patient at one time or over a series of treatments.

Exemplary antiviral agents include, for example darunavir (which may be used with ritonavir or cobicistat to increase darunavir levels), favilavir, lopinavir, ritonavir, remdesivir, galidesivir, ebastine, danoprevir, ASC09, emtricitabine, tenofovir, umifnovir, baloxavir marboxil, azvudine and/or ISR-50. Exemplary therapeutic antibodies include, for example, vascular growth factor inhibitors (e.g., bevacizumab), PD-1 blocking antibodies (e.g., thymosin, camrelizumab), CCR5 antagonists (e.g., leronlimab), IL-6 receptor antagonists (e.g., sarilumab, tocilizumab), IL-6 targeted inhibitors (e.g., siltuximab), anti-GMCSF antibodies (e.g., gimsilumab, TJM2), GMCSF receptor alpha blocking antibodies (e.g., mavrilimumab), anti-C5 antibodies (e.g., eculizumab, ravulizumab), and/or anti-C5a antibodies (IFX-1).

In some embodiments of the methods described herein, MASP-2 inhibitory agents (e.g., MASP-2 inhibitory antibodies, e.g., OMS646, or small molecule inhibitors of MASP-2) are used in combination with an antiviral agent such as remdesivir for the treatment of a subject suffering from COVID-19.

Other agents that may be efficacious for the treatment of coronavirus and/or influenza virus include, for example, chloroquine/hydroxychloroquine, camostat mesylate, ruxolinib, peginterferon alfa-2b, novaferon, ifenprodil, recombinant ACE2, APN01, brilacidin, BXT-25, BIO-11006, fingolimod, WP1122, interferon beta-1a, nafamostat, losartan and/or alteplase.

Pharmaceutical Carriers and Delivery Vehicles

In general, the MASP-2 inhibitory agent compositions of the present invention, combined with any other selected therapeutic agents, are suitably contained in a pharmaceutically acceptable carrier. The carrier is non-toxic, biocompatible and is selected so as not to detrimentally affect the biological activity of the MASP-2 inhibitory agent (and any other therapeutic agents combined therewith). Exemplary pharmaceutically acceptable carriers for peptides are described in U.S. Pat. No. 5,211,657 to Yamada. The anti-MASP-2 antibodies and inhibitory peptides useful in the invention may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO: PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular delivery, the MASP-2 inhibitory agent may be carried in above-described liquid or gel carriers that are injectable, above-described sustained-release delivery vehicles that are injectable, or a hyaluronic acid or hyaluronic acid derivative.

For oral administration of non-peptidergic agents, the MASP-2 inhibitory agent may be carried in an inert filler or diluent such as sucrose, cornstarch, or cellulose.

For topical administration, the MASP-2 inhibitory agent may be carried in ointment, lotion, cream, gel, drop, suppository, spray, liquid or powder, or in gel or microcapsular delivery systems via a transdermal patch.

Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavouring agents (for oral administration).

Pharmaceutical Carriers for Antibodies and Peptides

More specifically with respect to anti-MASP-2 antibodies and inhibitory peptides, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising anti-MASP-2 antibodies and inhibitory peptides. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-MASP-2 antibodies and inhibitory peptides can also be administered in the form of a depot injection or implant preparation that can be formulated in such a manner as to permit a sustained or pulsatile release of the active agents.

Pharmaceutically Acceptable Carriers for Expression Inhibitors

More specifically with respect to expression inhibitors useful in the methods of the invention, compositions are provided that comprise an expression inhibitor as described above and a pharmaceutically acceptable carrier or diluent. The composition may further comprise a colloidal dispersion system.

Pharmaceutical compositions that include expression inhibitors may include, but are not limited to, solutions, emulsions, and liposome-containing formulations. These compositions may be generated from a variety of components that include, but are not limited to, preformed liquids, self-emulsifying solids and self-emulsifying semisolids. The preparation of such compositions typically involves combining the expression inhibitor with one or more of the following: buffers, antioxidants, low molecular weight polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are examples of suitable diluents.

In some embodiments, the compositions may be prepared and formulated as emulsions which are typically heterogeneous systems of one liquid dispersed in another in the form of droplets (see, Idson, in *Pharmaceutical Dosage Forms*, Vol. 1, Rieger and Banker (eds.), Marcek Dekker, Inc., N.Y., 1988). Examples of naturally occurring emulsifiers used in emulsion formulations include acacia, beeswax, lanolin, lecithin and phosphatides.

In one embodiment, compositions including nucleic acids can be formulated as microemulsions. A microemulsion, as used herein refers to a system of water, oil, and amphiphile, which is a single optically isotropic and thermodynamically stable liquid solution (see Rosoff in *Pharmaceutical Dosage Forms*, Vol. 1). The method of the invention may also use liposomes for the transfer and delivery of antisense oligonucleotides to the desired site.

Pharmaceutical compositions and formulations of expression inhibitors for topical administration may include transdermal patches, ointments, lotions, creams, gels, drops, suppositories, sprays, liquids and powders. Conventional pharmaceutical carriers, as well as aqueous, powder or oily bases and thickeners and the like may be used.

Modes of Administration

The pharmaceutical compositions comprising MASP-2 inhibitory agents may be administered in a number of ways depending on whether a local or systemic mode of administration is most appropriate for the condition being treated. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

MASP-2 inhibitory antibodies and polypeptides can be delivered into a subject in need thereof by any suitable means. Methods of delivery of MASP-2 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-2 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-2 inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J. Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-2 inhibitory antibodies and polypeptides may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-2 inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-2 inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-2 inhibitory agent may be achieved in the context of surgical methods for treating disease or disorder caused or exacerbated by fibrosis and/or inflammation such as for example during procedures such as surgery.

Treatment Regimens

In prophylactic applications, the pharmaceutical compositions comprising a MASP-2 inhibitory agent (e.g., a MASP-2 inhibitory antibody or MASP-2 inhibitory small molecule compound) are administered to a subject susceptible to, or otherwise at risk of developing coronavirus-induced acute respiratory distress syndrome or influenza virus-induced acute respiratory distress syndrome in an amount sufficient to inhibit MASP-2-dependent complement activation and thereby reduce, eliminate or reduce the risk of developing symptoms of the respiratory syndrome. In both prophylactic and therapeutic regimens, compositions comprising MASP-2 inhibitory agents may be administered in several dosages until a sufficient therapeutic outcome has been achieved in the subject. Application of the MASP-2 inhibitory compositions of the present invention may be carried out by a single administration of the composition, or a limited sequence of administrations, for treatment of an acute condition associated with fibrosis and/or inflammation. Alternatively, the composition may be administered at periodic intervals over an extended period of time for treatment of chronic conditions associated with fibrosis and/or inflammation.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises a MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of a subject suffering from or at risk for developing a disease or disorder caused or exacerbated by fibrosis and/or inflammation. Alternatively, the composition may be administered at periodic intervals such as daily, biweekly, weekly, every other week, monthly or bimonthly over an extended period of time for treatment of a subject suffering from or at risk for developing a disease or disorder caused or exacerbated by fibrosis and/or inflammation.

In both prophylactic and therapeutic regimens, compositions comprising MASP-2 inhibitory agents may be administered in several dosages until a sufficient therapeutic outcome has been achieved in the subject.

VI. EXAMPLES

The following examples merely illustrate the best mode now contemplated for practicing the invention, but should not be construed to limit the invention. All literature citations herein are expressly incorporated by reference.

Example 1

This example describes the generation of a mouse strain deficient in MASP-2 (MASP-2−/−) but sufficient of MAp19 (MAp19+/+).

Figure 3:
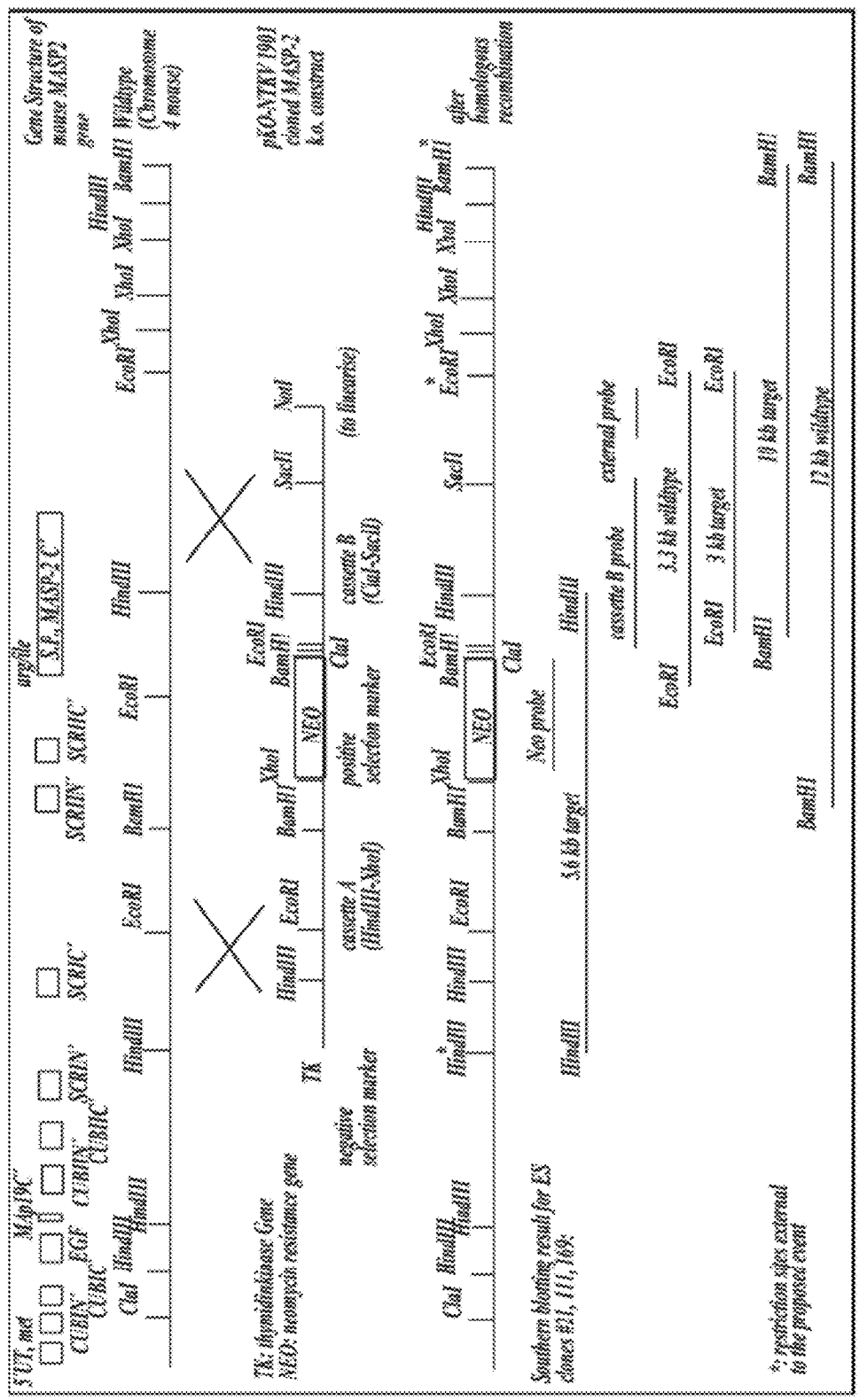
FIG. 3 is a diagram illustrating the murine MASP-2 knockout strategy.

Materials and Methods: The targeting vector pKO-NTKV 1901 was designed to disrupt the three exons coding for the C-terminal end of murine MASP-2, including the exon that encodes the serine protease domain, as shown in FIG. 3. PKO-NTKV 1901 was used to transfect the murine ES cell line E14.1a (SV129 Ola). Neomycin-resistant and Thymidine Kinase-sensitive clones were selected. 600 ES clones were screened and, of these, four different clones were identified and verified by southern blot to contain the expected selective targeting and recombination event as shown in FIG. 3. Chimeras were generated from these four positive clones by embryo transfer. The chimeras were then backcrossed in the genetic background C57/BL6 to create transgenic males. The transgenic males were crossed with females to generate F1s with 50% of the offspring showing heterozygosity for the disrupted MASP-2 gene. The heterozygous mice were intercrossed to generate homozygous MASP-2 deficient offspring, resulting in heterozygous and wild-type mice in the ration of 1:2:1, respectively.

Results and Phenotype: The resulting homozygous MASP-2−/− deficient mice were found to be viable and fertile and were verified to be MASP-2 deficient by southern blot to confirm the correct targeting event, by Northern blot to confirm the absence of MASP-2 mRNA, and by Western blot to confirm the absence of MASP-2 protein (data not shown). The presence of MAp19 mRNA and the absence of MASP-2 mRNA were further confirmed using time-resolved RT-PCR on a LightCycler machine. The MASP-2−/− mice do continue to express MAp19, MASP-1, and MASP-3 mRNA and protein as expected (data not shown). The presence and abundance of mRNA in the MASP-2−/− mice for Properdin, Factor B, Factor D, C4, C2, and C3 was assessed by LightCycler analysis and found to be identical to that of the wild-type littermate controls (data not shown). The plasma from homozygous MASP-2−/− mice is totally deficient of lectin-pathway-mediated complement activation as further described in Example 2.

Generation of a MASP-2−/− strain on a pure C57BL6 Background: The MASP-2−/− mice were back-crossed with a pure $C_{57}BL6$ line for nine generations prior to use of the MASP-2−/− strain as an experimental animal model.

Figure 4:
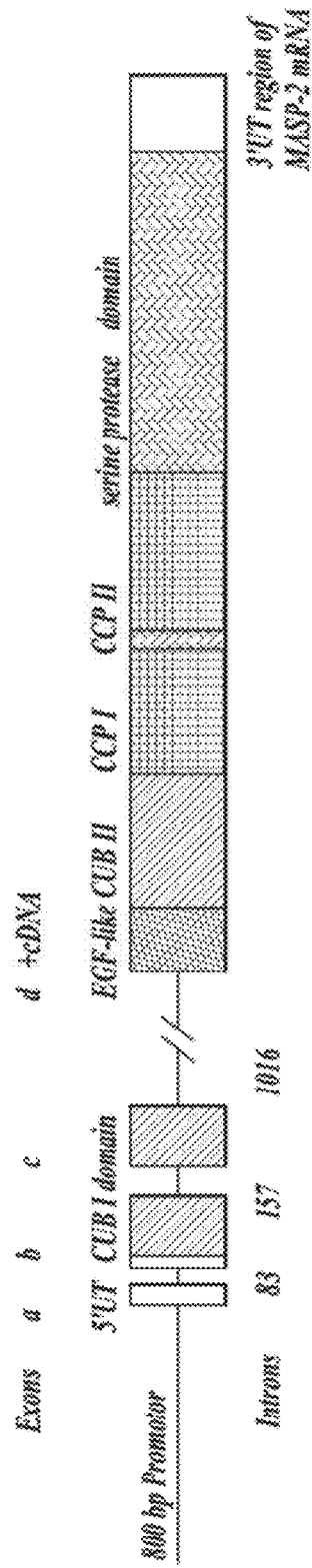
FIG. 4 is a diagram illustrating the human MASP-2 minigene construct.

A transgenic mouse strain that is murine MASP-2−/−, MAp19+/+ and that expresses a human MASP-2 transgene (a murine MASP-2 knock-out and a human MASP-2 knock-in) was also generated as follows:

Materials and Methods: A minigene encoding human MASP-2 called "mini hMASP-2" (SEQ ID NO:49) as shown in FIG. 4 was constructed which includes the promoter region of the human MASP 2 gene, including the first 3 exons (exon 1 to exon 3) followed by the cDNA sequence that represents the coding sequence of the following 8 exons, thereby encoding the full-length MASP-2 protein driven by its endogenous promoter. The mini hMASP-2 construct was injected into fertilized eggs of MASP-2−/− in order to replace the deficient murine MASP 2 gene by transgenically expressed human MASP-2.

Example 2

This example demonstrates that MASP-2 is required for complement activation via the lectin pathway.

Methods and Materials

Lectin pathway specific C4 Cleavage Assay: A C4 cleavage assay has been described by Petersen, et al., *J. Immunol. Methods* 257:107 (2001) that measures lectin pathway activation resulting from lipoteichoic acid (LTA) from *S. aureus*, which binds L-ficolin. The assay described by Petersen et al., (2001) was adapted to measure lectin pathway activation via MBL by coating the plate with LPS and mannan or zymosan prior to adding serum from MASP-2−/− mice as described below. The assay was also modified to remove the possibility of C4 cleavage due to the classical pathway. This was achieved by using a sample dilution buffer containing 1 M NaCl, which permits high affinity binding of lectin pathway recognition components to their ligands but prevents activation of endogenous C4, thereby excluding the participation of the classical pathway by dissociating the C1 complex. Briefly described, in the modified assay serum samples (diluted in high salt (1 M NaCl) buffer) are added to ligand-coated plates, followed by the addition of a constant amount of purified C4 in a buffer with a physiological concentration of salt. Bound recognition complexes containing MASP-2 cleave the C4, resulting in C4b deposition.

Assay Methods:
1) Nunc Maxisorb microtiter plates (MaxiSorb®, Nunc, Cat. No. 442404, Fisher Scientific) were coated with 1 μg/ml mannan (M7504 Sigma) or any other ligand (e.g., such as those listed below) diluted in coating buffer (15 mM $Na_2CO_3$, 35 mM $NaHCO_3$, pH 9.6).

The following reagents were used in the assay:
   a. mannan (1 μg/well mannan (M7504 Sigma) in 100 μl coating buffer):
   b. zymosan (1 μg/well zymosan (Sigma) in 100 μl coating buffer);
   c. LTA (1 μg/well in 100 μl coating buffer or 2 μg/well in 20 μl methanol)
   d. 1 μg of the H-ficolin specific Mab 4H5 in coating buffer
   e. PSA from *Aerococcus viridans* (2 μg/well in 100 μl coating buffer)
   f. 100 μl/well of formalin-fixed *S. aureus* DSM20233 ($OD_{550}$=0.5) in coating buffer.

2) The plates were incubated overnight at 4° C.
3) After overnight incubation, the residual protein binding sites were saturated by incubated the plates with 0.1% HSA-TBS blocking buffer (0.1% (w/v) HSA in 10 mM Tris-CL, 140 mM NaCl, 1.5 mM $NaN_3$, pH 7.4) for 1-3 hours, then washing the plates 3× with TBS/tween/$Ca^{2+}$ (TBS with 0.05% Tween 20 and 5 mM $CaCl_2$, 1 mM $MgCl_2$, pH 7.4).
4) Serum samples to be tested were diluted in MBL-binding buffer (1 M NaCl) and the diluted samples were added to the plates and incubated overnight at 4° C. Wells receiving buffer only were used as negative controls.
5) Following incubation overnight at 4° C., the plates were washed 3× with TBS/tween/$Ca^{2+}$. Human C4 (100 μl/well of 1 μg/ml diluted in BBS (4 mM barbital, 145 mM NaCl, 2 mM $CaCl_2$, 1 mM $MgCl_2$, pH 7.4)) was then added to the plates and incubated for 90 minutes at 37° C. The plates were washed again 3× with TBS/tween/$Ca^{2+}$.
6) C4b deposition was detected with an alkaline phosphatase-conjugated chicken anti-human C4c (diluted 1:1000 in TBS/tween/$Ca^{2+}$), which was added to the plates and incubated for 90 minutes at room temperature. The plates were then washed again 3× with TBS/tween/$Ca^{2+}$.
7) Alkaline phosphatase was detected by adding 100 μl of p-nitrophenyl phosphate substrate solution, incubating at room temperature for 20 minutes, and reading the $OD_{405}$ in a microtiter plate reader.

Figure 5A:
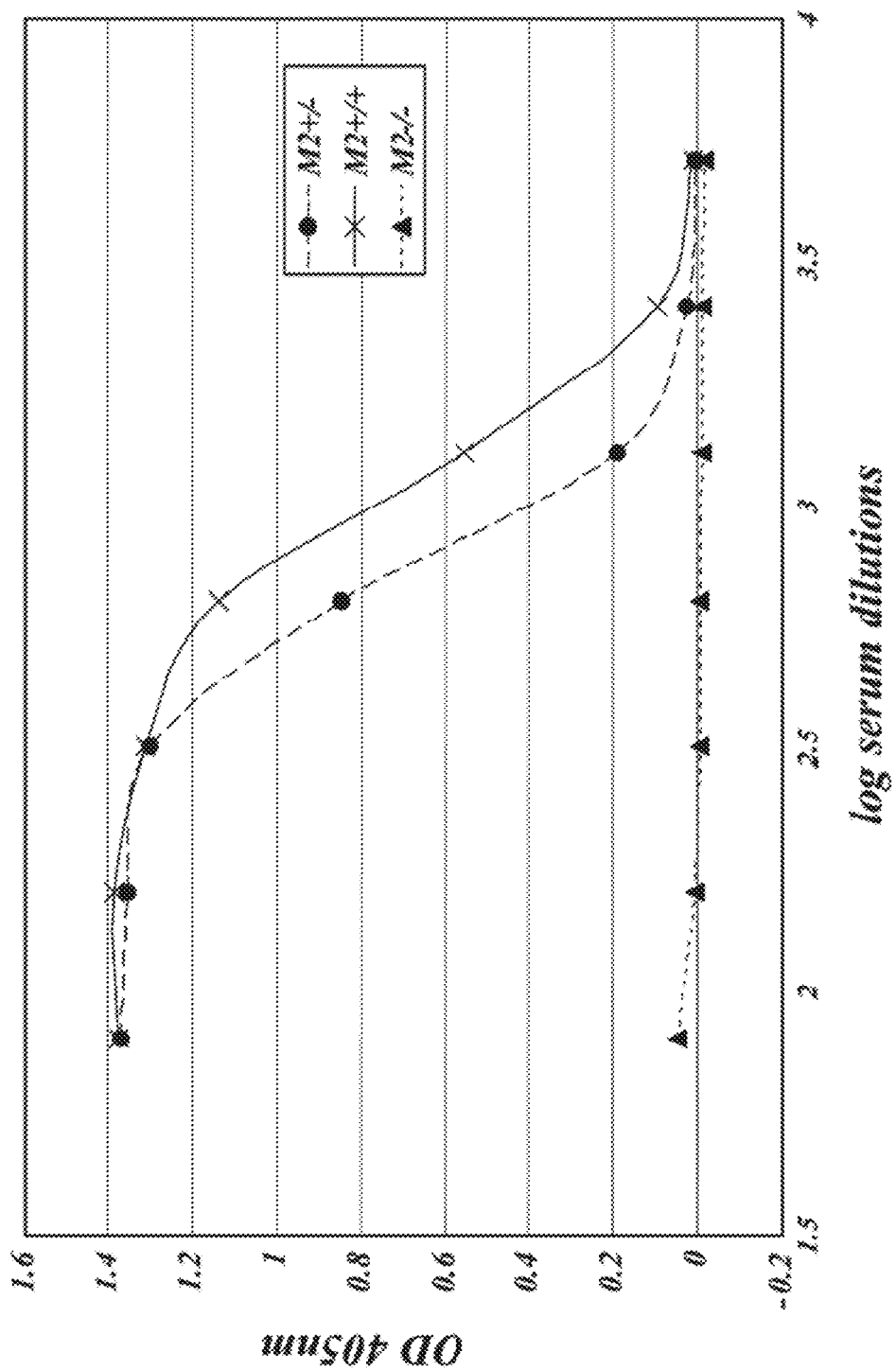
FIG. 5A presents results demonstrating that MASP-2-deficiency leads to the loss of lectin-pathway-mediated C4 activation as measured by lack of C4b deposition on mannan, as described in Example 2.
Figure 5B:
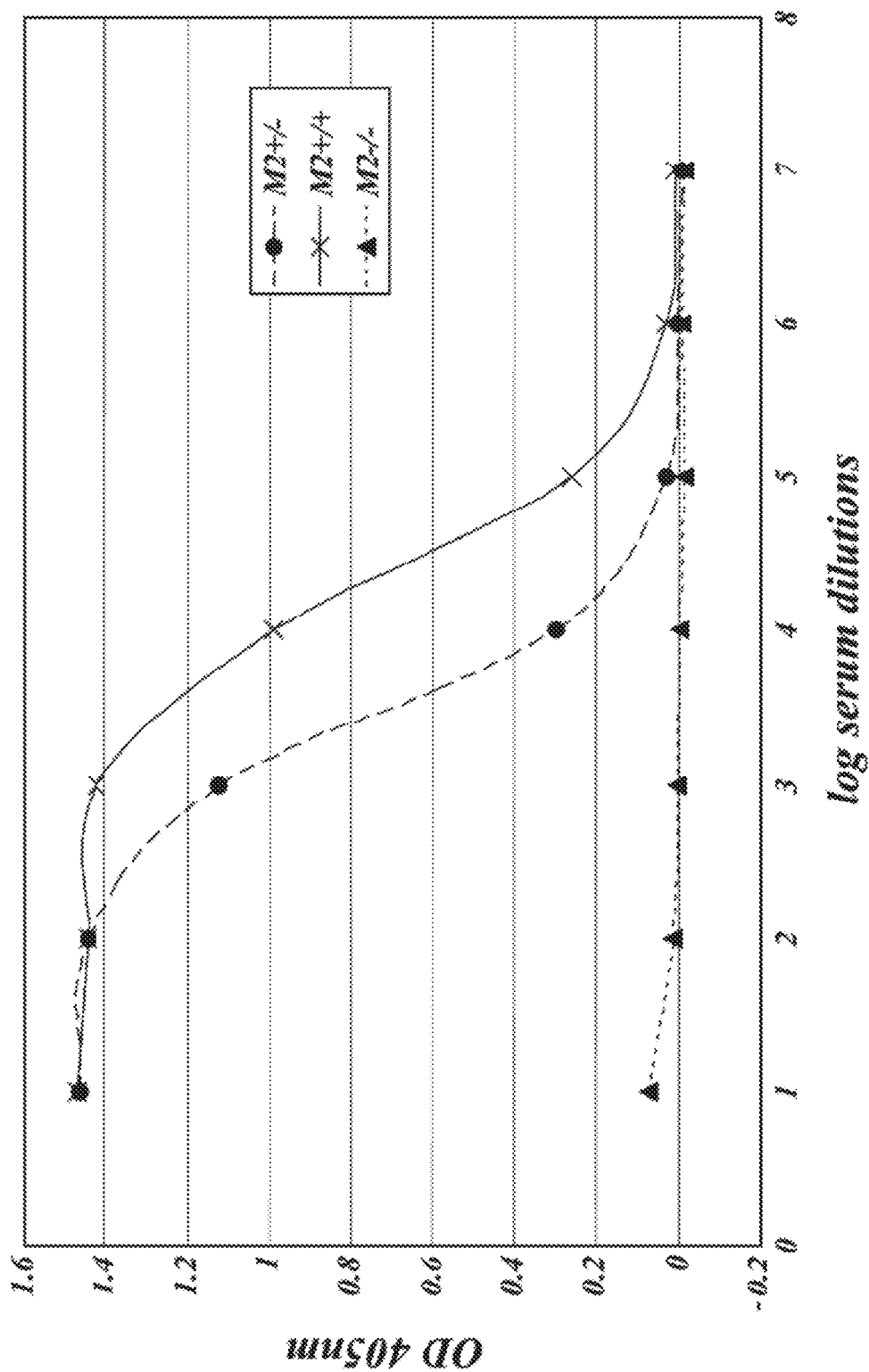
FIG. 5B presents results demonstrating that MASP-2-deficiency leads to the loss of lectin-pathway-mediated C4 activation as measured by lack of C4b deposition on zymosan, as described in Example 2.
Figure 5C:
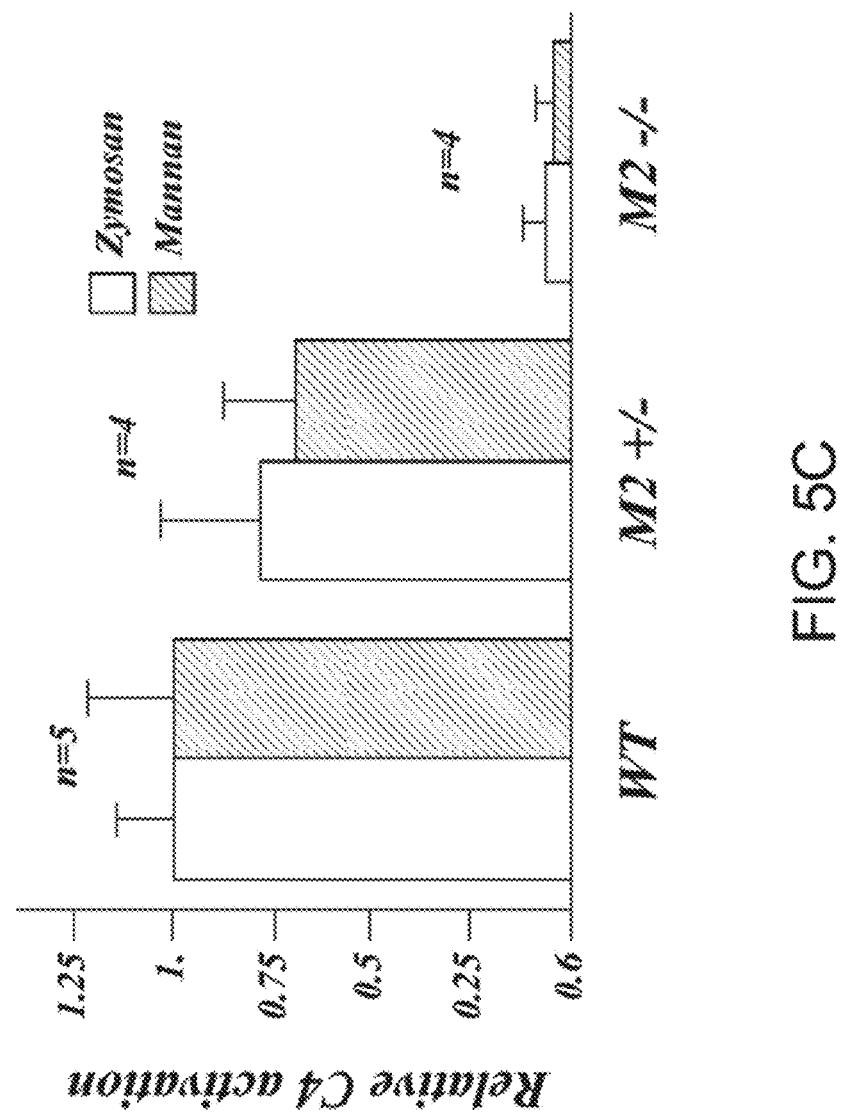
FIG. 5C presents results demonstrating the relative C4 activation levels of serum samples obtained from MASP-2+/−; MASP-2−/− and wild-type strains as measure by C4b deposition on mannan and on zymosan, as described in Example 2.

Results: FIGS. 5A-B show the amount of C4b deposition on mannan (FIG. 5A) and zymosan (FIG. 5B) in serum dilutions from MASP-2+/+(crosses), MASP-2+/−(closed circles) and MASP-2−/− (closed triangles). FIG. 5C shows the relative C4 convertase activity on plates coated with zymosan (white bars) or mannan (shaded bars) from MASP-2−/+ mice (n=5) and MASP-2−/− mice (n=4) relative to wild-type mice (n=5) based on measuring the amount of C4b deposition normalized to wild-type serum. The error bars represent the standard deviation. As shown in FIGS. 5A-C, plasma from MASP-2−/− mice is totally deficient in lectin-pathway-mediated complement activation on mannan and on zymosan coated plates. These results clearly demonstrate that MASP-2 is an effector component of the lectin pathway. Recombinant MASP-2 Reconstitutes Lectin Pathway-Dependent C4 Activation in Serum from the MASP-2−/− Mice In order to establish that the absence of MASP-2 was the direct cause of the loss of lectin pathway-dependent C4 activation in the MASP-2−/− mice, the effect of adding recombinant MASP-2 protein to serum samples was examined in the C4 cleavage assay described above. Functionally active murine MASP-2 and catalytically inactive murine MASP-2A (in which the active-site serine residue in the serine protease domain was substituted for the alanine residue) recombinant proteins were produced and purified as described below in Example 3. Pooled serum from 4 MASP-2−/− mice was pre-incubated with increasing protein concentrations of recombinant murine MASP-2 or inactive recombinant murine MASP-2A and C4 convertase activity was assayed as described above.

Figure 6:
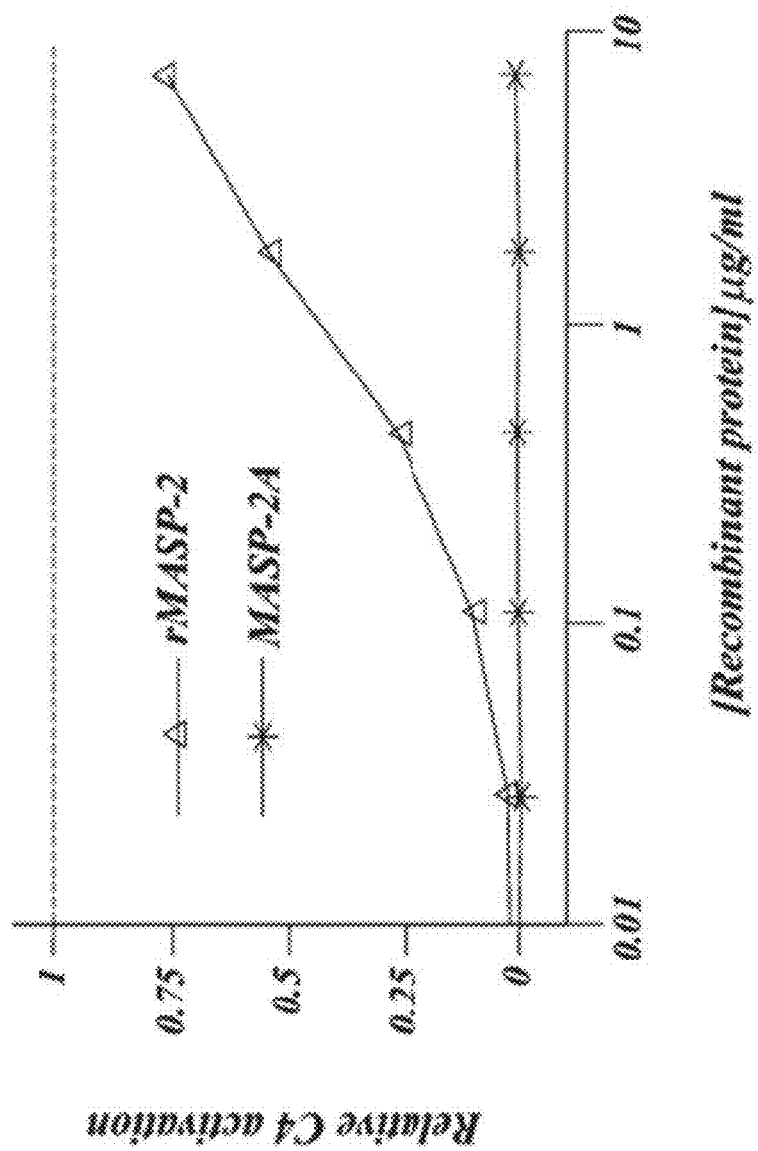
FIG. 6 presents results demonstrating that the addition of murine recombinant MASP-2 to MASP-2−/− serum samples recovers lectin-pathway-mediated C4 activation in a protein concentration dependent manner, as measured by C4b deposition on mannan, as described in Example 2.

Results: As shown in FIG. 6, the addition of functionally active murine recombinant MASP-2 protein (shown as open triangles) to serum obtained from the MASP-2−/− mice restored lectin pathway-dependent C4 activation in a protein concentration dependent manner, whereas the catalytically inactive murine MASP-2A protein (shown as stars) did not restore C4 activation. The results shown in FIG. 6 are normalized to the C4 activation observed with pooled wild-type mouse serum (shown as a dotted line).

Example 3

This example describes the recombinant expression and protein production of recombinant full-length human, rat and murine MASP-2, MASP-2 derived polypeptides, and catalytically inactivated mutant forms of MASP-2

Expression of Full-Length Human, Murine and Rat MASP-2:

The full length cDNA sequence of human MASP-2 (SEQ ID NO: 4) was also subcloned into the mammalian expression vector pCI-Neo (Promega), which drives eukaryotic expression under the control of the CMV enhancer/promoter region (described in Kaufman R. J. et al., *Nucleic Acids Research* 19:4485-90, 1991; Kaufman, *Methods in Enzymology*, 185:537-66 (1991)). The full length mouse cDNA (SEQ ID NO:50) and rat MASP-2 cDNA (SEQ ID NO:53) were each subcloned into the pED expression vector. The MASP-2 expression vectors were then transfected into the adherent Chinese hamster ovary cell line DXB1 using the standard calcium phosphate transfection procedure described in Maniatis et al., 1989. Cells transfected with these constructs grew very slowly, implying that the encoded protease is cytotoxic.

In another approach, the minigene construct (SEQ ID NO:49) containing the human cDNA of MASP-2 driven by its endogenous promoter is transiently transfected into Chinese hamster ovary cells (CHO). The human MASP-2 protein is secreted into the culture media and isolated as described below.

Expression of Full-Length Catalytically Inactive MASP-2:

Rationale: MASP-2 is activated by autocatalytic cleavage after the recognition subcomponents MBL or ficolins (either L-ficolin, H-ficolin or M-ficolin) bind to their respective carbohydrate pattern. Autocatalytic cleavage resulting in activation of MASP-2 often occurs during the isolation procedure of MASP-2 from serum, or during the purification following recombinant expression. In order to obtain a more stable protein preparation for use as an antigen, a catalytically inactive form of MASP-2, designed as MASP-2A was created by replacing the serine residue that is present in the catalytic triad of the protease domain with an alanine residue in rat (SEQ ID NO:55 Ser617 to Ala617); in mouse (SEQ ID NO:52 Ser617 to Ala617); or in human (SEQ ID NO:6 Ser618 to Ala618).

In order to generate catalytically inactive human and murine MASP-2A proteins, site-directed mutagenesis was carried out using the oligonucleotides shown in TABLE 5. The oligonucleotides in TABLE 5 were designed to anneal to the region of the human and murine cDNA encoding the enzymatically active serine and oligonucleotide contain a mismatch in order to change the serine codon into an alanine codon. For example, PCR oligonucleotides SEQ ID NOS: 56-59 were used in combination with human MASP-2 cDNA (SEQ ID NO:4) to amplify the region from the start codon to the enzymatically active serine and from the serine to the stop codon to generate the complete open reading from of the mutated MASP-2A containing the Ser618 to Ala618 mutation. The PCR products were purified after agarose gel electrophoresis and band preparation and single adenosine overlaps were generated using a standard tailing procedure. The adenosine tailed MASP-2A was then cloned into the pGEM-T easy vector, transformed into *E. coli*.

A catalytically inactive rat MASP-2A protein was generated by kinasing and annealing SEQ ID NO:64 and SEQ ID NO:65 by combining these two oligonucleotides in equal molar amounts, heating at 100° C. for 2 minutes and slowly cooling to room temperature. The resulting annealed fragment has Pst1 and Xba1 compatible ends and was inserted in place of the Pst1-Xba1 fragment of the wild-type rat MASP-2 cDNA (SEQ ID NO:53 to generate rat MASP-2A.

```
                                              (SEQ ID NO: 64)
   5' GAGGTGACGCAGGAGGGGCATTAGTGTTT 3'
                                              (SEQ ID NO: 65)
   5' CTAGAAACACTAATGCCCCTCCTGCGTCACCTCTGCA 3'
```

The human, murine and rat MASP-2A were each further subcloned into either of the mammalian expression vectors pED or pCI-Neo and transfected into the Chinese Hamster ovary cell line DXB1 as described below.

In another approach, a catalytically inactive form of MASP-2 is constructed using the method described in Chen et al., *J. Biol. Chem.*, 276(28):25894-25902, 2001. Briefly, the plasmid containing the full-length human MASP-2 cDNA (described in Thiel et al., *Nature* 386:506, 1997) is digested with Xho1 and EcoR1 and the MASP-2 cDNA (described herein as SEQ ID NO:4) is cloned into the corresponding restriction sites of the pFastBac1 baculovirus transfer vector (Life Technologies, NY). The MASP-2 serine protease active site at Ser618 is then altered to Ala618 by substituting the double-stranded oligonucleotides encoding the peptide region amino acid 610-625 (SEQ ID NO:13) with the native region amino acids 610 to 625 to create a MASP-2 full length polypeptide with an inactive protease domain.

Construction of Expression Plasmids Containing Polypeptide Regions Derived from Human Masp-2.

The following constructs are produced using the MASP-2 signal peptide (residues 1-15 of SEQ ID NO:5) to secrete various domains of MASP-2. A construct expressing the human MASP-2 CUBI domain (SEQ ID NO:8) is made by PCR amplifying the region encoding residues 1-121 of MASP-2 (SEQ ID NO:6) (corresponding to the N-terminal CUBI domain). A construct expressing the human MASP-2 CUBIEGF domain (SEQ ID NO:9) is made by PCR amplifying the region encoding residues 1-166 of MASP-2 (SEQ ID NO:6) (corresponding to the N-terminal CUBIEGF domain). A construct expressing the human MASP-2 CUBIEGFCUBII domain (SEQ ID NO:10) is made by PCR amplifying the region encoding residues 1-293 of MASP-2 (SEQ ID NO:6) (corresponding to the N-terminal CUBIEGFCUBII domain). The above mentioned domains are amplified by PCR using Vent$_R$ polymerase and pBS-MASP-2 as a template, according to established PCR methods. The 5' primer sequence of the sense primer (5'-CGG-GATCCATGAGGCTGCTGACCCTC-3' SEQ ID NO:34) introduces a BamHI restriction site (underlined) at the 5' end of the PCR products. Antisense primers for each of the MASP-2 domains, shown below in TABLE 5, are designed to introduce a stop codon (boldface) followed by an EcoRI site (underlined) at the end of each PCR product. Once amplified, the DNA fragments are digested with BamHI and EcoRI and cloned into the corresponding sites of the pFast-Bac1 vector. The resulting constructs are characterized by restriction mapping and confirmed by dsDNA sequencing.

TABLE 5

MASP-2 PCR PRIMERS

| MASP-2 domain | 5' PCR Primer | 3' PCR Primer |
|---|---|---|
| SEQ ID NO: 8 CUBI (aa 1-121 of SEQ ID NO: 6) | 5'CGGGATCCATGAG GCTGCTGACCCTC-3' (SEQ ID NO: 34) | 5'GGAATTCCTAGGCTGCA TA (SEQ ID NO: 35) |
| SEQ ID NO: 9 CUBIEGF (aa 1-166 of SEQ ID NO: 6) | 5'CGGGATCCATGAG GCTGCTGACCCTC-3' (SEQ ID NO: 34) | 5'GGAATTCCTACAGGGCG CT-3' (SEQ ID NO: 36) |
| SEQ ID NO: 10 CUBIEGFCUBII (aa 1-293 of SEQ ID NO: 6) | 5'CGGGATCCATGAG GCTGCTGACCCTC-3' (SEQ ID NO: 34) | 5'GGAATTCCTAGTAGTGG AT 3' (SEQ ID NO: 37) |
| SEQ ID NO: 4 human MASP-2 | 5'ATGAGGCTGCTGA CCCTCCTGGGCCTTC 3' (SEQ ID NO: 56) hMASP-2 forward | 5'TTAAAATCACTAATTAT GTTCTCGATC 3' (SEQ ID NO: 59) hMASP-2_reverse |
| SEQ ID NO: 4 human MASP-2 cDNA | 5'CAGAGGTGACGCA GGAGGGGCAC 3' (SEQ ID NO: 58) hMASP-2 ala forward | 5'GTGCCCCTCCTGCGTCA CCTCTG 3' (SEQ ID NO: 57) hMASP-2_ala_reverse |
| SEQ ID NO: 50 Murine MASP-2 cDNA | 5'ATGAGGCTACTCA TCTTCCTGG3' (SEQ ID NO: 60) mMASP-2_forward | 5'TTAGAAATTACTTATTAT GTTCTCAATCC3' (SEQ ID NO: 63) mMASP-2_reverse |
| SEQ ID NO: 50 Murine MASP-2 cDNA | 5'CCCCCCCTGCGTC ACCTCTGCAG3' (SEQ ID NO: 62) mMASP-2_ala_forward | 5'CTGCAGAGGTGACGCAG GGGGGG 3' (SEQ ID NO: 61) mMASP-2_ala_reverse |

Recombinant Eukaryotic Expression of MASP-2 and Protein Production of Enzymatically Inactive Mouse, Rat, and Human MASP-2A.

The MASP-2 and MASP-2A expression constructs described above were transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium for each of the three species.

MASP-2A protein purification: The MASP-2A (Ser-Ala mutant described above) was purified by affinity chromatography on MBP-A-agarose columns. This strategy enabled rapid purification without the use of extraneous tags. MASP-2A (100-200 ml of medium diluted with an equal volume of loading buffer (50 mM Tris-Cl, pH 7.5, containing 150 mM NaCl and 25 mM CaCl$_2$)) was loaded onto an MBP-agarose affinity column (4 ml) pre-equilibrated with 10 ml of loading buffer. Following washing with a further 10 ml of loading buffer, protein was eluted in 1 ml fractions with 50 mM Tris-Cl, pH 7.5, containing 1.25 M NaCl and 10 mM EDTA. Fractions containing the MASP-2A were identified by SDS-polyacrylamide gel electrophoresis. Where necessary, MASP-2A was purified further by ion-exchange chromatography on a MonoQ column (HR 5/5). Protein was dialyzed with 50 mM Tris-Cl pH 7.5, containing 50 mM NaCl and loaded onto the column equilibrated in the same buffer. Following washing, bound MASP-2A was eluted with a 0.05-1 M NaCl gradient over 10 ml.

Results: Yields of 0.25-0.5 mg of MASP-2A protein were obtained from 200 ml of medium. The molecular mass of 77.5 kDa determined by MALDI-MS is greater than the calculated value of the unmodified polypeptide (73.5 kDa) due to glycosylation. Attachment of glycans at each of the N-glycosylation sites accounts for the observed mass. MASP-2A migrates as a single band on SDS-polyacrylamide gels, demonstrating that it is not proteolytically processed during biosynthesis. The weight-average molecular mass determined by equilibrium ultracentrifugation is in agreement with the calculated value for homodimers of the glycosylated polypeptide.

Production of Recombinant Human MASP-2 Polypeptides

Another method for producing recombinant MASP-2 and MASP2A derived polypeptides is described in Thielens, N. M., et al., *J. Immunol.* 166:5068-5077, 2001. Briefly, the *Spodoptera frugiperda* insect cells (Ready-Plaque Sf9 cells obtained from Novagen, Madison, WI) are grown and maintained in Sf900II serum-free medium (Life Technologies) supplemented with 50 IU/ml penicillin and 50 mg/ml streptomycin (Life Technologies). The *Trichoplusia ni* (High Five) insect cells (provided by Jadwiga Chroboczek, Institut de Biologie Structurale, Grenoble, France) are maintained in TC100 medium (Life Technologies) containing 10% FCS (Dominique Dutscher, Brumath, France) supplemented with 50 IU/ml penicillin and 50 mg/ml streptomycin. Recombinant baculoviruses are generated using the Bac-to-Bac System® (Life Technologies). The bacmid DNA is purified using the Qiagen midiprep purification system (Qiagen) and is used to transfect Sf9 insect cells using cellfectin in Sf900 II SFM medium (Life Technologies) as described in the manufacturer's protocol. Recombinant virus particles are collected 4 days later, titrated by virus plaque assay, and amplified as described by King and Possee, in *The Baculovirus Expression System: A Laboratory Guide*, Chapman and Hall Ltd., London, pp. 111-114, 1992.

High Five cells ($1.75 \times 10^7$ cells/175-cm² tissue culture flask) are infected with the recombinant viruses containing MASP-2 polypeptides at a multiplicity of infection of 2 in Sf900 II SFM medium at 28° C. for 96 h. The supernatants are collected by centrifugation and diisopropyl phosphorofluoridate is added to a final concentration of 1 mM.

The MASP-2 polypeptides are secreted in the culture medium. The culture supernatants are dialyzed against 50 mM NaCl, 1 mM $CaCl_2$), 50 mM triethanolamine hydrochloride, pH 8.1, and loaded at 1.5 ml/min onto a Q-Sepharose Fast Flow column (Amersham Pharmacia Biotech) ($2.8 \times 12$ cm) equilibrated in the same buffer. Elution is conducted by applying a 1.2 liter linear gradient to 350 mM NaCl in the same buffer. Fractions containing the recombinant MASP-2 polypeptides are identified by Western blot analysis, precipitated by addition of $(NH_4)_2SO_4$ to 60% (w/v), and left overnight at 4° C. The pellets are resuspended in 145 mM NaCl, 1 mM $CaCl_2$), 50 mM triethanolamine hydrochloride, pH 7.4, and applied onto a TSK G3000 SWG column ($7.5 \times 600$ mm) (Tosohaas, Montgomeryville, PA) equilibrated in the same buffer. The purified polypeptides are then concentrated to 0.3 mg/ml by ultrafiltration on Microsep microconcentrators (m.w. cut-off=10,000) (Filtron, Karlstein, Germany).

Example 4

This example describes a method of producing polyclonal antibodies against MASP-2 polypeptides.

Materials and Methods

MASP-2 Antigens: Polyclonal anti-human MASP-2 antiserum is produced by immunizing rabbits with the following isolated MASP-2 polypeptides: human MASP-2 (SEQ ID NO:6) isolated from serum; recombinant human MASP-2 (SEQ ID NO:6), MASP-2A containing the inactive protease domain (SEQ ID NO:13), as described in Example 3; and recombinant CUBI (SEQ ID NO:8), CUBEGFI (SEQ ID NO:9), and CUBEGFCUBII (SEQ ID NO:10) expressed as described above in Example 3.

Polyclonal antibodies: Six-week old Rabbits, primed with BCG (*bacillus* Calmette-Guerin vaccine) are immunized by injecting 100 µg of MASP-2 polypeptide at 100 µg/ml in sterile saline solution. Injections are done every 4 weeks, with antibody titer monitored by ELISA assay as described in Example 5. Culture supernatants are collected for antibody purification by protein A affinity chromatography.

Example 5

This example describes a method for producing murine monoclonal antibodies against rat or human MASP-2 polypeptides.

Materials and Methods

Male A/J mice (Harlan, Houston, Tex.), 8-12 weeks old, are injected subcutaneously with 100 µg human or rat rMASP-2 or rMASP-2A polypeptides (made as described in Example 3) in complete Freund's adjuvant (Difco Laboratories, Detroit, Mich.) in 200 µl of phosphate buffered saline (PBS) pH 7.4. At two-week intervals the mice are twice injected subcutaneously with 50 µg of human or rat rMASP-2 or rMASP-2A polypeptide in incomplete Freund's adjuvant. On the fourth week the mice are injected with 50 µg of human or rat rMASP-2 or rMASP-2A polypeptide in PBS and are fused 4 days later.

For each fusion, single cell suspensions are prepared from the spleen of an immunized mouse and used for fusion with Sp2/0 myeloma cells. $5 \times 10^8$ of the Sp2/0 and $5 \times 10^8$ spleen cells are fused in a medium containing 50% polyethylene glycol (M.W. 1450) (Kodak, Rochester, N.Y.) and 5% dimethylsulfoxide (Sigma Chemical Co., St. Louis, Mo.). The cells are then adjusted to a concentration of $1.5 \times 10^5$ spleen cells per 200 µl of the suspension in Iscove medium (Gibco, Grand Island, N.Y.), supplemented with 10% fetal bovine serum, 100 units/ml of penicillin, 100 µg/ml of streptomycin, 0.1 mM hypoxanthine, 0.4 M aminopterin and 16 M thymidine. Two hundred microliters of the cell suspension are added to each well of about twenty 96-well microculture plates. After about ten days culture supernatants are withdrawn for screening for reactivity with purified factor MASP-2 in an ELISA assay.

ELISA Assay: Wells of Immulon®2 (Dynatech Laboratories, Chantilly, Va.) microtest plates are coated by adding 50 µl of purified hMASP-2 at 50 ng/ml or rat rMASP-2 (or rMASP-2A) overnight at room temperature. The low concentration of MASP-2 for coating enables the selection of high-affinity antibodies. After the coating solution is removed by flicking the plate, 200 µl of BLOTTO (non-fat dry milk) in PBS is added to each well for one hour to block the non-specific sites. An hour later, the wells are then washed with a buffer PBST (PBS containing 0.05% Tween 20). Fifty microliters of culture supernatants from each fusion well is collected and mixed with 50 µl of BLOTTO and then added to the individual wells of the microtest plates. After one hour of incubation, the wells are washed with PBST. The bound murine antibodies are then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma, St. Louis, Mo.) and 0.0003% hydrogen peroxide (Sigma) is added to the wells for color development for 30 minutes. The reaction is terminated by addition of 50 µl of 2M $H_2SO_4$ per well. The Optical Density at 450 nm of the reaction mixture is read with a BioTek® ELISA Reader (BioTek® Instruments, Winooski, Vt.).

MASP-2 Binding Assay:

Culture supernatants that test positive in the MASP-2 ELISA assay described above can be tested in a binding assay to determine the binding affinity the MASP-2 inhibitory agents have for MASP-2. A similar assay can also be used to determine if the inhibitory agents bind to other antigens in the complement system.

Polystyrene microtiter plate wells (96-well medium binding plates, Corning Costar, Cambridge, MA) are coated with MASP-2 (20 ng/100 l/well, Advanced Research Technology, San Diego, CA) in phosphate-buffered saline (PBS) pH 7.4 overnight at 4° C. After aspirating the MASP-2 solution, wells are blocked with PBS containing 1% bovine serum albumin (BSA; Sigma Chemical) for 2 h at room temperature. Wells without MASP-2 coating serve as the background controls. Aliquots of hybridoma supernatants or purified anti-MASP-2 MoAbs, at varying concentrations in blocking solution, are added to the wells. Following a 2 h incubation at room temperature, the wells are extensively rinsed with PBS. MASP-2-bound anti-MASP-2 MoAb is detected by the addition of peroxidase-conjugated goat anti-mouse IgG (Sigma Chemical) in blocking solution, which is allowed to incubate for 1 h at room temperature.

The plate is rinsed again thoroughly with PBS, and 100 µl of 3,3',5,5'-tetramethyl benzidine (TMB) substrate (Kirkegaard and Perry Laboratories, Gaithersburg, MD) is added. The reaction of TMB is quenched by the addition of 100 µl of 1M phosphoric acid, and the plate is read at 450 nm in a microplate reader (SPECTRA MAX 250, Molecular Devices, Sunnyvale, CA).

The culture supernatants from the positive wells are then tested for the ability to inhibit complement activation in a functional assay such as the C4 cleavage assay as described in Example 2. The cells in positive wells are then cloned by limiting dilution. The MoAbs are tested again for reactivity with hMASP-2 in an ELISA assay as described above. The selected hybridomas are grown in spinner flasks and the spent culture supernatant collected for antibody purification by protein A affinity chromatography.

Example 6

This example describes the generation and production of humanized murine anti-MASP-2 antibodies and antibody fragments.

A murine anti-MASP-2 monoclonal antibody is generated in Male A/J mice as described in Example 5. The murine antibody is then humanized as described below to reduce its immunogenicity by replacing the murine constant regions with their human counterparts to generate a chimeric IgG and Fab fragment of the antibody, which is useful for inhibiting the adverse effects of MASP-2-dependent complement activation in human subjects in accordance with the present invention.

1. Cloning of anti-MASP-2 variable region genes from murine hybridoma cells. Total RNA is isolated from the hybridoma cells secreting anti-MASP-2 MoAb (obtained as described in Example 7) using RNAzol following the manufacturer's protocol (Biotech, Houston, Tex.). First strand cDNA is synthesized from the total RNA using oligo dT as the primer. PCR is performed using the immunoglobulin constant C region-derived 3' primers and degenerate primer sets derived from the leader peptide or the first framework region of murine $V_H$ or $V_K$ genes as the 5' primers. Anchored PCR is carried out as described by Chen and Platsucas (Chen, P. F., *Scand. J. Immunol.* 35:539-549, 1992). For cloning the $V_K$ gene, double-stranded cDNA is prepared using a Not1-MAK1 primer (5'-TGCGGCCGCTGTAGGTGCTGTCTTT-3' SEQ ID NO:38). Annealed adaptors AD1 (5'-GGAATTCACTCGT-TATTCTCGGA-3' SEQ ID NO:39) and AD2 (5'-TCCGAGAATAACGAGTG-3' SEQ ID NO:40) are ligated to both 5' and 3' termini of the double-stranded cDNA. Adaptors at the 3' ends are removed by Not1 digestion. The digested product is then used as the template in PCR with the AD1 oligonucleotide as the 5' primer and MAK2 (5'-CAT-TGAAAGCTTTGGGGTAGAAGTTGTTC-3' SEQ ID NO:41) as the 3' primer. DNA fragments of approximately 500 bp are cloned into pUC19. Several clones are selected for sequence analysis to verify that the cloned sequence encompasses the expected murine immunoglobulin constant region. The Not1-MAK1 and MAK2 oligonucleotides are derived from the $V_K$ region and are 182 and 84 bp, respectively, downstream from the first base pair of the C kappa gene. Clones are chosen that include the complete $V_K$ and leader peptide.

For cloning the $V_H$ gene, double-stranded cDNA is prepared using the Not1 MAG1 primer (5'-CGCGGCCGCAGCTGCTCAGAGTGTAGA-3' SEQ ID NO:42). Annealed adaptors AD1 and AD2 are ligated to both 5' and 3' termini of the double-stranded cDNA. Adaptors at the 3' ends are removed by Not1 digestion. The digested product are used as the template in PCR with the AD1 oligonucleotide and MAG2 (5'-CGGTAAGCTT-CACTGGCTCAGGGAAATA-3' SEQ ID NO:43) as primers. DNA fragments of 500 to 600 bp in length are cloned into pUC19. The Not1-MAG1 and MAG2 oligonucleotides are derived from the murine Cγ.7.1 region, and are 180 and 93 bp, respectively, downstream from the first bp of the murine Cγ.7.1 gene. Clones are chosen that encompass the complete $V_H$ and leader peptide.

2. Construction of Expression Vectors for Chimeric MASP-2 IgG and Fab. The cloned $V_H$ and $V_K$ genes described above are used as templates in a PCR reaction to add the Kozak consensus sequence to the 5' end and the splice donor to the 3' end of the nucleotide sequence. After the sequences are analyzed to confirm the absence of PCR errors, the $V_H$ and $V_K$ genes are inserted into expression vector cassettes containing human C.γ1 and C. kappa respectively, to give pSV2neoV$_H$-huCγ1 and pSV2neoV-huCγ. CsCl gradient-purified plasmid DNAs of the heavy- and light-chain vectors are used to transfect COS cells by electroporation. After 48 hours, the culture supernatant is tested by ELISA to confirm the presence of approximately 200 ng/ml of chimeric IgG. The cells are harvested and total RNA is prepared. First strand cDNA is synthesized from the total RNA using oligo dT as the primer. This cDNA is used as the template in PCR to generate the Fd and kappa DNA fragments. For the Fd gene, PCR is carried out using 5'-AAGAAGCTTGCCGCCACCATGGATTGGCTGTG-GAACT-3' (SEQ ID NO:44) as the 5' primer and a CH1-derived 3' primer (5'-CGGGATCCTCAAACTTTCTTGTC-CACCTTGG-3' SEQ ID NO:45). The DNA sequence is confirmed to contain the complete $V_H$ and the CH1 domain of human IgG1. After digestion with the proper enzymes, the Fd DNA fragments are inserted at the HindIII and BamHI restriction sites of the expression vector cassette pSV2dhfr-TUS to give pSV2dhfrFd. The pSV2 plasmid is commercially available and consists of DNA segments from various sources: pBR322 DNA (thin line) contains the pBR322 origin of DNA replication (pBR ori) and the lactamase ampicillin resistance gene (Amp); SV40 DNA, represented by wider hatching and marked, contains the SV40 origin of DNA replication (SV40 ori), early promoter (5' to the dhfr and neo genes), and polyadenylation signal (3' to the dhfr and neo genes). The SV40-derived polyadenylation signal (pA) is also placed at the 3' end of the Fd gene.

For the kappa gene, PCR is carried out using 5'-AAGAAAGCTTGCCGCCACCATGTTCT-CACTAGCTCT-3' (SEQ ID NO:46) as the 5' primer and a $C_K$-derived 3' primer (5'-CGG-GATCCTTCTCCCTCTAACACTCT-3' SEQ ID NO:47). DNA sequence is confirmed to contain the complete $V_K$ and human $C_K$ regions. After digestion with proper restriction enzymes, the kappa DNA fragments are inserted at the HindIII and BamHI restriction sites of the expression vector cassette pSV2neo-TUS to give pSV2neoK. The expression of both Fd and .kappa genes are driven by the HCMV-derived enhancer and promoter elements. Since the Fd gene does not include the cysteine amino acid residue involved in the inter-chain disulfide bond, this recombinant chimeric Fab contains non-covalently linked heavy- and light-chains. This chimeric Fab is designated as cFab.

To obtain recombinant Fab with an inter-heavy and light chain disulfide bond, the above Fd gene may be extended to include the coding sequence for additional 9 amino acids (EPKSCDKTH SEQ ID NO:48) from the hinge region of human IgG1. The BstEII-BamHI DNA segment encoding 30 amino acids at the 3' end of the Fd gene may be replaced with DNA segments encoding the extended Fd, resulting in pSV2dhfrFd/9aa.

3. Expression and Purification of Chimeric Anti-MASP-2 IgG

To generate cell lines secreting chimeric anti-MASP-2 IgG, NSO cells are transfected with purified plasmid DNAs of pSV2neoV$_H$-huC.γ1 and pSV2neoV-huC kappa by electroporation. Transfected cells are selected in the presence of 0.7 mg/ml G418. Cells are grown in a 250 ml spinner flask using serum-containing medium.

Culture supernatant of 100 ml spinner culture is loaded on a 10-ml PROSEP-A column (Bioprocessing, Inc., Princeton, N.J.). The column is washed with 10 bed volumes of PBS. The bound antibody is eluted with 50 mM citrate buffer, pH 3.0. Equal volume of 1 M Hepes, pH 8.0 is added to the fraction containing the purified antibody to adjust the pH to 7.0. Residual salts are removed by buffer exchange with PBS by Millipore membrane ultrafiltration (M.W. cut-off: 3,000). The protein concentration of the purified antibody is determined by the BCA method (Pierce).

4. Expression and Purification of Chimeric Anti-MASP-2 Fab

To generate cell lines secreting chimeric anti-MASP-2 Fab, CHO cells are transfected with purified plasmid DNAs of pSV2dhfrFd (or pSV2dhfrFd/9aa) and pSV2neokappa, by electroporation. Transfected cells are selected in the presence of G418 and methotrexate. Selected cell lines are amplified in increasing concentrations of methotrexate. Cells are single-cell subcloned by limiting dilution. High-producing single-cell subcloned cell lines are then grown in 100 ml spinner culture using serum-free medium.

Chimeric anti-MASP-2 Fab is purified by affinity chromatography using a mouse anti-idiotypic MoAb to the MASP-2 MoAb. An anti-idiotypic MASP-2 MoAb can be made by immunizing mice with a murine anti-MASP-2 MoAb conjugated with keyhole limpet hemocyanin (KLH) and screening for specific MoAb binding that can be competed with human MASP-2. For purification, 100 ml of supernatant from spinner cultures of CHO cells producing cFab or cFab/9aa are loaded onto the affinity column coupled with an anti-idiotype MASP-2 MoAb. The column is then washed thoroughly with PBS before the bound Fab is eluted with 50 mM diethylamine, pH 11.5. Residual salts are removed by buffer exchange as described above. The protein concentration of the purified Fab is determined by the BCA method (Pierce).

The ability of the chimeric MASP-2 IgG, cFab, and cFAb/9aa to inhibit MASP-2-dependent complement pathways may be determined by using the inhibitory assays described in Example 2 or Example 7.

Example 7

This example describes an in vitro C4 cleavage assay used as a functional screen to identify MASP-2 inhibitory agents capable of blocking MASP-2-dependent complement activation via L-ficolin/P35, H-ficolin, M-ficolin or mannan.

C4 Cleavage Assay: A C4 cleavage assay has been described by Petersen, S. V., et al., *J. Immunol. Methods* 257:107, 2001, which measures lectin pathway activation resulting from lipoteichoic acid (LTA) from *S. aureus* which binds L-ficolin.

Reagents: Formalin-fixed *S. aureous* (DSM20233) is prepared as follows: bacteria is grown overnight at 37° C. in tryptic soy blood medium, washed three times with PBS, then fixed for 1 h at room temperature in PBS/0.5% formalin, and washed a further three times with PBS, before being resuspended in coating buffer (15 mM Na$_2$Co$_3$, 35 mM NaHCO$_3$, pH 9.6).

Assay: The wells of a Nunc MaxiSorb® microtiter plate (Nalgene Nunc International, Rochester, NY) are coated with: 100 µl of formalin-fixed *S. aureus* DSM20233 (OD$_{550}$=0.5) in coating buffer with 1 µg of L-ficolin in coating buffer. After overnight incubation, wells are blocked with 0.1% human serum albumin (HSA) in TBS (10 mM Tris-HCl, 140 mM NaCl, pH 7.4), then are washed with TBS containing 0.05% Tween 20 and 5 mM CaCl$_2$ (wash buffer). Human serum samples are diluted in 20 mM Tris-HCl, 1 M NaCl, 10 mM CaCl$_2$, 0.05% Triton X-100, 0.1% HSA, pH 7.4, which prevents activation of endogenous C4 and dissociates the C1 complex (composed of C1q, C1r and C1s). MASP-2 inhibitory agents, including anti-MASP-2 MoAbs and inhibitory peptides are added to the serum samples in varying concentrations. The diluted samples are added to the plate and incubated overnight at 4° C. After 24 hours, the plates are washed thoroughly with wash buffer, then 0.1 µg of purified human C4 (obtained as described in Dodds, A. W., *Methods Enzymol.* 223:46, 1993) in 100 µl of 4 mM barbital, 145 mM NaCl, 2 mM CaCl$_2$, 1 mM MgCl$_2$, pH 7.4 is added to each well. After 1.5 h at 37° C., the plates are washed again and C4b deposition is detected using alkaline phosphatase-conjugated chicken anti-human C4c (obtained from Immunsystem, Uppsala, Sweden) and measured using the colorimetric substrate p-nitrophenyl phosphate.

C4 Assay on mannan: The assay described above is adapted to measure lectin pathway activation via MBL by coating the plate with LSP and mannan prior to adding serum mixed with various MASP-2 inhibitory agents.

C4 assay on H-ficolin (Hakata Ag): The assay described above is adapted to measure lectin pathway activation via H-ficolin by coating the plate with LPS and H-ficolin prior to adding serum mixed with various MASP-2 inhibitory agents.

Example 8

The following assay demonstrates the presence of classical pathway activation in wild-type and MASP-2−/− mice.

Methods: Immune complexes were generated in situ by coating microtiter plates (MaxiSorb®, Nunc, cat. No. 442404, Fisher Scientific) with 0.1% human serum albumin in 10 mM Tris, 140 mM NaCl, pH 7.4 for 1 hours at room temperature followed by overnight incubation at 4° C. with sheep anti whole serum antiserum (Scottish Antibody Production Unit, Carluke, Scotland) diluted 1:1000 in TBS/tween/Ca$^{2+}$. Serum samples were obtained from wild-type and MASP-2−/− mice and added to the coated plates. Control samples were prepared in which C1q was depleted from wild-type and MASP-2−/− serum samples. C1q-depleted mouse serum was prepared using protein-A-coupled Dynabeads® (Dynal Biotech, Oslo, Norway) coated with rabbit anti-human C1q IgG (Dako, Glostrup, Denmark), according to the supplier's instructions. The plates were incubated for 90 minutes at 37° C. Bound C3b was detected with a polyclonal anti-human-C3c Antibody (Dako A 062) diluted in TBS/tw/Ca$^{++}$ at 1:1000. The secondary antibody is goat anti-rabbit IgG.

Figure 7:
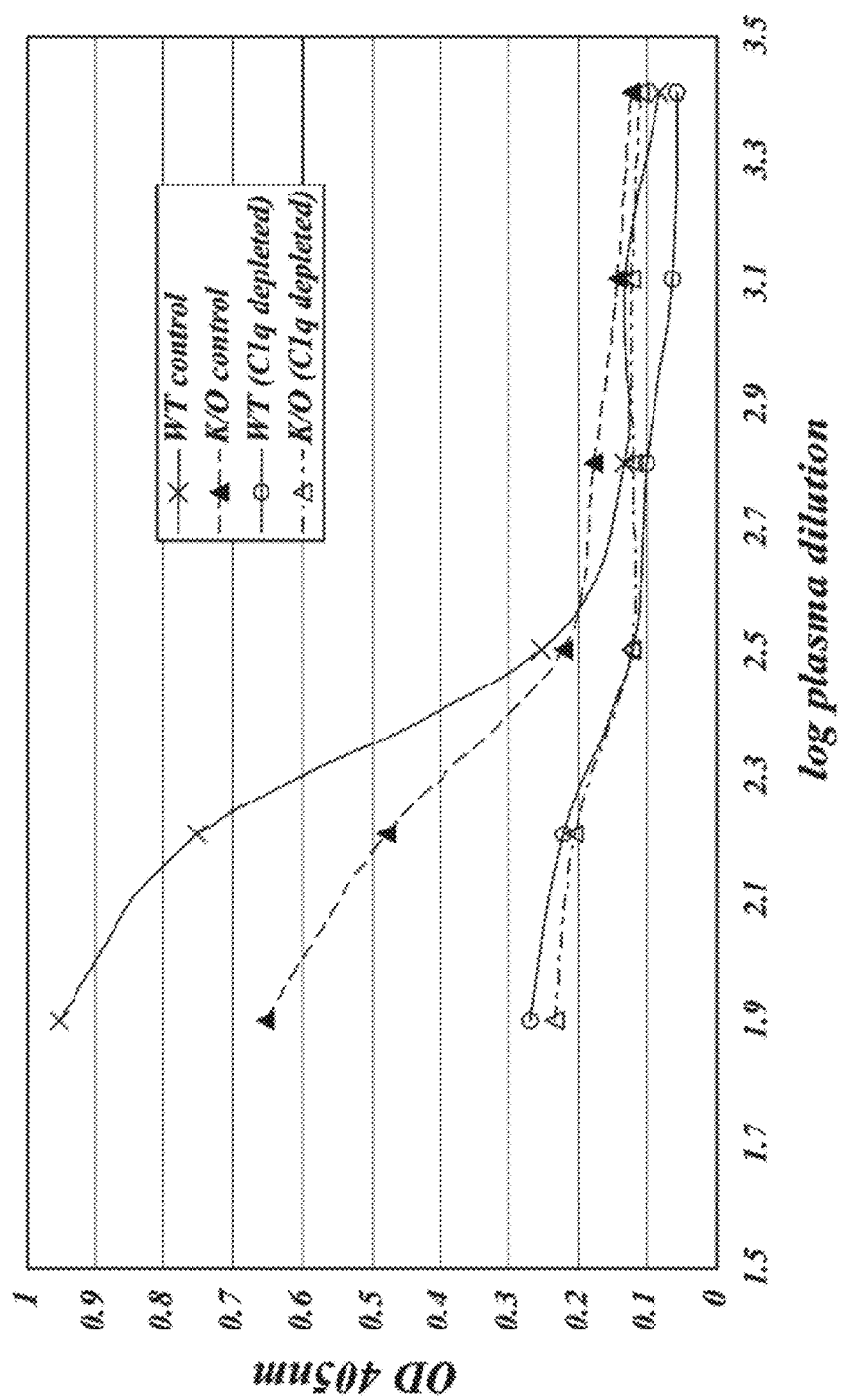
FIG. 7 presents results demonstrating that the classical pathway is functional in the MASP-2−/− strain, as described in Example 8.

Results: FIG. 7 shows the relative C3b deposition levels on plates coated with IgG in wild-type serum, MASP-2−/− serum, C1q-depleted wild-type and C1q-depleted MASP- 2-/- serum. These results demonstrate that the classical pathway is intact in the MASP-2-/- mouse strain.

Example 9

The following assay is used to test whether a MASP-2 inhibitory agent blocks the classical pathway by analyzing the effect of a MASP-2 inhibitory agent under conditions in which the classical pathway is initiated by immune complexes.

Methods: To test the effect of a MASP-2 inhibitory agent on conditions of complement activation where the classical pathway is initiated by immune complexes, triplicate 50 μl samples containing 90% NHS are incubated at 37° C. in the presence of 10 μg/ml immune complex (IC) or PBS, and parallel triplicate samples (+/–IC) are also included which contain 200 nM anti-properdin monoclonal antibody during the 37° C. incubation. After a two hour incubation at 37° C., 13 mM EDTA is added to all samples to stop further complement activation and the samples are immediately cooled to 5° C. The samples are then stored at –70° C. prior to being assayed for complement activation products (C3a and sC5b-9) using ELISA kits (Quidel, Catalog Nos. A015 and A009) following the manufacturer's instructions.

Example 10

This example describes the identification of high affinity anti-MASP-2 Fab2 antibody fragments that block MASP-2 activity.

Background and rationale: MASP-2 is a complex protein with many separate functional domains, including: binding site(s) for MBL and ficolins, a serine protease catalytic site, a binding site for proteolytic substrate C2, a binding site for proteolytic substrate C4, a MASP-2 cleavage site for auto-activation of MASP-2 zymogen, and two $Ca^{++}$ binding sites. Fab2 antibody fragments were identified that bind with high affinity to MASP-2, and the identified Fab2 fragments were tested in a functional assay to determine if they were able to block MASP-2 functional activity.

To block MASP-2 functional activity, an antibody or Fab2 antibody fragment must bind and interfere with a structural epitope on MASP-2 that is required for MASP-2 functional activity. Therefore, many or all of the high affinity binding anti-MASP-2 Fab2s may not inhibit MASP-2 functional activity unless they bind to structural epitopes on MASP-2 that are directly involved in MASP-2 functional activity.

A functional assay that measures inhibition of lectin pathway C3 convertase formation was used to evaluate the "blocking activity" of anti-MASP-2 Fab2s. It is known that the primary physiological role of MASP-2 in the lectin pathway is to generate the next functional component of the lectin-mediated complement pathway, namely the lectin pathway C3 convertase. The lectin pathway C3 convertase is a critical enzymatic complex (C4bC2a) that proteolytically cleaves C3 into C3a and C3b. MASP-2 is not a structural component of the lectin pathway C3 convertase (C4bC2a); however, MASP-2 functional activity is required in order to generate the two protein components (C4b, C2a) that comprise the lectin pathway C3 convertase. Furthermore, all of the separate functional activities of MASP-2 listed above appear to be required in order for MASP-2 to generate the lectin pathway C3 convertase. For these reasons, a preferred assay to use in evaluating the "blocking activity" of anti-MASP-2 Fab2s is believed to be a functional assay that measures inhibition of lectin pathway C3 convertase formation.

Generation of High Affinity Fab2s: A phage display library of human variable light and heavy chain antibody sequences and automated antibody selection technology for identifying Fab2s that react with selected ligands of interest was used to create high affinity Fab2s to rat MASP-2 protein (SEQ ID NO:55). A known amount of rat MASP-2 (~1 mg, >85% pure) protein was utilized for antibody screening. Three rounds of amplification were utilized for selection of the antibodies with the best affinity. Approximately 250 different hits expressing antibody fragments were picked for ELISA screening. High affinity hits were subsequently sequenced to determine uniqueness of the different antibodies.

Fifty unique anti-MASP-2 antibodies were purified and 250 μg of each purified Fab2 antibody was used for characterization of MASP-2 binding affinity and complement pathway functional testing, as described in more detail below.

Assays Used to Evaluate the Inhibitory (Blocking) Activity of Anti-MASP-2 Fab2s

1. Assay to Measure Inhibition of Formation of Lectin Pathway C3 Convertase:

Background: The lectin pathway C3 convertase is the enzymatic complex (C4bC2a) that proteolytically cleaves C3 into the two potent proinflammatory fragments, anaphylatoxin C3a and opsonic C3b. Formation of C3 convertase appears to a key step in the lectin pathway in terms of mediating inflammation. MASP-2 is not a structural component of the lectin pathway C3 convertase (C4bC2a); therefore anti-MASP-2 antibodies (or Fab2) will not directly inhibit activity of preexisting C3 convertase. However, MASP-2 serine protease activity is required in order to generate the two protein components (C4b, C2a) that comprise the lectin pathway C3 convertase. Therefore, anti-MASP-2 Fab2 which inhibit MASP-2 functional activity (i.e., blocking anti-MASP-2 Fab2) will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated for 30 min at 37° C. with diluted rat serum to activate the lectin pathway. The wells were then washed and assayed for C3b immobilized onto the wells using standard ELISA methods. The amount of C3b generated in this assay is a direct reflection of the de novo formation of lectin pathway C3 convertase. Anti-MASP-2 Fab2s at selected concentrations were tested in this assay for their ability to inhibit C3 convertase formation and consequent C3b generation.

Methods 96-well Costar Medium Binding plates were incubated overnight at 5° C. with mannan diluted in 50 mM carbonate buffer, pH 9.5 at 1 μg/50 μL/well. After overnight incubation, each well was washed three times with 200 μL PBS. The wells were then blocked with 100 μL/well of 1% bovine serum albumin in PBS and incubated for one hour at room temperature with gentle mixing. Each well was then washed three times with 200 μL of PBS. The anti-MASP-2 Fab2 samples were diluted to selected concentrations in $Ca^{++}$ and Mg++ containing GVB buffer (4.0 mM barbital, 141 mM NaCl, 1.0 mM MgCl$_2$, 2.0 mM CaCl$_2$), 0.1% gelatin, pH 7.4) at 5 C. A 0.5% rat serum was added to the above samples at 5° C. and 100 µL was transferred to each well. Plates were covered and incubated for 30 minutes in a 37 C waterbath to allow complement activation. The reaction was stopped by transferring the plates from the 37° C. waterbath to a container containing an ice-water mix. Each well was washed five times with 200 µL with PBS-Tween 20 (0.05% Tween 20 in PBS), then washed two times with 200 µL PBS. A 100 µL/well of 1:10,000 dilution of the primary antibody (rabbit anti-human C3c, DAKO A0062) was added in PBS containing 2.0 mg/ml bovine serum albumin and incubated 1 hr at room temperature with gentle mixing. Each well was washed 5×200 µL PBS. 100 µL/well of 1:10,000 dilution of the secondary antibody (peroxidase-conjugated goat anti-rabbit IgG, American Qualex A102PU) was added in PBS containing 2.0 mg/ml bovine serum albumin and incubated for one hour at room temperature on a shaker with gentle mixing. Each well was washed five times with 200 µL with PBS. 100 µL/well of the peroxidase substrate TMB (Kirkegaard & Perry Laboratories) was added and incubated at room temperature for 10 min. The peroxidase reaction was stopped by adding 100 µL/well of 1.0 M H$_3$PO$_4$ and the OD$_{450}$ was measured.

2. Assay to Measure Inhibition of MASP-2-Dependent C4 Cleavage

Background: The serine protease activity of MASP-2 is highly specific and only two protein substrates for MASP-2 have been identified; C2 and C4. Cleavage of C4 generates C4a and C4b. Anti-MASP-2 Fab2 may bind to structural epitopes on MASP-2 that are directly involved in C4 cleavage (e.g., MASP-2 binding site for C4; MASP-2 serine protease catalytic site) and thereby inhibit the C4 cleavage functional activity of MASP-2.

Yeast mannan is a known activator of the lectin pathway. In the following method to measure the C4 cleavage activity of MASP-2, plastic wells coated with mannan were incubated for 30 minutes at 37° C. with diluted rat serum to activate the lectin pathway. Since the primary antibody used in this ELISA assay only recognizes human C4, the diluted rat serum was also supplemented with human C4 (1.0 µg/ml). The wells were then washed and assayed for human C4b immobilized onto the wells using standard ELISA methods. The amount of C4b generated in this assay is a measure of MASP-2 dependent C4 cleavage activity. Anti-MASP-2 Fab2 at selected concentrations were tested in this assay for their ability to inhibit C4 cleavage.

Methods: 96-well Costar Medium Binding plates were incubated overnight at 5° C. with mannan diluted in 50 mM carbonate buffer, pH 9.5 at 1.0 µg/50 µL/well. Each well was washed 3× with 200 µL PBS. The wells were then blocked with 100 µL/well of 1% bovine serum albumin in PBS and incubated for one hour at room temperature with gentle mixing. Each well was washed 3× with 200 µL of PBS. Anti-MASP-2 Fab2 samples were diluted to selected concentrations in Ca++ and Mg++ containing GVB buffer (4.0 mM barbital, 141 mM NaCl, 1.0 mM MgCl$_2$, 2.0 mM CaCl$_2$), 0.1% gelatin, pH 7.4) at 5° C. 1.0 µg/ml human C4 (Quidel) was also included in these samples. 0.5% rat serum was added to the above samples at 5° C. and 100 µL was transferred to each well. The plates were covered and incubated for 30 minutes in a 37° C. waterbath to allow complement activation. The reaction was stopped by transferring the plates from the 37° C. waterbath to a container containing an ice-water mix. Each well was washed 5×200 µL with PBS-Tween 20 (0.05% Tween 20 in PBS), then each well was washed with 2× with 200 µL PBS. 100 µL/well of 1:700 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 µL PBS. 100 µL/well of 0.1 µg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 µL with PBS. 100 µL/well of the peroxidase substrate TMB (Kirkegaard & Perry Laboratories) was added and incubated at room temperature for 16 min. The peroxidase reaction was stopped by adding 100 µL/well of 1.0 M H$_3$PO$_4$ and the OD$_{450}$ was measured.

3. Binding Assay of Anti-Rat MASP-2 Fab2 to 'Native' Rat MASP-2

Background: MASP-2 is usually present in plasma as a MASP-2 dimer complex that also includes specific lectin molecules (mannose-binding protein (MBL) and ficolins). Therefore, if one is interested in studying the binding of anti-MASP-2 Fab2 to the physiologically relevant form of MASP-2, it is important to develop a binding assay in which the interaction between the Fab2 and 'native' MASP-2 in plasma is used, rather than purified recombinant MASP-2. In this binding assay the 'native' MASP-2-MBL complex from 10% rat serum was first immobilized onto mannan-coated wells. The binding affinity of various anti-MASP-2 Fab2s to the immobilized 'native' MASP-2 was then studied using a standard ELISA methodology.

Methods: 96-well Costar High Binding plates were incubated overnight at 5° C. with mannan diluted in 50 mM carbonate buffer, pH 9.5 at 1 µg/50 µL/well. Each well was washed 3× with 200 µL PBS. The wells were blocked with 100 µL/well of 0.5% nonfat dry milk in PBST (PBS with 0.05% Tween 20) and incubated for one hour at room temperature with gentle mixing. Each well was washed 3× with 200 µL of TBS/Tween/Ca++ Wash Buffer (Tris-buffered saline, 0.05% Tween 20, containing 5.0 mM CaCl$_2$), pH 7.4. 10% rat serum in High Salt Binding Buffer (20 mM Tris, 1.0 M NaCl, 10 mM CaCl$_2$), 0.05% Triton-X100, 0.1% (w/v) bovine serum albumin, pH 7.4) was prepared on ice. 100 µL/well was added and incubated overnight at 5° C. Wells were washed 3× with 200 µL of TBS/Tween/Ca++ Wash Buffer. Wells were then washed 2× with 200 µL PBS. 100 µL/well of selected concentration of anti-MASP-2 Fab2 diluted in Ca++ and Mg++ containing GVB Buffer (4.0 mM barbital, 141 mM NaCl, 1.0 mM MgCl$_2$, 2.0 mM CaCl$_2$), 0.1% gelatin, pH 7.4) was added and incubated for one hour at room temperature with gentle mixing. Each well was washed 5×200 µL PBS. 100 µL/well of H$_1$RP-conjugated goat anti-Fab2 (Biogenesis Cat No 0500-0099) diluted 1:5000 in 2.0 mg/ml bovine serum albumin in PBS was added and incubated for one hour at room temperature with gentle mixing. Each well was washed 5×200 µL PBS. 100 µL/well of the peroxidase substrate TMB (Kirkegaard & Perry Laboratories) was added and incubated at room temperature for 70 min. The peroxidase reaction was stopped by adding 100 µL/well of 1.0 M H$_3$PO$_4$ and OD$_{450}$ was measured.

Results

Approximately 250 different Fab2s that reacted with high affinity to the rat MASP-2 protein were picked for ELISA screening. These high affinity Fab2s were sequenced to determine the uniqueness of the different antibodies, and 50 unique anti-MASP-2 antibodies were purified for further analysis. 250 µg of each purified Fab2 antibody was used for characterization of MASP-2 binding affinity and complement pathway functional testing. The result of this analysis is shown below in TABLE 6.

TABLE 6

ANTI-MASP-2 FAB2 THAT BLOCK LECTIN PATHWAY COMPLEMENT ACTIVATION

| Fab2 antibody # | C3 Convertase ($IC_{50}$ (nM)) | $K_d$ | C4 Cleavage $IC_{50}$ (nM) |
|---|---|---|---|
| 88 | 0.32 | 4.1 | ND |
| 41 | 0.35 | 0.30 | 0.81 |
| 11 | 0.46 | 0.86 | <2 nM |
| 86 | 0.53 | 1.4 | ND |
| 81 | 0.54 | 2.0 | ND |
| 66 | 0.92 | 4.5 | ND |
| 57 | 0.95 | 3.6 | <2 nM |
| 40 | 1.1 | 7.2 | 0.68 |
| 58 | 1.3 | 2.6 | ND |
| 60 | 1.6 | 3.1 | ND |
| 52 | 1.6 | 5.8 | <2 nM |
| 63 | 2.0 | 6.6 | ND |
| 49 | 2.8 | 8.5 | <2 nM |
| 89 | 3.0 | 2.5 | ND |
| 71 | 3.0 | 10.5 | ND |
| 87 | 6.0 | 2.5 | ND |
| 67 | 10.0 | 7.7 | ND |

Figure 8A:
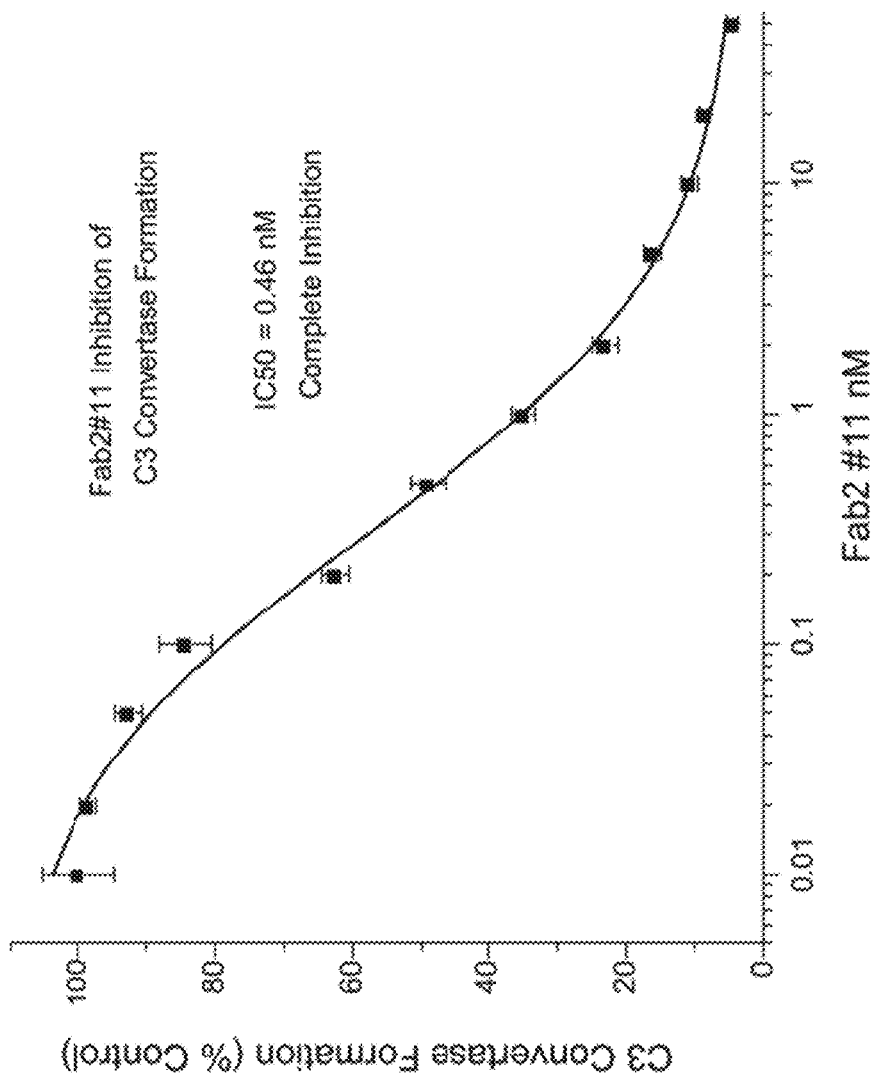
FIG. 8A presents results demonstrating that anti-MASP-2 Fab2 antibody #11 inhibits C3 convertase formation, as described in Example 10.

As shown above in TABLE 6, of the 50 anti-MASP-2 Fab2s tested, seventeen Fab2s were identified as MASP-2 blocking Fab2 that potently inhibit C3 convertase formation with $IC_{50}$ equal to or less than 10 nM Fab2s (a 34% positive hit rate). Eight of the seventeen Fab2s identified have $IC_{50}$s in the subnanomolar range. Furthermore, all seventeen of the MASP-2 blocking Fab2s shown in TABLE 6 gave essentially complete inhibition of C3 convertase formation in the lectin pathway C3 convertase assay. FIG. 8A graphically illustrates the results of the C3 convertase formation assay for Fab2 antibody #11, which is representative of the other Fab2 antibodies tested, the results of which are shown in TABLE 6. This is an important consideration, since it is theoretically possible that a "blocking" Fab2 may only fractionally inhibit MASP-2 function even when each MASP-2 molecule is bound by the Fab2.

Although mannan is a known activator of the lectin pathway, it is theoretically possible that the presence of anti-mannan antibodies in the rat serum might also activate the classical pathway and generate C3b via the classical pathway C3 convertase. However, each of the seventeen blocking anti-MASP-2 Fab2s listed in this example potently inhibits C3b generation (>95%), thus demonstrating the specificity of this assay for lectin pathway C3 convertase.

Figure 8B:
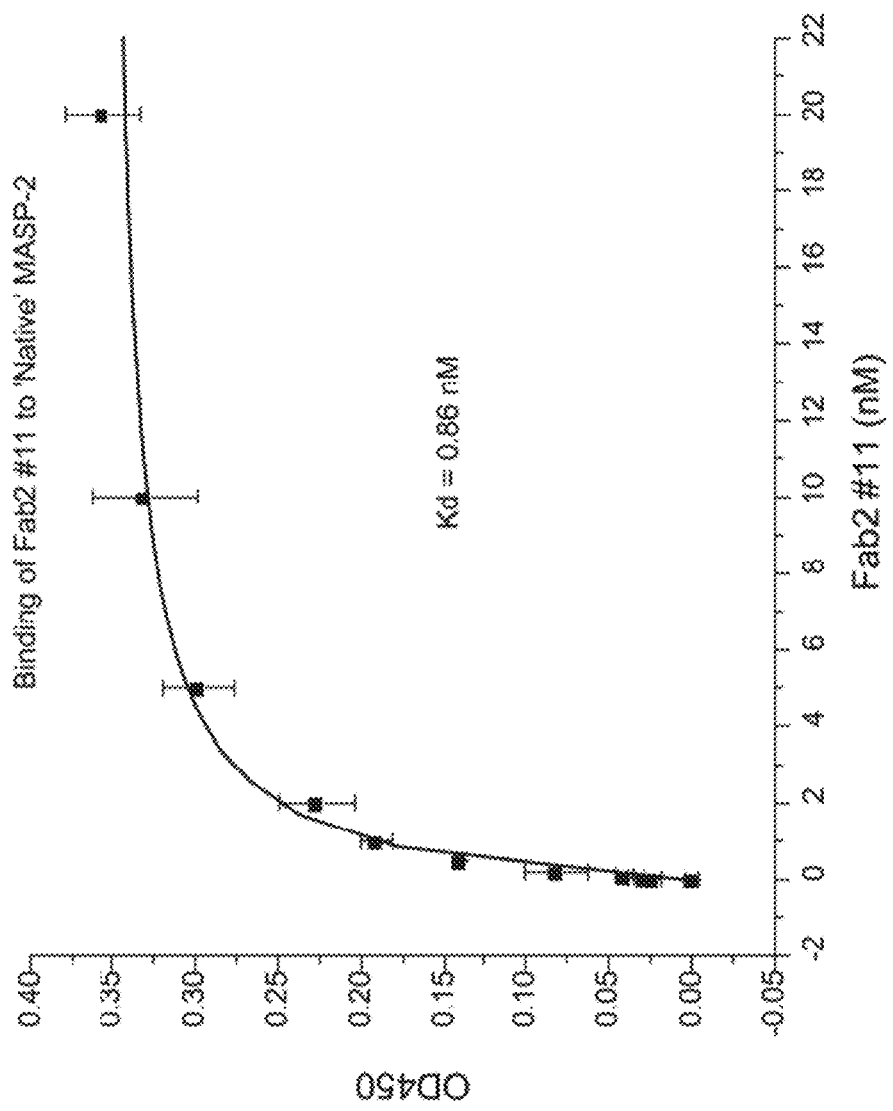
FIG. 8B presents results demonstrating that anti-MASP-2 Fab2 antibody #11 binds to native rat MASP-2, as described in Example 10.

Binding assays were also performed with all seventeen of the blocking Fab2s in order to calculate an apparent $K_d$ for each. The results of the binding assays of anti-rat MASP-2 Fab2s to native rat MASP-2 for six of the blocking Fab2s are also shown in TABLE 6. FIG. 8B graphically illustrates the results of a binding assay with the Fab2 antibody #11. Similar binding assays were also carried out for the other Fab2s, the results of which are shown in TABLE 6. In general, the apparent $K_d$s obtained for binding of each of the six Fab2s to 'native' MASP-2 corresponds reasonably well with the $IC_{50}$ for the Fab2 in the C3 convertase functional assay. There is evidence that MASP-2 undergoes a conformational change from an 'inactive' to an 'active' form upon activation of its protease activity (Feinberg et al., *EMBO J* 22:2348-59 (2003); Gal et al., *J. Biol. Chem.* 280:33435-44 (2005)). In the normal rat plasma used in the C3 convertase formation assay, MASP-2 is present primarily in the 'inactive' zymogen conformation. In contrast, in the binding assay, MASP-2 is present as part of a complex with MBL bound to immobilized mannan; therefore, the MASP-2 would be in the 'active' conformation (Petersen et al., *J. Immunol Methods* 257:107-16, 2001). Consequently, one would not necessarily expect an exact correspondence between the $IC_{50}$ and $K_d$ for each of the seventeen blocking Fab2 tested in these two functional assays since in each assay the Fab2 would be binding a different conformational form of MASP-2. Never-the-less, with the exception of Fab2 #88, there appears to be a reasonably close correspondence between the $IC_{50}$ and apparent Kd for each of the other sixteen Fab2 tested in the two assays (see TABLE 6).

Figure 8C:
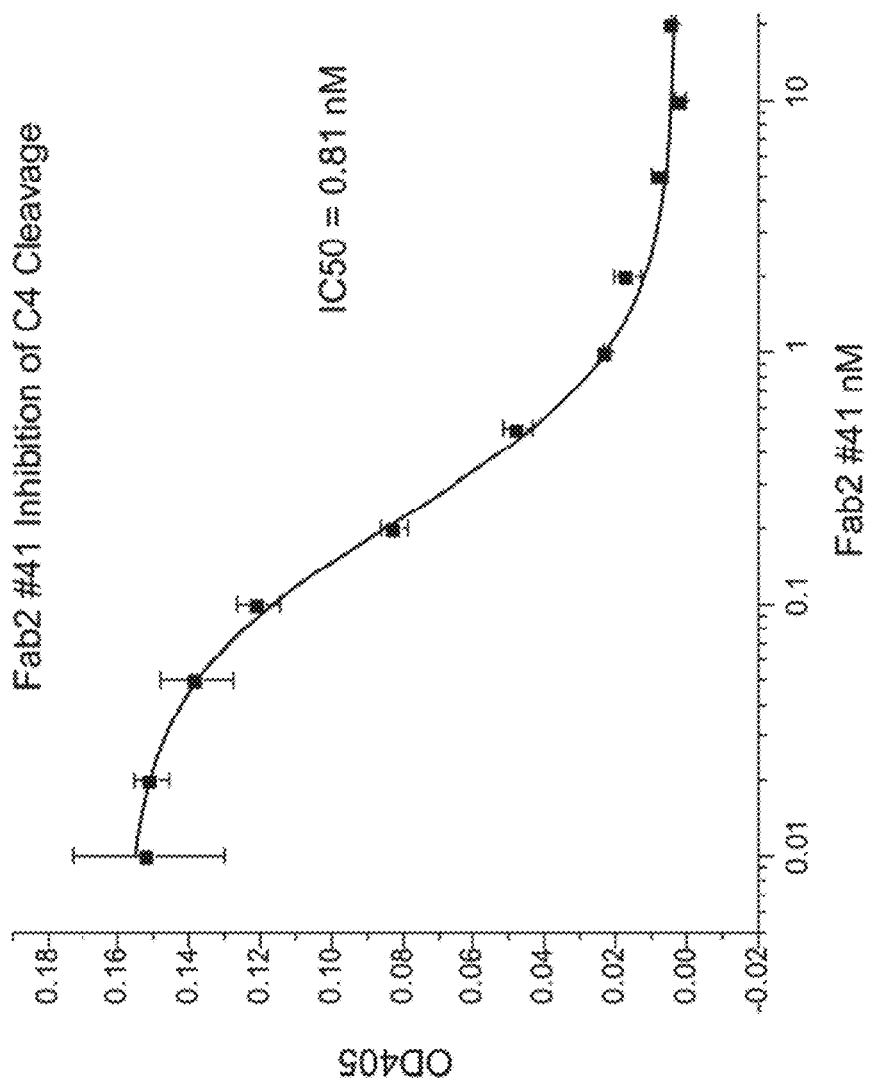
FIG. 8C presents results demonstrating that anti-MASP-2 Fab2 antibody #41 inhibits C4 cleavage, as described in Example 10.
Figure 9:
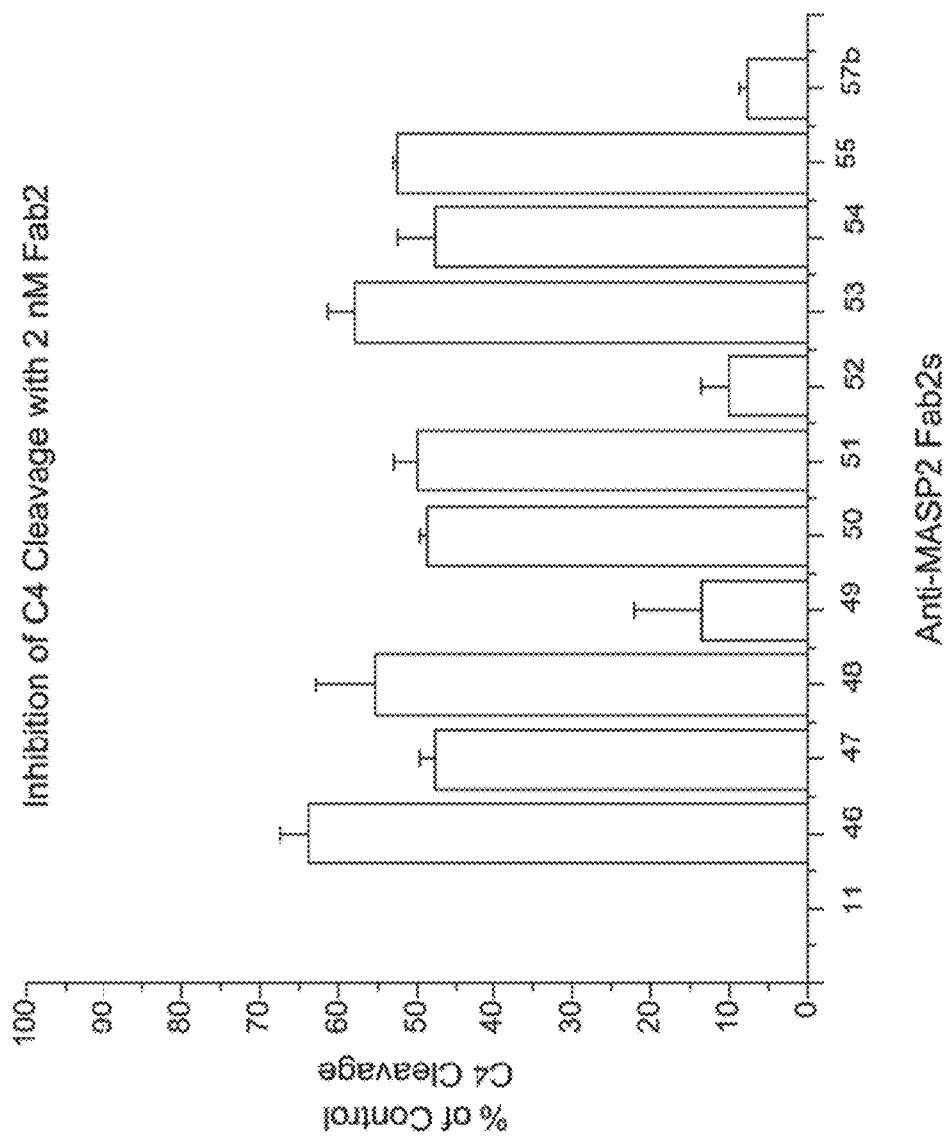
FIG. 9 presents results demonstrating that all of the anti-MASP-2 Fab2 antibodies tested that inhibited C3 convertase formation also were found to inhibit C4 cleavage, as described in Example 10.

Several of the blocking Fab2s were evaluated for inhibition of MASP-2 mediated cleavage of C4. FIG. 8C graphically illustrates the results of a C4 cleavage assay, showing inhibition with Fab2 #41, with an $IC_{50}$=0.81 nM (see TABLE 6). As shown in FIG. 9, all of the Fab2s tested were found to inhibit C4 cleavage with $IC_{50}$s similar to those obtained in the C3 convertase assay (see TABLE 6).

Although mannan is a known activator of the lectin pathway, it is theoretically possible that the presence of anti-mannan antibodies in the rat serum might also activate the classical pathway and thereby generate C4b by C1s-mediated cleavage of C4. However, several anti-MASP-2 Fab2s have been identified which potently inhibit C4b generation (>95%), thus demonstrating the specificity of this assay for MASP-2 mediated C4 cleavage. C4, like C3, contains an unusual and highly reactive thioester group as part of its structure. Upon cleavage of C4 by MASP-2 in this assay, the thioester group on C4b can form a covalent bond with hydroxyl or amino groups on macromolecules immobilized on the bottom of the plastic wells via ester or amide linkages, thus facilitating detection of C4b in the ELISA assay.

These studies clearly demonstrate the creation of high affinity Fab2s to rat MASP-2 protein that functionally block both C4 and C3 convertase activity, thereby preventing lectin pathway activation.

Example 11

This Example describes the epitope mapping for several of the blocking anti-rat MASP-2 Fab2 antibodies that were generated as described in Example 10.

Methods

Figure 10:
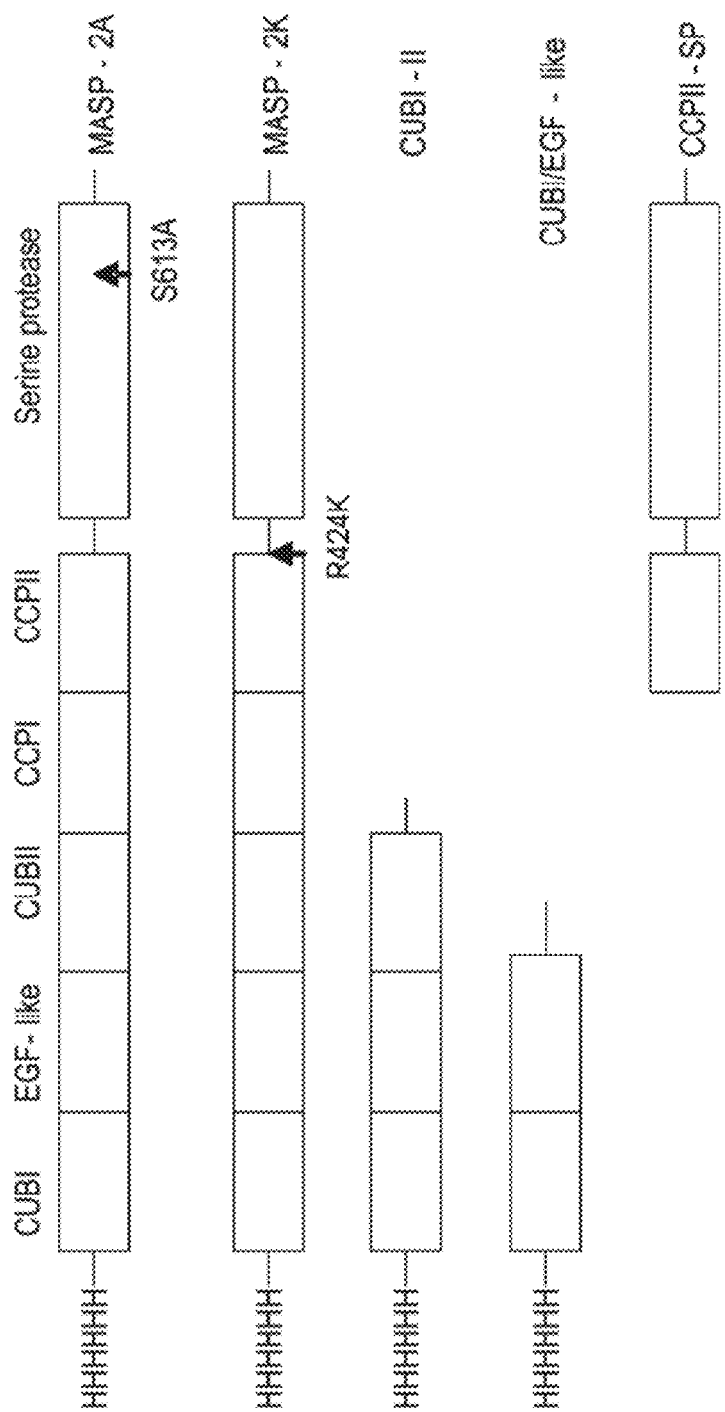
FIG. 10 is a diagram illustrating the recombinant polypeptides derived from rat MASP-2 that were used for epitope mapping of the MASP-2 blocking Fab2 antibodies, as described in Example 11.

As shown in FIG. 10, the following proteins, all with N-terminal 6× His tags were expressed in CHO cells using the pED4 vector:
  rat MASP-2A, a full length MASP-2 protein, inactivated by altering the serine at the active center to alanine (S613A);
  rat MASP-2K, a full-length MASP-2 protein altered to reduce autoactivation (R424K);
  CUBI-II, an N-terminal fragment of rat MASP-2 that contains the CUBI, EGF-like and CUBII domains only; and
  CUBI/EGF-like, an N-terminal fragment of rat MASP-2 that contains the CUBI and EGF-like domains only.
These proteins were purified from culture supernatants by nickel-affinity chromatography, as previously described (Chen et al., *J. Biol. Chem.* 276:25894-02 (2001)).

A C-terminal polypeptide (CCPII-SP), containing CCPII and the serine protease domain of rat MASP-2, was expressed in E. coli as a thioredoxin fusion protein using pTrxFus (Invitrogen). Protein was purified from cell lysates using Thiobond affinity resin. The thioredoxin fusion partner was expressed from empty pTrxFus as a negative control.

All recombinant proteins were dialyzed into TBS buffer and their concentrations determined by measuring the OD at 280 nm.

Dot Blot Analysis:

Serial dilutions of the five recombinant MASP-2 polypeptides described above and shown in FIG. 10 (and the thioredoxin polypeptide as a negative control for CCPII-serine protease polypeptide) were spotted onto a nitrocellulose membrane. The amount of protein spotted ranged from 100 ng to 6.4 µg, in five-fold steps. In later experiments, the amount of protein spotted ranged from 50 ng down to 16 µg, again in five-fold steps. Membranes were blocked with 5% skimmed milk powder in TBS (blocking buffer) then incubated with 1.0 µg/ml anti-MASP-2 Fab2s in blocking buffer (containing 5.0 mM $Ca^{2+}$). Bound Fab2s were detected using HRP-conjugated anti-human Fab (AbD/Serotec; diluted 1/10,000) and an ECL detection kit (Amersham). One membrane was incubated with polyclonal rabbit-anti human MASP-2 Ab (described in Stover et al., J Immunol 163:6848-59 (1999)) as a positive control. In this case, bound Ab was detected using HRP-conjugated goat anti-rabbit IgG (Dako; diluted 1/2,000).

MASP-2 Binding Assay

ELISA plates were coated with 1.0 µg/well of recombinant MASP-2A or CUBI-II polypeptide in carbonate buffer (pH 9.0) overnight at 4° C. Wells were blocked with 1% BSA in TBS, then serial dilutions of the anti-MASP-2 Fab2s were added in TBS containing 5.0 mM $Ca^{2+}$. The plates were incubated for one hour at RT. After washing three times with TBS/tween/$Ca^{2+}$, HRP-conjugated anti-human Fab (AbD/Serotec) diluted 1/10,000 in TBS/$Ca^{21}$ was added and the plates incubated for a further one hour at RT. Bound antibody was detected using a TMB peroxidase substrate kit (Biorad).

Results

Results of the dot blot analysis demonstrating the reactivity of the Fab2s with various MASP-2 polypeptides are provided below in TABLE 7. The numerical values provided in TABLE 7 indicate the amount of spotted protein required to give approximately half-maximal signal strength. As shown, all of the polypeptides (with the exception of the thioredoxin fusion partner alone) were recognized by the positive control Ab (polyclonal anti-human MASP-2 sera, raised in rabbits).

TABLE 7

REACTIVITY WITH VARIOUS RECOMBINANT RAT MASP-2 POLYPEPTIDES ON DOT BLOTS

| Fab2 Antibody # | MASP-2A | CUBI-II | CUBI/ EGF-like | CCPII-SP | Thioredoxin |
|---|---|---|---|---|---|
| 40 | 0.16 ng | NR | NR | 0.8 ng | NR |
| 41 | 0.16 ng | NR | NR | 0.8 ng | NR |
| 11 | 0.16 ng | NR | NR | 0.8 ng | NR |
| 49 | 0.16 ng | NR | NR | >20 ng | NR |
| 52 | 0.16 ng | NR | NR | 0.8 ng | NR |
| 57 | 0.032 ng | NR | NR | NR | NR |
| 58 | 0.4 ng | NR | NR | 2.0 ng | NR |
| 60 | 0.4 ng | 0.4 | NR | NR | NR |
| 63 | 0.4 ng | NR | NR | 2.0 ng | NR |
| 66 | 0.4 ng | NR | NR | 2.0 ng | NR |
| 67 | 0.4 ng | NR | NR | 2.0 ng | NR |
| 71 | 0.4 ng | NR | NR | 2.0 ng | NR |
| 81 | 0.4 ng | NR | NR | 2.0 ng | NR |
| 86 | 0.4 ng | NR | NR | 10 ng | NR |
| 87 | 0.4 ng | NR | NR | 2.0 ng | NR |
| Positive Control | <0.032 ng | 0.16 ng | 0.16 ng | <0.032 ng | NR |

NR = No reaction.
The positive control antibody is polyclonal anti-human MASP-2 sera, raised in rabbits.

Figure 11:
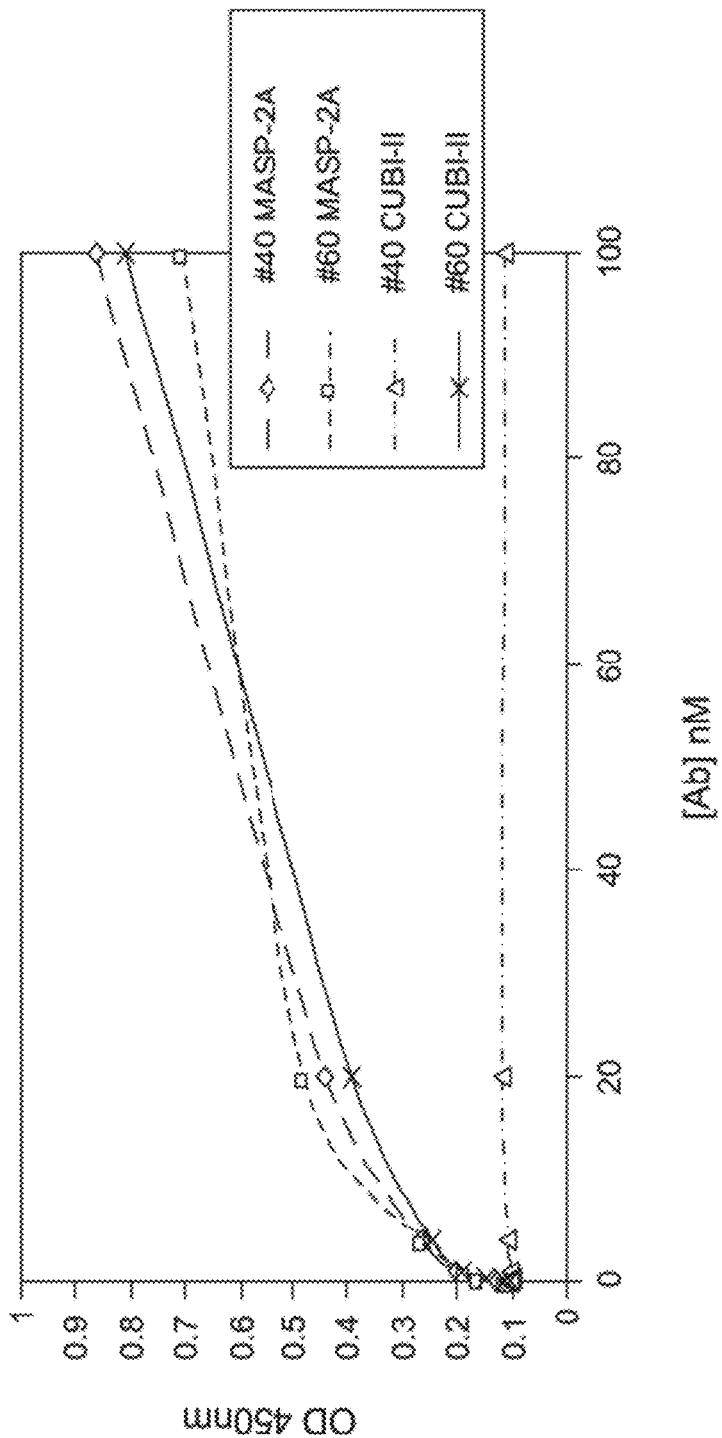
FIG. 11 presents results demonstrating the binding of anti-MASP-2 Fab2 #40 and #60 to rat MASP-2 polypeptides, as described in Example 11.

All of the Fab2s reacted with MASP-2A as well as MASP-2K (data not shown). The majority of the Fab2s recognized the CCPII-SP polypeptide but not the N-terminal fragments. The two exceptions are Fab2 #60 and Fab2 #57. Fab2 #60 recognizes MASP-2A and the CUBI-II fragment, but not the CUBI/EGF-like polypeptide or the CCPII-SP polypeptide, suggesting it binds to an epitope in CUBII, or spanning the CUBII and the EGF-like domain. Fab2 #57 recognizes MASP-2A but not any of the MASP-2 fragments tested, indicating that this Fab2 recognizes an epitope in CCP1. Fab2 #40 and #49 bound only to complete MASP-2A. In the ELISA binding assay shown in FIG. 11, Fab2 #60 also bound to the CUBI-II polypeptide, albeit with a slightly lower apparent affinity. These finding demonstrate the identification of unique blocking Fab2s to multiple regions of the MASP-2 protein.

Example 12

This example describes the identification, using phage display, of fully human scFv antibodies that bind to MASP-2 and inhibit lectin-mediated complement activation while leaving the classical (C1q-dependent) pathway component of the immune system intact.

Overview

Fully human, high-affinity MASP-2 antibodies were identified by screening a phage display library. The variable light and heavy chain fragments of the antibodies were isolated in both a scFv format and in a full-length IgG format. The human MASP-2 antibodies are useful for inhibiting cellular injury associated with lectin pathway-mediated complement pathway activation while leaving the classical (C1q-dependent) pathway component of the immune system intact. In some embodiments, the subject MASP-2 inhibitory antibodies have the following characteristics: (a) high affinity for human MASP-2 (e.g., a $K_D$ of 10 nM or less), and (b) inhibit MASP-2-dependent complement activity in 90% human serum with an $IC_{50}$ of 30 nM or less.

Methods

Expression of Full-Length Catalytically Inactive MASP-2:

The full-length cDNA sequence of human MASP-2 (SEQ ID NO: 4), encoding the human MASP-2 polypeptide with leader sequence (SEQ ID NO:5) was subcloned into the mammalian expression vector pCI-Neo (Promega), which drives eukaryotic expression under the control of the CMV enhancer/promoter region (described in Kaufman R. J. et al., Nucleic Acids Research 19:4485-90, 1991; Kaufman, *Methods in Enzymology*, 185:537-66 (1991)). In order to generate catalytically inactive human MASP-2A protein, site-directed mutagenesis was carried out as described in US2007/0172483, hereby incorporated herein by reference. The PCR products were purified after agarose gel electrophoresis and band preparation and single adenosine overlaps were generated using a standard tailing procedure. The adenosine-tailed MASP-2A was then cloned into the pGEM-T easy vector and transformed into *E. coli*. The human MASP-2A was further subcloned into either of the mammalian expression vectors pED or pCI-Neo.

The MASP-2A expression construct described above was transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium. The MASP-2A (Ser-Ala mutant described above) was purified by affinity chromatography on MBP-A-agarose columns MASP-2A ELISA on ScFv Candidate Clones Identified by Panning/scFv Conversion and Filter Screening A phage display library of human immunoglobulin light- and heavy-chain variable region sequences was subjected to antigen panning followed by automated antibody screening and selection to identify high-affinity scFv antibodies to human MASP-2 protein. Three rounds of panning the scFv phage library against HIS-tagged or biotin-tagged MASP-2A were carried out. The third round of panning was eluted first with MBL and then with TEA (alkaline). To monitor the specific enrichment of phages displaying scFv fragments against the target MASP-2A, a polyclonal phage ELISA against immobilized MASP-2A was carried out. The scFv genes from panning round 3 were cloned into a pHOG expression vector and run in a small-scale filter screening to look for specific clones against MASP-2A.

Bacterial colonies containing plasmids encoding scFv fragments from the third round of panning were picked, gridded onto nitrocellulose membranes and grown overnight on non-inducing medium to produce master plates. A total of 18,000 colonies were picked and analyzed from the third panning round, half from the competitive elution and half from the subsequent TEA elution. Panning of the scFv phagemid library against MASP-2A followed by scFv conversion and a filter screen yielded 137 positive clones. 108/137 clones were positive in an ELISA assay for MASP-2 binding (data not shown), of which 45 clones were further analyzed for the ability to block MASP-2 activity in normal human serum.

Assay to Measure Inhibition of Formation of Lectin Pathway C3 Convertase

A functional assay that measures inhibition of lectin pathway C3 convertase formation was used to evaluate the "blocking activity" of the MASP-2 scFv candidate clones. MASP-2 serine protease activity is required in order to generate the two protein components (C4b, C2a) that comprise the lectin pathway C3 convertase. Therefore, a MASP-2 scFv that inhibits MASP-2 functional activity (i.e., a blocking MASP-2 scFv), will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated with diluted human serum to activate the lectin pathway. The wells were then washed and assayed for C3b immobilized onto the wells using standard ELISA methods. The amount of C3b generated in this assay is a direct reflection of the de novo formation of lectin pathway C3 convertase. MASP-2 scFv clones at selected concentrations were tested in this assay for their ability to inhibit C3 convertase formation and consequent C3b generation.

Methods

The 45 candidate clones identified as described above were expressed, purified and diluted to the same stock concentration, which was again diluted in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) to assure that all clones had the same amount of buffer. The scFv clones were each tested in triplicate at the concentration of 2 µg/mL. The positive control was OMS100 Fab2 and was tested at 0.4 µg/mL. C3c formation was monitored in the presence and absence of the scFv/IgG clones.

Mannan was diluted to a concentration of 20 µg/mL (1 µg/well) in 50 mM carbonate buffer (15 mM $Na_2CO_3$+35 mM $NaHCO_3$+1.5 mM $NaN_3$), pH 9.5 and coated on an ELISA plate overnight at 4° C. The next day, the mannan-coated plates were washed 3 times with 200 µl PBS. 100 µl of 1% HSA blocking solution was then added to the wells and incubated for 1 hour at room temperature. The plates were washed 3 times with 200 µl PBS, and stored on ice with 200 µl PBS until addition of the samples.

Normal human serum was diluted to 0.5% in CaMgGVB buffer, and scFv clones or the OMS100 Fab2 positive control were added in triplicates at 0.01 µg/mL; 1 µg/mL (only OMS100 control) and 10 µg/mL to this buffer and preincubated 45 minutes on ice before addition to the blocked ELISA plate. The reaction was initiated by incubation for one hour at 37° C. and was stopped by transferring the plates to an ice bath. C3b deposition was detected with a Rabbit α-Mouse C3c antibody followed by Goat α-Rabbit $H_1RP$. The negative control was buffer without antibody (no antibody=maximum C3b deposition), and the positive control was buffer with EDTA (no C3b deposition). The background was determined by carrying out the same assay except that the wells were mannan-free. The background signal against plates without mannan was subtracted from the signals in the mannan-containing wells. A cut-off criterion was set at half of the activity of an irrelevant scFv clone (VZV) and buffer alone.

Results: Based on the cut-off criterion, a total of 13 clones were found to block the activity of MASP-2. All 13 clones producing >50% pathway suppression were selected and sequenced, yielding 10 unique clones. All ten clones were found to have the same light chain subclass, λ3, but three different heavy chain subclasses: VH2, VH3 and VH6. In the functional assay, five out of the ten candidate scFv clones gave $IC_{50}$ nM values less than the 25 nM target criteria using 0.5% human serum.

To identify antibodies with improved potency, the three mother scFv clones, identified as described above, were subjected to light-chain shuffling. This process involved the generation of a combinatorial library consisting of the VH of each of the mother clones paired up with a library of naive, human lambda light chains (VL) derived from six healthy donors. This library was then screened for scFv clones with improved binding affinity and/or functionality.

TABLE 8

Comparison of functional potency in IC$_{50}$ (nM) of the lead daughter clones and their respective clones (all in scFv format)

| scFv clone | 1% human serum C3 assay (IC$_{50}$ nM) | 90% human serum C3 assay (IC$_{50}$ nM) | 90% human serum C4 assay (IC$_{50}$ nM) |
|---|---|---|---|
| 17D20mc | 38 | nd | nd |
| 17D20m_d3521N11 | 26 | >1000 | 140 |
| 17N16mc | 68 | nd | nd |
| 17N16m d17N9 | 48 | 15 | 230 |

Presented below are the heavy-chain variable region (VH) sequences for the mother clones and daughter clones shown above in TABLE 8.

The Kabat CDRs (31-35 (H1), 50-65 (H2) and 95-107 (H3)) are bolded; and the Chothia CDRs (26-32 (H1), 52-56 (H2) and 95-101 (H3)) are underlined.

```
17D20_35VH-21N11VL heavy chain variable region
(VH) (SEQ ID NO:67, encoded by SEQ ID NO: 66)
QVTLKESGPVLVKPTETLTLTCTVSGFSLSRGKMGVSWIRQPPGKALEW
LAHIFSSDEKSYRTSLKSRLTISKDTSKNQVVLTMTNMDPVDTATYYCA
RIRRGGIDYWGQGTLVTVSS d17N9 heavy chain variable region (VH)
                                    (SEQ ID NO:68)
QVQLQQSGPGLVKPSQTLSLTCAISGDSVSSTSAAWNWIRQSPSRGLEW
LGRTYYRSKWYNDYAVSVKSRITINPDTSKNQFSLQLNSVTPEDTAVYY
CARDPFGVPFDIWGQGTMVTVSS
```

Presented below are the light-chain variable region (VL) sequences for the mother clones and daughter clones shown above in TABLE 8.

The Kabat CDRs (24-34 (L1); 50-56 (L2); and 89-97 (L3) are bolded; and the Chothia CDRs (24-34 (L1); 50-56 (L2) and 89-97 (L3) are underlined. These regions are the same whether numbered by the Kabat or Chothia system.

```
17D20m_d3521N11 light chain variable region (VL)
(SEQ ID NO: 69, encoded by SEQ ID NO: 70)
QPVLTQPPSLSVSPGQTASITCSGEKLGDKYAYWYQQKPGQSPVLVMYQ
DKQRPSGIPERFSGSNSGNTATLTISGTQAMDEADYYCQAWDSSTAVFG
GGTKLTVL 17N16m_d17N9 light chain variable region (VL)
                                    (SEQ ID NO: 71)
SYELIQPPSVSVAPGQTATITCAGDNLGKKRVHWYQQRPGQAPVLVIYD
DSDRPSGIPDRFSASNSGNTATLTITRGEAGDEADYYCQVWDIATDHVV
FGGGTKLTVLAAAGSEQKLISE
```

The MASP-2 antibodies OMS100 and MoAb_d3521N11VL, (comprising a heavy chain variable region set forth as SEQ ID NO:67 and a light chain variable region set forth as SEQ ID NO:69, also referred to as "OMS646" and "mAb6"), which have both been demonstrated to bind to human MASP-2 with high affinity and have the ability to block functional complement activity, were analyzed with regard to epitope binding by dot blot analysis. The results show that OMS646 and OMS100 antibodies are highly specific for MASP-2 and do not bind to MASP-1/3. Neither antibody bound to MAp19 nor to MASP-2 fragments that did not contain the CCP1 domain of MASP-2, leading to the conclusion that the binding sites encompass CCP1.

The MASP-2 antibody OMS646 was determined to avidly bind to recombinant MASP-2 (Kd 60-250 pM) with >5000 fold selectivity when compared to C1s, C1r or MASP-1 (see TABLE 9 below):

TABLE 9

Affinity and Specificity of OMS646 MASP-2 antibody-MASP-2 interaction as assessed by solid phase ELISA studies

| Antigen | $K_D$ (pM) |
|---|---|
| MASP-1 | >500,000 |
| MASP-2 | 62 ± 23* |
| MASP-3 | >500,000 |
| Purified human C1r | >500,000 |
| Purified human C1s | ~500,000 |

*Mean = SD;
n = 12

OMS646 Specifically Blocks Lectin-Dependent Activation of Terminal Complement Components Methods The effect of OMS646 on membrane attack complex (MAC) deposition was analyzed using pathway-specific conditions for the lectin pathway, the classical pathway and the alternative pathway. For this purpose, the Wieslab Comp300 complement screening kit (Wieslab, Lund, Sweden) was used following the manufacturer's instructions.

Results

Figure 12A:
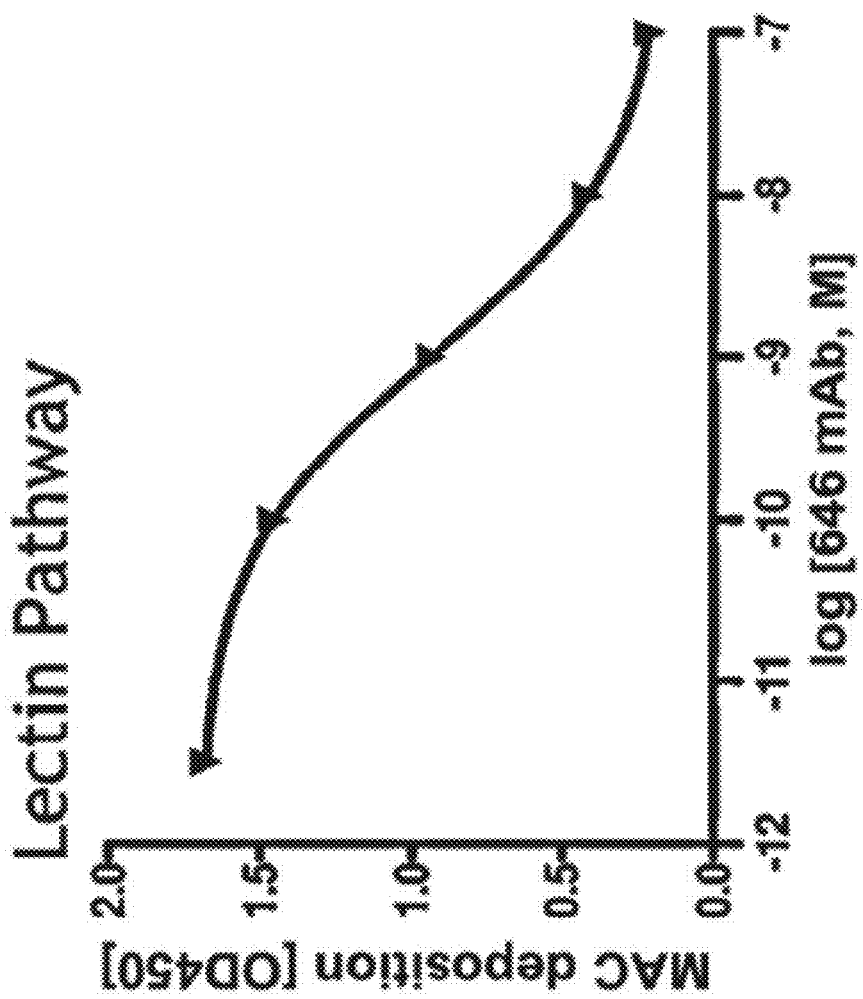
FIG. 12A graphically illustrates the level of MAC deposition in the presence or absence of human MASP-2 monoclonal antibody (OMS646) under lectin pathway-specific assay conditions, demonstrating that OMS646 inhibits lectin-mediated MAC deposition with an $IC_{50}$ value of approximately 1 nM, as described in Example 12.
Figure 12B:
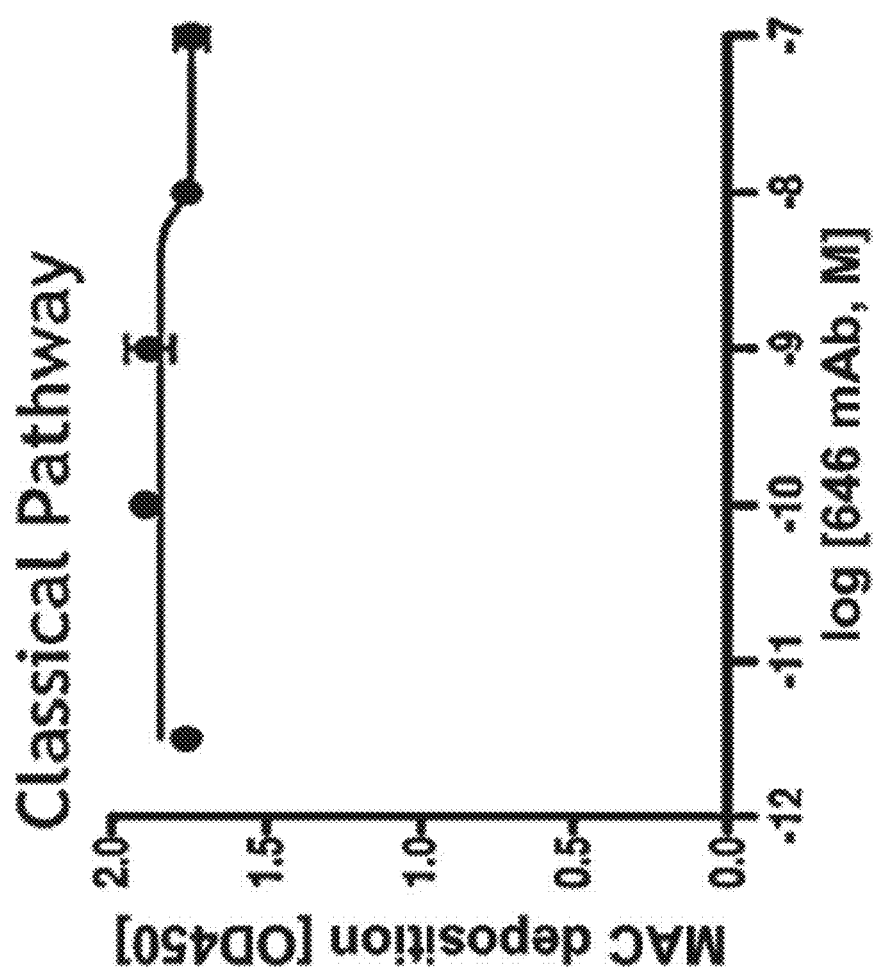
FIG. 12B graphically illustrates the level of MAC deposition in the presence or absence of human MASP-2 monoclonal antibody (OMS646) under classical pathway-specific assay conditions, demonstrating that OMS646 does not inhibit classical pathway-mediated MAC deposition, as described in Example 12.
Figure 12C:
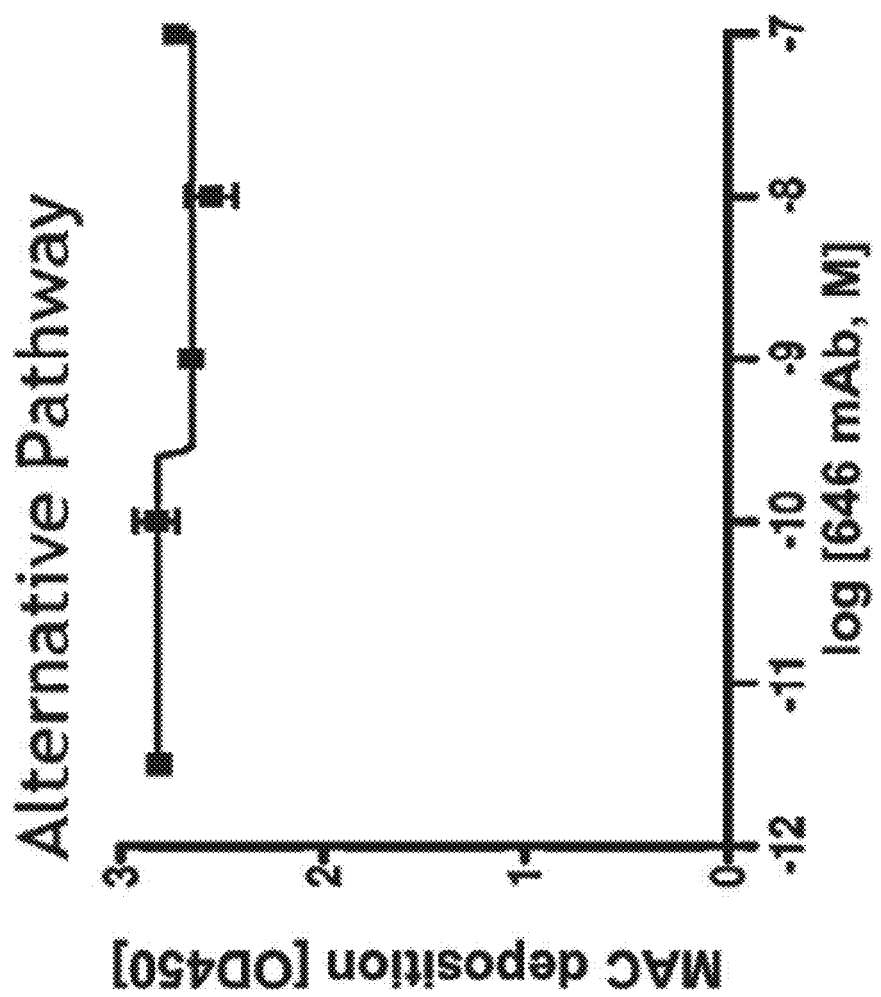
FIG. 12C graphically illustrates the level of MAC deposition in the presence or absence of human MASP-2 monoclonal antibody (OMS646) under alternative pathway-specific assay conditions, demonstrating that OMS646 does not inhibit alternative pathway-mediated MAC deposition, as described in Example 12.

FIG. 12A graphically illustrates the level of MAC deposition in the presence or absence of anti-MASP-2 antibody (OMS646) under lectin pathway-specific assay conditions. FIG. 12B graphically illustrates the level of MAC deposition in the presence or absence of anti-MASP-2 antibody (OMS646) under classical pathway-specific assay conditions. FIG. 12C graphically illustrates the level of MAC deposition in the presence or absence of anti-MASP-2 antibody (OMS646) under alternative pathway-specific assay conditions.

As shown in FIG. 12A, OMS646 blocks lectin pathway-mediated activation of MAC deposition with an IC$_{50}$ value of approximately 1 nM. However, OMS646 had no effect on MAC deposition generated from classical pathway-mediated activation (FIG. 12B) or from alternative pathway-mediated activation (FIG. 12C).

Pharmacokinetics and Pharmacodynamics of OMS646 Following Intravenous (IV) or Subcutaneous (SC) Administration to Mice The pharmacokinetics (PK) and pharmacodynamics (PD) of OMS646 were evaluated in a 28 day single dose PK/PD study in mice. The study tested dose levels of 5 mg/kg and 15 mg/kg of OMS646 administered subcutaneously (SC), as well as a dose level of 5 mg/kg OMS646 administered intravenously (IV).

Figure 13:
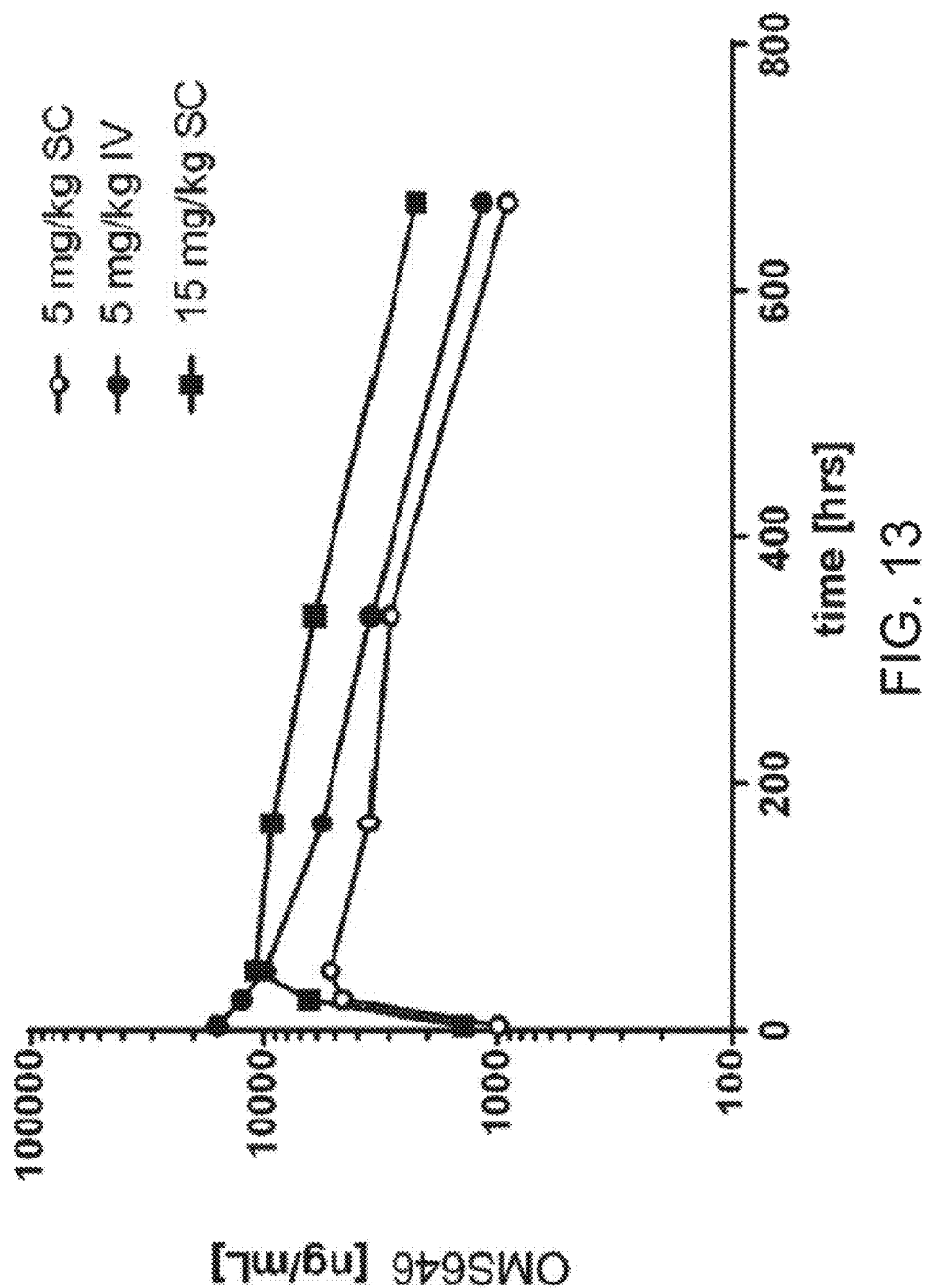
FIG. 13 graphically illustrates the pharmacokinetic (PK) profile of human MASP-2 monoclonal antibody (OMS646) in mice, showing the OMS646 concentration (mean of n=3 animals/groups) as a function of time after administration at the indicated dose, as described in Example 12.

With regard to the PK profile of OMS646, FIG. 13 graphically illustrates the OMS646 concentration (mean of n=3 animals/groups) as a function of time after administration of OMS646 at the indicated dose. As shown in FIG. 13, at 5 mg/kg SC, OMS646 reached the maximal plasma concentration of 5-6 μg/mL approximately 1-2 days after dosing. The bioavailability of OMS646 at 5 mg/kg SC was approximately 60%. As further shown in FIG. 13, at 15 mg/kg SC, OMS646 reached a maximal plasma concentration of 10-12 μg/mL approximately 1 to 2 days after dosing.

For all groups, the OMS646 was cleared slowly from systemic circulation with a terminal half-life of approximately 8-10 days. The profile of OMS646 is typical for human antibodies in mice.

Figure 14A:
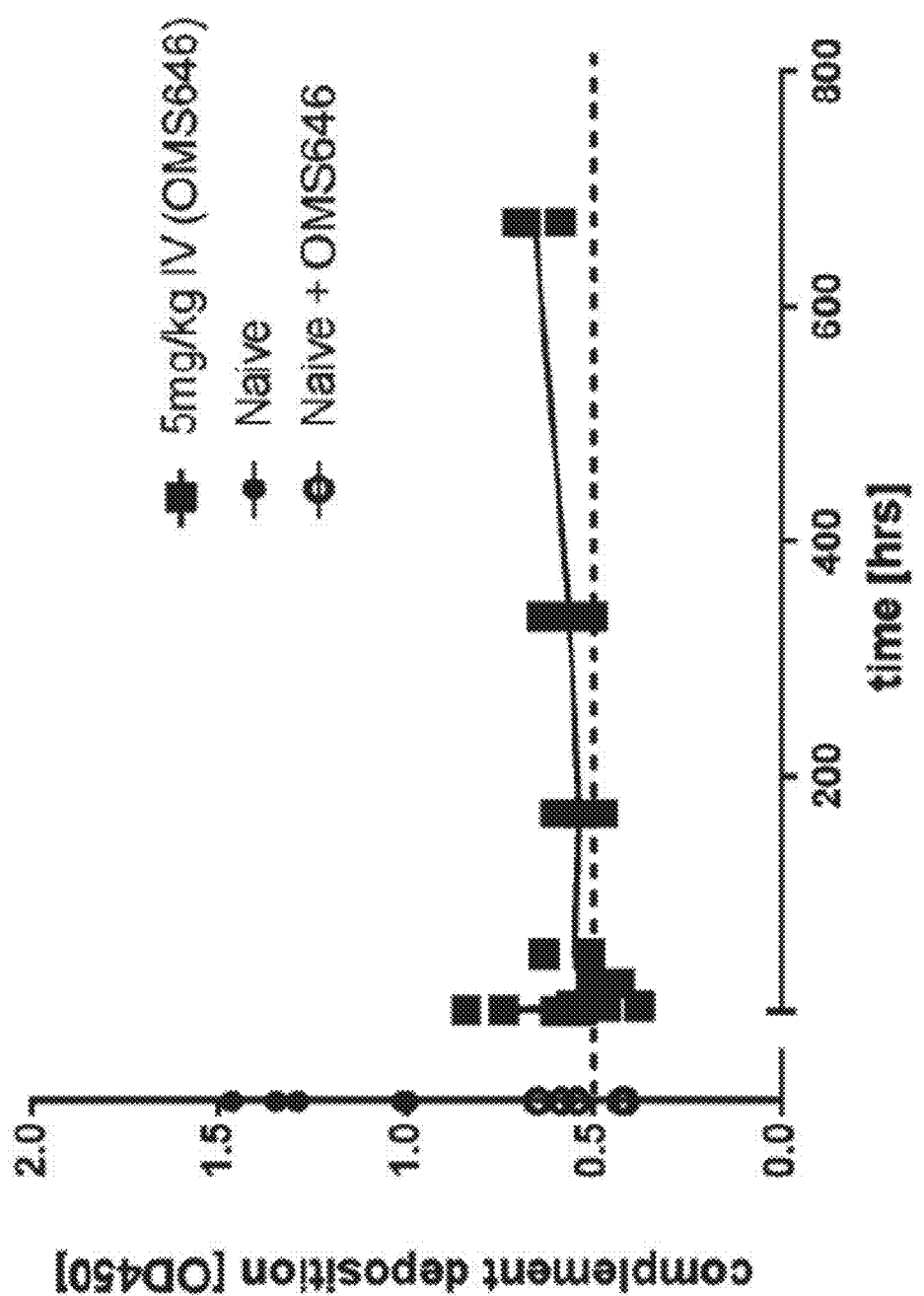
FIG. 14A graphically illustrates the pharmacodynamic (PD) response of human MASP-2 monoclonal antibody (OMS646), measured as a drop in systemic lectin pathway activity, in mice following intravenous administration, as described in Example 12.
Figure 14B:
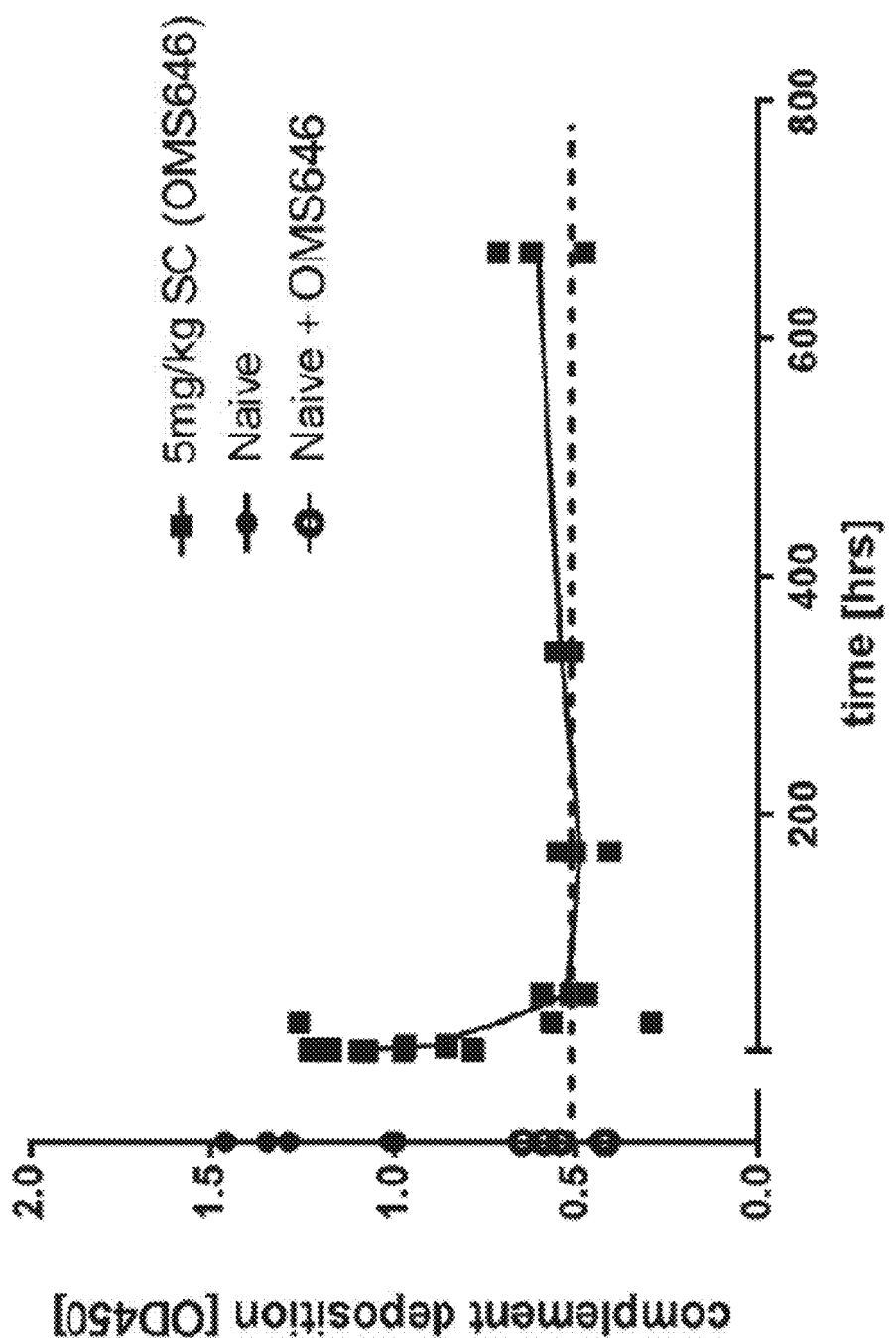
FIG. 14B graphically illustrates the pharmacodynamic (PD) response of human MASP-2 monoclonal antibody (OMS646), measured as a drop in systemic lectin pathway activity, in mice following subcutaneous administration, as described in Example 12.

The PD activity of OMS646 is graphically illustrated in FIGS. 14A and 14B. FIGS. 14A and 14B show the PD response (drop in systemic lectin pathway activity) for each mouse in the 5 mg/kg IV (FIG. 14A) and 5 mg/kg SC (FIG. 14B) groups. The dashed line indicates the baseline of the assay (maximal inhibition; naive mouse serum spiked in vitro with excess OMS646 prior to assay). As shown in FIG. 14A, following IV administration of 5 mg/kg of OMS646, systemic lectin pathway activity immediately dropped to near undetectable levels, and lectin pathway activity showed only a modest recovery over the 28 day observation period. As shown in FIG. 14B, in mice dosed with 5 mg/kg of OMS646 SC, time-dependent inhibition of lectin pathway activity was observed. Lectin pathway activity dropped to near-undetectable levels within 24 hours of drug administration and remained at low levels for at least 7 days. Lectin pathway activity gradually increased with time, but did not revert to pre-dose levels within the 28 day observation period. The lectin pathway activity versus time profile observed after administration of 15 mg/kg SC was similar to the 5 mg/kg SC dose (data not shown), indicating saturation of the PD endpoint. The data further indicated that weekly doses of 5 mg/kg of OMS646, administered either IV or SC, is sufficient to achieve continuous suppression of systemic lectin pathway activity in mice.

Example 13

This Example describes the generation of recombinant antibodies that inhibit MASP-2 comprising a heavy chain and/or a light chain variable region comprising one or more CDRs that specifically bind to MASP-2 and at least one SGMI core peptide sequence (also referred to as an SGMI-peptide bearing MASP-2 antibody or antigen binding fragment thereof).

Background/Rationale:

The generation of specific inhibitors of MASP-2, termed SGMI-2, is described in Heja et al., *J Biol Chem* 287:20290 (2012) and Heja et al., *PNAS* 109:10498 (2012), each of which is hereby incorporated herein by reference. SGMI-2 is a 36 amino acid peptide which was selected from a phage library of variants of the *Schistocerca gregaria* protease inhibitor 2 in which six of the eight positions of the protease binding loop were fully randomized. Subsequent in vitro evolution yielded mono-specific inhibitors with single digit nM Ki values (Heja et al., *J. Biol. Chem.* 287:20290, 2012). Structural studies revealed that the optimized protease binding loop forms the primary binding site that defines the specificity of the two inhibitors. The amino acid sequences of the extended secondary and internal binding regions are common to the two inhibitors and contribute to the contact interface (Heja et al., 2012. *J. Biol. Chem.* 287:20290). Mechanistically, SGMI-2 blocks the lectin pathway of complement activation without affecting the classical pathway (Heja et al., 2012. *Proc. Natl. Acad. Sci.* 109:10498).

The amino acid sequences of the SGMI-2 inhibitors are set forth below:

SGMI-2-full-length:

(SEQ ID NO: 72)
LEVTCEPGTTFKDKCNTCRCGSDGKSAVCTKLWCNQ

SGMI-2-medium:

(SEQ ID NO: 73)
TCEPGTTFKDKCNTCRCGSDGKSAVCTKLWCNQ

SGMI-2-short:

(SEQ ID NO: 74)
......................................TCRCGSDGKSA
VCTKLWCNQ

As described in this Example, and also described in WO2014/144542, SGMI-2 peptide-bearing MASP-2 antibodies and fragments thereof were generated by fusing the SGMI-2 peptide amino acid sequence (e.g., SEQ ID NO: 72, 73 or 74) onto the amino or carboxy termini of the heavy and/or light chains of a human MASP-2 antibody. The SGMI-2 peptide-bearing MASP-2 antibodies and fragments have enhanced inhibitory activity, as compared to the naked MASP-2 scaffold antibody that does not contain the SGMI-2 peptide sequence, when measured in a C3b or C4b deposition assay using human serum, as described in WO2014/144542, and also have enhanced inhibitory activity as compared to the naked MASP-2 scaffold antibody when measured in a mouse model in vivo. Methods of generating SGMI-2 peptide bearing MASP-2 antibodies are described below.

Methods

Expression constructs were generated to encode four exemplary SGMI-2 peptide bearing MASP-2 antibodies wherein the SGMI-2 peptide was fused either to the N- or C-terminus of the heavy or light chain of a representative MASP-2 inhibitory antibody OMS646 (generated as described in Example 12).

TABLE 10

MASP-2 antibody/SGMI-2 fusions

| Antibody reference | Peptide Location on Antibody | | | | SEQ ID NO: |
|---|---|---|---|---|---|
| | H-N | H-C | L-N | L-C | |
| HL-M2 (naked MASP-2 OMS646) | — | — | — | — | 67 + 70 |
| H-M2-SGMI-2-N | SGMI-2 | — | — | — | 75 + 70 |
| H-M2-SGMI-2-C | — | SGMI-2 | — | — | 76 + 70 |
| L-M2-SGMI-2-N | — | — | SGMI-2 | — | 67 + 77 |
| L-M2-SGMI-2-C | — | — | — | SGMI-2 | 67 + 78 |

Abbreviations in Table 10:
"H-N" = amino terminus of heavy chain
"H-C" = carboxyl terminus of heavy chain
"L-N" = amino terminus of light chain
"L-C" = carboxyl terminus of light chain
"M2" = MASP-2 ab scaffold (representative OMS646)

For the N-terminal fusions shown in TABLE 10, a peptide linker ('GTGGGSGSSS' SEQ ID NO: 79) was added between the SGMI-2 peptide and the variable region.

For the C-terminal fusions shown in TABLE 10, a peptide linker ('AAGGSG' SEQ ID NO: 80) was added between the constant region and the SGMI-2 peptide, and a second peptide "GSGA" (SEQ ID NO: 81) was added at the C-terminal end of the fusion polypeptide to protect C-terminal SGMI-2 peptides from degradation.

Amino acid sequences are provided below for the following representative MASP-2 antibody/SGMI-2 fusions:

H-M2ab6-SGMI-2-N (SEQ ID NO: 75, encoded by SEQ ID NO: 82):
LEVTCEPGTTFKDKCNTCRCGSDGKSAVCTKLWCNQ*GTGGGSGSSS*QVT
LKESGPVLVKPTETLTLTCTVSGFSLSRGKMGVSWIRQPPGKALEWLAH
IFSSDEKSYRTSLKSRLTISKDTSKNQVVLTMTNMDPVDTATYYCARIR
RGGIDYWGQGTLVTVSSASTKGPSVFPLAPCSRSTSESTAALGCLVKDY
FPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLG
K

[491 aa protein, aa 1-36=SGMI-2 (underlined), aa37-46=linker (italicized); aa47-164=heavy chain variable region of MASP-2 ab #6 (underlined); aa165-491=IgG4 constant region with hinge mutation.]

H-M2ab6-SGMI-2-C (SEQ ID NO: 76, encoded by SEQ ID NO: 83):
QVTLKESGPVLVKPTETLTLTCTVSGFSLSRGKMGVSWIRQPPGKALEW
LAHIFSSDEKSYRTSLKSRLTISKDTSKNQVVLTMTNMDPVDTATYYCA
RIRRGGIDYWGQGTLVTVSSASTKGPSVFPLAPCSRSTSESTAALGCLV
KDYFPEPVTVSWNSGALTSGVHTFPAVLQSSGLYSLSSVVTVPSSSLGT
KTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSL
SLGK*AAGGSG*LEVTCEPGTTFKDKCNTCRCGSDGKSAVCTKLWCNQ*GSG*
*A*

[491aa protein, aa1-118=heavy chain variable region of MASP-2 ab #6 (underlined); aa 119-445=IgG4 constant region with hinge mutation; aa 446–451=1st linker (italicized); aa 452-487=SGMI-2; aa488–491=2nd linker (italicized).]

L-M2ab6-SGMI-2-N (SEQ ID NO: 77, encoded by SEQ ID NO: 84);
LEVTCEPGTTFKDKCNTCRCGSDGKSAVCTKLWCNQ*GTGGGSGSSS*QPV
LTQPPSLSVSPGQTASITCSGEKLGDKYAYWYQQKPGQSPVLVMYQDKQ
RPSGIPERFSGSNSGNTATLTISGTQAMDEADYYCQAWDSSTAVFGGGT
KLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEG
STVEKTVAPTECS

[258aa protein, aa1-36=SGMI-2 (underlined); aa37-46=linker (italicized); aa47-152=light chain variable region of MASP-2 ab #6 (underlined); aa153-258=human Ig lambda constant region]

L-M2ab6-SGMI-2-C (SEQ ID NO: 78, encoded by SEQ ID NO: 85);
QPVLTQPPSLSVSPGQTASITCSGEKLGDKYAYWYQQKPGQSPVLVMYQ
DKQRPSGIPERFSGSNSGNTATLTISGTQAMDEADYYCQAWDSSTAVFG
GGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVT
HEGSTVEKTVAPTECS*AAGGSG*LEVTCEPGTTFKDKCNTCRCGSDGKSA
VCTKLWCNQ*GSGA*

[258aa protein, aa1-106=light chain variable region of MASP-2 ab #6 (underlined); aa 107-212=human Ig lambda constant region; aa 213–218=1st linker; aa219-254=SGMI-2; aa255-258=2nd linker]

Functional Assays:

The four MASP-2-SGMI-2 fusion antibody constructs were transiently expressed in Expi293F cells (Invitrogen), purified by Protein A affinity chromatography, and tested in 10% normal human serum for inhibition of C3b deposition in a mannan-coated bead assay as described below.

Testing the MASP-2-SGMI-2 Fusions in the Mannan-Coated Bead Assay for C3b Deposition The MASP-2-SGMI-2 fusion antibodies assessed for lectin pathway inhibition in an assay of C3b deposition on mannan-coated beads. This assay, which determines degree of activity by flow cytometry, offers greater resolution than the Wieslab® assay. The lectin pathway bead assay was carried out as follows: mannan was adsorbed to 7 μM-diameter polystyrene beads (Bangs Laboratories; Fishers, IN, USA) overnight at 4° C. in carbonate-bicarbonate buffer (pH 9.6). The beads were washed in PBS and exposed to 10% human serum, or 10% serum pre-incubated with antibodies or inhibitors. The serum-bead mixture was incubated at room temperature for one hour while agitating. Following the serum incubation, the beads were washed, and C3b deposition on the beads was measured by detection with an anti-C3c rabbit polyclonal antibody (Dako North America; Carpinteria, CA, USA) and a PE-Cγ5 conjugated goat anti-rabbit secondary antibody (Southern Biotech; Birmingham, AL, USA). Following the staining procedure, the beads were analyzed using a FACSCalibur flow cytometer. The beads were gated as a uniform population using forward and side scatter, and C3b deposition was apparent as FL3-positive particles (FL-3, or "FL-3 channel" indicates the 3rd or red channel on the cytometer). The Geometric Mean Fluorescence Intensity (MFI) for the population for each experimental condition was plotted relative to the antibody/inhibitor concentration to evaluate lectin pathway inhibition.

The $IC_{50}$ values were calculated using the GraphPad PRISM software. Specifically, $IC_{50}$ values were obtained by applying a variable slope (four parameter), nonlinear fit to log (antibody) versus mean fluorescence intensity curves obtained from the cytometric assay.

The results are shown in TABLE 11.

TABLE 11

C3b deposition (mannan-coated bead assay) in 10% human serum

| Construct | $IC_{50}$ (nM) |
|---|---|
| Naked N2 ab (mAb#6) | ≥3.63 nM |
| H-M2-SGMI-2-N | 2.11 nM |
| L-M2-SGMI-2-C | 1.99 nM |
| H-M2-SGMI-2-N | 2.24 nM |
| L-M2-SGMI-2-N | 3.71 nM |

Results

The control, non-SGMI-containing MASP-2 "naked" scaffold antibody (mAb #6), was inhibitory in this assay, with an IC50 value of ≥3.63 nM, which is consistent with the inhibitory results observed in Example 12. Remarkably, as shown in TABLE 11, all of the SGMI-2-MASP-2 antibody fusions that were tested improved the potency of the MASP-2 scaffold antibody in this assay, suggesting that increased valency may also be beneficial in the inhibition of C3b deposition.

Testing the MASP-2-SGMI-2 Fusions in the Mannan-Coated Bead Assay for C4b Deposition Assay with 10% Human Serum A C4b deposition assay was carried out with 10% human serum using the same assay conditions as described above for the C3b deposition assay with the following modifications. C4b detection and flow cytometric analysis was carried out by staining the deposition reaction with an anti-C4b mouse monoclonal antibody (1:500, Quidel) and staining with a secondary goat anti-mouse F(ab')2 conjugated to PE Cy5 (1:200, Southern Biotech) prior to flow cytometric analysis.

Results

The SGMI-2-bearing MASP-2-N-terminal antibody fusions (H-M2-SGMI-2-N: IC50=0.34 nM), L-M2-SGMI-2-N: IC50=0.41 nM)), both had increased potency as compared to the MASP-2 scaffold antibody (HL-M2: IC50=0.78 nM).

Similarly, the single SGMI-2 bearing C-terminal MASP-2 antibody fusions (H-M2-SGMI-2-C: $IC_{50}$=0.45 nM and L-M2-SGMI-2C: $IC_{50}$=0.47 nM) both had increased potency as compared to the MASP-2 scaffold antibody (HL-M2: $IC_{50}$=1.2 nM).

Testing the MASP-2-SGMI-2 Fusions in the Mannan-Coated Bead Assay for C3b Deposition with 10% Mouse Serum.

A mannan-coated bead assay for C3b deposition was carried out as described above with 10% mouse serum. Similar to the results observed in human serum, it was determined that the SGMI-2-bearing MASP-2 fusions had increased potency as compared to the MASP-2 scaffold antibody in mouse serum.

Summary of Results: The results in this Example demonstrate that all of the SGMI-2-MASP-2 antibody fusions that were tested improved the potency of the MASP-2 scaffold antibody.

Example 14

This Example provides results that were generated using a Unilateral Ureteric Obstruction (UUO) model of renal fibrosis in MASP-2-/- deficient and MASP-2+/+ sufficient mice to evaluate the role of the lectin pathway in renal fibrosis.

Background/Rationale:

Renal fibrosis and inflammation are prominent features of late stage kidney disease. Renal tubulointerstitial fibrosis is progressive process involving sustained cell injury, aberrant healing, activation of resident and infiltrating kidney cells, cytokine release, inflammation and phenotypic activation of kidney cells to produce extracellular matrix. Renal tubulointerstitial (TI) fibrosis is the common end point of multiple renal pathologies and represents a key target for potential therapies aimed at preventing progressive renal functional impairment in chronic kidney disease (CKD). Renal TI injury is closely linked to declining renal function in glomerular diseases (Risdon R. A. et al., *Lancet* 1: 363-366, 1968; Schainuck L. I. et al, *Hum Pathol* 1: 631-640, 1970; Nath K. A., *Am J Kid Dis* 20:1-17, 1992), and is characteristic of CKD where there is an accumulation of myofibroblasts, and the potential space between tubules and peritubular capillaries becomes occupied by matrix composed of collagens and other proteoglycans. The origin of TI myofibroblasts remains intensely controversial, but fibrosis is generally preceded by inflammation characterized initially by TI accumulation of T lymphocytes and then later by macrophages (Liu Y. et al., *Nat Rev Nephrol* 7:684-696, 2011; Duffield J. S., *J Clin Invest* 124:2299-2306, 2014).

The rodent model of UUO generates progressive renal fibrosis, a hallmark of progressive renal disease of virtually any etiology (Chevalier et al., Kidney International 75:1145-1152, 2009). It has been reported that C3 gene expression was increased in wild-type mice following UUO, and that collagen deposition was significantly reduced in C3-/- knockout mice following UUO as compared to wild-type mice, suggesting a role of complement activation in renal fibrosis (Fearn et al., *Mol Immunol* 48:1666-1733, 2011). It has also been reported that C5 deficiency led to a significant amelioration of major components of renal fibrosis in a model of tubulointerstitial injury (Boor P. et al., *J of Am Soc of Nephrology:* 18:1508-1515, 2007). However, prior to the study described herein carried out by the present inventors, the particular complement components involved in renal fibrosis were not well defined. Therefore, the following study was carried out to evaluate MASP-2 (-/-) and MASP-2 (+/+) male mice in a unilateral ureteral obstruction (UUO) model.

Methods

A MASP-2-/- mouse was generated as described in Example 1 and backcrossed for 10 generations with C57BL/6. Male wild-type (WT) C57BL/6 mice, and homozygous MASP-2 deficient (MASP-2-/-) mice on a C57BL/6 background were kept under standardized conditions of 12/12 day/night cycle, fed on standard food pellets and given free access to food and water. Ten-week-old mice, 6 per group, were anesthetized with 2.5% isoflurane in 1.5 L/min oxygen. The right ureters of two groups of ten-week-old male C56/BL6 mice, wild-type and MASP-2-/- were surgically ligated. The right kidney was exposed through a 1 cm flank incision. The right ureter was completely obstructed at two points using a 6/0 polyglactin suture. Buprenorphine analgesia was provided perioperatively every 12 hours for up to 5 doses depending on pain scoring. Local bupivacaine anesthetic was given once during the surgery.

Mice were sacrificed 7 days after the surgery and kidney tissues were collected, fixed and embedded in paraffin blocks. Blood was collected from the mice by cardiac puncture under anesthesia, and mice were culled by exsanguination after nephrectomy. Blood was allowed to clot on ice for 2 hours and serum was separated by centrifugation and kept frozen as aliquots at −80° C.

Immunohistochemistry of Kidney Tissue

To measure the degree of kidney fibrosis as indicated by collagen deposition, 5 micron paraffin embedded kidney sections were stained with picrosirius red, a collagen-specific stain, as described in Whittaker P. et al., *Basic Res Cardiol* 89:397-410, 1994. Briefly described, kidney sections were de-paraffinized, rehydrated and collagen stained for 1 hour with picrosirius red aqueous solution (0.5 gm Sirius red, Sigma, Dorset UK) in 500 mL saturated aqueous solution of picric acid. Slides were washed twice in acidified water (0.5% glacial acetic acid in distilled water) for 5 minutes each, then dehydrated and mounted.

To measure the degree of inflammation as indicated by macrophage infiltration, kidney sections were stained with macrophage-specific antibody F4/80 as follows. Formalin fixed, paraffin embedded, 5 micron kidney sections were deparaffinized and rehydrated. Antigen retrieval was performed in citrate buffer at 95° C. for 20 minutes followed by quenching of endogenous peroxidase activity by incubation in 3% $H_2O_2$ for 10 minutes. Tissue sections were incubated in blocking buffer (10% heat inactivated normal goat serum with 1% bovine serum albumin in phosphate buffered saline (PBS)) for 1 hour at room temperature followed by avidin/biotin blocking. Tissue sections were washed in PBS three times for 5 minutes after each step. F4/80 macrophage primary antibody (Santa Cruz, Dallas, TX, USA) diluted 1:100 in blocking buffer was applied for 1 hour. A biotinylated goat anti-rat secondary antibody, diluted 1:200, was then applied for 30 minutes followed by horse radish peroxidase (HRP) conjugated enzyme for 30 minutes. Staining color was developed using diaminobenzidine (DAB) substrate (Vector Labs, Peterborough UK) for 10 minutes and slides were washed in water, dehydrated and mounted without counter staining to facilitate the computer based analysis.

Image Analysis

The percentage of kidney cortical staining was determined as described in Furness P. N. et al., *J Clin Pathol* 50:118-122, 1997. Briefly described, 24 bit color images were captured from sequential non-overlapping fields of renal cortex just beneath the renal capsule around the entire periphery of the section of kidney. After each image capture NIH Image was used to extract the red channel as an 8 bit monochrome image. Unevenness in the background illumination was subtracted using a pre-recorded image of the illuminated microscope field with no section in place. The image was subjected to a fixed threshold to identify areas of the image corresponding to the staining positivity. The percentage of black pixels was then calculated, and after all the images around the kidney had been measured in this way the average percentage was recorded, providing a value corresponding to the percentage of stained area in the kidney section.

Gene Expression Analysis

Expression of several genes relevant to renal inflammation and fibrosis in mouse kidney were measured by quantitative PCR (qPCR) as follows. Total RNA was isolated from kidney cortex using Trizol© (ThermoFisher Scientific, Paisley, UK) according to the manufacturer's instructions. Extracted RNA was treated with the Turbo DNA-free kit (ThermoFisher Scientific) to eliminate DNA contamination, and then first strand cDNA was synthesized using AMV Reverse Transcription System (Promega, Madison, WI, USA). The cDNA integrity was confirmed by a single qPCR reaction using TaqMan GAPDH Assay (Applied Biosystems, Paisley UK) followed by qPCR reaction using Custom TaqMan Array 96-well Plates (Life Technologies, Paisley, UK).

Twelve Genes were Studied in this Analysis:
Collagen type IV alpha 1 (col4α1; assay ID: Mm01210125_m1)
Transforming growth factor beta-1 (TGFβ-1; assay ID: Mm01178820_m1);
Cadherin 1 (Cdh1; Assay ID: Mm01247357_m1);
Fibronectin 1 (Fn1; Assay ID:Mm01256744_m1);
Interleukin 6 (IL6; Assay ID Mm00446191_m1);
Interleukin 10 (IL10; Assay ID Mm00439614_m1);
Interleukin 12a (IL12a; Assay ID Mm00434165_m1);
Vimentin (Vim; Assay ID Mm01333430_m1);
Actinin alpha 1 (Actn1; Assay ID Mm01304398_m1);
Tumor necrosis factor-α (TNF-α; Assay ID Mm00443260_g1)
Complement component 3 (C3; Assay ID Mm00437838_m1);
Interferon gamma (Ifn-γ; Assay ID Mm01168134)

The Following Housekeeping Control Genes were Used:
Glyceraldehyde-3-phosphate dehydrogenase (GAPDH; Assay ID Mm99999915_g1);
Glucuronidase beta (Gusβ; Assay ID Mm00446953_m1);
Eukaryotic 18S rRNA (18S; Assay ID Hs99999901_s1);
Hypoxanthine guanine phosphoribosyl transferase (HPRT; Assay ID Mm00446968_m1)

Twenty μL reactions were amplified using TaqMan Fast Universal Master Mix (Applied Biosystems) for 40 cycles. Real time PCR amplification data were analyzed using Applied Biosystems 7000 SDS v1.4 software.

Results

Following unilateral ureteric obstruction (UUO), obstructed kidneys experience an influx of inflammatory cells, particularly macrophages, followed by the prompt development of fibrosis as evidenced by the accumulation of collagen alongside tubular dilatation and attenuation of the proximal tubular epithelium (see Chevalier R. L. et al., *Kidney Int* 75:1145-1152, 2009).

Figure 15:
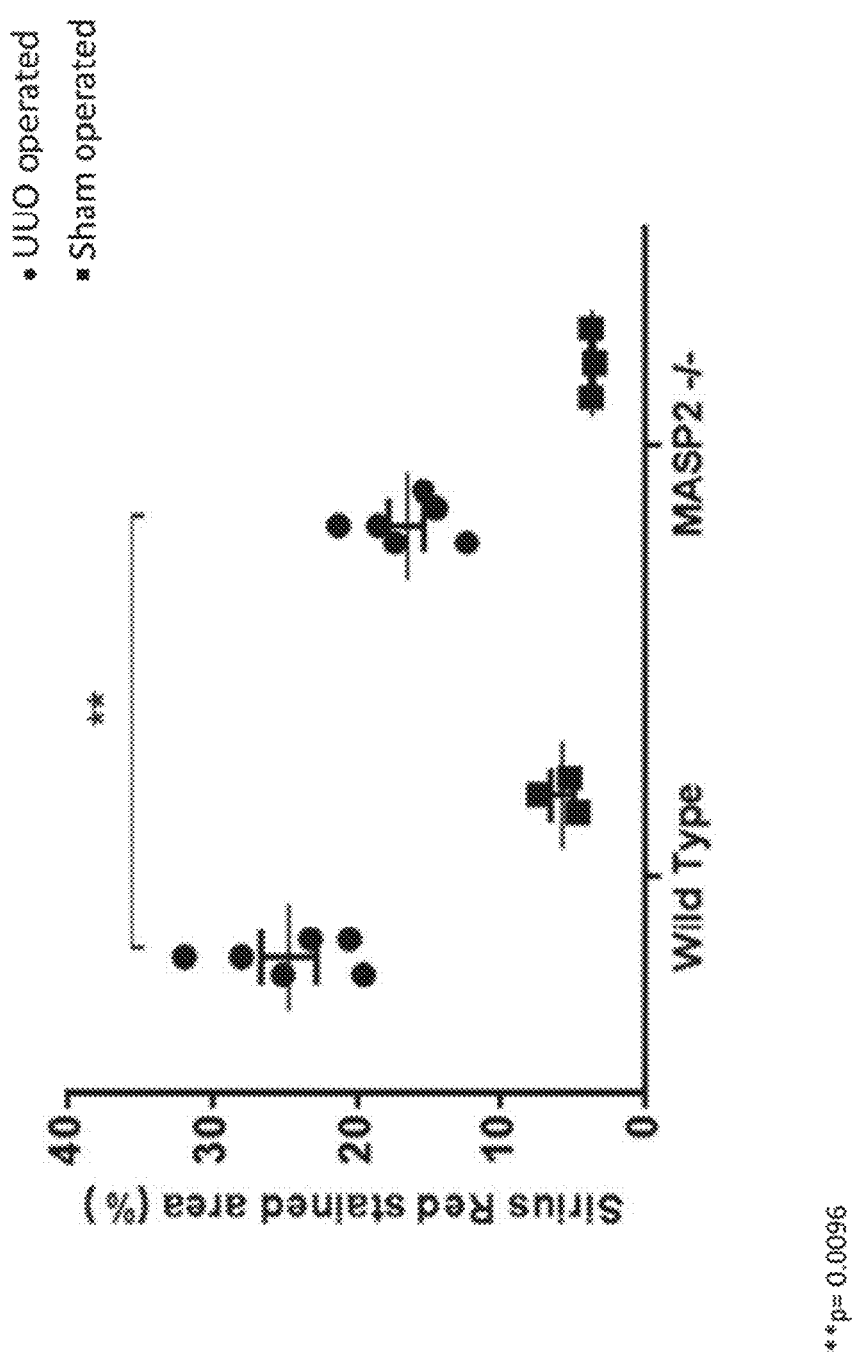
FIG. 15 graphically illustrates the results of computer-based image analysis of kidney tissue sections stained with Sirius red, wherein the tissue sections were obtained from wild-type and MASP-2−/− mice following 7 days of unilateral ureteric obstruction (UUO) and sham-operated wild-type and MASP-2−/− mice, as described in Example 14.

FIG. 15 graphically illustrates the results of computer-based image analysis of kidney tissue sections stained with Sirius red, wherein the tissue sections were obtained from wild-type and MASP-2−/− mice following 7 days of ureteric obstruction (UUO) or from sham-operated control mice. As shown in FIG. 15, kidney sections of wild-type mice following 7 days of ureteric obstruction showed significantly greater collagen deposition compared to MASP-2−/− mice (p value=0.0096). The mean values±standard error of means for UUO operated mice in wild-type and MASP-2−/− groups were 24.79±1.908 (n=6) and 16.58±1.3 (n=6), respectively. As further shown in FIG. 15, the tissue sections from the sham-operated control wild-type and the sham operated control MASP-2−/− mice showed very low levels of collagen staining, as expected.

Figure 16:
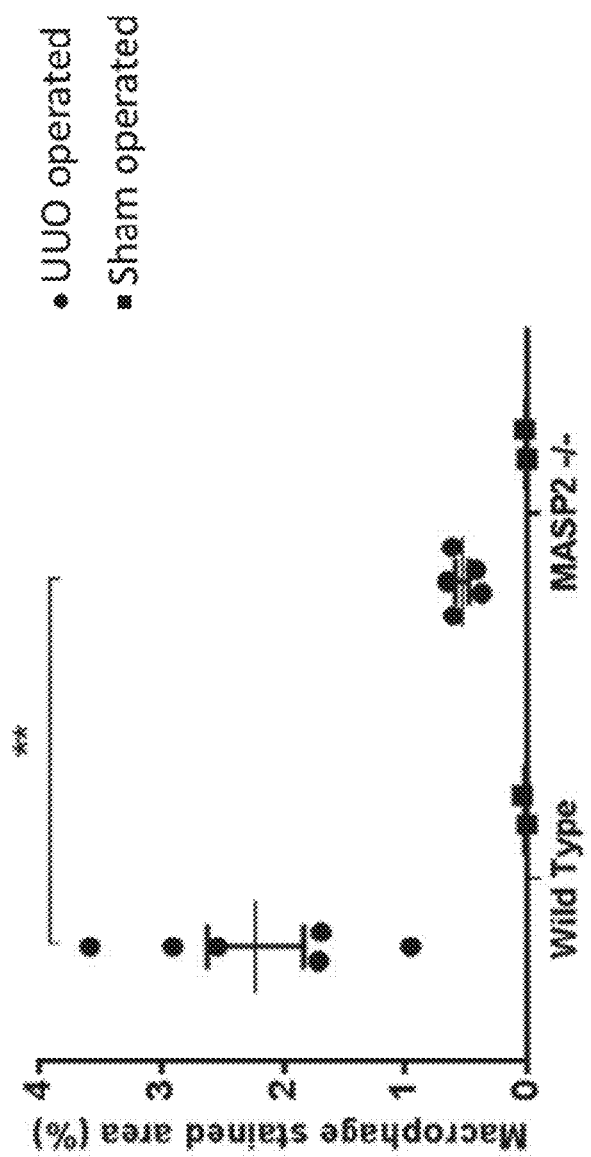
FIG. 16 graphically illustrates the results of computer-based image analysis of kidney tissue sections stained with the F4/80 macrophage-specific antibody, wherein the tissue sections were obtained from wild-type and MASP-2−/− mice following 7 days of unilateral ureteric obstruction (UUO) and sham-operated wild-type and MASP-2−/− mice, as described in Example 14.

FIG. 16 graphically illustrates the results of computer-based image analysis of kidney tissue sections stained with the F4/80 macrophage-specific antibody, wherein the tissue sections were obtained from wild-type and MASP-2−/− mice following 7 days of ureteric obstruction or from sham-operated control mice. As shown in FIG. 16, compared to wild-type mice, the tissue obtained from UUO kidneys from MASP-2−/− mice exhibited significantly less macrophage infiltration following 7 days of ureteric obstruction (% macrophage area stained in WT:2.23±0.4 vs MASP-2−/−: 0.53±0.06, p=0.0035). As further shown in FIG. 16, the tissue sections from the sham-operated wild-type and the sham-operated MASP-2−/− mice showed no detectable macrophage staining.

Figure 17:
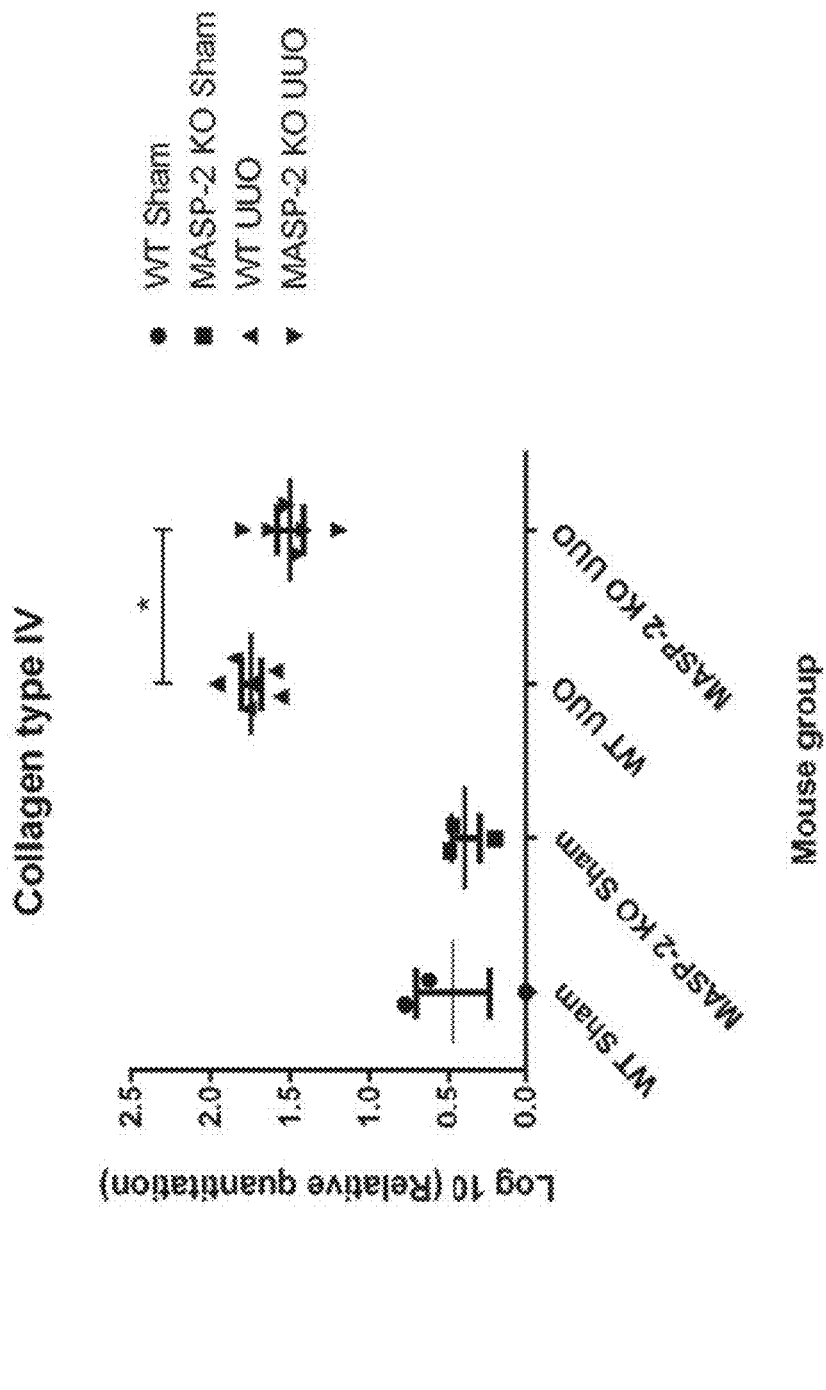
FIG. 17 graphically illustrates the relative mRNA expression levels of collagen-4, as measured by quantitative PCR (qPCR), in kidney tissue sections obtained from wild-type and MASP-2−/− mice following 7 days of unilateral ureteric obstruction (UUO) and sham-operated wild-type and MASP-2−/− mice, as described in Example 14.
Figure 18:
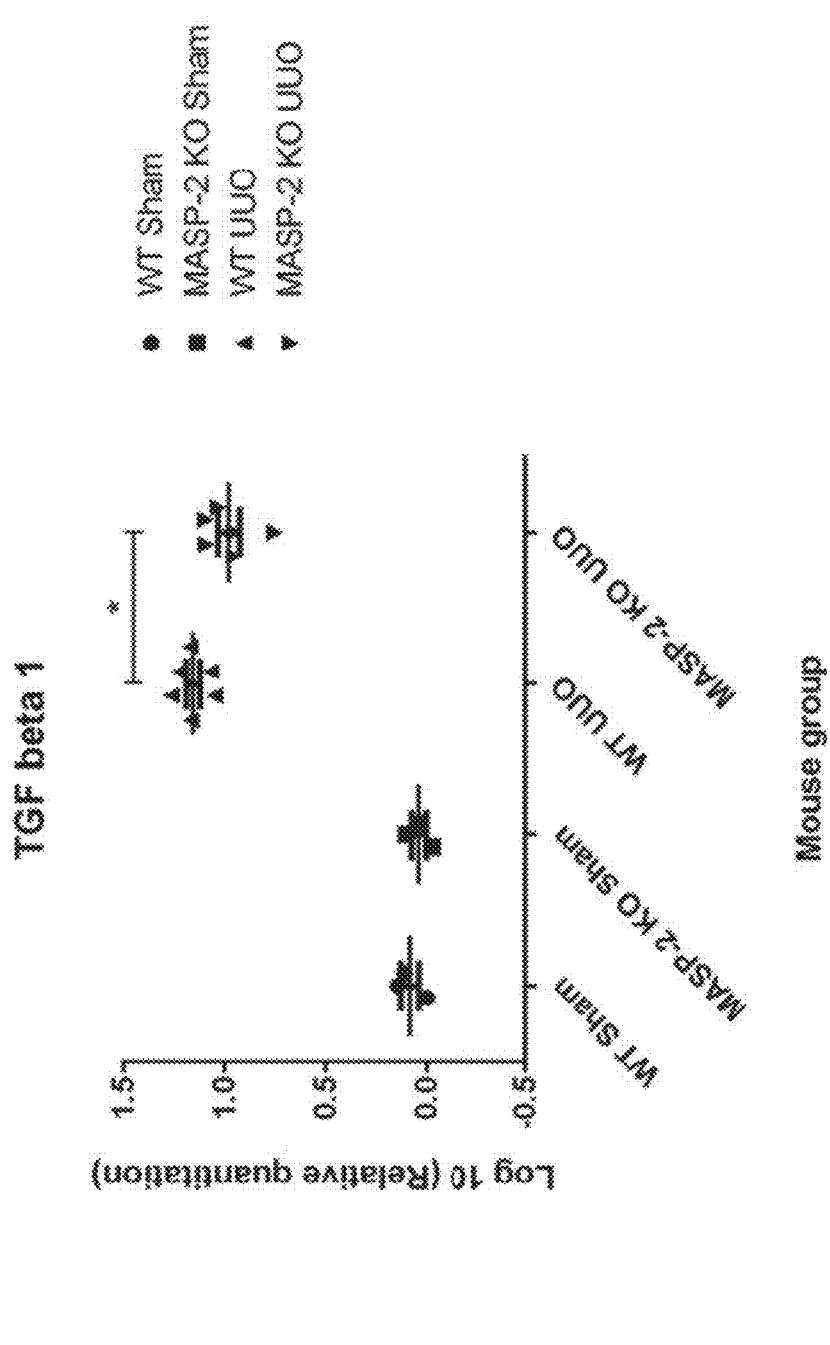
FIG. 18 graphically illustrates the relative mRNA expression levels of Transforming Growth Factor Beta-1 (TGFβ-1), as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.

Gene expression analysis of a variety of genes linked to renal inflammation and fibrosis was carried out in the kidney tissue sections obtained from wild-type and MASP-2−/− mice following 7 days of ureteric obstruction and sham-operated wild-type and MASP-2−/− mice. The data shown in FIGS. 17-20 are the Log 10 of relative quantitation to a wild-type sham operated sample and bars represent the standard error of means. With regard to the results of the gene expression analysis of the fibrosis-related genes, FIG. 17 graphically illustrates the relative mRNA expression levels of collagen type IV alpha 1 (collagen-4), as measured by qPCR in kidney tissue sections obtained from wild-type and MASP-2−/− mice following 7 days of ureteric obstruction and sham-operated control mice. FIG. 18 graphically illustrates the relative mRNA expression levels of Transforming Growth Factor Beta-1 (TGFβ-1), as measured by qPCR in kidney tissue sections obtained from wild-type and MASP-2−/− mice following 7 days of ureteric obstruction and sham-operated control mice. As shown in FIGS. 17 and 18, the obstructed kidneys from the wild-type mice demonstrated significantly increased expression of the fibrosis-related genes Collagen-type IV (FIG. 17) and TGFβ-1 (FIG. 18), as compared to the sham-operated kidneys in wild-type mice, demonstrating that these fibrosis-related genes are induced after UUO injury in wild-type mice, as expected. In contrast, as further shown in FIGS. 17 and 18, the obstructed kidneys from the MASP-2−/− subjected to the UUO injury exhibited a significant reduction in the expression of Collagen-type IV (FIG. 17, p=0.0388) and a significant reduction in the expression of TGFβ-1 (FIG. 18, p=0.0174), as compared to the wild-type mice subjected to the UUO injury.

Figure 19:
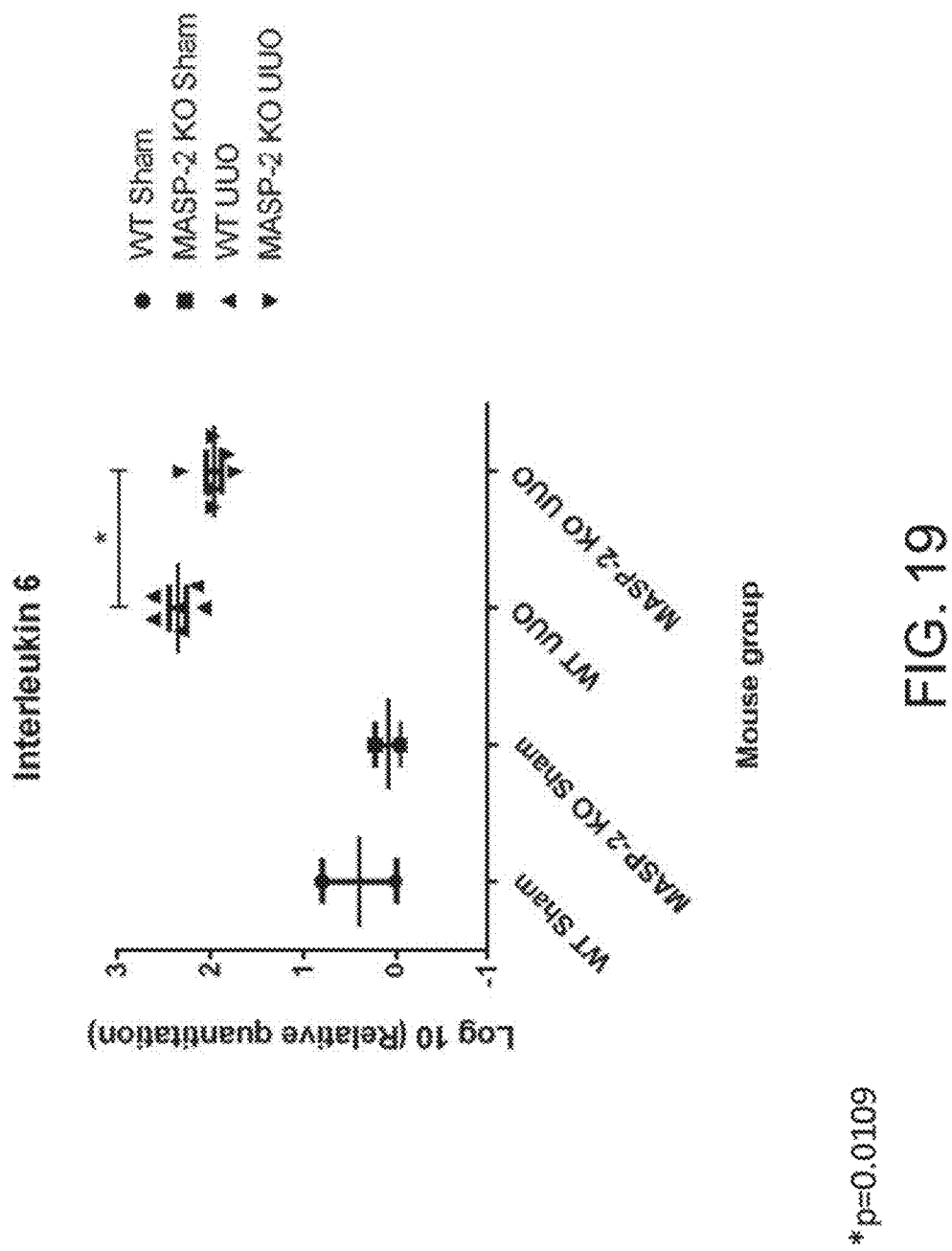
FIG. 19 graphically illustrates the relative mRNA expression levels of Interleukin-6 (IL-6), as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.
Figure 20:
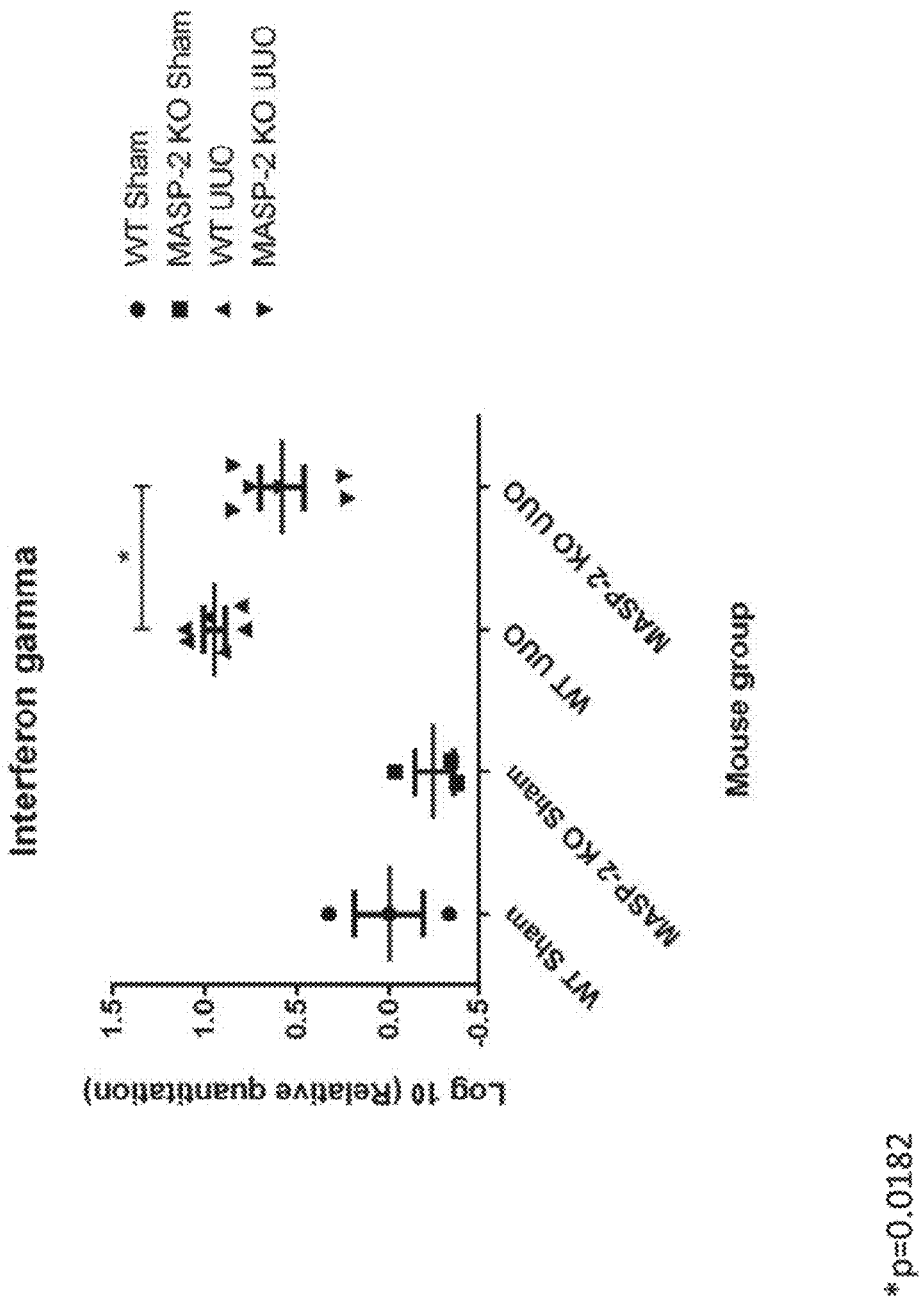
FIG. 20 graphically illustrates the relative mRNA expression levels of Interferon-γ, as measured by qPCR, in kidney tissue sections obtained from wild-type and MASP-2−/− mice following 7 days of unilateral ureteric obstruction (UUO) and sham-operated wild-type and MASP-2−/− mice, as described in Example 14.

With regard to the results of the gene expression analysis of the inflammation-related genes, FIG. 19 graphically illustrates the relative mRNA expression levels of Interleukin-6 (IL-6), as measured by qPCR in kidney tissue sections obtained from wild-type and MASP-2−/− mice following 7 days of ureteric obstruction and sham-operated control mice. FIG. 20 graphically illustrates the relative mRNA expression levels of Interferon-γ, as measured by qPCR in kidney tissue sections obtained from wild-type and MASP-2−/− mice following 7 days of ureteric obstruction and sham-operated control mice. As shown in FIGS. 19 and 20, the obstructed kidneys from the wild-type mice demonstrated significantly increased expression of the inflammation-related genes Interleukin-6 (FIG. 19) and Interferon-γ (FIG. 20), as compared to the sham-operated kidneys in wild-type mice, demonstrating that these inflammation-related genes are induced after UUO injury in wild-type mice. In contrast, as further shown in FIGS. 19 and 20, the obstructed kidneys from the MASP-2−/− subjected to the UUO injury exhibited a significant reduction in the expression of Interleukin-6 (FIG. 19, p=0.0109) and Interferon-γ (FIG. 20, p=0.0182) as compared to the wild-type mice subjected to the UUO injury.

It is noted that gene expression for Vim, Actn-1, TNFα, C3 and IL-10 were all found to be significantly up-regulated in the UUO kidneys obtained from both the wild-type and the MASP-2−/− mice, with no significant difference in the expression levels of these particular genes between the wild-type and MASP-2−/− mice (data not shown). The gene expression levels of Cdh-1 and IL-12a did not change in obstructed kidneys from animals in any group (data not shown).

Discussion

The UUO model in rodents is recognized to induce an early, active and profound injury in the obstructed kidney with reduced renal blood flow, interstitial inflammation and rapid fibrosis within one to two weeks following obstruction and has been used extensively to understand common mechanisms and mediators of inflammation and fibrosis in the kidney (see e.g., Chevalier R. L., *Kidney Int* 75:1145-1152, 2009; Yang H. et al., *Drug Discov Today Dis Models* 7:13-19, 2010).

The results described in this Example demonstrate that there is a significant reduction in collagen deposition and macrophage infiltration in UUO operated kidneys in the MASP-2(−/−) mice versus the wild-type (+/+) control mice. The unexpected results showing a significant reduction of renal injury at both the histological and gene expression levels in the MASP-2−/− animals demonstrates that the lectin pathway of complement activation contributes significantly to the development of inflammation and fibrosis in the obstructed kidney. While not wishing to be bound by a particular theory, it is believed that the lectin pathway contributes critically to the pathophysiology of fibrotic disease by triggering and maintaining pro-inflammatory stimuli that perpetuate a vicious cycle where cellular injury drives inflammation which in turn causes further cellular injury, scarring and tissue loss. In view of these results, it is expected that that inhibition or blockade of MASP-2 with an inhibitor would have a preventive and/or therapeutic effect in the inhibition or prevention of renal fibrosis, and for the inhibition or prevention of fibrosis in general (i.e., independent of the tissue or organ).

Example 15

This Example describes analysis of a monoclonal MASP-2 inhibitory antibody for efficacy in the Unilateral Ureteric Obstruction (UUO) model, a murine model of renal fibrosis.

Background/Rationale:

Amelioration of renal tubulointerstitial fibrosis, the common end point of multiple renal pathologies, represents a key target for therapeutic strategies aimed at preventing progressive renal diseases. Given the paucity of new and existing treatments targeting inflammatory pro-fibrotic pathways in renal disease, there is a pressing need to develop new therapies. Many patients with proteinuric renal disease exhibit tubulointerstitial inflammation and progressive fibrosis which closely parallels declining renal function. Proteinuria per se induces tubulointerstitial inflammation and the development of proteinuric nephropathy (Brunskill N. J. et al., *J Am Soc Nephrol* 15:504-505, 2004). Regardless of the primary renal disease, tubulointerstitial inflammation and fibrosis is invariably seen in patients with progressive renal impairment and is closely correlated with declining excretory function (Risdon R. A. et al., *Lancet* 1:363-366, 1968; Schainuck L. I., et al., *Hum Pathol* 1: 631-640, 1970). Therapies with the potential to interrupt the key common cellular pathways leading to fibrosis hold the promise of wide applicability in renal disorders.

As described in Example 14, in the UUO model of non-proteinuric renal fibrosis it was determined that MASP-2−/− mice exhibited significantly less renal fibrosis and inflammation compared to wild-type control animals, as shown by inflammatory cell infiltrates (75% reduction), and histological markers of fibrosis such as collagen (one third reduction), thereby establishing a key role of the lectin pathway in renal fibrosis.

As described in Example 13, a monoclonal MASP-2 antibody (OMS646-SGMI-2 fusion, comprising an SGMI-2 peptide fused to the C-terminus of the heavy chain of OMS646) was generated that specifically blocks the function of the human lectin pathway has also been shown to block the lectin pathway in mice. In this example, OMS646-SGMI-2 was analyzed in the UUO mouse model of renal fibrosis in wild-type mice to determine if a specific inhibitor of MASP-2 is able to inhibit renal fibrosis.

Methods

This study evaluated the effect of a MASP-2 inhibitory antibody (10 mg/kg OMS646-SGMI-2), compared to a human IgG4 isotype control antibody (10 mg/kg ET904), and a vehicle control in male WT C57BL/6 mice. The antibodies (10 mg/kg) were administered to groups of 9 mice by intraperitoneal (ip) injection on day 7, day 4 and day 1 prior to UUO surgery and again on day 2 post-surgery. Blood samples were taken prior to antibody administration and at the end of the experiment to assess lectin pathway functional activity.

The UUO surgery, tissue collection and staining with Sirius red and macrophage-specific antibody F4/80 were carried out using the methods described in Example 14.

Hydroxyproline content of mouse kidneys was measured using a specific colorimetric assay test kit (Sigma) according to manufacturer's instructions.

To assess the pharmacodynamic effect of the MASP-2 inhibitory mAb in mice, systemic lectin pathway activity was evaluated by quantitating lectin-induced C3 activation in minimally diluted serum samples collected at the indicated time after MASP-2 mAb or control mAb i.p. administration to mice. Briefly described, 7 μM diameter polystyrene microspheres (Bangs Laboratories, Fisher IN, USA) were coated with mannan by overnight incubation with 30 μg/mL mannan (Sigma) in sodium bicarbonate buffer (pH 9.6), then washed, blocked with 1% fetal bovine serum in PBS and resuspended in PBS at a final concentration of $1 \times 10^8$ beads/mL. Complement deposition reactions were initiated by the addition of 2.5 μL of mannan-coated beads (~250,000 beads) to 50 μL of minimally diluted mouse serum samples (90% final serum concentration), followed by incubation for 40 minutes at 4° C. Following termination of the deposition reaction by the addition of 250 μL of ice-cold flow cytometry buffer (FB: PBS containing 0.1% fetal bovine serum), beads were collected by centrifugation and washed two more times with 300 μL of ice-cold FB.

To quantify lectin-induced C3 activation, beads were incubated for 1 hour at 4° C. with 50 μL of rabbit anti-human C3c antibody (Dako, Carpenteria, CA, USA) diluted in FB. Following two washes with FB to remove unbound material, the beads were incubated for 30 minutes at 4° C. with 50 μL of goat anti-rabbit antibody conjugated to PE-Cy5 (Southern Biotech, Birmingham, AL, USA) diluted in FB. Following two washes with FB to remove unbound material, the beads were resuspended in FB and analyzed by a FACS Calibur cytometer. The beads were gated as a uniform population using forward and side scatter, and C3b deposition in each sample was quantitated as mean fluorescent intensity (MFI).

Results

Figure 21:
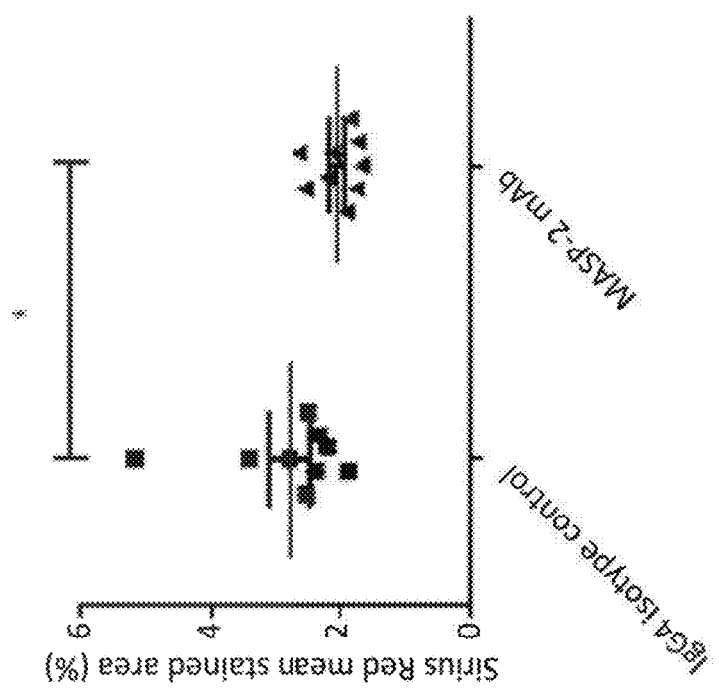
FIG. 21 graphically illustrates the results of computer-based image analysis of kidney tissue sections stained with Siruis red, wherein the tissue sections were obtained following 7 days of unilateral ureteric obstruction (UUO) from wild-type mice treated with a MASP-2 inhibitory antibody and an isotype control antibody, as described in Example 15.

Assessment of Collagen Deposition:

FIG. 21 graphically illustrates the results of computer-based image analysis of kidney tissue sections stained with Siruis red, wherein the tissue sections were obtained following 7 days of ureteric obstruction from wild-type mice treated with either a MASP-2 inhibitory antibody or an isotype control antibody. As shown in FIG. 21, tissue sections from kidneys harvested 7 days after obstruction (UUO) obtained from wild-type mice treated with MASP-2 inhibitory antibody showed a significant reduction (p=0.0477) in collagen deposition as compared with the amount of collagen deposition in tissue sections from obstructed kidneys obtained from wild-type mice treated with an IgG4 isotype control.

Assessment of Hydroxy Proline Content:

Hydroxy proline was measured in kidney tissues as an indicator of collagen content. Hydroxy proline is a parameter which is highly indicative of the pathophysiological progression of disease induced in this model.

Figure 22:
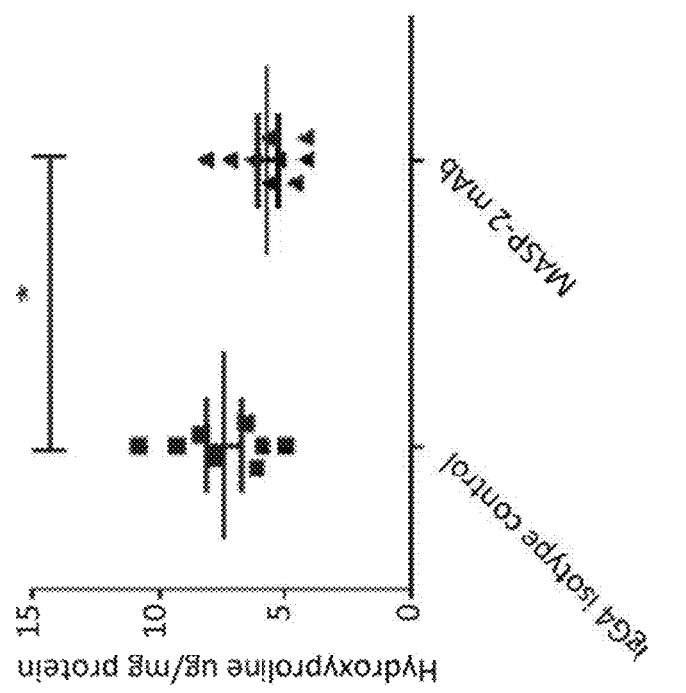
FIG. 22 graphically illustrates the hydroxyl proline content from kidneys harvested 7 days after unilateral ureteric obstruction (UUO) obtained from wild-type mice treated with MASP-2 inhibitory antibody as compared with the level of hydroxyl proline in tissue from obstructed kidneys obtained from wild-type mice treated with an IgG4 isotype control, as described in Example 15.

FIG. 22 graphically illustrates the hydroxyl proline content from kidneys harvested 7 days after obstruction (UUO) obtained from wild-type mice treated with either a MASP-2 inhibitory antibody or an isotype control antibody. As shown in FIG. 22, the obstructed kidney tissues from mice treated with MASP-2 inhibitory antibody demonstrated significantly less hydroxyl proline, an indicator of collagen content, than the kidneys from mice treated with the IgG4 isotype control mAb (p=0.0439).

Assessment of Inflammation:

Obstructed kidneys from wild-type, isotype control antibody-treated animals, and wild-type animals treated with MASP-2 inhibitory antibody demonstrated a brisk infiltrate of macrophages. Careful quantification revealed no significant difference in macrophage percentage stained area between these two groups (data not shown). However, despite equivalent numbers of infiltrating macrophages, the obstructed kidneys from the MASP-2 inhibitory antibody-injected animals exhibited significantly less fibrosis as judged by Sirius red staining, compared to obstructed kidneys from isotype control injected animals, which result is consistent with the results that obstructed kidney tissues from mice treated with MASP-2 inhibitory antibody had significantly less hydroxyl proline than the kidneys treated with the IgG4 isotype control mAb.

Discussion

The results described in this Example demonstrate that the use of a MASP-2 inhibitory antibody provides protection against renal fibrosis in the UUO model, which is consistent with the results described in Example 14 demonstrating that MASP-2−/− mice have significantly reduced renal fibrosis and inflammation in the UUO model as compared to wild-type mice. The results in this Example showing reduced fibrosis in the mice treated with the MASP-2 inhibitory antibody. The finding of reduced fibrosis in the UUO kidneys in animals with a reduction or blockade of MASP-2-dependent lectin pathway activity is highly significant novel finding. Taken together, the results presented in Example 14 and in this Example demonstrate a beneficial effect of MASP-2 inhibition on renal tubulointerstitial inflammation, tubular cell injury, profibrotic cytokine release and scarring. The relief of renal fibrosis remains a key goal for renal therapeutics. The UUO model is a severe model of accelerated renal fibrosis, and an intervention that reduces fibrosis in this model, such as the use of MASP-2 inhibitory antibodies, is likely to be used to inhibit or prevent renal fibrosis. The results from the UUO model are likely to be transferable to renal disease characterized by glomerular and/or proteinuric tubular injury.

Example 16

This Example provides results that were generated using a protein overload proteinurea model of renal fibrosis, inflammation and tubulointerstital injury in MASP-2-/- and wild-type mice to evaluate the role of the lectin pathway in proteinuric nephropathy.
Background/Rationale:

Proteinuria is a risk factor for the development of renal fibrosis and loss of renal excretory function, regardless of the primary renal disease (Tryggvason K. et al., *J Intern Med* 254:216-224, 2003, Williams M., *Am J. Nephrol* 25:77-94, 2005). The concept of proteinuric nephropathy describes the toxic effects of excess protein entering the proximal tubule as a result of the impaired glomerular permselectivity (Brunskill N. J., *J Am Soc Nephrol* 15:504-505, 2004, Baines R. J., *Nature Rev Nephrol* 7:177-180, 2011). This phenomenon, common to many glomerular diseases, results in a pro-inflammatory scarring environment in the kidney and is characterized by alterations in proximal tubular cell growth, apoptosis, gene transcription and inflammatory cytokine production as a consequence of dysregulated signaling pathways stimulated by proteinuric tubular fluid. Proteinuric nephropathy is generally recognized to be a key contributor to progressive renal injury common to diverse primary renal pathologies.

Chronic kidney disease affects greater than 15% of the adult population in the United States and accounts for approximately 750,000 deaths each year worldwide (Lozano R. et al., *Lancet* vol 380, Issue 9859:2095-2128, 2012). Proteinuria is an indicator of chronic kidney disease as well as a factor promoting disease progression. Many patients with proteinuric renal disease exhibit tubulointerstitial inflammation and progressive fibrosis which closely parallels declining renal function. Proteinuria per se induces tubulointerstitial inflammation and the development of proteinuric nephropathy (Brunskill N. J. et al., *J Am Soc Nephrol* 15:504-505, 2004). In proteinuric kidney diseases, excessive amounts of albumin and other macromolecules are filtered through the glomeruli and reabsorbed by proximal tubular epithelial cells. This causes an inflammatory vicious cycle mediated by complement activation leading to cytokine and leukocyte infiltrates that cause tubule-interstitial injury and fibrosis, thereby exacerbating proteinuria and leading to loss of renal function and eventually progression to end-stage renal failure (see, e.g., Clark et al., *Canadian Medical Association Journal* 178:173-175, 2008). Therapies that modulate this detrimental cycle of inflammation and proteinuria are expected to improve outcomes in chronic kidney disease.

In view of the beneficial effects of MASP-2 inhibition in the UUO model of tubulointerstital injury, the following experiment was carried out to determine if MASP-2 inhibition would reduce renal injury in a protein overload model. This study employed protein overload to induce proteinuric kidney disease as described in Ishola et al., *European Renal Association* 21:591-597, 2006.

Methods

A MASP-2-/- mouse was generated as described in Example 1 and backcrossed for 10 generations with BALB/c. The current study compared the results of wild-type and MASP-2-/- BALB/c mice in a protein overload proteinuria model as follows.

One week prior to the experiment, mice were unilaterally nephrectomised before protein overload challenge in order to see an optimal response. The proteinuria inducing agent used was a low endotoxin bovine serum albumin (BSA, Sigma) given i.p. in normal saline to WT (n=7) and MASP-2-/- mice (n=7) at the following doses: one dose each of 2 mg BSA/gm, 4 mg BSA/gm, 6 mg BSA/gm, 8 mg BSA/gm, 10 mg BSA/gm and 12 mg BSA/gm body weight, and 9 doses of 15 mg BSA/gm body weight, for a total of 15 doses administered i.p. over a period of 15 days. The control WT (n=4) and MASP-2-/- (n=4) mice received saline only administered i.p. After administration of the last dose, animals were caged separately in metabolic cages for 24 hours to collect urine. Blood was collected by cardiac puncture under anesthesia, blood was allowed to clot on ice for 2 hours and serum was separated by centrifugation. Serum and urine samples were collected at the end of the experiment on day 15, stored and frozen for analysis.

Mice were sacrificed 24 hours after the last BSA administration on day 15 and various tissues were collected for analysis. Kidneys were harvested and processed for H&E and immunostaining. Immunohistochemistry staining was carried out as follows. Formalin fixed, paraffin-embedded 5 micron kidney tissue sections from each mouse were deparaffinized and rehydrated. Antigen retrieval was performed in citrate buffer at 95° C. for 20 minutes followed by incubating tissues in 3% $H_2O_2$ for 10 minutes. Tissues were then incubated in blocking buffer (10% serum from the species the secondary antibody was raised in and 1% BSA in PBS) with 10% avidin solution for 1 hour at room temperature. Sections were washed in PBS three times, 5 minutes each, after each step. Primary antibody was then applied in blocking buffer with 10% biotin solution for 1 hour at a concentration of 1:100 for the antibodies F4/80 (Santa Cruz cat #sc-25830), TGFβ (Santa Cruz cat #sc-7892), IL-6 (Santa Cruz cat #sc-1265) and at 1:50 for the TNFα antibody (Santa Cruz cat #sc-1348). A biotinylated secondary antibody was then applied for 30 minutes at a concentration of 1:200 for the F4/80, TGFβ and TL-6 sections and 1:100 for the TNFα section followed by HRP conjugate enzyme for another 30 minutes. The color was developed using diaminobenzidine (DAB) substrate kit (Vector labs) for 10 minutes and slides were washed in water, dehydrated and mounted without counter staining to facilitate computer-based image analysis. Stained tissue sections from the renal cortex were analyzed by digital image capture followed by quantification using automated image analysis software.

Apoptosis was assessed in the tissue sections by staining with terminal deoxynucleotidyl transferase dUTP nick end labeling (TUNEL) as follows. Apoptotic cells in the kidney sections were stained using ApopTag® Peroxidase kit (Millipore) as follows. Parrafin embedded, formalin fixed kidney sections from each mouse were deparaffinized, rehydrated and then protein permeabilized using proteinase K (20 μg/mL) which was applied to each specimen for 15 minutes at room temperature. Specimens were washed in PBS between steps. Endogenous peroxidase activity was quenched by incubating tissues in 3% $H_2O_2$ for 10 minutes. Tissues were then incubated in equilibration buffer followed by incubation with TdT enzyme for 1 hour at 37° C. After washing in stop/wash buffer for 10 minutes, anti-digoxigenin conjugate was applied for 30 minutes at room temperature followed by washing. Color was developed in DAB substrate kit for 4 minutes followed by washing in water. Tissues were counter stained in haematoxylin and mounted in DBX. The frequency of TUNEL stained (brown colored) apoptotic cells were manually counted in serially selected 20 high power fields from the cortex using Leica DBXM light microscope.

Results

Assessment of Proteinuria

To confirm the presence of proteinuria in the mice, the total protein in serum was analyzed at day 15 and the total excreted proteins in urine was measured in urine samples collected over a 24 hour period on day 15 of the study.

Figure 23:
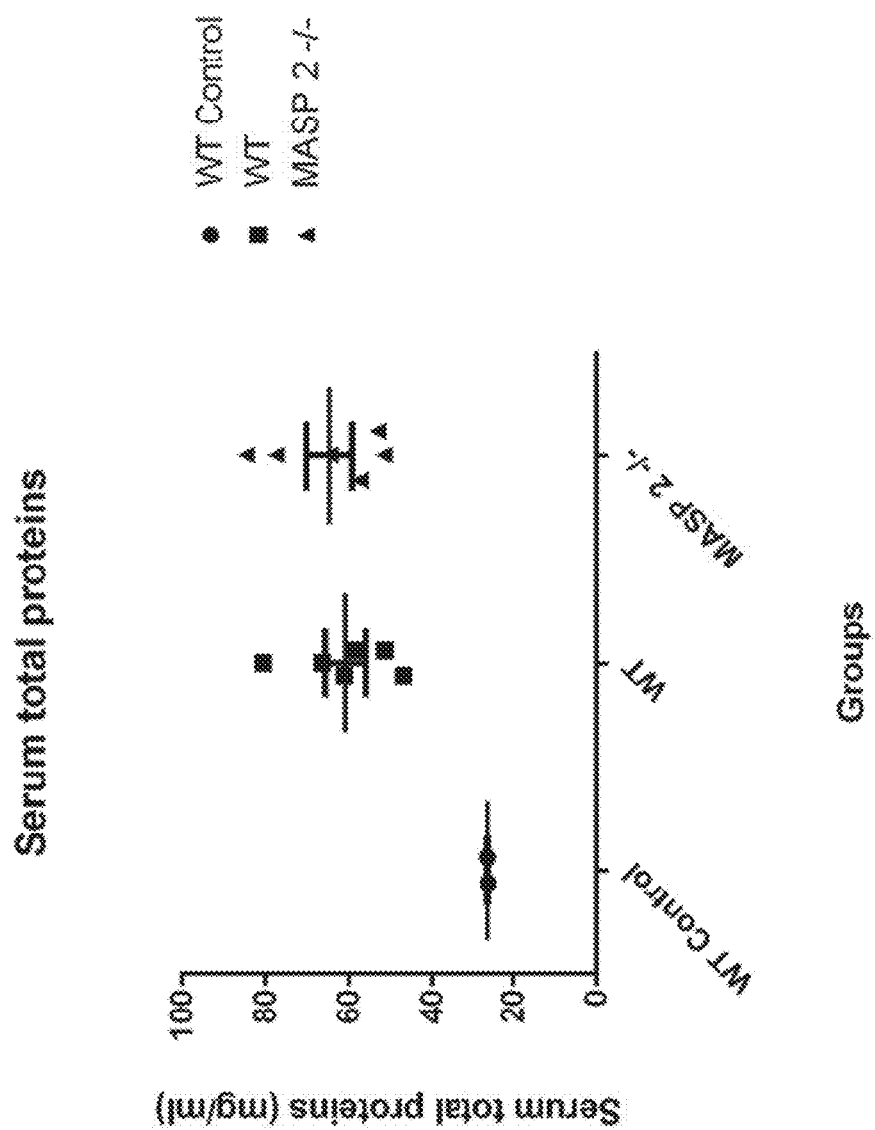
FIG. 23 graphically illustrates the total amount of serum proteins (mg/ml) measured on day 15 of the protein overload study in wild-type control mice (n=2) that received saline only, wild-type mice that received BSA (n=6) and MASP-2−/− mice that received BSA (n=6), as described in Example 16.

FIG. 23 graphically illustrates the total amount of serum proteins (mg/ml) measured at day 15 in the wild-type control mice (n=2) that received saline only, the wild-type mice that received BSA (n=6) and the MASP-2-/- mice that received BSA (n=6). As shown in FIG. 23, administration of BSA increased the serum total protein level in both wild-type and MASP-2-/- groups to more than double the concentration of the control group that received only saline, with no significant difference between the treated groups.

Figure 24:
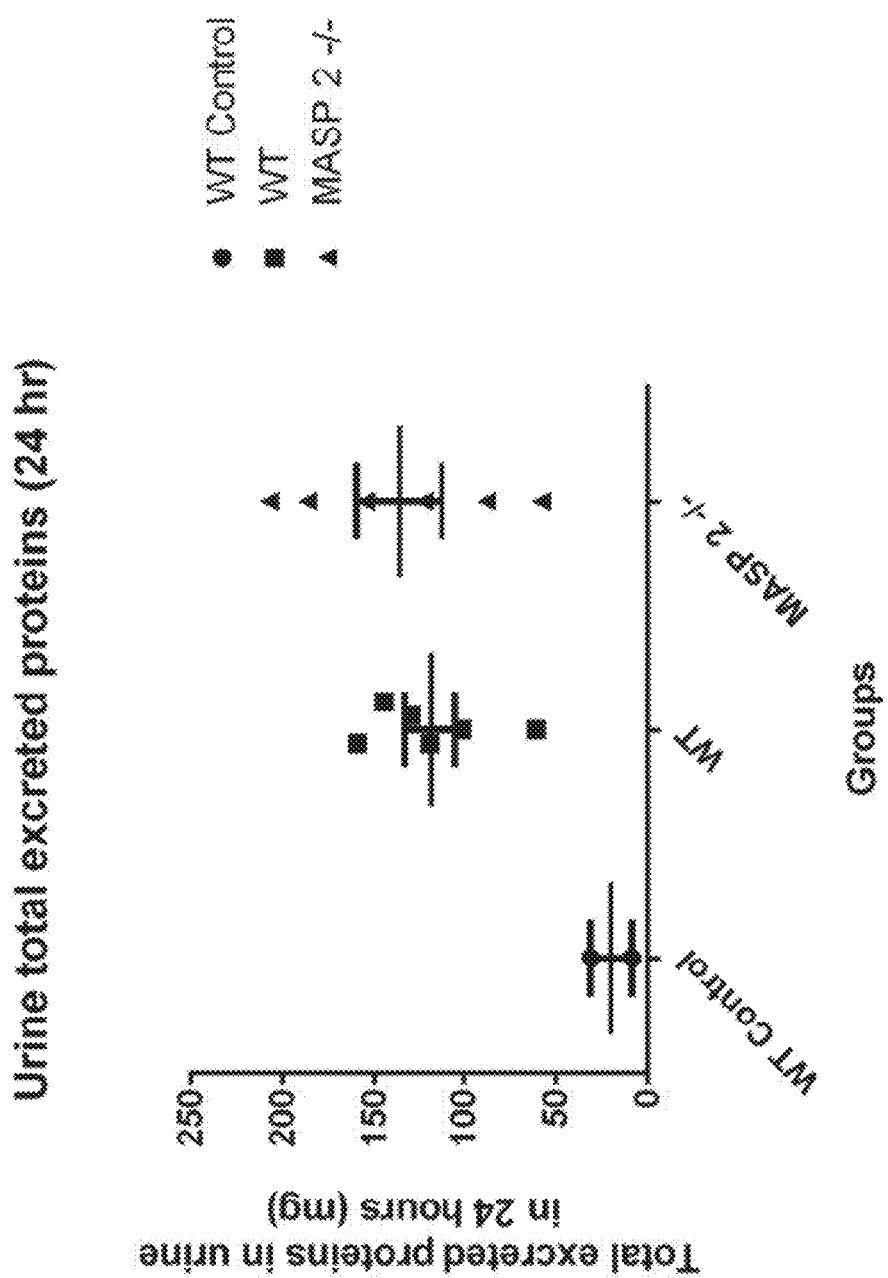
FIG. 24 graphically illustrates the total amount of excreted protein (mg) in urine collected over a 24 hour period on day 15 of the protein overload study from wild-type control mice (n=2) that received saline only, wild-type that received BSA (n=6) and MASP-2−/− mice that received BSA (n=6), as described in Example 16.

FIG. 24 graphically illustrates the total amount of excreted protein (mg) in urine collected over a 24 hour period on day 15 of the study from the wild-type control mice (n=2) that received saline only, the wild-type mice that received BSA (n=6) and the MASP-2-/- mice that received BSA (n=6). As shown in FIG. 24, on day 15 of this study, there was an approximately six-fold increase in total excreted proteins in urine in the BSA treated groups as compared to the sham-treated control group that received saline only. The results shown in FIGS. 23 and 24 demonstrate that the proteinuria model was working as expected.

Assessment of Histological Changes in the Kidney

Figure 25:
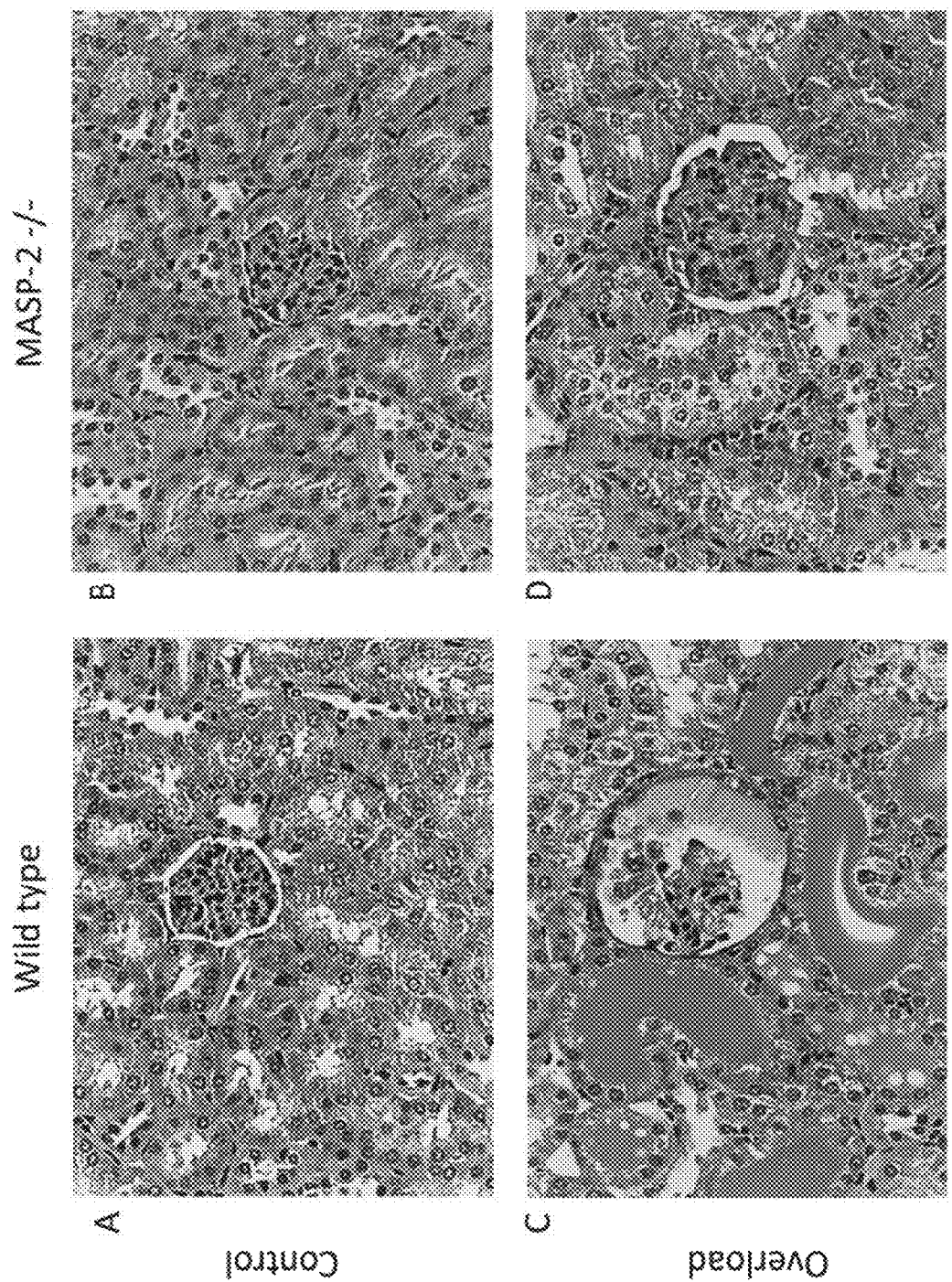
FIG. 25 shows representative hematoxylin and eosin (H&E) stained renal tissue sections from the following groups of mice on day 15 of the protein overload study as follows: (panel A) wild-type control mice; (panel B) MASP-2−/− control mice, (panel C) wild-type mice treated with BSA; and (panel D) MASP-2−/− mice treated with bovine serum albumin (BSA), as described in Example 16.

FIG. 25 shows representative H&E stained renal tissue sections that were harvested on day 15 of the protein overload study from the following groups of mice: (panel A) wild-type control mice; (panel B) MASP-2-/- control mice; (panel C) wild-type mice treated with BSA; and (panel D) MASP-2-/- mice treated with BSA. As shown in FIG. 25, there is a much higher degree of tissue preservation in the MASP-2-/- overload group (panel D) compared to the wild-type overload group (panel C) at the same level of protein overload challenge. For example, Bowman's capsules in the wild-type mice treated with BSA (overload) were observed to be greatly expanded (panel C) as compared to Bowman's capsules in the wild-type control group (panel A). In contrast, Bowman's capsules in the MASP-2-/- mice (overload) treated with the same level of BSA (panel D) retained morphology similar to the MASP-2-/- control mice (panel B) and wild-type control mice (panel A). As further shown in FIG. 25, large protein cast structures have accumulated in proximal and distal tubules of the wild-type kidney sections (panel C), which are larger and more abundant as compared to MASP-2-/- mice (panel D).

It is also noted that analysis of renal sections from this study by transmitting electron microscope showed that the mice treated with BSA had overall damage to the ciliary borders of distal and proximal tubular cells, with cellular content and nuclei bursting into the tubule lumen. In contrast, the tissue was preserved in the MASP-2-/- mice treated with BSA.

Assessment of Macrophage Infiltration in the Kidney

To measure the degree of inflammation, as indicated by macrophage infiltration, the tissue sections of the harvested kidneys were also stained with macrophage-specific antibody F4/80 using methods as described in Boor et al., *J of Am Soc of Nephrology* 18:1508-1515, 2007.

Figure 26:
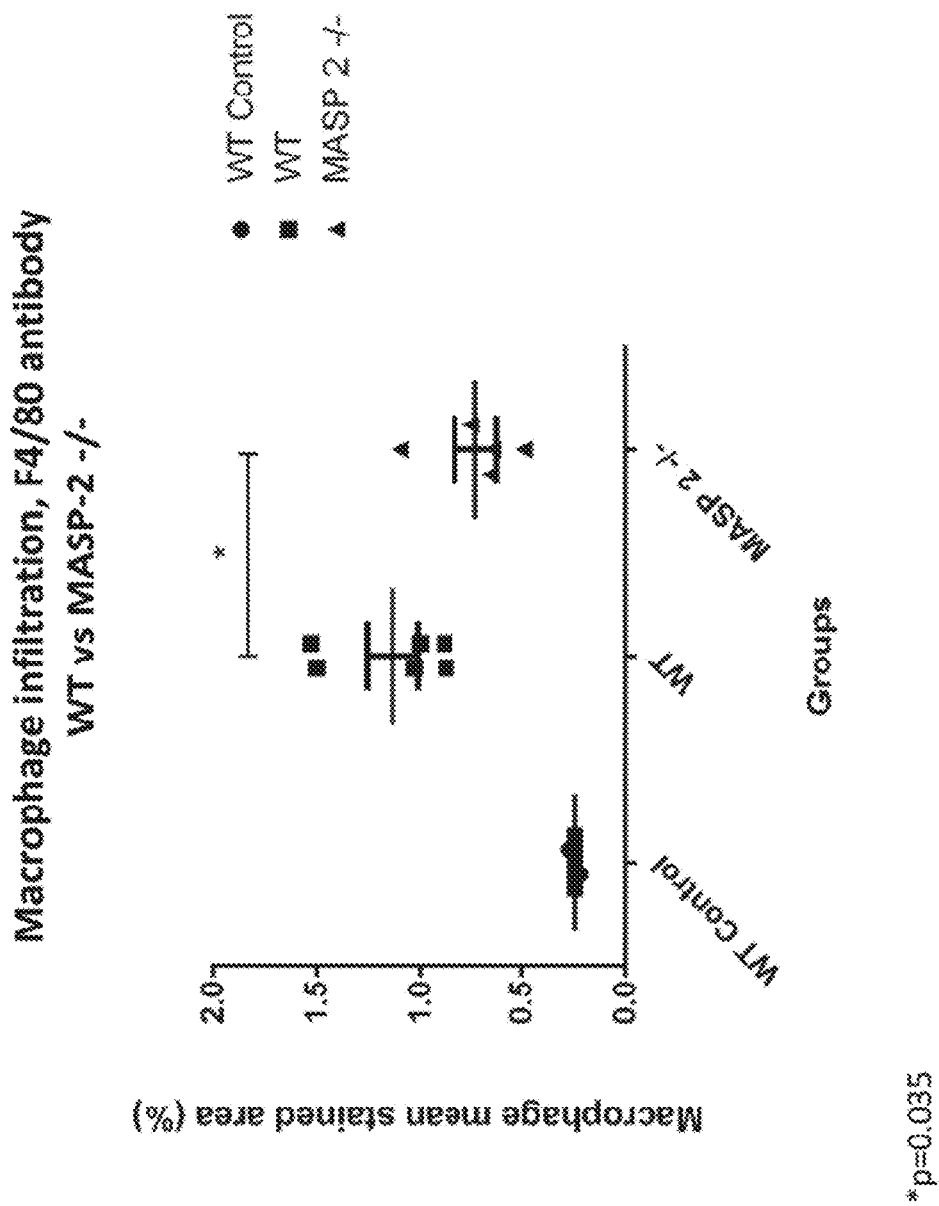
FIG. 26 graphically illustrates the results of computer-based image analysis of kidney tissue sections stained with macrophage-specific antibody F4/80, showing the macrophage mean stained area (%), wherein the tissue sections were obtained on day 15 of the protein overload study from wild-type control mice (n=2), wild-type mice treated with BSA (n=6), and MASP-2−/− mice treated with BSA (n=5), as described in Example 16.

FIG. 26 graphically illustrates the results of computer-based image analysis of kidney tissue sections stained with macrophage-specific antibody F4/80, showing the macrophage mean stained area (%), wherein the tissue sections were obtained at day 15 of the protein overload study from wild-type control mice (n=2), wild-type mice treated with BSA (n=6), and MASP-2-/- mice treated with BSA (n=5). As shown in FIG. 26, kidney tissue sections stained with F4/80 anti-macrophage antibody showed that while both groups treated with BSA showed a significant increase in the kidney macrophage infiltration (measured as % F4/80 antibody-stained area) compared to the wild-type sham control, a significant reduction in macrophage infiltration was observed in tissue sections from BSA-treated MASP-2-/- mice as compared with macrophage infiltration in tissue sections from BSA-treated wild-type mice (p value=0.0345).

Figure 27A:
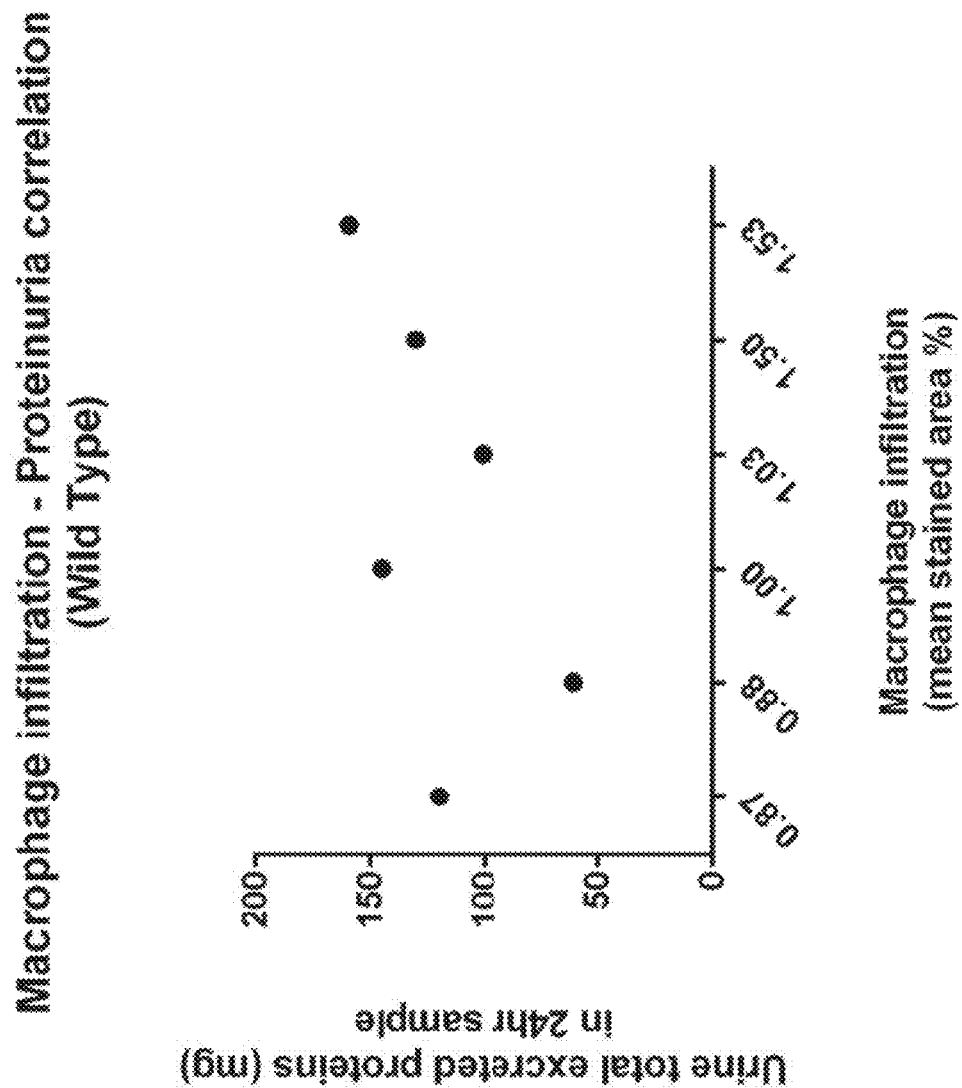
FIG. 27A graphically illustrates the analysis for the presence of a macrophage-proteinuria correlation in each wild-type mouse (n=6) treated with BSA by plotting the total excreted proteins measured in urine from a 24-hour sample versus the macrophage infiltration (mean stained area %), as described in Example 16.

FIG. 27A graphically illustrates the analysis for the presence of a macrophage-proteinuria correlation in each wild-type mouse (n=6) treated with BSA by plotting the total excreted proteins measured in urine from a 24 hour sample versus the macrophage infiltration (mean stained area %). As shown in FIG. 27A, most of the samples from the wild-type kidneys showed a positive correlation between the level of proteinuria present and the degree of macrophage infiltration.

Figure 27B:
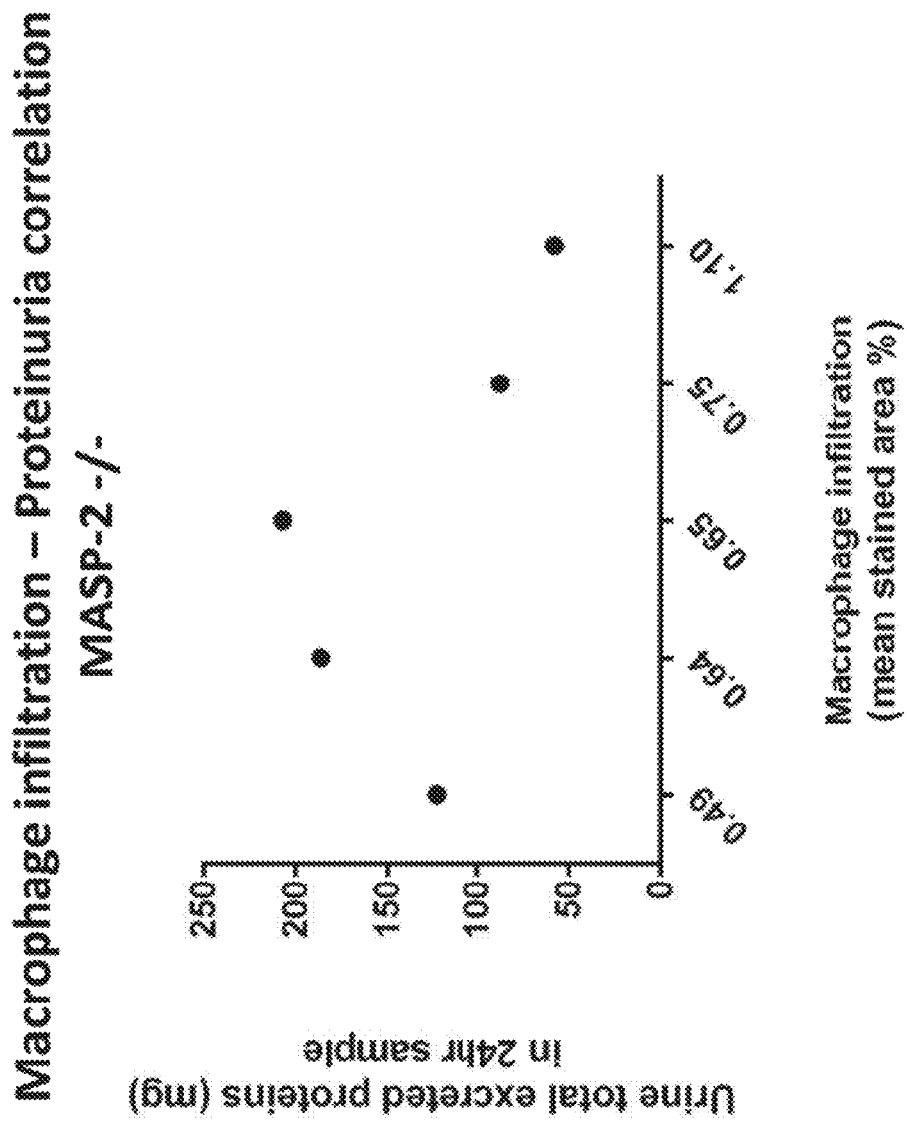
FIG. 27B graphically illustrates the analysis for the presence of a macrophage-proteinuria correlation in each MASP-2−/− mouse (n=5) treated with BSA by plotting the total excreted proteins in urine in a 24-hour sample versus the macrophage infiltration (mean stained area %), as described in Example 16.

FIG. 27B graphically illustrates the analysis for the presence of a macrophage-proteinuria correlation in each MASP-2-/- mouse (n=5) treated with BSA by plotting the total excreted proteins in urine in a 24 hour sample versus the macrophage infiltration (mean stained area %). As shown in FIG. 27B, the positive correlation observed in wild-type mice between the level of proteinuria and the degree of macrophage infiltration (shown in FIG. 27A) was not observed in MASP-2-/- mice. While not wishing to be bound by any particular theory, these results may indicate the presence of a mechanism of inflammation clearance at high levels of proteinuria in MASP-2-/- mice.

Assessment of Cytokine Infiltration

Interleukin 6 (IL-6), Transforming Growth Factor Beta (TGFβ) and Tumor Necrosis Factor Alpha (TNFα) are pro-inflammatory cytokines known to be up-regulated in proximal tubules of wild-type mice in a model of proteinuria (Abbate M. et al., *Journal of the American Society of Nephrology:* JASN, 17: 2974-2984, 2006; David S. et al., Nephrology, Didalysis, Transplantation, Official Publication of the European Dialysis and Transplant Association—European Renal Association 12: 51-56, 1997). The tissue sections of kidneys were stained with cytokine-specific antibodies as described above.

Figure 28:
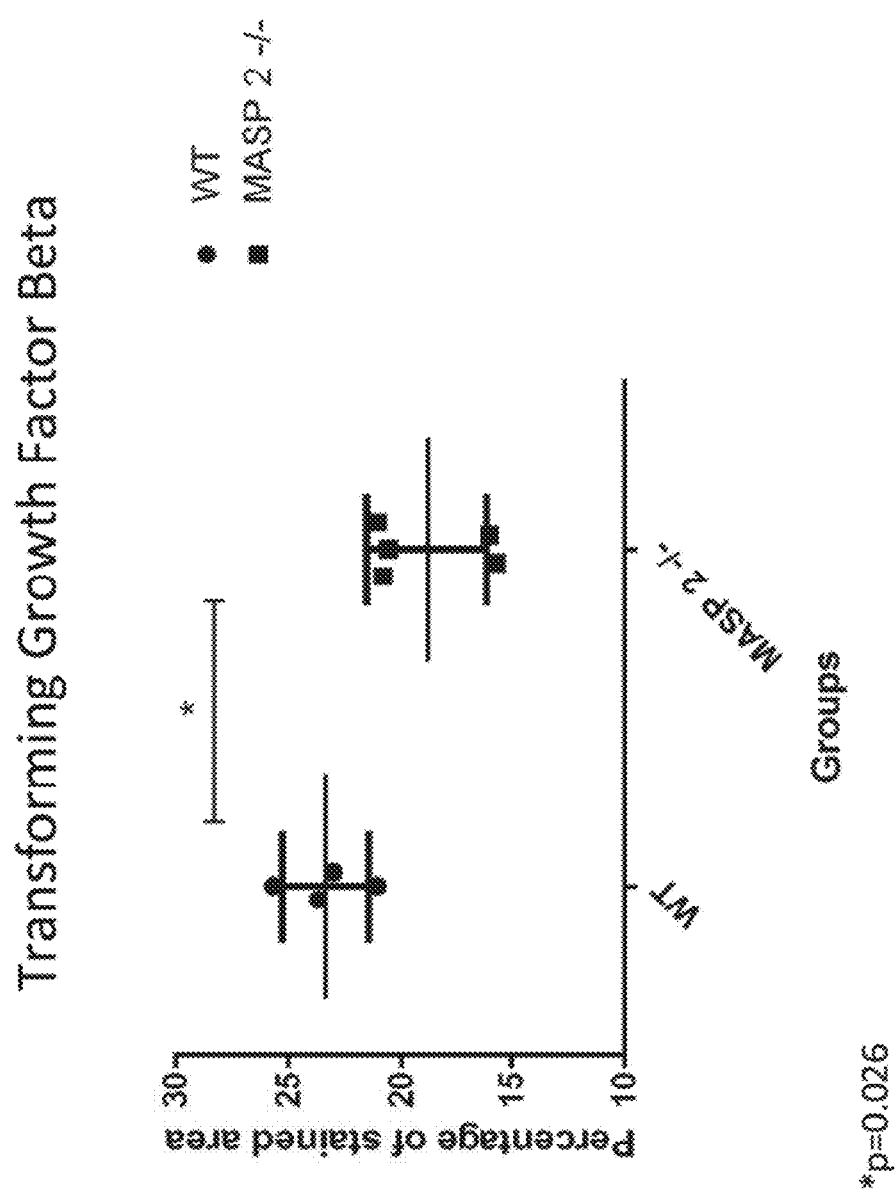
FIG. 28 graphically illustrates the results of computer-based image analysis of stained tissue sections with anti-TGFβ antibody (measured as % TGFβ antibody-stained area) in wild-type mice treated with BSA (n=4) and MASP-2−/− mice treated with BSA (n=5), as described in Example 16.

FIG. 28 graphically illustrates the results of computer-based image analysis of stained tissue sections with anti-TGFβ antibody (measured as % TGFβ antibody-stained area) in wild-type mice treated with BSA (n=4) and MASP-2-/- mice treated with BSA (n=5). As shown in FIG. 28, a significant increase in the staining of TGFβ was observed in the wild-type BSA treated (overload) group as compared to the MASP-2-/- BSA treated (overload) group (p=0.026).

Figure 29:
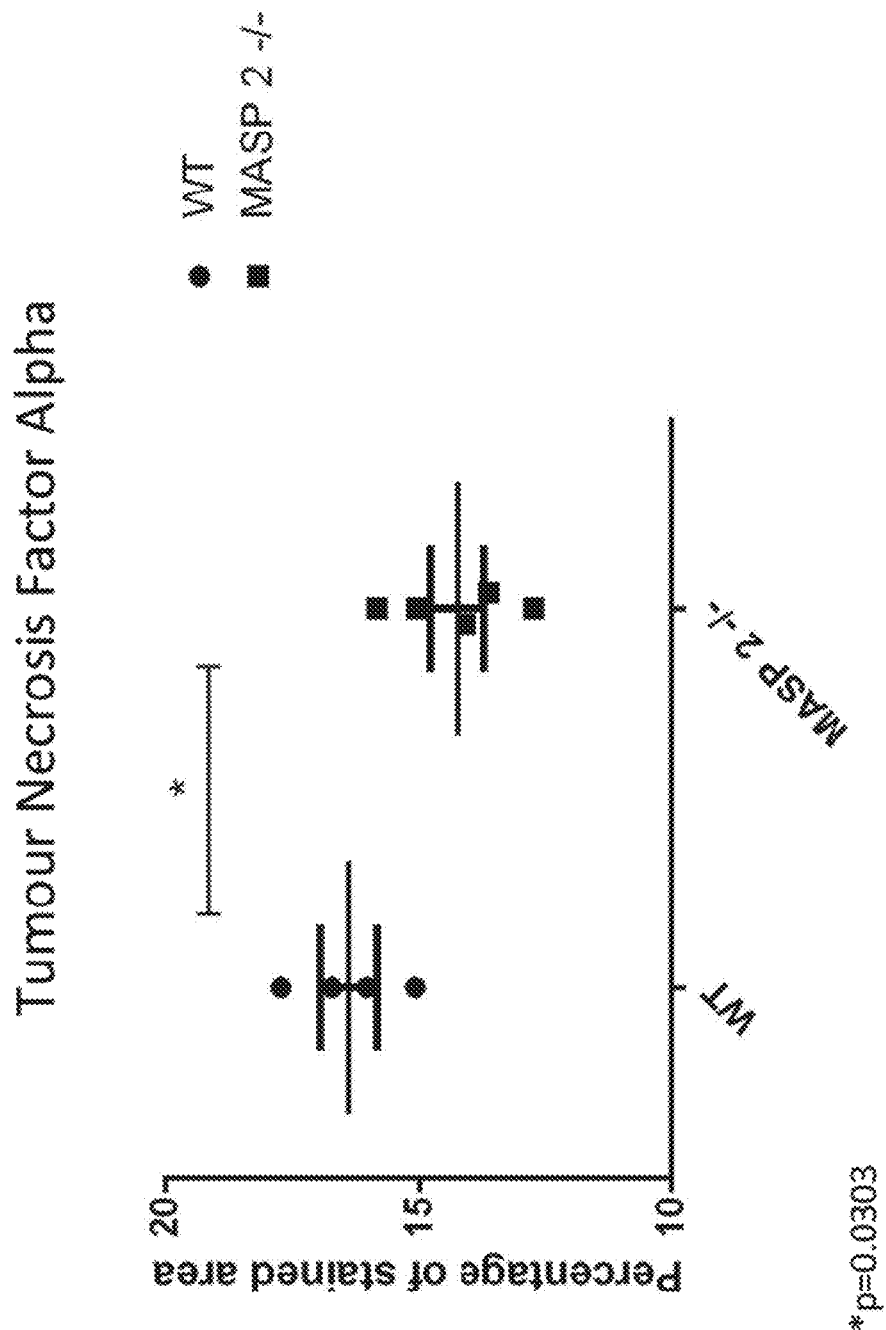
FIG. 29 graphically illustrates the results of computer-based image analysis of stained tissue sections with anti-TNFα antibody (measured as % TNFα antibody-stained area) in wild-type mice treated with BSA (n=4) and MASP-2−/− mice treated with BSA (n=5), as described in Example 16.

FIG. 29 graphically illustrates the results of computer-based image analysis of stained tissue sections with anti-TNFα antibody (measured as % TNFα antibody-stained area) in wild-type mice treated with BSA (n=4) and MASP-2−/− mice treated with BSA (n=5). As shown in FIG. 29, a significant increase in the staining of TNFα was observed in the wild-type BSA treated (overload) group as compared to the MASP-2−/− BSA treated (overload) group (p=0.0303).

Figure 30:
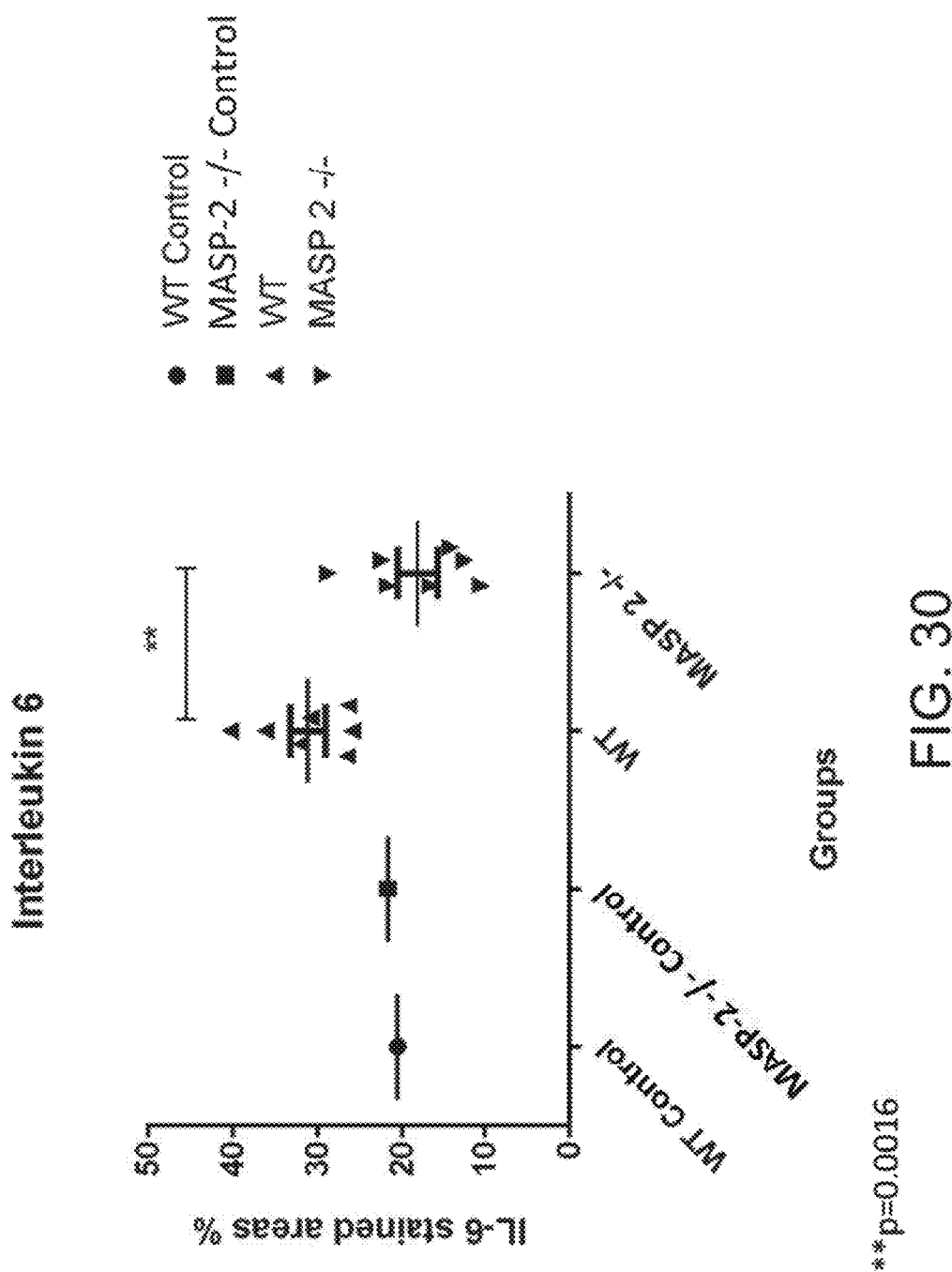
FIG. 30 graphically illustrates the results of computer-based image analysis of stained tissue sections with anti-IL-6 antibody (measured as % IL-6 antibody-stained area) in wild-type control mice, MASP-2−/− control mice, wild-type mice treated with BSA (n=7) and MASP-2−/− mice treated with BSA (n=7), as described in Example 16.

FIG. 30 graphically illustrates the results of computer-based image analysis of stained tissue sections with anti-IL-6 antibody (measured as % IL-6 antibody-stained area) in wild-type control mice, MASP-2−/− control mice, wild-type mice treated with BSA (n=7) and MASP-2−/− mice treated with BSA (n=7). As shown in FIG. 30, a highly significant increase in the staining of IL-6 was observed in the wild-type BSA treated group as compared to the MASP-2−/− BSA treated group (p=0.0016).

Assessment of Apoptosis

Apoptosis was assessed in the tissue sections by staining with terminal deoxynucleotidyl transferase dUTP nick end labeling (TUNEL) and the frequency of TUNEL stained apoptotic cells were counted in serially selected 20 high power fields (HPFs) from the cortex.

Figure 31:
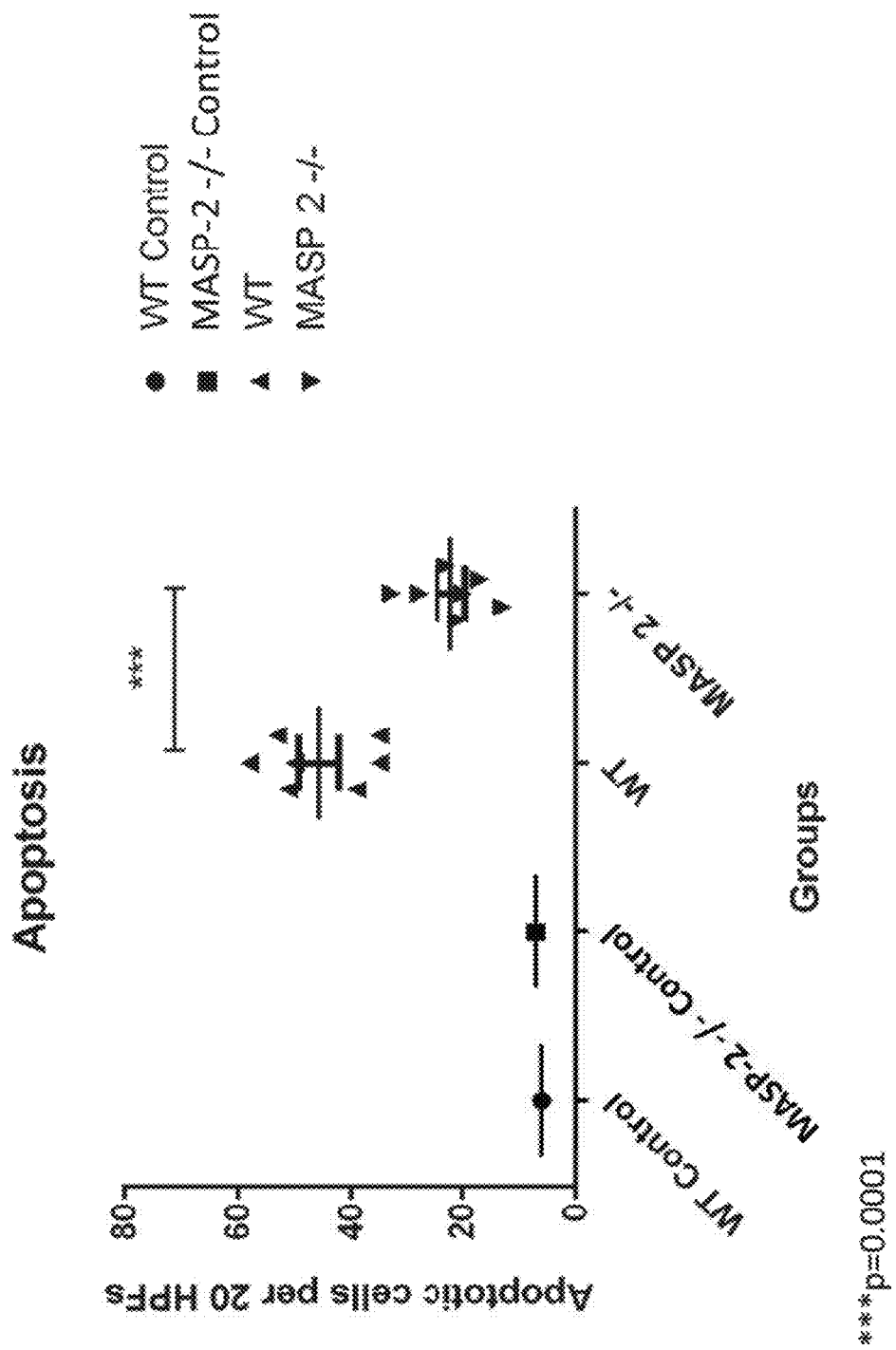
FIG. 31 graphically illustrates the frequency of TUNEL apoptotic cells counted in serially selected 20 high power fields (HPFs) from tissue sections from the renal cortex in wild-type control mice (n=1), MASP-2−/− control mice (n=1), wild-type mice treated with BSA (n=6) and MASP-2−/− mice treated with BSA (n=7), as described in Example 16.

FIG. 31 graphically illustrates the frequency of TUNEL apoptotic cells counted in serially selected 20 high power fields (HPFs) from tissue sections from the renal cortex in wild-type control mice (n=1), MASP-2−/− control mice (n=1), wild-type mice treated with BSA (n=6) and MASP-2−/− mice treated with BSA (n=7). As shown in FIG. 31, a significantly higher rate of apoptosis in the cortex was observed in kidneys obtained from wild-type mice treated with BSA as compared to kidneys obtained from the MASP-2−/− mice treated with BSA (p=0.0001).

Overall Summary of Results and Conclusions

The results in this Example demonstrate that MASP-2−/− mice have reduced renal injury in a protein overload model. Therefore, MASP-2 inhibitory agents, such as MASP-2 inhibitory antibodies would be expected to inhibit or prevent the detrimental cycle of inflammation and proteinuria and improve outcomes in chronic kidney disease.

Example 17

This Example describes analysis of a monoclonal MASP-2 inhibitory antibody for efficacy in reducing and/or preventing renal inflammation and tubulointerstitial injury in a mouse protein overload proteinurea model in wild-type mice.

Background/Rationale:

As described in Example 16, in a protein overload model of proteinuria it was determined that MASP-2−/− mice exhibited significantly better outcomes (e.g., less tubulointerstitial injury and less renal inflammation) than wild-type mice, implicating a pathogenic role for the lectin pathway in proteinuric kidney disease.

As described in Example 13, a monoclonal MASP-2 inhibitory antibody (OMS646-SGMI-2) was generated that specifically blocks the function of the human lectin pathway and has also been shown to block the lectin pathway in mice. In this example, the MASP-2 inhibitory antibody OMS646-SGMI-2 was analyzed in a mouse protein overload protein-urea model for efficacy in reducing and/or preventing renal inflammation and tubulointerstitial injury in wild-type mice.

Methods

This study evaluated the effect of MASP-2 inhibitory antibody (10 mg/kg OMS646-SGMI-2), compared to a human IgG4 isotype control antibody, ET904 (10 mg/kg), and a saline control.

Similar to the study described in Example 16, this study employed protein overload to induce proteinuric kidney disease (Ishola et al., *European Renal Association* 21:591-597, 2006). Proteinuria was induced in unilaterally nephrectomized Balb/c mice by daily i.p. injections with escalating doses (2 g/kg to 15 g/kg) of low endotoxin bovine serum albumin (BSA) for a total of 15 days, as described in Example 16.

Antibody treatments were administered by biweekly i.p. injection starting 7 days before proteinuria induction and continued throughout the study. This dosing scheme was selected based on previous PK/PD and pharmacoclogy studies demonstrating sustained lectin pathway suppression (data not shown). Mice were sacrificed on day 15 and kidneys were harvested and processed for H&E and immunostaining. Stained tissue sections from the renal cortex were analyzed by digital image capture followed by quantification using automated image analysis software.

Immunohistochemistry staining and apoptosis assessment were carried out as described in Example 16.

Results

Assessment of Proteinuria

To confirm the presence of proteinuria in the mice, the total excreted proteins in urine was measured in urine samples collected over a 24 hour period at day 15 (the end of the experiment). It was determined that the urine samples showed a mean of almost a six-fold increase in total protein levels in the groups that were treated with BSA as compared to the control groups not treated with BSA (data not shown), confirming the presence of proteinuria in the mice treated with BSA. No significant difference was observed in the protein levels between the BSA-treated groups.

Assessment of Histological Changes

Figure 32:
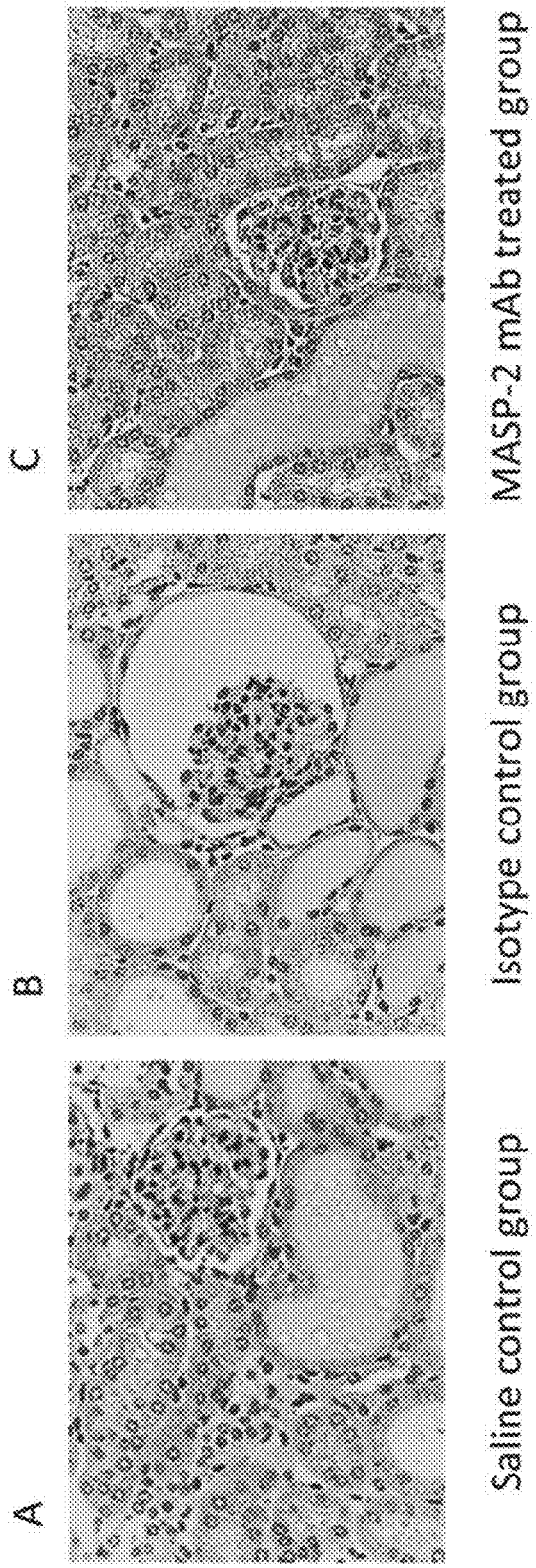
FIG. 32 shows representative H&E stained tissue sections from the following groups of mice at day 15 after treatment with BSA: (panel A) wild-type control mice treated with saline, (panel B) isotype antibody treated control mice and (panel C) wild-type mice treated with a MASP-2 inhibitory antibody, as described in Example 17.

FIG. 32 shows representative H&E stained tissue sections from the following groups of mice at day 15 after treatment with BSA: (panel A) wild-type control mice treated with saline; (panel B) isotype antibody treated control mice; and (panel C) wild-type mice treated with MASP-2 inhibitory antibody.

As shown in FIG. 32, there is a much higher degree of tissue preservation in the MASP-2 inhibitory antibody-treated group (panel C) as compared to the wild-type group treated with saline (panel A) or isotype control (panel B) at the same level of protein overload challenge.

Assessment of Apoptosis

Figure 33:
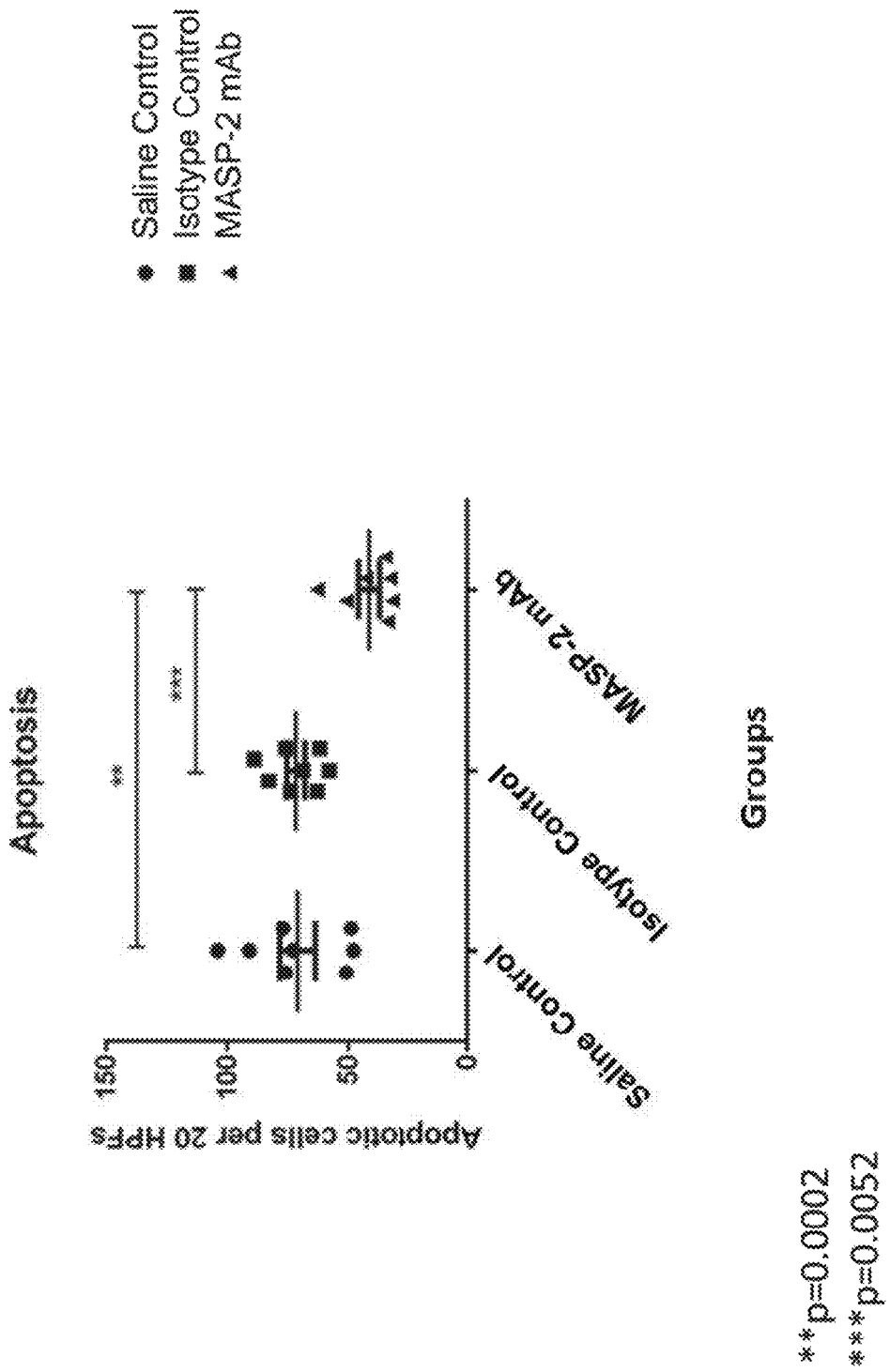
FIG. 33 graphically illustrates the frequency of TUNEL apoptotic cells counted in serially selected 20 high power fields (HPFs) from tissue sections from the renal cortex in wild-type mice treated with saline control and BSA (n=8), wild-type mice treated with the isotype control antibody and BSA (n=8) and wild-type mice treated with a MASP-2 inhibitory antibody and BSA (n=7), as described in Example 17.

Apoptosis was assessed in the tissue sections by staining with terminal deoxynucleotidyl transferase dUTP nick end labeling (TUNEL) and the frequency of TUNEL stained apoptotic cells were counted in serially selected 20 high power fields (HPFs) from the cortex. FIG. 33 graphically illustrates the frequency of TUNEL apoptotic cells counted in serially selected 20 high power fields (HPFs) from tissue sections from the renal cortex in wild-type mice treated with saline control and BSA (n=8), wild-type mice treated with the isotype control antibody and BSA (n=8) and wild-type mice treated with the MASP-2 inhibitory antibody and BSA (n=7). As shown in FIG. 33, a highly significantly decrease in the rate of apoptosis in the cortex was observed in kidneys obtained from the MASP-2 inhibitory antibody treated group as compared to the saline and isotype control treated group (p=0.0002 for saline control v MASP-2 inhibitory antibody; p=0.0052 for isotype control v. MASP-2 inhibitory antibody).

Assessment of Cytokine Infiltration

Interleukin 6 (IL-6), Transforming Growth Factor Beta (TGFβ) and Tumor Necrosis Factor Alpha (TNFα), which are pro-inflammatory cytokines known to be up-regulated in proximal tubules of wild-type mice in a model of proteinuria, were assessed in the kidney tissue sections obtained in this study.

Figure 34:
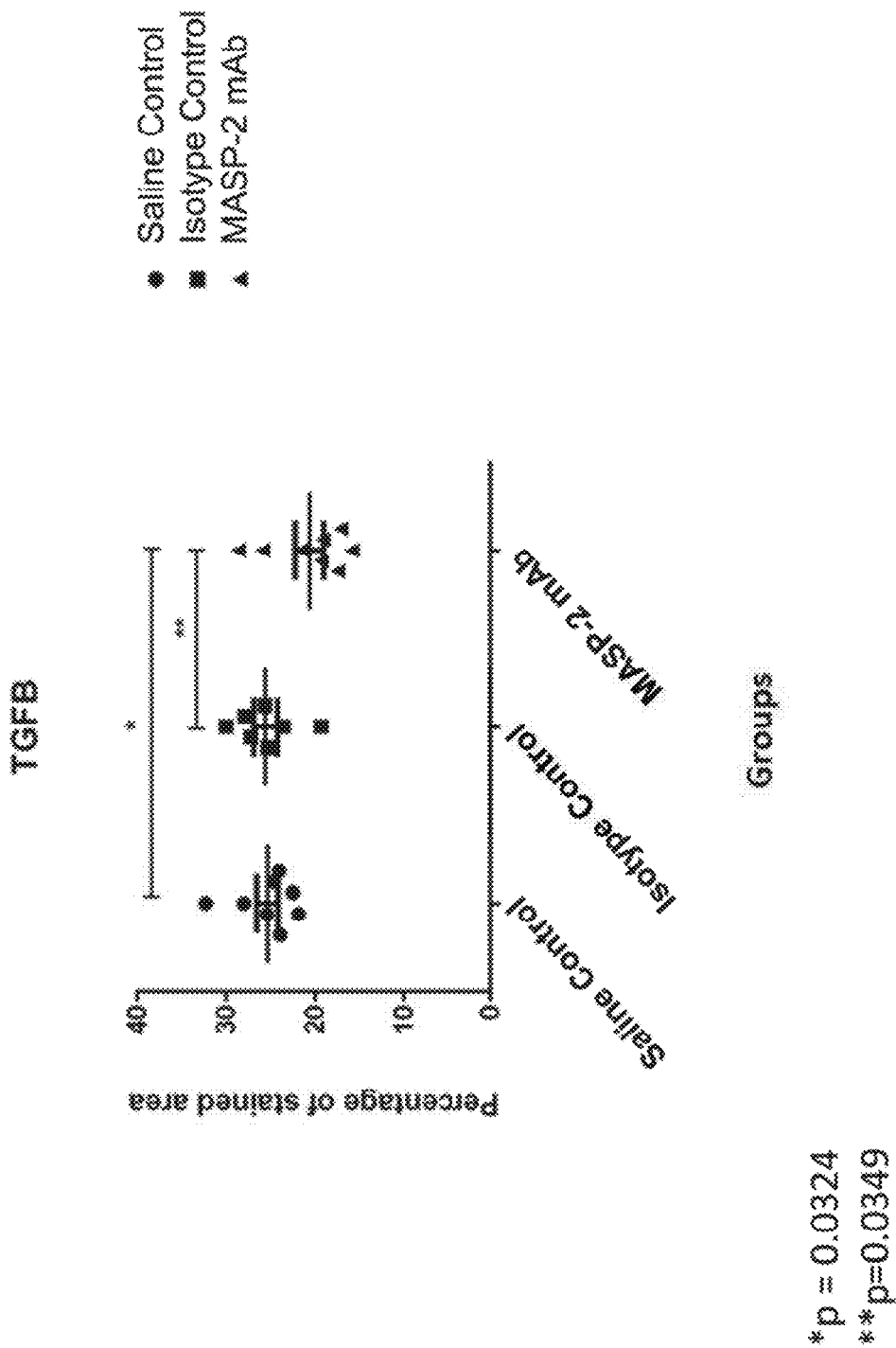
FIG. 34 graphically illustrates the results of computer-based image analysis of stained tissue sections with anti-TGFβ antibody (measured as % TGFβ antibody-stained area) in wild-type mice treated with BSA and saline (n=8), wild-type mice treated with BSA and isotype control antibody (n=7) and wild-type mice treated with BSA and MASP-2 inhibitory antibody (n=8), as described in Example 17.

FIG. 34 graphically illustrates the results of computer-based image analysis of stained tissue sections with anti-TGFβ antibody (measured as % TGFβ antibody-stained area) in wild-type mice treated with BSA and saline (n=8), wild-type mice treated with BSA and isotype control antibody (n=7) and wild-type mice treated with BSA and MASP-2 inhibitory antibody (n=8). As shown in FIG. 34, quantification of the TGFβ stained areas showed a significant reduction in the levels of TGFβ in the MASP-2 inhibitory antibody-treated mice as compared to the saline and isotype control antibody-treated control groups (p values=0.0324 and 0.0349, respectively).

Figure 35:
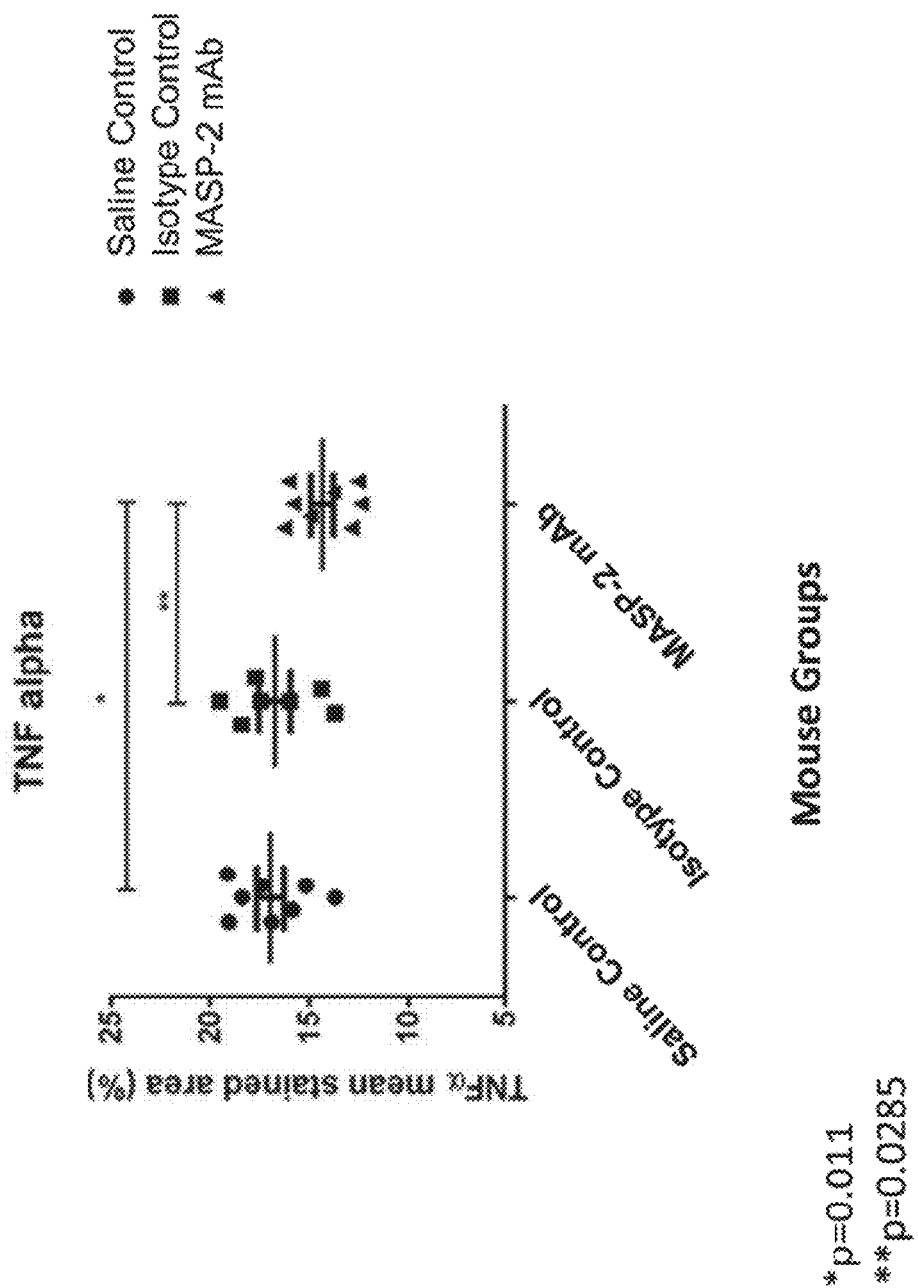
FIG. 35 graphically illustrates the results of computer-based image analysis of stained tissue sections with anti-TNFα antibody (measured as % TNFα antibody-stained area) in wild-type mice treated with BSA and saline (n=8), BSA and isotype control antibody (n=7) and wild-type mice treated with BSA and MASP-2 inhibitory antibody (n=8), as described in Example 17.

FIG. 35 graphically illustrates the results of computer-based image analysis of stained tissue sections with anti-TNFα antibody (measured as % TNFα antibody-stained area) in wild-type mice treated with BSA and saline (n=8), BSA and isotype control antibody (n=7) and wild-type mice treated with BSA and MASP-2 inhibitory antibody (n=8). As shown in FIG. 35, analysis of stained sections showed a significant reduction in the level of TNFα in the MASP-2 inhibitory antibody-treated group as compared to the saline control group (p=0.011) as well as the isotype control group (p=0.0285).

Figure 36:
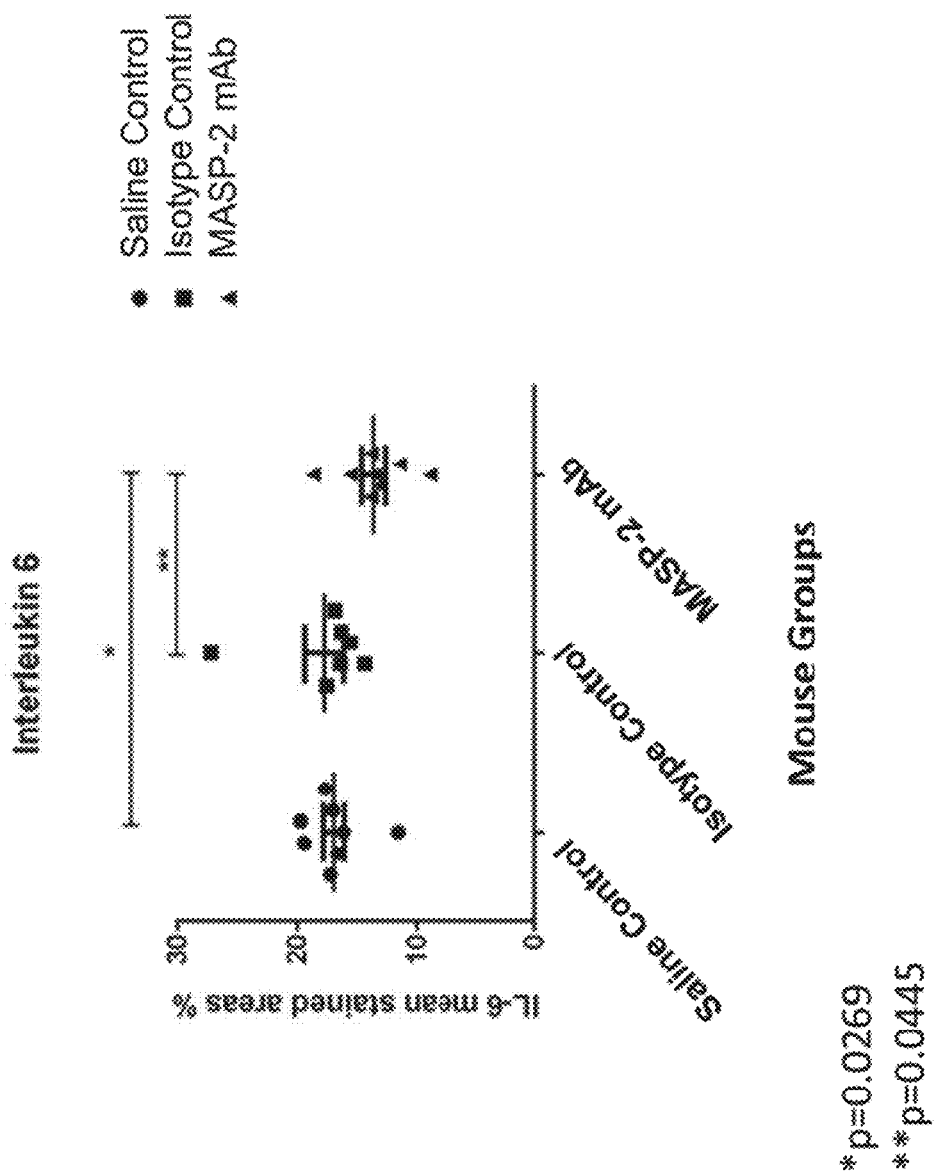
FIG. 36 graphically illustrates the results of computer-based image analysis of stained tissue sections with anti-IL-6 antibody (measured as % IL-6 antibody-stained area) in in wild-type mice treated with BSA and saline (n=8), BSA and isotype control antibody (n=7) and wild-type mice treated with BSA and MASP-2 inhibitory antibody (n=8), as described in Example 17.

FIG. 36 graphically illustrates the results of computer-based image analysis of stained tissue sections with anti-IL-6 antibody (measured as % IL-6 antibody-stained area) in in wild-type mice treated with BSA and saline (n=8), BSA and isotype control antibody (n=7) and wild-type mice treated with BSA and MASP-2 inhibitory antibody (n=8). As shown in FIG. 36, analysis of stained sections showed a significant reduction in the level of IL-6 in the MASP-2 inhibitory antibody-treated group as compared to the saline control group (p=0.0269) as well as to the isotype control group (p=0.0445).

Overall Summary of Results and Conclusions

The results in this Example demonstrate that the use of a MASP-2 inhibitory antibody provides protection against renal injury in a protein overload model, which is consistent with the results described in Example 16 demonstrating that MASP-2–/– mice have reduced renal injury in the proteinuria model.

Example 18

This Example provides results generated using an Adriamycin-induced nephrology model of renal fibrosis, inflammation and tubulointerstitial injury in MASP-2–/– and wild-type mice to evaluate the role of the lectin pathway in Adriamycin-induced nephropathy.

Background/Rationale:

Adriamycin is an anthracycline antitumor antibiotic used in the treatment of a wide range of cancers, including hematological malignancies, soft tissue sarcomas and many types of carcinomas. Adriamycin-induced nephropathy is well established rodent model of chronic kidney disease that has enabled a better understanding of the progression of chronic proteinuria (Lee and Harris, *Nephrology,* 16:30-38, 2011). The type of structural and functional injury in Adriamycin-induced nephropathy is very similar to that of chronic proteinuric renal disease in humans (Pippin et al., *American Journal of Renal Physiology* 296:F213-29, 2009).

Adriamycin-induced nephropathy is characterized by an injury to the podocytes followed by glomerulosclerosis, tubulointerstitial inflammation and fibrosis. It has been shown in many studies that Adriamycin-induced nephropathy is modulated by both immune and non-immune derived mechanisms (Lee and Harris, *Nephrology,* 16:30-38, 2011). Adriamycin-induced nephropathy has several strengths as a model of kidney disease. First, it is a highly reproducible and predicable model of renal injury. This is because it is characterized by the induction of renal injury within a few days of drug administration, which allows for ease of experimental design as the timing of injury is consistent. It is also a model in which the degree of tissue injury is severe while associated with acceptable mortality (<5%) and morbidity (weight loss). Therefore, due to the severity and timing of renal injury in Adriamycin-induced nephropathy, it is a model suitable for testing interventions that protect against renal injury.

As described in Examples 16 and 17, in a protein overload model of proteinuria it was determined that MASP-2–/– mice and mice treated with a MASP-2 inhibitory antibody exhibited significantly better outcomes (e.g., less tubulointerstitial injury, and less renal inflammation) than wild-type mice, implicating a pathogenic role for the lectin pathway in proteinuric kidney disease.

In this example, MASP-2–/– mice were analyzed in comparison with wild-type mice in the Adriamycin-induced nephrology model (AN) to determine if MASP-2 deficiency reduces and/or prevents renal inflammation and tubulointerstitial injury induced by Adriamycin.

Methods

1. Dosage and Time Point Optimization

An initial experiment was carried out to determine the dose of Adriamycin and time point at which BALB/c mice develop a level of renal inflammation suitable for testing therapeutic intervention.

Three groups of wild-type BALB/c mice (n=8) were injected with a single dose of Adriamycin (10.5 mg/kg) administered IV. Mice were culled at three time points: one week, two weeks and four weeks after Adriamycin administration. Control mice were injected with saline only.

Results: All mice in the three groups showed signs of glomerulosclerosis and proteinuria, as determined by H&E staining, with incrementally increasing degree of tissue inflammation as measured by macrophage infiltration in the kidney (data not shown). The degree of tissue injury was mild in the one week group, moderate in the two week group and severe in the four week group (data not shown). The two week time point was selected for the rest of the study.

2. Analysis of Adriamycin-Induced Nephrology in Wild-Type and MASP-2–/– Mice

In order to elucidate the role of the lectin pathway of complement in the Adriamycin-induced nephrology, a group of MASP-2–/– mice (BALB/c) were compared to wild-type mice (BALB/c) at the same dose of Adriamycin. The MASP-2–/– mice were backcrossed with BALB/c mice for 10 generations.

Wild-type (n=8) and MASP-2−/− (n=8) were injected IV with Adriamycin (10.5 mg/kg) and three mice of each strain were give saline only as a control. All mice were culled two weeks after the treatment and tissues were collected. The degree of histopatholigical injury was assessed by H&E staining.

Results

Figure 37:
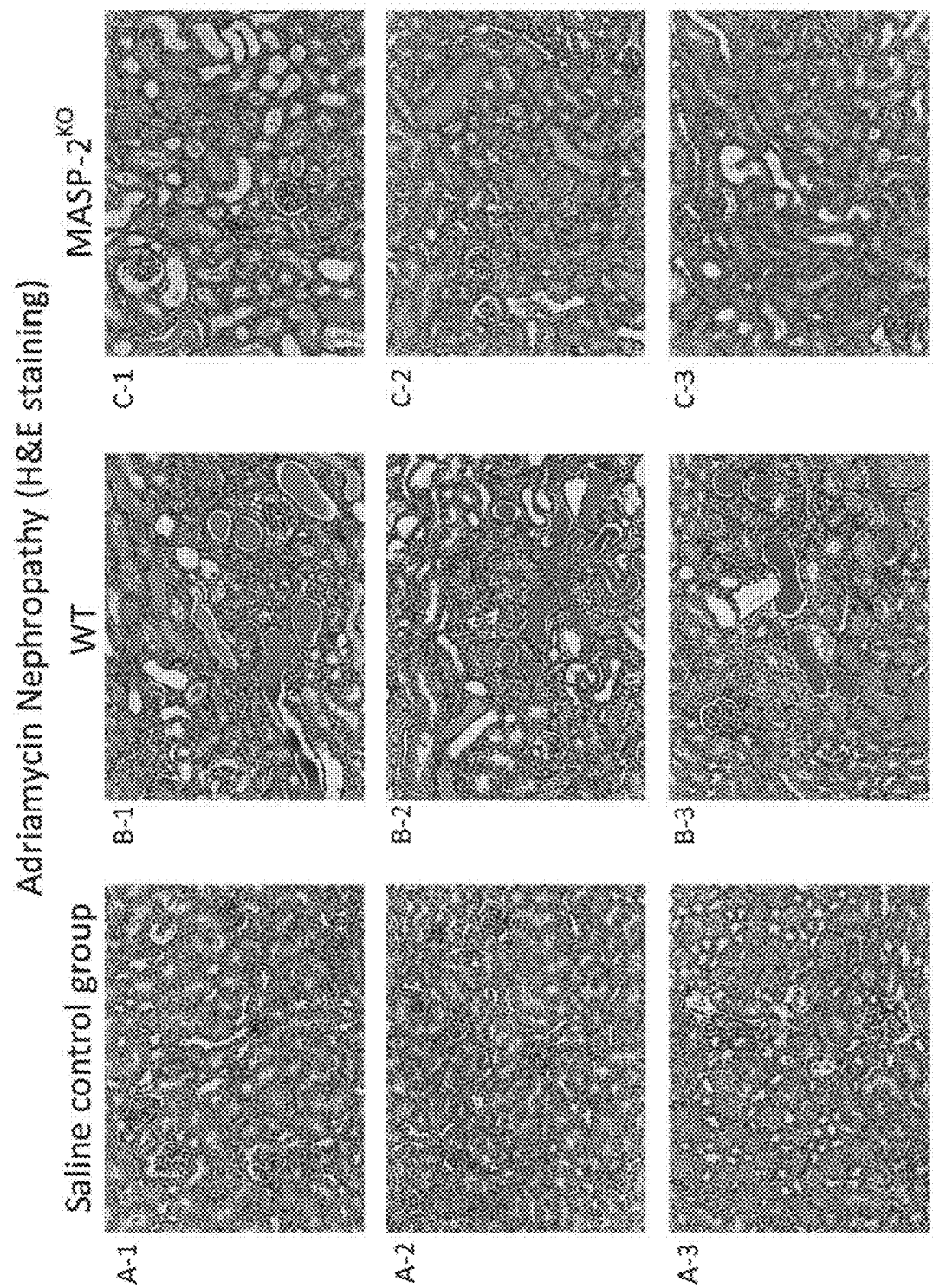
FIG. 37 shows representative H&E stained tissue sections from the following groups of mice at day 14 after treatment with Adriamycin or saline only (control): (panels A-1, A-2, A-3) wild-type control mice treated with only saline; (panels B-1, B-2, B-3) wild-type mice treated with Adriamycin; and (panels C-1, C-2, C-3) MASP-2−/− mice treated with Adriamycin, as described in Example 18.

FIG. 37 shows representative H&E stained tissue sections from the following groups of mice at day 14 after treatment with Adriamycin or saline only (control): (panels A-1, A-2, A-3) wild-type control mice treated with only saline; (panels B-1, B-2, B-3) wild-type mice treated with Adriamycin; and (panels C-1, C-2, C-3) MASP-2−/− mice treated with Adriamycin. Each photo (e.g., panel A-1, A-2, A-3) represents a different mouse.

As shown in FIG. 37, there is a much higher degree of tissue preservation in the MASP-2−/− group treated with Adriamycin as compared to the wild-type group treated with the same dose of Adriamycin.

Figure 38:
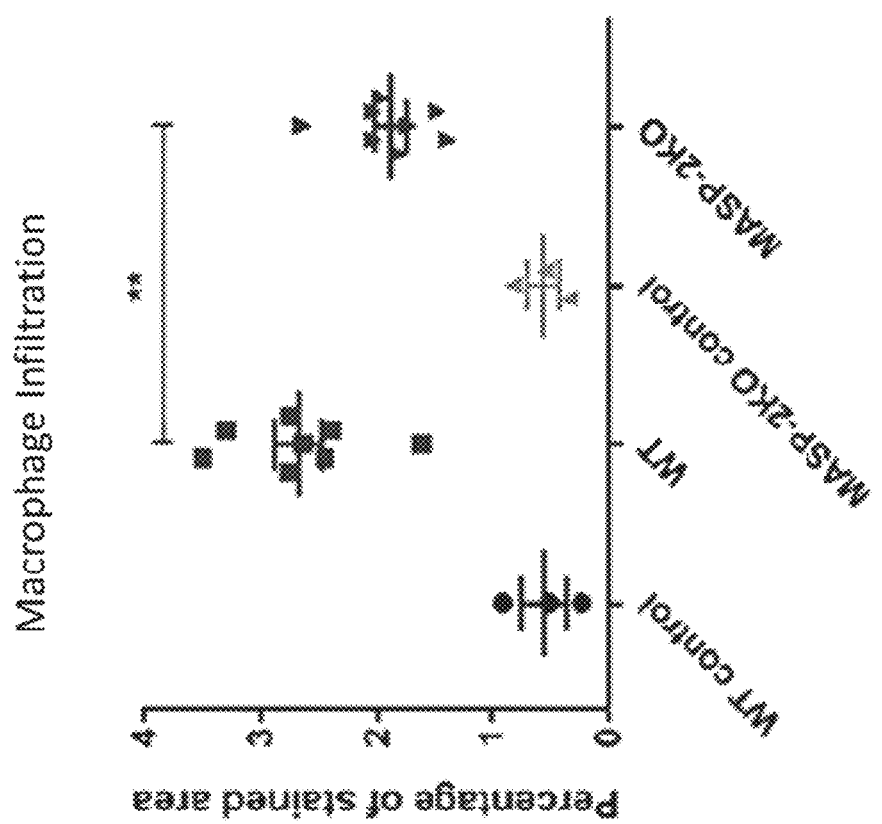
FIG. 38 graphically illustrates the results of computer-based image analysis of kidney tissue sections stained with macrophage-specific antibody F4/80 showing the macrophage mean stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin, wherein **p=0.007, as described in Example 18.

FIG. 38 graphically illustrates the results of computer-based image analysis of kidney tissue sections stained with macrophage-specific antibody F4/80 showing the macrophage mean stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin. As shown in FIG. 38, MASP-2−/− mice treated with Adriamycin have reduced macrophage infiltration (**$p=0.007$) compared to wild-type mice treated with Adriamycin.

Figure 39:
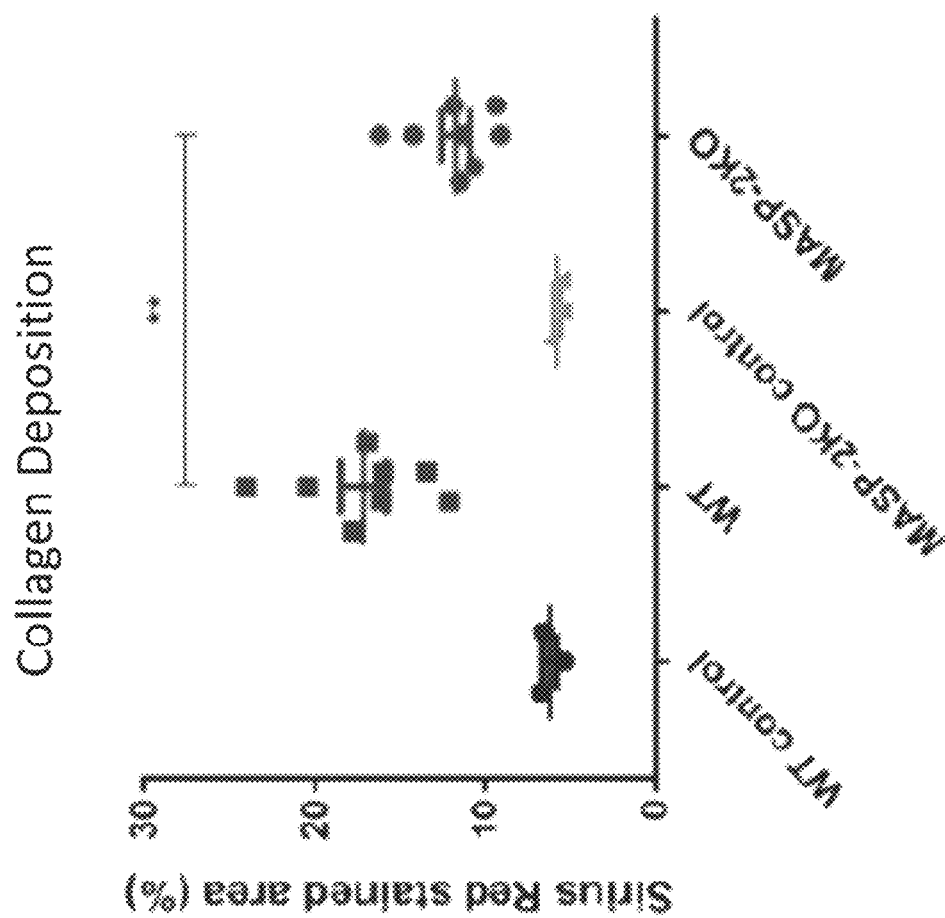
FIG. 39 graphically illustrates the results of computer-based image analysis of kidney tissue sections stained with Sirius Red, showing the collagen deposition stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin, wherein p=0.005, as described in Example 18.

FIG. 39 graphically illustrates the results of computer-based image analysis of kidney tissue sections stained with Sirius Red, showing the collagen deposition stained area (%) from the following groups of mice at day 14 after treatment with Adriamycin or saline only (wild-type control): wild-type control mice treated with only saline; wild-type mice treated with Adriamycin; MASP-2−/− mice treated with saline only, and MASP-2−/− mice treated with Adriamycin. As shown in FIG. 39, MASP-2−/− mice treated with Adriamycin have reduced collagen deposition (**$p=0.005$) compared to wild-type mice treated with Adriamycin.

Overall Summary and Conclusions

The amelioration of renal tubulointerstitial inflammation is a key target for the treatment of kidney disease. The results presented herein indicate that the lectin pathway of complement activation contributes significantly to the development of renal tubulointerstitial inflammation. As further demonstrated herein, a MASP-2 inhibitory agent, such as a MASP-2 inhibitory antibody, may be used as a novel therapeutic approach in the treatment of proteinuric nephropathy, Adriamycin nephropathy and amelioration of renal tubulointerstitial inflammation.

Example 19

This Example describes the initial results of an ongoing Phase 2 clinical trial to evaluate the safety and clinical efficacy of a fully human monoclonal MASP-2 inhibitory antibody in adults with steroid-dependent immunoglobulin A nephropathy (IgAN) and in adults with steroid-dependent membranous nephropathy (MN).

Background

Chronic kidney diseases affect more than 20 million people in the United States (Drawz P. et al., *Ann Intern Med* 162(11); ITC1-16, 2015). Glomerulonephropathies (GNs), including IgAN and MN are kidney diseases in which the glomeruli are damaged and frequently lead to end-stage renal disease and dialysis. Several types of primary GNs exist, the most common being IgAN. Many of these patients have persistent renal inflammation and progressive deterioration. Often these patients are treated with corticosteroids or immunosuppressive agents, which have many serious long-term adverse consequences. Many patients continue to deteriorate even on these treatments. No treatments are approved for the treatment of IgAN or MN.

IgA Nephropathy

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., *N Engl J Med* 368(25):2402-14, 2013). Clinical markers such as impaired kidney function, sustained hypertension, and heavy proteinuria (over 1 g per day) are associated with poor prognosis (Goto M et al., *Nephrol Dial Transplant* 24(10):3068-74, 2009; Berthoux F. et al., *J Am Soc Nephrol* 22(4):752-61, 2011). Proteinuria is the strongest prognostic factor independent of other risk factors in multiple large observational studies and prospective trials (Coppo R. et al., *J Nephrol* 18(5):503-12, 2005; Reich H. N., et al., *J Am Soc Nephrol* 18(12):3177-83, 2007). It is estimated that 15-20% of patients reach ESRD within 10 years of disease onset if left untreated (D'Amico G., *Am J Kidney Dis* 36(2):227-37, 2000).

The diagnostic hallmark of IgAN is the predominance of IgA deposits, alone or with IgG, IgM, or both, in the glomerular mesangium. In IgAN, renal biopsies reveal glomerular deposition of mannan-binding lectin (MBL), a key recognition molecule for activation of MASP-2, the effector enzyme of the complement system's lectin pathway. Glomerular MBL deposits, usually co-localized with IgA and indicating complement activation, and high levels of urinary MBL are associated with an unfavorable prognosis in IgAN, with these patients demonstrating more severe histological changes and mesangial proliferation than patients without MBL deposition or high levels of urinary MBL (Matsuda M. et al., *Nephron* 80(4):408-13, 1998; Liu L L et al., *Clin Exp Immunol* 169(2):148-155, 2012; Roos A. et al., *J Am Soc Nephrol* 17(6):1724-34, 2006; Liu L L et al., *Clin Exp Immunol* 174(1):152-60, 2013). Remission rates also are substantially lower for patients with MBL deposition (Liu L L et al., *Clin Exp Immunol* 174(1):152-60, 2013).

Current therapy for IgAN includes blood pressure control and, frequently, corticosteroids and/or other immunosuppressive agents, such as cyclophosphamide, azathioprine, or mycofenolate mofetil, for severe disease (e.g., crescentic IgAN). The Kidney Disease Improving Global Outcomes (KDIGO) Guidelines for Glomerulonephritis (*Int. Soc of Nephrol* 2(2):139-274, 2012) recommend that corticosteroids should be administered to patients with proteinuria of greater than or equal to 1 g/day, with a usual treatment duration of 6 months. However, even with aggressive immunosuppressive treatment, which is associated with serious long-term sequelae, some patients have progressive deterioration of renal function. There is no approved treatment for IgAN, and even with the use of angiotensin-converting enzyme (ACE) inhibitors or angiotensin receptor blockers (ARBs) to control blood pressure, increased proteinuria persists in some patients. None of these treatments have been shown to stop or even slow the progression of IgAN in patients who are at risk for rapid progression of the disease.

Membranous Nephropathy

The annual incidence of membranous nephropathy (MN) is approximately 10-12 per 1,000,000. Patients with MN can have a variable clinical course, but approximately 25% will develop end-stage renal disease.

Membranous nephropathy is an immune-mediated glomerular disease and one of the most common causes of the nephrotic syndrome in adults. The disease is characterized by the formation of immune deposits, primarily IgG4, on the outer aspect of the glomerular basement membrane, which contain podocyte antigens and antibodies specific to those antigens, resulting in complement activation. Initial manifestations of MN are related to the nephrotic syndrome: proteinuria, hypoalbuminemia, hyperlipidemia, and edema.

Although MN may spontaneously remit without treatment, as many as one third of patients demonstrate progressive loss of kidney function and progress to ESRD at a median of 5 years after diagnosis. Often, corticosteroids are used to treat MN and there is a need to develop alternative therapies. Additionally, patients determined to be at moderate risk for progression, based on severity of proteinuria, are treated with prednisone in conjunction with cyclophosphamide or a calcinuerin inhibitor, and these two treatments together are often associated with severe systemic adverse effects.

Methods

Two Phase 1 clinical trials carried out in healthy volunteers have demonstrated that both intravenous and subcutaneous dosing of a MASP-2 inhibitory antibody, OMS646, resulted in sustained lectin pathway inhibition.

This Example describes interim results from an ongoing Phase 2, uncontrolled, multicenter study of a MASP-2 inhibitory antibody, OMS646, in subjects with IgAN and MN. Inclusion criteria require that all patients in this study, regardless of renal disease subtype, have been maintained on a stable dose of corticosteroids for at least 12 weeks prior to study enrollment (i.e., the patients are steroid-dependent). The study is a single-arm pilot study with 12 weeks of treatment and a 6-week follow-up period.

Approximately four subjects are planned to be enrolled per disease. The study is designed to evaluate whether OMS646 may improve renal function (e.g., improve proteinuria) and decrease corticosteroid needs in subjects with IgAN and MN. To date, 2 patients with IgA nephropathy and 2 patients with membranous nephropathy have completed treatment in the study.

At study entry each subject must have high levels of protein in the urine despite ongoing treatment with a stable corticosteroid dose. These criteria select for patients who are unlikely to spontaneously improve during the study period.

The subjects were age ≥18 at screening and were only included in the study if they had a diagnosis of one of the following: IgAN diagnosed on kidney biopsy or primary MN diagnosed on kidney biopsy. The enrolled patients also had to meet all of the following inclusion criteria:

(1) have average urine albumin/creatinine ratio >0.6 from three samples collected consecutively and daily prior to each of 2 visits during the screening period;
(2) have been on ≥10 mg of prednisone or equivalent dose for at least 12 weeks prior to screening visit 1;
(3) if on immunosuppressive treatment (e.g., cyclophosphamide, mycophenolate mofetil), have been on a stable dose for at least 2 months prior to Screening Visit 1 with no expected change in the dose for the study duration;
(4) have an estimated glomerular filtration rate (eGFR)≥30 mL/min/1.73 m² calculated by the MDRD equation[1];
(5) are on a physician-directed, stable, optimized treatment with angiotensin converting enzyme inhibitors (ACEI) and/or angiotensin receptor blockers (ARB) and have a systolic blood pressure of <150 mmHg and a diastolic blood pressure of <90 mmHg at rest;
(6) have not used belimumab, eculizumab or rituzimab within 6 months of screening visit 1; and
(7) do not have a history of renal transplant.

[1]MDRD Equation: eGFR (mL/min/1.73 m²)=175×(SCr)$^{-1.154}$×(Age)$^{-0.203}$×(0.742 if female)×(1.212 if African American). Note: SCr=Serum Creatinine measurement should be mg/dL.

The monoclonal antibody used in this study, OMS646, is a fully human IgG4 monoclonal antibody that binds to and inhibits human MASP-2. MASP-2 is the effector enzyme of the lectin pathway. As demonstrated in Example 12, OMS646 avidly binds to recombinant MASP-2 (apparent equilibrium dissociation constant in the range of 100 µM) and exhibits greater than 5,000-fold selectivity over the homologous proteins C1s, C1r, and MASP-1. In functional assays, OMS646 inhibits the human lectin pathway with nanomolar potency (concentration leading to 50% inhibition [IC$_{50}$] of approximately 3 nM) but has no significant effect on the classical pathway. OMS646 administered either by intravenous (IV) or subcutaneous (SC) injection to mice, non-human primates, and humans resulted in high plasma concentrations that were associated with suppression of lectin pathway activation in an ex vivo assay.

In this study, the OMS646 drug substance was provided at a concentration of 100 mg/mL, which was further diluted for IV administration. The appropriate calculated volume of OMS646 100 mg/mL injection solution was withdrawn from the vial using a syringe for dose preparation. The infusion bag was administered within four hours of preparation.

The study consists of screening (28 days), treatment (12 weeks) and follow-up (6 weeks) periods, as shown in the Study Design Schematic shown in FIG. 54.

Within the screening period and before the first OMS646 dose, consented subjects provided three urine samples (collected once daily) on each of two three-consecutive-day periods to establish baseline values of the urine albumin-to-creatinine ratio. Following the screening period, eligible subjects received OMS646 4 mg/kg IV once weekly for 12 weeks (treatment period). There was a 6-week follow-up period after the last dose of OMS646.

During the initial 4 weeks of treatment with OMS646, subjects were maintained on their stable pre-study dose of corticosteroids. At the end of the initial 4-weeks of the 12-week treatment period, subjects underwent corticosteroid taper (i.e., the corticosteroid dose was reduced), if tolerated, over 4 weeks, followed by 4 weeks during which the resultant corticosteroid dose was maintained. The target was a taper to ≤6 mg prednisone (or equivalent dose) daily. Over this period, the taper was discontinued in subjects who had deterioration of renal function, as determined by the investigator. Subjects were treated with OMS646 through the corticosteroid taper and through the full 12 weeks of treatment. The patients were then followed for an additional 6 weeks after their last treatment. The taper of corticosteroids and OMS646 treatment permitted assessment of whether OMS646 allowed for a decrease in the dose of corticosteroid required to maintain stable renal function.

The key efficacy measures in this study are the change in urine albumin-to-creatinine ratio (uACR) and 24-hour protein levels from baseline to 12 weeks. Measurement of urinary protein or albumin is routinely used to assess kidney involvement and persistent high levels of urinary protein correlates with renal disease progression. The uACR is used clinically to assess proteinuria.

Efficacy Analyses

The analysis value for uACR is defined as the average of all the values obtained for a time point. The planned number of uACRs is three at each scheduled time point. The baseline value of the uACR is defined as the average of the analysis values at the two screening visits.

Results

Figure 40:
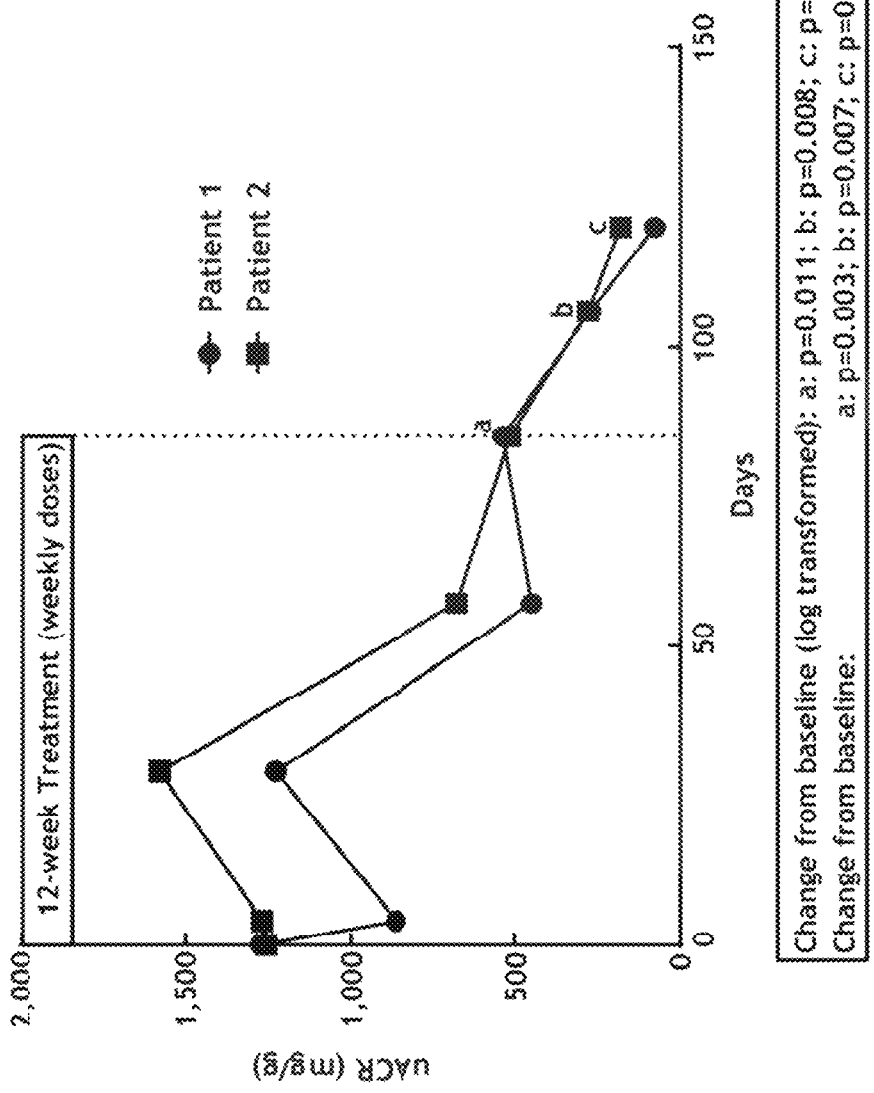
FIG. 40** graphically illustrates the urine albumin/creatinine ratio (uACR) in two IgA patients during the course of a twelve-week study with weekly treatment with a MASP-2 inhibitory antibody (OMS646), as described in Example 19.

FIG. 40 graphically illustrates the uACRin two IgAN patients during the course of a twelve week study with weekly treatment with 4 mg/kg MASP-2 inhibitory antibody (OMS646). As shown in FIG. 40, the change from baseline is statistically significant at time point "a" (p=0.003); time point "b" (p=0.007) and a time point "c" (p=0.033) by the untransformed analysis. TABLE 12 provides the 24-hour urine-protein data for the two IgAN patients treated with OMS646.

TABLE 12

24-hour Urine Protein (mg/day) in OMS646-treated IgAN Patients

| Time of Sample | Patient #1 (mg/24 hours) | Patient #2 (mg/24 hours) | Mean |
|---|---|---|---|
| Baseline | 3876 | 2437 | 3156 |
| Day 85 | 1783 | 455 | 1119 | p = 0.017

As shown in FIG. 40 and TABLE 12, the patients with IgAN demonstrated a clinically and statistically significant improvement in kidney function over the course of the study. There were statistically significant decreases in both uACR (see FIG. 40) and 24-hour urine protein concentration (see TABLE 12). As shown in the uACR data in FIG. 40, the mean baseline uACR was 1264 mg/g and reached 525 mg/g at the end of treatment (p=0.011) decreasing to 128 mg/g at the end of the follow-up period. As further shown in FIG. 40, the treatment effect was maintained throughout the follow-up period. Measures of 24-hour urine protein excretion tracked uACRs, with a mean reduction from 3156 mg/24 hours to 1119 mg/24 hours (p=0.017). Treatment effects across the two patients were highly consistent. Both patients experienced reductions of approximately 2000 mg/day and both achieved a partial remission (defined as greater than 50 percent reduction in 24-hour urine protein excretion and/or resultant protein exretion less than 1000 mg/day; complete remission defined as protein excretion less than 300 mg/day). The magnitude of the 24-hour proteinuria reductions in both IgA nephropathy patients is associated with a significant improvement in renal survival. Both IgA nephropathy patients were also able to taper their steroids substantially, each reducing the daily dose to ≤5 mg (60 mg to 0 mg; 30 mg to 5 mg).

The two MN patients also demonstrated reductions in uACR during treatment with OMS646. One MN patient had a decrease in uACR from 1003 mg/g to 69 mg/g and maintained this low level throughout the follow-up period. The other MN patient had a decrease in uACR from 1323 mg/g to 673 mg/g, with a variable course after treatment. The first MN patient showed a marked reduction in 24-hour urine protein level (10,771 mg/24 hours at baseline to 325 mg/24 hours on Day 85), achieving partial and nearly complete remission, while the other remained essentially unchanged (4272 mg/24 hours at baseline to 4502 mg/24 on Day 85). Steroids were tapered in the two MN patients from 30 mg to 15 mg and from 10 mg to 5 mg.

In summary, consistent improvements in renal function were observed in IgAN and MN subjects treated with the MASP-2 inhibitory antibody OMS646. The effects of OMS646 treatment in the patients with IgAN are robust and consistent, suggesting a strong efficacy signal. These effects are supported by the results in MN patients. The time course and magnitude of the uACR changes during treatment were consistent between all four patients with IgAN and MN. No significant safety concerns have been observed. Patients in this study represent a difficult-to-treat group and a therapeutic effect in these patients is believed to be predictive of efficacy with a MASP-2 inhibitory antibody, such as OMS646, in IgAN and MN patients, such as patients suffering from steroid-dependent IgAN and MN (i.e., patients undergoing treatment with a stable corticosteroid dose prior to treatment with a MASP-2 inhibitory antibody), including those at risk for rapid progression to end-stage renal disease.

In accordance with the foregoing, in one embodiment, the invention provides a method of treating a human subject suffering from IgAN or MN comprising administering to the subject a composition comprising an amount of a MASP-2 inhibitory antibody effective to inhibit MASP-2-dependent complement activation. In one embodiment, the method comprises administering to the human subject suffering from IgAN or MN an amount of a MASP-2 inhibitory antibody sufficient to improve renal function (e.g., improve proteinuria). In one embodiment, the subject is suffering from steroid-dependent IgAN. In one embodiment, the subject is suffering from steroid-dependent MN. In one embodiment, the MASP-2 inhibitory antibody is administered to the subject suffering from steroid-dependent IgAN or steroid-dependent MN in an amount sufficient to improve renal function and/or decrease corticosteroid dosage in said subject.

In one embodiment, the method further comprises identifying a human subject suffering from steroid-dependent IgAN prior to the step of administering to the subject a composition comprising an amount of a MASP-2 inhibitory antibody effective to inhibit MASP-2-dependent complement activation.

In one embodiment, the method further comprises identifying a human subject suffering from steroid-dependent MN prior to the step of administering to the subject a composition comprising an amount of a MASP-2 inhibitory antibody effective to inhibit MASP-2-dependent complement activation.

In accordance with any of the disclosed embodiments herein, the MASP-2 inhibitory antibody exhibits at least one or more of the following characteristics: said antibody binds human MASP-2 with a $K_D$ of 10 nM or less, said antibody binds an epitope in the CCP1 domain of MASP-2, said antibody inhibits C3b deposition in an in vitro assay in 1% human serum at an $IC_{50}$ of 10 nM or less, said antibody inhibits C3b deposition in 90% human serum with an $IC_{50}$ of 30 nM or less, wherein the antibody is an antibody fragment selected from the group consisting of Fv, Fab, Fab', $F(ab)_2$ and $F(ab')_2$ wherein the antibody is a single-chain molecule, wherein said antibody is an IgG2 molecule, wherein said antibody is an IgG1 molecule, wherein said antibody is an IgG4 molecule, wherein the IgG4 molecule comprises a S228P mutation. In one embodiment, the antibody binds to MASP-2 and selectively inhibits the lectin pathway and does not substantially inhibit the classical pathway (i.e., inhibits the lectin pathway while leaving the classical complement pathway intact).

In one embodiment, the MASP-2 inhibitory antibody is administered in an amount effective to improve at least one or more clinical parameters associated renal function, such as an improvement in proteinuria (e.g., a decrease in uACR and/or a decrease in 24-hour urine protein concentration, such as greater than 20 percent reduction in 24-hour urine protein excretion, or such as greater than 30 percent reduction in 24-hour urine protein excretion, or such as greater than 40 percent reduction in 24-hour urine protein excretion, or such as greater than 50 percent reduction in 24-hour urine protein excretion).

In some embodiments, the method comprises administering a MASP-2 inhibitory antibody to a subject suffering from IgAN (such as steroid-dependent IgAN), via a catheter (e.g., intravenously) for a first time period (e.g., at least one day to a week or two weeks or three weeks or four weeks or longer) followed by administering a MASP-2 inhibitory antibody to the subject subcutaneously for a second time period (e.g., a chronic phase of at least two weeks or longer).

In some embodiments, the method comprises administering a MASP-2 inhibitory agent to a subject suffering from MN (such as steroid-dependent MN), via a catheter (e.g., intravenously) for a first time period (e.g., at least one day to a week or two weeks or three weeks or four weeks or longer) followed by administering a MASP-2 inhibitory antibody to the subject subcutaneously for a second time period (e.g., a chronic phase of at least two weeks or longer).

In some embodiments, the method comprises administering a MASP-2 inhibitory antibody to a subject suffering from IgAN (such as steroid-dependent IgAN) or MN (such as steroid-dependent MN) either intravenously, intramuscularly, or subcutaneously. Treatment may be chronic and administered daily to monthly, but preferably at least every two weeks, or at least once a week, such as twice a week or three times a week.

In one embodiment, the method comprises treating a subject suffering from IgAN (such as steroid-dependent IgAN) or MN (such as steroid-dependent MN) comprising administering to the subject a composition comprising an amount of a MASP-2 inhibitory antibody, or antigen binding fragment thereof, comprising a heavy chain variable region comprising CDR-H1, CDR-H2 and CDR-H3 of the amino acid sequence set forth as SEQ ID NO:67 and a light-chain variable region comprising CDR-L1, CDR-L2 and CDR-L3 of the amino acid sequence set forth as SEQ ID NO:69. In some embodiments, the composition comprises a MASP-2 inhibitory antibody comprising (a) a heavy-chain variable region comprising: i) a heavy-chain CDR-H1 comprising the amino acid sequence from 31-35 of SEQ ID NO:67; and ii) a heavy-chain CDR-H2 comprising the amino acid sequence from 50-65 of SEQ ID NO:67; and iii) a heavy-chain CDR-H3 comprising the amino acid sequence from 95-107 of SEQ ID NO:67 and b) a light-chain variable region comprising: i) a light-chain CDR-L1 comprising the amino acid sequence from 24-34 of SEQ ID NO:69; and ii) a light-chain CDR-L2 comprising the amino acid sequence from 50-56 of SEQ ID NO:69; and iii) a light-chain CDR-L3 comprising the amino acid sequence from 89-97 of SEQ ID NO:69, or (II) a variant thereof comprising a heavy-chain variable region with at least 90% identity to SEQ ID NO:67 (e.g., at least 91%, at least 92%, at least 93%, at least 94%, at least 95%, at least 96%, at least 97%, at least 98%, at least 99% identity to SEQ ID NO:67) and a light-chain variable region with at least 90% identity (e.g., at least 91%, at least 92%, at least 93%, at least 94%, at least 95%, at least 96%, at least 97%, at least 98%, at least 99% identity to SEQ ID NO:69.

In some embodiments, the method comprises administering to the subject a composition comprising an amount of a MASP-2 inhibitory antibody, or antigen binding fragment thereof, comprising a heavy-chain variable region comprising the amino acid sequence set forth as SEQ ID NO:67 and a light-chain variable region comprising the amino acid sequence set forth as SEQ ID NO:69.

In some embodiments, the method comprises administering to the subject a composition comprising a MASP-2 inhibitory antibody, or antigen binding fragment thereof, that specifically recognizes at least part of an epitope on human MASP-2 recognized by reference antibody OMS646 comprising a heavy-chain variable region as set forth in SEQ ID NO:67 and a light-chain variable region as set forth in SEQ ID NO:69.

In some embodiments, the method comprises administering to a subject suffering from, or at risk for developing IgAN (such as steroid-dependent IgAN) or MN (such as steroid-dependent MN), a composition comprising a MASP-2 inhibitory antibody, or antigen binding fragment thereof comprising a heavy-chain variable region comprising the amino acid sequence set forth as SEQ ID NO:67 and a light-chain variable region comprising the amino acid sequence set forth as SEQ ID NO:69 in a dosage from 1 mg/kg to 10 mg/kg (i.e., 1 mg/kg, 2 mg/kg, 3 mg/kg, 4 mg/kg, 5 mg/kg, 6 mg/kg, 7 mg/kg, 8 mg/kg, 9 mg/kg or 10 mg/kg) at least once weekly (such as at least twice weekly or at least three times weekly) for a period of at least 3 weeks, or for at least 4 weeks, or for at least 5 weeks, or for at least 6 weeks, or for at least 7 weeks, or for at least 8 weeks, or for at least 9 weeks, or for at least 10 weeks, or for at least 11 weeks, or for at least 12 weeks.

Example 20

This Example describes a study using a MASP-2 inhibitory antibody, OMS646, in the treatment of a subject suffering from, or at risk for developing, coronavirus-induced acute respiratory distress syndrome.

Background/Rationale:

Acute respiratory distress syndrome is a severe complication of coronavirus infection. SARS-CoV emerged in 2002 and 2003 from coronavirus circulating in animal markets in China, leading to a global outbreak of respiratory disease, with over 8,000 human cases and 10% mortality (Rota P. A. et al., Science 300:1394-1999, 2003). In 2012, a new related coronavirus was identified in the Middle East, designated as the Middle East respiratory syndrome coronavirus (MERS-CoV), causing severe respiratory disease with greater than 35% mortality (Zaki A. M. et al., N Engl J Med 367:1814-1820, 2012). Coronavirus disease 2019 (COVID-19) is an infectious disease that emerged in 2019 and is caused by severe acute respiratory syndrome coronavirus 2 (SARS coronavirus 2 or SARS-CoV-2), a virus that is closely related to the SARS virus (World Health Organization, 2/11/2020, Novel Coronavirus Situation Report 22). COVID-19, SARS-CoV and MERS-CoV all cause a range of disease from asymptomatic cases to severe acute respiratory distress syndrome (coronavirus-induced ARDS) and respiratory failure. Those affected by COVID-19 may develop a fever, dry cough, fatigue and shortness of breath. Findings on computed tomography can show pulmonary ground glass opacities and bilateral patchy shadowing. Cases can progress to respiratory dysfunction, including pneumonia, severe acute respiratory distress syndrome, which can lead to multi-organ failure and septic shock, and death in the most vulnerable (see e.g., Hui D. S. et al., Int J Infect Dis 91:264-266, Jan. 14, 2020 and Guan et al. OI:10.1056/NEJMoa2002032). There is no vaccine or specific antiviral treatment, with management involving treatment of symptoms and supportive care. Thus, there is an urgent need to develop therapeutically effective agents to treat, inhibit and/or prevent coronavirus-induced acute respiratory distress syndrome.

It has been observed that complement activation contributes to the pathogenesis of coronavirus-induced severe acute respiratory syndrome. It was found that SARS-CoV-infected mice deficient in complement component 3 (C3−/− mice) exhibited significantly less weight loss and less respiratory dysfunction in comparison to SARS-CoV-infected C57BL/6J control mice, despite equivalent viral loads in the lung (Gralinski L. E. et al., mBio 9:e01753-18, 2018). It was further observed that there were significantly fewer neutrophils and inflammatory monocytes in the lungs of SARS-CoV-infected C3−/− mice than in the infected control mice as well as reduced lung pathology and lower cytokine and chemokine levels (e.g., IL-5, IL-6) in the lungs of the SARS-CoV-infected C3−/− mice as compared to the infected control mice (Gralinski L. E. et al., mBio 9:e01753-18, 2018).

Studies have also shown that many survivors of SARS-CoV infection develop pulmonary fibrosis, with a higher prevalence in older patients (Hui D. S. et al., Chest 128: 2247-2261, 2005). There are limited options for treating pulomonary fibrosis, such as coronavirus-induced fibrosis. Traditionally, corticosteroids are used to treat ARDS and pulmonary fibrosis, however, during a viral infection, this treatment dampens the immune response and can result in worsened disease (Gross T. J. et al., N Engl J Med 345:517-525, 2001).

As noted previously, no effective treatment for COVID-19 is known, and the disease is spreading rapidly. Although mortality assessments are still early, the World Health Organization reported a mortality rate of 3.4% in early March 2020 (worldwideweb.who.int/dg/speeches/detail/who-director-general-s-opening-remarks-at-the-media-briefing-on-covid-19-3-march-2020). Effective treatment is needed for patients with severe COVID-19 infection.

As described herein, the lectin pathway is one of the three activation pathways of complement. The other pathways are the classical pathway and alternative pathway. All activation pathways result in the creation of the anaphylatoxins C3a and C5a and in the creation of C5b-9 or membrane attack complex (MAC) on target cells.

The lectin pathway is part of the innate immune system and is activated by microorganisms or injured cells. Microorganisms display carbohydrate-based pathogen-associated molecular patterns (PAMPs) and injured host cells display damage-associated molecular patterns (DAMPs). DAMPs are not displayed on healthy cells but become exposed with cell injury.

Circulating lectins, such as mannose-binding lectin (MBL), ficolins, and collectins recognize and bind to PAMPs and DAMPs. Lectin binding to the PAMPs or DAMPs localizes the complement activation to the vicinity of the cell membrane. These lectins carry mannan-binding lectin-associated serine protease 2 (MASP-2), that, cleaves complement factors 2 and 4 to create the C3 convertase, which itself, then cleaves C3 to form the C5 convertase. In addition to the lectin pathway activation, the alternative pathway can also be activated and amplifies complement activation. All of this leads to insertion of the MAC into the membrane of the injured cell, further injuring the cell with more DAMP exposure. The circulating lectins carrying MASP-2 recognize and bind to the DAMPs, causing further lectin pathway activation and additional cell injury. In this manner, the lectin pathway could magnify and worsen cell injury caused by initial complement activation.

As described herein, OMS646 (also known as OMS721 or narsoplimab) is an investigational human IgG4 monoclonal antibody directed against MASP-2. As further described herein, by blocking MASP-2, activation of the lectin pathway is inhibited. This may break the cycle of complement-mediated cellular injury described above. To date, OMS646 has been administered to approximately 230 healthy volunteers, patients with thrombotic microangiopathies (TMA), and patients with glomerulonephropathies (e.g., immuno-globulin A [IgA] nephropathy.

The lectin pathway may play a key role in initiating and perpetuating complement activation in coronavirus-induced ARDS, and inhibition of the lectin pathway via a MASP-2 inhibitory agent such as the MASP-2 inhibitory antibody OMS646 may address complement-mediated pulmonary injury related to coronavirus infection. As described herein, the inventors discovered that inhibition of mannan-binding lectin-associated serine protease-2 (MASP-2), the key regulator of the lectin pathway of the complement system, significantly reduces inflammation and fibrosis in various animal models of fibrotic disease. For example, the results presented in Examples 14 and 15 herein demonstrate a beneficial effect of MASP-2 inhibition on renal tubulointerstitial inflammation, tubular cell injury, profibrotic cytokine release and scarring. As described in Example 17, in an analysis of a monoclonal MASP-2 inhibitory antibody for efficacy in reducing and/or preventing renal inflammation and tubulointerstitial injury in a mouse protein-overload proteinuria model in wild-type mice, it was determined that there was a significant reduction in the level of IL-6 in the MASP-2 inhibitory antibody-treated group as compared to the saline control group ($p=0.0269$) as well as to the isotype control group ($p=0.0445$), as shown in FIG. 36.

Methods

The following study is carried out to analyze the use of OMS646 in the treatment of one or more patients suffering from coronavirus (e.g., COVID-19-virus) infection in order to measure the efficacy of OMS646 for treating, inhibiting, alleviating or preventing acute respiratory distress syndrome in said patient(s).

The methods involve identifying a subject infected with coronavirus, such as SARS-CoV-2, MERS-CoV or SARS-CoV, which may be determined by carrying out a diagnostic test, such as a molecular test (e.g., rRT-PCR) or a serology test, or by reference to a database containing such information. Exemplary tests for SARS-CoV-2, MERS-CoV and SARS-CoV are found on the Centers For Disease Control website (world-wide-web.cdc.gov/coronavirus/mers/lab/lab-testing.html#molecular).

The subject may be suffering from COVID-19-induced ARDS, or at risk for developing ARDS, such as a subject suffering from pneumonia. Pneumonia is the most common risk factor for the development of ARDS (Sweeney R. M. and McAuley, D. F., *Lancet* vol 388:2416-30, 2016).

COVID-19-induced ARDS is defined as a clinical syndrome that develops after infection with SARS-CoV-2 and fulfills one or more of the following criteria for ARDS (Sweeney R. M. and McAuley, D. F., *Lancet* vol 388:2416-30, 2016), based on the Berlin Definition (*JAMA* 307:2526, 2012):

Oxygenation (mm Hg): mild ($PaO_2/FiO_2$ 200-300); moderate ($PaO_2/Fi\ O_2$ 100-199); severe ($PaO_2/FiO_2$<100)
Positive end-expiratory pressure (PEEP) (cm $H_2O$): minimum PEEP of 5 required
Infiltrates on chest radiograph: bilateral infiltrates involving two or more quadrants on a frontal chest radiograph or CT
Heart failure: left ventricular failure insufficient to solely account for clinical state
Severity: based on oxygenation criteria Treatment Administration Subjects suffering from COVID-19 and experiencing one or more respiratory symptoms, such as those criteria listed above, are dosed with 4 mg/kg of OMS646 via intravenous infusion. Treatment is administered twice weekly. The dose frequency is guided by patient response to therapy. If the patient demonstrates clinical improvement that is maintained for 4 weeks, the dose may be decreased to 4 mg/kg once weekly. If the patient maintains the treatment response while receiving 4 mg/kg once weekly for 4 weeks, treatment may be discontinued.

A positive response to treatment is determined when an improvement is observed in respiratory function, for example, in one or more respiratory symptoms, such as in one or more criteria for ARDS.

In accordance with the foregoing, in one aspect, the present invention provides a method for treating, inhibiting, alleviating or preventing acute respiratory distress syndrome or other manifestation of the disease in a mammalian subject infected with coronavirus, comprising administering to the subject an amount of a MASP-2 inhibitory agent effective to inhibit MASP-2-dependent complement activation (i.e., inhibit lectin pathway activation). In some embodiments, the subject is suffering from one or more respiratory symptoms and the method comprises administering to the subject an amount of a MASP-2 inhibitory agent effective to improve at least one respiratory symptom (i.e., improve respiratory function).

In one embodiment, the method comprises administering the composition to a subject infected with SARS-CoV-2. In one embodiment, the method comprises administering the composition to a subject infected with SARS-CoV. In one embodiment, the method comprises administering the composition to a subject infected with MERS-CoV. In one embodiment, the subject is identified as having coronavirus (i.e., SARS-CoV-2, SARS-CoV or MERS-CoV) prior to administration of the MASP-2 inhibitory agent.

In one embodiment, the MASP-2 inhibitory agent is a small molecule that inhibits MASP-2-dependent complement activation.

In one embodiment, the MASP-2 inhibitory agent is an expression inhibitor of MASP-2.

In one embodiment, the MASP-2 inhibitory antibody is a monoclonal antibody, or fragment thereof that specifically binds to human MASP-2. In one embodiment, the MASP-2 inhibitory antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum with an $IC_{50}$ of 30 nM or less.

In one embodiment, the MASP-2 inhibitory antibody or antigen-binding fragment thereof, comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69. In one embodiment, the MASP-2 inhibitory antibody or antigen-binding fragment thereof comprises a heavy chain variable region comprising the amino acid sequence set forth as SEQ ID NO:67 and a light chain variable region comprising the amino acid sequence set forth as SEQ ID NO:69.

In some embodiments, the method comprises administering to a subject infected with coronavirus a composition comprising a MASP-2 inhibitory antibody, or antigen binding fragment thereof comprising a heavy-chain variable region comprising the amino acid sequence set forth as SEQ ID NO:67 and a light-chain variable region comprising the amino acid sequence set forth as SEQ ID NO:69 in a dosage from 1 mg/kg to 10 mg/kg (i.e., 1 mg/kg, 2 mg/kg, 3 mg/kg, 4 mg/kg, 5 mg/kg, 6 mg/kg, 7 mg/kg, 8 mg/kg, 9 mg/kg or 10 mg/kg) at least once weekly (such as at least twice weekly or at least three times weekly) for a period of at least 2 weeks (such as for at least 3 weeks, or for at least 4 weeks, or for at least 5 weeks, or for at least 6 weeks, or for at least 7 weeks, or for at least 8 weeks, or at least 9 weeks, or at least 10 weeks, or at least 11 weeks, or at least 12 weeks).

In one embodiment, the dosage of MASP-2 inhibitory antibody is about 4 mg/kg (i.e., from 3.6 mg/kg to 4.4 mg/kg).

In one embodiment, dosage of the MASP-2 inhibitory antibody is a fixed dose from about 300 mg to about 450 mg (i.e., from about 300 mg to about 400 mg, or from about 350 mg to about 400 mg), such as about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg or about 450 mg). In one embodiment, the dosage of the MASP-2 inhibitory antibody is a fixed dose of about 370 mg (±10%).

In one embodiment, the method comprises administering a fixed dosage of MASP-2 inhibitory antibody at about 370 mg (±10%) to a subject infected with coronavirus twice weekly intravenously for a treatment period of at least 8 weeks.

In one embodiment, the MASP-2 inhibitory agent is delivered to the subject systemically. In one embodiment, the MASP-2 inhibitory agent is administered orally, subcutaneously, intraperitoneally, intra-muscularly, intra-arterially, intravenously, or as an inhalant.

Example 21

OMS646 (Narsoplimab) Treatment in COVID-19 Patients

This Example describes the use of narsoplimab (OMS646) in the treatment of COVID-19 patients using the methods described in Example 20. The results described in this Example confirm the efficacy of narsoplimab in COVID-19 patients described in Example 20.

Background/Rationale:

Severe acute respiratory syndrome coronavirus 2 (SARS-CoV-2; COVID-19) was identified as a clinical syndrome in Hubei province China in December 2019 and spread rapidly (Zhou F, Yu T, Du R, et al. Clinical course and risk factors for mortality of adult inpatients with COVID-19 in Wuhan, China: a retrospective cohort study. Lancet, 395: 1054-62, 2020). By late February 2020, a fast-growing number of COVID-19 cases were diagnosed in the northern Italian region of Lombardy (Remuzzi A, Remuzzi G. COVID-19 and Italy: what next?*The Lancet*). A primary cause of death in COVID-19 is severe respiratory dysfunction. Lung tissue in patients who have died of COVID-19 shows high concentration of SARS-CoV RNA (Wichmann D. et al., *Ann Intern Med,* 2020) and the same intense inflammatory changes seen in previously reported coronaviruses SARS-CoV (SARS) and MERS-CoV (MERS), and anti-inflammatory strategies are being evaluated for COVID-19 treatment (Xu Z. et al., *Lancet Respir Med,* 8(4):420-2, 2020; Horby P. et al., *medRxiv* 2020: 2020.06.22.20137273; Gritti G. et al., *medRxiv* 2020: 2020.04.01.20048561). Thrombosis has also been reported in SARS and SARS-CoV-2 infection (Wichmann D. et al., *Ann Intern Med* 2020; Magro C. et al., *Transl Res* 2020; Ding Y. et al., *J Pathol* 200(3):28209, 2003). Like SARS and MERS, COVID-19 can cause life-threatening acute respiratory distress syndrome (ARDS) (Guan W. J, Ni Z. Y, Hu Y, et al. Clinical Characteristics of Coronavirus Disease 2019 in China. *N Engl J Med* 2020 [Epub ahead of print]).

A central pathological component of COVID-19 and of the exudative phase of ARDS is endothelial injury and activation (Varga Z. et al., *Lancet* 2020; Ackermann M. et al., *N Engl J Med* 2020; Green S. J. et al., *Microbes Infect* 22(4-5):149-50, 2020; Teuwen L. A. et al., *Nat Rev Immunol* 20(7):389-91, 2020; Goshua G. et al., *Lancet Haematol* 2020; Thompson B. T. et al., *N Engl J Med* 377(19):1904-5, 2017). The underlying cause of increased capillary permeability and pulmonary edema in ARDS, endothelial injury can also cause microvascular angiopathy and thrombosis. Endothelial injury can also cause microvascular angiopathy and thrombosis. Endothelial activation further enhances the local inflammatory environment. Importantly, as demonstrated in human in vitro and animal studies, endothelial injury specifically activates the lectin pathway of complement on the endothelial cell surface (Collard C D, Väkevä A, Morrissey M A, et al. Complement Activation after Oxidative Stress: Role of the Lectin Complement Pathway. *Am J Pathol* 2000; 156(5):1549-1556).

As described in Example 20, OMS646 (also known as narsoplimab), a high affinity monoclonal antibody that binds to MASP-2 and blocks lectin pathway activation, was expected to be effective for the treatment of COVID-19 patients. Consistent with the description in Example 20, MASP-2 has been directly linked to the lung injury in coronavirus infection in an animal model. See Gao et al., *medRxiv* 3/30/2020. MASP-2 also acts directly on the coagulation cascade and the contact system, cleaving prothrombin to thrombin and forming fibrin clots. Narsoplimab not only inhibits lectin pathway activation but also blocks microvascular injury associated thrombus formation as well as MASP-2-mediated activation of kallikrein and factor XII.

No disease-specific therapies have been shown effective for the treatment of COVID-19. In view of the heavy disease burden in Italy, we treated patients with severe COVID-19 infection and ARDS with narsoplimab under a compassionate use program at Papa Giovanni XXIII Hospital in Bergamo. This represents the first time that a lectin pathway inhibitor has been used to treat patients with COVID-19. Here we report this initial clinical experience.

Methods

Study Oversight

The investigation described in this Example was conducted at the Azienda Socio-Sanitaria Territoriale Papa Giovanni XXIII in Bergamo, Italy and approved by the institutional Ethics Committee and the Agenzia Italiana del Farmaco. Laboratory values including blood counts, LDH, C Reactive protein (CRP) were collected as per standard clinical practice. All patients treated with narsoplimab (OMS646) provided informed consent. This study was carried out using the methods described in Example 20, as further described below.

Histopathology

Standard Haematoxylin and Eosin staining (H&E) and immunohistochemistry were performed on formalin fixed-paraffin embedded samples obtained from pathological autopsies of patients with COVID-19. H&E stained sections were reviewed by two pathologists. In order to confirm diagnosis and immunohistochemical analysis of the human endothelial cell marker (CD34) was performed with Bond Ready-to-Use Antibody CD34 (Clone QBEnd/10, Leica Biosystems, Germany), a ready to use product that has been specifically optimized for use with Bond Polymer Refine Detection. The assay was performed on an automated stainer platform (Leica Bond-3, Leica, Germany) using a heat-based antigen retrieval technique as recommended by the manufacturer (Bond Epitope Retrieval solution 2 for 20 minutes). Cytoplasmatic staining of endothelium in the capillaries of pulmonary alveoli indicated positive results.

Circulating Endothelial Cells (CEC) Identification and Count

CEC were tested by flow cytometry analysis performed on peripheral blood samples collected with EDTA. After an erythrocyte-lysis step, samples were labeled with the following monoclonal antibodies: anti-CD45 V500 (clone 2D1, Becton Dickinson, San Jose', CA), anti-CD34 PerCP-CY5.5 (clone 8G12, Becton Dickinson, San Jose', CA), anti-CD146 PE (clone P1H12BD, Pharmingen, CA), for 20 min at room temperature. At least $1 \times 10^6$ events/sample with total leucocyte morphology were acquired by flow cytometry (FACSLyric, BD Biosciences). To reduce operator-induced variability, all the samples in this study were always analyzed by the same laboratory technician. CEC/ml numbers were calculated by a dual-platform counting method using the lymphocyte subset as reference population as previously reported (Almici C. et al., *Bone Marrow Transplant* 52:1637-42, 2017).

Serum Levels of Cytokines

Levels of interleukin-8 (IL-8), interleukin-1β (IL-1β), interleukin-6 (IL-6), interleukin-10 (IL-10), tumor necrosis factor (TNF), and interleukin-12p70 (IL-12p70) were analyzed in a single sample of serum by flow cytometry (BD CBA Human Inflammatory Cytokines Kit, Becton Dickinson, San Jose, CA).

Patients

All narsoplimab-treated patients were admitted to the hospital between March 11 and Mar. 23, 2020. Over this 13-day span, the total daily number of COVID-19 patients hospitalized on the wards ranged from 405 to 542. During this same time period, an average of 140 Helmet-continuous passive airway pressure (CPAP) devises were utilized on a daily basis, and a median of 82 patients (range 66-91) were managed each day in the ICU. Of these ICU patients, 61 met the Berlin criteria for ARDS (PaO2/FiO2 ratio <100 is severe ARDS; 100-200 is moderate; >200 and ≤300 is mild) (Ferguson N. D et al., *Intensive Care Med* 38(10): 1573-82, 2012; Fagiuoli S. et al., *N Engl J Med* 382(21)e71, 2020) on Mar. 11, 2020 and 80 on Mar. 23, 2020.

All patients treated in this study had laboratory-confirmed SARS-CoV-2 infection diagnosed by quantitative reverse-transcriptase-polymerase-chain-reaction assay. SARS-CoV-2 genome from nasal and respiratory samples was detected by different molecular methods including GeneFinder™ Covid-19 Plus RealAmp Kit (ELIThech Group, 92800 Puteaux, France) and Allplex™ 2019-nCoV Assay (Seegene Inc, Arrow Diagnostics S.r.l., Italy). After purification of viral RNA from clinical samples, detection of RdRp, E and N viral genes was obtained by real-time polymerase chain reaction according to World Health Organization protocol (Corman V. M. et al., Euro Surveill 25, 2020). To be eligible for treatment with narsoplimab, COVID-19-confirmed patients were required to be adults (>18 years of age), to have ARDS according to the Berlin criteria (Ferguson N D, et al. *Intensive Care* 38(10):1573-1582, 2012; see also Sweeney R. M. and McAuley, D. F., *Lancet* vol 388:2416-30, 2016; *JAMA* 307:2526, 2012) and to require non-invasive mechanical ventilation by continuous positive airway pressure (CPAP) according to the institutional guidelines for respiratory support. While all enrolled patients empirically received azithromycin 500 mg once daily, patients with active systemic bacterial or fungal infections requiring antimicrobial therapy were not eligible for narsoplimab treatment.

Narsoplimab Treatment, Supportive Therapy and Outcome Assessment

As described in Example 20, narsoplimab (OMS646) is a fully human monoclonal antibody comprised of immunoglobulin gamma 4 (IgG4) heavy-chain and lambda light-chain constant regions. It binds to and inhibits MASP-2 with sub-nanomolar affinity. In accordance with the methods described in Example 20, narsoplimab was administered to six patients infected with COVID-19 at a dosage of 4 mg/kg intravenously twice weekly for 2 to 4 weeks, with a maximum of 6 to 8 doses (for two weeks, three weeks or four weeks). At study initiation, dosing duration was set at 2 weeks but was increased empirically when the first patient treated with narsoplimab experienced a clinical and laboratory-marker recurrence after cessation of treatment at 2 weeks, subsequently resolving with an additional week of dosing. All patients received standard supportive care per the hospital's guidelines at the time of the study, including prophylactic enoxaparin (Clexane, Sanofi Aventis) 4,000 IU/0 4 mL, azithromycin (Zitromax, Pfizer SpA, Italy) 500 mg once daily, hydroxychloroquine (Plaquenil, Sanofi Aventis) 200 mg twice daily, darunavir and cobicistat (Rezolsta, Janssen-Cilag S.p. A., Italy) 800/150 mg once daily. Beginning March 27, per updated institutional guidelines, all COVID-19 patients in the hospital received methylprednisolone 1 mg/kg. Accordingly, a total of five of the six narsoplimab-treated patients also received systemic corticosteroids (methylprednisolone 1 mg/kg) following initiation of narsoplimab treatment. All respiratory support was provided according to institutional treatment algorithms. The clinical characteristics of these six patients are summarized below in Table 13.

In addition to CEC counts and cytokine levels, clinical and laboratory measures, including blood counts, LDH and C-reactive protein (CRP) levels, were collected on all narsoplimab-treated patients per standard clinical practice. Routine blood examinations were collected prior to each narsoplimab dose and then twice weekly. Respiratory function was evaluated daily. Chest computed tomograph (CT) scan was performed on all patients at hospital admission to document the typical interstitial pneumonia and to document pulmonary embolism if clinically indicated. Chest radiography was performed as per clinical requirement during the course of treatment.

Statistical Analysis

Demographic and clinical patient data are presented as frequency with percentage for categorical variables and median with range for continuous ones. Difference in CEC values between normal and COVID-19 patients was assessed with Mann-Whitney U-test. Repeated measures analysis was performed to test differences in CEC and cytokine levels during narsoplimab treatment at appropriate timepoints; non-parametric Friedman test was used, and pairwise-comparisons were performed using paired Wilcoxon signed-rank test. Decreasing trend of LDH and CRP levels during treatment were evaluated with non-parametric Spearman test between the observations and time. Significance at 5% was fixed. Analysis was performed using R software (version 3•6•2).

Table 13 summarizes the clinical characteristics of the six narsoplimab-treated patients.

TABLE 13

Demographics of COVID-19 Patients Treated with narsoplimab

| Clinical Characteristics | All patients (N = 6) |
|---|---|
| Age - years, median (range) | 56.5 years (47-63) |
| Sex - number (%) | |
| Female | 1 (17%) |
| Male | 5 (83%) |
| Weight- kilograms, median (range) | 86 (82-100) |
| BMI- kilograms/$m^2$, median (range) | 28 (26.8-32) |
| Time from disease onset to hospital admission - days, median (range) | 8.5 (3-12) |
| Fever[##] on admission to the hospital - number (%) | 6 (100%) |
| Other Symptoms - number (%) | |
| Cough | 1 (17%) |
| Anorexia | 2 (33%) |
| Fatigue | 4 (67%) |
| Shortness of breath | 5 (83%) |
| Nausea or Vomiting | 1 (17%) |
| Diarrhea | 2 (33%) |
| Headache | 1 (17%) |
| Coexisting disorder - number (%) | |
| Diabetes | 1 (17%)[#] |
| Hypertension | 1 (17%) |
| Dyslipidemia | 2 (33%) |
| Obesity (BMI) ≥30 kg/$m^2$ | 2 (33%) |
| Overweight ≥25 kg/$m^2$ | 4 (66%) |
| ARDS severity at enrollment - number (%) | |
| Mild | 3 (50%) |
| Moderate | 2 (33%) |
| Severe | 1 (17%) |

TABLE 13-continued

Demographics of COVID-19 Patients Treated with narsoplimab

| Clinical Characteristics | All patients (N = 6) |
|---|---|
| Time from hospitalization to start of treatment - days, median (range) | 2 days (1-4) |
| Time from CPAP placement to start of treatment - number (%) | |
| 0-24 hours | 4 (67%) |
| 24-48 hours | 2 (33%) |
| Radiologic findings | |
| Abnormality on chest radiology - number (%) | |
| Bilateral interstitial abnormalities | 6 (100%) |
| Laboratory findings | |
| $PaO_2$:$FiO_2$ ratio - median (range) | 175 (57.5-288) |
| Circulating endothelial cell count - median (range) | 334 (0-9315) |
| White cell count - per $mm^3$, median (range) | 8335 (6420-10,120) |
| >10,000 per $mm^3$ - number (%) | 2 (33%) |
| <4000 per $mm^3$ - number (%) | 0 (0) |
| Lymphocyte count- per $mm^3$ median (range) | 875 (410-1290) |
| Platelet count × $10^3$ per $mm^3$ median (range) | 282 (199-390) |
| Hemoglobin - g/dL, median (range) | 13.4 (13.2-14.1) |
| Distribution of other findings (laboratory reference ranges) | |
| C-reactive protein (0.0-1.0 mg/dL) | 14 (9.5-31.3) |
| Lactate dehydrogenase (120/246 U/L) | 518.5 (238-841) |
| Aspartate aminotransferase (13-40 U/L) | 78.5 (51-141) |
| Alanine aminotransferase (7-40 U/L) | 73 (37-183) |
| Creatinine (0.3-1.3 mg/dL) | 0.85 (0.38-1.33) |
| D-dimer* (<500 ng/mL) | 1250.5 (943-1454) |
| Haptoglobin (36-195 mg/dL) | 368.5 (270-561) |
| Complement C3** (79-152 mg/dL) | 101 (60-126) |
| Complement C4** (16-38 mg/dL) | 21 (2-37) |
| Concomitant Treatments | |
| Anti-retroviral Therapy - number (%) | |
| Darunavir + Cobicistat | 6 (100%) |
| Systemic steroid therapy - number (%) | 5 (83%) |
| After the $1^{st}$ dose of narsoplimab | 2 (33%) |
| After the $2^{nd}$ dose of narsoplimab | 1 (17%) |
| After the $3^{rd}$ dose of narsoplimab | 1 (17%) |
| After the $4^{th}$ dose of narsoplimab | 1 (17%) |

ARDS: Acute Respiratory Distress Syndrome;
ICU: Intensive Care Unit;
CPAP: Continuous Positive Airway Pressure.
*data available only for 4 patients
**data available only for 5 patients
several patients were initially categorized as having diabetes, but were later recategorized as being overweight but not having diabetes.
defined as body temperature >37.5° C.

Results

Thrombosis and Endothelial Cell Damage in COVID-19 Patients

From March 13 to March 16, soon after the dramatic beginning of the COVID-19 outbreak in Bergamo area, the Pathology department of the hospital started to perform autopsies in an initial group of 20 deceased patients. Prior to their deaths, all of these patients, as did the patients treated with narsoplimab in the current study, required advanced respiratory support with CPAP or invasive mechanical ventilation. In keeping with the clinical picture of frequently lethal pulmonary thromboembolism, the lungs and the liver of many patients were found extensively affected by thrombotic events, as described below.

At the histopathological level an arterial involvement by thrombotic process was evident in septal blood vessels of the lung in COVID-19 patients, including also areas unaffected by destructive inflammatory process. Immunohistochemical staining for CD34 (endothelial marker) demonstrated severe endothelial damage with cell shrinkage, degenerated hydropic cytoplasm and adhesion of lymphocytes on endothelial surface as shown in FIGS. 41A-D.

FIGS. 41A-D show representative images of the immunohistochemistry analysis of tissue sections taken from COVID-19 patients, showing vascular damage in these patients.

Figure 41A:
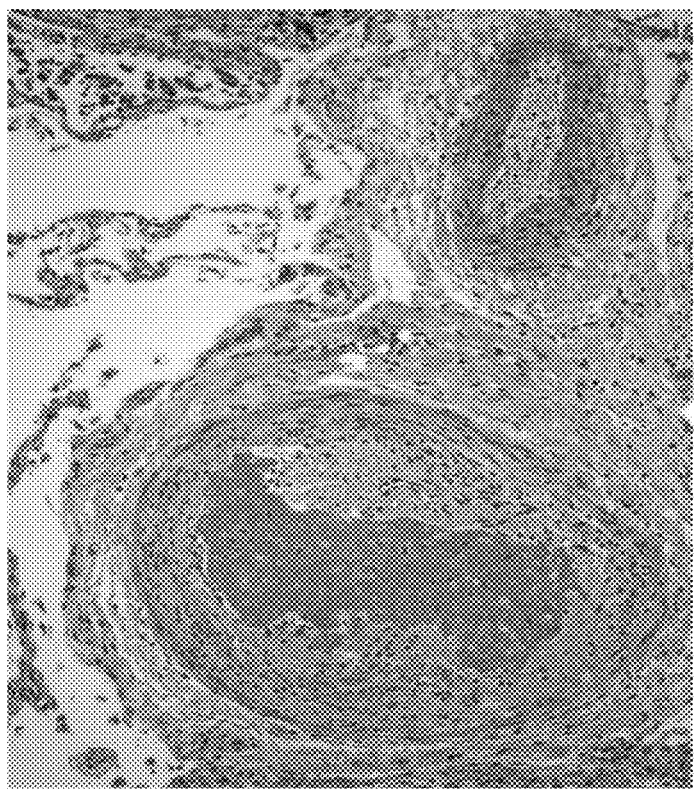
FIG. 41A shows a representative image of the immunohistochemistry analysis of tissue sections of septal blood vessels from the lung of a COVID-19 patient (H&E, 400×), as described in Example 21.

FIG. 41A shows a representative image of the immunohistochemistry analysis of tissue sections of septal blood vessels from the lung of a COVID-19 patient. As shown in FIG. 41A, there is arterial involvement by thrombotic process in septal blood vessels of the lung; note initial organization of the thrombus in arterial lumen (H&E, 400×).

Figure 41B:
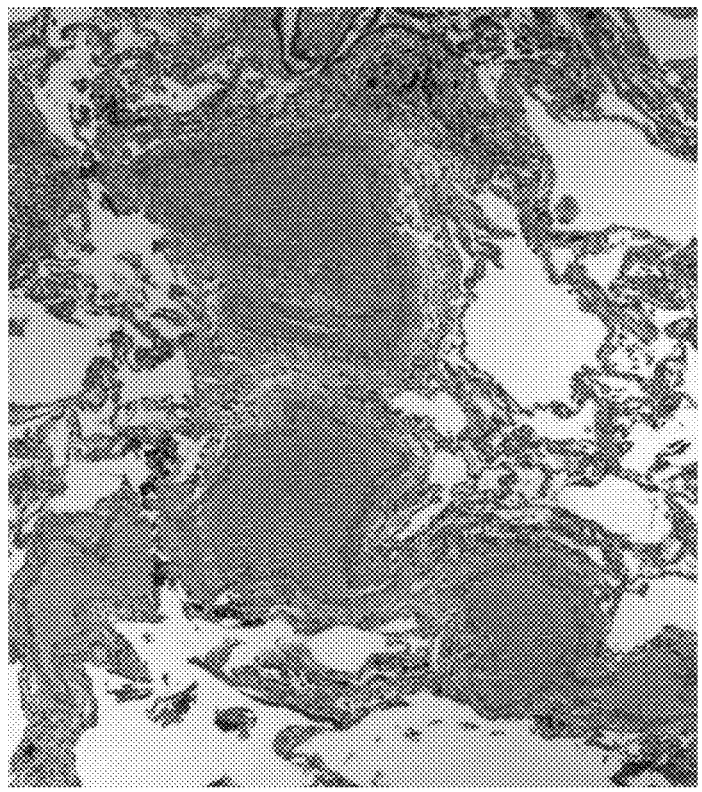
FIG. 41B shows a representative image of the immunohistochemistry analysis of tissue sections of septal blood vessels from the lung of a COVID-19 patient (H&E, 400×), as described in Example 21.

FIG. 41B shows a representative image of the immunohistochemistry analysis of tissue sections of septal blood vessels from the lung of a COVID-19 patient. As shown in FIG. 41B, similar pathologic features as shown in FIG. 41A are extensively notable in most septal vessels in lung area unaffected by destructive inflammatory process (H&E, 400×).

Figure 41C:
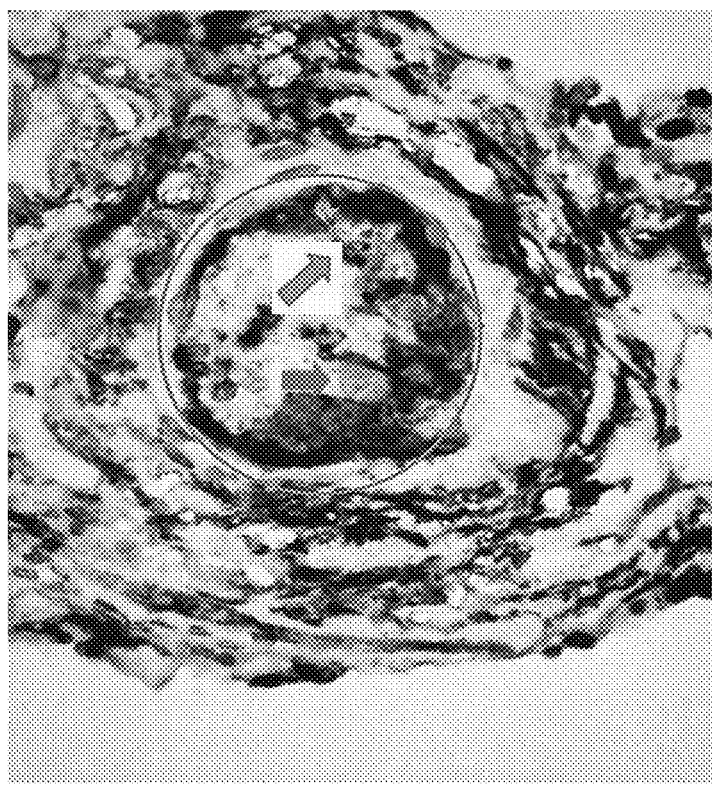
FIG. 41C shows a representative image of the immunohistochemistry analysis of tissue sections of medium diameter lung septal blood vessels from a COVID-19 patient, as described in Example 21.

FIG. 41C shows a representative image of the immunohistochemistry analysis of tissue sections of medium diameter lung septal blood vessels from a COVID-19 patient. As shown in FIG. 41C, medium diameter lung septal blood vessel (circled) with complete lumen thrombosis; immunohistochemical brown staining for CD34 (endothelial marker) demonstrated severe endothelial damage with cell shrinkage, degenerated hydropic cytoplasm (see arrow on the right) and adhesion of lymphocytes on endothelial surface (see arrow on the left).

Figure 41D:
FIG. 41D shows a representative image of the immunohistochemistry analysis of tissue sections of liver parenchyma from a COVID-19 patient (H&E, 400×), as described in Example 21.

FIG. 41D shows a representative image of the immunohistochemistry analysis of tissue sections of liver parenchyma from a COVID-19 patient. As shown in FIG. 41D, vascular alteration was also observed in liver parenchyma with large vessel partial lumen thrombosis (H&E, 400×).

Circulating Endothelial Cells (CEC) Identification and Count

Circulating endothelial cells (CEC) have been used as a biomarker for endothelial cell dysfunction (see Farinacci M et al., *Res Pract Thromb Haemost* 3:49-58, 2019), and it has been shown that CEC counts are elevated in patients with sepsis-related ARDS compared to those with sepsis without ARDS (Moussa M et al., *Intensive Care Med* 41(2):231-8, 2015). Results have also been published in the setting of acute Graft versus Host Disease (GvHD) where an immune-mediated attack of vascular endothelial cells leads to their detachment from the vessel wall and mobilization into the blood stream (see, e.g, Almici et al., *Bone Marrow Transplant* 52:1637-1642, 2017).

Based on these initial observations and published findings in acute graft-versus-host disease (GvHD), prior to the initiation of the study with narsoplimab, we began measuring CEC counts in a non-study cohort of molecularly confirmed COVID-19 patients randomly selected in our hospital. In this non-study cohort of 33 COVID-19 patients, we found that CEC/mL of peripheral blood (median 110, range 38-877) were significantly increased compared to healthy controls (median 7, range 0-37 (P=0.0004), as shown in FIG. 42A.

In this study, the number of CEC/ml was measured in COVID-19 patients before and after treatment with narsoplimab. As noted above, interestingly, it was determined that the number of CEC/ml of peripheral blood (median 110, range 38-877) was significantly increased in an independent cohort of COVID-19 patients when compared to healthy normal subjects (median 7, range 0-37) (see FIG. 42A). An increased number of CEC/ml (median 334, range 0-9315) was also confirmed in the six patients that were selected for the treatment with narsoplimab. After treatment with narsoplimab, a rapid decrease in the number of CEC/ml was documented after the first two doses (median 92 CEC/mL, range 18-460) and confirmed after the fourth dose (median 73, range 0-593), as shown in FIG. 42B. It was further confirmed that the number of CEC/mL was also decreased after the sixth dose of narsoplimab (median 59, range 15-276) (data not shown in FIG. 42B).

Figure 42A:
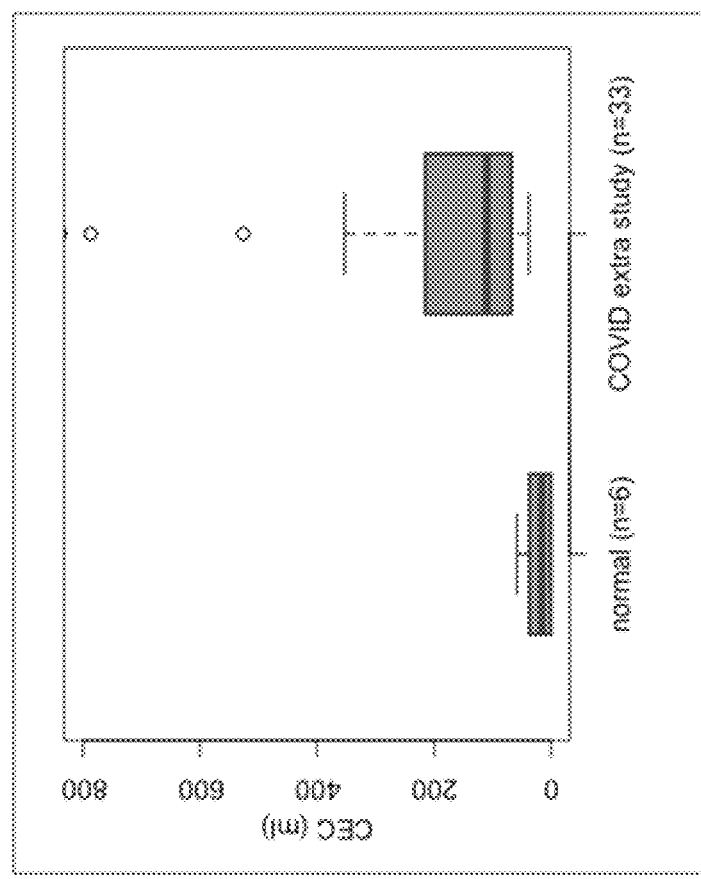
FIG. 42A graphically illustrates the circulating endothelial cell (CEC)/ml counts in the peripheral blood of normal healthy controls (n-6) as compared to the CEC/ml counts in COVID-19 patients that were not part of this study (n=33), as described in Example 21.
Figure 42B:
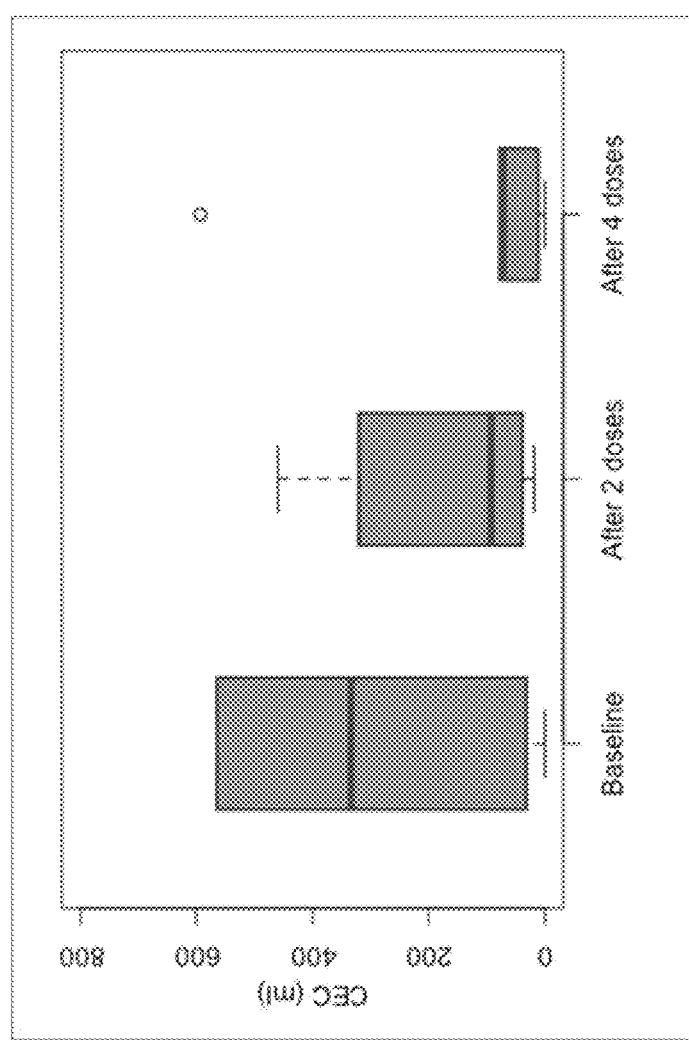
FIG. 42B graphically illustrates the CEC/ml counts in the 6 patients selected for this study before (baseline) and after treatment with narsoplimab, boxes represent values from the first to the third quartile, horizontal line shows the median value and the whiskers indicate the min and max value, as described in Example 21.

FIG. 42A graphically illustrates the CEC/ml counts in normal healthy controls (n=6) as compared to the CEC/ml counts in COVID-19 patients that were not part of this study (n=33). As shown in FIG. 42A, when compared to healthy normal subjects, it was determined that the number of CEC/ml was significantly increased in this independent cohort of COVID-19 patients.

FIG. 42B graphically illustrates the CEC/ml counts in the 6 patients selected for this study before (baseline) and after treatment with narsoplimab, boxes represent values from the first to the third quartile, horizontal line shows the median value and the whiskers indicate the min and max value. As shown in FIG. 42B, an increased CEC/ml was also confirmed in the six patients that were selected for the treatment with narsoplimab, which rapidly decreased after treatment with narsoplimab.

Because our hospital established guidelines implementing standard steroid use for COVID-19 patients 16 days after the initiation of this study, steroid treatment was given to five of the six patients as part of the supportive therapy, beginning 2 to 10 days following initiation of narsoplimab. For this reason, the number of CEC/ml were also evaluated in a separate group of four patients (all female, median age 83 years with a range of 62 to 90 years, three requiring oxygen by mask and one on CPAP) who received only steroids. In these four patients, the CEC counts evaluated after 48 hours were found to be unaffected by steroid administration (p=0•38). In two additional patients receiving only steroids, CEC counts were evaluated at baseline and after 4 weeks of steroid-inclusive supportive treatment. In the first patient, whose clinical course progressively worsened, CEC counts remained unaffected (271/mL vs. 247/mL) while, in the second, clinical improvement was accompanied by a simultaneous decrease of CEC (165 vs. 65/mL).

In the six narsoplimab-treated patients, CEC/mL were markedly increased at baseline (median 334, range 0-9315). With narsoplimab, CEC counts rapidly decreased after the second (median 92 CEC/mL, range 18-460), fourth (median 7•2 5, range 0-593) and sixth (median 59, range 15-276) doses of treatment (p=0•01). Serum concentrations of IL-6, IL-8, CRP and LDH also markedly decreased with narsoplimab treatment as further described below.

Figure 43:
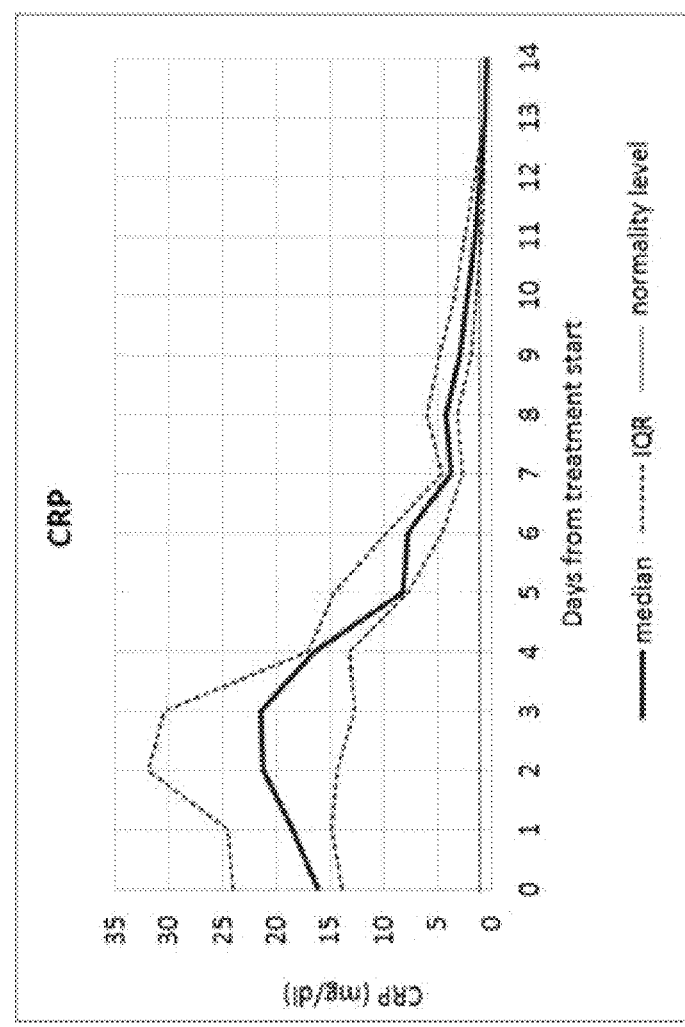
FIG. 43 graphically illustrates the serum level of C Reactive Protein (CRP) (median; interquartile range (IQR)) in 6 COVID-19 patients at baseline prior to treatment (day 0) and at different time points after treatment with narsoplimab, as described in Example 21.

Serum Levels of C Reactive Protein (CRP), Lactate Dehydrogenase (LDH) and Cytokines FIG. 43 graphically illustrates the serum level of C Reactive Protein (CRP) (median; interquartile range (IQR)) in 6 patients with COVID-19 at baseline prior to treatment (day 0) and at different time points after treatment with narsoplimab. As shown in Table 13, the serum level of CRP in healthy subjects is in the range of (0.0-1.0 mg/dl) and the median level of CRP in the 6 COVID-19 patients prior to start of treatment was 14 mg/dl. As shown in FIG. 43, after 2 weeks of treatment with narsoplimab, the level of CRP in the 6 COVID-19 patients was reduced to a median level of nearly 0.0 mg/dl, which is within the normal range of healthy subjects.

Figure 44:
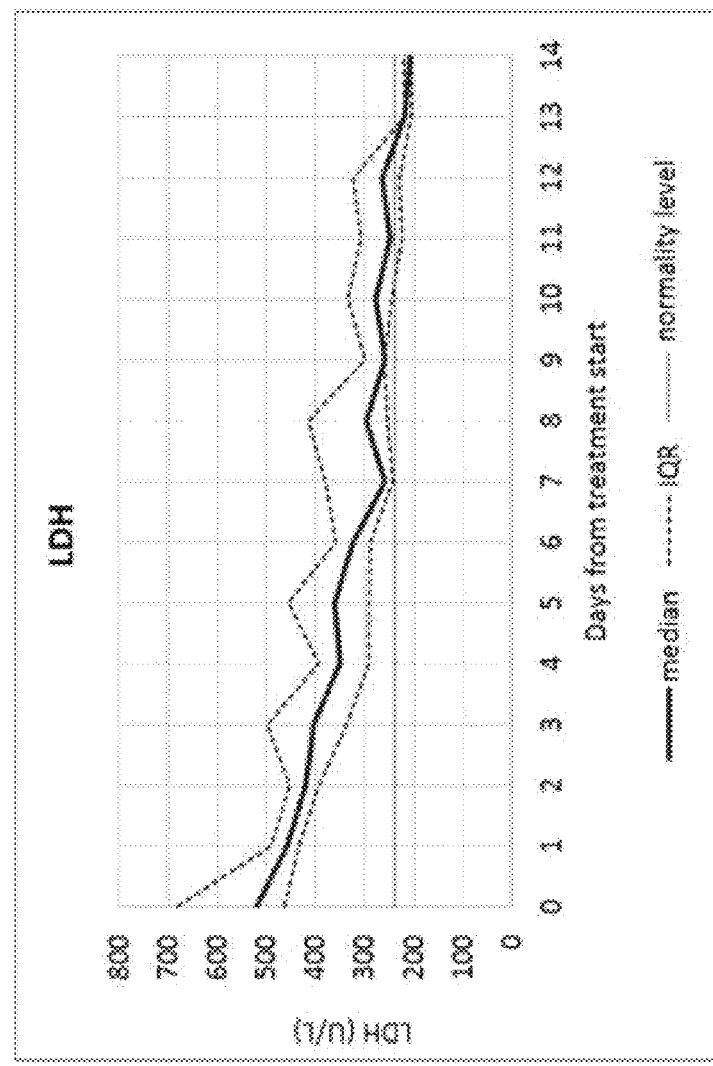
FIG. 44 graphically illustrates the serum level of Lactate Dehydrogenase (LDH) (median; IQR) in 6 COVID-19 patients at baseline prior to treatment (day 0) and at different time points after treatment with narsoplimab, as described in Example 21.

FIG. 44 graphically illustrates the serum level of Lactate Dehydrogenase (LDH) (median; IQR) in 6 patients with COVID-19 at baseline prior to treatment (day 0) and at different time points after treatment with narsoplimab. As shown in Table 13, the serum level of LDH in healthy subjects is in the range of (120-246 U/l) and the median level of LDH in the 6 COVID-19 patients prior to start of treatment was 518 U/1. As shown in FIG. 44, after 2 weeks of treatment with narsoplimab, the level of LDH in the COVID-19 patients was reduced to a median level of about 200 U/1, which is within the normal range of healthy subjects.

Figure 45:
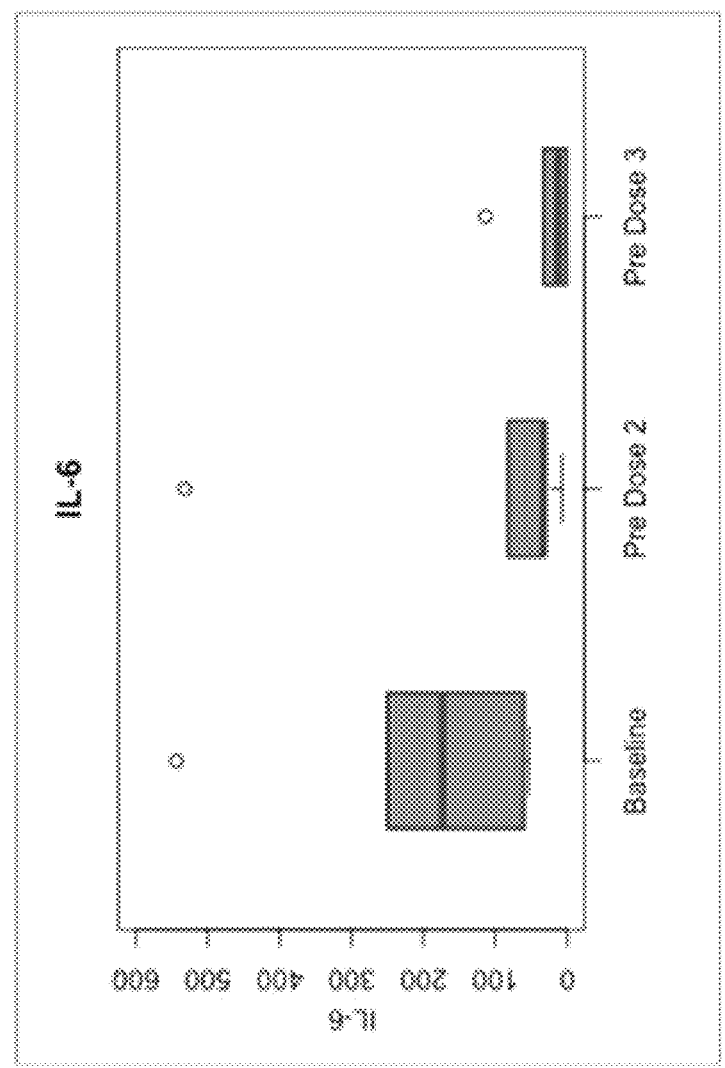
FIG. 45 graphically illustrates the serum level of Interleukin 6 (IL-6) (median; interquartile range (IQR)) in 6

FIG. 45 graphically illustrates the serum level of Interleukin 6 (IL-6) pg/mL (median; interquartile range (IQR)) in 6 patients with COVID-19 at baseline prior to treatment (day 0) and at different time points after treatment with narsoplimab. As shown in FIG. 45, the median level of IL-6 in the COVID-19 patients at baseline prior to treatment was about 180 μg/mL. After 1 dose of narsoplimab (pre-dose 2), the median level of IL-6 in the COVID-19 patients was reduced to about 40 μg/mL and after 2 doses of narsoplimab (pre-dose 3), the median level of IL-6 in the COVID-19 patients was further reduced to about 10 μg/mL.

FIG. 46 graphically illustrates the serum level of Interleukin 8 (IL-8) pg/mL (median; interquartile range (IQR)) in 6 patients with COVID-19 at baseline prior to treatment (day 0) and at different time points after treatment with narsoplimab. Treatment with narsoplimab was given on Day 1, Day 4, Day 7, Day 11 and Day 14. As shown in FIG. 46, the median level of IL-8 in the COVID-19 patients at baseline prior to treatment was about 30 pg/mL. After 1 dose of narsoplimab (pre-dose 2), the median level of IL-8 in the COVID-19 patients was reduced to about 20 pg/mL and after 2 doses of narsoplimab (pre-dose 3), the median level of IL-8 in the COVID-19 patients was further reduced to about 15 pg/mL.

Clinical Outcomes after Treatment with Narsoplimab

The clinical characteristics of the 6 patients selected for treatment with narsoplimab are summarized in Table 13. The median age was 56.5 years and most of the patients were males (83%). All patients were overweight or obese based on a body mass index (BMI) ≥25 and ≥30, respectively. At enrollment, all patients had pneumonia/ARDS requiring CPAP, with two patients rapidly deteriorating and requiring intubation soon after enrollment. Treatment with narsoplimab started within 48 hours from the beginning of non-invasive ventilation with CPAP. A summary of the clinical outcome observed in these patients treated with narsoplimab is presented below in Table 14, which has been updated to reflect the patient status after treatment. Patients received narsoplimab administration twice weekly. Following treatment, the respiratory distress of 4 patients (67%) improved and they reduced the ventilatory support from CPAP to high flow oxygen after a median of 3 narsoplimab doses (range 2-3). Oxygen support was then decreased and stopped until discharge in 3 patients. As documented by a contrast enhanced CT scan, patient #4 developed a massive pulmonary embolism at day 4 after treatment start. For this reason, low molecular weight heparin was added on the top of the ongoing narsoplimab and a rapid improvement of the clinical and CT scan picture was documented after 7 days. In the last two patients (#5 and #6) a rapid and progressive worsening of severe ARDS was documented soon after the enrolment. In case #5 the severe ARDS (with a $PiO_2/FiO_2$ value of 57) lead the patient to be intubated at day 4. Nonetheless, the subsequent clinical outcome was rapidly favorable and the patient was discharged from the ICU after 3 days. After 2 days of CPAP he is now stable with low flow oxygen support. In case #6, severe ARDS developed 4 days after the enrolment and the patient required intubation. Similar to the previous case, she was placed back in CPAP and subsequently in high flow oxygen due to a rapid clinical improvement and later discharged.

No treatment-related adverse events were reported in this study.

TABLE 14

Patient Outcomes to Date

| Patient | Dosing of narsoplimab | Outome to Date |
|---|---|---|
| 1 | 6 doses | Discontinued CPAP within 1 week of treatment initiation, discharged on Day 18, no steroids |
| 2 | 5 doses | Discontinued CPAP within 1 week of treatment initiation, steroids started on day 10, discharged on Day 16 |
| 3 | 5 doses <br> *updated: 7 doses | Was at home greater than 1 week with rapidly progressive respiratory distress before admission; discontinued CPAP within 11 days after treatment initiation, started steroids on day 10, discharged on Day 22* |
| 4 | 4 doses so far, dosing continues <br> **updated: 8 doses | Course complicated by multiple pulmonary emboli determined to predate narsoplimab treatment; started steroids on day 1, developed pulmonary embolism on day 4, improved by day 7 with improved CT scan, discontinued CPAP within 12 days, stabilized with narsoplimab, still improving and dosing continues <br> **updated: nasal cannula on day 26, room air on day 28 and discharged on day 33. |
| 5 | 3 doses so far, dosing continues <br> ***updated: 8 doses | Started steroids on day 3, was able to receive only 2 doses of narsoplimab before requiring intubation and transfer to ICU on day 4; stabilized with narsoplimab, improved, extubated and transferred to step-down unit back to CPAP on Day 7, discontinued CPAP on day 9, still improving and dosing continues <br> ***updated :nasal cannula on day 25, room air on day 27 anddischarged on day 33. |
| 6 | 3 doses so far, dosing continues <br> ****updated: 8 doses | Started steroids on day 1, was able to receive only 1 dose of narsoplimab before requiring intubation and transfer to ICU on day 3, stabilized on narsoplimab and remains intubated; improving and dosing continues <br> ****updated: extubated and transferred to CPAP on day 20, discontinued CPAP on day 82 and moved to nasal cannula, room air on day 85, discharged on day 90. |

*, , *, ****, see updates on patients 3-6 described below.

Discussion

The findings in this study indicate that endothelial injury and thrombosis are central to the pathophysiology of COVID-19-related lung injury. Patients with severe respiratory failure demonstrated not only markedly elevated levels of CRP, LDH, IL-6 and IL-8 but also of circulating endothelial cells (CEC). This novel observation is in keeping with the histopathological findings detected in the lung and the liver that showed a marked endothelial injury and thrombosis in COVID-19 patients. The multi-organ microvascular histopathological changes, specifically the formation of microvascular thrombi, resemble those of HSCT-TMA, further supporting the role of endothelial injury in COVID-19-related pulmonary injury. Endothelial injury is known to be a central component of the pathophysiology of complement activation that is present in ARDS (Thompson B T, et al., N Engl J Med, 377(6):562-572, 2017). Complement activation has also been reported in models of SARS and MERS and is important in other conditions characterized by endothelial injury. Endothelial injury, the underlying cause of increased capillary permeability and pulmonary edema in ARDS, can also cause microvascular angiopathy and thrombosis.

The complement system is an important part of the immune system. Three pathways activate complement in response to distinct initiating events: the classical, lectin, and alternative pathways. The lectin pathway of complement is part of the innate immune response. A pattern-recognition system, activation of the lectin pathway is initiated by members of the MASP enzyme family (MASP-1, MASP-2 and MASP-3). These proteases are synthesized as proenzymes that form a complex in blood with lectins, specifically mannan-binding lectin (MBL), the ficolins, and collectins. These lectins recognize and bind to carbohydrate patterns found on the surfaces of pathogenic microorganisms or injured host cells, targeting MASPs to their site(s) of action and leading to their activation. In this way, lectin pathway activation occurs on the surface of damaged endothelial cells. As described in Example 20, the lectin pathway activation was expected to occur in the setting of COVID-19-related endothelial injury.

MASP-2 is the key enzyme responsible for activation of the lectin pathway, Once activated, MASP-2 cleaves complement component 2 (C2) and C4, initiating a series of enzymatic steps that result in the activation of C3 and C5, yielding the anaphylatoxins C3a and C5a, and the formation of C5b-9 (the membrane attack complex). Preclinically, C3a and C5a have induced endothelial activation associated with endothelial injury and pro-inflammatory changes, leukocyte recruitment, and endothelial apoptosis. Membrane-bound C5b-9 also can cause cell lysis. Even when sub-lytic, C5b-9 causes additional cell injury that induces secretion of prothrombotic factors, platelet activation, upregulation of adhesion molecules, and dysfunctional morphological changes in the endothelium (Kerr H, Richards A. *Immunobiology* 217(2):195-203, 2012). These complement-mediated activities can amplify endothelial injury and dysfunction, causing or worsening clinical condition. A recent publication by Gao et al. *medRxiv* 2020, reports the core involvement of MASP-2 and the lectin pathway in the pathophysiology of SARS and MERS in animal models. However, with regard to the mouse model of LPS-induced lung injury described in Gao et al. (which is not a model of ARDS, but rather is a model of sepsis) the mice were first infected with Ad-SARS N, then on Day 6 were injected with 200 μg/kg anti-MASP-2 antibody and 30 minutes later were induced with LPS and mouse survival was measured. It is further noted that the anti-MASP-2 antibody (200 μg/kg) used in this animal model described in Gao et al. (i.e., HyCult Biotech (HBT) anti-MASP-2 antibody clone 8B5 or clone 6G12) were assayed for C3b inhibitory activity and it was determined that neither mAb 8B5 nor 6G12 were capable of inhibiting C3b deposition in normal human or mouse serum whereas the positive control antibody OMS646 was capable of inhibiting C3b deposition in both normal human and mouse serum in the same assay).

MASP-2, the key enzyme responsible for lectin pathway activation, binds and undergoes activation by the COVID-19 N protein (Gao et al., *medRxiv* 2020, 2020.03.29.20041962) and has been found in the microvasculature of lung tissue in patients with severe COVID-19 (Magro C., et al., *Transl Res* 2020; doi.org/10.1016/j.trsl.2020.04.007). Activated MASP-2 initiates a series of enzymatic steps that results in production of the anaphylatoxins C3a and C5a and in formation of the membrane attack complex C5b-9 (Dobo et al., *Front Immunol* 9:1851, 2018), which can induce proinflammatory responses and cause cell lysis and death. MASP-2 can also cleave C3 directly through the C4 bypass (Yaseen S. et al., *FASEB J* 31(5):2210-9, 2017). Importantly, MASP-2 is located upstream in the lectin pathway, so inhibition of MASP-2 does not interfere with the lytic arm of the classical pathway (i.e., C1r/C1s-driven formation of the C3 and C5 convertases), preserving the adaptive immune response needed to fight infection (Schwaeble et al., *Proc Natl Acad Sci* 108(18):7523-8, 2011).

In addition to its role in complement, MASP-2 acts directly on the coagulation cascade and the contact system, cleaving prothrombin to thrombin and forming fibrin clots (Gulla K. C., *Immunology* 129(4):482-95, 2010; Krarup A. et al., *PLoS One* 2(7):e623, 2007). Narsoplimab not only inhibits lectin pathway activation but also blocks microvascular injury-associated thrombus formation as well as MASP-2-mediated activation of kallikrein and factor XII, as described in WO2019246367, hereby incorporated herein by reference. These activities could contribute to beneficial effects by inhibiting microvascular thrombosis, which may have played an important therapeutic role in the narsoplimab-treated patients, particularly those who suffered massive pulmonary thromboses. Narsoplimab does not prolong bleeding time nor does it affect prothrombin or activated partial thromboplastin times, and no bleeding was observed in the narsoplimab-treated patients. While not wishing to be bound by any particular theory, it is believed that narsoplimab may block coagulation resulting from endothelial damage (associated with factor XII activation) but not extracellular matrix related (factor VII-driven) coagulation.

Lectin pathway inhibition has not previously been investigated as a treatment for COVID-19. All patients in this study had COVID-19-related respiratory failure. In the current study, inhibition of MASP-2 and the lectin pathway by narsoplimab was associated with clinical improvement and survival in all COVID-19 patients treated with the drug. Following treatment with the MASP-2 inhibitor narsoplimab, all six patients recovered and were able to be discharged from the hospital. The clinical improvement observed in patients suffering from COVID-19-related respiratory failure following treatment with narsoplimab, which inhibits MASP-2 and lectin pathway activation, further supports an important role of the lectin pathway in COVID-19 pathophysiology. As described in this Example, all six COVID-19 patients demonstrated clinical improvement following narsoplimab treatment. In each case, COVID-19 lung injury had progressed to ARDS prior to narsoplimab treatment and all patients were receiving non-invasive mechanical ventilation, initiated for each at the time of hospital admission. Two patients experienced continued deterioration following the first dose of narsoplimab and required invasive mechanical ventilation. Both of these patients were subsequently able to discontinue mechanical ventilation entirely with continued narsoplimab treatment. Two patients (one intubated and the other on CPAP) experienced massive bilateral pulmonary thromboses, and both patients completely recovered with narsoplimab, possibly benefitting from the drug's anticoagulant effects. The temporal patterns of laboratory markers (CEC, IL-6, IL-8, CRP and LDH) were consistent with the observed clinical improvement and with the proposed mechanism of action of narsoplimab. In particular, CEC counts appear to be a reliable tool to evaluate endothelial damage and treatment response in this disease. Notably, improvement in IL-6 levels and IL-8 levels also correlated temporally with narsoplimab treatment, suggesting that lectin pathway activation may precede cytokine storm elevation in COVID-19 and that lectin pathway inhibition has a potential beneficial effect on the cytokine storm described in patients with COVID-19 infection (Xiong Y, et al., *Emerg Microbes Infect* 9(1):761-770, 2020). Two weeks of narsoplimab dosing was planned initially but was increased to 3 to 4 weeks following the rise in CEC in patient #1 when dosing was first discontinued. Rebound pulmonary signs and symptoms have not been observed following 3 to 4 weeks of narsoplimab treatment. We saw no evidence of impaired viral defense in the narsoplimab-treated patients, and no narsoplimab-related adverse events were observed Notably, narsoplimab does not inhibit the alternative or classical complement pathways and does not interfere with the adaptive immune response or antigen-antibody complexing. No evidence of narsoplimab-related infection risk has been observed in clinical trials. In addition to inhibiting lectin pathway activation, narsoplmab has been demonstrated to block MASP-2-mediated cleavage of prothrombin to thrombin (Krarup A, et al., *PLoS One;* 2(7):e623, 2007), activation of kallikrein, and autoactivation of factor XII to XIIa. These activities could contribute to beneficial effects by inhibiting microvascular thrombosis. Narsoplimab does not prolong bleeding time nor does it affect either prothrombin or activated partial thromboplastin times. (Krarup PLoS One 2007)

The results described in this Example strongly implicate MASP-2-mediated lectin pathway activation caused by endothelial injury in the pathophysiology of COVID-19-related lung injury. The improvement in the clinical status and laboratory findings following narsoplimab treatment is notable. These findings strongly suggest meaningful clinical efficacy with supportive evidence related to the drug's mechanism of action and the pathophysiology of the disease. Lectin pathway inhibition by narsoplimab appears to be a promising potential treatment of COVID-19-related lung injury.

Supplemental Data from the Clinical Study Described in this Example

As described above in this Example, six patients with laboratory-confirmed COVID-19 and ARDS (per the Berlin criteria) were treated with narsoplimab (4 mg/kg intravenously (IV) twice weekly for 3 to 4 weeks. All patients received standard supportive care including prophylactic enoxaparin (Clexane, Sanofi Aventis) 4,000 IU/0.4 mL, azithromycin (Zitromax, Pfizer SpA, Italy) 500 mg once daily, hydroxychloroquine (Plaquenil, Sanofi Aventis) 200 mg twice daily, and darunavir and cobicistat (Rezolsta, Janssen-Cilag S.p. A., Italy) 800/150 mg once daily. Beginning March 27, per updated institutional guidelines, all Covid-19 patients in our hospital received methylprednisolone (1 mg/kg), which was administered to 5 of the 6 narsoplimab-treated patients.

Histopathological evaluation was performed on deceased COVID-19 patients who were not treated with narsoplimab. Clinical and laboratory measures, including blood counts, LDH and CRP levels, were collected per standard practice on narsoplimab-treated and patients not treated with narsoplimab. Routine blood examinations were collected prior to each narsoplimab dose and then twice weekly. Circulating endothelial cell counts and IL-6 and IL-8 levels were serially assessed by flow cytometry. Respiratory function was evaluated daily. All patients received chest computed tomography (CT) at hospital admission to document interstitial pneumonia, and if clinically indicated, during hospitalization to document pulmonary embolism. Chest radiography was also performed as clinically indicated.

Data are presented as frequency with percentage for categorical variables and median with range for continuous variables. Differences in clinical and laboratory measures between time points were evaluated with non-parametric Friedman test. Pairwise-comparisons were performed using paired Wilcoxon signed-rank test. Significance at 5% was fixed. Analysis was performed using R software (version 3.6.2).

As described in this Example, autopsies were performed on an initial group of 20 deceased COVID-19 patients. Consistent with the clinical picture of frequently lethal pulmonary thromboembolism, the lungs and liver of most patients were found to be extensively affected by thromboses. Histologically, arterial thromboses were evident in septal vessels of the lung, including areas unaffected by the destructive inflammatory process. Immunohistochemical staining for CD34 (an endothelial cell marker) demonstrated severe endothelial damage with cell shrinkage, degenerated hydropic cytoplasm and adhesion of lymphocytes to endothelial cells, as shown in FIGS. 41A-D.

As described in this Example, inhibition of the lectin pathway of complement by narsoplimab was associated with clinical improvement in this study. Treatment with narsoplimab was associated with a rapid and sustained reduction of CEC paralleled by a concomitant reduction of serum IL-6, IL-8, CRP and LDH. In particular, CEC counts appear to be a reliable tool to evaluate the endothelial damage and treatment response in this disease. The temporal improvement of IL-6 and IL-8 with narsoplimab treatment suggests a potential beneficial effect on the cytokine storm described in patients with Covid-19 infection ((Xiong Y, et al., *Emerg Microbes Infect* 9(1):761-770, 2020). This study's findings indicate that endothelial injury is central to the pathophysiology of COVID-19-related lung injury. Patients with severe respiratory failure demonstrated not only markedly elevated levels of C-reactive protein (CRP) and lactate dehydrogenase (LDH), but also IL-6, IL-8 and circulating endothelial cells (CEC). This novel observation is consistent with the histopathological finding in the lung and liver showing marked endothelial injury and thrombosis in COVID-19 patients. The microvascular histopathological changes are very similar to those of the endothelial injury syndrome HSCT-TMA, further supporting the role of endothelial injury in COVID-19-related pulmonary injury.

Two weeks of dosing was planned initially but was increased to 3-4 weeks following the rise in CEC in patient #1 when dosing was first discontinued. With the third week of dosing, the patient's CEC counts again improved. Rebound pulmonary signs and symptoms have not been observed following 4 weeks of narsoplimab treatment. We saw no evidence of impaired viral defense in the narsoplimab-treated patients. Notably, narsoplimab does not inhibit the classical or alternative complement pathways and does not interfere with the adaptive immune response or antigen-antibody complexing. No evidence of narsoplimab-related infection risk has been observed in clinical trials. In addition to inhibiting lectin pathway activation, narsoplimab has been shown to block MASP-2-mediated cleavage of prothrombin to thrombin, activation of kallikrein, and auto-activation of factor XII to XIIa. These activities could contribute to beneficial effects by inhibiting microvascular thrombosis, and this could have played an important therapeutic role, particularly in those patients who suffered massive pulmonary thrombosis. Narsoplimab does not prolong bleeding time nor does it affect prothrombin or activated partial thromboplastin times, and no bleeding was observed in the patients we treated.

Our findings strongly implicate lectin pathway activation caused by endothelial injury in the pathophysiology of Covid-19-related lung injury. Inhibition of the lectin pathway of complement by narsoplimab was associated with clinical improvement in all patients in this study. Narsoplimab was well tolerated, and no adverse drug reactions were reported. All patients improved during treatment and survived. The improvements in clinical status and laboratory findings following narsoplimab treatment are notable. These findings strongly suggest meaningful clinical efficacy with supportive evidence related to the drug's mechanism of action and the pathophysiology of the disease. Lectin pathway inhibition by narsoplimab appears to be a promising potential treatment of Covid-19-related lung injury.

Additional Data is Provided from the Clinical Study Described in this Example.

The clinical characteristics of the 6 narsoplimab-treated patients are summarized in Table 13. Narsoplimab 4 mg/kg was administered intravenously twice weekly for 3 to 4 weeks. Following treatment, all patients improved clinically.

In 4 patients, enoxaparin was given at therapeutic doses (100 IU/kg twice daily) due to CT scan-documented pulmonary embolism (patients #4 and #6), medical decision (patient #3) and rapid deterioration of respiratory function requiring intubation (patient #5). Median follow-up was 27 days (16-90), and patients were administered narsoplimab twice weekly with a median of 8 total narsoplimab doses (range 5-8). Following treatment, all patients improved clinically. Four patients (67%) reduced ventilatory support from CPAP to high-flow oxygen (non-rebreather or Venturi oxygen mask) after a median of 3 narsoplimab doses (range 2-3).

FIG. 50 graphically illustrates the clinical outcome of six COVID-19 patients treated with narsoplimab.

As shown in FIG. 50, in 3 of these patients, oxygen support was weaned and then discontinued, and they were discharged following a median of 6 (5-8) total narsoplimab doses.

In patient #4, massive bilateral pulmonary emboli were documented by contrast-enhanced CT scan 4 days following enrollment. Enoxaparin was added to the ongoing narsoplimab dosing, and rapid clinical and radiographic (repeat CT scan) improvement was documented 11 days later (FIG. 47A and FIG. 47B) and was subsequently discharged.

In the 2 remaining patients (#5 and #6), rapid and progressively worsening severe ARDS was documented soon after enrollment.

In patient #5, severe ARDS ($PaO_2/FiO_2$ of 55) led to intubation at day 4. Nonetheless, the subsequent clinical outcome was rapidly favorable, and the patient was discharged from the intensive care unit after 3 days. Following 2 days of CPAP, he stabilized with low-flow oxygen support. He subsequently required no oxygen and was discharged.

Patient #6 had PaO2/FiO2 of 60 and severe ARDS at enrollment and required intubation 2 days later. Her course was complicated by massive bilateral pulmonary thrombosis and nosocomical methicillin-resistant *Staphylococcus aureus* (MRSA) infection. Her condition improved and, after 18 days, she was extubated, tracheostomized (due to claustrophobia) and supported with low-flow oxygen. Her condition improved, oxygen support was removed and, at day 90, she was discharged. (day 33 to day 90 not shown in FIG. 50) No treatment-related adverse events were reported in this study.

As described above, in patient #4, massive bilateral pulmonary emboli were documented by contrast-enhanced CT scan 4 days following enrollment. Enoxaparin was added to the ongoing narsoplimab dosing, and rapid clinical and radiographic (repeat CT scan) improvement was documented 11 days later as shown in FIG. 47A,B.

FIG. 47A and FIG. 47B are images from CT-scans taken of the lungs of patient #4 with COVID-19 pneumonia treated with narsoplimab.

FIG. 47A shows the CT-scan of patient #4 on Day 5 since enrollment (i.e., after treatment with narsoplimab) wherein the patient is observed to have severe interstitial pneumonia with diffuse ground-glass opacity involving both the peripheral and central regions. Consolidation in lower lobes, especially in the left lung. Massive bilateral pulmonary embolism with filling defects in interlobar and segmental arteries (not shown).

FIG. 47B shows the CT-scan of patient #4 on Day 16 since enrollment (i.e., after treatment with narsoplimab) in which the ground-glass opacity is significantly reduced with almost complete resolution of parenchymal consolidation. "Crazy-paving" pattern is observed with peripheral distribution, especially in the lower lobes. Evident pneumomediastinum. Minimal filing defects in subsegmental arteries of the right lung (not shown).

FIG. 48 graphically illustrates the serum levels of IL-6 (pg/mL) at baseline and at different time points after narsoplimab treatment (after 2 doses, after four doses) in the patients treated with narsoplimab. Boxes represent values from the first to the third quartile, horizontal line shows the median value, and dots show all patient values. FIG. 48 provides an update of the IL-6 data presented in FIG. 45.

FIG. 49 graphically illustrates the serum levels of IL-8 (pg/mL) at baseline and at different time points after narsoplimab treatment (after two doses, after 4 doses) in the patients treated with narsoplimab. Boxes represent values from the first to the third quartile, horizontal line shows the median value, and dots show all patient values. FIG. 49 provides an update of the IL-8 data presented in FIG. 46.

FIG. 50 graphically illustrates the clinical outcome of six COVID-19 patients treated with narsoplimab. The bar colors indicate the different oxygen support (CPAP: yellow; mechanical ventilation with intubation: red; non-rebreather oxygen mask: green; low-flow oxygen by nasal cannula: light green; room air: blue). Narsoplimab doses are marked by blue arrows. Black circle indicates the beginning of steroid treatment. Diamond symbol indicates TEP. Astericks (*) indicate discharged from the hospital. CPAP=continuous positive airway pressure. NRM=non-rebreather oxygen mask. VM=Venturi mask. TEP=pulmonary thromboembolism.

FIG. 51A graphically illustrates the serum levels of Aspartate aminotransferase (AST) (Units/Liter, U/L) values before and after narsoplimab treatment. Black lines represent median and interquartile range (IQR). The red line represents normality level and dots show all patient values.

FIG. 51B graphically illustrates the serum levels of D-Dimer values (ng/ml), in the four patients in whom base line values were available before treatment with narsoplimab started. Black circles indicate when steroid treatment was initiated. The red line represents normality level.

In summary, in this study, the first time a lectin-pathway inhibitor was used to treat COVID-19, six COVID-19 patients with ARDS requiring continuous positive airway pressure (CPAP) or intubation received narsoplimab. The median age of the patients was 57 years (range 47-63 years), 83 percent were men, and all had comorbidities. At baseline, circulating endothelial cell (CEC) counts and serum levels of interleukin-6 (IL-6), interleukin-8 (IL-8), C-reactive protein (CRP), lactate dehydrogenase (LDH), D-dimer and aspartate transaminase (AST)—all markers of endothelial/cellular damage and/or inflammation—were significantly elevated. Narsoplimab treatment was begun within 48 hours of initiation of mechanical ventilation. Dosing was twice weekly for two to four weeks.

Study Results

All narsoplimab-treated patients fully recovered, survived and were discharged from the hospital Narsoplimab treatment was associated with rapid and sustained reduction/normalization across all assessed markers of endothelial/cellular damage and/or inflammation—CEC, IL-6, IL-8, CRP LDH, D-dimer and AST Temporal patterns of laboratory markers were consistent with the observed clinical improvement In particular, CEC counts appear to be a reliable tool to evaluate endothelial damage and treatment response in this disease The temporal improvement of IL-6 and IL-8 with narsoplimab treatment suggests that lectin pathway activation may precede cytokine elevation in COVID-19 and that lectin pathway inhibition has a beneficial effect on the cytokine storm described in patients with COVID-19 infection The courses of two patients (one intubated and the other on CPAP) were further complicated by massive bilateral pulmonary thromboses, and both patients completely recovered with narsoplimab, possibly benefitting from the drug's anticoagulant effects Narsoplimab was well tolerated in the study and no adverse drug reactions were reported Two control groups with similar entry criteria and baseline characteristics were used for retrospective comparison, both showing substantial mortality rates at 32 percent and 53 percent.

Conclusion

As demonstrated in this Example, inhibiting the lectin pathway of complement with narsoplimab may represent an effective treatment for Covid-19 patients by reducing Covid-19-related endothelial cell damage and thus the inflammatory status and thrombotic risk. Lectin pathway inhibition has not previously been investigated as a treatment for COVID-19. All patients in this study had COVID-19-related respiratory failure. Following treatment with the MASP-2 inhibitor narsoplimab, all patients recovered and were able to be discharged from the hospital, further supporting the importance of the lectin pathway in COVID-19 pathophysiology.

Use of other complement inhibitors in COVID-19 have been reported. AMY-101, a compstatin-based C3 inhibitor (Mastaglio S. et al., *Clin Immunol* 215:108450, 2020) was used in one patient and eculizumab was administered together with antiviral and anticoagulant therapy to four patients (Diurno F. et al., *Eur Rev Med Pharmacol Sci* 24(7):4040-7, 2020. These five patients were on CPAP and survived. Two COVID-19 patients on high-flow nasal oxygen received a C5a antibody in conjunction with supportive therapy, including antiviral therapy, following steroid treatment and these two patients also survived. Collectively, these reports support our findings with narsoplimab. However, unlike C3 and C5 inhibitors, the MASP-2 antibody narsoplimab fully maintains classical complement pathway function and does not interfere with the adaptive immune response or the antigen-antibody complex-mediated lytic response (Schwaeble W. et al., *Proc Natl Acad Sci* 108(18): 7523-8, 2011). No evidence of narsoplimab-related infection risk has been observed in narsoplimab clinical trials.

While this was a compassionate use, single-arm study, two different control groups provide a retrospective comparison. The first was described in a recently published article by Gritti et al (*medRxiv* 2020:2020.04.01.20048561) evaluating the use of siltuximab, an IL-6 inhibitor, in COVID-19 patients. The siltuximab study and our narsoplimab study share the same lead investigators (G. G. and A. R.), entry criteria and patient characteristics (i.e., demographics, symptoms, comorbidities, ARDS severity, laboratory values and respiratory support at enrollment). In that study, mortality rates in the siltuximab-treated and the control groups were 33% and 53%, respectively. The second retrospective comparator is represented by the 33 patients who were randomly selected within our hospital to assess the viability of CEC measurements in COVID-19 patients. Of these 33 patients, 22 met the same entry criteria and had similar baseline characteristics as the narsoplimab-treated patients. Median baseline CEC count, however, in the control group compared to that in the narsoplimab-treated group was 101/mL versus 334/mL, respectively. Interestingly, 20 of these 22 patients (91%) were treated with IL-6 inhibitors (tocilizumab or siltuximab) and/or steroids, and the group had an overall 30-day mortality of 32%. The mortality rate was still 31% when the outcome analysis was restricted to 16 patients matched for age to narsoplimab-treated patients (median 58 years, range 51-65 years). In this latter group, 94% received IL-6 and/or steroid therapy and the median baseline CEC count at 55/mL was six-fold lower than in the narsoplimab-treated patients.

The use of steroids in COVID-19 has resulted in reports of mixed outcomes (Veronese N. et al., Front Med (Lausanne) 7:170, 2020). Most recently, the Randomised Evaluation of COVID-19 therapy (RECOVERY) trial, demonstrated that dexamethasone reduced 28-day mortality in patients on invasive mechanical ventilation by 28.7% (29.0% versus 40.7% with usual care), by 14% (21.5% versus 25.0% with usual care) in those receiving oxygen support without invasive mechanical ventilation and had no effect on mortality in patients not receiving respiratory support at randomization (17.0% versus 13.2% with usual care) (Horby P. et al., *medRxiv* 2020:2020.06.22.20137273). Based on these data and the experience at our hospital, we believe that steroids have a role to play in treating COVID-19 patients with respiratory dysfunction, acting to tamp down the inflammatory response. In the narsoplimab-treated group, one (patient #1) of the six patients did not receive steroids. Subsequently, in late March, institutional guidelines were updated, requiring that all patients in our hospital receive steroids. Of the five narsoplimab-treated patients who received steroids, two (patients #2 and #3) initiated them after already improving such that CPAP was no longer required or was discontinued the following day. As described previously, we evaluated CEC counts in a separate group of four patients receiving only steroids for a short duration, and the counts were found to be unaffected by steroid administration. This suggests that any beneficial effect of steroids on COVID-19-associated endothelial damage may be delayed and had little effect on the recovery course of patients #2 and #3.

In conclusion, our findings strongly suggest that endothelial injury-induced activation of MASP-2 and the lectin pathway play a central role in the pathophysiology of COVID-19-related lung injury. The improvements in clinical status and laboratory findings following narsoplimab treatment are notable. There findings strongly suggest meaningful clinical efficacy and provide supportive evidence related to the drug's mechanism of action and the pathophysiology of the disease. Lectin pathway inhibition by narsoplimab appears to be a promising treatment of COVID-19-related lung injury and endothelial damage-associated thromboses.

Further Supplemental Data from the Clinical Study Described in this Example

As described above in this Example, six patients with laboratory-confirmed COVID-19 and ARDS (per the Berlin criteria) were treated with narsoplimab (4 mg/kg intravenously (IV) twice weekly for 3 to 4 weeks. As described in this Example, all six patients in this study had COVID-19-related respiratory failure. Following treatment with the MASP-2 inhibitor narsoplimab, all patients recovered and were able to be discharged from the hospital. These patients have been monitored since discharge from the hospital. As of Oct. 22, 2020, (5 to 6 months following treatment with narsoplimab), all six patients are clinically normal with no evidence of any long-term sequelae that has been reported in COVID-19 patients not treated with narsoplimab. The clinical laboratory measures for all six patients are also normal as of Oct. 22, 2020, including serum levels of D-Dimers, were all found to be in the normal range (see Table 15 below).

Table 15 shows the baseline laboratory measures taken from the six COVID-19 patients at hospital admission (baseline) prior to treatment with narsoplimab, as compared to the laboratory measures taken in October, 2020, five to six months later.

Table 15 summarizes the clinical characteristics of the six narsoplimab-treated patients at baseline (prior to treatment, see also Table 13) and as measured in October 2020, five to six months post-treatment.

TABLE 15

Laboratory Measures of COVID-19 Patients (#1-6) Treated with narsoplimab

| Laboratory Findings | Baseline:All Patients Prior to narsoplimab treatment (March-June, 2020) (N = 6) | Last Evaluation (October 2020) (N = 6) (5-6 months post-discharge) |
|---|---|---|
| White cell count-per mm$^3$, median (range) | 8335 (6420-10,120) | 7320 (3200-8770) |
| . . . >10,000 per mm$^3$-number (%) | 2 (33) | 0 (0) |
| . . . <4000 per mm$^3$-number (%) | 0 (0) | 1 (17) |
| Lymphocyte count-per mm$^3$ median (range) | 875 (410-1290) | 2815 (810-3780) |
| Platelet count × 10$^3$ per mm$^3$ median (range) | 282 (199-390) | 238 (170-354) |
| Hemoglobin-g/dL, median (range) | 13.4 (13.2-14.1) | 14.8 (13.4-15.8) |
| Distribution of other findings (laboratory reference ranges) | | |
| C-reactive protein (0.0-1.0 mg/dL) | 14 (9.5-31.3) | 0.15 (0-0.5) |
| Lactate dehydrogenase (120/246 U/L) | 518.5 (238-841) | 212 (119-249) |
| Aspartate aminotransferase (13-40 U/L) | 78.5 (51-141) | 18 (12-29) |
| Alanine aminotransferase (7-40 U/L) | 73 (37-183) | 22.5 (20-67) |
| Creatinine (0.3-1.3 mg/dL) | 0.85 (0.38-1.33) | 0.94 (0.51-1.07) |
| D-dimer (<500 ng/mL) | | |
| <190-no. (%) | 0 (0) | 3 (50) |
| >190-median (range) | 1250.5 (943-1454) | 324 (202-390) |

These results demonstrate that treatment of COVID-19 patients with narsoplimab in these six patients has led to a complete recovery in these patients with no evidence of any long-term COVID sequelae.

As widely reported, many COVID-19 patients, including those with mild symptoms as well as those with severe COVID-19 related lung injury such as ARDS and/or thrombosis, suffer from immediate complications from COVID-19 infection as well as long-term sequelae even after recovery from the initial infection, also referred to as "long-haulers." As described in Marshall M., ("The lasting misery of coronavirus long-haulers," *Nature* Vol 585, Sep. 17, 2020, page 339-341) people with more severe COVID-19 infections may experience long-term damage in their lungs, heart, immune system, brain, central nervous system, kidneys, gut and elsewhere, and even mild cases of COVID-19 infection can cause a lingering malaise similar to chronic fatigue syndrome. As further described in Marshall (2020), immediate and long-term sequelae from COVID-19 infection include cardiovascular complications (including myocardial injury, cardiomyopathy, myocarditis, intravascular coagulation, stroke, venous and arterial complications, and pulmonary thrombosis); neurological complications (including cognitive difficulties, confusion, memory loss, also referred to as "brain fog", headache, stroke, dizziness, syncope, seizure, anorexia, insomnia, anosmia, ageusia, myoclonus, neuropathic pain, myalgias; development of neurological disease such as Alzheimer's disease, Guillian Barre Syndrome, Miller-Fisher Syndrome, Parkinson's disease); kidney injury (such as acute kidney injury (AKI), pulmonary complications including lung fibrosis, dyspnea, pulmonary embolism); inflammatory conditions such as Kawasaki disease, Kawasaki-like disease, multisystem inflammatory syndrome in children; and multi-system organ failure. See also Troyer A. et al., *Brain, Behavior and Immunity* 87:43-39, 2020; Babapoor-Farrokhram S. et al., *Life Sciences* 253: 117723, 2020; and Heneka M. et al., *Alzheimer's Research & Therapy*, vol 12:69, 2020. As further described in Yelin D. et al., *Lancet Infect Dis* 2020, 9/1/2020, long-term complaints of people recovering from acute COVID-19 include: extreme fatigue, muscle weakness, low grade fever, inability to concentrate, memory lapses, changes in mood, sleep difficulties, needle pains in arms and legs, diarrhea and vomiting, loss of taste and smell, sore throat and difficulties in swallowing, new onset of diabetes and hypertension, skin rash, shortness of breath, chest pains and palpitations.

As described in this Example, treatment of COVID-19 patients with narsoplimab in these six patients has led to a complete recovery in these patients with no evidence of any long-term sequelae from COVID-19 infection.

Example 22

OMS646 (Narsoplimab) Treatment in COVID-19 Patient #7

This Example describes the use of narsoplimab (OMS646) in the treatment of a seventh COVID-19 patient (patient #7) using the methods described in Example 20 and Example 21. The results described in this Example are consistent with the results observed with the six COVID-19 patients in Example 21 and further confirm the efficacy of narsoplimab in the treatment of COVID-19-infected patients.

Methods and Results

Patient #7 is a SARS-CoV-2 infected 76-year-old obese, diabetic man with a long history of smoking and COPD who had also undergone surgery for prostate cancer (i.e., a patient classified as "high risk" for COVID-19 related complications). The patient entered the hospital in Bergamo initially requiring oxygen by nasal cannulae. His respiratory status quickly deteriorated, first requiring oxygenation by mask followed by mechanical ventilation with continuous positive airway pressure and then intubation. After intubation, treatment was initiated with narsoplimab (OMS646), a fully human monoclonal antibody comprised of immunoglobulin gamma 4 (IgG4) heavy-chain and lambda light-chain constant regions. Narsoplimab binds to and inhibits MASP-2 with sub-nanomolar affinity. Treatment of patient #7 with narsoplimab was carried out in accordance with the methods described in Example 20 and Example 21 at a dosage of 4 mg/kg administered intravenously twice weekly for 2 to 4 weeks, with a maximum of 6 to 8 doses (i.e., a dosing duration of two weeks, three weeks or four weeks). To date, patient #7 has received 4 doses of narsoplimab. After treatment with narsoplimab patient #7 rapidly improved and he was extubated after the second dose. His laboratory findings are show in FIG. 52A-E, described below, with the dosing denoted by the vertical arrows on each graph.

FIG. 52A graphically illustrates the serum level of D-dimer values (ng/mL) in patient #7, critically ill with COVID-19, at baseline prior to treatment (day 0) and at different time points after treatment with narsoplimab. Dosing with narsoplimab is indicated by the vertical arrows. The red horizontal line represents normality level.

FIG. 52B graphically illustrates the serum level of C reactive protein (CRP) in patient #7, critically ill with COVID-19. at baseline prior to treatment (day 0) and at different time points after treatment with narsoplimab. Dosing with narsoplimab is indicated by the vertical arrows. The red horizontal line represents normality level FIG. 52C graphically illustrates the serum level of aspartate aminotransferase (AST) (Units/Liter, U/L) in patient #7, critically ill with COVID-19, at baseline prior to treatment (day 0) and at different time points after narsoplimab treatment. Dosing with narsoplimab is indicated by the vertical arrows. The red horizontal line represents normality level.

FIG. 52D graphically illustrates the serum level of alanine transaminase (ALT) (Units/Liter, U/L) in patient #7, critically ill with COVID-19, at baseline prior to treatment (day 0) and at different time points after narsoplimab treatment. Dosing with narsoplimab is indicated by the vertical arrows. The red horizontal line represents normality level.

FIG. 52E graphically illustrates the serum level of lactate dehydrogenase (LDH) in patient #7 with severe COVID-19 at baseline prior to treatment (day 0) and at different time points after treatment with narsoplimab. Dosing with narsoplimab is indicated by the vertical arrows. The red horizontal line represents normality level.

Summary of Results

As shown in FIGS. 52A to 52E, at the time of hospital admission and prior to treatment with narsoplimab, patient #7 had a high serum level of D-dimer (considered the premier marker of coagulability in COVID-19), a high serum level of C-reactive protein (a marker of inflammation), a high serum level of aspartate aminotransferase (an enzyme marker of critical illness in COVID-19), a high serum level of alanine transaminase (a marker of liver function), and a high serum level of lactate dehydrogenase (a marker of cellular death). As further shown in FIGS. 52A to 52E, patient #7 improved following the first dose of narsoplimab, with all the above laboratory measures dropping near or to normal levels after the fourth dose. He was extubated after the second dose of narsoplimab. The ICU staff were amazed with his rapid improvement following treatment with narsoplimab. The rapid improvement of patient #7 reported in this Example is consistent with the recovery of COVID-19 patients #1-6 after treatment with narsoplimab as described in Example 21.

Additional Data are Provided from the Clinical Study Described in this Example:

As described in this Example, patient #7 improved following the first dose of narsoplimab, he was extubated after the second dose, and all the above laboratory measures dropped near or to normal levels after the fourth dose. As an update, patient #7 received a total of 6 narsoplimab doses and was discharged from the hospital. As shown in FIG. 53, serology data from patient #7 over time indicate that appropriately high titers of anti-SARS-CoV-2 antibodies were generated during treatment with narsoplimab, indicating that narsoplimab does not impede effector function of the adaptive immune response.

In addition to patients #1-7 described herein, numerous additional COVID-19 patients suffering from ARDS (total of n=19) have been treated with narsoplimab under compassionate use in accordance with the methods described in Example 20 and Example 21 at a dosage of 4 mg/kg administered intravenously twice weekly for 2 weeks to 4 weeks or 5 weeks, with a maximum of 4 to 10 doses (for two weeks, three weeks, four weeks or 5 weeks). All the additional patients described in this example were severely ill with COVID-19-associated ARDS prior to treatment, all were intubated, with the majority initiating narsoplimab multiple days after intubation and all had failed other therapies prior to initiating narsoplimab. Strikingly positive outcomes were observed in most patients treated with narsoplimab, similar to those observed with patients #1-7 described herein. Most COVID-19 patients treated with narsoplimab showed rapid and marked improvement in clinical symptoms and laboratory values and were subsequently discharged from the hospital. Importantly, narsoplimab-treated COVID-19 patients for whom follow-up data (5-6 months after cessation of narsoplimab treatment) are available show no observed clinical or laboratory evidence of long-term sequelae. It was also observed that COVID-19 patients treated with narsoplimab that survived developed appropriately high anti-SARS-CoV-2 antibodies as described above for patient #7. These results demonstrate that treatment with narsoplimab, which specifically inhibits the lectin pathway and leaves the alternative pathway and the classical pathway of complement fully functional, preserves the infection-fighting effector function of the adaptive immune response and maintains the antigen-antibody complex-mediated lytic response that plays an important role in killing virus-infected cells.

A brief description of the treatment course of the critically ill COVID-19 patients #8-15 treated with narsoplimab in Bergamo, Italy and patients #1-4 treated with narsoplimab in the U.S. are provided below:

Patient #8 (Bergamo, Italy)

Patient #8 was a 76-year-old obese man with congestive heart failure, hypertension, dyslipidemia and severe COVID-19. He began narsoplimab treatment 3 days after intubation and died of complications of pre-existing cardiomyopathy following the $3^{rd}$ dose. His D-dimer and LDH levels were improved after 1 to 2 doses of narsoplimab. Serology data indicate that he did not develop a high titer of anti-SARS-CoV-2 antibodies.

Patient #9 (Bergamo, Italy)

Patient #9 is a 41-year-old overweight man with severe COVID-19. He began narsoplimab treatment 2 days after intubation and was extubated after the 3rd dose. He received a total of 6 doses and was discharged from the hospital. His D-dimer levels and LDH levels were improved after 1 to 2 doses of narsoplimab. Serology data indicate that he developed appropriately high titers of anti-SARS-CoV-2 antibodies during the course of treatment with narsoplimab.

Patient #10 (Bergamo, Italy)

Patient #10 is a 65-year-old overweight man with severe COVID-19. He began narsoplimab treatment 3 days after intubation and was extubated after the $4^{th}$ dose. He received a total of 8 doses of narsoplimab and was discharged from the hospital. His D-dimer levels and LDH levels were improved after 1 to 2 doses of narsoplimab. Serology data indicate that he developed appropriately high titers of anti-SARS-CoV-2 antibodies during the course of treatment with narsoplimab.

Patient #11 (Bergamo, Italy)

Patient #11 was a 68-year-old overweight man with hypertension, dyslipidemia and severe COVID-19. He began narsoplimab treatment 13 days after intubation. He received a total of 7 doses and died of multi-organ failure. Serology data indicate that he did not develop a high titer of anti-SARS-CoV-2 antibodies.

Patient #12 (Bergamo, Italy)

Patient #12 is a 62-year-old overweight man with diabetes, hypertension, dyslipidemia and severe COVID-19. He began narsoplimab treatment 2 days after intubation and was extubated after 5 doses. He received a total of 6 narsoplimab doses, then developed nosocomial infection, requiring re-intubation and tracheostomy, which was removed 9 days later. He was discharged from the hospital to a rehabilitation facility on low-flow oxygen. Serology data indicate that he developed appropriately high titers of anti-SARS-CoV-2 antibodies during the course of treatment with narsoplimab.

Patient #13 (Bergamo, Italy)

Patient #13 is a 62-year-old overweight man with hypertension and severe COVID-19. He began narsoplimab treatment 3 days after intubation and was tracheostomized after the $6^{th}$ dose. He received a total of 8 doses of narsoplimab, the tracheostomy was subsequently removed and he was discharged from the hospital on room air. Serology data indicate that he developed appropriately high titers of anti-SARS-CoV-2 antibodies during the course of treatment with narsoplimab.

Patient #14 (Bergamo, Italy)

Patient #14 is a SARS-CoV-2 infected 64-year-old overweight man with hypertension and severe COVID-19. He began narsoplimab treatment 6 days after intubation. He was tracheostomized after the $7^{th}$ dose. He received a total of 8 doses of narsoplimab, the tracheostomy was subsequently removed and he was discharged from the hospital on room air. Serology data indicate that he developed appropriately high titers of anti-SARS-CoV-2 antibodies during the course of treatment with narsoplimab.

Patient #15 (Bergamo, Italy)

Patient #15 is a 79-year-old overweight man with hypertension and severe COVID-19. He began narsoplimab treatment 3 days after intubation. He was extubated after 3 doses of narsoplimab. He received a total of 6 narsoplimab doses and was discharged from the hospital. Serology data indicate that he developed appropriately high titers of anti-SARS-CoV-2 antibodies during the course of treatment with narsoplimab.

Patient #1 (U.S.)

Patient #1 is a 53-year-old man with severe COVID-19 who had been intubated for about 2 weeks after failing other therapy regimens including remdesivir, tocilizumab, initial steroid therapy and convalescent plasma. He began treatment with narsoplimab and concurrently received enoxaparin and methylprednisolone. He responded quickly and was extubated soon after the $5^{th}$ dose of narsoplimab. He was discharged to a rehabilitation facility for physical therapy, continued to improve and returned to work last month. He reportedly has no longer-term sequelae of COVID-19.

Patient #2 (U.S.)

Patient #2 is a 55-year-old African American woman with rapidly deteriorating respiratory function as a result of severe COVID-19. She began treatment with narsoplimab several days after intubation. Her oxygen requirement was successfully weaned but, due to mask intolerance, a tracheostomy was placed for low-level oxygen support and a feeding tube was inserted. She was discharged to an acute care facility and then to home. The tracheostomy and feeding tube were removed and she is reportedly doing well without evidence of longer-term clinical sequelae.

Patient #3 (U.S.)

Patient #3 was an 80-year-old man with severe COVID-19. He began treatment with narsoplimab several days after intubation. He died after the $3^{rd}$ or $4^{th}$ dose of narsoplimab. His death was reportedly associated with barotrauma and related complications secondary to mechanical ventilation. His family declined extracorporeal membrane oxygenation (ECMO) treatment for religious reasons.

Patient #4 (U.S.)

Patient #4 was a 61-year-old man with hypertension and severe COVID-19. Prior to initiation of narsoplimab treatment, he had been intubated for 8 days and undergoing ECMO. He had failed treatment with remdesivir, baricitinib and high-dose steroids. He received three doses of narsoplimab and died.

In summary, narsoplimab has been used to treat 19 patients described herein with striking results. All COVID-19 patients treated with narsoplimab had ARDS requiring mechanical ventilation—CPAP (4) or intubation (14). All patients had high-risk characteristics/comorbidities. Most COVID-19 patients treated with narsoplimab showed rapid and marked improvement in symptoms (i.e., no longer requiring supplemental oxygen) and laboratory values and were subsequently discharged from the hospital. As further described herein, narsoplimab-treated COVID-19 patients for whom follow-up (5-6 month) data are available show no observed clinical or laboratory evidence of longer-term COVID seqeulae. Narsoplimab-treated COVID-19 patients develop appropriately high titers of SARS-CoV-2 antibodies, indicating that narsoplimab, unlike treatment with other complement inhibitors, does not impede effector function of the adaptive immune response.

TABLE 16

Clinical Characteristics of Patients #7-#15 (Bergamo, Italy)

| Clinical characteristics | Patient #7 | Patient #8 | Patient #9 | Patient #10 | Patient #11 | Patient #12 | Patient #13 | Patient #14 | Patient #15 |
|---|---|---|---|---|---|---|---|---|---|
| Age (years) | 76 | 76 | 41 | 65 | 68 | 62 | 62 | 64 | 79 |
| Male/Female | M | M | M | M | M | M | M | M | M |
| Weight (kg) | 90 | 100 | 90 | 90 | 85 | 85 | 90 | 105 | 75 |
| BMI (kg/m2) | 32 | >30 | 29 | 27.8 | 29 | n/a | 27.8 | 32.5 | 26.0 |
| Time from disease onset to hospital admission (days) | 10 | n/a | 4 | 7 | 4 | 2 | 5 | 7 | 1 |
| Time from admission to intensive care (days) | 6 | 0 | 2 | 2 | 1 | 1 | 13 | 5 | 2 |
| Fever on admission to the hospital | Yes | Yes | Yes | Yes | Yes | Yes | Yes | Yes | No |
| ARDS severity at enrollment | moderate | severe | moderate | moderate | severe | moderate | moderate | moderate | mild |
| Time from hospitalization to start of treatment w/ narsoplimab | 6 | 3 | 4 | 5 | 14 | 3 | 16 | 11 | 5 |
| Time from intubation to start of treatment w/ narsoplimab | 0-24 hrs | 0-24 hrs | 0-24 hrs | >48 hrs | >48 hrs | >48 hrs | >48 hrs | >48 hrs | 24-48 hrs |
| Bilateral interstitial abnormalities on chest radiography | Yes | Yes | Yes | Yes | Yes | Yes | Yes | Yes | Yes |
| Laboratory Findings | | | | | | | | | |
| PaO2:FiO2 ratio | 130 | 45 | 186 | 110 | 95 | 119 | 160 | 162 | 250 |
| White cell count--per $mm^3$, | 7480 | 7410 | 10270 | 10620 | 19640 | 8190 | 21520 | 8810 | 8470 |
| Lymphocyte count-per $mm^3$, | 550 | 480 | 1320 | 700 | 390 | 500 | 1940 | 490 | 350 |
| Platelet count × $10^3$ per $mm^3$ | 181 | 192 | 313 | 268 | 307 | 154 | 247 | 205 | 210 |
| Hemoglobin-g/dL | 13.3 | 11.4 | 13.0 | 12.0 | 10.9 | 15.4 | 12.4 | 12.7 | 11.3 |
| C-reactive protein (0.0-1.0 mg/dL) | 16 | 16.4 | 6 | 17.3 | 12 | 6.1 | 6.8 | 16.3 | 14.5 |
| Lactate dehydrogenase (120/246 U/L) | 496 | 623 | 582 | 491 | 354 | 513 | 315 | 360 | 350 |
| Aspartate aminotransferase (13-40 U/L) | 81 | 149 | 19 | 55 | 52 | 69 | 89 | 37 | 71 |
| Alanine aminotransferase (7-40 U/L) | 70 | 68 | 24 | 22 | 86 | 30 | 252 | 44 | 54 |
| Creatinine (0.3-1.3 mg/dL) | 0.82 | 1.4 | 0.48 | 0.71 | 0.35 | 0.79 | 0.79 | 0.88 | 1.13 |
| D-dimer (<500 ng/mL) | 3949 | 2026 | 4299 | 4471 | 1126 | 808 | 429 | 2410 | 354 |
| Results of treatment with narsoplimab | | | | | | | | | |
| Total Number of doses of narsoplimab | 6 | 3 | 5 | 8 | 8 | 6 | 8 | 8 | 6 |
| Discharged from the hospital | Yes | No, died | Yes | Yes | No, died | Yes | Yes | Yes | Yes |

Influenza Virus

As described in Examples 20, 21 and 22, it has been demonstrated that the lectin pathway contributes to the pulmonary injury in COVID-19 infection and that a representative MASP-2 inhibitory antibody, narsoplimab, is effective to alleviate the pulmonary symptoms in COVID-19 patients. Complement activation has also been demonstrated to contribute to pulmonary injury in a model of Influenza H5N1 virus infection. Pulmonary histopathological changes are very similar in patients with H5N1 infection and SARS-CoV infection In the H5N1 murine model, expression of MASP-2 RNA, C3a receptor RNA and C5a receptor RNA were all increased by the first day following infection Complement inhibition with the use of a C3aR antagonist or cobra venom factor attenuated lung injury and clinical signs. Survival was also increased (see Sun et al., Am J Respir Cell Mol Biol 49(2):221-30, 2013). Accordingly, it is expected that a MASP-2 inhibitory agent will also be effective for use in methods for treating, inhibiting, alleviating or preventing acute respiratory distress syndrome or other manifestation of the disease in a mammalian subject infected with influenza virus.

Example 23

Enzymatic Assay for MASP-2

The MASP-2 assay utilizes a fluorogenic substrate, based on the cleavage site for its natural substrate C2. The assay was run at room temperature in an assay buffer containing 20 mM Hepes, pH 7.4, 140 mM NaCl and 0.1% Tween 20. Assay parameters were adjusted such that the assay was linear with respect to time, enzyme and substrate concentrations. Under these optimized assays conditions, $IC_{50}$ values were equivalent to Ki values, except in a few cases of "tight binding" inhibitors. Cases of "tight binding" or possible "slow binding" inhibitors were handled by the methods described in Copeland R. A. (2013) Evaluation of Enzyme Inhibitors in Drug Discovery. 2nd Ed., John Wiley and Sons, Inc., Chapters 5-7.

The MASP-2 assay protocol was carried out as follows. Test compounds were serially diluted in DMSO and then 100 nL of each dilution was transferred to the assay plate(s). 10 μL of Assay Buffer was added, followed by 15 μL of Enzyme (MASP-2 (CCP1-CCP2-SP) in Assay Buffer. 15 μL of Substrate in Assay Buffer was then added and mixed to start the reactions. After 20 min at room temperature, 15 μL of a stop solution (0.1 M acetic acid) was added, mixed and the plates were read on a SpectraMax i3x Microplate Reader and exported as Excel files. Each assay plate included a "no inhibitor" (DMSO Only) control, a "no enzyme" control and a reference inhibitor control. % Activity values=100*(ave. test comp. fluorescence–ave. "no enz" fluorescence)/(ave. "DMSO only" fluorescence–ave."no enz" fluorescence). $IC_{50}$ and Ki values were very reproducible, falling well within 2-fold.

Example 24

Lectin Pathway Activation Assay in Human Serum Treated with Small Compounds

Microtiter ELISA plate was coated with mannan from Saccharomyces cerevisiae (Sigma-Aldrich, M7504) for overnight at 4° C. in coating buffer [15 mM $Na_2CO_3$, 35 mM $NaHCO_3$]. Plate was blocked with 1% bovine serum albumin (BSA) (Sigma-Aldrich, A3294) in Tris-buffered Saline (TBS) [10 mM Tris-HCl, 140 mM NaCl] for 2 hours at room temperature. 1% human serum was incubated with serial dilutions of small compounds in GVB++ [4 mM Barbital, 145 mM NaCl, 0.2 mM $MgCl_2$, 0.2 mM $CaCl_2$), 1% Gelatin] and incubated for 15 minutes at room temperature. 100 μL of this mixture were then added to the plate and plate was incubated at 37° C. for up to an hour with gentle shaking, 200 rpm. After that, plate was washed thrice in wash buffer [TBS containing 5 mM $CaCl_2$) and 0.05% Tween-20] and 100 L of rabbit anti human C3c (Dako, A0062) diluted 1:5000 in wash buffer were added and incubated at 37° C. for 30 minutes. Plate was washed and 100 L of HRP goat anti rabbit IgG (Southern Biotech, 4050-05) diluted 1:8000 in wash buffer were added and incubated at room temperature for 30 minutes. After that, plate was washed three times and 100 μL/well of TMB Colorimetric substrate (Thermo Scientific, 34029) were added and incubated at room temperature for 5 minutes and the reaction was stop by adding 100 μL/well of 0.1 N sulfuric acid (BDH7230) and the absorbance was measured at 450 nm.

Example 25. Enzymatic Assay for Thrombin

The thrombin assay utilizes a fluorogenic peptide substrate (Boc-VPR-AMC (R&D Systems) and was run at room temperature in an assay buffer containing 20 mM Hepes, pH 7.4, 140 mM NaCl and 0.1% Tween 20. Assay parameters were adjusted such that the assay was linear with respect to time, enzyme and substrate concentrations. Under these optimized assays conditions, $IC_{50}$ values were equivalent to Ki values, except in a few cases of "tight binding" inhibitors. Cases of "tight binding" or possible "slow binding" inhibitors were handled by the methods described in Copeland R. A. (2013) Evaluation of Enzyme Inhibitors in Drug Discovery. 2nd Ed. John Wiley and Sons, Inc., Chapters 5-7.

The thrombin assay protocol was carried out as follows. Test compounds were serially diluted in DMSO and then 100 nl of each dilution was transferred to the assay plate(s). 10 μL of Assay Buffer was added, followed by 15 μL of enzyme (human α-thrombin (BioPharm Lab.)) in assay buffer. 15 μL of substrate in assay buffer were then added and mixed to start the reactions. After 20 min at room temperature, 15 μL of a stop solution (0.1 M acetic acid) was added, mixed and the plates were read on a SpectraMax i3x Microplate Reader and exported as Excel files. Each assay plate included a "no inhibitor" (DMSO Only) control, a "no enzyme" control and a reference inhibitor control. % Activity values=100*(ave. test comp. fluorescence–ave."no enz" fluorescence)/(ave. "DMSO only" fluorescence–ave. "no enz" fluorescence). $IC_{50}$ and Ki values were very reproducible, falling well within ±2-fold.

The results of biological assays for the compounds listed in Tables 4A-4E are listed in Tables 17A, 17B and 17C below.

TABLE 17A

MASP-2/Thrombin/Lectin Pathway Inhibition for Compounds 1000-1229

| Compound | MASP-2 $K_i$ (μM) | mMASP-2 $K_i$ (μM) | Thrombin $K_i$ (μM) | Lectin Pathway $IC_{50}$ (μM) | MASP-2 vs. thrombin selectivity |
|---|---|---|---|---|---|
| 1000 | *** | ND | *** | ND | + |
| 1001 | ** | ND | *** | ND | — |
| 1002 | ** | ND | **** | ND | ND |
| 1003 | *** | ND | **** | ND | — |
| 1004 | *** | ND | **** | ND | — |
| 1005 | ** | ND | **** | ND | — |
| 1006 | **** | **** | **** | ND | — |
| 1007 | **** | ** | * | ND | *** |
| 1008 | *** | ND | **** | + | — |
| 1009 | ** | ND | *** | ND | — |
| 1010 | **** | ND | — | ND | **** |
| 1011 | **** | ND | **** | ++ | — |
| 1012 | *** | ND | — | ND | *** |
| 1013 | ** | ND | * | ND | ** |
| 1014 | ** | ND | — | ND | ** |
| 1015 | *** | * | — | + | * |
| 1016 | *** | * | — | + | ** |
| 1017 | **** | ND | **** | ND | — |
| 1018 |  | ND | /*** | — | — |
| 1019 | *** | ND | *** | ND | — |
| 1020 | **** | ND | **** | ND | — |
| 1021 | ** | — | — | — | *** |
| 1022 | * | ND | *** | ND | — |
| 1023 | *** | ND | **** | + | — |
| 1024 | **** | ND | **** | +++/++++ | ** |
| 1025 | **** | ND | — | ++ | **** |
| 1026 | *** | ND | **** | ND | ** |
| 1027 | **** | ND | **** | ++/+++ | — |
| 1028 | ** | ND | **** | ND | — |
| 1029 | * * | ND | *** | ND | — |
| 1030 | **** | **** | ** | ++ | *** |
| 1031 | *** | ND | * | ND | ** |
| 1032 | **** | ND | ** | ND | **** |
| 1033 | ** | ND | ** | ND | — |
| 1034 | **** | ND | *** | +/++ | * |
| 1035 | **** | ND | **** | ++++ | ** |
| 1036 | ** |  | */ | +++/++++ | ** |
| 1037 | **** | ND | *** | ND | *** |
| 1038 | **** | ND | **** | +++/++++ | * |
| 1039 | ** | * | — | ND | *** |
| 1040 | **** | **** | — | ++ | **** |
| 1041 | *** | ND | **** | + | — |
| 1042 | **** | ND | **** | ++++ | ** |
| 1043 | **** | **** | *** | ++/+++ | ** |
| 1044 | **** | **** | **** | ND | ** |
| 1045 | **** | **** | **** | ND | ** |
| 1046 | **** | **** | **** | ND | ** |
| 1047 | **** | **** | *** | ++/+++ | ** |
| 1048 | **** | **** | **** | ++/+++ | ** |
| 1049 | **** | ND | **** | ND | ** |
| 1050 | **** | ND | ** | ND | ND |
| 1051 | ** | ND | **** | + | — |
| 1053 | **** | ND | ** | ++ | ** |
| 1054 | *** | ND | ** | + | * |
| 1055 | *** | ND | **** | + | — |
| 1056 | **** | ND | *** | ND | **** |
| 1057 | **** | ND | *** | ND | **** |
| 1058 | **** | ND | **** | ++/+++ | — |
| 1059 | **** | **** | — | ++/+++ | **** |

TABLE 17A-continued

MASP-2/Thrombin/Lectin Pathway Inhibition for Compounds 1000-1229

| Compound | MASP-2 $K_i$ (μM) | mMASP-2 $K_i$ (μM) | Thrombin $K_i$ (μM) | Lectin Pathway IC$_{50}$ (μM) | MASP-2 vs. thrombin selectivity |
|---|---|---|---|---|---|
| 1060 | **/* | — | — | — | *** |
| 1061 | **** | ND | *** | ND | * |
| 1062 | *** | ND | * | ND | *** |
| 1063 | **** | ND | *** | ND | ** |
| 1064 | *** | ND | ** | ND | ** |
| 1065 | **** | **** | * | ++++ | **** |
| 1066 | **** | ND | — | ND | *** |
| 1067 | **** | **** | ** | ND | **** |
| 1068 | *** | ND | * | ND | ** |
| 1069 | **** | ND | **** | ++ | — |
| 1070 | ** | ND | — | ND | * |
| 1071 | **** | **** | ** | ND | *** |
| 1072 | **** | **** | **** | ND | ** |
| 1073 | **** | **** | **** | ND | ** |
| 1074 | **** | **** | **** | ND | ** |
| 1075 | **** | **** | **** | ND | ** |
| 1076 | **** | ND | **** | ND | ** |
| 1077 | ** | ND | **** | ND | — |
| 1078 | **** | ND | ND | ++ | ND |
| 1079 | **** | ND | ND | + | ND |
| 1080 | **** | **** | **** | ++/+++ | ** |
| 1081 | **** | **** | **** | ++/+++ | ** |
| 1082 | **** | ND | **** | ND | * |
| 1083 | **** | ND | **** | + | — |
| 1084 | **** | ND | **** | ND | ** |
| 1085 | **** | ND | **** | ND | ** |
| 1086 | **** | ND | **** | ND | ** |
| 1087 | **** | ND | **** | ND | ** |
| 1088 | **** | **** | *** | +++ | ** |
| 1089 | **** | ND | ** | ND | *** |
| 1090 | **** | **** | **/* | ++ | *** |
| 1091 | *** | **** | — | + | *** |
| 1092 | **** | **** | **** | ++/+++ | — |
| 1093 | **** | ND | **** | ND | — |
| 1094 | **** | ND | **** | + | — |
| 1095 | ** | ND | ** | ND | * |
| 1096 | *** | ND | **** | +/++ | — |
| 1097 | **** | **** | **** | ND | *** |
| 1098 | **** | ND | ND | ++++ | ND |
| 1099 | **** | ND | **** | +++ | — |
| 1100 | *** | ND | **** | ND | — |
| 1101 | **** | **** | *** | ND | * |
| 1102 | *** | ND | **** | ND | — |
| 1103 | **** | **** | **** | +++ | ** |
| 1104 | * | ND | *** | ND | — |
| 1105 | ** | ND | *** | ND | — |
| 1106 | *** | ND | **** | ND | — |
| 1107 | **** | ND | **** | ++/+ | — |
| 1108 | **** | **** | **** | ND | * |
| 1109 | ** | ND | **** | — | — |
| 1110 | **** | ND | **** | +++/++++ | * |
| 1111 | **** | ND | **** | ND | * |
| 1112 | **** | ND | **** | ND | ** |
| 1113 | ** | ND | *** | ND | — |
| 1114 | **** | ND | **** | ++ | — |
| 1115 | **** | ND | **** | ++ | — |
| 1116 | *** | ND | **** | + | — |
| 1117 | ** | ND | **** | ND | — |
| 1118 | **** | **** | **** | ND | ** |
| 1119 | **** | ND | *** | ND | ** |
| 1120 | **** | ND | **** | ND | ** |
| 1121 | ** | ND | *** | ND | — |
| 1122 | **** | ND | **** | ND | — |
| 1123 | **** | ND | *** | ++ | ** |
| 1124 | **** | ND | **** | +++/++++ | — |
| 1125 | **** | **** | **** | ND | — |
| 1126 | **** | ND | ND | ND | — |
| 1127 | *** | ND | **** | + | — |
| 1128 | **** | ND | **** | ND | * |
| 1129 | **** | ND | **** | ++ | — |
| 1130 | **** | ND | **** | ND | — |
| 1131 | **** | ND | **** | ++ | — |
| 1132 | *** | ND | ND | ND | ND |
| 1133 | **** | ND | **** | + | — |
| 1134 | **** | **** | **** | ND | — |
| 1135 | **** | ND | *** | ND | * |
| 1136 | **** | ND | *** | ND | *** |
| 1137 | *** | ND | ND | — | ND |
| 1138 | ** | ND | **** | ND | — |
| 1139 | **** | ** | *** | + | * |
| 1140 | **** | ND | **** | ND | — |
| 1141 | **** | ND | **** | ND | — |
| 1142 | **** | ND | **** | ND | * |
| 1143 | **** | **** | **** | ND | — |
| 1144 | *** | ND | ND | ND | ND |
| 1145 | **** | ND | ND | +++ | ND |
| 1146 | **** | ND | *** | ND | * |
| 1147 | *** | ND | *** | ND | * |
| 1148 | **** | ND | ND | ND | ND |
| 1149 | **** | **** | **** | ND | ** |
| 1151 | **** | ND | **** | ND | — |
| 1152 | **** | ND | **** | ND | * |
| 1153 | **** | ND | **** | ND | **** |
| 1154 | **** | ND | **** | ND | — |
| 1156 | * | ND | */** | ND | — |
| 1157 | * | ND | — | ND | * |
| 1158 | * | ND | **** | ND | — |
| 1170 | **** | * | — | ND | **** |
| 1171 | * | * | — | — | * |
| 1192 | * | ND | — | ND | * |
| 1194 | * | ND | ** | ND | — |
| 1195 | * | ND | * | ND | — |
| 1207 | ** | ND | *** | ND | — |
| 1211 | **** | ND | **** | ND | — |
| 1213 | * | ND | — | ND | * |
| 1215 | ** | * | — | ND | * |
| 1218 | **** | ND | **** | ND | — |
| 1223 | **** | **** | **** | ND | *** |
| 1229 | ** | ND | ** | ND | * |
| 999 (melagatran control) | **** | **** | **** | +/++ | — |

MASP-2 Inhibition and Thrombin Inhibition Ki Values:
* $K_i$ of less than 25 μM
** $K_i$ of less than 10 μM
*** $K_i$ of less than 2.5 μM
**** $K_i$ of less than 0.5 μM
— $K_i$ of >25 μM
Lectin Pathway Inhibition
— IC$_{50}$ value > 50 μM
+ IC$_{50}$ value in the range of 5 μM to 50 μM
++ IC$_{50}$ value in the range of 0.5 μM to 5 μM
+++ IC$_{50}$ value in the range of 0.05 μM to 0.5 μM
++++ IC$_{50}$ value < 0.05 μM
Selectivity of compound for MASP-2 inhibition versus thrombin:
— less than 1.0-fold
* 1.0 to 5.0-fold
** 5.0 to 25-fold
*** 25 to 100-fold
**** >100-fold
ND Not determined

TABLE 17B

MASP-2/Thrombin/Lectin Pathway Inhibition for Compounds 1230-1497

| Compound | MASP-2 $K_i$ (μM) | mMASP-2 $K_i$ (μM) | Thrombin $K_i$ (μM) | Lectin Pathway IC$_{50}$ (μM) | MASP-2 vs. thrombin selectivity |
|---|---|---|---|---|---|
| 1230 | **** | **** | * | ++++ | **** |
| 1231 | **** | **** | ** | ND | **** |
| 1232 | *** | ND | **** | ND | — |
| 1233 | **** | **** | *** | ND | * |
| 1234 | **** | **** | * | ND | *** |

TABLE 17B-continued

MASP-2/Thrombin/Lectin Pathway Inhibition for Compounds 1230-1497

| Compound | MASP-2 $K_i$ (μM) | mMASP-2 $K_i$ (μM) | Thrombin $K_i$ (μM) | Lectin Pathway $IC_{50}$ (μM) | MASP-2 vs. thrombin selectivity |
|---|---|---|---|---|---|
| 1235 | **** | ND | * | ND | *** |
| 1236 | **** | **** | **** | ND | * |
| 1237 | * | ND | *** | ND | — |
| 1238 | **** | **** | ** | ND | *** |
| 1239 | **** | **** | ** | ++ | ** |
| 1240 | *** | ND | * | ++ | ** |
| 1241 | **** | **** | **** | ND | * |
| 1242 | *** | ** | ** | ND | ** |
| 1243 | * | ND | — | ND | ND |
| 1244 | *** | ND | — | ND | ** |
| 1245 | **** | * | * | ND | **** |
| 1246 | * | ND | * | ND | * |
| 1247 | **** | **** | *** | ND | *** |
| 1248 | **** | **** | *** | ND | ** |
| 1249 | **** | **** | * | ND | **** |
| 1250 | **** | **** | **** | ND | * |
| 1251 | *** | ND | **** | ND | — |
| 1252 | **** | ND | ** | ND | *** |
| 1253 | **** | *** | — | +++ | ND |
| 1254 | **** | ND | * | ND | *** |
| 1255 | *** | ND | — | ND | ND |
| 1256 | **** | ND | **** | ND | * |
| 1257 | **** | * | — | ND | *** |
| 1258 | ** | ND | — | ND | ND |
| 1259 | ** | ND | — | ND | ND |
| 1260 | ** | ND | — | ND | ND |
| 1261 | * | * | — | ND | * |
| 1262 | **** | ND | *** | ND | *** |
| 1263 | ** | ** | — | ND | ND |
| 1264 | ** | * | — | ND | ND |
| 1265 | **** | ** | — | ND | **** |
| 1266 | *** | — | — | ND | ** |
| 1267 | ** | — | — | ND | ND |
| 1268 | **** | **** | **** | ND | * |
| 1269 | *** | * | — | ND | ** |
| 1270 | **** | **** | **** | ND | ** |
| 1271 | ** | — | — | ND | ND |
| 1272 | **** | **** | *** | ND | *** |
| 1273 | * | * | — | ND | ND |
| 1274 | ** | * | — | ND | ** |
| 1275 | *** | — | — | ND | *** |
| 1276 | **** | **** | *** | ND | *** |
| 1277 | **** | **** | **** | ND | ** |
| 1278 | **** | **** | ** | ND | *** |
| 1279 | *** | — | ** | ND | ** |
| 1280 | ** | * | — | ND | ND |
| 1281 | ** | — | — | ND | ND |
| 1282 | * | — | — | ND | ND |
| 1283 | **** | *** | ** | ND | *** |
| 1284 | **** | **** | **** | ND | * |
| 1285 | *** | *** | ** | ND | ** |
| 1286 | ** | **** | *** | ND | — |
| 1287 | * | — | — | ND | ND |
| 1288 | ** | ** | — | ND | ND |
| 1289 | **** | **** | **** | ND | — |
| 1290 | **** | **** | *** | ND | ** |
| 1291 | *** | * | — | ND | ND |
| 1292 | ** | * | — | ND | ND |
| 1293 | ** | ** | — | ND | * |
| 1294 | ** | ** | — | ND | ND |
| 1295 | **** | **** | ** | ND | *** |
| 1296 | ** | — | — | ND | ** |
| 1297 | **** | **** | * | ND | **** |
| 1298 | **** | ** | — | ND | ND |
| 1299 | **** | **** | * | ND | **** |
| 1300 | **** | **** | ** | ND | *** |
| 1301 | ** | — | — | ND | ND |
| 1302 | **** | **** | — | ND | *** |
| 1303 | **** | ** | — | ND | *** |
| 1304 | **** | *** | *** | +++ | *** |
| 1305 | *** | **** | — | ND | ** |
| 1306 | **** | **** | **** | ND | * |
| 1307 | **** | **** | — | +++ | **** |
| 1308 | *** | *** | * | ND | ** |
| 1309 | **** | **** | — | ND | **** |
| 1310 | *** | — | — | ND | *** |
| 1311 | ** | ** | — | ND | * |
| 1312 | **** | **** | **** | ND | * |
| 1313 | ** | — | * | ND | * |
| 1314 | * | — | — | ND | * |
| 1315 | *** | **** | ** | ND | * |
| 1316 | **** | **** | *** | ND | *** |
| 1317 | **** | *** | — | ND | ND |
| 1318 | **** | **** | ** | ND | **** |
| 1319 | **** | * | ** | ND | ** |
| 1320 | **** | *** | *** | ND | ** |
| 1321 | * | — | — | ND | ND |
| 1322 | **** | *** | * | ND | *** |
| 1323 | — | * | — | ND | ND |
| 1324 | **** | **** | *** | +++ | *** |
| 1325 | *** | * | **** | ND | — |
| 1326 | **** | **** | * | ND | *** |
| 1327 | **** | **** | **** | ND | *** |
| 1328 | **** | **** | *** | +++ | **** |
| 1329 | **** | **** | *** | ND | * |
| 1330 | **** | **** | **** | ND | *** |
| 1331 | **** | **** | — | +++ | **** |
| 1332 | * | ** | — | ND | ND |
| 1333 | ** | * | — | ND | ND |
| 1334 | **** | **** | **** | +++ | — |
| 1335 | **** | **** | ** | ND | *** |
| 1336 | * | — | — | ND | ND |
| 1337 | **** | **** | *** | ++ | **** |
| 1338 | **** | **** | — | +++ | *** |
| 1339 | **** | **** | **** | ++++ | ** |
| 1340 | **** | **** | **** | ND | ** |
| 1341 | * | — | *** | ND | — |
| 1342 | **** | *** | * | ND | **** |
| 1343 | **** | **** | ** | +++ | **** |
| 1344 | **** | **** | ** | ND | **** |
| 1345 | **** | **** | **** | ++++ | **** |
| 1346 | * | — | — | ND | ND |
| 1347 | **** | **** | *** | ++++ | *** |
| 1348 | **** | **** | **** | ++++ | *** |
| 1349 | *** | ** | — | ND | ** |
| 1350 | **** | **** | ** | ++ | **** |
| 1351 | **** | **** | — | ++++ | **** |
| 1352 | **** | **** | *** | +++ | *** |
| 1353 | **** | **** | **** | ++++ | *** |
| 1354 | **** | *** | ** | ND | *** |
| 1355 | **** | * | — | ND | ND |
| 1356 | **** | **** | — | +++ | **** |
| 1357 | **** | **** | — | ++++ | **** |
| 1358 | *** | — | — | ND | ND |
| 1359 | *** | * | — | ND | ** |
| 1360 | **** | **** | — | +++ | **** |
| 1361 | **** | **** | — | ++++ | **** |
| 1362 | *** | *** | *** | ND | * |
| 1363 | **** | **** | ** | +++ | **** |
| 1364 | *** | * | — | ND | ND |
| 1365 | **** | **** | — | ++++ | **** |
| 1366 | ** | ** | — | ND | ND |
| 1367 | **** | * | — | ND | ND |
| 1368 | *** | * | — | +++ | ** |
| 1369 | **** | **** | — | ND | **** |
| 1370 | **** | *** | — | +++ | ND |
| 1371 | **** | **** | **** | +++ | — |
| 1372 | **** | **** | **** | +++ | ** |
| 1373 | **** | **** | *** | +++ | *** |
| 1374 | **** | **** | — | ND | ND |
| 1375 | *** | * | * | ++ | ** |
| 1376 | *** | — | — | ND | ND |
| 1377 | *** | — | * | ND | ** |
| 1378 | **** | **** | *** | ++ | * |
| 1379 | **** | **** | — | ++ | **** |
| 1380 | *** | **** | — | — | *** |
| 1381 | *** | * | * | ++ | ** |
| 1382 | **** | ** | — | + | *** |

TABLE 17B-continued

MASP-2/Thrombin/Lectin Pathway Inhibition for Compounds 1230-1497

| Compound | MASP-2 $K_i$ (µM) | mMASP-2 $K_i$ (µM) | Thrombin $K_i$ (µM) | Lectin Pathway $IC_{50}$ (µM) | MASP-2 vs. thrombin selectivity |
|---|---|---|---|---|---|
| 1383 | *** | ** | — | + | ND |
| 1384 | * | — | — | ND | * |
| 1385 | **** | **** | **** | +++ | ** |
| 1386 | * | — | — | ND | ND |
| 1387 | ** | * | — | ND | ND |
| 1388 | **** | **** | — | ++++ | **** |
| 1389 | **** | ** | — | ++ | **** |
| 1390 | ** | — | — | ND | ND |
| 1391 | **** | **** | — | ++ | **** |
| 1392 | **** | **** | *** | ++ | *** |
| 1393 | **** | **** | **** | +++ | * |
| 1394 | ** | — | * | ND | * |
| 1395 | *** | ** | — | + | ND |
| 1396 | **** | **** | — | ++ | **** |
| 1397 | **** | **** | — | +++ | **** |
| 1398 | **** | **** | — | +++ | ND |
| 1399 | **** | **** | * | +++ | **** |
| 1400 | **** | ** | — | ++ | ND |
| 1401 | **** | *** | — | ND | ND |
| 1402 | **** | *** | **** | ND | * |
| 1403 | **** | *** | — | ND | ND |
| 1404 | **** | **** | **** | ND | ** |
| 1405 | **** | *** | *** | ND | ** |
| 1406 | **** | **** | ** | +++ | **** |
| 1407 | **** | **** | ** | +++ | **** |
| 1408 | **** | ** | ** | ND | ** |
| 1409 | **** | ** | **** | ++ | * |
| 1410 | **** | *** | *** | ++ | *** |
| 1411 | **** | **** | — | +++ | ND |
| 1412 | **** | ** | — | ND | ND |
| 1413 | *** | ** | — | ND | *** |
| 1414 | **** | **** | **** | +++ | — |
| 1415 | **** | **** | **** | +++ | * |
| 1416 | **** | **** | **** | +++ | ** |
| 1417 | *** | ** | — | ND | ND |
| 1418 | ** | * | — | ND | ND |
| 1419 | **** | **** | **** | ++++ | * |
| 1420 | **** | **** | ** | +++ | **** |
| 1421 | **** | *** | * | ND | **** |
| 1422 | **** | **** | ** | ++ | **** |
| 1423 | **** | **** | ** | +++ | **** |
| 1424 | *** | *** | **** | ND | ND |
| 1425 | ** | *** | — | ND | ND |
| 1426 | **** | *** | *** | ++++ | *** |
| 1427 | **** | **** | — | ND | **** |
| 1428 | **** | *** | * | ++ | **** |
| 1429 | **** | **** | ** | ++ | **** |
| 1430 | **** | **** | — | ++ | **** |
| 1431 | **** | **** | * | +++ | **** |
| 1432 | **** | **** | * | ++ | **** |
| 1433 | **** | **** | *** | +++ | **** |
| 1434 | * | * | — | ND | ND |
| 1435 | **** | **** | * | ++ | **** |
| 1436 | *** | — | * | ND | ** |
| 1437 | *** | ** | — | ND | ** |
| 1438 | **** | *** | **** | ++ | ** |
| 1439 | **** | ** | — | ND | ND |
| 1440 | **** | ** | — | ND | ND |
| 1441 | **** | **** | — | +++ | ND |
| 1442 | **** | **** | — | ++ | ND |
| 1443 | **** | **** | *** | ++ | *** |
| 1444 | **** | **** | **** | ++ | ** |
| 1445 | **** | *** | — | + | **** |
| 1446 | **** | *** | — | + | **** |
| 1447 | **** | **** | ** | ++ | **** |
| 1448 | **** | ** | — | ND | **** |
| 1449 | **** | **** | ** | ++ | **** |
| 1450 | **** | **** | ** | +++ | **** |
| 1451 | **** | **** | * | ++ | **** |
| 1452 | **** | **** | *** | ++ | **** |
| 1453 | **** | **** | * | ++++ | **** |
| 1454 | **** | **** | *** | ++ | *** |
| 1455 | **** | **** | — | ND | **** |
| 1456 | **** | *** | — | — | ND |
| 1457 | * | ** | — | ND | ND |
| 1458 | **** | **** | — | ND | **** |
| 1459 | **** | **** | ** | ND | **** |
| 1460 | **** | **** | — | ND | **** |
| 1461 | **** | **** | *** | ND | **** |
| 1462 | *** | ** | * | ND | ** |
| 1463 | **** | **** | — | ND | ND |
| 1464 | **** | **** | — | ND | ND |
| 1465 | **** | *** | **** | ND | * |
| 1466 | **** | **** | * | ND | **** |
| 1467 | **** | *** | — | ND | **** |
| 1468 | **** | **** | — | ND | **** |
| 1469 | **** | **** | ** | ND | **** |
| 1470 | **** | **** | ** | ND | **** |
| 1471 | ** | ** | — | ND | ND |
| 1472 | **** | **** | ** | ND | **** |
| 1473 | **** | **** | — | ND | ND |
| 1474 | **** | **** | — | ND | **** |
| 1475 | **** | **** | * | ND | **** |
| 1476 | **** | **** | ** | ND | **** |
| 1477 | **** | **** | * | ND | **** |
| 1478 | **** | **** | * | ND | **** |
| 1479 | **** | **** | * | ND | **** |
| 1480 | **** | **** | — | ND | **** |
| 1481 | **** | **** | ** | ND | **** |
| 1482 | **** | **** | *** | ND | *** |
| 1483 | **** | **** | * | ND | **** |
| 1484 | *** | *** | — | ND | ND |
| 1485 | **** | **** | *** | ND | ** |
| 1486 | *** | **** | ** | ND | ** |
| 1487 | **** | ND | — | ND | *** |
| 1488 | **** | ** | **** | ++ | — |
| 1489 | **** | *** | **** | ND | — |
| 1490 | **** | ** | **** | + | — |
| 1491 | *** | **** | **** | + | — |
| 1492 | **** | **** | **** | +++ | ** |
| 1493 | * | — | * | ND | * |
| 1494 | **** | **** | ** | ND | **** |
| 1495 | ** | *** | — | ND | ** |
| 1496 | **** | *** | — | ND | ND |
| 1497 | **** | ** | ** | ND | ** |

MASP-2 Inhibition and Thrombin Inhibition Ki Values:
* 10 µM < $K_i$ ≤ 25 µM
** 2.5 µM ≤ $K_i$ < 10 µM
*** 0.5 µM ≤ $K_i$ < 2.5 µM
**** $K_i$ < 0.5 µM
— $K_i$ of > 25 µM
ND Not determined
Lectin Pathway Inhibition
+ 5 µM < $IC_{50}$ ≤ 50 µM
++ 0.5 µM ≤ $IC_{50}$ < 5 µM
+++ 0.05 µM ≤ $K_i$ < 0.5 µM
++++ $K_i$ < 0.05 µM
— $IC_{50}$ > 50 µM
Selectivity of compound for MASP-2 inhibition versus thrombin:
— <1.0-fold
* ≥1.0 to <5.0-fold
** ≥5.0 to <25-fold
*** ≥25 to <100-fold
**** ≥100-fold
ND Not determined

TABLE 17C

MASP-2/Thrombin/Lectin Pathway Inhibition

| Compound No. | MASP-2 $K_i$ (µM) | Thrombin $K_i$ (µM) | Lectin $K_i$ | MASP-2 versus thrombin selectivity |
|---|---|---|---|---|
| 2000 | **** (+Zn) — (+EDTA) | ** (+Zn) — (+EDTA) | ND | ++ (+Zn) |

TABLE 17C-continued

MASP-2/Thrombin/Lectin Pathway Inhibition

| Compound No. | MASP-2 K$_i$ (μM) | Thrombin K$_i$ (μM) | Lectin K$_i$ | MASP-2 versus thrombin selectivity |
|---|---|---|---|---|
| 2001 | **** (+Zn) — (+EDTA) | *** (+Zn) — (+EDTA) | ND | ++ (+Zn) |
| 2002 | *** (+Zn) — (+EDTA) | * (+Zn) — (+EDTA) | ND | ++ (+Zn) |
| 2003 | ***** (+Zn) — (+EDTA) | *** (+Zn) — (+EDTA) | ND | +++ (+Zn) |
| 2004 | **** (+Zn) — (+EDTA) | **** (+Zn) — (+EDTA) | ND | + (+Zn) |
| 2005 | ***** (+Zn) — (+EDTA) | ***** (+Zn) — (+EDTA) | ND | + (+Zn) |
| 2006 | ** (+Zn) — (+EDTA) | — (+Zn) — (+EDTA) | ND | + (+Zn) |
| 2007 | **** (+Zn) — (+EDTA) | *** (+Zn) — (+EDTA) | ND | ++ (+Zn) |
| 2008 | **** (+Zn) —(+EDTA) | ** (+Zn) —(+EDTA) | ND | +++ (+Zn) |
| 2009 | **** (+Zn) — (+EDTA) | *** (+Zn) * (+EDTA) | ND | ++ (+Zn) |
| 2010 | ***** (+Zn) — (+EDTA) | *** (+Zn) * (+EDTA) | ND | ++ (+Zn) |
| 2011 | **** (+Zn) — (+EDTA) | *** (+Zn) — (+EDTA) | ND | ++ (+Zn) |
| 2012 | ***** (+Zn) — (+EDTA) | **** (+Zn) — (+EDTA) | ND | + (+Zn) |
| 2013 | **** (+Zn) — (+EDTA) | ** (+Zn) — (+EDTA) | ND | ++++ (+Zn) |
| 2014 | **** (+Zn) — (+EDTA) | *** (+Zn) * (+EDTA) | ND | +++ (+Zn) |
| 2015 | ** (−Zn) ***** (+Zn) — (+EDTA)] | *** (−Zn) **** (+Zn) — (+EDTA)] | ND | + (+Zn) |
| 2016 | **** (+Zn) — (+EDTA) | * (+Zn) * (+EDTA) | ND | +++ (+Zn) |
| 2017 | *** | — | ND | >++ |
| 2018 | *** | — | ND | >++ |
| 2019 | ** | — | ND | >+ |
| 2020 | * | — | ND | >+ |
| 2021 | ** | — | + | >++ |

MASP-2 Inhibition and Thrombin Inhibition Ki values:
* K$_i$ of less than 25 μM
** K$_i$ of less than 10 μM
*** K$_i$ of less than 2.5 μM
**** K$_i$ of less than 0.5 μM
***** K$_i$ of less than 0.05 μM
— K$_i$ of >25 μM
Lectin Pathway Inhibition:
— IC$_{50}$ value > 50 μM
+ IC$_{50}$ value in the range of 5 μM to 50 μM
Selectivity of compound for MASP-2 versus thrombin:
— less than 1.0-fold
+ 1.0 to 5.0-fold
++ 5.0 to 25-fold
+++ 25 to 100-fold
++++ >100-fold
ND Not determined In accordance with the foregoing, in one aspect, the present invention provides a method for treating, inhibiting, alleviating or preventing acute respiratory distress syndrome or other manifestation of the disease, such as thrombosis, in a mammalian subject infected with coronavirus or influenza virus, comprising administering to the subject an amount of a MASP-2 inhibitory agent effective to inhibit MASP-2-dependent complement activation (i.e., inhibit lectin pathway activation). In some embodiments, the subject is suffering from one or more respiratory symptoms and/or thrombosis and the method comprises administering to the subject an amount of a MASP-2 inhibitory agent effective to improve at least one respiratory symptom (i.e., improve respiratory function) and/or alleviate thrombosis.

In one embodiment, the method comprises administering the composition to a subject infected with COVID-19. In one embodiment, the method comprises administering the composition to a subject infected with SARS-CoV. In one embodiment, the method comprises administering the composition to a subject infected with MERS-CoV. In one embodiment, the subject is identified as having coronavirus (i.e., COVID-19, SARS-CoV or MERS-CoV) prior to administration of the MASP-2 inhibitory agent. In one embodiment, the subject is identified as being infected with COVID-19 and is in need of supplemental oxygen and the MASP-2 inhibitory agent, such as a MASP-2 inhibitory antibody, such as, for example, narsoplimab, is administered to the subject at a dosage and time period effective to eliminate the need for supplemental oxygen.

In one embodiment, the subject is identified as having COVID-19 and is suffering from, or at risk for developing, COVID-19-induced thrombosis and the method comprises administering a composition comprising a MASP-2 inhibitory agent (e.g., a MASP-2 inhibitory antibody such as narsoplimab) in a therapeutically effective amount to treat, prevent or reduce the severity of coagulation or thrombosis in said subject. In some embodiments, the methods of the invention provide anticoagulation and/or antithrombosis and/or antithrombogenesis without affecting hemostasis. In one embodiment, the level of D-Dimer is measured in a subject suffering from COVID-19 to determine the presence or absence of thrombosis in said subject, wherein a D-Dimer level higher than the standard range is indicative of the presence of thrombosis and the subject is treated with a MASP-2 inhibitory agent (e.g., a MASP-2 inhibitory antibody such as narsoplimab) in a therapeutically effective amount to treat, prevent or reduce the severity of coagulation or thrombosis in said subject, which can be measured, for example, by a reduction in the level of D-Dimer level into the normal range of a healthy subject.

In one embodiment, the method comprises administering the composition to a subject infected with influenza virus, such as influenza A virus (H1N1 (caused the "Spanish Flu" in 1918 and "Swine Flu" in 2009); H2N2 (caused the "Asian Flu" in 1957), H3N2 (caused the "Hong Kong Flu" in 1968), H5N1 (caused the "Bird Flu in 2004), H7N7, H1N2, H9N2, H7N2, H7N3, H10N7, H7N9 and H6N1); or influenza B virus, or influenza virus C virus. In one embodiment, the subject is identified as having influenza virus prior to administration of the MASP-2 inhibitory agent.

In one embodiment, the subject is determined to have an increased level of circulating endothelial cells in a blood sample obtained from the subject prior to treatment with the MASP-2 inhibitory agent as compared to the level of circulating endothelial cells in a control healthy subject or population. In some embodiments, the method comprises administering an amount of a MASP-2 inhibitory agent in an amount sufficient to reduce the number of circulating endothelial cells in a subject infected with coronavirus or influenza virus.

In one embodiment, the MASP-2 inhibitory agent is a small molecule that inhibits MASP-2-dependent complement activation.

In one embodiment, the MASP-2 inhibitory agent is an expression inhibitor of MASP-2.

In one embodiment, the MASP-2 inhibitory antibody is a monoclonal antibody, or fragment thereof that specifically binds to human MASP-2. In one embodiment, the MASP-2 inhibitory antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum with an $IC_{50}$ of 30 nM or less.

In one embodiment, the MASP-2 inhibitory antibody or antigen-binding fragment thereof, comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69. In one embodiment, the MASP-2 inhibitory antibody or antigen-binding fragment thereof comprises a heavy chain variable region comprising the amino acid sequence set forth as SEQ ID NO:67 and a light chain variable region comprising the amino acid sequence set forth as SEQ ID NO:69.

In some embodiments, the method comprises administering to a subject infected with coronavirus or influenza virus a composition comprising a MASP-2 inhibitory antibody, or antigen binding fragment thereof comprising a heavy-chain variable region comprising the amino acid sequence set forth as SEQ ID NO:67 and a light-chain variable region comprising the amino acid sequence set forth as SEQ ID NO:69 in a dosage from 1 mg/kg to 10 mg/kg (i.e., 1 mg/kg, 2 mg/kg, 3 mg/kg, 4 mg/kg, 5 mg/kg, 6 mg/kg, 7 mg/kg, 8 mg/kg, 9 mg/kg or 10 mg/kg) at least once weekly (such as at least twice weekly or at least three times weekly) for a period of at least 2 weeks (such as for at least 3 weeks, or for at least 4 weeks, or for at least 5 weeks, or for at least 6 weeks, or for at least 7 weeks, or for at least 8 weeks, or at least 9 weeks, or at least 10 weeks, or at least 11 weeks, or at least 12 weeks).

In one embodiment, the dosage of MASP-2 inhibitory antibody is about 4 mg/kg (i.e., from 3.6 mg/kg to 4.4 mg/kg).

In one embodiment, the dosage of MASP-2 inhibitory antibody (e.g., narsoplimab) is administered to a subject suffering from COVID-19 at a dosage of about 4 mg/kg (i.e., from 3.6 mg/kg to 4.4 mg/kg) at least twice a week for a time period of at least two weeks, or at least three weeks, or at least four weeks (e.g., from two weeks to four weeks).

In one embodiment, dosage of the MASP-2 inhibitory antibody is a fixed dose from about 300 mg to about 450 mg (i.e., from about 300 mg to about 400 mg, or from about 350 mg to about 400 mg), such as about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg or about 450 mg). In one embodiment, the dosage of the MASP-2 inhibitory antibody is a fixed dose of about 370 mg (±10%).

In one embodiment, the method comprises administering a fixed dosage of MASP-2 inhibitory antibody at about 370 mg (±10%) to a subject infected with coronavirus or influenza virus twice weekly intravenously for a treatment period of at least 8 weeks.

In one embodiment, the MASP-2 inhibitory agent is delivered to the subject systemically. In one embodiment, the MASP-2 inhibitory agent is administered orally, subcutaneously, intraperitoneally, intra-muscularly, intra-arterially, intravenously, or as an inhalant.

In one embodiment, the subject is suffering from COVID-19-induced pneumonia or ARDS and the MASP-2 inhibitory agent (e.g., MASP-2 inhibitory antibody) is administered for a time sufficient to alleviate one or more symptoms of pneumonia or ARDS. In one embodiment, the subject is on a mechanical ventilator and the MASP-2 inhibitory agent (e.g., MASP-2 inhibitory antibody) is administered at a dosage and for a time period sufficient to discontinue the need for mechanical ventilation. In one embodiment the subject is on an invasive mechanical ventilator. In one embodiment, the subject is on a non-invasive mechanical ventilator. In one embodiment, the MASP-2 inhibitory agent (e.g., MASP-2 inhibitory antibody) is administered at a dosage and for a time period sufficient to discontinue the use of supplemental oxygen.

In one embodiment, the MASP-2 inhibitory agent (e.g., MASP-2 inhibitory antibody) is administered to a subject infected with coronavirus or influenza virus as a monotherapy. In some embodiments, the MASP-2 inhibitory agent (e.g., MASP-2 inhibitory antibody) is administered to a subject infected with coronavirus or influenza virus in combination with one or more additional therapeutic agents, such as in a pharmaceutical composition comprising a MASP-2 inhibitory agent and one or more antiviral agents, or one or more anti-coagulants, or one or more therapeutic antibodies or one or more therapeutic small molecule compounds. In some embodiments, the MASP-2 inhibitory agent (e.g., MASP-2 inhibitory antibody) is administered to a subject infected with coronavirus or influenza virus, wherein the subject is undergoing treatment with one or more additional therapeutic agents, such as one or more antiviral agents or one or more anti-coagulants, or one or more therapeutic antibodies or one or more therapeutic small molecule compounds.

In accordance with the foregoing, in another aspect, the present invention provides a method for treating, ameliorating, preventing or reducing the risk of developing one or more long-term sequelae in a mammalian subject infected with coronavirus or influenza virus, comprising administering to the subject an amount of a MASP-2 inhibitory agent effective to inhibit MASP-2-dependent complement activation (i.e., inhibit lectin pathway activation). In some embodiments, the subject is suffering from one or more respiratory symptoms and/or thrombosis and the method comprises administering to the subject an amount of a MASP-2 inhibitory agent effective to improve at least one respiratory symptom (i.e., improve respiratory function) and/or alleviate thrombosis.

In one embodiment, the method comprises administering the composition to a subject infected with COVID-19. In one embodiment, the method comprises administering the composition to a subject infected with SARS-CoV. In one embodiment, the method comprises administering the composition to a subject infected with MERS-CoV. In one embodiment, the subject is identified as having coronavirus (i.e., COVID-19, SARS-CoV or MERS-CoV) prior to administration of the MASP-2 inhibitory agent. In one embodiment, the subject is identified as being infected with SARS-CoV-2 and is in need of supplemental oxygen and the MASP-2 inhibitory agent, such as a MASP-2 inhibitory antibody, such as, for example, narsoplimab, is administered to the subject at a dosage and time period effective to eliminate the need for supplemental oxygen.

In one embodiment, the subject is identified as being infected with COVID-19 and experiences mild symptoms and the MASP-2 inhibitory agent, such as a MASP-2 inhibitory antibody, such as, for example, narsoplimab, is administered to the subject at a dosage and time period effective to treat, ameliorate, prevent or reduce the risk of developing one or more COVID-19 related long-term sequelae in said subject. In some embodiments, the method is useful for treating, ameliorating, preventing or reducing the risk of developing one or more COVID-19 related long term sequelae in a subject suffering from, or previously infected with COVID-19, wherein the long term sequelae are selected from the group consisting of cardiovascular complications (including myocardial injury, cardiomyopathy, myocarditis, intravascular coagulation, stroke, venous and arterial complications and pulmonary thrombosis); neurological complications (including cognitive difficulties, confusion, memory loss, also referred to as "brain fog" headache, stroke, dizziness, syncope, seizure, anorexia, insomnia, anosmia, ageusia, myoclonus, neuropathic pain, myalgias; development of neurological disease such as Alzheimer's disease, Guillian Barre Syndrome, Miller-Fisher Syndrome, Parkinson's disease); kidney injury (such as acute kidney injury (AKI); pulmonary complications including lung fibrosis, dyspnea, pulmonary embolism) and inflammatory conditions such as Kawasaki disease, Kawasaki-like disease, multisystem inflammatory syndrome in children (MIS-C) and multi-system organ failure in a subject that has been infected with COVID-19. Recently published data show that SARS-CoV-2 infection in children results in high incidence of TMA, independent of clinical severity (see Diorio C. et al., *Blood Advances* vol 4(23), Dec. 8, 2020). It has also been reported that SARS-CoV-2 infection in children can result in multi-system inflammatory syndrome (MIS-C) (see Radia T. et al., *Paediatr Respri Rev* Aug. 11, 2020).

Multiple international groups have recently published reports that more than 60% of "recovered" COVID-19 patients have serious sequelae, including cognitive/CNS, pulmonary, cardiac, hepatic and other abnormalities (see e.g., Bonow et al., *JAMA Cardiology* vol 5(7) July 2020; Del Rio et al., *JAMA* vol 324 (17), November 2020; Lindner et al., *JAMA Cardiology* vol 5(11), November 2020; Marchiano S. et al., *bioRxiv*, Aug. 30, 2020; Puntmann V. et al., *JAMA Cardiology* vol 5 (11), November 2020; Xiong Q. et al., *Clin Microbial Infect* 2020). For example, as described in Yelin D. et al., *Lancet Infect Dis* 2020, 9/1/2020, long-term complaints of people recovering from acute COVID-19 include: extreme fatigue, muscle weakness, low grade fever, inability to concentrate, memory lapses, changes in mood, sleep difficulties, needle pains in arms and legs, diarrhea and vomiting, loss of taste and smell, sore throat and difficulties in swallowing, new onset of diabetes and hypertension, skin rash, shortness of breath, chest pains and palpitations. Remarkably, as described in Examples 21 and 22 herein, 5- to 6-month follow-up on the initial 6 Bergamo study COVID-19 patients treated with narsoplimab showed no clinical or laboratory evidence of longer-term COVID-19 sequelae.

In one embodiment, the subject is determined to have an increased level of circulating endothelial cells in a blood sample obtained from the subject prior to treatment with the MASP-2 inhibitory agent as compared to the level of circulating endothelial cells in a control healthy subject or population. In some embodiments, the method comprises administering an amount of a MASP-2 inhibitory agent in an amount sufficient to reduce the number of circulating endothelial cells in a subject infected with coronavirus or influenza virus.

In one embodiment, the MASP-2 inhibitory agent is a small molecule that inhibits MASP-2-dependent complement activation.

In one embodiment, the MASP-2 inhibitory agent is an expression inhibitor of MASP-2.

In one embodiment, the MASP-2 inhibitory antibody is a monoclonal antibody, or fragment thereof that specifically binds to human MASP-2. In one embodiment, the MASP-2 inhibitory antibody or fragment thereof is selected from the group consisting of a recombinant antibody, an antibody having reduced effector function, a chimeric antibody, a humanized antibody, and a human antibody. In one embodiment, the MASP-2 inhibitory antibody does not substantially inhibit the classical pathway. In one embodiment, the MASP-2 inhibitory antibody inhibits C3b deposition in 90% human serum with an $IC_{50}$ of 30 nM or less.

In one embodiment, the MASP-2 inhibitory antibody or antigen-binding fragment thereof, comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69. In one embodiment, the MASP-2 inhibitory antibody or antigen-binding fragment thereof comprises a heavy chain variable region comprising the amino acid sequence set forth as SEQ ID NO:67 and a light chain variable region comprising the amino acid sequence set forth as SEQ ID NO:69.

In some embodiments, the method comprises administering to a subject infected with coronavirus or influenza virus a composition comprising a MASP-2 inhibitory antibody, or antigen binding fragment thereof comprising a heavy-chain variable region comprising the amino acid sequence set forth as SEQ ID NO:67 and a light-chain variable region comprising the amino acid sequence set forth as SEQ ID NO:69 in a dosage from 1 mg/kg to 10 mg/kg (i.e., 1 mg/kg, 2 mg/kg, 3 mg/kg, 4 mg/kg, 5 mg/kg, 6 mg/kg, 7 mg/kg, 8 mg/kg, 9 mg/kg or 10 mg/kg) at least once weekly (such as at least twice weekly or at least three times weekly) for a period of at least 2 weeks (such as for at least 3 weeks, or for at least 4 weeks, or for at least 5 weeks, or for at least 6 weeks, or for at least 7 weeks, or for at least 8 weeks, or at least 9 weeks, or at least 10 weeks, or at least 11 weeks, or at least 12 weeks).

In one embodiment, the dosage of MASP-2 inhibitory antibody is about 4 mg/kg (i.e., from 3.6 mg/kg to 4.4 mg/kg).

In one embodiment, the dosage of MASP-2 inhibitory antibody (e.g., narsoplimab) is administered to a subject suffering from COVID-19 at a dosage of about 4 mg/kg (i.e., from 3.6 mg/kg to 4.4 mg/kg) at least twice a week for a time period of at least two weeks, or at least three weeks, or at least four weeks or at least five weeks or at least 6 weeks or at least 7 weeks or at least 8 weeks (e.g., from two weeks to four weeks, or from two weeks to five weeks or from two to six weeks or from two weeks to seven weeks or from two weeks to eight weeks).

In one embodiment, dosage of the MASP-2 inhibitory antibody is a fixed dose from about 300 mg to about 450 mg (i.e., from about 300 mg to about 400 mg, or from about 350 mg to about 400 mg), such as about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg or about 450 mg). In one embodiment, the dosage of the MASP-2 inhibitory antibody is a fixed dose of about 370 mg (±10%).

In one embodiment, the method comprises administering a fixed dosage of MASP-2 inhibitory antibody at about 370 mg (±10%) to a subject infected with coronavirus or influenza virus twice weekly intravenously for a treatment period of at least 8 weeks.

In one embodiment, the MASP-2 inhibitory agent is delivered to the subject systemically. In one embodiment, the MASP-2 inhibitory agent is administered orally, subcutaneously, intraperitoneally, intra-muscularly, intra-arterially, intravenously, or as an inhalant.

In one embodiment, the subject is suffering from COVID-19-induced pneumonia or ARDS and the MASP-2 inhibitory agent (e.g., MASP-2 inhibitory antibody) is administered for a time sufficient to alleviate one or more symptoms of pneumonia or ARDS and to alleviate or prevent COVID-19-related long term sequelae. In one embodiment, the subject is on a mechanical ventilator and the MASP-2 inhibitory agent (e.g., MASP-2 inhibitory antibody) is administered at a dosage and for a time period sufficient to discontinue the need for mechanical ventilation. In one embodiment the subject is on an invasive mechanical ventilator. In one embodiment, the subject is on a non-invasive mechanical ventilator. In one embodiment, the MASP-2 inhibitory agent (e.g., MASP-2 inhibitory antibody) is administered at a dosage and for a time period sufficient to discontinue the use of supplemental oxygen.

In one embodiment, the MASP-2 inhibitory agent (e.g., MASP-2 inhibitory antibody) is administered to a subject infected with coronavirus or influenza virus as a monotherapy. In some embodiments, the MASP-2 inhibitory agent (e.g., MASP-2 inhibitory antibody) is administered to a subject infected with coronavirus or influenza virus in combination with one or more additional therapeutic agents, such as in a pharmaceutical composition comprising a MASP-2 inhibitory agent and one or more antiviral agents, or one or more anti-coagulants, or one or more therapeutic antibodies or one or more therapeutic small molecule compounds. In some embodiments, the MASP-2 inhibitory agent (e.g., MASP-2 inhibitory antibody) is administered to a subject infected with coronavirus or influenza virus, wherein the subject is undergoing treatment with one or more additional therapeutic agents, such as one or more antiviral agents or one or more anti-coagulants, or one or more therapeutic antibodies or one or more therapeutic small molecule compounds.

Other Embodiments

I. Methods for Treating, Inhibiting, Alleviating or Preventing Acute Respiratory Distress Syndrome in a Subject Infected with Coronavirus.

1. A method for treating, inhibiting, alleviating, or preventing acute respiratory distress syndrome, pneumonia, or some other pulmonary or other manifestation of coronavirus infection, such as thrombosis, in a mammalian subject infected with coronavirus, comprising administering to the subject an amount of a MASP-2 inhibitory agent effective to inhibit MASP-2-dependent complement activation.

2. The method of paragraph 1, wherein the MASP-2 inhibitory agent is a MASP-2 antibody or fragment thereof.

3. The method of paragraph 2, wherein the MASP-2 inhibitory agent is a MASP-2 monoclonal antibody, or fragment thereof that specifically binds to a portion of SEQ ID NO:6.

4. The method of paragraph 2, wherein the MASP-2 antibody or fragment thereof specifically binds to a polypeptide comprising SEQ ID NO:6 with an affinity of at least 10 times greater than it binds to a different antigen in the complement system.

5. The method of paragraph 2, wherein the antibody or fragment thereof is selected from the group consisting of a recombinant antibody, an antibody having reduced effector function, a chimeric antibody, a humanized antibody and a human antibody.

6. The method of paragraph 2, wherein the MASP-2 inhibitory antibody selectively inhibits lectin pathway complement activation without substantially inhibiting C1q-dependent complement activation.

7. The method of paragraph 2, wherein the MASP-2 inhibitory antibody inhibits C3b deposition in 10% human serum with an $IC_{50}$ of 30 nM or less.

8. The method of paragraph 2, wherein the MASP-2 inhibitory antibody inhibits C3b deposition in 90% human serum with an $IC_{50}$ of 30 nM or less.

9. The method of paragraph 2, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

10. The method of paragraph 2, wherein the MASP-2 inhibitory antibody or antigen-binding fragment thereof comprises a heavy chain variable region comprising SEQ ID NO:67 and a light chain variable region comprising SEQ ID NO:69.

11. The method of paragraph 1, wherein the MASP-2 inhibitory agent is a small molecule MASP-2 inhibitory compound.

12. The method of paragraph 11, wherein the MASP-2 inhibitory compound is a synthetic or semi-synthetic small molecule.

13. The method of paragraph 1, wherein the MASP-2 inhibitory agent is an expression inhibitor of MASP-2.

14. The method of paragraph 11, wherein the small molecule MASP-2 inhibitory compound is a compound of any one of the Formulae (IA), (IB), (IIA), (IIB), (III), (IV), (VA), (VB), (VIA), (VB), (VIIA), or (VIIB).

15. The method of paragraph 11, wherein the small molecule MASP-2 inhibitory compound is a compound having the following structure:

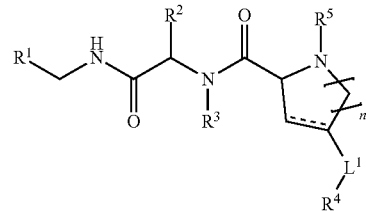

or a stereoisomer, tautomer, or pharmaceutically acceptable salt thereof, wherein:
    ==== represents a double or single bond;
    $R^1$ is a substituted or unsubstituted aryl or a substituted or unsubstituted heteroaryl;
    $R^2$ is hydrogen, alkyl, alkoxy, haloalkyl, hydroxyalkyl, haloalkoxy, or cycloalkyl;
    $R^3$ is hydrogen, alkyl, haloalkyl, or cycloalkyl, or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or substituted or unsubstituted heterocyclyl;

$R^5$ is hydrogen, alkyl, haloalkyl, cycloalkyl, phosphonalkyl, $(CH_2)_mC(=O)OR^6$, $C(=O)R^6$, $C(=O)OR^6$, $(CH_2)_mNR^6S(O)_2R^7$, or $C(=O)NR^6R^7$;

$R^6$ and $R^7$ are, at each occurrence, independently hydrogen, alkyl, haloalkyl, cycloalkyl, or arylalkyl;

$L^1$ is a direct bond, $-CR^{8a}R^{8b}-$, $-S(O)_t-$, $NR^{8c}$, or $-O-$;

$R^{8a}$ and $R^{8b}$ are each independently hydrogen, alkyl, or $R^{8a}$ and $R^{8b}$, together with the carbon to which they are attached form an optionally substituted 3-6 membered cycloalkyl;

$R^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;

n is 1 or 2;

m is 1, 2, 3, 4, 5, or 6; and t is 0, 1, or 2.

16. The method of paragraph 11, wherein the small molecule MASP-2 inhibitory compound is a compound of Table 4A, 4B, 4C, 4D, or 4E.

17. The method of paragraph 11, wherein the small molecule MASP-2 inhibitory compound a small molecule with a molecular weight from 200 Da to 2,000 Da, from 250 Da to 2,000 Da, from 300 Da to 2,000 Da, from 300 Da to 1,000 Da, from 300 Da to 600 Da, from 350 Da to 2,000 Da, from 350 Da to 1,500 Da, from 350 Da to 1,200 Da, from 350 Da to 1,000 Da, from 350 Da to 900 Da, from 350 Da to 800 Da, from 350 Da to 700 Da, from 350 Da to 600 Da.

18. The method of paragraph 11, wherein the small molecule MASP-2 inhibitory compound has zero to one basic groups selected from guanidine and benzamidine groups.

19. The method of paragraph 11, wherein the small molecule MASP-2 inhibitory compound has a MASP-2 inhibition Ki value of less than about 25 µM, less than about 10 µM, less than about 2.5 µM, less than about 1 µM, less than about 0.5 µM, or less than about 0.1 µM.

20. The method of paragraph 11, wherein the small molecule MASP-2 inhibitory compound is a lectin pathway inhibitor with a lectin pathway inhibition $IC_{50}$ of less than about 50 µM, less than about 5 µM, less than about 1 µM, less than about 0.5 µM, or less than about 0.05 µM.

21. The method of paragraph 11, wherein the small molecule MASP-2 inhibitory compound is a selective MASP-2 inhibitor with a selectivity for MASP-2 inhibition versus thrombin inhibition of greater than about 2-fold, greater than about 5-fold, greater than about 10-fold, greater than about 25-fold, greater than about 50-fold, or greater than about 100-fold.

22. The method of paragraph 11, wherein the small molecule MASP-2 inhibitory compound has a greater affinity for MASP-2 for thrombin with the selectivity ratio of MAASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

22. The method of paragraph 11, wherein the small molecule MASP-2 inhibitory compound is not a covalent inhibitor of MASP-2.

23. The method of paragraph 11, wherein the small molecule MASP-2 inhibitory compound is not an endogenous MASP-2 ligand or substrate.

24. The method of any of paragraphs 1 to 23, wherein the MASP-2 inhibitory agent is administered subcutaneously, intraperitoneally, intra-muscularly, intra-arterially, intravenously, orally, or as an inhalant.

25. The method of any of paragraphs 1 to 24, wherein the coronavirus is severe acute respiratory syndrome coronavirus 2 (otherwise referred to as SARS coronavirus 2 or SARS-CoV-2).

26. The method of any of paragraphs 1 to 24, wherein the coronavirus is severe acute respiratory syndrome coronavirus (SARS-CoV).

27. The method of any of paragraphs 1 to 24, wherein the coronavirus is Middle East respiratory syndrome coronavirus (MERS-CoV).

28. The method of any of paragraphs 1 to 27, wherein the subject is identified as having coronavirus prior to administration of the MASP-2 inhibitory agent.

29. The method of any of paragraphs 1 to 28, wherein the MASP-2 inhibitory antibody or antigen-binding fragment thereof is administered in an amount effective to improve respiratory function.

30. The method of any of paragraphs 1 to 29, wherein the mammalian subject is a human subject.

II. Methods for Treating a Human Subject Suffering from COVID-19 Induced Acute Respiratory Distress Syndrome (ARDS) or Pneumonia 1. A method for treating a human subject suffering from COVID-19 induced acute respiratory distress syndrome (ARDS) or pneumonia, comprising administering to the subject an amount of a MASP-2 inhibitory agent effective to inhibit MASP-2-dependent complement activation.

2. The method of paragraph 1, wherein the subject is on a mechanical ventilator prior to treatment and the MASP-2 inhibitory agent is administered at a dosage and for a time period sufficient to discontinue the need for mechanical ventilation.

3. The method of paragraph 2, wherein the subject is on an invasive mechanical ventilator.

4. The method of paragraph 2, wherein the subject is on a non-invasive mechanical ventilator.

5. The method of paragraph 1, wherein the subject requires supplemental oxygen prior to treatment and the MASP-2 inhibitory agent is administered at a dosage and for a time period sufficient to discontinue the use of supplemental oxygen.

6. The method of any of paragraphs 1 to 5, wherein the MASP-2 inhibitory agent is a MASP-2 antibody or fragment thereof.

7. The method of paragraph 6, wherein the MASP-2 inhibitory agent is a MASP-2 monoclonal antibody, or fragment thereof that specifically binds to a portion of SEQ ID NO:6.

8. The method of paragraph 6 or 7, wherein the MASP-2 antibody or fragment thereof specifically binds to a polypeptide comprising SEQ ID NO:6 with an affinity of at least 10 times greater than it binds to a different antigen in the complement system.

9. The method of any of paragraphs 6 to 8, wherein the antibody or fragment thereof is selected from the group consisting of a recombinant antibody, an antibody having reduced effector function, a chimeric antibody, a humanized antibody and a human antibody.

10. The method of any of paragraphs 6 to 9, wherein the MASP-2 inhibitory antibody selectively inhibits lectin pathway complement activation without substantially inhibiting C1q-dependent complement activation.

11. The method of any of paragraphs 6 to 10, wherein the MASP-2 inhibitory antibody inhibits C3b deposition in 10% human serum with an $IC_{50}$ of 30 nM or less.

12. The method of any of paragraphs 6 to 10, wherein the MASP-2 inhibitory antibody inhibits C3b deposition in 90% human serum with an $IC_{50}$ of 30 nM or less.

13. The method of any of paragraphs 6 to 12, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

14. The method of any of paragraphs 6 to 13, wherein the MASP-2 inhibitory antibody or antigen-binding fragment thereof comprises a heavy chain variable region comprising SEQ ID NO:67 and a light chain variable region comprising SEQ ID NO:69.

15. The method of any of paragraphs 1 to 5, wherein the MASP-2 inhibitory agent is a small molecule MASP-2 inhibitory compound.

16. The method of paragraph 15, wherein the MASP-2 inhibitory compound is a synthetic or semi-synthetic small molecule.

17. The method of paragraph 1, wherein the MASP-2 inhibitory agent is an expression inhibitor of MASP-2.

18. The method of paragraph 15, wherein the small molecule MASP-2 inhibitory compound is a compound of any one of the Formulae (IA), (IB), (IIA), (IIB), (III), (IV), (VA), (VB), (VIA), (VB), (VIIA), or (VIIB).

19. The method of paragraph 15, wherein the small molecule MASP-2 inhibitory compound is a compound having the following structure:

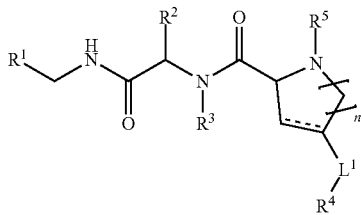

or a stereoisomer, tautomer, or pharmaceutically acceptable salt thereof, wherein:
==== represents a double or single bond;
$R^1$ is a substituted or unsubstituted aryl or a substituted or unsubstituted heteroaryl;
$R^2$ is hydrogen, alkyl, alkoxy, haloalkyl, hydroxyalkyl, haloalkoxy, or cycloalkyl;
$R^3$ is hydrogen, alkyl, haloalkyl, or cycloalkyl, or $R^2$ and $R^3$, together with the carbon and nitrogen to which they are attached, respectively, form an optionally substituted 4-7 membered heterocyclyl;
$R^4$ is a substituted or unsubstituted aryl, substituted or unsubstituted heteroaryl, substituted or unsubstituted cycloalkyl, or substituted or unsubstituted heterocyclyl;
$R^5$ is hydrogen, alkyl, haloalkyl, cycloalkyl, phosphonalkyl, $(CH_2)_mC(=O)OR^6$, $C(=O)R^6$, $C(=O)OR^6$, $(CH_2)_mNR^6S(O)_2R^7$, or $C(=O)NR^6R^7$;
$R^6$ and $R^7$ are, at each occurrence, independently hydrogen, alkyl, haloalkyl, cycloalkyl, or arylalkyl;
$L^1$ is a direct bond, $-CR^{8a}R^{8b}-$, $-S(O)_t-$, $NR^{8c}$, or $-O-$;
$R^{8a}$ and $R^{8b}$ are each independently hydrogen, alkyl, or $R^{8a}$ and $R^{8b}$, together with the carbon to which they are attached form an optionally substituted 3-6 membered cycloalkyl;
$R^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;
n is 1 or 2;
m is 1, 2, 3, 4, 5, or 6; and
t is 0, 1, or 2.

20. The method of paragraph 15, wherein the small molecule MASP-2 inhibitory compound is a compound of Table 4A, 4B, 4C, 4D, or 4E.

21. The method of paragraph 15, wherein the small molecule MASP-2 inhibitory compound a small molecule with a molecular weight from 200 Da to 2,000 Da, from 250 Da to 2,000 Da, from 300 Da to 2,000 Da, from 300 Da to 1,000 Da, from 300 Da to 600 Da, from 350 Da to 2,000 Da, from 350 Da to 1,500 Da, from 350 Da to 1,200 Da, from 350 Da to 1,000 Da, from 350 Da to 900 Da, from 350 Da to 800 Da, from 350 Da to 700 Da, from 350 Da to 600 Da.

22. The method of paragraph 15, wherein the small molecule MASP-2 inhibitory compound has zero to one basic groups selected from guanidine and benzamidine groups.

23. The method of paragraph 15, wherein the small molecule MASP-2 inhibitory compound has a MASP-2 inhibition Ki value of less than about 25 µM, less than about 10 µM, less than about 2.5 µM, less than about 1 µM, less than about 0.5 µM, or less than about 0.1 µM.

24. The method of paragraph 15, wherein the small molecule MASP-2 inhibitory compound is a lectin pathway inhibitor with a lectin pathway inhibition $IC_{50}$ of less than about 50 µM, less than about 5 µM, less than about 1 µM, less than about 0.5 µM, or less than about 0.05 µM.

25. The method of paragraph 15, wherein the small molecule MASP-2 inhibitory compound is a selective MASP-2 inhibitor with a selectivity for MASP-2 inhibition versus thrombin inhibition of greater than about 2-fold, greater than about 5-fold, greater than about 10-fold, greater than about 25-fold, greater than about 50-fold, or greater than about 100-fold.

26. The method of paragraph 15, wherein the small molecule MASP-2 inhibitory compound has a greater affinity for MASP-2 for thrombin with the selectivity ratio of MAASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

27. The method of paragraph 15, wherein the small molecule MASP-2 inhibitory compound is not a covalent inhibitor of MASP-2.

28. The method of paragraph 15, wherein the small molecule MASP-2 inhibitory compound is not an endogenous MASP-2 ligand or substrate.

29. The method of any of paragraphs 1 to 28, wherein the MASP-2 inhibitory agent is administered subcutaneously, intraperitoneally, intra-muscularly, intra-arterially, intravenously, orally, or as an inhalant.

III. A Method for Treating, Inhibiting, Alleviating or Preventing Thrombosis in a Human Subject Infected with SARS-CoV-2

1. A method for treating, preventing or reducing the severity or coagulation or thrombosis in a human subject infected with SARS-CoV-2 comprising administering to the subject an amount of a MASP-2 inhibitory agent effective to treat, prevent or reduce the severity of coagulation or thrombosis in said subject.

2. The method of paragraph 1, wherein the subject has a D-Dimer level higher than the standard range prior to treatment and the MASP-2 inhibitory agent is administered in an amount and for a time sufficient to reduce the level of D-Dimer in said subject into the normal range of a healthy subject.

3. The method of paragraph 1 or 2, wherein the MASP-2 inhibitory agent provides anticoagulation and/or antithrombosis effects without affecting hemostasis.

4. The method of any of paragraphs 1 to 3, wherein the MASP-2 inhibitory agent is a MASP-2 antibody or fragment thereof.

5. The method of paragraph 4, wherein the MASP-2 inhibitory agent is a MASP-2 monoclonal antibody, or fragment thereof that specifically binds to a portion of SEQ ID NO:6.

6. The method of paragraph 4 or 5, wherein the MASP-2 antibody or fragment thereof specifically binds to a polypeptide comprising SEQ ID NO:6 with an affinity of at least 10 times greater than it binds to a different antigen in the complement system.

7. The method of any of paragraphs 4 to 6, wherein the antibody or fragment thereof is selected from the group consisting of a recombinant antibody, an antibody having reduced effector function, a chimeric antibody, a humanized antibody and a human antibody.

8. The method of any of paragraphs 4 to 7, wherein the MASP-2 inhibitory antibody selectively inhibits lectin pathway complement activation without substantially inhibiting C1q-dependent complement activation.

9. The method of any of paragraphs 4 to 8, wherein the MASP-2 inhibitory antibody inhibits C3b deposition in 10% human serum with an $IC_{50}$ of 30 nM or less.

10. The method of any of paragraphs 4 to 9, wherein the MASP-2 inhibitory antibody inhibits C3b deposition in 90% human serum with an $IC_{50}$ of 30 nM or less.

11. The method of any of paragraphs 4 to 10, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

12. The method of any of paragraphs 4 to 11, wherein the MASP-2 inhibitory antibody or antigen-binding fragment thereof comprises a heavy chain variable region comprising SEQ ID NO:67 and a light chain variable region comprising SEQ ID NO:69.

13. The method of any of paragraphs 1 to 3, wherein the MASP-2 inhibitory agent is a small molecule MASP-2 inhibitory compound.

14. The method of paragraph 13, wherein the MASP-2 inhibitory compound is a synthetic or semi-synthetic small molecule.

15. The method of paragraph 1, wherein the MASP-2 inhibitory agent is an expression inhibitor of MASP-2.

16. The method of paragraph 13, wherein the small molecule MASP-2 inhibitory compound is a compound of any one of the Formulae (IA), (IB), (IIA), (IIB), (III), (IV), (VA), (VB), (VIA), (VB), (VIIA), or (VIIB).

17. The method of paragraph 13, wherein the small molecule MASP-2 inhibitory compound is a compound having the following structure:

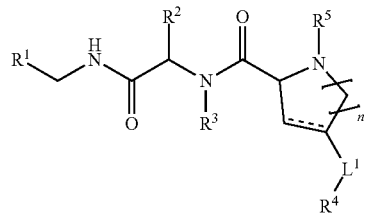

or a stereoisomer, tautomer, or pharmaceutically acceptable salt thereof, wherein:

==== represents a double or single bond;

$R^1$ is a substituted or unsubstituted aryl or a substituted or unsubstituted heteroaryl;

$R^2$ is hydrogen, alkyl, alkoxy, haloalkyl, hydroxyalkyl, haloalkoxy, or cycloalkyl;

$R^3$ is hydrogen, alkyl, haloalkyl, or cycloalkyl, or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or substituted or unsubstituted heterocyclyl;

$R^5$ is hydrogen, alkyl, haloalkyl, cycloalkyl, phosphonalkyl, $(CH_2)_mC(=O)OR^6$, $C(=O)R^6$, $C(=O)OR^6$, $(CH_2)_mNR^6S(O)_2R^7$, or $C(=O)NR^6R^7$;

$R^6$ and $R^7$ are, at each occurrence, independently hydrogen, alkyl, haloalkyl, cycloalkyl, or arylalkyl;

$L^1$ is a direct bond, $-CR^{8a}R^{8b}-$, $-S(O)_t-$, $NR^{8c}$, or $-O-$;

$R^{8a}$ and $R^{8b}$ are each independently hydrogen, alkyl, or $R^{8a}$ and $R^{8b}$, together with the carbon to which they are attached form an optionally substituted 3-6 membered cycloalkyl;

$R^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;

n is 1 or 2;

m is 1, 2, 3, 4, 5, or 6; and t is 0, 1, or 2.

18. The method of paragraph 13, wherein the small molecule MASP-2 inhibitory compound is a compound of Table 4A, 4B, 4C, 4D, or 4E.

19. The method of paragraph 13, wherein the small molecule MASP-2 inhibitory compound a small molecule with a molecular weight from 200 Da to 2,000 Da, from 250 Da to 2,000 Da, from 300 Da to 2,000 Da, from 300 Da to 1,000 Da, from 300 Da to 600 Da, from 350 Da to 2,000 Da, from 350 Da to 1,500 Da, from 350 Da to 1,200 Da, from 350 Da to 1,000 Da, from 350 Da to 900 Da, from 350 Da to 800 Da, from 350 Da to 700 Da, from 350 Da to 600 Da.

20. The method of paragraph 13, wherein the small molecule MASP-2 inhibitory compound has zero to one basic groups selected from guanidine and benzamidine groups.

21. The method of paragraph 13, wherein the small molecule MASP-2 inhibitory compound has a MASP-2 inhibition Ki value of less than about 25 µM, less than about 10 µM, less than about 2.5 µM, less than about 1 µM, less than about 0.5 µM, or less than about 0.1 µM.

22. The method of paragraph 13, wherein the small molecule MASP-2 inhibitory compound is a lectin pathway inhibitor with a lectin pathway inhibition $IC_{50}$ of less than about 50 µM, less than about 5 µM, less than about 1 µM, less than about 0.5 µM, or less than about 0.05 µM.

23. The method of paragraph 13, wherein the small molecule MASP-2 inhibitory compound is a selective MASP-2 inhibitor with a selectivity for MASP-2 inhibition versus thrombin inhibition of greater than about 2-fold, greater than about 5-fold, greater than about 10-fold, greater than about 25-fold, greater than about 50-fold, or greater than about 100-fold.

24. The method of paragraph 13, wherein the small molecule MASP-2 inhibitory compound has a greater affinity for MASP-2 for thrombin with the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

25. The method of paragraph 13, wherein the small molecule MASP-2 inhibitory compound is not a covalent inhibitor of MASP-2.

26. The method of paragraph 13, wherein the small molecule MASP-2 inhibitory compound is not an endogenous MASP-2 ligand or substrate.

27. The method of any of paragraphs 1 to 26, wherein the MASP-2 inhibitory agent is administered subcutaneously, intraperitoneally, intra-muscularly, intra-arterially, intravenously, orally, or as an inhalant.

IV. A Method for Treating, Ameliorating, Preventing or Reducing the Risk of Developing One or More COVID-19-Related Long-Term Sequelae in a Human Subject that has been Infected with SARS-CoV-2

1. A method for treating, ameliorating, preventing or reducing the risk of developing one or more COVID-19-related long-term sequelae in a human subject that is currently infected with SARS-CoV-2 or has been infected with SARS-CoV-2, comprising administering to the subject an amount of a MASP-2 inhibitory agent effective to inhibit MASP-2-dependent complement activation.

2. The method of paragraph 1, wherein the subject is suffering from COVID-19-induced pneumonia or ARDS and the MASP-2 inhibitory agent is administered in an amount effective to improve respiratory function.

3. The method of paragraph 1, wherein the subject is suffering from COVID-19-induced coagulation or thrombosis and the MASP-2 inhibitory agent is administered to the subject in an amount effective to treat, prevent or reduce the severity of coagulation or thrombosis in said subject.

4. The method of any of paragraphs 1 to 3, wherein the MASP-2 inhibitory agent is a MASP-2 antibody or fragment thereof.

5. The method of paragraph 4, wherein the MASP-2 inhibitory agent is a MASP-2 monoclonal antibody, or fragment thereof that specifically binds to a portion of SEQ ID NO:6.

6. The method of paragraph 4 or 5, wherein the MASP-2 antibody or fragment thereof specifically binds to a polypeptide comprising SEQ ID NO:6 with an affinity of at least 10 times greater than it binds to a different antigen in the complement system.

7. The method of any of paragraphs 4 to 6, wherein the antibody or fragment thereof is selected from the group consisting of a recombinant antibody, an antibody having reduced effector function, a chimeric antibody, a humanized antibody and a human antibody.

8. The method of any of paragraphs 4 to 7, wherein the MASP-2 inhibitory antibody selectively inhibits lectin pathway complement activation without substantially inhibiting C1q-dependent complement activation.

9. The method of any of paragraphs 4 to 8, wherein the MASP-2 inhibitory antibody inhibits C3b deposition in 10% human serum with an $IC_{50}$ of 30 nM or less.

10. The method of any of paragraphs 4 to 9, wherein the MASP-2 inhibitory antibody inhibits C3b deposition in 90% human serum with an $IC_{50}$ of 30 nM or less.

11. The method of any of paragraphs 4 to 10, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

12. The method of any of paragraphs 4 to 11, wherein the MASP-2 inhibitory antibody or antigen-binding fragment thereof comprises a heavy chain variable region comprising SEQ ID NO:67 and a light chain variable region comprising SEQ ID NO:69.

13. The method of any of paragraphs 1 to 3, wherein the MASP-2 inhibitory agent is a small molecule MASP-2 inhibitory compound.

14. The method of paragraph 13, wherein the MASP-2 inhibitory compound is a synthetic or semi-synthetic small molecule.

15. The method of paragraph 1, wherein the MASP-2 inhibitory agent is an expression inhibitor of MASP-2.

16. The method of paragraph 13, wherein the small molecule MASP-2 inhibitory compound is a compound of any one of the Formulae (IA), (IB), (IIA), (IIB), (III), (IV), (VA), (VB), (VIA), (VB), (VIIA), or (VIIB).

17. The method of paragraph 13, wherein the small molecule MASP-2 inhibitory compound is a compound having the following structure:

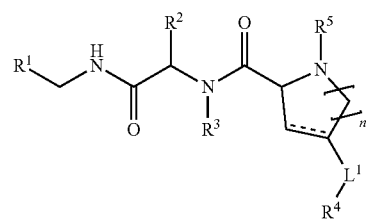

or a stereoisomer, tautomer, or pharmaceutically acceptable salt thereof, wherein:

==== represents a double or single bond;

$R^1$ is a substituted or unsubstituted aryl or a substituted or unsubstituted heteroaryl;

$R^2$ is hydrogen, alkyl, alkoxy, haloalkyl, hydroxyalkyl, haloalkoxy, or cycloalkyl;

$R^3$ is hydrogen, alkyl, haloalkyl, or cycloalkyl, or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or substituted or unsubstituted heterocyclyl;

$R^5$ is hydrogen, alkyl, haloalkyl, cycloalkyl, phosphonalkyl, $(CH_2)_m C(=O)OR^6$, $C(=O)R^6$, $C(=O)OR^6$, $(CH_2)_m NR^6 S(O)_2 R^7$, or $C(=O)NR^6 R^7$;

$R^6$ and $R^7$ are, at each occurrence, independently hydrogen, alkyl, haloalkyl, cycloalkyl, or arylalkyl;

$L^1$ is a direct bond, $-CR^{8a}R^{8b}-$, $-S(O)_t-$, $NR^{8c}$, or $-O-$;

$R^{8a}$ and $R^{8b}$ are each independently hydrogen, alkyl, or $R^{8a}$ and $R^{8b}$, together with the carbon to which they are attached form an optionally substituted 3-6 membered cycloalkyl;

$R^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;

n is 1 or 2;

m is 1, 2, 3, 4, 5, or 6; and t is 0, 1, or 2.

18. The method of paragraph 13, wherein the small molecule MASP-2 inhibitory compound is a compound of Table 4A, 4B, 4C, 4D, or 4E.

19. The method of paragraph 13, wherein the small molecule MASP-2 inhibitory compound a small molecule with a molecular weight from 200 Da to 2,000 Da, from 250 Da to 2,000 Da, from 300 Da to 2,000 Da, from 300 Da to 1,000 Da, from 300 Da to 600 Da, from 350 Da to 2,000 Da, from 350 Da to 1,500 Da, from 350 Da to 1,200 Da, from 350 Da to 1,000 Da, from 350 Da to 900 Da, from 350 Da to 800 Da, from 350 Da to 700 Da, from 350 Da to 600 Da.

20. The method of paragraph 13, wherein the small molecule MASP-2 inhibitory compound has zero to one basic groups selected from guanidine and benzamidine groups.

21. The method of paragraph 13, wherein the small molecule MASP-2 inhibitory compound has a MASP-2 inhibition Ki value of less than about 25 µM, less than about 10 µM, less than about 2.5 µM, less than about 1 µM, less than about 0.5 µM, or less than about 0.1 µM.

22. The method of paragraph 13, wherein the small molecule MASP-2 inhibitory compound is a lectin pathway inhibitor with a lectin pathway inhibition $IC_{50}$ of less than about 50 µM, less than about 5 µM, less than about 1 µM, less than about 0.5 µM, or less than about 0.05 µM.

23. The method of paragraph 13, wherein the small molecule MASP-2 inhibitory compound is a selective MASP-2 inhibitor with a selectivity for MASP-2 inhibition versus thrombin inhibition of greater than about 2-fold, greater than about 5-fold, greater than about 10-fold, greater than about 25-fold, greater than about 50-fold, or greater than about 100-fold.

24. The method of paragraph 13, wherein the small molecule MASP-2 inhibitory compound has a greater affinity for MASP-2 for thrombin with the selectivity ratio of MASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

25. The method of paragraph 13, wherein the small molecule MASP-2 inhibitory compound is not a covalent inhibitor of MASP-2.

26. The method of paragraph 13, wherein the small molecule MASP-2 inhibitory compound is not an endogenous MASP-2 ligand or substrate.

27. The method of any of paragraphs 1 to 26, wherein the MASP-2 inhibitory agent is administered subcutaneously, intraperitoneally, intra-muscularly, intra-arterially, intravenously, orally, or as an inhalant.

28. The method of any of paragraphs 1 to 27, wherein the one or more COVID-19 related long term sequelae is selected from the group consisting of a cardiovascular complication (including myocardial injury, cardiomyopathy, myocarditis, intravascular coagulation, stroke, venous and arterial complications and pulmonary thrombosis); a neurological complication (including cognitive difficulties, confusion, memory loss, also referred to as "brain fog," headache, stroke, dizziness, syncope, seizure, anorexia, insomnia, anosmia, ageusia, myoclonus, neuropathic pain, myalgias, development of neurological disease such as Alzheimer's disease, Guillian Barre Syndrome, Miller-Fisher Syndrome, Parkinson's disease) kidney injury (such as acute kidney injury (AKI); a pulmonary complication (including lung fibrosis, dyspnea, pulmonary embolism), an inflammatory condition such as Kawasaki disease, Kawasaki-like disease, multisystem inflammatory syndrome in children, multi-system organ failure, extreme fatigue, muscle weakness, low grade fever, inability to concentrate, memory lapses, changes in mood, sleep difficulties, needle pains in arms and legs, diarrhea and vomiting, loss of taste and smell, sore throat and difficulties in swallowing, new onset of diabetes and hypertension, skin rash, shortness of breath, chest pains and palpitations.

29. The method of Claim 28, wherein the subject has recovered from COVID-19 induced pneumonia or ARDS and the MASP-2 inhibitory agent is administered in an amount to treat or ameliorate one or more long-term sequelae.

30. The method of Claim 28, wherein the subject has recovered from COVID-19 induced coagulation or thrombosis and the MASP-2 inhibitory agent is administered in an amount to treat or ameliorate one or more long-term sequelae.

V. A Method for Treating, Inhibiting, Alleviating or Preventing Acute Respiratory Distress Syndrome, Pneumonia or Some Other Pulmonary or Other Manifestation of Influenza Virus Infection, in a Mammalian Subject Infected with Influenza Virus 1. A method for treating, inhibiting, alleviating or preventing acute respiratory distress syndrome, pneumonia or some other pulmonary or other manifestation of influenza virus infection, in a mammalian subject infected with influenza virus, comprising administering to the subject an amount of a MASP-2 inhibitory agent effective to inhibit MASP-2-dependent complement activation.

2. The method of paragraph 1, wherein the influenza virus is influenza virus A, influenza virus B or influenza virus C.

3. The method of paragraph 2, wherein the influenza virus A is selected from the group consisting of H1N1, H2N2, H3N2, H5N1, H7N7, H1N2, H9N2, H7N2, H7N3, H10N7, H7N9 and H6N1.

4. The method of any of paragraphs 1 to 3, wherein the subject is identified as having influenza virus prior to administration of the MASP-2 inhibitory agent.

5. The method of any of paragraphs 1 to 4, wherein the MASP-2 inhibitory agent is administered in an amount effective to improve respiratory function.

6. The method of any of paragraphs 1 to 5, wherein the MASP-2 inhibitory agent is a MASP-2 antibody or fragment thereof.

7. The method of paragraph 6, wherein the MASP-2 inhibitory agent is a MASP-2 monoclonal antibody, or fragment thereof that specifically binds to a portion of SEQ ID NO:6.

8. The method of paragraph 6 or 7, wherein the MASP-2 antibody or fragment thereof specifically binds to a polypeptide comprising SEQ ID NO:6 with an affinity of at least 10 times greater than it binds to a different antigen in the complement system.

9. The method of any of paragraphs 6 to 8, wherein the antibody or fragment thereof is selected from the group consisting of a recombinant antibody, an antibody having reduced effector function, a chimeric antibody, a humanized antibody and a human antibody.

10. The method of any of paragraphs 6 to 9, wherein the MASP-2 inhibitory antibody selectively inhibits lectin pathway complement activation without substantially inhibiting C1q-dependent complement activation.

11. The method of any of paragraphs 6 to 10, wherein the MASP-2 inhibitory antibody inhibits C3b deposition in 10% human serum with an IC$_{50}$ of 30 nM or less.

12. The method of any of paragraphs 6 to 10, wherein the MASP-2 inhibitory antibody inhibits C3b deposition in 90% human serum with an IC$_{50}$ of 30 nM or less.

13. The method of any of paragraphs 6 to 12, wherein the MASP-2 inhibitory antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

14. The method of any of paragraphs 6 to 13, wherein the MASP-2 inhibitory antibody or antigen-binding fragment thereof comprises a heavy chain variable region comprising SEQ ID NO:67 and a light chain variable region comprising SEQ ID NO:69.

15. The method of any of paragraphs 1 to 5, wherein the MASP-2 inhibitory agent is a small molecule MASP-2 inhibitory compound.

16. The method of paragraph 15, wherein the MASP-2 inhibitory compound is a synthetic or semi-synthetic small molecule.

17. The method of paragraph 1, wherein the MASP-2 inhibitory agent is an expression inhibitor of MASP-2.

18. The method of paragraph 15, wherein the small molecule MASP-2 inhibitory compound is a compound of any one of the Formulae (IA), (IB), (IIA), (IIB), (III), (IV), (VA), (VB), (VIA), (VB), (VIIA), or (VIIB).

19. The method of paragraph 15, wherein the small molecule MASP-2 inhibitory compound is a compound having the following structure:

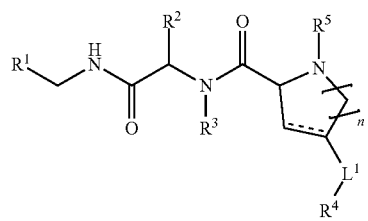

or a stereoisomer, tautomer, or pharmaceutically acceptable salt thereof, wherein:
 ⸺ represents a double or single bond;
R$^1$ is a substituted or unsubstituted aryl or a substituted or unsubstituted heteroaryl;
R$^2$ is hydrogen, alkyl, alkoxy, haloalkyl, hydroxyalkyl, haloalkoxy, or cycloalkyl;
R$^3$ is hydrogen, alkyl, haloalkyl, or cycloalkyl, or R$^2$ and R$^3$, together with the carbon and nitrogen to which they are attached, respectively, form an optionally substituted 4-7 membered heterocyclyl;
R$^4$ is a substituted or unsubstituted aryl, substituted or unsubstituted heteroaryl, substituted or unsubstituted cycloalkyl, or substituted or unsubstituted heterocyclyl;
R$^5$ is hydrogen, alkyl, haloalkyl, cycloalkyl, phosphonalkyl, (CH$_2$)$_m$C(=O)OR$^6$, C(=O)R$^6$, C(=O)OR$^6$, (CH$_2$)$_m$NR$^6$S(O)$_2$R$^7$, or C(=O)NR$^6$R$^7$;
R$^6$ and R$^7$ are, at each occurrence, independently hydrogen, alkyl, haloalkyl, cycloalkyl, or arylalkyl;
L$^1$ is a direct bond, —CR$^{8a}$R$^{8b}$—, —S(O)$_t$—, NR$^{8c}$, or —O—;
R$^{8a}$ and R$^{8b}$ are each independently hydrogen, alkyl, or R$^{8a}$ and R$^{8b}$, together with the carbon to which they are attached form an optionally substituted 3-6 membered cycloalkyl;
R$^{8c}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl;
n is 1 or 2;
m is 1, 2, 3, 4, 5, or 6; and
t is 0, 1, or 2.

20. The method of paragraph 15, wherein the small molecule MASP-2 inhibitory compound is a compound of Table 4A, 4B, 4C, 4D, or 4E.

21. The method of paragraph 15, wherein the small molecule MASP-2 inhibitory compound a small molecule with a molecular weight from 200 Da to 2,000 Da, from 250 Da to 2,000 Da, from 300 Da to 2,000 Da, from 300 Da to 1,000 Da, from 300 Da to 600 Da, from 350 Da to 2,000 Da, from 350 Da to 1,500 Da, from 350 Da to 1,200 Da, from 350 Da to 1,000 Da, from 350 Da to 900 Da, from 350 Da to 800 Da, from 350 Da to 700 Da, from 350 Da to 600 Da.

22. The method of paragraph 15, wherein the small molecule MASP-2 inhibitory compound has zero to one basic groups selected from guanidine and benzamidine groups.

23. The method of paragraph 15, wherein the small molecule MASP-2 inhibitory compound has a MASP-2 inhibition Ki value of less than about 25 μM, less than about 10 μM, less than about 2.5 μM, less than about 1 μM, less than about 0.5 μM, or less than about 0.1 μM.

24. The method of paragraph 15, wherein the small molecule MASP-2 inhibitory compound is a lectin pathway inhibitor with a lectin pathway inhibition $IC_{50}$ of less than about 50 μM, less than about 5 μM, less than about 1 μM, less than about 0.5 μM, or less than about 0.05 μM.

25. The method of paragraph 15, wherein the small molecule MASP-2 inhibitory compound is a selective MASP-2 inhibitor with a selectivity for MASP-2 inhibition versus thrombin inhibition of greater than about 2-fold, greater than about 5-fold, greater than about 10-fold, greater than about 25-fold, greater than about 50-fold, or greater than about 100-fold.

26. The method of paragraph 15, wherein the small molecule MASP-2 inhibitory compound has a greater affinity for MASP-2 for thrombin with the selectivity ratio of MAASP-2:thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

27. The method of paragraph 15, wherein the small molecule MASP-2 inhibitory compound is not a covalent inhibitor of MASP-2.

28. The method of paragraph 15, wherein the small molecule MASP-2 inhibitory compound is not an endogenous MASP-2 ligand or substrate.

29. The method of any of paragraphs 1 to 28, wherein the MASP-2 inhibitory agent is administered subcutaneously, intraperitoneally, intra-muscularly, intra-arterially, intravenously, orally, or as an inhalant.

All publications, patent applications, and patents mentioned in this specification are herein incorporated by reference.

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for improving respiratory function in a human subject suffering from COVID-19 induced acute respiratory distress syndrome (ARDS) wherein said subject requires mechanical ventilation, comprising administering to the subject an amount of a MASP-2 inhibitory monoclonal antibody or antigen-binding fragment thereof and for a time period sufficient to discontinue the need for mechanical ventilation, wherein the MASP-2 inhibitory monoclonal antibody or antigen-binding fragment thereof comprises a heavy chain variable region comprising CDR-H1, CDR-H2 and CDR-H3 of the amino acid sequence set forth as SEQ ID NO:67 and a light chain variable region comprising CDR-L1, CDR-L2 and CDR-L3 of the amino acid sequence set forth as SEQ ID NO:69.

2. The method of claim 1, wherein the subject requires supplemental oxygen prior to treatment and the MASP-2 inhibitory monoclonal antibody or antigen-binding fragment thereof is administered at a dosage and for a time period sufficient to discontinue the use of supplemental oxygen.

3. The method of claim 1, wherein the antibody or fragment thereof is selected from the group consisting of a recombinant antibody, an antibody having reduced effector function, a chimeric antibody, a humanized antibody and a human antibody.

4. The method of claim 1, wherein the MASP-2 inhibitory antibody selectively inhibits lectin pathway complement activation without substantially inhibiting C1q-dependent complement activation.

5. The method of claim 1, wherein the MASP-2 inhibitory antibody inhibits C3b deposition in 10% human serum with an $IC_{50}$ of 30 nM or less.

6. The method of claim 1 wherein the MASP-2 inhibitory antibody or antigen-binding fragment thereof comprises a heavy chain variable region comprising SEQ ID NO:67 and a light chain variable region comprising SEQ ID NO:69.

* * * * *